US009890368B2

(12) United States Patent
Bouvier et al.

(10) Patent No.: US 9,890,368 B2
(45) Date of Patent: Feb. 13, 2018

(54) POLYPEPTIDE FRAGMENTS COMPRISING ENDONUCLEASE ACTIVITY AND THEIR USE

(71) Applicants: European Molecular Biology Laboratory (EMBL), Heidelberg (DE); Universite Grenoble Alpes, Saint Martin d'Heres (FR); Centre National de la Recherche Scientifique, Paris (FR)

(72) Inventors: Denis Bouvier, Meylan (FR); Thibaut Crepin, Grenoble (FR); Rob Ruigrok, Sassenage (FR); Aelxander Dias, Voiron (FR); Stephen Cusack, Seyssinet-Pariset (FR)

(73) Assignees: European Molecular Biology Laboratory (EMBL), Heidelberg (DE); Centre National de la Recherche Scientifique, Paris (FR); Universite Grenoble Alpes, Saint Martin d'Heres (FR)

( * ) Notice: Subject to any disclaimer, the term of this patent is extended or adjusted under 35 U.S.C. 154(b) by 0 days.

(21) Appl. No.: 14/519,525

(22) Filed: Oct. 21, 2014

(65) Prior Publication Data

US 2015/0105315 A1 Apr. 16, 2015

Related U.S. Application Data

(63) Continuation of application No. 13/140,626, filed as application No. PCT/EP2009/009161 on Dec. 18, 2009, now abandoned.

(Continued)

(51) Int. Cl.

| | |
|---|---|
| *C12N 9/22* | (2006.01) |
| *A61K 31/192* | (2006.01) |

(Continued)

(52) U.S. Cl.

CPC .............. *C12N 9/22* (2013.01); *A61K 31/192* (2013.01); *C12N 9/127* (2013.01); *C12Q 1/44* (2013.01);

(Continued)

(58) Field of Classification Search

None

See application file for complete search history.

(56) References Cited

U.S. PATENT DOCUMENTS 7,074,414 B2 * 7/2006 Dowling .............. A61K 39/145 424/186.1
2005/0143402 A1 6/2005 Cheetham et al.

FOREIGN PATENT DOCUMENTS

JP 2006-504415 2/2006
JP 2006-525032 11/2006

(Continued)

OTHER PUBLICATIONS

The active sites of the influenza cap-dependent endonuclease are on different polymerase subunits: Mei-Ling Li et al., The EMBO journal vol. 20 No. 8 pp. 2078-2086, 2001.

(Continued)

*Primary Examiner* — Paul J Holland

(74) *Attorney, Agent, or Firm* — Barnes & Thornburg LLP

(57) ABSTRACT

The present invention relates to polypeptide fragments comprising an amino-terminal fragment of the PA subunit of a viral RNA-dependent RNA polymerase or variants thereof possessing endonuclease activity, wherein said PA subunit is from a virus belonging to the Orthomyxoviridae family. This invention also relates to (i) crystals of the polypeptide fragments which are suitable for structure determination of said polypeptide fragments using X-ray crystallography and (ii) computational methods using the structural coordinates (Continued)

of said polypeptide to screen for and design compounds that modulate, preferably inhibit the endonucleolytically active site within the polypeptide fragment. In addition, this invention relates to methods identifying compounds that bind to the PA polypeptide fragments possessing endonuclease activity and preferably inhibit said endonucleolytic activity, preferably in a high throughput setting. This invention also relates to compounds and pharmaceutical compositions comprising the identified compounds for the treatment of disease conditions due to viral infections caused by viruses of the Orthomyxoviridae family.

18 Claims, 143 Drawing Sheets

Related U.S. Application Data

(60) Provisional application No. 61/203,259, filed on Dec. 19, 2008.

(51) Int. Cl.

| | |
|---|---|
| ***C12N 9/12*** | (2006.01) |
| ***C12Q 1/44*** | (2006.01) |
| ***G06F 19/12*** | (2011.01) |
| ***G06F 19/16*** | (2011.01) |

(52) U.S. Cl.

CPC .............. *G06F 19/12* (2013.01); *G06F 19/16* (2013.01); *C07K 2299/00* (2013.01); *G01N 2333/922* (2013.01); *G01N 2500/02* (2013.01)

(56) References Cited

FOREIGN PATENT DOCUMENTS

| | | | |
|---|---|---|---|
| JP | 2008-526263 | | 7/2008 |
| KR | 10-2003-0013451 | | 2/2003 |
| WO | 02/00884 | A2 | 1/2002 |
| WO | 2002/00884 | | 1/2002 |

OTHER PUBLICATIONS

Influenza Polymerase Fragment, Database PDB (Online), Dec. 17, 2008, retrieved from EBI, Database accession No. 2W69.
Fodor et al., A single amino acid mutation in the PA subunit of the influenza virus RNA polymerase inhibits endonucleolytic cleavage of capped RNAs, Journal of Virology, 2002, 8989-9001, 76(18).
Sanz-Ezquerro et al., The amino-terminal one-third of the influenza virus PA protein is responsible for the induction of proteolysis, Journal of Virology, 1996, 1905-1911, 70(3).
Hara Koyu et al., Amino acid residues in the N-terminal region of the PA subunit of influenza A virus RNA polymerase play a critical role in protein stability, endonuclease activity, cap binding and virion RNA promoter binding, Journal of Virology, 2006, 7789-7798, 80(16).
Zürcher et al., "Mutational analysis of the influenza virus A/Victoria/3/75 PA protein: studies of the interaction with PB1 protein and identification of a dominant negative mutant," Journal of General Virology, 1996, vol. 77, pp. 1745-1749.
Thathaisong et al., "Human Monoclonal Single Chain Anti-bodies (HuScFv) that Bind to the Polymerase Proteins of Influenza A Virus," Asian Pacific Journal of Allergy and Immunology, Mar. 2008, vol. 26, No. 1, pp. 23-25.
Nakazawa et al., "PA subunit of RNA polymerase as a promising target for anti-influenza virus agents," Antiviral Research, 2008-06, vol. 78, No. 3, pp. 194-201.
Ochoa et al., "Epitope mapping of cross-reactive monoclonal antibodies specific for the influenza A virus PA and PB2 polypeptides," Virus Research, Aug. 1995, vol. 37, No. 3, pp. 305-315.
Dias et al., "The cap-snatching endonuclease of influenza virus polymerase resides in the PA Subunit," Nature, pub. in print Apr. 16, 2009, Epub Feb. 4, 1995, vol. 458, No. 7240, pp. 914-918.
Kuzuhara et al., Green tea catechins inhibit the endonuclease activity of influenza A virus RNA polymerase, PLoS Currents, Oct. 13, 2009, 1:RRN1052.
Zhao et al., "Nucleoside Monophosphate Complex Structures of the Endonuclease Domain from the Influenza Virus Polymerase PA Subunit Reveal the Substrate Binding Site Inside the Catalytic Center," Journal of Virology, Jul. 8, 2009, vol. 83, No. 18, pp. 9024-9030.
Yuan et al., "Crystal structure of an avian influenza polymerase PAN reveals an endonuclease active site," Nature Letters, 2009, 458: pp. 909-913.
Fodor et al, "A Single Amino Acid Mutation in the PA Subunit of the Influenza Virus RNA Polymerase Inhibits Endonucleolytic Cleavage of Capped RNAs," Journal of Virology, 76(18): 8989-9001.
Database PDB, "Influenza Polymerase Fragment," 2008, pp. 1-157.
Sanz-Ezquerro et al., "The amino-terminal one-third of the influenza virus PA protein is responsible for the induction of proteolysis," Journal of Virology, 1996, 70(3): 1905-1911.
Singapore Search Report for Corresponding Singapore Patent Application No. 201104461-7, dated Aug. 25, 2012.
Von Itzstein et al., "Rational Design of potent sialidase-based inhibitors of influenza virus replication", Nature, 363:418-423.
Magden et al., 2005, "Inhibitors of virus replication: recent developments and prospects", Appl. Microbiol. Biotechnol., 66:612-621.
Eriksson et al., 1977, Antimicrob. Agents Chemother., 11:946-951.
Furuta et al., 2005, Antimicrob. Agents Chemother., 49:981-986.
Plotch et al., 1981, Cell, 23:847-858.
Kukkonen et al., 2005, Arch. Virol., 150:533-556.
Leahy et al., 1997, J. Virol., 71:8347-8351.
Noah and Krug, 2005, Adv. Virus Res., 65:121-145.
Fechter et al., 2003, J. Biol. Chem., 278:20381-20388.
Guilligay et al., 2008 Nat. Struct. Mol. Biol., 15:500-506.
Ghanem et al., 2007, J. Virol., 81:7801-7804.
Tisdale et al., 1995, Antimicrob. Agents Chemother., 39:2454-2458.
Tomassini et al., 1994, Antimicrob. Agents Chemother., 38:2827-2837.
Tomassini et al., 1996, Antimicrob. Agents Chemother., 40:1189-1193.
He et al., 2008, Nature, 454:1123-1126.
Obayashi et al., 2008, Nature, 454:1127-1131.
S. M. Berge et al., 1977, "Pharmaceutical Salts", J. Pharm. Sci., 66:1-19.
Terwilliger, 2000, Acta Cryst. D. Biol. Crystallogr, 56:965-972.
Perrakis et al., 1999, Nat. Struct. Biol., 6:458-63.
Murshudov, 1997, Acta Crystallogr. D. Bio. Crystallogr. 53:240-255.
Sali and Blundell, 1993, J. Mol. Biol., 234:779-815.
Goodsell et al., 1990, Proteins: Struct., Funct., Genet., 8: 195-202.
Kuntz et al., 1982, J. Mol. Biol., 161:269-288.
Lauri and Bartlett, 1994, J. Comp. Aid. Mol. Des., 8:51-66.
Martin, 1992, J. Med. Chem., 35:2145-2154.
Eisen et al., 1994, Proteins: Struct., Funct., Genet., 19:199-221.
Meng et al., 1992, J. Comp. Chem., 13:505-524.
Bohm, 1992, J. Comp. Aid. Mol. Des., 6:61-78.
Gillet et al., 1993, J. Comp. Aid Mol. Des., 7:127-153.
Rotstein and Murcko, 1993, J. Med. Chem., 36:1700-1710.
Moon and Howe, 1991, Proteins, 11:314-328.
Cohen et al., 1990, J. Med. Chem., 33:883-894.
Navia and Murcko, 1992, Curr. Opin. Struct. Biol., 2:202-210.
Guida, 1994, Curr. Opin. Struct. Bio., 4:777-781.
Jorgensen & Duffy, 2000, Bioorg. Med. Chem. Lett., 10:1155-1158.
Lipinski et al., 1997, Adv. Drug Deliv. Rev., 23:3-25.
Saito et al., 2008, Nature, 454:523-527.
Baudin et al., 1994, EMBO J., 13:3158-3165.
Doan et al., 1999, Biochemistry, 38:5612-5619.
Kabsch, 1993, J. Appl. Cryst., 26:795-800.
Schneider and Sheidrick, 2002, Acta Crystallogr. D. Biol. Crystallogr. 58:1772-1779.
Pape and Schneider, 2004, J. Appl. Cryst., 37:843-844.

(56) References Cited

OTHER PUBLICATIONS de La Fortelle et al., 1997, Methods in Enzymology, 276:472-494.
Terwilliger, 2002, Acta Crystallogr. D. Biol. Crystallogr. 58:2213-2215.
Terwilliger, 2003, Acta Crystallogr. D. Biol. Crystallogr. 59:45-49.
Jones et al., 1991, Acta Crystallogr. A, 47:110-119.
Lovell et al., 2003, Proteins, 50:437-450.
Rocchia et al., 2002, J. Comput. Chem, 23:128-137.
Nishino et al., 2001, Structure, 9:197-204.
Li et al, 2001, The EMBO Journal, 20(8): 2078-2086.
Blundell et al., 1976, "Protein Crystallography," Academic Press, New York. [Book Reference Available Only Upon Request].
Drenth, 1999, Princrples of Protein X-Ray Crystallography, 2nd Ed., Sprlnger Advanced Texts In Chemlstry, New York. [Book Reference Available Only Upon Request].
Vonrhein et al., 2006, Methods Mol. Biol., 364:215-30.
Jorgensen, 1998, Encyclopedia of Computational Chemistry, Schleyer, Ed., Wiley, New York, Vol. 3, pp. 1986-1989. [Book Reference Available Only Upon Request].
Balbes et al., 1994, Reviews in Computational Chemistry, vol. 5. [Book Reference Available Only Upon Request].
Cowtan, 1994, Joint CCP4 and ESF-EACBM Newsletter on Protein Crystallography, 31 :34-38.
Collaborative Computational Project, 1994, Acta Crystallogr. D. Biol. Crystallogr. 50:760-763.
Gouet et al., 1999, Bioinformatics, 15:305-308.
Schulz et al., 1985. "Principles of Protein Structure," Springer Verlag, New York. [Book Reference Available Only Upon Request].
Balbes et al., 1994, Reviews in Computational Chemistry, vol. V(5), Lipkowitz and Boyd, Eds., VCH, New York, pp. 337-380.
Cowtan. 1994, Joint CCP4 and ESF-EACBM Newsletter on Protein Crystallography, 31 :34-38.
Collaborative Computational Project, No. 4, 1994, The CCP4 Suite: Programs for Protein Crystallography, *Acta Crzst.* D50:760-763.
Gouet et al., 1999, ESpript: analysis of multiple sequence alignments in PostScript, Bioinformatics, 15(4):305-308.
Bartlett et al., 1989, Molecular Recognition in Chemical and Biological Problems, Special Publication, Royal Chem. Soc. 78:182-196.
Vonrhein et al., 2006, Automated Structure with autoSharp. Macromolecular Crystallography Protocols: vol 2: Structure Determination; Methods Mol. Biol., 364:215-30; Double Ed., Humana Press, Inc., Totowa, NJ.

* cited by examiner

Figure 2

| Type of metal | Tm (°C) |
| --- | --- |
| No metal | 44 |
| **$CaCl_2$** | **52** |
| **$MgCl_2$** | **50** |
| **$MnCl_2$** | **57** |
| $NiCl_2$ | 48 |
| $FeCl_2$ | 45 |
| $CuCl_2$ | 44 |
| $ZnCl_2$ | 39 |

37°C, 40 min, 1 mM $Mn^{2+}$

37°C, 40 min, 1 mM $Mn^{2+}$

```
COMPND    --REMARK   3
REMARK   3 REFINEMENT.
REMARK   3   PROGRAM     : REFMAC 5.2.0019
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.05
REMARK   3   RESOLUTION RANGE LOW  (ANGSTROMS) :  75.81
REMARK   3   DATA CUTOFF            (SIGMA(F)) : NONE
REMARK   3   COMPLETENESS FOR RANGE        (%) :  93.18
REMARK   3   NUMBER OF REFLECTIONS             :   39713
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.21971
REMARK   3   R VALUE            (WORKING SET) :  0.21716
REMARK   3   FREE R VALUE                     :  0.26750
REMARK   3   FREE R VALUE TEST SET SIZE   (%) :  5.1
REMARK   3   FREE R VALUE TEST SET COUNT      :  2118
REMARK   3
REMARK   3  FIT IN THE HIGHEST RESOLUTION BIN.
REMARK   3   TOTAL NUMBER OF BINS USED           :       20
REMARK   3   BIN RESOLUTION RANGE HIGH           :    2.050
REMARK   3   BIN RESOLUTION RANGE LOW            :    2.103
REMARK   3   REFLECTION IN BIN     (WORKING SET) :     3094
REMARK   3   BIN COMPLETENESS (WORKING+TEST) (%) :    99.42
REMARK   3   BIN R VALUE           (WORKING SET) :    0.278
REMARK   3   BIN FREE R VALUE SET COUNT          :      169
REMARK   3   BIN FREE R VALUE                    :    0.320
REMARK   3
REMARK   3  NUMBER OF NON-HYDROGEN ATOMS USED IN REFINEMENT.
REMARK   3   ALL ATOMS                :     4939
REMARK   3
REMARK   3  B VALUES.
REMARK   3   FROM WILSON PLOT           (A**2) : NULL
REMARK   3   MEAN B VALUE      (OVERALL, A**2) :  45.800
REMARK   3   OVERALL ANISOTROPIC B VALUE.
REMARK   3    B11 (A**2) :    -0.36
REMARK   3    B22 (A**2) :    -0.36
REMARK   3    B33 (A**2) :     0.71
REMARK   3    B12 (A**2) :     0.00
REMARK   3    B13 (A**2) :     0.00
REMARK   3    B23 (A**2) :     0.00
REMARK   3
REMARK   3  ESTIMATED OVERALL COORDINATE ERROR.
REMARK   3   ESU BASED ON R VALUE                            (A):   0.231
REMARK   3   ESU BASED ON FREE R VALUE                       (A):   0.201
REMARK   3   ESU BASED ON MAXIMUM LIKELIHOOD                 (A):   0.156
REMARK   3   ESU FOR B VALUES BASED ON MAXIMUM LIKELIHOOD (A**2):  11.611
REMARK   3
REMARK   3 CORRELATION COEFFICIENTS.
REMARK   3   CORRELATION COEFFICIENT FO-FC      :   0.943
REMARK   3   CORRELATION COEFFICIENT FO-FC FREE :   0.914
REMARK   3
REMARK   3  RMS DEVIATIONS FROM IDEAL VALUES        COUNT    RMS    WEIGHT
REMARK   3   BOND LENGTHS REFINED ATOMS        (A):  4869 ; 0.014 ; 0.022
REMARK   3   BOND LENGTHS OTHERS               (A):  3354 ; 0.002 ; 0.020
REMARK   3   BOND ANGLES REFINED ATOMS   (DEGREES):  6555 ; 1.363 ; 1.946
REMARK   3   BOND ANGLES OTHERS          (DEGREES):  8117 ; 0.981 ; 3.000
REMARK   3   TORSION ANGLES, PERIOD 1    (DEGREES):   573 ; 5.789 ; 5.000
REMARK   3   TORSION ANGLES, PERIOD 2    (DEGREES):   259 ;36.576 ;23.977
REMARK   3   TORSION ANGLES, PERIOD 3    (DEGREES):   895 ;16.069 ;15.000
REMARK   3   TORSION ANGLES, PERIOD 4    (DEGREES):    37 ;18.457 ;15.000
REMARK   3   CHIRAL-CENTER RESTRAINTS       (A**3):   701 ; 0.081 ; 0.200
REMARK   3   GENERAL PLANES REFINED ATOMS      (A):  5348 ; 0.005 ; 0.020
REMARK   3   GENERAL PLANES OTHERS             (A):  1043 ; 0.002 ; 0.020
REMARK   3   NON-BONDED CONTACTS REFINED ATOMS (A):  1019 ; 0.215 ; 0.200
REMARK   3   NON-BONDED CONTACTS OTHERS        (A):  3369 ; 0.194 ; 0.200
REMARK   3   NON-BONDED TORSION REFINED ATOMS  (A):  2308 ; 0.178 ; 0.200
REMARK   3   NON-BONDED TORSION OTHERS         (A):  2563 ; 0.084 ; 0.200
REMARK   3   H-BOND (X...Y) REFINED ATOMS      (A):   179 ; 0.180 ; 0.200
REMARK   3   SYMMETRY VDW REFINED ATOMS        (A):    25 ; 0.239 ; 0.200
REMARK   3   SYMMETRY VDW OTHERS               (A):    50 ; 0.274 ; 0.200
REMARK   3   SYMMETRY H-BOND REFINED ATOMS     (A):     5 ; 0.192 ; 0.200
```

FIG. 18

```
REMARK   3
REMARK   3  ISOTROPIC THERMAL FACTOR RESTRAINTS.     COUNT   RMS    WEIGHT
REMARK   3   MAIN-CHAIN BOND REFINED ATOMS  (A**2):  3179 ; 1.590 ; 2.000
REMARK   3   MAIN-CHAIN BOND OTHER ATOMS    (A**2):  1159 ; 0.347 ; 2.000
REMARK   3   MAIN-CHAIN ANGLE REFINED ATOMS (A**2):  4635 ; 2.247 ; 3.000
REMARK   3   SIDE-CHAIN BOND REFINED ATOMS  (A**2):  2210 ; 1.426 ; 2.000
REMARK   3   SIDE-CHAIN ANGLE REFINED ATOMS (A**2):  1918 ; 1.974 ; 3.000
REMARK   3
REMARK   3  NCS RESTRAINTS STATISTICS
REMARK   3   NUMBER OF DIFFERENT NCS GROUPS :   2
REMARK   3
REMARK   3  NCS GROUP NUMBER               :   1
REMARK   3     CHAIN NAMES                    : A B
REMARK   3     NUMBER OF COMPONENTS NCS GROUP :    8
REMARK   3       COMPONENT C  SSSEQI  TO  C   SSSEQI   CODE
REMARK   3           1     A      1       A      8       1
REMARK   3           1     B      1       B      8       1
REMARK   3           2     A     12       A     17       1
REMARK   3           2     B     12       B     17       1
REMARK   3           3     A     33       A     45       1
REMARK   3           3     B     33       B     45       1
REMARK   3           4     A    110       A    116       1
REMARK   3           4     B    110       B    116       1
REMARK   3           5     A    122       A    132       1
REMARK   3           5     B    122       B    132       1
REMARK   3           6     A    144       A    150       1
REMARK   3           6     B    144       B    150       1
REMARK   3           7     A    154       A    163       1
REMARK   3           7     B    154       B    163       1
REMARK   3           8     A    174       A    192       1
REMARK   3           8     B    174       B    192       1
REMARK   3                  GROUP CHAIN        COUNT   RMS     WEIGHT
REMARK   3   TIGHT POSITIONAL    1    A    (A):   1143 ;  0.06 ;  0.05
REMARK   3   TIGHT THERMAL       1    A (A**2):   1143 ;  0.17 ;  0.50
REMARK   3
REMARK   3  NCS GROUP NUMBER               :   2
REMARK   3     CHAIN NAMES                    : B D
REMARK   3     NUMBER OF COMPONENTS NCS GROUP :    5
REMARK   3       COMPONENT C  SSSEQI  TO  C   SSSEQI   CODE
REMARK   3           1     B     33       B     45       2
REMARK   3           1     D     33       D     45       2
REMARK   3           2     B    121       B    133       2
REMARK   3           2     D    121       D    133       2
REMARK   3           3     B    144       B    150       2
REMARK   3           3     D    144       D    150       2
REMARK   3           4     B    161       B    164       2
REMARK   3           4     D    161       D    164       2
REMARK   3           5     B    168       B    183       2
REMARK   3           5     D    168       D    183       2
REMARK   3                  GROUP CHAIN        COUNT   RMS     WEIGHT
REMARK   3   TIGHT POSITIONAL    2    B    (A):    317 ;  0.04 ;  0.05
REMARK   3   MEDIUM POSITIONAL   2    B    (A):    443 ;  0.24 ;  0.50
REMARK   3   TIGHT THERMAL       2    B (A**2):    317 ;  0.18 ;  0.50
REMARK   3   MEDIUM THERMAL      2    B (A**2):    443 ;  0.69 ;  2.00
REMARK   3
REMARK   3
REMARK   3  TLS DETAILS
REMARK   3   NUMBER OF TLS GROUPS  :    3
REMARK   3   ATOM RECORD CONTAINS SUM OF TLS AND RESIDUAL B FACTORS
REMARK   3   ANISOU RECORD CONTAINS SUM OF TLS AND RESIDUAL U FACTORS
REMARK   3
REMARK   3   TLS GROUP :     1
REMARK   3    NUMBER OF COMPONENTS GROUP :    2
REMARK   3    COMPONENTS          C SSSEQI   TO  C SSSEQI
REMARK   3    RESIDUE RANGE :   A     0         A   196
REMARK   3    RESIDUE RANGE :   A   301         A   402
REMARK   3    ORIGIN FOR THE GROUP (A):   0.4380  31.9220  84.5340
REMARK   3    T TENSOR
REMARK   3      T11:   0.0340 T22:   0.1320
REMARK   3      T33:  -0.0452 T12:  -0.0193
REMARK   3      T13:   0.0298 T23:   0.0543
REMARK   3    L TENSOR
REMARK   3      L11:   2.6068 L22:   2.0135
REMARK   3      L33:   2.5508 L12:   1.0612
REMARK   3      L13:   0.0150 L23:  -0.1527
REMARK   3    S TENSOR
REMARK   3      S11:  -0.1001 S12:   0.2362 S13:  -0.0361
REMARK   3      S21:  -0.1237 S22:   0.1658 S23:   0.0784
REMARK   3      S31:   0.0830 S32:  -0.2500 S33:  -0.0657
```

FIG. 18 (continued)

```
REMARK   3
REMARK   3   TLS GROUP :     2
REMARK   3    NUMBER OF COMPONENTS GROUP :    2
REMARK   3    COMPONENTS          C SSSEQI    TO  C SSSEQI
REMARK   3    RESIDUE RANGE :   B     0          B   196
REMARK   3    RESIDUE RANGE :   B   301          B   403
REMARK   3    ORIGIN FOR THE GROUP (A):  22.5390  42.1420 102.7410
REMARK   3    T TENSOR
REMARK   3      T11:   0.0404 T22:   0.0842
REMARK   3      T33:  -0.0604 T12:   0.0210
REMARK   3      T13:   0.0303 T23:  -0.0277
REMARK   3    L TENSOR
REMARK   3      L11:   2.8576 L22:   2.1021
REMARK   3      L33:   3.1067 L12:   0.1958
REMARK   3      L13:  -0.8397 L23:  -0.3874
REMARK   3    S TENSOR
REMARK   3      S11:   0.0073 S12:  -0.2765 S13:   0.2133
REMARK   3      S21:   0.0189 S22:   0.0880 S23:  -0.1481
REMARK   3      S31:   0.0012 S32:   0.2691 S33:  -0.0953
REMARK   3
REMARK   3   TLS GROUP :     3
REMARK   3    NUMBER OF COMPONENTS GROUP :    2
REMARK   3    COMPONENTS          C SSSEQI    TO  C SSSEQI
REMARK   3    RESIDUE RANGE :   D     0          D   196
REMARK   3    RESIDUE RANGE :   D   301          D   403
REMARK   3    ORIGIN FOR THE GROUP (A): -22.4770  20.8930 102.3720
REMARK   3    T TENSOR
REMARK   3      T11:   0.1570 T22:   0.1217
REMARK   3      T33:   0.1402 T12:  -0.0869
REMARK   3      T13:   0.1110 T23:  -0.0160
REMARK   3    L TENSOR
REMARK   3      L11:   2.5483 L22:   2.0767
REMARK   3      L33:   8.2665 L12:   0.0117
REMARK   3      L13:   0.0498 L23:   0.6732
REMARK   3    S TENSOR
REMARK   3      S11:  -0.2912 S12:  -0.3117 S13:  -0.2484
REMARK   3      S21:   0.2341 S22:  -0.4001 S23:  -0.1232
REMARK   3      S31:   0.6684 S32:  -0.3291 S33:   0.6913
REMARK   3
REMARK   3
REMARK   3  BULK SOLVENT MODELLING.
REMARK   3   METHOD USED :  MASK
REMARK   3   PARAMETERS FOR MASK CALCULATION
REMARK   3   VDW PROBE RADIUS   :   1.20
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3  HYDROGENS HAVE BEEN ADDED IN THE RIDING POSITIONS
REMARK   3
LINK             LEU A  71                 LYS A  73                gap
LINK             SER A 140                 THR A 143                gap
LINK             VAL D  62                 HIS D  74                gap
LINK             LYS D 139                 THR D 143                gap
CRYST1   67.130   67.130  302.950  90.00  90.00  90.00 P 43 21 2
SCALE1      0.014896  0.000000  0.000000        0.00000
SCALE2      0.000000  0.014896  0.000000        0.00000
SCALE3      0.000000  0.000000  0.003301        0.00000
ATOM      1  N   ALA A   0       9.315  10.382  90.066  1.00 50.72           N
ANISOU    1  N   ALA A   0     7389   3921   7962    611     76    464       N
ATOM      2  CA  ALA A   0      10.124  11.028  88.989  1.00 50.07           C
ANISOU    2  CA  ALA A   0     7165   3975   7882    726    202    231       C
ATOM      4  CB  ALA A   0      10.165  10.148  87.721  1.00 52.25           C
ANISOU    4  CB  ALA A   0     7530   4037   8286    741    344    -42       C
ATOM      8  C   ALA A   0       9.671  12.452  88.645  1.00 46.70           C
ANISOU    8  C   ALA A   0     6647   3914   7182    603    245    183       C
ATOM      9  O   ALA A   0      10.538  13.316  88.477  1.00 47.00           O
ANISOU    9  O   ALA A   0     6529   4129   7199    713    272    143       O
ATOM     13  N   MET A   1       8.350  12.713  88.567  1.00 44.40           N
ANISOU   13  N   MET A   1     6441   3734   6694    381    247    197       N
ATOM     14  CA  MET A   1       7.837  14.031  88.151  1.00 42.59           C
ANISOU   14  CA  MET A   1     6131   3825   6226    272    288    149       C
ATOM     16  CB  MET A   1       6.338  14.001  87.763  1.00 42.12           C
ANISOU   16  CB  MET A   1     6168   3833   6002     37    307    119       C
ATOM     19  CG  MET A   1       5.743  15.382  87.386  1.00 38.09           C
ANISOU   19  CG  MET A   1     5567   3643   5263    -59    334     97       C
ATOM     22  SD  MET A   1       6.495  16.073  85.893  1.00 38.49           S
ANISOU   22  SD  MET A   1     5531   3825   5269      1    455   -136       S
ATOM     23  CE  MET A   1       5.333  15.561  84.636  1.00 37.87           C
```

FIG. 18 (continued)

| | | | | | | | | | | | | |
|---|---|---|---|---|---|---|---|---|---|---|---|---|
| ANISOU | 23 | CE | MET | A | 1 | 5562 | 3744 | 5084 | -209 | 520 | -306 | C |
| ATOM | 27 | C | MET | A | 1 | 8.057 | 15.081 | 89.228 | 1.00 | 41.39 | | C |
| ANISOU | 27 | C | MET | A | 1 | 5876 | 3876 | 5975 | 306 | 199 | 335 | C |
| ATOM | 28 | O | MET | A | 1 | 8.385 | 16.224 | 88.905 | 1.00 | 39.08 | | O |
| ANISOU | 28 | O | MET | A | 1 | 5471 | 3802 | 5576 | 328 | 235 | 283 | O |
| ATOM | 30 | N | GLU | A | 2 | 7.854 | 14.717 | 90.492 | 1.00 | 42.43 | | N |
| ANISOU | 30 | N | GLU | A | 2 | 6056 | 3939 | 6127 | 292 | 86 | 548 | N |
| ATOM | 31 | CA | GLU | A | 2 | 8.073 | 15.657 | 91.571 | 1.00 | 43.33 | | C |
| ANISOU | 31 | CA | GLU | A | 2 | 6087 | 4242 | 6132 | 309 | 3 | 712 | C |
| ATOM | 33 | CB | GLU | A | 2 | 7.656 | 15.061 | 92.913 | 1.00 | 46.20 | | C |
| ANISOU | 33 | CB | GLU | A | 2 | 6540 | 4521 | 6492 | 249 | -115 | 945 | C |
| ATOM | 36 | CG | GLU | A | 2 | 7.491 | 16.108 | 94.002 | 1.00 | 45.99 | | C |
| ANISOU | 36 | CG | GLU | A | 2 | 6459 | 4732 | 6282 | 198 | -179 | 1088 | C |
| ATOM | 39 | CD | GLU | A | 2 | 7.296 | 15.490 | 95.355 | 1.00 | 47.39 | | C |
| ANISOU | 39 | CD | GLU | A | 2 | 6719 | 4838 | 6448 | 146 | -297 | 1325 | C |
| ATOM | 40 | OE1 | GLU | A | 2 | 6.846 | 14.324 | 95.413 | 1.00 | 50.77 | | O |
| ANISOU | 40 | OE1 | GLU | A | 2 | 7269 | 5051 | 6970 | 89 | -318 | 1387 | O |
| ATOM | 41 | OE2 | GLU | A | 2 | 7.570 | 16.174 | 96.362 | 1.00 | 48.11 | | O |
| ANISOU | 41 | OE2 | GLU | A | 2 | 6765 | 5089 | 6427 | 145 | -371 | 1450 | O |
| ATOM | 42 | C | GLU | A | 2 | 9.537 | 16.090 | 91.591 | 1.00 | 42.82 | | C |
| ANISOU | 42 | C | GLU | A | 2 | 5884 | 4218 | 6169 | 499 | -14 | 694 | C |
| ATOM | 43 | O | GLU | A | 2 | 9.835 | 17.264 | 91.719 | 1.00 | 40.12 | | O |
| ANISOU | 43 | O | GLU | A | 2 | 5439 | 4094 | 5710 | 504 | -13 | 693 | O |
| ATOM | 45 | N | ASP | A | 3 | 10.448 | 15.138 | 91.413 | 1.00 | 44.73 | | N |
| ANISOU | 45 | N | ASP | A | 3 | 6115 | 4242 | 6638 | 654 | -22 | 668 | N |
| ATOM | 46 | CA | ASP | A | 3 | 11.880 | 15.449 | 91.280 | 1.00 | 45.34 | | C |
| ANISOU | 46 | CA | ASP | A | 3 | 6031 | 4358 | 6840 | 844 | -21 | 628 | C |
| ATOM | 48 | CB | ASP | A | 3 | 12.704 | 14.167 | 91.109 | 1.00 | 49.33 | | C |
| ANISOU | 48 | CB | ASP | A | 3 | 6538 | 4574 | 7631 | 1025 | -26 | 604 | C |
| ATOM | 51 | CG | ASP | A | 3 | 12.855 | 13.393 | 92.403 | 1.00 | 52.53 | | C |
| ANISOU | 51 | CG | ASP | A | 3 | 6995 | 4815 | 8147 | 1079 | -195 | 862 | C |
| ATOM | 52 | OD1 | ASP | A | 3 | 12.810 | 14.021 | 93.478 | 1.00 | 53.28 | | O |
| ANISOU | 52 | OD1 | ASP | A | 3 | 7062 | 5075 | 8108 | 1024 | -313 | 1051 | O |
| ATOM | 53 | OD2 | ASP | A | 3 | 13.016 | 12.161 | 92.343 | 1.00 | 56.60 | | O |
| ANISOU | 53 | OD2 | ASP | A | 3 | 7590 | 5033 | 8881 | 1171 | -209 | 874 | O |
| ATOM | 54 | C | ASP | A | 3 | 12.177 | 16.363 | 90.099 | 1.00 | 42.26 | | C |
| ANISOU | 54 | C | ASP | A | 3 | 5540 | 4147 | 6370 | 841 | 114 | 417 | C |
| ATOM | 55 | O | ASP | A | 3 | 12.991 | 17.287 | 90.189 | 1.00 | 41.12 | | O |
| ANISOU | 55 | O | ASP | A | 3 | 5252 | 4179 | 6192 | 900 | 107 | 419 | O |
| ATOM | 57 | N | PHE | A | 4 | 11.537 | 16.073 | 88.984 | 1.00 | 41.38 | | N |
| ANISOU | 57 | N | PHE | A | 4 | 5509 | 3988 | 6225 | 759 | 233 | 238 | N |
| ATOM | 58 | CA | PHE | A | 4 | 11.670 | 16.923 | 87.821 | 1.00 | 40.24 | | C |
| ANISOU | 58 | CA | PHE | A | 4 | 5294 | 4024 | 5972 | 722 | 358 | 53 | C |
| ATOM | 60 | CB | PHE | A | 4 | 10.836 | 16.386 | 86.665 | 1.00 | 41.11 | | C |
| ANISOU | 60 | CB | PHE | A | 4 | 5523 | 4063 | 6036 | 607 | 466 | -127 | C |
| ATOM | 63 | CG | PHE | A | 4 | 10.797 | 17.308 | 85.529 | 1.00 | 40.25 | | C |
| ANISOU | 63 | CG | PHE | A | 4 | 5360 | 4162 | 5769 | 533 | 573 | -280 | C |
| ATOM | 64 | CD1 | PHE | A | 4 | 11.880 | 17.401 | 84.679 | 1.00 | 42.34 | | C |
| ANISOU | 64 | CD1 | PHE | A | 4 | 5524 | 4460 | 6103 | 636 | 685 | -442 | C |
| ATOM | 66 | CE1 | PHE | A | 4 | 11.872 | 18.304 | 83.633 | 1.00 | 40.40 | | C |
| ANISOU | 66 | CE1 | PHE | A | 4 | 5235 | 4424 | 5692 | 549 | 781 | -563 | C |
| ATOM | 68 | CZ | PHE | A | 4 | 10.794 | 19.105 | 83.448 | 1.00 | 38.66 | | C |
| ANISOU | 68 | CZ | PHE | A | 4 | 5068 | 4363 | 5260 | 381 | 752 | -514 | C |
| ATOM | 70 | CE2 | PHE | A | 4 | 9.728 | 19.045 | 84.307 | 1.00 | 38.18 | | C |
| ANISOU | 70 | CE2 | PHE | A | 4 | 5087 | 4272 | 5148 | 300 | 643 | -360 | C |
| ATOM | 72 | CD2 | PHE | A | 4 | 9.730 | 18.149 | 85.341 | 1.00 | 38.74 | | C |
| ANISOU | 72 | CD2 | PHE | A | 4 | 5205 | 4151 | 5364 | 366 | 561 | -248 | C |
| ATOM | 74 | C | PHE | A | 4 | 11.273 | 18.381 | 88.119 | 1.00 | 37.76 | | C |
| ANISOU | 74 | C | PHE | A | 4 | 4927 | 3981 | 5438 | 618 | 327 | 128 | C |
| ATOM | 75 | O | PHE | A | 4 | 12.027 | 19.306 | 87.806 | 1.00 | 34.70 | | O |
| ANISOU | 75 | O | PHE | A | 4 | 4418 | 3754 | 5013 | 658 | 363 | 81 | O |
| ATOM | 77 | N | VAL | A | 5 | 10.097 | 18.571 | 88.723 | 1.00 | 36.13 | | N |
| ANISOU | 77 | N | VAL | A | 5 | 4812 | 3818 | 5099 | 483 | 267 | 241 | N |
| ATOM | 78 | CA | VAL | A | 5 | 9.572 | 19.908 | 88.996 | 1.00 | 34.93 | | C |
| ANISOU | 78 | CA | VAL | A | 5 | 4625 | 3893 | 4753 | 389 | 249 | 298 | C |
| ATOM | 80 | CB | VAL | A | 5 | 8.135 | 19.854 | 89.650 | 1.00 | 33.81 | | C |
| ANISOU | 80 | CB | VAL | A | 5 | 4584 | 3771 | 4490 | 245 | 202 | 407 | C |
| ATOM | 82 | CG1 | VAL | A | 5 | 7.674 | 21.216 | 90.170 | 1.00 | 31.16 | | C |
| ANISOU | 82 | CG1 | VAL | A | 5 | 4205 | 3648 | 3986 | 184 | 181 | 476 | C |
| ATOM | 86 | CG2 | VAL | A | 5 | 7.098 | 19.313 | 88.674 | 1.00 | 33.46 | | C |
| ANISOU | 86 | CG2 | VAL | A | 5 | 4624 | 3681 | 4407 | 127 | 268 | 301 | C |
| ATOM | 90 | C | VAL | A | 5 | 10.542 | 20.662 | 89.894 | 1.00 | 34.74 | | C |
| ANISOU | 90 | C | VAL | A | 5 | 4495 | 3968 | 4737 | 474 | 177 | 401 | C |
| ATOM | 91 | O | VAL | A | 5 | 10.910 | 21.788 | 89.618 | 1.00 | 33.00 | | O |
| ANISOU | 91 | O | VAL | A | 5 | 4194 | 3911 | 4435 | 466 | 206 | 361 | O |
| ATOM | 93 | N | ARG | A | 6 | 10.953 | 20.025 | 90.982 | 1.00 | 37.74 | | N |
| ANISOU | 93 | N | ARG | A | 6 | 4881 | 4245 | 5213 | 542 | 72 | 542 | N |
| ATOM | 94 | CA | ARG | A | 6 | 11.827 | 20.670 | 91.955 | 1.00 | 39.90 | | C |
| ANISOU | 94 | CA | ARG | A | 6 | 5060 | 4622 | 5478 | 600 | -22 | 656 | C |

FIG. 18 (continued)

| | | | | | | | | | | | | |
|---|---|---|---|---|---|---|---|---|---|---|---|---|
| ATOM | 96 | CB | ARG | A | 6 | 11.981 | 19.791 | 93.190 | 1.00 | 41.23 | | C |
| ANISOU | 96 | CB | ARG | A | 6 | 5272 | 4669 | 5725 | 641 | -156 | 843 | C |
| ATOM | 99 | CG | ARG | A | 6 | 10.697 | 19.651 | 93.975 | 1.00 | 40.79 | | C |
| ANISOU | 99 | CG | ARG | A | 6 | 5351 | 4617 | 5531 | 498 | -195 | 958 | C |
| ATOM | 102 | CD | ARG | A | 6 | 10.928 | 18.851 | 95.278 | 1.00 | 42.89 | | C |
| ANISOU | 102 | CD | ARG | A | 6 | 5664 | 4785 | 5848 | 521 | -340 | 1172 | C |
| ATOM | 105 | NE | ARG | A | 6 | 9.652 | 18.568 | 95.912 | 1.00 | 43.90 | | N |
| ANISOU | 105 | NE | ARG | A | 6 | 5925 | 4907 | 5848 | 368 | -353 | 1271 | N |
| ATOM | 107 | CZ | ARG | A | 6 | 8.902 | 19.457 | 96.546 | 1.00 | 42.02 | | C |
| ANISOU | 107 | CZ | ARG | A | 6 | 5708 | 4857 | 5402 | 242 | -346 | 1309 | C |
| ATOM | 108 | NH1 | ARG | A | 6 | 9.316 | 20.704 | 96.693 | 1.00 | 40.53 | | N |
| ANISOU | 108 | NH1 | ARG | A | 6 | 5434 | 4855 | 5109 | 250 | -339 | 1262 | N |
| ATOM | 111 | NH2 | ARG | A | 6 | 7.734 | 19.083 | 97.060 | 1.00 | 42.78 | | N |
| ANISOU | 111 | NH2 | ARG | A | 6 | 5910 | 4947 | 5396 | 105 | -341 | 1391 | N |
| ATOM | 114 | C | ARG | A | 6 | 13.208 | 21.030 | 91.402 | 1.00 | 41.92 | | C |
| ANISOU | 114 | C | ARG | A | 6 | 5160 | 4932 | 5836 | 720 | 12 | 568 | C |
| ATOM | 115 | O | ARG | A | 6 | 13.807 | 22.008 | 91.844 | 1.00 | 41.81 | | O |
| ANISOU | 115 | O | ARG | A | 6 | 5054 | 5073 | 5759 | 716 | -31 | 608 | O |
| ATOM | 117 | N | GLN | A | 7 | 13.689 | 20.255 | 90.429 | 1.00 | 44.86 | | N |
| ANISOU | 117 | N | GLN | A | 7 | 5502 | 5182 | 6361 | 813 | 99 | 437 | N |
| ATOM | 118 | CA | GLN | A | 7 | 14.980 | 20.509 | 89.794 | 1.00 | 47.32 | | C |
| ANISOU | 118 | CA | GLN | A | 7 | 5649 | 5553 | 6778 | 926 | 160 | 333 | C |
| ATOM | 120 | CB | GLN | A | 7 | 15.596 | 19.206 | 89.265 | 1.00 | 50.83 | | C |
| ANISOU | 120 | CB | GLN | A | 7 | 6067 | 5789 | 7458 | 1081 | 214 | 243 | C |
| ATOM | 123 | CG | GLN | A | 7 | 16.042 | 18.245 | 90.381 | 1.00 | 55.13 | | C |
| ANISOU | 123 | CG | GLN | A | 7 | 6603 | 6162 | 8182 | 1209 | 69 | 419 | C |
| ATOM | 126 | CD | GLN | A | 7 | 16.546 | 16.882 | 89.861 | 1.00 | 59.09 | | C |
| ANISOU | 126 | CD | GLN | A | 7 | 7099 | 6405 | 8947 | 1378 | 126 | 329 | C |
| ATOM | 127 | OE1 | GLN | A | 7 | 16.678 | 16.665 | 88.642 | 1.00 | 62.39 | | O |
| ANISOU | 127 | OE1 | GLN | A | 7 | 7506 | 6788 | 9411 | 1404 | 289 | 108 | O |
| ATOM | 128 | NE2 | GLN | A | 7 | 16.824 | 15.959 | 90.790 | 1.00 | 61.66 | | N |
| ANISOU | 128 | NE2 | GLN | A | 7 | 7441 | 6543 | 9443 | 1492 | -9 | 499 | N |
| ATOM | 131 | C | GLN | A | 7 | 14.864 | 21.532 | 88.674 | 1.00 | 44.06 | | C |
| ANISOU | 131 | C | GLN | A | 7 | 5206 | 5308 | 6227 | 834 | 288 | 182 | C |
| ATOM | 132 | O | GLN | A | 7 | 15.798 | 22.282 | 88.440 | 1.00 | 43.88 | | O |
| ANISOU | 132 | O | GLN | A | 7 | 5046 | 5421 | 6206 | 862 | 316 | 145 | O |
| ATOM | 134 | N | CYS | A | 8 | 13.713 | 21.608 | 88.006 | 1.00 | 41.71 | | N |
| ANISOU | 134 | N | CYS | A | 8 | 5033 | 5013 | 5802 | 712 | 354 | 112 | N |
| ATOM | 135 | CA | CYS | A | 8 | 13.632 | 22.405 | 86.780 | 1.00 | 41.63 | | C |
| ANISOU | 135 | CA | CYS | A | 8 | 5001 | 5141 | 5673 | 632 | 474 | -28 | C |
| ATOM | 137 | CB | CYS | A | 8 | 13.175 | 21.523 | 85.634 | 1.00 | 44.73 | | C |
| ANISOU | 137 | CB | CYS | A | 8 | 5476 | 5432 | 6086 | 607 | 584 | -188 | C |
| ATOM | 140 | SG | CYS | A | 8 | 14.467 | 20.295 | 85.173 | 1.00 | 52.87 | | S |
| ANISOU | 140 | SG | CYS | A | 8 | 6419 | 6299 | 7370 | 794 | 670 | -327 | S |
| ATOM | 142 | C | CYS | A | 8 | 12.851 | 23.730 | 86.821 | 1.00 | 37.13 | | C |
| ANISOU | 142 | C | CYS | A | 8 | 4468 | 4738 | 4901 | 495 | 456 | 26 | C |
| ATOM | 143 | O | CYS | A | 8 | 12.992 | 24.544 | 85.907 | 1.00 | 36.80 | | O |
| ANISOU | 143 | O | CYS | A | 8 | 4392 | 4822 | 4768 | 436 | 534 | -55 | O |
| ATOM | 145 | N | PHE | A | 9 | 12.076 | 23.962 | 87.882 | 1.00 | 34.09 | | N |
| ANISOU | 145 | N | PHE | A | 9 | 4149 | 4353 | 4449 | 448 | 358 | 162 | N |
| ATOM | 146 | CA | PHE | A | 9 | 11.500 | 25.282 | 88.136 | 1.00 | 29.79 | | C |
| ANISOU | 146 | CA | PHE | A | 9 | 3620 | 3951 | 3748 | 354 | 336 | 217 | C |
| ATOM | 148 | CB | PHE | A | 9 | 9.991 | 25.175 | 88.443 | 1.00 | 28.54 | | C |
| ANISOU | 148 | CB | PHE | A | 9 | 3575 | 3776 | 3495 | 265 | 312 | 273 | C |
| ATOM | 151 | CG | PHE | A | 9 | 9.169 | 24.801 | 87.252 | 1.00 | 25.87 | | C |
| ANISOU | 151 | CG | PHE | A | 9 | 3292 | 3425 | 3113 | 196 | 385 | 177 | C |
| ATOM | 152 | CD1 | PHE | A | 9 | 8.712 | 25.773 | 86.385 | 1.00 | 26.33 | | C |
| ANISOU | 152 | CD1 | PHE | A | 9 | 3346 | 3607 | 3052 | 121 | 430 | 136 | C |
| ATOM | 154 | CE1 | PHE | A | 9 | 7.961 | 25.434 | 85.252 | 1.00 | 26.62 | | C |
| ANISOU | 154 | CE1 | PHE | A | 9 | 3431 | 3655 | 3029 | 41 | 482 | 55 | C |
| ATOM | 156 | CZ | PHE | A | 9 | 7.648 | 24.110 | 84.998 | 1.00 | 28.44 | | C |
| ANISOU | 156 | CZ | PHE | A | 9 | 3722 | 3762 | 3321 | 27 | 498 | -6 | C |
| ATOM | 158 | CE2 | PHE | A | 9 | 8.086 | 23.119 | 85.848 | 1.00 | 29.05 | | C |
| ANISOU | 158 | CE2 | PHE | A | 9 | 3816 | 3688 | 3535 | 107 | 463 | 28 | C |
| ATOM | 160 | CD2 | PHE | A | 9 | 8.862 | 23.479 | 86.986 | 1.00 | 29.88 | | C |
| ANISOU | 160 | CD2 | PHE | A | 9 | 3863 | 3793 | 3698 | 197 | 400 | 131 | C |
| ATOM | 162 | C | PHE | A | 9 | 12.225 | 25.984 | 89.283 | 1.00 | 29.37 | | C |
| ANISOU | 162 | C | PHE | A | 9 | 3502 | 3962 | 3694 | 383 | 249 | 318 | C |
| ATOM | 163 | O | PHE | A | 9 | 12.692 | 25.361 | 90.216 | 1.00 | 29.17 | | O |
| ANISOU | 163 | O | PHE | A | 9 | 3457 | 3874 | 3753 | 448 | 167 | 400 | O |
| ATOM | 165 | N | ASN | A | 10 | 12.285 | 27.297 | 89.197 | 1.00 | 27.08 | | N |
| ANISOU | 165 | N | ASN | A | 10 | 3189 | 3797 | 3304 | 322 | 261 | 315 | N |
| ATOM | 166 | CA | ASN | A | 10 | 12.898 | 28.112 | 90.216 | 1.00 | 29.20 | | C |
| ANISOU | 166 | CA | ASN | A | 10 | 3412 | 4137 | 3546 | 316 | 185 | 389 | C |
| ATOM | 168 | CB | ASN | A | 10 | 12.948 | 29.565 | 89.738 | 1.00 | 30.10 | | C |
| ANISOU | 168 | CB | ASN | A | 10 | 3515 | 4358 | 3563 | 238 | 228 | 352 | C |
| ATOM | 171 | CG | ASN | A | 10 | 13.991 | 29.772 | 88.634 | 1.00 | 33.67 | | C |
| ANISOU | 171 | CG | ASN | A | 10 | 3864 | 4863 | 4064 | 246 | 304 | 266 | C |
| ATOM | 172 | OD1 | ASN | A | 10 | 13.776 | 30.548 | 87.672 | 1.00 | 35.92 | | O |

FIG. 18 (continued)

| | | | | | | | | | | | | |
|---|---|---|---|---|---|---|---|---|---|---|---|---|
| ANISOU | 172 | OD1 | ASN | A | 10 | 4167 | 5205 | 4276 | 177 | 375 | 218 | O |
| ATOM | 173 | ND2 | ASN | A | 10 | 15.130 | 29.076 | 88.763 | 1.00 | 35.79 | | N |
| ANISOU | 173 | ND2 | ASN | A | 10 | 4020 | 5121 | 4459 | 330 | 289 | 253 | N |
| ATOM | 176 | C | ASN | A | 10 | 12.223 | 27.971 | 91.586 | 1.00 | 27.94 | | C |
| ANISOU | 176 | C | ASN | A | 10 | 3329 | 3955 | 3331 | 294 | 94 | 501 | C |
| ATOM | 177 | O | ASN | A | 10 | 11.046 | 27.661 | 91.681 | 1.00 | 26.18 | | O |
| ANISOU | 177 | O | ASN | A | 10 | 3198 | 3695 | 3055 | 256 | 107 | 521 | O |
| ATOM | 179 | N | PRO | A | 11 | 13.006 | 28.085 | 92.655 | 1.00 | 29.58 | | N |
| ANISOU | 179 | N | PRO | A | 11 | 3492 | 4197 | 3551 | 311 | -2 | 577 | N |
| ATOM | 180 | CA | PRO | A | 11 | 12.460 | 27.811 | 93.973 | 1.00 | 28.66 | | C |
| ANISOU | 180 | CA | PRO | A | 11 | 3450 | 4070 | 3368 | 281 | -88 | 687 | C |
| ATOM | 182 | CB | PRO | A | 11 | 13.627 | 28.106 | 94.913 | 1.00 | 31.75 | | C |
| ANISOU | 182 | CB | PRO | A | 11 | 3764 | 4532 | 3768 | 291 | -197 | 754 | C |
| ATOM | 185 | CG | PRO | A | 11 | 14.853 | 27.909 | 94.052 | 1.00 | 31.76 | | C |
| ANISOU | 185 | CG | PRO | A | 11 | 3623 | 4531 | 3912 | 374 | -175 | 696 | C |
| ATOM | 188 | CD | PRO | A | 11 | 14.464 | 28.338 | 92.693 | 1.00 | 30.86 | | C |
| ANISOU | 188 | CD | PRO | A | 11 | 3520 | 4417 | 3790 | 353 | -40 | 571 | C |
| ATOM | 191 | C | PRO | A | 11 | 11.208 | 28.574 | 94.358 | 1.00 | 26.61 | | C |
| ANISOU | 191 | C | PRO | A | 11 | 3292 | 3859 | 2960 | 190 | -54 | 687 | C |
| ATOM | 192 | O | PRO | A | 11 | 10.325 | 27.973 | 94.985 | 1.00 | 24.43 | | O |
| ANISOU | 192 | O | PRO | A | 11 | 3093 | 3550 | 2640 | 163 | -72 | 752 | O |
| ATOM | 193 | N | MET | A | 12 | 11.095 | 29.848 | 93.984 | 1.00 | 26.22 | | N |
| ANISOU | 193 | N | MET | A | 12 | 3241 | 3880 | 2842 | 145 | -1 | 619 | N |
| ATOM | 194 | CA | MET | A | 12 | 9.903 | 30.635 | 94.385 | 1.00 | 28.23 | | C |
| ANISOU | 194 | CA | MET | A | 12 | 3579 | 4171 | 2977 | 82 | 38 | 613 | C |
| ATOM | 196 | CB | MET | A | 12 | 10.081 | 32.171 | 94.254 | 1.00 | 32.63 | | C |
| ANISOU | 196 | CB | MET | A | 12 | 4137 | 4783 | 3477 | 41 | 70 | 552 | C |
| ATOM | 199 | CG | MET | A | 12 | 10.074 | 32.766 | 92.830 | 1.00 | 34.41 | | C |
| ANISOU | 199 | CG | MET | A | 12 | 4335 | 5000 | 3740 | 46 | 143 | 487 | C |
| ATOM | 202 | SD | MET | A | 12 | 11.555 | 32.239 | 91.976 | 1.00 | 42.95 | | S |
| ANISOU | 202 | SD | MET | A | 12 | 5307 | 6083 | 4930 | 82 | 136 | 460 | S |
| ATOM | 203 | CE | MET | A | 12 | 11.763 | 33.541 | 90.745 | 1.00 | 41.59 | | C |
| ANISOU | 203 | CE | MET | A | 12 | 5120 | 5945 | 4736 | 31 | 210 | 399 | C |
| ATOM | 207 | C | MET | A | 12 | 8.653 | 30.147 | 93.665 | 1.00 | 24.85 | | C |
| ANISOU | 207 | C | MET | A | 12 | 3190 | 3702 | 2551 | 80 | 105 | 597 | C |
| ATOM | 208 | O | MET | A | 12 | 7.596 | 30.147 | 94.238 | 1.00 | 21.72 | | O |
| ANISOU | 208 | O | MET | A | 12 | 2846 | 3322 | 2083 | 45 | 120 | 626 | O |
| ATOM | 210 | N | ILE | A | 13 | 8.812 | 29.709 | 92.423 | 1.00 | 23.59 | | N |
| ANISOU | 210 | N | ILE | A | 13 | 2996 | 3501 | 2465 | 109 | 147 | 547 | N |
| ATOM | 211 | CA | ILE | A | 13 | 7.721 | 29.165 | 91.627 | 1.00 | 23.37 | | C |
| ANISOU | 211 | CA | ILE | A | 13 | 3000 | 3443 | 2436 | 90 | 198 | 526 | C |
| ATOM | 213 | CB | ILE | A | 13 | 8.155 | 28.825 | 90.165 | 1.00 | 24.53 | | C |
| ANISOU | 213 | CB | ILE | A | 13 | 3112 | 3565 | 2644 | 107 | 248 | 444 | C |
| ATOM | 215 | CG1 | ILE | A | 13 | 8.633 | 30.091 | 89.404 | 1.00 | 26.07 | | C |
| ANISOU | 215 | CG1 | ILE | A | 13 | 3268 | 3832 | 2804 | 93 | 286 | 397 | C |
| ATOM | 218 | CD1 | ILE | A | 13 | 7.533 | 31.193 | 89.236 | 1.00 | 24.60 | | C |
| ANISOU | 218 | CD1 | ILE | A | 13 | 3116 | 3699 | 2531 | 49 | 307 | 414 | C |
| ATOM | 222 | CG2 | ILE | A | 13 | 7.023 | 28.099 | 89.423 | 1.00 | 23.39 | | C |
| ANISOU | 222 | CG2 | ILE | A | 13 | 3008 | 3391 | 2486 | 65 | 283 | 422 | C |
| ATOM | 226 | C | ILE | A | 13 | 7.229 | 27.894 | 92.309 | 1.00 | 22.73 | | C |
| ANISOU | 226 | C | ILE | A | 13 | 2965 | 3296 | 2377 | 82 | 162 | 591 | C |
| ATOM | 227 | O | ILE | A | 13 | 6.021 | 27.711 | 92.492 | 1.00 | 22.24 | | O |
| ANISOU | 227 | O | ILE | A | 13 | 2943 | 3247 | 2261 | 29 | 182 | 617 | O |
| ATOM | 229 | N | VAL | A | 14 | 8.172 | 27.038 | 92.728 | 1.00 | 23.62 | | N |
| ANISOU | 229 | N | VAL | A | 14 | 3064 | 3338 | 2574 | 131 | 105 | 629 | N |
| ATOM | 230 | CA | VAL | A | 14 | 7.813 | 25.784 | 93.357 | 1.00 | 24.71 | | C |
| ANISOU | 230 | CA | VAL | A | 14 | 3257 | 3384 | 2749 | 123 | 60 | 711 | C |
| ATOM | 232 | CB | VAL | A | 14 | 9.035 | 24.866 | 93.522 | 1.00 | 27.10 | | C |
| ANISOU | 232 | CB | VAL | A | 14 | 3525 | 3583 | 3188 | 212 | -4 | 746 | C |
| ATOM | 234 | CG1 | VAL | A | 14 | 8.680 | 23.609 | 94.318 | 1.00 | 26.89 | | C |
| ANISOU | 234 | CG1 | VAL | A | 14 | 3574 | 3442 | 3203 | 199 | -69 | 864 | C |
| ATOM | 238 | CG2 | VAL | A | 14 | 9.639 | 24.470 | 92.119 | 1.00 | 25.97 | | C |
| ANISOU | 238 | CG2 | VAL | A | 14 | 3331 | 3371 | 3165 | 279 | 64 | 622 | C |
| ATOM | 242 | C | VAL | A | 14 | 7.093 | 26.013 | 94.706 | 1.00 | 25.47 | | C |
| ANISOU | 242 | C | VAL | A | 14 | 3406 | 3544 | 2727 | 54 | 23 | 809 | C |
| ATOM | 243 | O | VAL | A | 14 | 6.178 | 25.303 | 95.056 | 1.00 | 23.75 | | O |
| ANISOU | 243 | O | VAL | A | 14 | 3246 | 3295 | 2484 | -4 | 26 | 866 | O |
| ATOM | 245 | N | GLU | A | 15 | 7.550 | 27.014 | 95.444 | 1.00 | 25.34 | | N |
| ANISOU | 245 | N | GLU | A | 15 | 3371 | 3623 | 2635 | 50 | -4 | 820 | N |
| ATOM | 246 | CA | GLU | A | 15 | 6.969 | 27.398 | 96.721 | 1.00 | 28.74 | | C |
| ANISOU | 246 | CA | GLU | A | 15 | 3852 | 4138 | 2930 | -20 | -21 | 883 | C |
| ATOM | 248 | CB | GLU | A | 15 | 7.850 | 28.494 | 97.302 | 1.00 | 29.23 | | C |
| ANISOU | 248 | CB | GLU | A | 15 | 3889 | 4284 | 2934 | -18 | -57 | 860 | C |
| ATOM | 251 | CG | GLU | A | 15 | 7.467 | 29.092 | 98.642 | 1.00 | 32.33 | | C |
| ANISOU | 251 | CG | GLU | A | 15 | 4339 | 4779 | 3167 | -97 | -69 | 891 | C |
| ATOM | 254 | CD | GLU | A | 15 | 8.460 | 30.216 | 98.988 | 1.00 | 32.87 | | C |
| ANISOU | 254 | CD | GLU | A | 15 | 4382 | 4913 | 3192 | -105 | -105 | 839 | C |
| ATOM | 255 | OE1 | GLU | A | 15 | 9.671 | 29.977 | 98.958 | 1.00 | 32.55 | | O |
| ANISOU | 255 | OE1 | GLU | A | 15 | 4286 | 4861 | 3222 | -71 | -193 | 873 | O |

FIG. 18 (continued)

| | | | | | | | | | | | | | |
|---|---|---|---|---|---|---|---|---|---|---|---|---|---|
| ATOM | 256 | OE2 | GLU | A | 15 | 8.036 | 31.362 | 99.223 | 1.00 | 36.39 | | | O |
| ANISOU | 256 | OE2 | GLU | A | 15 | 4860 | 5417 | 3551 | -142 | -43 | 758 | | O |
| ATOM | 257 | C | GLU | A | 15 | 5.532 | 27.855 | 96.544 | 1.00 | 26.04 | | | C |
| ANISOU | 257 | C | GLU | A | 15 | 3533 | 3852 | 2510 | -75 | 72 | 842 | | C |
| ATOM | 258 | O | GLU | A | 15 | 4.665 | 27.393 | 97.259 | 1.00 | 27.52 | | | O |
| ANISOU | 258 | O | GLU | A | 15 | 3764 | 4065 | 2629 | -141 | 82 | 905 | | O |
| ATOM | 260 | N | LEU | A | 16 | 5.302 | 28.726 | 95.577 | 1.00 | 25.65 | | | N |
| ANISOU | 260 | N | LEU | A | 16 | 3444 | 3826 | 2476 | -50 | 136 | 748 | | N |
| ATOM | 261 | CA | LEU | A | 16 | 3.965 | 29.244 | 95.252 | 1.00 | 24.91 | | | C |
| ANISOU | 261 | CA | LEU | A | 16 | 3343 | 3789 | 2334 | -78 | 216 | 713 | | C |
| ATOM | 263 | CB | LEU | A | 16 | 4.048 | 30.344 | 94.195 | 1.00 | 24.76 | | | C |
| ANISOU | 263 | CB | LEU | A | 16 | 3282 | 3783 | 2341 | -36 | 257 | 632 | | C |
| ATOM | 266 | CG | LEU | A | 16 | 4.731 | 31.643 | 94.615 | 1.00 | 24.47 | | | C |
| ANISOU | 266 | CG | LEU | A | 16 | 3250 | 3776 | 2271 | -15 | 256 | 592 | | C |
| ATOM | 268 | CD1 | LEU | A | 16 | 4.989 | 32.523 | 93.431 | 1.00 | 23.58 | | | C |
| ANISOU | 268 | CD1 | LEU | A | 16 | 3107 | 3650 | 2203 | 16 | 282 | 538 | | C |
| ATOM | 272 | CD2 | LEU | A | 16 | 3.812 | 32.369 | 95.689 | 1.00 | 25.23 | | | C |
| ANISOU | 272 | CD2 | LEU | A | 16 | 3375 | 3939 | 2271 | -38 | 305 | 583 | | C |
| ATOM | 276 | C | LEU | A | 16 | 3.058 | 28.125 | 94.804 | 1.00 | 25.87 | | | C |
| ANISOU | 276 | C | LEU | A | 16 | 3470 | 3874 | 2486 | -122 | 231 | 745 | | C |
| ATOM | 277 | O | LEU | A | 16 | 1.904 | 28.030 | 95.283 | 1.00 | 26.98 | | | O |
| ANISOU | 277 | O | LEU | A | 16 | 3613 | 4076 | 2564 | -181 | 270 | 775 | | O |
| ATOM | 279 | N | ALA | A | 17 | 3.573 | 27.212 | 93.970 | 1.00 | 23.75 | | | N |
| ANISOU | 279 | N | ALA | A | 17 | 3204 | 3507 | 2312 | -104 | 204 | 734 | | N |
| ATOM | 280 | CA | ALA | A | 17 | 2.773 | 26.040 | 93.554 | 1.00 | 24.45 | | | C |
| ANISOU | 280 | CA | ALA | A | 17 | 3318 | 3538 | 2434 | -166 | 211 | 754 | | C |
| ATOM | 282 | CB | ALA | A | 17 | 3.521 | 25.270 | 92.413 | 1.00 | 23.02 | | | C |
| ANISOU | 282 | CB | ALA | A | 17 | 3143 | 3241 | 2364 | -128 | 201 | 692 | | C |
| ATOM | 286 | C | ALA | A | 17 | 2.388 | 25.061 | 94.675 | 1.00 | 27.68 | | | C |
| ANISOU | 286 | C | ALA | A | 17 | 3786 | 3911 | 2818 | -234 | 178 | 863 | | C |
| ATOM | 287 | O | ALA | A | 17 | 1.245 | 24.559 | 94.729 | 1.00 | 28.32 | | | O |
| ANISOU | 287 | O | ALA | A | 17 | 3878 | 4015 | 2868 | -327 | 206 | 894 | | O |
| ATOM | 289 | N | GLU | A | 18 | 3.357 | 24.729 | 95.548 | 1.00 | 29.66 | | | N |
| ANISOU | 289 | N | GLU | A | 18 | 4073 | 4112 | 3086 | -201 | 109 | 934 | | N |
| ATOM | 290 | CA | GLU | A | 18 | 3.113 | 23.885 | 96.731 | 1.00 | 32.10 | | | C |
| ANISOU | 290 | CA | GLU | A | 18 | 4450 | 4395 | 3352 | -272 | 61 | 1067 | | C |
| ATOM | 292 | CB | GLU | A | 18 | 4.406 | 23.580 | 97.499 | 1.00 | 33.49 | | | C |
| ANISOU | 292 | CB | GLU | A | 18 | 4649 | 4513 | 3564 | -213 | -42 | 1151 | | C |
| ATOM | 295 | CG | GLU | A | 18 | 5.222 | 22.443 | 96.915 | 1.00 | 35.82 | | | C |
| ANISOU | 295 | CG | GLU | A | 18 | 4958 | 4620 | 4032 | -139 | -98 | 1169 | | C |
| ATOM | 298 | CD | GLU | A | 18 | 6.444 | 22.109 | 97.750 | 1.00 | 36.93 | | | C |
| ANISOU | 298 | CD | GLU | A | 18 | 5099 | 4712 | 4220 | -70 | -216 | 1279 | | C |
| ATOM | 299 | OE1 | GLU | A | 18 | 7.464 | 22.788 | 97.585 | 1.00 | 40.01 | | | O |
| ANISOU | 299 | OE1 | GLU | A | 18 | 5413 | 5148 | 4640 | 16 | -239 | 1228 | | O |
| ATOM | 300 | OE2 | GLU | A | 18 | 6.393 | 21.154 | 98.540 | 1.00 | 38.83 | | | O |
| ANISOU | 300 | OE2 | GLU | A | 18 | 5410 | 4871 | 4473 | -108 | -292 | 1427 | | O |
| ATOM | 301 | C | GLU | A | 18 | 2.124 | 24.513 | 97.689 | 1.00 | 34.60 | | | C |
| ANISOU | 301 | C | GLU | A | 18 | 4768 | 4867 | 3513 | -358 | 111 | 1099 | | C |
| ATOM | 302 | O | GLU | A | 18 | 1.250 | 23.809 | 98.246 | 1.00 | 37.00 | | | O |
| ANISOU | 302 | O | GLU | A | 18 | 5111 | 5182 | 3764 | -466 | 124 | 1181 | | O |
| ATOM | 304 | N | LYS | A | 19 | 2.264 | 25.818 | 97.886 | 1.00 | 36.99 | | | N |
| ANISOU | 304 | N | LYS | A | 19 | 5029 | 5281 | 3745 | -318 | 147 | 1029 | | N |
| ATOM | 305 | CA | LYS | A | 19 | 1.304 | 26.583 | 98.680 | 1.00 | 39.73 | | | C |
| ANISOU | 305 | CA | LYS | A | 19 | 5366 | 5775 | 3956 | -377 | 224 | 1016 | | C |
| ATOM | 307 | CB | LYS | A | 19 | 1.658 | 28.076 | 98.712 | 1.00 | 39.96 | | | C |
| ANISOU | 307 | CB | LYS | A | 19 | 5361 | 5876 | 3945 | -309 | 261 | 914 | | C |
| ATOM | 310 | CG | LYS | A | 19 | 0.928 | 28.921 | 99.792 | 1.00 | 41.11 | | | C |
| ANISOU | 310 | CG | LYS | A | 19 | 5514 | 6160 | 3946 | -355 | 342 | 883 | | C |
| ATOM | 313 | CD | LYS | A | 19 | 0.895 | 30.421 | 99.365 | 1.00 | 42.09 | | | C |
| ANISOU | 313 | CD | LYS | A | 19 | 5595 | 6311 | 4084 | -273 | 406 | 755 | | C |
| ATOM | 316 | CE | LYS | A | 19 | 0.107 | 31.338 | 100.341 | 1.00 | 43.50 | | | C |
| ANISOU | 316 | CE | LYS | A | 19 | 5777 | 6607 | 4142 | -297 | 513 | 688 | | C |
| ATOM | 319 | NZ | LYS | A | 19 | -0.326 | 32.646 | 99.663 | 1.00 | 42.49 | | | N |
| ANISOU | 319 | NZ | LYS | A | 19 | 5593 | 6471 | 4080 | -200 | 591 | 575 | | N |
| ATOM | 323 | C | LYS | A | 19 | -0.073 | 26.352 | 98.058 | 1.00 | 39.62 | | | C |
| ANISOU | 323 | C | LYS | A | 19 | 5302 | 5797 | 3954 | -429 | 302 | 995 | | C |
| ATOM | 324 | O | LYS | A | 19 | -0.961 | 25.842 | 98.727 | 1.00 | 39.77 | | | O |
| ANISOU | 324 | O | LYS | A | 19 | 5334 | 5877 | 3902 | -532 | 336 | 1061 | | O |
| ATOM | 326 | N | ALA | A | 20 | -0.223 | 26.685 | 96.768 | 1.00 | 38.37 | | | N |
| ANISOU | 326 | N | ALA | A | 20 | 5085 | 5612 | 3880 | -373 | 322 | 914 | | N |
| ATOM | 327 | CA | ALA | A | 20 | -1.500 | 26.511 | 96.061 | 1.00 | 37.94 | | | C |
| ANISOU | 327 | CA | ALA | A | 20 | 4967 | 5608 | 3840 | -426 | 375 | 896 | | C |
| ATOM | 329 | CB | ALA | A | 20 | -1.368 | 26.873 | 94.530 | 1.00 | 36.88 | | | C |
| ANISOU | 329 | CB | ALA | A | 20 | 4784 | 5439 | 3790 | -363 | 368 | 815 | | C |
| ATOM | 333 | C | ALA | A | 20 | -2.097 | 25.117 | 96.265 | 1.00 | 38.18 | | | C |
| ANISOU | 333 | C | ALA | A | 20 | 5036 | 5595 | 3874 | -551 | 359 | 980 | | C |
| ATOM | 334 | O | ALA | A | 20 | -3.279 | 24.991 | 96.568 | 1.00 | 41.92 | | | O |
| ANISOU | 334 | O | ALA | A | 20 | 5463 | 6172 | 4295 | -642 | 414 | 1009 | | O |
| ATOM | 336 | N | MET | A | 21 | -1.283 | 24.068 | 96.171 | 1.00 | 39.05 | | | N |

FIG. 18 (continued)

| | | | | | | | | | | | | |
|---|---|---|---|---|---|---|---|---|---|---|---|---|
| ANISOU | 336 | N | MET | A | 21 | 5230 | 5551 | 4055 | -558 | 285 | 1025 | N |
| ATOM | 337 | CA | MET | A | 21 | -1.788 | 22.702 | 96.299 | 1.00 | 38.52 | | C |
| ANISOU | 337 | CA | MET | A | 21 | 5224 | 5400 | 4014 | -681 | 263 | 1107 | C |
| ATOM | 339 | CB | MET | A | 21 | -0.778 | 21.695 | 95.755 | 1.00 | 38.62 | | C |
| ANISOU | 339 | CB | MET | A | 21 | 5317 | 5200 | 4156 | -639 | 189 | 1110 | C |
| ATOM | 342 | CG | MET | A | 21 | -0.687 | 21.739 | 94.239 | 1.00 | 35.47 | | C |
| ANISOU | 342 | CG | MET | A | 21 | 4884 | 4753 | 3841 | -596 | 205 | 980 | C |
| ATOM | 345 | SD | MET | A | 21 | 0.362 | 20.453 | 93.625 | 1.00 | 39.81 | | S |
| ANISOU | 345 | SD | MET | A | 21 | 5528 | 5049 | 4550 | -551 | 150 | 956 | S |
| ATOM | 346 | CE | MET | A | 21 | -0.856 | 19.178 | 93.255 | 1.00 | 39.90 | | C |
| ANISOU | 346 | CE | MET | A | 21 | 5603 | 4977 | 4582 | -737 | 161 | 972 | C |
| ATOM | 350 | C | MET | A | 21 | -2.188 | 22.324 | 97.729 | 1.00 | 42.81 | | C |
| ANISOU | 350 | C | MET | A | 21 | 5814 | 6000 | 4451 | -786 | 267 | 1235 | C |
| ATOM | 351 | O | MET | A | 21 | -3.102 | 21.504 | 97.932 | 1.00 | 40.74 | | O |
| ANISOU | 351 | O | MET | A | 21 | 5568 | 5742 | 4167 | -928 | 285 | 1304 | O |
| ATOM | 353 | N | LYS | A | 22 | -1.488 | 22.897 | 98.711 | 1.00 | 44.96 | | N |
| ANISOU | 353 | N | LYS | A | 22 | 6112 | 6322 | 4647 | -735 | 246 | 1268 | N |
| ATOM | 354 | CA | LYS | A | 22 | -1.806 | 22.648 | 100.100 | 1.00 | 48.37 | | C |
| ANISOU | 354 | CA | LYS | A | 22 | 6596 | 6838 | 4945 | -843 | 252 | 1386 | C |
| ATOM | 356 | CB | LYS | A | 22 | -0.727 | 23.210 | 101.039 | 1.00 | 48.58 | | C |
| ANISOU | 356 | CB | LYS | A | 22 | 6666 | 6896 | 4895 | -781 | 196 | 1416 | C |
| ATOM | 359 | CG | LYS | A | 22 | -0.641 | 22.465 | 102.378 | 1.00 | 51.38 | | C |
| ANISOU | 359 | CG | LYS | A | 22 | 7121 | 7268 | 5134 | -900 | 139 | 1588 | C |
| ATOM | 362 | CD | LYS | A | 22 | 0.454 | 23.060 | 103.288 | 1.00 | 51.62 | | C |
| ANISOU | 362 | CD | LYS | A | 22 | 7188 | 7354 | 5072 | -853 | 65 | 1616 | C |
| ATOM | 365 | CE | LYS | A | 22 | 0.468 | 22.433 | 104.691 | 1.00 | 54.38 | | C |
| ANISOU | 365 | CE | LYS | A | 22 | 7638 | 7762 | 5263 | -991 | 5 | 1798 | C |
| ATOM | 368 | NZ | LYS | A | 22 | 1.414 | 23.155 | 105.593 | 1.00 | 55.29 | | N |
| ANISOU | 368 | NZ | LYS | A | 22 | 7780 | 7975 | 5253 | -969 | -63 | 1807 | N |
| ATOM | 372 | C | LYS | A | 22 | -3.165 | 23.271 | 100.388 | 1.00 | 49.24 | | C |
| ANISOU | 372 | C | LYS | A | 22 | 6618 | 7146 | 4945 | -921 | 378 | 1344 | C |
| ATOM | 373 | O | LYS | A | 22 | -4.017 | 22.651 | 101.022 | 1.00 | 50.12 | | O |
| ANISOU | 373 | O | LYS | A | 22 | 6743 | 7322 | 4977 | -1069 | 416 | 1432 | O |
| ATOM | 375 | N | GLU | A | 23 | -3.363 | 24.486 | 99.892 | 1.00 | 49.84 | | N |
| ANISOU | 375 | N | GLU | A | 23 | 6598 | 7312 | 5026 | -820 | 444 | 1213 | N |
| ATOM | 376 | CA | GLU | A | 23 | -4.602 | 25.224 | 100.118 | 1.00 | 52.80 | | C |
| ANISOU | 376 | CA | GLU | A | 23 | 6865 | 7870 | 5326 | -851 | 569 | 1157 | C |
| ATOM | 378 | CB | GLU | A | 23 | -4.446 | 26.647 | 99.587 | 1.00 | 53.64 | | C |
| ANISOU | 378 | CB | GLU | A | 23 | 6896 | 8017 | 5470 | -697 | 611 | 1023 | C |
| ATOM | 381 | CG | GLU | A | 23 | -4.252 | 27.619 | 100.703 | 1.00 | 56.62 | | C |
| ANISOU | 381 | CG | GLU | A | 23 | 7293 | 8494 | 5726 | -668 | 674 | 976 | C |
| ATOM | 384 | CD | GLU | A | 23 | -3.453 | 28.803 | 100.299 | 1.00 | 57.33 | | C |
| ANISOU | 384 | CD | GLU | A | 23 | 7383 | 8536 | 5865 | -525 | 660 | 871 | C |
| ATOM | 385 | OE1 | GLU | A | 23 | -3.765 | 29.392 | 99.231 | 1.00 | 57.26 | | O |
| ANISOU | 385 | OE1 | GLU | A | 23 | 7292 | 8506 | 5958 | -436 | 677 | 805 | O |
| ATOM | 386 | OE2 | GLU | A | 23 | -2.527 | 29.138 | 101.078 | 1.00 | 59.20 | | O |
| ANISOU | 386 | OE2 | GLU | A | 23 | 7703 | 8762 | 6027 | -518 | 625 | 864 | O |
| ATOM | 387 | C | GLU | A | 23 | -5.879 | 24.610 | 99.528 | 1.00 | 54.24 | | C |
| ANISOU | 387 | C | GLU | A | 23 | 6960 | 8103 | 5547 | -954 | 613 | 1176 | C |
| ATOM | 388 | O | GLU | A | 23 | -6.848 | 24.378 | 100.251 | 1.00 | 52.18 | | O |
| ANISOU | 388 | O | GLU | A | 23 | 6657 | 7975 | 5195 | -1076 | 692 | 1224 | O |
| ATOM | 390 | N | TYR | A | 24 | -5.888 | 24.371 | 98.216 | 1.00 | 54.13 | | N |
| ANISOU | 390 | N | TYR | A | 24 | 6913 | 7999 | 5655 | -920 | 566 | 1135 | N |
| ATOM | 391 | CA | TYR | A | 24 | -7.117 | 23.923 | 97.537 | 1.00 | 56.06 | | C |
| ANISOU | 391 | CA | TYR | A | 24 | 7057 | 8312 | 5932 | -1023 | 596 | 1138 | C |
| ATOM | 393 | CB | TYR | A | 24 | -7.128 | 24.376 | 96.073 | 1.00 | 55.46 | | C |
| ANISOU | 393 | CB | TYR | A | 24 | 6909 | 8209 | 5954 | -934 | 563 | 1049 | C |
| ATOM | 396 | CG | TYR | A | 24 | -7.039 | 25.884 | 95.813 | 1.00 | 54.06 | | C |
| ANISOU | 396 | CG | TYR | A | 24 | 6644 | 8111 | 5785 | -767 | 601 | 964 | C |
| ATOM | 397 | CD1 | TYR | A | 24 | -8.131 | 26.606 | 95.329 | 1.00 | 55.06 | | C |
| ANISOU | 397 | CD1 | TYR | A | 24 | 6608 | 8381 | 5929 | -738 | 652 | 931 | C |
| ATOM | 399 | CE1 | TYR | A | 24 | -8.038 | 27.983 | 95.056 | 1.00 | 54.09 | | C |
| ANISOU | 399 | CE1 | TYR | A | 24 | 6420 | 8296 | 5836 | -577 | 679 | 865 | C |
| ATOM | 401 | CZ | TYR | A | 24 | -6.846 | 28.647 | 95.270 | 1.00 | 54.39 | | C |
| ANISOU | 401 | CZ | TYR | A | 24 | 6557 | 8234 | 5873 | -466 | 662 | 822 | C |
| ATOM | 402 | OH | TYR | A | 24 | -6.714 | 30.017 | 95.011 | 1.00 | 53.12 | | O |
| ANISOU | 402 | OH | TYR | A | 24 | 6352 | 8082 | 5748 | -320 | 687 | 760 | O |
| ATOM | 404 | CE2 | TYR | A | 24 | -5.750 | 27.938 | 95.740 | 1.00 | 53.28 | | C |
| ANISOU | 404 | CE2 | TYR | A | 24 | 6562 | 7976 | 5708 | -504 | 610 | 849 | C |
| ATOM | 406 | CD2 | TYR | A | 24 | -5.861 | 26.568 | 95.998 | 1.00 | 53.90 | | C |
| ANISOU | 406 | CD2 | TYR | A | 24 | 6700 | 8011 | 5769 | -642 | 578 | 923 | C |
| ATOM | 408 | C | TYR | A | 24 | -7.310 | 22.392 | 97.659 | 1.00 | 57.80 | | C |
| ANISOU | 408 | C | TYR | A | 24 | 7368 | 8430 | 6165 | -1201 | 548 | 1242 | C |
| ATOM | 409 | O | TYR | A | 24 | -8.220 | 21.814 | 97.060 | 1.00 | 59.88 | | O |
| ANISOU | 409 | O | TYR | A | 24 | 7572 | 8722 | 6459 | -1321 | 553 | 1249 | O |
| ATOM | 411 | N | GLY | A | 25 | -6.452 | 21.739 | 98.435 | 1.00 | 58.14 | | N |
| ANISOU | 411 | N | GLY | A | 25 | 7555 | 8349 | 6187 | -1224 | 493 | 1329 | N |
| ATOM | 412 | CA | GLY | A | 25 | -6.660 | 20.356 | 98.823 | 1.00 | 59.62 | | C |
| ANISOU | 412 | CA | GLY | A | 25 | 7845 | 8432 | 6377 | -1396 | 453 | 1455 | C |

FIG. 18 (continued)

| | | | | | | | | | | | | |
|---|---|---|---|---|---|---|---|---|---|---|---|---|
| ATOM | 415 | C | GLY | A | 25 | -6.280 | 19.359 | 97.758 | 1.00 | 60.24 | | C |
| ANISOU | 415 | C | GLY | A | 25 | 8002 | 8288 | 6599 | -1412 | 370 | 1437 | C |
| ATOM | 416 | O | GLY | A | 25 | -7.006 | 18.387 | 97.531 | 1.00 | 61.72 | | O |
| ANISOU | 416 | O | GLY | A | 25 | 8213 | 8425 | 6812 | -1580 | 366 | 1482 | O |
| ATOM | 418 | N | GLU | A | 26 | -5.140 | 19.603 | 97.101 | 1.00 | 58.49 | | N |
| ANISOU | 418 | N | GLU | A | 26 | 7819 | 7934 | 6469 | -1247 | 314 | 1360 | N |
| ATOM | 419 | CA | GLU | A | 26 | -4.573 | 18.654 | 96.153 | 1.00 | 57.03 | | C |
| ANISOU | 419 | CA | GLU | A | 26 | 7724 | 7520 | 6423 | -1238 | 248 | 1322 | C |
| ATOM | 421 | CB | GLU | A | 26 | -4.273 | 19.345 | 94.815 | 1.00 | 56.28 | | C |
| ANISOU | 421 | CB | GLU | A | 26 | 7559 | 7441 | 6386 | -1118 | 257 | 1163 | C |
| ATOM | 424 | CG | GLU | A | 26 | -5.398 | 20.266 | 94.273 | 1.00 | 56.09 | | C |
| ANISOU | 424 | CG | GLU | A | 26 | 7379 | 7640 | 6293 | -1148 | 319 | 1096 | C |
| ATOM | 427 | CD | GLU | A | 26 | -6.391 | 19.557 | 93.373 | 1.00 | 57.17 | | C |
| ANISOU | 427 | CD | GLU | A | 26 | 7489 | 7782 | 6452 | -1307 | 316 | 1063 | C |
| ATOM | 428 | OE1 | GLU | A | 26 | -6.124 | 18.402 | 92.969 | 1.00 | 57.88 | | O |
| ANISOU | 428 | OE1 | GLU | A | 26 | 7696 | 7680 | 6618 | -1385 | 274 | 1055 | O |
| ATOM | 429 | OE2 | GLU | A | 26 | -7.434 | 20.174 | 93.052 | 1.00 | 57.39 | | O |
| ANISOU | 429 | OE2 | GLU | A | 26 | 7374 | 8006 | 6427 | -1351 | 353 | 1041 | O |
| ATOM | 430 | C | GLU | A | 26 | -3.294 | 18.067 | 96.757 | 1.00 | 55.47 | | C |
| ANISOU | 430 | C | GLU | A | 26 | 7655 | 7128 | 6292 | -1156 | 167 | 1406 | C |
| ATOM | 431 | O | GLU | A | 26 | -2.421 | 18.804 | 97.216 | 1.00 | 54.68 | | O |
| ANISOU | 431 | O | GLU | A | 26 | 7542 | 7068 | 6166 | -1020 | 148 | 1407 | O |
| ATOM | 433 | N | ASP | A | 27 | -3.181 | 16.744 | 96.754 | 1.00 | 56.04 | | N |
| ANISOU | 433 | N | ASP | A | 27 | 7850 | 6985 | 6458 | -1238 | 114 | 1479 | N |
| ATOM | 434 | CA | ASP | A | 27 | -1.972 | 16.071 | 97.227 | 1.00 | 57.03 | | C |
| ANISOU | 434 | CA | ASP | A | 27 | 8090 | 6896 | 6683 | -1143 | 23 | 1570 | C |
| ATOM | 436 | CB | ASP | A | 27 | -2.331 | 14.714 | 97.844 | 1.00 | 60.81 | | C |
| ANISOU | 436 | CB | ASP | A | 27 | 8706 | 7201 | 7198 | -1302 | -27 | 1735 | C |
| ATOM | 439 | CG | ASP | A | 27 | -1.117 | 13.949 | 98.349 | 1.00 | 63.20 | | C |
| ANISOU | 439 | CG | ASP | A | 27 | 9124 | 7263 | 7627 | -1194 | -138 | 1857 | C |
| ATOM | 440 | OD1 | ASP | A | 27 | -0.059 | 14.571 | 98.576 | 1.00 | 63.01 | | O |
| ANISOU | 440 | OD1 | ASP | A | 27 | 9056 | 7272 | 7615 | -1018 | -179 | 1849 | O |
| ATOM | 441 | OD2 | ASP | A | 27 | -1.231 | 12.712 | 98.526 | 1.00 | 67.60 | | O |
| ANISOU | 441 | OD2 | ASP | A | 27 | 9814 | 7594 | 8279 | -1289 | -189 | 1968 | O |
| ATOM | 442 | C | ASP | A | 27 | -0.954 | 15.894 | 96.083 | 1.00 | 54.84 | | C |
| ANISOU | 442 | C | ASP | A | 27 | 7824 | 6441 | 6572 | -982 | 0 | 1431 | C |
| ATOM | 443 | O | ASP | A | 27 | -1.196 | 15.121 | 95.144 | 1.00 | 53.52 | | O |
| ANISOU | 443 | O | ASP | A | 27 | 7707 | 6124 | 6505 | -1035 | 13 | 1345 | O |
| ATOM | 445 | N | LEU | A | 28 | 0.187 | 16.584 | 96.190 | 1.00 | 52.54 | | N |
| ANISOU | 445 | N | LEU | A | 28 | 7487 | 6172 | 6303 | -801 | -29 | 1405 | N |
| ATOM | 446 | CA | LEU | A | 28 | 1.171 | 16.640 | 95.104 | 1.00 | 51.53 | | C |
| ANISOU | 446 | CA | LEU | A | 28 | 7335 | 5935 | 6310 | -644 | -25 | 1257 | C |
| ATOM | 448 | CB | LEU | A | 28 | 2.194 | 17.790 | 95.311 | 1.00 | 51.51 | | C |
| ANISOU | 448 | CB | LEU | A | 28 | 7240 | 6056 | 6276 | -482 | -38 | 1228 | C |
| ATOM | 451 | CG | LEU | A | 28 | 3.419 | 17.618 | 96.227 | 1.00 | 52.17 | | C |
| ANISOU | 451 | CG | LEU | A | 28 | 7339 | 6064 | 6418 | -366 | -136 | 1350 | C |
| ATOM | 453 | CD1 | LEU | A | 28 | 4.457 | 16.720 | 95.582 | 1.00 | 54.19 | | C |
| ANISOU | 453 | CD1 | LEU | A | 28 | 7622 | 6080 | 6889 | -234 | -170 | 1305 | C |
| ATOM | 457 | CD2 | LEU | A | 28 | 4.050 | 18.952 | 96.586 | 1.00 | 50.01 | | C |
| ANISOU | 457 | CD2 | LEU | A | 28 | 6968 | 5982 | 6052 | -280 | -140 | 1324 | C |
| ATOM | 461 | C | LEU | A | 28 | 1.859 | 15.299 | 94.898 | 1.00 | 52.19 | | C |
| ANISOU | 461 | C | LEU | A | 28 | 7527 | 5716 | 6585 | -595 | -79 | 1281 | C |
| ATOM | 462 | O | LEU | A | 28 | 2.400 | 15.051 | 93.825 | 1.00 | 49.56 | | O |
| ANISOU | 462 | O | LEU | A | 28 | 7192 | 5266 | 6374 | -507 | -48 | 1131 | O |
| ATOM | 464 | N | LYS | A | 29 | 1.805 | 14.418 | 95.903 | 1.00 | 54.37 | | N |
| ANISOU | 464 | N | LYS | A | 29 | 7905 | 5864 | 6891 | -658 | -154 | 1468 | N |
| ATOM | 465 | CA | LYS | A | 29 | 2.234 | 13.028 | 95.714 | 1.00 | 56.67 | | C |
| ANISOU | 465 | CA | LYS | A | 29 | 8321 | 5829 | 7383 | -632 | -204 | 1504 | C |
| ATOM | 467 | CB | LYS | A | 29 | 2.332 | 12.281 | 97.053 | 1.00 | 60.77 | | C |
| ANISOU | 467 | CB | LYS | A | 29 | 8942 | 6236 | 7913 | -681 | -313 | 1765 | C |
| ATOM | 470 | CG | LYS | A | 29 | 3.331 | 12.882 | 98.074 | 1.00 | 61.40 | | C |
| ANISOU | 470 | CG | LYS | A | 29 | 8961 | 6420 | 7947 | -548 | -405 | 1902 | C |
| ATOM | 473 | CD | LYS | A | 29 | 4.776 | 12.965 | 97.533 | 1.00 | 61.64 | | C |
| ANISOU | 473 | CD | LYS | A | 29 | 8918 | 6343 | 8159 | -299 | -438 | 1812 | C |
| ATOM | 476 | CE | LYS | A | 29 | 5.749 | 13.516 | 98.602 | 1.00 | 61.76 | | C |
| ANISOU | 476 | CE | LYS | A | 29 | 8866 | 6476 | 8125 | -193 | -550 | 1965 | C |
| ATOM | 479 | NZ | LYS | A | 29 | 7.214 | 13.367 | 98.263 | 1.00 | 62.01 | | N |
| ANISOU | 479 | NZ | LYS | A | 29 | 8817 | 6380 | 8363 | 45 | -608 | 1930 | N |
| ATOM | 483 | C | LYS | A | 29 | 1.298 | 12.264 | 94.757 | 1.00 | 56.76 | | C |
| ANISOU | 483 | C | LYS | A | 29 | 8408 | 5720 | 7438 | -784 | -139 | 1386 | C |
| ATOM | 484 | O | LYS | A | 29 | 1.749 | 11.380 | 94.015 | 1.00 | 58.33 | | O |
| ANISOU | 484 | O | LYS | A | 29 | 8685 | 5660 | 7816 | -726 | -134 | 1289 | O |
| ATOM | 486 | N | ILE | A | 30 | 0.010 | 12.602 | 94.772 | 1.00 | 55.11 | | N |
| ANISOU | 486 | N | ILE | A | 30 | 8170 | 5700 | 7068 | -977 | -89 | 1385 | N |
| ATOM | 487 | CA | ILE | A | 30 | -0.979 | 11.965 | 93.888 | 1.00 | 55.91 | | C |
| ANISOU | 487 | CA | ILE | A | 30 | 8324 | 5736 | 7182 | -1155 | -39 | 1278 | C |
| ATOM | 489 | CB | ILE | A | 30 | -2.405 | 11.956 | 94.530 | 1.00 | 57.14 | | C |
| ANISOU | 489 | CB | ILE | A | 30 | 8468 | 6060 | 7182 | -1401 | -23 | 1397 | C |
| ATOM | 491 | CG1 | ILE | A | 30 | -2.431 | 11.085 | 95.795 | 1.00 | 60.05 | | C |

FIG. 18 (continued)

| | | | | | | | | | | | | |
|---|---|---|---|---|---|---|---|---|---|---|---|---|
| ANISOU | 491 | CG1 | ILE | A | 30 | 8960 | 6285 | 7570 | -1491 | -93 | 1636 | C |
| ATOM | 494 | CD1 | ILE | A | 30 | -3.644 | 11.334 | 96.706 | 1.00 | 60.30 | | C |
| ANISOU | 494 | CD1 | ILE | A | 30 | 8948 | 6551 | 7412 | -1706 | -64 | 1777 | C |
| ATOM | 498 | CG2 | ILE | A | 30 | -3.452 | 11.454 | 93.541 | 1.00 | 57.27 | | C |
| ANISOU | 498 | CG2 | ILE | A | 30 | 8504 | 6060 | 7195 | -1597 | 23 | 1275 | C |
| ATOM | 502 | C | ILE | A | 30 | -1.020 | 12.725 | 92.559 | 1.00 | 52.50 | | C |
| ANISOU | 502 | C | ILE | A | 30 | 7791 | 5441 | 6715 | -1107 | 35 | 1049 | C |
| ATOM | 503 | O | ILE | A | 30 | -0.714 | 12.178 | 91.495 | 1.00 | 52.50 | | O |
| ANISOU | 503 | O | ILE | A | 30 | 7846 | 5279 | 6821 | -1084 | 63 | 887 | O |
| ATOM | 505 | N | GLU | A | 31 | -1.356 | 14.005 | 92.638 | 1.00 | 49.19 | | N |
| ANISOU | 505 | N | GLU | A | 31 | 7230 | 5315 | 6143 | -1087 | 68 | 1037 | N |
| ATOM | 506 | CA | GLU | A | 31 | -1.551 | 14.817 | 91.451 | 1.00 | 46.29 | | C |
| ANISOU | 506 | CA | GLU | A | 31 | 6765 | 5107 | 5717 | -1065 | 125 | 860 | C |
| ATOM | 508 | CB | GLU | A | 31 | -2.580 | 15.937 | 91.723 | 1.00 | 47.00 | | C |
| ANISOU | 508 | CB | GLU | A | 31 | 6718 | 5504 | 5635 | -1138 | 154 | 900 | C |
| ATOM | 511 | CG | GLU | A | 31 | -3.867 | 15.553 | 92.458 | 1.00 | 50.43 | | C |
| ANISOU | 511 | CG | GLU | A | 31 | 7151 | 6021 | 5991 | -1342 | 156 | 1024 | C |
| ATOM | 514 | CD | GLU | A | 31 | -4.996 | 15.056 | 91.550 | 1.00 | 54.58 | | C |
| ANISOU | 514 | CD | GLU | A | 31 | 7666 | 6578 | 6495 | -1541 | 173 | 946 | C |
| ATOM | 515 | OE1 | GLU | A | 31 | -5.591 | 14.009 | 91.877 | 1.00 | 58.90 | | O |
| ANISOU | 515 | OE1 | GLU | A | 31 | 8299 | 7011 | 7067 | -1720 | 157 | 1018 | O |
| ATOM | 516 | OE2 | GLU | A | 31 | -5.314 | 15.713 | 90.526 | 1.00 | 56.75 | | O |
| ANISOU | 516 | OE2 | GLU | A | 31 | 7845 | 6996 | 6719 | -1534 | 195 | 825 | O |
| ATOM | 517 | C | GLU | A | 31 | -0.201 | 15.423 | 91.018 | 1.00 | 42.27 | | C |
| ANISOU | 517 | C | GLU | A | 31 | 6212 | 4579 | 5270 | -842 | 134 | 766 | C |
| ATOM | 518 | O | GLU | A | 31 | -0.042 | 16.653 | 90.984 | 1.00 | 37.78 | | O |
| ANISOU | 518 | O | GLU | A | 31 | 5530 | 4214 | 4610 | -761 | 154 | 746 | O |
| ATOM | 520 | N | THR | A | 32 | 0.776 | 14.582 | 90.687 | 1.00 | 40.10 | | N |
| ANISOU | 520 | N | THR | A | 32 | 6020 | 4058 | 5157 | -742 | 125 | 707 | N |
| ATOM | 521 | CA | THR | A | 32 | 2.094 | 15.118 | 90.374 | 1.00 | 40.90 | | C |
| ANISOU | 521 | CA | THR | A | 32 | 6058 | 4157 | 5325 | -534 | 138 | 631 | C |
| ATOM | 523 | CB | THR | A | 32 | 3.208 | 14.074 | 90.532 | 1.00 | 44.16 | | C |
| ANISOU | 523 | CB | THR | A | 32 | 6549 | 4283 | 5948 | -398 | 107 | 638 | C |
| ATOM | 525 | OG1 | THR | A | 32 | 3.063 | 13.429 | 91.789 | 1.00 | 46.29 | | O |
| ANISOU | 525 | OG1 | THR | A | 32 | 6893 | 4438 | 6256 | -433 | 21 | 848 | O |
| ATOM | 527 | CG2 | THR | A | 32 | 4.559 | 14.761 | 90.531 | 1.00 | 45.28 | | C |
| ANISOU | 527 | CG2 | THR | A | 32 | 6585 | 4474 | 6145 | -187 | 107 | 609 | C |
| ATOM | 531 | C | THR | A | 32 | 2.173 | 15.838 | 89.010 | 1.00 | 37.44 | | C |
| ANISOU | 531 | C | THR | A | 32 | 5549 | 3851 | 4826 | -517 | 214 | 435 | C |
| ATOM | 532 | O | THR | A | 32 | 2.959 | 16.768 | 88.855 | 1.00 | 35.16 | | O |
| ANISOU | 532 | O | THR | A | 32 | 5166 | 3676 | 4515 | -389 | 231 | 400 | O |
| ATOM | 534 | N | ASN | A | 33 | 1.349 | 15.437 | 88.050 | 1.00 | 36.73 | | N |
| ANISOU | 534 | N | ASN | A | 33 | 5503 | 3759 | 4695 | -663 | 252 | 319 | N |
| ATOM | 535 | CA | ASN | A | 33 | 1.246 | 16.169 | 86.786 | 1.00 | 35.92 | | C |
| ANISOU | 535 | CA | ASN | A | 33 | 5336 | 3819 | 4492 | -684 | 309 | 162 | C |
| ATOM | 537 | CB | ASN | A | 33 | 0.452 | 15.366 | 85.759 | 1.00 | 37.30 | | C |
| ANISOU | 537 | CB | ASN | A | 33 | 5593 | 3936 | 4641 | -862 | 336 | 29 | C |
| ATOM | 540 | CG | ASN | A | 33 | 1.250 | 14.204 | 85.166 | 1.00 | 40.42 | | C |
| ANISOU | 540 | CG | ASN | A | 33 | 6110 | 4057 | 5191 | -815 | 383 | -126 | C |
| ATOM | 541 | OD1 | ASN | A | 33 | 2.451 | 14.299 | 84.935 | 1.00 | 40.77 | | O |
| ANISOU | 541 | OD1 | ASN | A | 33 | 6131 | 4034 | 5326 | -640 | 427 | -203 | O |
| ATOM | 542 | ND2 | ASN | A | 33 | 0.562 | 13.105 | 84.884 | 1.00 | 42.22 | | N |
| ANISOU | 542 | ND2 | ASN | A | 33 | 6462 | 4127 | 5454 | -979 | 381 | -183 | N |
| ATOM | 545 | C | ASN | A | 33 | 0.655 | 17.581 | 86.961 | 1.00 | 32.68 | | C |
| ANISOU | 545 | C | ASN | A | 33 | 4799 | 3695 | 3923 | -700 | 298 | 236 | C |
| ATOM | 546 | O | ASN | A | 33 | 1.146 | 18.544 | 86.370 | 1.00 | 30.17 | | O |
| ANISOU | 546 | O | ASN | A | 33 | 4405 | 3506 | 3551 | -620 | 327 | 173 | O |
| ATOM | 548 | N | LYS | A | 34 | -0.380 | 17.698 | 87.787 | 1.00 | 33.13 | | N |
| ANISOU | 548 | N | LYS | A | 34 | 4834 | 3841 | 3913 | -800 | 262 | 370 | N |
| ATOM | 549 | CA | LYS | A | 34 | -0.987 | 18.992 | 88.106 | 1.00 | 32.07 | | C |
| ANISOU | 549 | CA | LYS | A | 34 | 4578 | 3951 | 3655 | -796 | 259 | 442 | C |
| ATOM | 551 | CB | LYS | A | 34 | -2.261 | 18.796 | 88.953 | 1.00 | 32.73 | | C |
| ANISOU | 551 | CB | LYS | A | 34 | 4643 | 4113 | 3680 | -935 | 240 | 566 | C |
| ATOM | 554 | CG | LYS | A | 34 | -3.130 | 20.026 | 89.096 | 1.00 | 32.91 | | C |
| ANISOU | 554 | CG | LYS | A | 34 | 4529 | 4386 | 3588 | -944 | 253 | 612 | C |
| ATOM | 557 | CD | LYS | A | 34 | -4.372 | 19.746 | 89.990 | 1.00 | 33.73 | | C |
| ANISOU | 557 | CD | LYS | A | 34 | 4597 | 4576 | 3641 | -1083 | 254 | 726 | C |
| ATOM | 560 | CE | LYS | A | 34 | -5.480 | 18.934 | 89.267 | 1.00 | 36.01 | | C |
| ANISOU | 560 | CE | LYS | A | 34 | 4886 | 4881 | 3914 | -1285 | 242 | 694 | C |
| ATOM | 563 | NZ | LYS | A | 34 | -6.680 | 18.663 | 90.150 | 1.00 | 36.38 | | N |
| ANISOU | 563 | NZ | LYS | A | 34 | 4878 | 5033 | 3913 | -1434 | 253 | 809 | N |
| ATOM | 567 | C | LYS | A | 34 | 0.022 | 19.945 | 88.814 | 1.00 | 30.19 | | C |
| ANISOU | 567 | C | LYS | A | 34 | 4288 | 3757 | 3425 | -622 | 256 | 495 | C |
| ATOM | 568 | O | LYS | A | 34 | 0.016 | 21.141 | 88.579 | 1.00 | 28.05 | | O |
| ANISOU | 568 | O | LYS | A | 34 | 3932 | 3646 | 3081 | -571 | 271 | 482 | O |
| ATOM | 570 | N | PHE | A | 35 | 0.860 | 19.404 | 89.690 | 1.00 | 30.61 | | N |
| ANISOU | 570 | N | PHE | A | 35 | 4396 | 3665 | 3569 | -543 | 226 | 562 | N |
| ATOM | 571 | CA | PHE | A | 35 | 1.952 | 20.158 | 90.295 | 1.00 | 30.02 | | C |
| ANISOU | 571 | CA | PHE | A | 35 | 4275 | 3620 | 3510 | -393 | 209 | 600 | C |

FIG. 18 (continued)

| | | | | | | | | | | | | |
|---|---|---|---|---|---|---|---|---|---|---|---|---|
| ATOM | 573 | CB | PHE | A | 35 | 2.723 | 19.217 | 91.241 | 1.00 | 32.73 | | C |
| ANISOU | 573 | CB | PHE | A | 35 | 4687 | 3782 | 3965 | -334 | 152 | 696 | C |
| ATOM | 576 | CG | PHE | A | 35 | 3.857 | 19.866 | 92.046 | 1.00 | 31.98 | | C |
| ANISOU | 576 | CG | PHE | A | 35 | 4542 | 3725 | 3885 | -199 | 109 | 761 | C |
| ATOM | 577 | CD1 | PHE | A | 35 | 3.804 | 21.188 | 92.476 | 1.00 | 31.05 | | C |
| ANISOU | 577 | CD1 | PHE | A | 35 | 4350 | 3797 | 3649 | -184 | 116 | 781 | C |
| ATOM | 579 | CE1 | PHE | A | 35 | 4.854 | 21.747 | 93.212 | 1.00 | 31.16 | | C |
| ANISOU | 579 | CE1 | PHE | A | 35 | 4326 | 3846 | 3669 | -86 | 69 | 832 | C |
| ATOM | 581 | CZ | PHE | A | 35 | 5.974 | 20.982 | 93.538 | 1.00 | 31.16 | | C |
| ANISOU | 581 | CZ | PHE | A | 35 | 4337 | 3705 | 3797 | 9 | 5 | 880 | C |
| ATOM | 583 | CE2 | PHE | A | 35 | 6.040 | 19.668 | 93.130 | 1.00 | 33.92 | | C |
| ANISOU | 583 | CE2 | PHE | A | 35 | 4751 | 3854 | 4283 | 20 | -1 | 869 | C |
| ATOM | 585 | CD2 | PHE | A | 35 | 4.976 | 19.112 | 92.385 | 1.00 | 33.99 | | C |
| ANISOU | 585 | CD2 | PHE | A | 35 | 4822 | 3813 | 4281 | -91 | 56 | 802 | C |
| ATOM | 587 | C | PHE | A | 35 | 2.861 | 20.812 | 89.220 | 1.00 | 28.76 | | C |
| ANISOU | 587 | C | PHE | A | 35 | 4062 | 3498 | 3369 | -295 | 250 | 468 | C |
| ATOM | 588 | O | PHE | A | 35 | 3.106 | 22.015 | 89.251 | 1.00 | 27.23 | | O |
| ANISOU | 588 | O | PHE | A | 35 | 3794 | 3444 | 3109 | -242 | 259 | 470 | O |
| ATOM | 590 | N | ALA | A | 36 | 3.266 | 20.030 | 88.220 | 1.00 | 29.13 | | N |
| ANISOU | 590 | N | ALA | A | 36 | 4152 | 3423 | 3495 | -289 | 284 | 346 | N |
| ATOM | 591 | CA | ALA | A | 36 | 4.033 | 20.555 | 87.092 | 1.00 | 28.71 | | C |
| ANISOU | 591 | CA | ALA | A | 36 | 4051 | 3422 | 3437 | -227 | 341 | 210 | C |
| ATOM | 593 | CB | ALA | A | 36 | 4.535 | 19.393 | 86.164 | 1.00 | 27.40 | | C |
| ANISOU | 593 | CB | ALA | A | 36 | 3952 | 3081 | 3378 | -218 | 393 | 60 | C |
| ATOM | 597 | C | ALA | A | 36 | 3.246 | 21.604 | 86.303 | 1.00 | 26.67 | | C |
| ANISOU | 597 | C | ALA | A | 36 | 3740 | 3363 | 3030 | -309 | 364 | 179 | C |
| ATOM | 598 | O | ALA | A | 36 | 3.804 | 22.616 | 85.883 | 1.00 | 26.96 | | O |
| ANISOU | 598 | O | ALA | A | 36 | 3714 | 3507 | 3023 | -253 | 387 | 150 | O |
| ATOM | 600 | N | ALA | A | 37 | 1.949 | 21.366 | 86.104 | 1.00 | 26.67 | | N |
| ANISOU | 600 | N | ALA | A | 37 | 3761 | 3414 | 2959 | -445 | 350 | 196 | N |
| ATOM | 601 | CA | ALA | A | 37 | 1.102 | 22.313 | 85.378 | 1.00 | 26.47 | | C |
| ANISOU | 601 | CA | ALA | A | 37 | 3673 | 3579 | 2805 | -517 | 351 | 191 | C |
| ATOM | 603 | CB | ALA | A | 37 | -0.284 | 21.666 | 85.021 | 1.00 | 26.28 | | C |
| ANISOU | 603 | CB | ALA | A | 37 | 3669 | 3588 | 2727 | -687 | 328 | 192 | C |
| ATOM | 607 | C | ALA | A | 37 | 0.913 | 23.646 | 86.133 | 1.00 | 24.12 | | C |
| ANISOU | 607 | C | ALA | A | 37 | 3293 | 3415 | 2457 | -452 | 331 | 300 | C |
| ATOM | 608 | O | ALA | A | 37 | 0.871 | 24.698 | 85.520 | 1.00 | 24.65 | | O |
| ANISOU | 608 | O | ALA | A | 37 | 3305 | 3604 | 2457 | -436 | 338 | 292 | O |
| ATOM | 610 | N | ILE | A | 38 | 0.801 | 23.598 | 87.460 | 1.00 | 24.50 | | N |
| ANISOU | 610 | N | ILE | A | 38 | 3342 | 3435 | 2532 | -421 | 309 | 400 | N |
| ATOM | 611 | CA | ILE | A | 38 | 0.678 | 24.832 | 88.245 | 1.00 | 24.59 | | C |
| ANISOU | 611 | CA | ILE | A | 38 | 3290 | 3557 | 2496 | -360 | 304 | 476 | C |
| ATOM | 613 | CB | ILE | A | 38 | 0.338 | 24.545 | 89.746 | 1.00 | 25.30 | | C |
| ANISOU | 613 | CB | ILE | A | 38 | 3398 | 3630 | 2586 | -370 | 287 | 579 | C |
| ATOM | 615 | CG1 | ILE | A | 38 | -1.039 | 23.903 | 89.862 | 1.00 | 26.63 | | C |
| ANISOU | 615 | CG1 | ILE | A | 38 | 3560 | 3836 | 2721 | -499 | 289 | 621 | C |
| ATOM | 618 | CD1 | ILE | A | 38 | -1.263 | 23.155 | 91.222 | 1.00 | 26.37 | | C |
| ANISOU | 618 | CD1 | ILE | A | 38 | 3577 | 3750 | 2691 | -548 | 275 | 723 | C |
| ATOM | 622 | CG2 | ILE | A | 38 | 0.386 | 25.839 | 90.570 | 1.00 | 25.16 | | C |
| ANISOU | 622 | CG2 | ILE | A | 38 | 3330 | 3714 | 2516 | -301 | 297 | 623 | C |
| ATOM | 626 | C | ILE | A | 38 | 1.958 | 25.644 | 88.180 | 1.00 | 22.71 | | C |
| ANISOU | 626 | C | ILE | A | 38 | 3036 | 3315 | 2279 | -248 | 313 | 446 | C |
| ATOM | 627 | O | ILE | A | 38 | 1.906 | 26.842 | 87.993 | 1.00 | 24.59 | | O |
| ANISOU | 627 | O | ILE | A | 38 | 3226 | 3649 | 2469 | -217 | 322 | 453 | O |
| ATOM | 629 | N | CYS | A | 39 | 3.093 | 24.971 | 88.338 | 1.00 | 23.42 | | N |
| ANISOU | 629 | N | CYS | A | 39 | 3160 | 3286 | 2452 | -191 | 308 | 418 | N |
| ATOM | 630 | CA | CYS | A | 39 | 4.409 | 25.599 | 88.109 | 1.00 | 23.82 | | C |
| ANISOU | 630 | CA | CYS | A | 39 | 3176 | 3341 | 2535 | -99 | 320 | 376 | C |
| ATOM | 632 | CB | CYS | A | 39 | 5.570 | 24.609 | 88.281 | 1.00 | 23.03 | | C |
| ANISOU | 632 | CB | CYS | A | 39 | 3093 | 3104 | 2555 | -28 | 312 | 348 | C |
| ATOM | 635 | SG | CYS | A | 39 | 5.779 | 24.064 | 90.011 | 1.00 | 24.90 | | S |
| ANISOU | 635 | SG | CYS | A | 39 | 3357 | 3262 | 2840 | 9 | 233 | 485 | S |
| ATOM | 637 | C | CYS | A | 39 | 4.513 | 26.272 | 86.771 | 1.00 | 21.59 | | C |
| ANISOU | 637 | C | CYS | A | 39 | 2864 | 3138 | 2202 | -119 | 363 | 296 | C |
| ATOM | 638 | O | CYS | A | 39 | 4.981 | 27.414 | 86.691 | 1.00 | 20.99 | | O |
| ANISOU | 638 | O | CYS | A | 39 | 2747 | 3134 | 2093 | -85 | 370 | 305 | O |
| ATOM | 640 | N | THR | A | 40 | 4.083 | 25.581 | 85.720 | 1.00 | 24.21 | | N |
| ANISOU | 640 | N | THR | A | 40 | 3225 | 3456 | 2516 | -189 | 389 | 221 | N |
| ATOM | 641 | CA | THR | A | 40 | 4.177 | 26.130 | 84.384 | 1.00 | 24.15 | | C |
| ANISOU | 641 | CA | THR | A | 40 | 3201 | 3540 | 2436 | -230 | 426 | 149 | C |
| ATOM | 643 | CB | THR | A | 40 | 3.782 | 25.078 | 83.318 | 1.00 | 26.04 | | C |
| ANISOU | 643 | CB | THR | A | 40 | 3493 | 3749 | 2653 | -324 | 455 | 43 | C |
| ATOM | 645 | OG1 | THR | A | 40 | 4.591 | 23.911 | 83.435 | 1.00 | 27.23 | | O |
| ANISOU | 645 | OG1 | THR | A | 40 | 3686 | 3744 | 2918 | -276 | 490 | -40 | O |
| ATOM | 647 | CG2 | THR | A | 40 | 3.905 | 25.623 | 81.912 | 1.00 | 26.28 | | C |
| ANISOU | 647 | CG2 | THR | A | 40 | 3514 | 3895 | 2575 | -387 | 492 | -29 | C |
| ATOM | 651 | C | THR | A | 40 | 3.294 | 27.384 | 84.249 | 1.00 | 24.25 | | C |
| ANISOU | 651 | C | THR | A | 40 | 3173 | 3686 | 2352 | -262 | 397 | 229 | C |
| ATOM | 652 | O | THR | A | 40 | 3.698 | 28.418 | 83.683 | 1.00 | 22.06 | | O |

FIG. 18 (continued)

| | | | | | | | | | | | | |
|---|---|---|---|---|---|---|---|---|---|---|---|---|
| ANISOU | 652 | O | THR | A | 40 | 2869 | 3483 | 2028 | -250 | 409 | 233 | O |
| ATOM | 654 | N | HIS | A | 41 | 2.054 | 27.272 | 84.728 | 1.00 | 24.75 | | N |
| ANISOU | 654 | N | HIS | A | 41 | 3230 | 3780 | 2395 | -305 | 361 | 296 | N |
| ATOM | 655 | CA | HIS | A | 41 | 1.110 | 28.358 | 84.580 | 1.00 | 22.71 | | C |
| ANISOU | 655 | CA | HIS | A | 41 | 2918 | 3640 | 2072 | -318 | 334 | 371 | C |
| ATOM | 657 | CB | HIS | A | 41 | -0.263 | 27.955 | 85.102 | 1.00 | 24.08 | | C |
| ANISOU | 657 | CB | HIS | A | 41 | 3063 | 3851 | 2237 | -372 | 308 | 428 | C |
| ATOM | 660 | CG | HIS | A | 41 | -1.261 | 29.062 | 85.040 | 1.00 | 24.23 | | C |
| ANISOU | 660 | CG | HIS | A | 41 | 3002 | 3988 | 2219 | -357 | 283 | 507 | C |
| ATOM | 661 | ND1 | HIS | A | 41 | -1.632 | 29.795 | 86.150 | 1.00 | 23.09 | | N |
| ANISOU | 661 | ND1 | HIS | A | 41 | 2815 | 3857 | 2101 | -282 | 295 | 568 | N |
| ATOM | 663 | CE1 | HIS | A | 41 | -2.472 | 30.743 | 85.778 | 1.00 | 23.45 | | C |
| ANISOU | 663 | CE1 | HIS | A | 41 | 2785 | 3995 | 2129 | -259 | 275 | 624 | C |
| ATOM | 665 | NE2 | HIS | A | 41 | -2.683 | 30.623 | 84.481 | 1.00 | 25.84 | | N |
| ANISOU | 665 | NE2 | HIS | A | 41 | 3078 | 4357 | 2382 | -329 | 235 | 620 | N |
| ATOM | 667 | CD2 | HIS | A | 41 | -1.915 | 29.603 | 83.990 | 1.00 | 23.45 | | C |
| ANISOU | 667 | CD2 | HIS | A | 41 | 2854 | 3994 | 2062 | -397 | 247 | 536 | C |
| ATOM | 669 | C | HIS | A | 41 | 1.627 | 29.625 | 85.279 | 1.00 | 22.14 | | C |
| ANISOU | 669 | C | HIS | A | 41 | 2821 | 3574 | 2016 | -222 | 338 | 422 | C |
| ATOM | 670 | O | HIS | A | 41 | 1.649 | 30.696 | 84.699 | 1.00 | 21.61 | | O |
| ANISOU | 670 | O | HIS | A | 41 | 2732 | 3564 | 1913 | -210 | 332 | 447 | O |
| ATOM | 672 | N | LEU | A | 42 | 2.092 | 29.466 | 86.508 | 1.00 | 23.49 | | N |
| ANISOU | 672 | N | LEU | A | 42 | 3006 | 3679 | 2239 | -167 | 341 | 437 | N |
| ATOM | 673 | CA | LEU | A | 42 | 2.716 | 30.555 | 87.262 | 1.00 | 23.66 | | C |
| ANISOU | 673 | CA | LEU | A | 42 | 3021 | 3698 | 2272 | -96 | 344 | 464 | C |
| ATOM | 675 | CB | LEU | A | 42 | 3.180 | 30.029 | 88.639 | 1.00 | 24.26 | | C |
| ANISOU | 675 | CB | LEU | A | 42 | 3120 | 3712 | 2384 | -65 | 333 | 481 | C |
| ATOM | 678 | CG | LEU | A | 42 | 2.066 | 29.837 | 89.672 | 1.00 | 24.99 | | C |
| ANISOU | 678 | CG | LEU | A | 42 | 3213 | 3832 | 2451 | -85 | 331 | 537 | C |
| ATOM | 680 | CD1 | LEU | A | 42 | 2.546 | 28.992 | 90.907 | 1.00 | 24.15 | | C |
| ANISOU | 680 | CD1 | LEU | A | 42 | 3148 | 3667 | 2363 | -85 | 308 | 571 | C |
| ATOM | 684 | CD2 | LEU | A | 42 | 1.447 | 31.179 | 90.141 | 1.00 | 24.98 | | C |
| ANISOU | 684 | CD2 | LEU | A | 42 | 3181 | 3895 | 2414 | -49 | 353 | 559 | C |
| ATOM | 688 | C | LEU | A | 42 | 3.871 | 31.210 | 86.537 | 1.00 | 23.89 | | C |
| ANISOU | 688 | C | LEU | A | 42 | 3048 | 3725 | 2302 | -79 | 358 | 426 | C |
| ATOM | 689 | O | LEU | A | 42 | 3.889 | 32.453 | 86.402 | 1.00 | 22.28 | | O |
| ANISOU | 689 | O | LEU | A | 42 | 2836 | 3552 | 2078 | -62 | 358 | 456 | O |
| ATOM | 691 | N | GLU | A | 43 | 4.818 | 30.379 | 86.044 | 1.00 | 25.62 | | N |
| ANISOU | 691 | N | GLU | A | 43 | 3275 | 3905 | 2553 | -85 | 377 | 360 | N |
| ATOM | 692 | CA | GLU | A | 43 | 5.987 | 30.882 | 85.344 | 1.00 | 26.73 | | C |
| ANISOU | 692 | CA | GLU | A | 43 | 3398 | 4064 | 2695 | -80 | 407 | 316 | C |
| ATOM | 694 | CB | GLU | A | 43 | 6.968 | 29.755 | 84.980 | 1.00 | 29.59 | | C |
| ANISOU | 694 | CB | GLU | A | 43 | 3750 | 4376 | 3117 | -64 | 443 | 229 | C |
| ATOM | 697 | CG | GLU | A | 43 | 8.201 | 30.291 | 84.313 | 1.00 | 32.74 | | C |
| ANISOU | 697 | CG | GLU | A | 43 | 4106 | 4818 | 3517 | -63 | 490 | 180 | C |
| ATOM | 700 | CD | GLU | A | 43 | 9.435 | 29.411 | 84.398 | 1.00 | 34.73 | | C |
| ANISOU | 700 | CD | GLU | A | 43 | 4311 | 5018 | 3869 | -2 | 524 | 105 | C |
| ATOM | 701 | OE1 | GLU | A | 43 | 10.525 | 29.968 | 84.162 | 1.00 | 39.37 | | O |
| ANISOU | 701 | OE1 | GLU | A | 43 | 4835 | 5653 | 4469 | 5 | 557 | 81 | O |
| ATOM | 702 | OE2 | GLU | A | 43 | 9.341 | 28.207 | 84.649 | 1.00 | 38.05 | | O |
| ANISOU | 702 | OE2 | GLU | A | 43 | 4749 | 5349 | 4361 | 36 | 521 | 73 | O |
| ATOM | 703 | C | GLU | A | 43 | 5.584 | 31.682 | 84.104 | 1.00 | 25.14 | | C |
| ANISOU | 703 | C | GLU | A | 43 | 3197 | 3943 | 2410 | -139 | 419 | 327 | C |
| ATOM | 704 | O | GLU | A | 43 | 6.123 | 32.761 | 83.844 | 1.00 | 23.62 | | O |
| ANISOU | 704 | O | GLU | A | 43 | 2997 | 3779 | 2198 | -143 | 426 | 351 | O |
| ATOM | 706 | N | VAL | A | 44 | 4.647 | 31.158 | 83.317 | 1.00 | 26.30 | | N |
| ANISOU | 706 | N | VAL | A | 44 | 3357 | 4131 | 2505 | -199 | 413 | 318 | N |
| ATOM | 707 | CA | VAL | A | 44 | 4.189 | 31.881 | 82.087 | 1.00 | 24.47 | | C |
| ANISOU | 707 | CA | VAL | A | 44 | 3127 | 3995 | 2176 | -268 | 402 | 350 | C |
| ATOM | 709 | CB | VAL | A | 44 | 3.228 | 30.998 | 81.259 | 1.00 | 25.56 | | C |
| ANISOU | 709 | CB | VAL | A | 44 | 3277 | 4187 | 2248 | -355 | 386 | 321 | C |
| ATOM | 711 | CG1 | VAL | A | 44 | 2.518 | 31.809 | 80.181 | 1.00 | 27.31 | | C |
| ANISOU | 711 | CG1 | VAL | A | 44 | 3490 | 4524 | 2363 | -425 | 341 | 396 | C |
| ATOM | 715 | CG2 | VAL | A | 44 | 3.995 | 29.789 | 80.657 | 1.00 | 25.16 | | C |
| ANISOU | 715 | CG2 | VAL | A | 44 | 3260 | 4104 | 2196 | -397 | 449 | 182 | C |
| ATOM | 719 | C | VAL | A | 44 | 3.573 | 33.257 | 82.469 | 1.00 | 24.35 | | C |
| ANISOU | 719 | C | VAL | A | 44 | 3095 | 3995 | 2160 | -229 | 358 | 464 | C |
| ATOM | 720 | O | VAL | A | 44 | 3.861 | 34.275 | 81.871 | 1.00 | 24.34 | | O |
| ANISOU | 720 | O | VAL | A | 44 | 3102 | 4023 | 2123 | -246 | 353 | 511 | O |
| ATOM | 722 | N | CYS | A | 45 | 2.756 | 33.291 | 83.516 | 1.00 | 22.47 | | N |
| ANISOU | 722 | N | CYS | A | 45 | 2840 | 3728 | 1971 | -174 | 334 | 505 | N |
| ATOM | 723 | CA | CYS | A | 45 | 2.133 | 34.539 | 83.947 | 1.00 | 24.10 | | C |
| ANISOU | 723 | CA | CYS | A | 45 | 3028 | 3931 | 2197 | -117 | 310 | 589 | C |
| ATOM | 725 | CB | CYS | A | 45 | 1.122 | 34.312 | 85.078 | 1.00 | 24.08 | | C |
| ANISOU | 725 | CB | CYS | A | 45 | 2994 | 3920 | 2236 | -67 | 307 | 608 | C |
| ATOM | 728 | SG | CYS | A | 45 | -0.429 | 33.526 | 84.567 | 1.00 | 25.97 | | S |
| ANISOU | 728 | SG | CYS | A | 45 | 3169 | 4256 | 2443 | -123 | 271 | 644 | S |
| ATOM | 730 | C | CYS | A | 45 | 3.166 | 35.577 | 84.402 | 1.00 | 24.89 | | C |
| ANISOU | 730 | C | CYS | A | 45 | 3160 | 3968 | 2331 | -78 | 329 | 589 | C |

FIG. 18 (continued)

| | | | | | | | | | | | | |
|---|---|---|---|---|---|---|---|---|---|---|---|---|
| ATOM | 731 | O | CYS | A | 45 | 3.111 | 36.748 | 83.970 | 1.00 | 26.01 | | O |
| ANISOU | 731 | O | CYS | A | 45 | 3314 | 4101 | 2469 | -71 | 312 | 651 | O |
| ATOM | 733 | N | PHE | A | 46 | 4.116 | 35.127 | 85.229 | 1.00 | 22.58 | | N |
| ANISOU | 733 | N | PHE | A | 46 | 2879 | 3628 | 2073 | -62 | 353 | 528 | N |
| ATOM | 734 | CA | PHE | A | 46 | 5.219 | 35.987 | 85.681 | 1.00 | 23.67 | | C |
| ANISOU | 734 | CA | PHE | A | 46 | 3038 | 3720 | 2236 | -51 | 364 | 517 | C |
| ATOM | 736 | CB | PHE | A | 46 | 6.053 | 35.293 | 86.766 | 1.00 | 25.34 | | C |
| ANISOU | 736 | CB | PHE | A | 46 | 3243 | 3901 | 2484 | -30 | 368 | 465 | C |
| ATOM | 739 | CG | PHE | A | 46 | 5.299 | 35.093 | 88.070 | 1.00 | 24.62 | | C |
| ANISOU | 739 | CG | PHE | A | 46 | 3164 | 3788 | 2403 | 12 | 356 | 478 | C |
| ATOM | 740 | CD1 | PHE | A | 46 | 4.466 | 36.076 | 88.571 | 1.00 | 26.61 | | C |
| ANISOU | 740 | CD1 | PHE | A | 46 | 3432 | 4027 | 2651 | 44 | 361 | 505 | C |
| ATOM | 742 | CE1 | PHE | A | 46 | 3.793 | 35.891 | 89.777 | 1.00 | 28.54 | | C |
| ANISOU | 742 | CE1 | PHE | A | 46 | 3683 | 4273 | 2888 | 73 | 371 | 502 | C |
| ATOM | 744 | CZ | PHE | A | 46 | 3.941 | 34.710 | 90.484 | 1.00 | 25.98 | | C |
| ANISOU | 744 | CZ | PHE | A | 46 | 3358 | 3961 | 2553 | 56 | 359 | 496 | C |
| ATOM | 746 | CE2 | PHE | A | 46 | 4.784 | 33.740 | 90.002 | 1.00 | 26.44 | | C |
| ANISOU | 746 | CE2 | PHE | A | 46 | 3405 | 4008 | 2633 | 34 | 338 | 484 | C |
| ATOM | 748 | CD2 | PHE | A | 46 | 5.465 | 33.945 | 88.797 | 1.00 | 25.62 | | C |
| ANISOU | 748 | CD2 | PHE | A | 46 | 3286 | 3906 | 2544 | 19 | 344 | 463 | C |
| ATOM | 750 | C | PHE | A | 46 | 6.100 | 36.490 | 84.554 | 1.00 | 25.50 | | C |
| ANISOU | 750 | C | PHE | A | 46 | 3274 | 3979 | 2436 | -112 | 380 | 518 | C |
| ATOM | 751 | O | PHE | A | 46 | 6.507 | 37.660 | 84.559 | 1.00 | 28.56 | | O |
| ANISOU | 751 | O | PHE | A | 46 | 3687 | 4333 | 2831 | -124 | 377 | 552 | O |
| ATOM | 753 | N | MET | A | 47 | 6.372 | 35.638 | 83.577 | 1.00 | 24.45 | | N |
| ANISOU | 753 | N | MET | A | 47 | 3124 | 3903 | 2263 | -161 | 403 | 478 | N |
| ATOM | 754 | CA | MET | A | 47 | 7.125 | 36.034 | 82.414 | 1.00 | 27.52 | | C |
| ANISOU | 754 | CA | MET | A | 47 | 3514 | 4347 | 2595 | -237 | 434 | 474 | C |
| ATOM | 756 | CB | MET | A | 47 | 7.456 | 34.795 | 81.550 | 1.00 | 29.96 | | C |
| ANISOU | 756 | CB | MET | A | 47 | 3803 | 4716 | 2864 | -281 | 482 | 383 | C |
| ATOM | 759 | CG | MET | A | 47 | 8.508 | 33.845 | 82.087 | 1.00 | 29.99 | | C |
| ANISOU | 759 | CG | MET | A | 47 | 3764 | 4686 | 2945 | -237 | 526 | 285 | C |
| ATOM | 762 | SD | MET | A | 47 | 8.844 | 32.417 | 80.998 | 1.00 | 35.52 | | S |
| ANISOU | 762 | SD | MET | A | 47 | 4452 | 5426 | 3617 | -273 | 603 | 152 | S |
| ATOM | 763 | CE | MET | A | 47 | 9.609 | 33.306 | 79.673 | 1.00 | 24.48 | | C |
| ANISOU | 763 | CE | MET | A | 47 | 3044 | 4147 | 2110 | -380 | 667 | 148 | C |
| ATOM | 767 | C | MET | A | 47 | 6.336 | 37.073 | 81.558 | 1.00 | 26.50 | | C |
| ANISOU | 767 | C | MET | A | 47 | 3419 | 4246 | 2403 | -278 | 397 | 581 | C |
| ATOM | 768 | O | MET | A | 47 | 6.878 | 38.113 | 81.143 | 1.00 | 24.05 | | O |
| ANISOU | 768 | O | MET | A | 47 | 3134 | 3932 | 2073 | -325 | 399 | 634 | O |
| ATOM | 770 | N | TYR | A | 48 | 5.060 | 36.795 | 81.321 | 1.00 | 25.62 | | N |
| ANISOU | 770 | N | TYR | A | 48 | 3304 | 4164 | 2267 | -265 | 354 | 624 | N |
| ATOM | 771 | CA | TYR | A | 48 | 4.168 | 37.681 | 80.553 | 1.00 | 27.91 | | C |
| ANISOU | 771 | CA | TYR | A | 48 | 3607 | 4486 | 2511 | -285 | 295 | 746 | C |
| ATOM | 773 | CB | TYR | A | 48 | 2.771 | 37.068 | 80.540 | 1.00 | 27.09 | | C |
| ANISOU | 773 | CB | TYR | A | 48 | 3462 | 4430 | 2400 | -261 | 247 | 772 | C |
| ATOM | 776 | CG | TYR | A | 48 | 1.830 | 37.470 | 79.414 | 1.00 | 27.00 | | C |
| ANISOU | 776 | CG | TYR | A | 48 | 3439 | 4509 | 2311 | -311 | 172 | 887 | C |
| ATOM | 777 | CD1 | TYR | A | 48 | 1.387 | 36.525 | 78.482 | 1.00 | 27.73 | | C |
| ANISOU | 777 | CD1 | TYR | A | 48 | 3518 | 4721 | 2296 | -410 | 150 | 860 | C |
| ATOM | 779 | CE1 | TYR | A | 48 | 0.488 | 36.877 | 77.493 | 1.00 | 27.94 | | C |
| ANISOU | 779 | CE1 | TYR | A | 48 | 3525 | 4852 | 2240 | -466 | 61 | 977 | C |
| ATOM | 781 | CZ | TYR | A | 48 | 0.029 | 38.194 | 77.406 | 1.00 | 28.84 | | C |
| ANISOU | 781 | CZ | TYR | A | 48 | 3628 | 4934 | 2396 | -404 | -9 | 1138 | C |
| ATOM | 782 | OH | TYR | A | 48 | -0.859 | 38.577 | 76.412 | 1.00 | 32.13 | | O |
| ANISOU | 782 | OH | TYR | A | 48 | 4014 | 5457 | 2735 | -452 | -118 | 1282 | O |
| ATOM | 784 | CE2 | TYR | A | 48 | 0.447 | 39.129 | 78.314 | 1.00 | 28.18 | | C |
| ANISOU | 784 | CE2 | TYR | A | 48 | 3566 | 4706 | 2436 | -295 | 23 | 1156 | C |
| ATOM | 786 | CD2 | TYR | A | 48 | 1.331 | 38.760 | 79.320 | 1.00 | 27.08 | | C |
| ANISOU | 786 | CD2 | TYR | A | 48 | 3449 | 4479 | 2359 | -258 | 113 | 1025 | C |
| ATOM | 788 | C | TYR | A | 48 | 4.146 | 39.121 | 81.136 | 1.00 | 27.96 | | C |
| ANISOU | 788 | C | TYR | A | 48 | 3642 | 4389 | 2592 | -223 | 272 | 830 | C |
| ATOM | 789 | O | TYR | A | 48 | 4.295 | 40.092 | 80.419 | 1.00 | 24.17 | | O |
| ANISOU | 789 | O | TYR | A | 48 | 3199 | 3901 | 2084 | -265 | 247 | 922 | O |
| ATOM | 791 | N | SER | A | 49 | 4.009 | 39.208 | 82.458 | 1.00 | 31.66 | | N |
| ANISOU | 791 | N | SER | A | 49 | 4105 | 4775 | 3151 | -133 | 285 | 789 | N |
| ATOM | 792 | CA | SER | A | 49 | 3.940 | 40.462 | 83.221 | 1.00 | 30.51 | | C |
| ANISOU | 792 | CA | SER | A | 49 | 3995 | 4511 | 3085 | -67 | 279 | 826 | C |
| ATOM | 794 | CB | SER | A | 49 | 3.389 | 40.155 | 84.639 | 1.00 | 30.79 | | C |
| ANISOU | 794 | CB | SER | A | 49 | 4010 | 4507 | 3183 | 25 | 300 | 763 | C |
| ATOM | 797 | OG | SER | A | 49 | 4.270 | 39.342 | 85.400 | 1.00 | 32.22 | | O |
| ANISOU | 797 | OG | SER | A | 49 | 4189 | 4697 | 3356 | 2 | 333 | 667 | O |
| ATOM | 799 | C | SER | A | 49 | 5.282 | 41.202 | 83.332 | 1.00 | 30.80 | | C |
| ANISOU | 799 | C | SER | A | 49 | 4086 | 4486 | 3131 | -125 | 305 | 805 | C |
| ATOM | 800 | O | SER | A | 49 | 5.309 | 42.391 | 83.653 | 1.00 | 30.72 | | O |
| ANISOU | 800 | O | SER | A | 49 | 4129 | 4365 | 3176 | -104 | 296 | 845 | O |
| ATOM | 802 | N | ASP | A | 50 | 6.368 | 40.483 | 83.044 | 1.00 | 30.09 | | N |
| ANISOU | 802 | N | ASP | A | 50 | 3975 | 4464 | 2995 | -201 | 340 | 738 | N |
| ATOM | 803 | CA | ASP | A | 50 | 7.739 | 40.932 | 83.181 | 1.00 | 31.26 | | C |

FIG. 18 (continued)

| | | | | | | | | | | | | |
|---|---|---|---|---|---|---|---|---|---|---|---|---|
| ANISOU | 803 | CA | ASP | A | 50 | 4136 | 4592 | 3149 | -270 | 370 | 703 | C |
| ATOM | 805 | CB | ASP | A | 50 | 8.054 | 42.111 | 82.221 | 1.00 | 34.46 | | C |
| ANISOU | 805 | CB | ASP | A | 50 | 4596 | 4975 | 3523 | -359 | 361 | 801 | C |
| ATOM | 808 | CG | ASP | A | 50 | 9.556 | 42.306 | 82.011 | 1.00 | 34.45 | | C |
| ANISOU | 808 | CG | ASP | A | 50 | 4580 | 5010 | 3501 | -472 | 406 | 763 | C |
| ATOM | 809 | OD1 | ASP | A | 50 | 10.316 | 41.354 | 82.227 | 1.00 | 35.00 | | O |
| ANISOU | 809 | OD1 | ASP | A | 50 | 4576 | 5157 | 3567 | -477 | 445 | 667 | O |
| ATOM | 810 | OD2 | ASP | A | 50 | 9.999 | 43.423 | 81.703 | 1.00 | 38.36 | | O |
| ANISOU | 810 | OD2 | ASP | A | 50 | 5130 | 5450 | 3996 | -553 | 400 | 831 | O |
| ATOM | 811 | C | ASP | A | 50 | 8.034 | 41.309 | 84.629 | 1.00 | 32.60 | | C |
| ANISOU | 811 | C | ASP | A | 50 | 4325 | 4673 | 3390 | -223 | 368 | 649 | C |
| ATOM | 812 | O | ASP | A | 50 | 8.832 | 42.191 | 84.895 | 1.00 | 29.95 | | O |
| ANISOU | 812 | O | ASP | A | 50 | 4024 | 4280 | 3075 | -278 | 371 | 646 | O |
| ATOM | 814 | N | PHE | A | 51 | 7.355 | 40.628 | 85.547 | 1.00 | 33.02 | | N |
| ANISOU | 814 | N | PHE | A | 51 | 4358 | 4723 | 3466 | -140 | 363 | 606 | N |
| ATOM | 815 | CA | PHE | A | 51 | 7.507 | 40.828 | 86.979 | 1.00 | 35.93 | | C |
| ANISOU | 815 | CA | PHE | A | 51 | 4748 | 5034 | 3870 | -104 | 362 | 549 | C |
| ATOM | 817 | CB | PHE | A | 51 | 6.453 | 39.989 | 87.711 | 1.00 | 39.13 | | C |
| ANISOU | 817 | CB | PHE | A | 51 | 5130 | 5462 | 4276 | -24 | 363 | 530 | C |
| ATOM | 820 | CG | PHE | A | 51 | 6.493 | 40.131 | 89.192 | 1.00 | 40.63 | | C |
| ANISOU | 820 | CG | PHE | A | 51 | 5348 | 5617 | 4472 | 1 | 368 | 473 | C |
| ATOM | 821 | CD1 | PHE | A | 51 | 6.038 | 41.293 | 89.790 | 1.00 | 43.02 | | C |
| ANISOU | 821 | CD1 | PHE | A | 51 | 5713 | 5832 | 4801 | 32 | 385 | 457 | C |
| ATOM | 823 | CE1 | PHE | A | 51 | 6.075 | 41.438 | 91.155 | 1.00 | 43.28 | | C |
| ANISOU | 823 | CE1 | PHE | A | 51 | 5783 | 5847 | 4815 | 38 | 399 | 387 | C |
| ATOM | 825 | CZ | PHE | A | 51 | 6.595 | 40.423 | 91.939 | 1.00 | 42.62 | | C |
| ANISOU | 825 | CZ | PHE | A | 51 | 5672 | 5840 | 4682 | 8 | 378 | 359 | C |
| ATOM | 827 | CE2 | PHE | A | 51 | 7.072 | 39.256 | 91.341 | 1.00 | 41.58 | | C |
| ANISOU | 827 | CE2 | PHE | A | 51 | 5473 | 5777 | 4548 | -8 | 350 | 392 | C |
| ATOM | 829 | CD2 | PHE | A | 51 | 7.024 | 39.122 | 89.985 | 1.00 | 40.74 | | C |
| ANISOU | 829 | CD2 | PHE | A | 51 | 5334 | 5682 | 4465 | -10 | 354 | 435 | C |
| ATOM | 831 | C | PHE | A | 51 | 8.936 | 40.456 | 87.440 | 1.00 | 32.80 | | C |
| ANISOU | 831 | C | PHE | A | 51 | 4318 | 4674 | 3470 | -164 | 362 | 489 | C |
| ATOM | 832 | O | PHE | A | 51 | 9.499 | 39.477 | 86.993 | 1.00 | 33.31 | | O |
| ANISOU | 832 | O | PHE | A | 51 | 4317 | 4815 | 3524 | -179 | 371 | 470 | O |
| ATOM | 834 | N | HIS | A | 52 | 9.527 | 41.300 | 88.271 | 1.00 | 31.67 | | N |
| ANISOU | 834 | N | HIS | A | 52 | 4216 | 4475 | 3342 | -200 | 351 | 460 | N |
| ATOM | 835 | CA | HIS | A | 52 | 10.856 | 41.077 | 88.838 | 1.00 | 30.90 | | C |
| ANISOU | 835 | CA | HIS | A | 52 | 4072 | 4424 | 3244 | -263 | 331 | 413 | C |
| ATOM | 837 | CB | HIS | A | 52 | 11.741 | 42.308 | 88.619 | 1.00 | 32.49 | | C |
| ANISOU | 837 | CB | HIS | A | 52 | 4308 | 4583 | 3454 | -372 | 330 | 417 | C |
| ATOM | 840 | CG | HIS | A | 52 | 12.132 | 42.526 | 87.188 | 1.00 | 33.35 | | C |
| ANISOU | 840 | CG | HIS | A | 52 | 4391 | 4726 | 3554 | -437 | 361 | 470 | C |
| ATOM | 841 | ND1 | HIS | A | 52 | 13.010 | 41.699 | 86.520 | 1.00 | 33.92 | | N |
| ANISOU | 841 | ND1 | HIS | A | 52 | 4357 | 4917 | 3615 | -471 | 386 | 456 | N |
| ATOM | 843 | CE1 | HIS | A | 52 | 13.164 | 42.124 | 85.281 | 1.00 | 34.70 | | C |
| ANISOU | 843 | CE1 | HIS | A | 52 | 4463 | 5041 | 3683 | -544 | 423 | 505 | C |
| ATOM | 845 | NE2 | HIS | A | 52 | 12.409 | 43.197 | 85.114 | 1.00 | 37.35 | | N |
| ANISOU | 845 | NE2 | HIS | A | 52 | 4908 | 5267 | 4018 | -553 | 407 | 571 | N |
| ATOM | 847 | CD2 | HIS | A | 52 | 11.751 | 43.469 | 86.290 | 1.00 | 36.58 | | C |
| ANISOU | 847 | CD2 | HIS | A | 52 | 4869 | 5071 | 3957 | -477 | 374 | 542 | C |
| ATOM | 849 | C | HIS | A | 52 | 10.725 | 40.738 | 90.337 | 1.00 | 29.53 | | C |
| ANISOU | 849 | C | HIS | A | 52 | 3914 | 4250 | 3057 | -229 | 300 | 367 | C |
| ATOM | 850 | O | HIS | A | 52 | 10.238 | 41.517 | 91.110 | 1.00 | 29.94 | | O |
| ANISOU | 850 | O | HIS | A | 52 | 4044 | 4233 | 3098 | -225 | 303 | 340 | O |
| ATOM | 852 | N | PHE | A | 53 | 11.175 | 39.552 | 90.710 | 1.00 | 28.41 | | N |
| ANISOU | 852 | N | PHE | A | 53 | 3698 | 4182 | 2913 | -206 | 273 | 360 | N |
| ATOM | 853 | CA | PHE | A | 53 | 11.117 | 39.067 | 92.076 | 1.00 | 28.00 | | C |
| ANISOU | 853 | CA | PHE | A | 53 | 3657 | 4150 | 2831 | -188 | 231 | 342 | C |
| ATOM | 855 | CB | PHE | A | 53 | 11.217 | 37.539 | 92.101 | 1.00 | 29.97 | | C |
| ANISOU | 855 | CB | PHE | A | 53 | 3834 | 4453 | 3101 | -132 | 208 | 369 | C |
| ATOM | 858 | CG | PHE | A | 53 | 9.920 | 36.809 | 91.838 | 1.00 | 32.27 | | C |
| ANISOU | 858 | CG | PHE | A | 53 | 4149 | 4726 | 3388 | -67 | 241 | 392 | C |
| ATOM | 859 | CD1 | PHE | A | 53 | 9.570 | 36.398 | 90.541 | 1.00 | 32.38 | | C |
| ANISOU | 859 | CD1 | PHE | A | 53 | 4135 | 4739 | 3430 | -45 | 281 | 401 | C |
| ATOM | 861 | CE1 | PHE | A | 53 | 8.393 | 35.686 | 90.323 | 1.00 | 32.06 | | C |
| ANISOU | 861 | CE1 | PHE | A | 53 | 4108 | 4693 | 3381 | -6 | 300 | 420 | C |
| ATOM | 863 | CZ | PHE | A | 53 | 7.562 | 35.360 | 91.407 | 1.00 | 31.73 | | C |
| ANISOU | 863 | CZ | PHE | A | 53 | 4099 | 4648 | 3308 | 14 | 289 | 435 | C |
| ATOM | 865 | CE2 | PHE | A | 53 | 7.901 | 35.751 | 92.690 | 1.00 | 32.50 | | C |
| ANISOU | 865 | CE2 | PHE | A | 53 | 4227 | 4751 | 3368 | -3 | 261 | 427 | C |
| ATOM | 867 | CD2 | PHE | A | 53 | 9.081 | 36.457 | 92.903 | 1.00 | 33.84 | | C |
| ANISOU | 867 | CD2 | PHE | A | 53 | 4391 | 4924 | 3541 | -44 | 232 | 402 | C |
| ATOM | 869 | C | PHE | A | 53 | 12.262 | 39.618 | 92.940 | 1.00 | 24.66 | | C |
| ANISOU | 869 | C | PHE | A | 53 | 3228 | 3754 | 2387 | -275 | 177 | 312 | C |
| ATOM | 870 | O | PHE | A | 53 | 12.277 | 39.379 | 94.147 | 1.00 | 26.28 | | O |
| ANISOU | 870 | O | PHE | A | 53 | 3456 | 3988 | 2542 | -284 | 131 | 300 | O |
| ATOM | 872 | N | ILE | A | 54 | 13.269 | 40.243 | 92.323 | 1.00 | 24.42 | | N |
| ANISOU | 872 | N | ILE | A | 54 | 3157 | 3734 | 2385 | -352 | 175 | 306 | N |

FIG. 18 (continued)

| | | | | | | | | | | | | |
|---|---|---|---|---|---|---|---|---|---|---|---|---|
| ATOM | 873 | CA | ILE | A | 54 | 14.328 | 40.925 | 93.065 | 1.00 | 24.07 | | C |
| ANISOU | 873 | CA | ILE | A | 54 | 3106 | 3719 | 2321 | -462 | 120 | 275 | C |
| ATOM | 875 | CB | ILE | A | 54 | 15.773 | 40.475 | 92.694 | 1.00 | 24.49 | | C |
| ANISOU | 875 | CB | ILE | A | 54 | 3007 | 3879 | 2421 | -508 | 83 | 293 | C |
| ATOM | 877 | CG1 | ILE | A | 54 | 15.969 | 38.980 | 92.940 | 1.00 | 25.84 | | C |
| ANISOU | 877 | CG1 | ILE | A | 54 | 3074 | 4120 | 2626 | -408 | 44 | 327 | C |
| ATOM | 880 | CD1 | ILE | A | 54 | 17.447 | 38.528 | 92.683 | 1.00 | 26.89 | | C |
| ANISOU | 880 | CD1 | ILE | A | 54 | 3027 | 4361 | 2828 | -430 | 7 | 339 | C |
| ATOM | 884 | CG2 | ILE | A | 54 | 16.871 | 41.300 | 93.491 | 1.00 | 23.74 | | C |
| ANISOU | 884 | CG2 | ILE | A | 54 | 2894 | 3829 | 2298 | -652 | 12 | 263 | C |
| ATOM | 888 | C | ILE | A | 54 | 14.165 | 42.399 | 92.795 | 1.00 | 26.55 | | C |
| ANISOU | 888 | C | ILE | A | 54 | 3526 | 3930 | 2632 | -541 | 157 | 246 | C |
| ATOM | 889 | O | ILE | A | 54 | 14.046 | 42.814 | 91.648 | 1.00 | 25.14 | | O |
| ANISOU | 889 | O | ILE | A | 54 | 3353 | 3709 | 2490 | -547 | 206 | 277 | O |
| ATOM | 891 | N | ASN | A | 55 | 14.169 | 43.184 | 93.873 | 1.00 | 26.33 | | N |
| ANISOU | 891 | N | ASN | A | 55 | 3590 | 3858 | 2555 | -608 | 131 | 185 | N |
| ATOM | 892 | CA | ASN | A | 55 | 14.033 | 44.631 | 93.768 | 1.00 | 26.16 | | C |
| ANISOU | 892 | CA | ASN | A | 55 | 3691 | 3704 | 2545 | -684 | 163 | 143 | C |
| ATOM | 894 | CB | ASN | A | 55 | 13.366 | 45.210 | 95.057 | 1.00 | 24.59 | | C |
| ANISOU | 894 | CB | ASN | A | 55 | 3625 | 3433 | 2286 | -687 | 171 | 50 | C |
| ATOM | 897 | CG | ASN | A | 55 | 14.295 | 45.235 | 96.278 | 1.00 | 25.40 | | C |
| ANISOU | 897 | CG | ASN | A | 55 | 3724 | 3623 | 2302 | -814 | 92 | -12 | C |
| ATOM | 898 | OD1 | ASN | A | 55 | 15.511 | 45.081 | 96.164 | 1.00 | 25.83 | | O |
| ANISOU | 898 | OD1 | ASN | A | 55 | 3679 | 3774 | 2361 | -914 | 23 | 16 | O |
| ATOM | 899 | ND2 | ASN | A | 55 | 13.718 | 45.501 | 97.459 | 1.00 | 22.69 | | N |
| ANISOU | 899 | ND2 | ASN | A | 55 | 3490 | 3257 | 1874 | -821 | 103 | -101 | N |
| ATOM | 902 | C | ASN | A | 55 | 15.340 | 45.344 | 93.366 | 1.00 | 27.10 | | C |
| ANISOU | 902 | C | ASN | A | 55 | 3773 | 3839 | 2686 | -844 | 135 | 146 | C |
| ATOM | 903 | O | ASN | A | 55 | 16.428 | 44.729 | 93.266 | 1.00 | 25.14 | | O |
| ANISOU | 903 | O | ASN | A | 55 | 3383 | 3729 | 2441 | -895 | 88 | 171 | O |
| ATOM | 905 | N | GLU | A | 56 | 15.259 | 46.655 | 93.142 | 1.00 | 27.09 | | N |
| ANISOU | 905 | N | GLU | A | 56 | 3893 | 3693 | 2708 | -926 | 164 | 123 | N |
| ATOM | 906 | CA | GLU | A | 56 | 16.419 | 47.371 | 92.625 | 1.00 | 27.66 | | C |
| ANISOU | 906 | CA | GLU | A | 56 | 3935 | 3771 | 2802 | -1096 | 147 | 140 | C |
| ATOM | 908 | CB | GLU | A | 56 | 16.022 | 48.757 | 92.108 | 1.00 | 31.50 | | C |
| ANISOU | 908 | CB | GLU | A | 56 | 4581 | 4051 | 3337 | -1154 | 191 | 149 | C |
| ATOM | 911 | CG | GLU | A | 56 | 15.215 | 48.684 | 90.833 | 1.00 | 33.75 | | C |
| ANISOU | 911 | CG | GLU | A | 56 | 4874 | 4282 | 3669 | -1047 | 245 | 252 | C |
| ATOM | 914 | CD | GLU | A | 56 | 15.966 | 48.036 | 89.631 | 1.00 | 37.52 | | C |
| ANISOU | 914 | CD | GLU | A | 56 | 5203 | 4914 | 4140 | -1090 | 258 | 339 | C |
| ATOM | 915 | OE1 | GLU | A | 56 | 17.235 | 47.987 | 89.609 | 1.00 | 39.97 | | O |
| ANISOU | 915 | OE1 | GLU | A | 56 | 5410 | 5341 | 4437 | -1229 | 237 | 330 | O |
| ATOM | 916 | OE2 | GLU | A | 56 | 15.256 | 47.567 | 88.696 | 1.00 | 39.44 | | O |
| ANISOU | 916 | OE2 | GLU | A | 56 | 5426 | 5172 | 4387 | -986 | 294 | 410 | O |
| ATOM | 917 | C | GLU | A | 56 | 17.540 | 47.468 | 93.633 | 1.00 | 28.01 | | C |
| ANISOU | 917 | C | GLU | A | 56 | 3933 | 3912 | 2797 | -1244 | 67 | 78 | C |
| ATOM | 918 | O | GLU | A | 56 | 18.716 | 47.665 | 93.268 | 1.00 | 24.70 | | O |
| ANISOU | 918 | O | GLU | A | 56 | 3414 | 3577 | 2392 | -1386 | 38 | 101 | O |
| ATOM | 920 | N | GLN | A | 57 | 17.183 | 47.325 | 94.909 | 1.00 | 27.64 | | N |
| ANISOU | 920 | N | GLN | A | 57 | 3949 | 3871 | 2682 | -1222 | 29 | 1 | N |
| ATOM | 921 | CA | GLN | A | 57 | 18.153 | 47.339 | 96.010 | 1.00 | 25.76 | | C |
| ANISOU | 921 | CA | GLN | A | 57 | 3671 | 3748 | 2369 | -1365 | -68 | -54 | C |
| ATOM | 923 | CB | GLN | A | 57 | 17.487 | 47.911 | 97.281 | 1.00 | 26.60 | | C |
| ANISOU | 923 | CB | GLN | A | 57 | 3954 | 3765 | 2386 | -1392 | -68 | -175 | C |
| ATOM | 926 | CG | GLN | A | 57 | 16.938 | 49.378 | 97.107 | 1.00 | 27.17 | | C |
| ANISOU | 926 | CG | GLN | A | 57 | 4230 | 3592 | 2501 | -1444 | 11 | -258 | C |
| ATOM | 929 | CD | GLN | A | 57 | 15.507 | 49.424 | 96.565 | 1.00 | 22.87 | | C |
| ANISOU | 929 | CD | GLN | A | 57 | 3766 | 2899 | 2024 | -1245 | 115 | -237 | C |
| ATOM | 930 | OE1 | GLN | A | 57 | 14.942 | 48.415 | 96.230 | 1.00 | 22.60 | | O |
| ANISOU | 930 | OE1 | GLN | A | 57 | 3641 | 2947 | 1998 | -1091 | 132 | -164 | O |
| ATOM | 931 | NE2 | GLN | A | 57 | 14.943 | 50.627 | 96.461 | 1.00 | 26.95 | | N |
| ANISOU | 931 | NE2 | GLN | A | 57 | 4451 | 3189 | 2599 | -1252 | 180 | -299 | N |
| ATOM | 934 | C | GLN | A | 57 | 18.751 | 45.935 | 96.271 | 1.00 | 24.69 | | C |
| ANISOU | 934 | C | GLN | A | 57 | 3340 | 3824 | 2217 | -1303 | -145 | 11 | C |
| ATOM | 935 | O | GLN | A | 57 | 19.511 | 45.756 | 97.196 | 1.00 | 26.48 | | O |
| ANISOU | 935 | O | GLN | A | 57 | 3509 | 4172 | 2380 | -1398 | -246 | -7 | O |
| ATOM | 937 | N | GLY | A | 58 | 18.390 | 44.945 | 95.460 | 1.00 | 25.39 | | N |
| ANISOU | 937 | N | GLY | A | 58 | 3334 | 3947 | 2365 | -1145 | -102 | 88 | N |
| ATOM | 938 | CA | GLY | A | 58 | 19.081 | 43.669 | 95.443 | 1.00 | 23.98 | | C |
| ANISOU | 938 | CA | GLY | A | 58 | 2963 | 3934 | 2215 | -1079 | -162 | 154 | C |
| ATOM | 941 | C | GLY | A | 58 | 18.506 | 42.605 | 96.371 | 1.00 | 25.23 | | C |
| ANISOU | 941 | C | GLY | A | 58 | 3126 | 4140 | 2322 | -962 | -212 | 176 | C |
| ATOM | 942 | O | GLY | A | 58 | 19.249 | 41.680 | 96.776 | 1.00 | 24.79 | | O |
| ANISOU | 942 | O | GLY | A | 58 | 2926 | 4215 | 2277 | -939 | -303 | 231 | O |
| ATOM | 944 | N | GLU | A | 59 | 17.230 | 42.763 | 96.743 | 1.00 | 22.57 | | N |
| ANISOU | 944 | N | GLU | A | 59 | 2944 | 3698 | 1932 | -896 | -157 | 139 | N |
| ATOM | 945 | CA | GLU | A | 59 | 16.540 | 41.872 | 97.667 | 1.00 | 25.49 | | C |
| ANISOU | 945 | CA | GLU | A | 59 | 3345 | 4108 | 2234 | -811 | -188 | 159 | C |
| ATOM | 947 | CB | GLU | A | 59 | 16.125 | 42.588 | 98.975 | 1.00 | 27.46 | | C |

FIG. 18 (continued)

| | | | | | | | | | | | | |
|---|---|---|---|---|---|---|---|---|---|---|---|---|
| ANISOU | 947 | CB | GLU | A | 59 | 3747 | 4341 | 2348 | -903 | -204 | 71 | C |
| ATOM | 950 | CG | GLU | A | 59 | 17.300 | 43.101 | 99.767 | 1.00 | 28.40 | | C |
| ANISOU | 950 | CG | GLU | A | 59 | 3842 | 4552 | 2395 | -1081 | -315 | 37 | C |
| ATOM | 953 | CD | GLU | A | 59 | 16.891 | 43.853 | 101.024 | 1.00 | 31.33 | | C |
| ANISOU | 953 | CD | GLU | A | 59 | 4383 | 4907 | 2613 | -1190 | -318 | -77 | C |
| ATOM | 954 | OE1 | GLU | A | 59 | 17.064 | 45.096 | 101.021 | 1.00 | 34.12 | | O |
| ANISOU | 954 | OE1 | GLU | A | 59 | 4839 | 5166 | 2959 | -1310 | -285 | -182 | O |
| ATOM | 955 | OE2 | GLU | A | 59 | 16.440 | 43.217 | 102.009 | 1.00 | 28.23 | | O |
| ANISOU | 955 | OE2 | GLU | A | 59 | 4027 | 4593 | 2104 | -1170 | -352 | -64 | O |
| ATOM | 956 | C | GLU | A | 59 | 15.314 | 41.274 | 97.041 | 1.00 | 24.02 | | C |
| ANISOU | 956 | C | GLU | A | 59 | 3189 | 3848 | 2088 | -657 | -97 | 188 | C |
| ATOM | 957 | O | GLU | A | 59 | 14.549 | 41.949 | 96.319 | 1.00 | 22.20 | | O |
| ANISOU | 957 | O | GLU | A | 59 | 3036 | 3505 | 1893 | -624 | -5 | 159 | O |
| ATOM | 959 | N | SER | A | 60 | 15.111 | 40.008 | 97.364 | 1.00 | 22.25 | | N |
| ANISOU | 959 | N | SER | A | 60 | 2909 | 3687 | 1860 | -569 | -136 | 254 | N |
| ATOM | 960 | CA | SER | A | 60 | 13.896 | 39.301 | 96.995 | 1.00 | 22.85 | | C |
| ANISOU | 960 | CA | SER | A | 60 | 3016 | 3710 | 1955 | -445 | -65 | 282 | C |
| ATOM | 962 | CB | SER | A | 60 | 14.030 | 37.786 | 97.305 | 1.00 | 21.97 | | C |
| ANISOU | 962 | CB | SER | A | 60 | 2824 | 3664 | 1861 | -371 | -130 | 372 | C |
| ATOM | 965 | OG | SER | A | 60 | 13.811 | 37.490 | 98.690 | 1.00 | 24.84 | | O |
| ANISOU | 965 | OG | SER | A | 60 | 3246 | 4085 | 2109 | -410 | -195 | 394 | O |
| ATOM | 967 | C | SER | A | 60 | 12.640 | 39.944 | 97.633 | 1.00 | 21.33 | | C |
| ANISOU | 967 | C | SER | A | 60 | 2968 | 3456 | 1680 | -443 | 4 | 219 | C |
| ATOM | 968 | O | SER | A | 60 | 12.653 | 40.375 | 98.764 | 1.00 | 20.58 | | O |
| ANISOU | 968 | O | SER | A | 60 | 2948 | 3390 | 1480 | -519 | -23 | 168 | O |
| ATOM | 970 | N | ILE | A | 61 | 11.562 | 40.016 | 96.867 | 1.00 | 22.00 | | N |
| ANISOU | 970 | N | ILE | A | 61 | 3082 | 3464 | 1813 | -357 | 95 | 217 | N |
| ATOM | 971 | CA | ILE | A | 61 | 10.318 | 40.650 | 97.320 | 1.00 | 25.14 | | C |
| ANISOU | 971 | CA | ILE | A | 61 | 3585 | 3801 | 2166 | -328 | 176 | 156 | C |
| ATOM | 973 | CB | ILE | A | 61 | 10.153 | 42.039 | 96.678 | 1.00 | 25.28 | | C |
| ANISOU | 973 | CB | ILE | A | 61 | 3668 | 3696 | 2243 | -337 | 236 | 98 | C |
| ATOM | 975 | CG1 | ILE | A | 61 | 10.433 | 41.934 | 95.154 | 1.00 | 25.66 | | C |
| ANISOU | 975 | CG1 | ILE | A | 61 | 3642 | 3715 | 2391 | -305 | 241 | 168 | C |
| ATOM | 978 | CD1 | ILE | A | 61 | 9.640 | 42.917 | 94.273 | 1.00 | 27.70 | | C |
| ANISOU | 978 | CD1 | ILE | A | 61 | 3956 | 3851 | 2717 | -258 | 308 | 169 | C |
| ATOM | 982 | CG2 | ILE | A | 61 | 11.045 | 43.056 | 97.374 | 1.00 | 25.04 | | C |
| ANISOU | 982 | CG2 | ILE | A | 61 | 3707 | 3643 | 2165 | -465 | 202 | 17 | C |
| ATOM | 986 | C | ILE | A | 61 | 9.064 | 39.795 | 97.007 | 1.00 | 24.11 | | C |
| ANISOU | 986 | C | ILE | A | 61 | 3432 | 3674 | 2054 | -222 | 231 | 203 | C |
| ATOM | 987 | O | ILE | A | 61 | 8.009 | 40.341 | 96.626 | 1.00 | 26.04 | | O |
| ANISOU | 987 | O | ILE | A | 61 | 3710 | 3854 | 2331 | -161 | 311 | 177 | O |
| ATOM | 989 | N | VAL | A | 62 | 9.157 | 38.475 | 97.229 | 1.00 | 24.31 | | N |
| ANISOU | 989 | N | VAL | A | 62 | 3400 | 3772 | 2063 | -204 | 182 | 276 | N |
| ATOM | 990 | CA | VAL | A | 62 | 7.990 | 37.565 | 97.066 | 1.00 | 25.04 | | C |
| ANISOU | 990 | CA | VAL | A | 62 | 3477 | 3874 | 2162 | -135 | 226 | 322 | C |
| ATOM | 992 | CB | VAL | A | 62 | 8.370 | 36.080 | 97.311 | 1.00 | 26.36 | | C |
| ANISOU | 992 | CB | VAL | A | 62 | 3594 | 4091 | 2329 | -132 | 153 | 411 | C |
| ATOM | 994 | CG1 | VAL | A | 62 | 7.126 | 35.151 | 97.315 | 1.00 | 25.73 | | C |
| ANISOU | 994 | CG1 | VAL | A | 62 | 3516 | 4020 | 2242 | -96 | 197 | 457 | C |
| ATOM | 998 | CG2 | VAL | A | 62 | 9.379 | 35.639 | 96.270 | 1.00 | 23.78 | | C |
| ANISOU | 998 | CG2 | VAL | A | 62 | 3184 | 3743 | 2108 | -107 | 111 | 440 | C |
| ATOM | 1002 | C | VAL | A | 62 | 6.783 | 37.943 | 97.917 | 1.00 | 24.77 | | C |
| ANISOU | 1002 | C | VAL | A | 62 | 3508 | 3855 | 2051 | -129 | 302 | 274 | C |
| ATOM | 1003 | O | VAL | A | 62 | 5.588 | 37.771 | 97.514 | 1.00 | 22.52 | | O |
| ANISOU | 1003 | O | VAL | A | 62 | 3201 | 3560 | 1794 | -67 | 372 | 285 | O |
| ATOM | 1005 | N | VAL | A | 63 | 7.096 | 38.510 | 99.073 | 1.00 | 25.45 | | N |
| ANISOU | 1005 | N | VAL | A | 63 | 3663 | 3973 | 2035 | -199 | 295 | 212 | N |
| ATOM | 1006 | CA | VAL | A | 63 | 6.096 | 39.054 | 99.984 | 1.00 | 27.31 | | C |
| ANISOU | 1006 | CA | VAL | A | 63 | 3967 | 4228 | 2182 | -204 | 388 | 130 | C |
| ATOM | 1008 | CB | VAL | A | 63 | 6.784 | 39.675 | 101.209 | 1.00 | 25.58 | | C |
| ANISOU | 1008 | CB | VAL | A | 63 | 3836 | 4051 | 1831 | -313 | 360 | 48 | C |
| ATOM | 1010 | CG1 | VAL | A | 63 | 7.470 | 40.992 | 100.811 | 1.00 | 26.25 | | C |
| ANISOU | 1010 | CG1 | VAL | A | 63 | 3966 | 4032 | 1975 | -339 | 360 | -41 | C |
| ATOM | 1014 | CG2 | VAL | A | 63 | 5.786 | 39.862 | 102.345 | 1.00 | 28.91 | | C |
| ANISOU | 1014 | CG2 | VAL | A | 63 | 4327 | 4536 | 2122 | -336 | 460 | -33 | C |
| ATOM | 1018 | C | VAL | A | 63 | 5.104 | 40.076 | 99.354 | 1.00 | 26.94 | | C |
| ANISOU | 1018 | C | VAL | A | 63 | 3929 | 4087 | 2222 | -114 | 498 | 60 | C |
| ATOM | 1019 | O | VAL | A | 63 | 3.999 | 40.296 | 99.879 | 1.00 | 27.90 | | O |
| ANISOU | 1019 | O | VAL | A | 63 | 4065 | 4229 | 2308 | -76 | 598 | 4 | O |
| ATOM | 1021 | N | GLU | A | 64 | 5.493 | 40.712 | 98.263 | 1.00 | 27.38 | | N |
| ANISOU | 1021 | N | GLU | A | 64 | 3969 | 4044 | 2390 | -80 | 483 | 68 | N |
| ATOM | 1022 | CA | GLU | A | 64 | 4.672 | 41.766 | 97.677 | 1.00 | 29.23 | | C |
| ANISOU | 1022 | CA | GLU | A | 64 | 4219 | 4172 | 2717 | 6 | 563 | 23 | C |
| ATOM | 1024 | CB | GLU | A | 64 | 5.510 | 42.714 | 96.809 | 1.00 | 30.76 | | C |
| ANISOU | 1024 | CB | GLU | A | 64 | 4442 | 4249 | 2995 | -14 | 526 | 24 | C |
| ATOM | 1027 | CG | GLU | A | 64 | 6.369 | 43.615 | 97.662 | 1.00 | 33.75 | | C |
| ANISOU | 1027 | CG | GLU | A | 64 | 4924 | 4582 | 3319 | -113 | 516 | -80 | C |
| ATOM | 1030 | CD | GLU | A | 64 | 7.247 | 44.555 | 96.848 | 1.00 | 35.99 | | C |
| ANISOU | 1030 | CD | GLU | A | 64 | 5241 | 4751 | 3682 | -162 | 479 | -73 | C |

FIG. 18 (continued)

| | | | | | | | | | | | | |
|---|---|---|---|---|---|---|---|---|---|---|---|---|
| ATOM | 1031 | OE1 | GLU | A | 64 | 6.940 | 44.839 | 95.659 | 1.00 | 38.30 | | O |
| ANISOU | 1031 | OE1 | GLU | A | 64 | 5505 | 4970 | 4078 | -99 | 487 | -1 | O |
| ATOM | 1032 | OE2 | GLU | A | 64 | 8.252 | 45.010 | 97.418 | 1.00 | 40.17 | | O |
| ANISOU | 1032 | OE2 | GLU | A | 64 | 5828 | 5277 | 4160 | -281 | 437 | -133 | O |
| ATOM | 1033 | C | GLU | A | 64 | 3.506 | 41.205 | 96.882 | 1.00 | 27.19 | | C |
| ANISOU | 1033 | C | GLU | A | 64 | 3870 | 3935 | 2525 | 103 | 599 | 97 | C |
| ATOM | 1034 | O | GLU | A | 64 | 2.590 | 41.952 | 96.526 | 1.00 | 27.12 | | O |
| ANISOU | 1034 | O | GLU | A | 64 | 3850 | 3862 | 2594 | 193 | 664 | 77 | O |
| ATOM | 1036 | N | LEU | A | 65 | 3.497 | 39.898 | 96.648 | 1.00 | 25.89 | | N |
| ANISOU | 1036 | N | LEU | A | 65 | 3640 | 3859 | 2338 | 85 | 553 | 182 | N |
| ATOM | 1037 | CA | LEU | A | 65 | 2.341 | 39.257 | 95.992 | 1.00 | 26.97 | | C |
| ANISOU | 1037 | CA | LEU | A | 65 | 3691 | 4035 | 2520 | 147 | 581 | 246 | C |
| ATOM | 1039 | CB | LEU | A | 65 | 2.643 | 37.824 | 95.554 | 1.00 | 26.93 | | C |
| ANISOU | 1039 | CB | LEU | A | 65 | 3639 | 4089 | 2505 | 106 | 515 | 332 | C |
| ATOM | 1042 | CG | LEU | A | 65 | 3.668 | 37.645 | 94.426 | 1.00 | 26.38 | | C |
| ANISOU | 1042 | CG | LEU | A | 65 | 3553 | 3977 | 2491 | 90 | 446 | 370 | C |
| ATOM | 1044 | CD1 | LEU | A | 65 | 3.991 | 36.143 | 94.234 | 1.00 | 25.60 | | C |
| ANISOU | 1044 | CD1 | LEU | A | 65 | 3420 | 3920 | 2387 | 58 | 395 | 427 | C |
| ATOM | 1048 | CD2 | LEU | A | 65 | 3.198 | 38.260 | 93.092 | 1.00 | 26.60 | | C |
| ANISOU | 1048 | CD2 | LEU | A | 65 | 3548 | 3962 | 2595 | 140 | 457 | 397 | C |
| ATOM | 1052 | C | LEU | A | 65 | 1.157 | 39.293 | 96.925 | 1.00 | 27.94 | | C |
| ANISOU | 1052 | C | LEU | A | 65 | 3801 | 4219 | 2597 | 177 | 675 | 200 | C |
| ATOM | 1053 | O | LEU | A | 65 | 0.056 | 39.678 | 96.525 | 1.00 | 29.11 | | O |
| ANISOU | 1053 | O | LEU | A | 65 | 3887 | 4361 | 2812 | 261 | 735 | 200 | O |
| ATOM | 1055 | N | ASP | A | 66 | 1.381 | 38.914 | 98.178 | 1.00 | 29.74 | | N |
| ANISOU | 1055 | N | ASP | A | 66 | 4078 | 4516 | 2704 | 104 | 687 | 164 | N |
| ATOM | 1056 | CA | ASP | A | 66 | 0.323 | 38.886 | 99.181 | 1.00 | 29.92 | | C |
| ANISOU | 1056 | CA | ASP | A | 66 | 4091 | 4624 | 2651 | 107 | 792 | 112 | C |
| ATOM | 1058 | CB | ASP | A | 66 | 0.530 | 37.691 | 100.122 | 1.00 | 31.42 | | C |
| ANISOU | 1058 | CB | ASP | A | 66 | 4305 | 4929 | 2706 | -3 | 759 | 166 | C |
| ATOM | 1061 | CG | ASP | A | 66 | 0.130 | 36.346 | 99.481 | 1.00 | 31.92 | | C |
| ANISOU | 1061 | CG | ASP | A | 66 | 4291 | 5031 | 2806 | -17 | 711 | 292 | C |
| ATOM | 1062 | OD1 | ASP | A | 66 | -0.242 | 36.296 | 98.253 | 1.00 | 28.23 | | O |
| ANISOU | 1062 | OD1 | ASP | A | 66 | 3751 | 4518 | 2457 | 46 | 697 | 331 | O |
| ATOM | 1063 | OD2 | ASP | A | 66 | 0.180 | 35.340 | 100.242 | 1.00 | 31.45 | | O |
| ANISOU | 1063 | OD2 | ASP | A | 66 | 4255 | 5046 | 2649 | -105 | 685 | 354 | O |
| ATOM | 1064 | C | ASP | A | 66 | 0.209 | 40.183 | 99.997 | 1.00 | 31.68 | | C |
| ANISOU | 1064 | C | ASP | A | 66 | 4388 | 4804 | 2844 | 131 | 888 | -36 | C |
| ATOM | 1065 | O | ASP | A | 66 | -0.821 | 40.455 | 100.606 | 1.00 | 31.73 | | O |
| ANISOU | 1065 | O | ASP | A | 66 | 4369 | 4863 | 2825 | 171 | 1009 | -107 | O |
| ATOM | 1067 | N | ASP | A | 67 | 1.242 | 41.001 | 100.002 | 1.00 | 32.12 | | N |
| ANISOU | 1067 | N | ASP | A | 67 | 4533 | 4763 | 2908 | 103 | 843 | -92 | N |
| ATOM | 1068 | CA | ASP | A | 67 | 1.215 | 42.268 | 100.732 | 1.00 | 34.27 | | C |
| ANISOU | 1068 | CA | ASP | A | 67 | 4899 | 4965 | 3159 | 113 | 930 | -249 | C |
| ATOM | 1070 | CB | ASP | A | 67 | 1.958 | 42.076 | 102.055 | 1.00 | 36.09 | | C |
| ANISOU | 1070 | CB | ASP | A | 67 | 5228 | 5285 | 3201 | -31 | 910 | -314 | C |
| ATOM | 1073 | CG | ASP | A | 67 | 1.643 | 43.166 | 103.078 | 1.00 | 39.18 | | C |
| ANISOU | 1073 | CG | ASP | A | 67 | 5720 | 5647 | 3519 | -42 | 1035 | -508 | C |
| ATOM | 1074 | OD1 | ASP | A | 67 | 0.833 | 44.065 | 102.757 | 1.00 | 40.11 | | O |
| ANISOU | 1074 | OD1 | ASP | A | 67 | 5824 | 5655 | 3760 | 84 | 1145 | -591 | O |
| ATOM | 1075 | OD2 | ASP | A | 67 | 2.220 | 43.116 | 104.201 | 1.00 | 41.11 | | O |
| ANISOU | 1075 | OD2 | ASP | A | 67 | 6058 | 5977 | 3585 | -178 | 1020 | -576 | O |
| ATOM | 1076 | C | ASP | A | 67 | 1.876 | 43.390 | 99.906 | 1.00 | 34.58 | | C |
| ANISOU | 1076 | C | ASP | A | 67 | 4988 | 4827 | 3324 | 147 | 891 | -272 | C |
| ATOM | 1077 | O | ASP | A | 67 | 2.994 | 43.832 | 100.203 | 1.00 | 34.93 | | O |
| ANISOU | 1077 | O | ASP | A | 67 | 5124 | 4826 | 3322 | 51 | 833 | -319 | O |
| ATOM | 1079 | N | PRO | A | 68 | 1.227 | 43.818 | 98.825 | 1.00 | 34.97 | | N |
| ANISOU | 1079 | N | PRO | A | 68 | 4974 | 4784 | 3529 | 270 | 909 | -221 | N |
| ATOM | 1080 | CA | PRO | A | 68 | 1.922 | 44.750 | 97.918 | 1.00 | 37.05 | | C |
| ANISOU | 1080 | CA | PRO | A | 68 | 5289 | 4886 | 3904 | 281 | 853 | -201 | C |
| ATOM | 1082 | CB | PRO | A | 68 | 1.007 | 44.786 | 96.695 | 1.00 | 33.89 | | C |
| ANISOU | 1082 | CB | PRO | A | 68 | 4785 | 4448 | 3643 | 410 | 852 | -92 | C |
| ATOM | 1085 | CG | PRO | A | 68 | -0.317 | 44.483 | 97.241 | 1.00 | 34.86 | | C |
| ANISOU | 1085 | CG | PRO | A | 68 | 4826 | 4659 | 3761 | 497 | 952 | -127 | C |
| ATOM | 1088 | CD | PRO | A | 68 | -0.101 | 43.470 | 98.323 | 1.00 | 35.15 | | C |
| ANISOU | 1088 | CD | PRO | A | 68 | 4872 | 4855 | 3630 | 387 | 963 | -161 | C |
| ATOM | 1091 | C | PRO | A | 68 | 2.064 | 46.170 | 98.469 | 1.00 | 42.28 | | C |
| ANISOU | 1091 | C | PRO | A | 68 | 6077 | 5388 | 4601 | 290 | 921 | -349 | C |
| ATOM | 1092 | O | PRO | A | 68 | 1.343 | 46.559 | 99.383 | 1.00 | 38.83 | | O |
| ANISOU | 1092 | O | PRO | A | 68 | 5670 | 4949 | 4136 | 336 | 1037 | -478 | O |
| ATOM | 1093 | N | ASN | A | 69 | 2.982 | 46.913 | 97.863 | 1.00 | 46.43 | | N |
| ANISOU | 1093 | N | ASN | A | 69 | 6673 | 5778 | 5188 | 239 | 856 | -330 | N |
| ATOM | 1094 | CA | ASN | A | 69 | 3.057 | 48.359 | 98.000 | 1.00 | 54.20 | | C |
| ANISOU | 1094 | CA | ASN | A | 69 | 7781 | 6552 | 6260 | 260 | 907 | -439 | C |
| ATOM | 1096 | CB | ASN | A | 69 | 4.522 | 48.789 | 97.921 | 1.00 | 55.32 | | C |
| ANISOU | 1096 | CB | ASN | A | 69 | 8019 | 6633 | 6365 | 94 | 818 | -448 | C |
| ATOM | 1099 | CG | ASN | A | 69 | 5.350 | 48.138 | 98.990 | 1.00 | 56.44 | | C |
| ANISOU | 1099 | CG | ASN | A | 69 | 8184 | 6935 | 6326 | -60 | 778 | -513 | C |
| ATOM | 1100 | OD1 | ASN | A | 69 | 4.981 | 48.182 | 100.169 | 1.00 | 58.37 | | O |

FIG. 18 (continued)

| | | | | | | | | | | | | |
|---|---|---|---|---|---|---|---|---|---|---|---|---|
| ANISOU | 1100 | OD1 | ASN | A | 69 | 8483 | 7229 | 6466 | -78 | 852 | -648 | O |
| ATOM | 1101 | ND2 | ASN | A | 69 | 6.459 | 47.499 | 98.595 | 1.00 | 56.12 | | N |
| ANISOU | 1101 | ND2 | ASN | A | 69 | 8094 | 6990 | 6240 | -171 | 661 | -414 | N |
| ATOM | 1104 | C | ASN | A | 69 | 2.194 | 49.016 | 96.914 | 1.00 | 56.82 | | C |
| ANISOU | 1104 | C | ASN | A | 69 | 8070 | 6737 | 6782 | 424 | 926 | -353 | C |
| ATOM | 1105 | O | ASN | A | 69 | 1.017 | 48.687 | 96.782 | 1.00 | 58.09 | | O |
| ANISOU | 1105 | O | ASN | A | 69 | 8122 | 6955 | 6994 | 561 | 981 | -319 | O |
| ATOM | 1107 | N | ALA | A | 70 | 2.760 | 49.923 | 96.124 | 1.00 | 60.58 | | N |
| ANISOU | 1107 | N | ALA | A | 70 | 8622 | 7036 | 7361 | 402 | 874 | -301 | N |
| ATOM | 1108 | CA | ALA | A | 70 | 1.972 | 50.635 | 95.119 | 1.00 | 62.44 | | C |
| ANISOU | 1108 | CA | ALA | A | 70 | 8830 | 7117 | 7777 | 553 | 875 | -199 | C |
| ATOM | 1110 | CB | ALA | A | 70 | 2.731 | 51.858 | 94.614 | 1.00 | 64.29 | | C |
| ANISOU | 1110 | CB | ALA | A | 70 | 9206 | 7115 | 8107 | 493 | 835 | -181 | C |
| ATOM | 1114 | C | ALA | A | 70 | 1.572 | 49.699 | 93.957 | 1.00 | 62.05 | | C |
| ANISOU | 1114 | C | ALA | A | 70 | 8629 | 7213 | 7735 | 595 | 797 | -5 | C |
| ATOM | 1115 | O | ALA | A | 70 | 2.137 | 48.603 | 93.790 | 1.00 | 60.11 | | O |
| ANISOU | 1115 | O | ALA | A | 70 | 8323 | 7145 | 7370 | 492 | 738 | 48 | O |
| ATOM | 1117 | N | LEU | A | 71 | 0.568 | 50.129 | 93.193 | 1.00 | 63.56 | | N |
| ANISOU | 1117 | N | LEU | A | 71 | 8756 | 7325 | 8067 | 751 | 797 | 95 | N |
| ATOM | 1118 | CA | LEU | A | 71 | 0.032 | 49.356 | 92.077 | 1.00 | 63.39 | | C |
| ANISOU | 1118 | CA | LEU | A | 71 | 8595 | 7440 | 8053 | 790 | 721 | 271 | C |
| ATOM | 1120 | CB | LEU | A | 71 | -1.456 | 49.087 | 92.298 | 1.00 | 64.17 | | C |
| ANISOU | 1120 | CB | LEU | A | 71 | 8551 | 7613 | 8216 | 960 | 783 | 270 | C |
| ATOM | 1123 | CG | LEU | A | 71 | -1.806 | 48.307 | 93.566 | 1.00 | 64.20 | | C |
| ANISOU | 1123 | CG | LEU | A | 71 | 8509 | 7770 | 8113 | 947 | 883 | 126 | C |
| ATOM | 1125 | CD1 | LEU | A | 71 | -3.320 | 48.263 | 93.765 | 1.00 | 65.50 | | C |
| ANISOU | 1125 | CD1 | LEU | A | 71 | 8524 | 7995 | 8368 | 1119 | 962 | 121 | C |
| ATOM | 1129 | CD2 | LEU | A | 71 | -1.203 | 46.908 | 93.510 | 1.00 | 61.39 | | C |
| ANISOU | 1129 | CD2 | LEU | A | 71 | 8114 | 7616 | 7594 | 797 | 822 | 168 | C |
| ATOM | 1133 | C | LEU | A | 71 | 0.234 | 50.123 | 90.770 | 1.00 | 65.14 | | C |
| ANISOU | 1133 | C | LEU | A | 71 | 8854 | 7525 | 8371 | 797 | 631 | 435 | C |
| ATOM | 1134 | O | LEU | A | 71 | 0.408 | 49.526 | 89.703 | 1.00 | 65.15 | | O |
| ANISOU | 1134 | O | LEU | A | 71 | 8793 | 7639 | 8321 | 737 | 544 | 579 | O |
| ATOM | 1136 | N | LYS | A | 73 | 2.755 | 50.516 | 88.990 | 1.00 | 57.68 | | N |
| ANISOU | 1136 | N | LYS | A | 73 | 8068 | 6523 | 7324 | 459 | 466 | 624 | N |
| ATOM | 1137 | CA | LYS | A | 73 | 4.127 | 50.939 | 88.742 | 1.00 | 59.28 | | C |
| ANISOU | 1137 | CA | LYS | A | 73 | 8373 | 6669 | 7482 | 280 | 436 | 629 | C |
| ATOM | 1139 | CB | LYS | A | 73 | 5.084 | 50.317 | 89.781 | 1.00 | 59.35 | | C |
| ANISOU | 1139 | CB | LYS | A | 73 | 8388 | 6786 | 7376 | 160 | 467 | 473 | C |
| ATOM | 1142 | CG | LYS | A | 73 | 4.898 | 50.867 | 91.216 | 1.00 | 61.37 | | C |
| ANISOU | 1142 | CG | LYS | A | 73 | 8728 | 6931 | 7658 | 199 | 543 | 290 | C |
| ATOM | 1145 | CD | LYS | A | 73 | 5.860 | 50.248 | 92.232 | 1.00 | 60.40 | | C |
| ANISOU | 1145 | CD | LYS | A | 73 | 8610 | 6936 | 7402 | 66 | 549 | 161 | C |
| ATOM | 1148 | CE | LYS | A | 73 | 5.454 | 50.604 | 93.678 | 1.00 | 62.52 | | C |
| ANISOU | 1148 | CE | LYS | A | 73 | 8950 | 7146 | 7658 | 107 | 631 | -24 | C |
| ATOM | 1151 | NZ | LYS | A | 73 | 6.288 | 49.979 | 94.796 | 1.00 | 62.08 | | N |
| ANISOU | 1151 | NZ | LYS | A | 73 | 8901 | 7236 | 7452 | -25 | 623 | -141 | N |
| ATOM | 1155 | C | LYS | A | 73 | 4.568 | 50.597 | 87.305 | 1.00 | 58.49 | | C |
| ANISOU | 1155 | C | LYS | A | 73 | 8232 | 6671 | 7322 | 183 | 359 | 801 | C |
| ATOM | 1156 | O | LYS | A | 73 | 5.327 | 51.345 | 86.692 | 1.00 | 59.71 | | O |
| ANISOU | 1156 | O | LYS | A | 73 | 8472 | 6726 | 7487 | 70 | 326 | 876 | O |
| ATOM | 1158 | N | HIS | A | 74 | 4.059 | 49.494 | 86.758 | 1.00 | 56.23 | | N |
| ANISOU | 1158 | N | HIS | A | 74 | 7819 | 6579 | 6967 | 217 | 335 | 860 | N |
| ATOM | 1159 | CA | HIS | A | 74 | 4.466 | 49.028 | 85.425 | 1.00 | 54.38 | | C |
| ANISOU | 1159 | CA | HIS | A | 74 | 7545 | 6473 | 6646 | 114 | 277 | 992 | C |
| ATOM | 1161 | CB | HIS | A | 74 | 5.345 | 47.787 | 85.598 | 1.00 | 55.24 | | C |
| ANISOU | 1161 | CB | HIS | A | 74 | 7586 | 6772 | 6630 | 9 | 298 | 903 | C |
| ATOM | 1164 | CG | HIS | A | 74 | 6.685 | 48.098 | 86.193 | 1.00 | 56.85 | | C |
| ANISOU | 1164 | CG | HIS | A | 74 | 7850 | 6938 | 6812 | -117 | 323 | 811 | C |
| ATOM | 1165 | ND1 | HIS | A | 74 | 7.636 | 48.843 | 85.525 | 1.00 | 58.49 | | N |
| ANISOU | 1165 | ND1 | HIS | A | 74 | 8122 | 7089 | 7011 | -257 | 306 | 875 | N |
| ATOM | 1167 | CE1 | HIS | A | 74 | 8.703 | 48.980 | 86.292 | 1.00 | 58.24 | | C |
| ANISOU | 1167 | CE1 | HIS | A | 74 | 8118 | 7048 | 6965 | -358 | 327 | 770 | C |
| ATOM | 1169 | NE2 | HIS | A | 74 | 8.475 | 48.358 | 87.436 | 1.00 | 57.72 | | N |
| ANISOU | 1169 | NE2 | HIS | A | 74 | 8014 | 7027 | 6889 | -287 | 350 | 647 | N |
| ATOM | 1171 | CD2 | HIS | A | 74 | 7.219 | 47.799 | 87.400 | 1.00 | 56.54 | | C |
| ANISOU | 1171 | CD2 | HIS | A | 74 | 7812 | 6917 | 6755 | -139 | 355 | 669 | C |
| ATOM | 1173 | C | HIS | A | 74 | 3.277 | 48.741 | 84.503 | 1.00 | 49.58 | | C |
| ANISOU | 1173 | C | HIS | A | 74 | 6853 | 5939 | 6047 | 210 | 222 | 1131 | C |
| ATOM | 1174 | O | HIS | A | 74 | 2.127 | 48.782 | 84.934 | 1.00 | 48.65 | | O |
| ANISOU | 1174 | O | HIS | A | 74 | 6681 | 5793 | 6010 | 364 | 230 | 1124 | O |
| ATOM | 1176 | N | ARG | A | 75 | 3.572 | 48.433 | 83.242 | 1.00 | 44.38 | | N |
| ANISOU | 1176 | N | ARG | A | 75 | 6175 | 5392 | 5294 | 106 | 168 | 1252 | N |
| ATOM | 1177 | CA | ARG | A | 75 | 2.538 | 48.162 | 82.238 | 1.00 | 42.84 | | C |
| ANISOU | 1177 | CA | ARG | A | 75 | 5906 | 5293 | 5077 | 158 | 96 | 1397 | C |
| ATOM | 1179 | CB | ARG | A | 75 | 3.150 | 47.803 | 80.876 | 1.00 | 43.33 | | C |
| ANISOU | 1179 | CB | ARG | A | 75 | 5975 | 5498 | 4992 | -6 | 53 | 1500 | C |
| ATOM | 1182 | CG | ARG | A | 75 | 2.130 | 47.102 | 79.983 | 1.00 | 44.41 | | C |
| ANISOU | 1182 | CG | ARG | A | 75 | 6015 | 5800 | 5057 | 17 | -17 | 1598 | C |

FIG. 18 (continued)

| | | | | | | | | | | | | |
|---|---|---|---|---|---|---|---|---|---|---|---|---|
| ATOM | 1185 | CD | ARG | A | 75 | 2.519 | 46.931 | 78.567 | 1.00 | 45.17 | | C |
| ANISOU | 1185 | CD | ARG | A | 75 | 6132 | 6031 | 4999 | -141 | -67 | 1714 | C |
| ATOM | 1188 | NE | ARG | A | 75 | 1.378 | 46.422 | 77.814 | 1.00 | 45.60 | | N |
| ANISOU | 1188 | NE | ARG | A | 75 | 6101 | 6229 | 4997 | -112 | -153 | 1815 | N |
| ATOM | 1190 | CZ | ARG | A | 75 | 1.427 | 46.073 | 76.541 | 1.00 | 47.50 | | C |
| ANISOU | 1190 | CZ | ARG | A | 75 | 6343 | 6633 | 5073 | -249 | -208 | 1910 | C |
| ATOM | 1191 | NH1 | ARG | A | 75 | 2.573 | 46.188 | 75.854 | 1.00 | 49.50 | | N |
| ANISOU | 1191 | NH1 | ARG | A | 75 | 6675 | 6930 | 5202 | -420 | -170 | 1917 | N |
| ATOM | 1194 | NH2 | ARG | A | 75 | 0.330 | 45.625 | 75.944 | 1.00 | 47.45 | | N |
| ANISOU | 1194 | NH2 | ARG | A | 75 | 6252 | 6760 | 5015 | -228 | -298 | 1996 | N |
| ATOM | 1197 | C | ARG | A | 75 | 1.554 | 47.059 | 82.634 | 1.00 | 38.70 | | C |
| ANISOU | 1197 | C | ARG | A | 75 | 5254 | 4912 | 4539 | 252 | 107 | 1333 | C |
| ATOM | 1198 | O | ARG | A | 75 | 0.341 | 47.192 | 82.413 | 1.00 | 39.11 | | O |
| ANISOU | 1198 | O | ARG | A | 75 | 5233 | 4974 | 4654 | 369 | 60 | 1421 | O |
| ATOM | 1200 | N | PHE | A | 76 | 2.081 | 45.963 | 83.171 | 1.00 | 36.37 | | N |
| ANISOU | 1200 | N | PHE | A | 76 | 4923 | 4731 | 4165 | 195 | 163 | 1194 | N |
| ATOM | 1201 | CA | PHE | A | 76 | 1.246 | 44.862 | 83.653 | 1.00 | 33.46 | | C |
| ANISOU | 1201 | CA | PHE | A | 76 | 4449 | 4485 | 3780 | 258 | 181 | 1127 | C |
| ATOM | 1203 | CB | PHE | A | 76 | 1.709 | 43.524 | 83.110 | 1.00 | 31.10 | | C |
| ANISOU | 1203 | CB | PHE | A | 76 | 4109 | 4356 | 3351 | 145 | 181 | 1088 | C |
| ATOM | 1206 | CG | PHE | A | 76 | 1.627 | 43.410 | 81.639 | 1.00 | 29.66 | | C |
| ANISOU | 1206 | CG | PHE | A | 76 | 3918 | 4272 | 3079 | 58 | 117 | 1205 | C |
| ATOM | 1207 | CD1 | PHE | A | 76 | 0.388 | 43.326 | 80.996 | 1.00 | 30.89 | | C |
| ANISOU | 1207 | CD1 | PHE | A | 76 | 4001 | 4504 | 3231 | 102 | 43 | 1314 | C |
| ATOM | 1209 | CE1 | PHE | A | 76 | 0.316 | 43.224 | 79.611 | 1.00 | 32.24 | | C |
| ANISOU | 1209 | CE1 | PHE | A | 76 | 4173 | 4788 | 3291 | -1 | -28 | 1427 | C |
| ATOM | 1211 | CZ | PHE | A | 76 | 1.484 | 43.191 | 78.864 | 1.00 | 32.12 | | C |
| ANISOU | 1211 | CZ | PHE | A | 76 | 4231 | 4809 | 3165 | -145 | -6 | 1419 | C |
| ATOM | 1213 | CE2 | PHE | A | 76 | 2.710 | 43.271 | 79.488 | 1.00 | 31.38 | | C |
| ANISOU | 1213 | CE2 | PHE | A | 76 | 4193 | 4641 | 3090 | -179 | 77 | 1308 | C |
| ATOM | 1215 | CD2 | PHE | A | 76 | 2.780 | 43.376 | 80.872 | 1.00 | 30.54 | | C |
| ANISOU | 1215 | CD2 | PHE | A | 76 | 4084 | 4422 | 3096 | -79 | 128 | 1207 | C |
| ATOM | 1217 | C | PHE | A | 76 | 1.186 | 44.788 | 85.167 | 1.00 | 32.17 | | C |
| ANISOU | 1217 | C | PHE | A | 76 | 4288 | 4262 | 3673 | 333 | 257 | 985 | C |
| ATOM | 1218 | O | PHE | A | 76 | 2.199 | 44.857 | 85.870 | 1.00 | 33.20 | | O |
| ANISOU | 1218 | O | PHE | A | 76 | 4485 | 4344 | 3787 | 276 | 300 | 886 | O |
| ATOM | 1220 | N | GLU | A | 77 | -0.016 | 44.647 | 85.676 | 1.00 | 32.14 | | N |
| ANISOU | 1220 | N | GLU | A | 77 | 4205 | 4280 | 3727 | 450 | 273 | 976 | N |
| ATOM | 1221 | CA | GLU | A | 77 | -0.171 | 44.271 | 87.074 | 1.00 | 33.86 | | C |
| ANISOU | 1221 | CA | GLU | A | 77 | 4409 | 4501 | 3954 | 495 | 353 | 838 | C |
| ATOM | 1223 | CB | GLU | A | 77 | -1.243 | 45.118 | 87.751 | 1.00 | 37.44 | | C |
| ANISOU | 1223 | CB | GLU | A | 77 | 4832 | 4864 | 4529 | 651 | 399 | 821 | C |
| ATOM | 1226 | CG | GLU | A | 77 | -1.225 | 45.001 | 89.267 | 1.00 | 38.59 | | C |
| ANISOU | 1226 | CG | GLU | A | 77 | 5002 | 4996 | 4666 | 676 | 499 | 663 | C |
| ATOM | 1229 | CD | GLU | A | 77 | 0.136 | 45.324 | 89.826 | 1.00 | 40.39 | | C |
| ANISOU | 1229 | CD | GLU | A | 77 | 5363 | 5139 | 4846 | 578 | 516 | 573 | C |
| ATOM | 1230 | OE1 | GLU | A | 77 | 0.607 | 46.454 | 89.560 | 1.00 | 41.10 | | O |
| ANISOU | 1230 | OE1 | GLU | A | 77 | 5545 | 5071 | 5001 | 579 | 504 | 590 | O |
| ATOM | 1231 | OE2 | GLU | A | 77 | 0.739 | 44.448 | 90.511 | 1.00 | 41.39 | | O |
| ANISOU | 1231 | OE2 | GLU | A | 77 | 5498 | 5356 | 4875 | 493 | 533 | 496 | O |
| ATOM | 1232 | C | GLU | A | 77 | -0.538 | 42.798 | 87.187 | 1.00 | 32.58 | | C |
| ANISOU | 1232 | C | GLU | A | 77 | 4158 | 4509 | 3710 | 453 | 357 | 810 | C |
| ATOM | 1233 | O | GLU | A | 77 | -1.537 | 42.356 | 86.606 | 1.00 | 30.66 | | O |
| ANISOU | 1233 | O | GLU | A | 77 | 3817 | 4363 | 3469 | 479 | 321 | 882 | O |
| ATOM | 1235 | N | ILE | A | 78 | 0.247 | 42.061 | 87.983 | 1.00 | 32.80 | | N |
| ANISOU | 1235 | N | ILE | A | 78 | 4221 | 4567 | 3674 | 385 | 394 | 711 | N |
| ATOM | 1236 | CA | ILE | A | 78 | -0.013 | 40.658 | 88.267 | 1.00 | 32.17 | | C |
| ANISOU | 1236 | CA | ILE | A | 78 | 4082 | 4611 | 3530 | 343 | 401 | 680 | C |
| ATOM | 1238 | CB | ILE | A | 78 | 1.144 | 39.917 | 89.004 | 1.00 | 35.15 | | C |
| ANISOU | 1238 | CB | ILE | A | 78 | 4512 | 4996 | 3846 | 265 | 417 | 599 | C |
| ATOM | 1240 | CG1 | ILE | A | 78 | 2.490 | 40.514 | 88.694 | 1.00 | 37.61 | | C |
| ANISOU | 1240 | CG1 | ILE | A | 78 | 4896 | 5239 | 4154 | 209 | 399 | 587 | C |
| ATOM | 1243 | CD1 | ILE | A | 78 | 3.566 | 39.515 | 88.868 | 1.00 | 38.45 | | C |
| ANISOU | 1243 | CD1 | ILE | A | 78 | 5006 | 5393 | 4211 | 135 | 389 | 545 | C |
| ATOM | 1247 | CG2 | ILE | A | 78 | 1.154 | 38.400 | 88.582 | 1.00 | 34.89 | | C |
| ANISOU | 1247 | CG2 | ILE | A | 78 | 4434 | 5064 | 3759 | 199 | 393 | 608 | C |
| ATOM | 1251 | C | ILE | A | 78 | -1.210 | 40.502 | 89.183 | 1.00 | 29.43 | | C |
| ANISOU | 1251 | C | ILE | A | 78 | 3666 | 4307 | 3211 | 419 | 454 | 652 | C |
| ATOM | 1252 | O | ILE | A | 78 | -1.377 | 41.215 | 90.153 | 1.00 | 31.03 | | O |
| ANISOU | 1252 | O | ILE | A | 78 | 3895 | 4446 | 3449 | 483 | 515 | 588 | O |
| ATOM | 1254 | N | ILE | A | 79 | -2.013 | 39.518 | 88.876 | 1.00 | 27.25 | | N |
| ANISOU | 1254 | N | ILE | A | 79 | 3299 | 4146 | 2907 | 395 | 437 | 688 | N |
| ATOM | 1255 | CA | ILE | A | 79 | -3.133 | 39.155 | 89.698 | 1.00 | 27.32 | | C |
| ANISOU | 1255 | CA | ILE | A | 79 | 3224 | 4230 | 2927 | 435 | 492 | 667 | C |
| ATOM | 1257 | CB | ILE | A | 79 | -4.463 | 39.464 | 88.988 | 1.00 | 27.34 | | C |
| ANISOU | 1257 | CB | ILE | A | 79 | 3095 | 4298 | 2996 | 507 | 465 | 752 | C |
| ATOM | 1259 | CG1 | ILE | A | 79 | -4.508 | 40.982 | 88.680 | 1.00 | 28.36 | | C |
| ANISOU | 1259 | CG1 | ILE | A | 79 | 3244 | 4305 | 3228 | 627 | 458 | 787 | C |
| ATOM | 1262 | CD1 | ILE | A | 79 | -5.606 | 41.394 | 87.959 | 1.00 | 29.36 | | C |

FIG. 18 (continued)

| | | | | | | | | | | | | |
|---|---|---|---|---|---|---|---|---|---|---|---|---|
| ANISOU | 1262 | CD1 | ILE | A | 79 | 3249 | 4476 | 3432 | 710 | 412 | 889 | C |
| ATOM | 1266 | CG2 | ILE | A | 79 | -5.677 | 38.964 | 89.866 | 1.00 | 25.69 | | C |
| ANISOU | 1266 | CG2 | ILE | A | 79 | 2766 | 4199 | 2794 | 533 | 536 | 726 | C |
| ATOM | 1270 | C | ILE | A | 79 | -2.969 | 37.684 | 90.137 | 1.00 | 26.09 | | C |
| ANISOU | 1270 | C | ILE | A | 79 | 3070 | 4155 | 2689 | 330 | 496 | 640 | C |
| ATOM | 1271 | O | ILE | A | 79 | -3.153 | 37.383 | 91.287 | 1.00 | 25.54 | | O |
| ANISOU | 1271 | O | ILE | A | 79 | 3004 | 4110 | 2589 | 325 | 556 | 590 | O |
| ATOM | 1273 | N | GLU | A | 80 | -2.603 | 36.797 | 89.205 | 1.00 | 27.04 | | N |
| ANISOU | 1273 | N | GLU | A | 80 | 3197 | 4306 | 2771 | 245 | 434 | 673 | N |
| ATOM | 1274 | CA | GLU | A | 80 | -2.247 | 35.410 | 89.501 | 1.00 | 25.71 | | C |
| ANISOU | 1274 | CA | GLU | A | 80 | 3055 | 4167 | 2548 | 151 | 429 | 649 | C |
| ATOM | 1276 | CB | GLU | A | 80 | -1.877 | 34.695 | 88.187 | 1.00 | 26.30 | | C |
| ANISOU | 1276 | CB | GLU | A | 80 | 3139 | 4256 | 2598 | 75 | 369 | 668 | C |
| ATOM | 1279 | CG | GLU | A | 80 | -1.644 | 33.183 | 88.331 | 1.00 | 26.98 | | C |
| ANISOU | 1279 | CG | GLU | A | 80 | 3253 | 4345 | 2653 | -14 | 363 | 641 | C |
| ATOM | 1282 | CD | GLU | A | 80 | -2.775 | 32.428 | 89.021 | 1.00 | 26.25 | | C |
| ANISOU | 1282 | CD | GLU | A | 80 | 3105 | 4318 | 2551 | -55 | 384 | 662 | C |
| ATOM | 1283 | OE1 | GLU | A | 80 | -3.686 | 31.964 | 88.326 | 1.00 | 27.76 | | O |
| ANISOU | 1283 | OE1 | GLU | A | 80 | 3231 | 4582 | 2733 | -113 | 357 | 691 | O |
| ATOM | 1284 | OE2 | GLU | A | 80 | -2.749 | 32.242 | 90.268 | 1.00 | 29.66 | | O |
| ANISOU | 1284 | OE2 | GLU | A | 80 | 3559 | 4738 | 2972 | -49 | 424 | 652 | O |
| ATOM | 1285 | C | GLU | A | 80 | -1.040 | 35.329 | 90.445 | 1.00 | 25.80 | | C |
| ANISOU | 1285 | C | GLU | A | 80 | 3160 | 4108 | 2535 | 140 | 447 | 593 | C |
| ATOM | 1286 | O | GLU | A | 80 | -0.112 | 36.125 | 90.330 | 1.00 | 28.39 | | O |
| ANISOU | 1286 | O | GLU | A | 80 | 3543 | 4369 | 2877 | 163 | 439 | 571 | O |
| ATOM | 1288 | N | GLY | A | 81 | -1.014 | 34.339 | 91.326 | 1.00 | 24.70 | | N |
| ANISOU | 1288 | N | GLY | A | 81 | 3038 | 3988 | 2357 | 90 | 460 | 583 | N |
| ATOM | 1289 | CA | GLY | A | 81 | 0.128 | 34.155 | 92.217 | 1.00 | 24.30 | | C |
| ANISOU | 1289 | CA | GLY | A | 81 | 3066 | 3889 | 2278 | 73 | 453 | 552 | C |
| ATOM | 1292 | C | GLY | A | 81 | -0.065 | 34.738 | 93.590 | 1.00 | 26.10 | | C |
| ANISOU | 1292 | C | GLY | A | 81 | 3319 | 4134 | 2464 | 92 | 505 | 519 | C |
| ATOM | 1293 | O | GLY | A | 81 | 0.738 | 34.510 | 94.488 | 1.00 | 27.55 | | O |
| ANISOU | 1293 | O | GLY | A | 81 | 3564 | 4305 | 2601 | 60 | 489 | 505 | O |
| ATOM | 1295 | N | ARG | A | 82 | -1.118 | 35.518 | 93.748 | 1.00 | 27.05 | | N |
| ANISOU | 1295 | N | ARG | A | 82 | 3389 | 4289 | 2598 | 146 | 566 | 504 | N |
| ATOM | 1296 | CA | ARG | A | 82 | -1.416 | 36.204 | 94.995 | 1.00 | 28.37 | | C |
| ANISOU | 1296 | CA | ARG | A | 82 | 3579 | 4477 | 2723 | 171 | 642 | 443 | C |
| ATOM | 1298 | CB | ARG | A | 82 | -2.036 | 37.567 | 94.725 | 1.00 | 30.64 | | C |
| ANISOU | 1298 | CB | ARG | A | 82 | 3832 | 4728 | 3083 | 278 | 696 | 404 | C |
| ATOM | 1301 | CG | ARG | A | 82 | -1.248 | 38.495 | 93.789 | 1.00 | 31.98 | | C |
| ANISOU | 1301 | CG | ARG | A | 82 | 4045 | 4786 | 3321 | 318 | 644 | 408 | C |
| ATOM | 1304 | CD | ARG | A | 82 | -1.879 | 39.904 | 93.894 | 1.00 | 32.65 | | C |
| ANISOU | 1304 | CD | ARG | A | 82 | 4120 | 4803 | 3482 | 430 | 708 | 363 | C |
| ATOM | 1307 | NE | ARG | A | 82 | -1.185 | 40.812 | 93.014 | 1.00 | 32.54 | | N |
| ANISOU | 1307 | NE | ARG | A | 82 | 4159 | 4672 | 3534 | 454 | 657 | 386 | N |
| ATOM | 1309 | CZ | ARG | A | 82 | -0.297 | 41.733 | 93.386 | 1.00 | 32.86 | | C |
| ANISOU | 1309 | CZ | ARG | A | 82 | 4304 | 4602 | 3580 | 445 | 664 | 322 | C |
| ATOM | 1310 | NH1 | ARG | A | 82 | 0.042 | 41.898 | 94.651 | 1.00 | 35.06 | | N |
| ANISOU | 1310 | NH1 | ARG | A | 82 | 4652 | 4877 | 3792 | 412 | 716 | 220 | N |
| ATOM | 1313 | NH2 | ARG | A | 82 | 0.286 | 42.486 | 92.460 | 1.00 | 31.75 | | N |
| ANISOU | 1313 | NH2 | ARG | A | 82 | 4205 | 4362 | 3498 | 447 | 614 | 366 | N |
| ATOM | 1316 | C | ARG | A | 82 | -2.475 | 35.429 | 95.705 | 1.00 | 28.05 | | C |
| ANISOU | 1316 | C | ARG | A | 82 | 3484 | 4544 | 2630 | 129 | 697 | 463 | C |
| ATOM | 1317 | O | ARG | A | 82 | -3.285 | 34.760 | 95.071 | 1.00 | 29.62 | | O |
| ANISOU | 1317 | O | ARG | A | 82 | 3601 | 4796 | 2858 | 109 | 687 | 519 | O |
| ATOM | 1319 | N | ASP | A | 83 | -2.514 | 35.598 | 97.017 | 1.00 | 28.35 | | N |
| ANISOU | 1319 | N | ASP | A | 83 | 3565 | 4624 | 2581 | 104 | 762 | 413 | N |
| ATOM | 1320 | CA | ASP | A | 83 | -3.654 | 35.190 | 97.838 | 1.00 | 31.75 | | C |
| ANISOU | 1320 | CA | ASP | A | 83 | 3936 | 5177 | 2949 | 67 | 852 | 413 | C |
| ATOM | 1322 | CB | ASP | A | 83 | -3.415 | 35.686 | 99.285 | 1.00 | 33.97 | | C |
| ANISOU | 1322 | CB | ASP | A | 83 | 4298 | 5497 | 3111 | 38 | 928 | 328 | C |
| ATOM | 1325 | CG | ASP | A | 83 | -4.642 | 35.701 | 100.095 | 1.00 | 39.62 | | C |
| ANISOU | 1325 | CG | ASP | A | 83 | 4942 | 6343 | 3768 | 26 | 1062 | 291 | C |
| ATOM | 1326 | OD1 | ASP | A | 83 | -4.828 | 34.764 | 100.916 | 1.00 | 43.86 | | O |
| ANISOU | 1326 | OD1 | ASP | A | 83 | 5500 | 6981 | 4185 | -94 | 1078 | 340 | O |
| ATOM | 1327 | OD2 | ASP | A | 83 | -5.418 | 36.655 | 99.925 | 1.00 | 41.34 | | O |
| ANISOU | 1327 | OD2 | ASP | A | 83 | 5079 | 6564 | 4062 | 138 | 1154 | 217 | O |
| ATOM | 1328 | C | ASP | A | 83 | -4.937 | 35.752 | 97.216 | 1.00 | 29.35 | | C |
| ANISOU | 1328 | C | ASP | A | 83 | 3493 | 4917 | 2740 | 159 | 917 | 405 | C |
| ATOM | 1329 | O | ASP | A | 83 | -4.970 | 36.904 | 96.801 | 1.00 | 28.64 | | O |
| ANISOU | 1329 | O | ASP | A | 83 | 3389 | 4760 | 2735 | 272 | 935 | 357 | O |
| ATOM | 1331 | N | ARG | A | 84 | -5.980 | 34.922 | 97.126 | 1.00 | 31.59 | | N |
| ANISOU | 1331 | N | ARG | A | 84 | 3671 | 5312 | 3018 | 106 | 940 | 463 | N |
| ATOM | 1332 | CA | ARG | A | 84 | -7.229 | 35.297 | 96.445 | 1.00 | 32.89 | | C |
| ANISOU | 1332 | CA | ARG | A | 84 | 3671 | 5546 | 3281 | 183 | 977 | 479 | C |
| ATOM | 1334 | CB | ARG | A | 84 | -8.252 | 34.137 | 96.428 | 1.00 | 36.23 | | C |
| ANISOU | 1334 | CB | ARG | A | 84 | 3983 | 6108 | 3675 | 71 | 988 | 551 | C |
| ATOM | 1337 | CG | ARG | A | 84 | -8.340 | 33.474 | 95.063 | 1.00 | 36.13 | | C |
| ANISOU | 1337 | CG | ARG | A | 84 | 3927 | 6078 | 3721 | 27 | 869 | 635 | C |

FIG. 18 (continued)

| | | | | | | | | | | | | |
|---|---|---|---|---|---|---|---|---|---|---|---|---|
| ATOM | 1340 | CD | ARG | A | 84 | -9.437 | 32.463 | 95.010 | 1.00 | 37.46 | | C |
| ANISOU | 1340 | CD | ARG | A | 84 | 3979 | 6383 | 3872 | -91 | 880 | 696 | C |
| ATOM | 1343 | NE | ARG | A | 84 | -10.636 | 32.982 | 94.346 | 1.00 | 37.69 | | N |
| ANISOU | 1343 | NE | ARG | A | 84 | 3810 | 6520 | 3990 | -21 | 892 | 719 | N |
| ATOM | 1345 | CZ | ARG | A | 84 | -10.858 | 32.908 | 93.044 | 1.00 | 36.67 | | C |
| ANISOU | 1345 | CZ | ARG | A | 84 | 3618 | 6394 | 3921 | -21 | 787 | 775 | C |
| ATOM | 1346 | NH1 | ARG | A | 84 | -9.997 | 32.317 | 92.221 | 1.00 | 35.58 | | N |
| ANISOU | 1346 | NH1 | ARG | A | 84 | 3600 | 6157 | 3762 | -92 | 679 | 797 | N |
| ATOM | 1349 | NH2 | ARG | A | 84 | -11.977 | 33.393 | 92.562 | 1.00 | 37.40 | | N |
| ANISOU | 1349 | NH2 | ARG | A | 84 | 3516 | 6602 | 4092 | 44 | 789 | 811 | N |
| ATOM | 1352 | C | ARG | A | 84 | -7.914 | 36.537 | 96.984 | 1.00 | 32.60 | | C |
| ANISOU | 1352 | C | ARG | A | 84 | 3565 | 5532 | 3291 | 315 | 1101 | 388 | C |
| ATOM | 1353 | O | ARG | A | 84 | -8.390 | 37.347 | 96.197 | 1.00 | 32.12 | | O |
| ANISOU | 1353 | O | ARG | A | 84 | 3414 | 5437 | 3355 | 440 | 1091 | 396 | O |
| ATOM | 1355 | N | THR | A | 85 | -7.977 | 36.698 | 98.309 | 1.00 | 30.52 | | N |
| ANISOU | 1355 | N | THR | A | 85 | 3345 | 5322 | 2929 | 289 | 1218 | 301 | N |
| ATOM | 1356 | CA | THR | A | 85 | -8.495 | 37.946 | 98.862 | 1.00 | 34.33 | | C |
| ANISOU | 1356 | CA | THR | A | 85 | 3786 | 5798 | 3460 | 423 | 1353 | 178 | C |
| ATOM | 1358 | CB | THR | A | 85 | -8.484 | 37.956 | 100.403 | 1.00 | 37.53 | | C |
| ANISOU | 1358 | CB | THR | A | 85 | 4264 | 6289 | 3709 | 352 | 1488 | 69 | C |
| ATOM | 1360 | OG1 | THR | A | 85 | -9.124 | 36.776 | 100.904 | 1.00 | 40.39 | | O |
| ANISOU | 1360 | OG1 | THR | A | 85 | 4559 | 6824 | 3963 | 211 | 1524 | 136 | O |
| ATOM | 1362 | CG2 | THR | A | 85 | -9.276 | 39.150 | 100.899 | 1.00 | 40.37 | | C |
| ANISOU | 1362 | CG2 | THR | A | 85 | 4547 | 6658 | 4135 | 500 | 1657 | -76 | C |
| ATOM | 1366 | C | THR | A | 85 | -7.710 | 39.158 | 98.361 | 1.00 | 33.08 | | C |
| ANISOU | 1366 | C | THR | A | 85 | 3720 | 5449 | 3398 | 543 | 1307 | 127 | C |
| ATOM | 1367 | O | THR | A | 85 | -8.283 | 40.169 | 97.955 | 1.00 | 33.53 | | O |
| ANISOU | 1367 | O | THR | A | 85 | 3698 | 5447 | 3595 | 699 | 1350 | 95 | O |
| ATOM | 1369 | N | MET | A | 86 | -6.389 | 39.044 | 98.359 | 1.00 | 33.51 | | N |
| ANISOU | 1369 | N | MET | A | 86 | 3937 | 5406 | 3390 | 469 | 1215 | 132 | N |
| ATOM | 1370 | CA | MET | A | 86 | -5.556 | 40.156 | 97.935 | 1.00 | 33.43 | | C |
| ANISOU | 1370 | CA | MET | A | 86 | 4024 | 5221 | 3456 | 547 | 1172 | 88 | C |
| ATOM | 1372 | CB | MET | A | 86 | -4.090 | 39.935 | 98.325 | 1.00 | 34.23 | | C |
| ANISOU | 1372 | CB | MET | A | 86 | 4291 | 5264 | 3452 | 432 | 1095 | 72 | C |
| ATOM | 1375 | CG | MET | A | 86 | -3.173 | 41.133 | 98.013 | 1.00 | 35.36 | | C |
| ANISOU | 1375 | CG | MET | A | 86 | 4541 | 5233 | 3661 | 482 | 1061 | 15 | C |
| ATOM | 1378 | SD | MET | A | 86 | -3.793 | 42.675 | 98.790 | 1.00 | 40.15 | | S |
| ANISOU | 1378 | SD | MET | A | 86 | 5178 | 5750 | 4328 | 608 | 1219 | -159 | S |
| ATOM | 1379 | CE | MET | A | 86 | -3.531 | 43.774 | 97.412 | 1.00 | 40.55 | | C |
| ANISOU | 1379 | CE | MET | A | 86 | 5239 | 5596 | 4571 | 724 | 1140 | -99 | C |
| ATOM | 1383 | C | MET | A | 86 | -5.687 | 40.396 | 96.432 | 1.00 | 31.58 | | C |
| ANISOU | 1383 | C | MET | A | 86 | 3720 | 4915 | 3364 | 624 | 1072 | 194 | C |
| ATOM | 1384 | O | MET | A | 86 | -5.658 | 41.534 | 96.014 | 1.00 | 32.98 | | O |
| ANISOU | 1384 | O | MET | A | 86 | 3913 | 4965 | 3652 | 738 | 1075 | 170 | O |
| ATOM | 1386 | N | ALA | A | 87 | -5.781 | 39.327 | 95.631 | 1.00 | 30.33 | | N |
| ANISOU | 1386 | N | ALA | A | 87 | 3502 | 4830 | 3193 | 551 | 979 | 310 | N |
| ATOM | 1387 | CA | ALA | A | 87 | -6.031 | 39.433 | 94.181 | 1.00 | 29.64 | | C |
| ANISOU | 1387 | CA | ALA | A | 87 | 3340 | 4716 | 3206 | 598 | 882 | 415 | C |
| ATOM | 1389 | CB | ALA | A | 87 | -6.051 | 38.041 | 93.501 | 1.00 | 26.74 | | C |
| ANISOU | 1389 | CB | ALA | A | 87 | 2935 | 4442 | 2785 | 474 | 795 | 508 | C |
| ATOM | 1393 | C | ALA | A | 87 | -7.304 | 40.220 | 93.857 | 1.00 | 30.57 | | C |
| ANISOU | 1393 | C | ALA | A | 87 | 3306 | 4858 | 3453 | 745 | 928 | 434 | C |
| ATOM | 1394 | O | ALA | A | 87 | -7.275 | 41.092 | 92.977 | 1.00 | 30.95 | | O |
| ANISOU | 1394 | O | ALA | A | 87 | 3347 | 4806 | 3608 | 840 | 871 | 485 | O |
| ATOM | 1396 | N | TRP | A | 88 | -8.395 | 39.950 | 94.585 | 1.00 | 32.58 | | N |
| ANISOU | 1396 | N | TRP | A | 88 | 3434 | 5243 | 3702 | 765 | 1032 | 400 | N |
| ATOM | 1397 | CA | TRP | A | 88 | -9.641 | 40.724 | 94.437 | 1.00 | 35.11 | | C |
| ANISOU | 1397 | CA | TRP | A | 88 | 3580 | 5598 | 4163 | 927 | 1095 | 404 | C |
| ATOM | 1399 | CB | TRP | A | 88 | -10.846 | 40.059 | 95.131 | 1.00 | 38.65 | | C |
| ANISOU | 1399 | CB | TRP | A | 88 | 3856 | 6249 | 4580 | 900 | 1203 | 385 | C |
| ATOM | 1402 | CG | TRP | A | 88 | -11.446 | 38.916 | 94.345 | 1.00 | 38.41 | | C |
| ANISOU | 1402 | CG | TRP | A | 88 | 3698 | 6370 | 4527 | 787 | 1107 | 514 | C |
| ATOM | 1403 | CD1 | TRP | A | 88 | -11.518 | 37.597 | 94.733 | 1.00 | 37.92 | | C |
| ANISOU | 1403 | CD1 | TRP | A | 88 | 3640 | 6433 | 4337 | 605 | 1111 | 534 | C |
| ATOM | 1405 | NE1 | TRP | A | 88 | -12.125 | 36.851 | 93.741 | 1.00 | 38.39 | | N |
| ANISOU | 1405 | NE1 | TRP | A | 88 | 3576 | 6593 | 4417 | 530 | 1007 | 648 | N |
| ATOM | 1407 | CE2 | TRP | A | 88 | -12.461 | 37.677 | 92.700 | 1.00 | 38.38 | | C |
| ANISOU | 1407 | CE2 | TRP | A | 88 | 3483 | 6557 | 4544 | 663 | 928 | 713 | C |
| ATOM | 1408 | CD2 | TRP | A | 88 | -12.065 | 38.986 | 93.046 | 1.00 | 38.67 | | C |
| ANISOU | 1408 | CD2 | TRP | A | 88 | 3589 | 6442 | 4660 | 833 | 988 | 640 | C |
| ATOM | 1409 | CE3 | TRP | A | 88 | -12.296 | 40.036 | 92.118 | 1.00 | 40.65 | | C |
| ANISOU | 1409 | CE3 | TRP | A | 88 | 3778 | 6610 | 5059 | 993 | 915 | 710 | C |
| ATOM | 1411 | CZ3 | TRP | A | 88 | -12.935 | 39.746 | 90.925 | 1.00 | 40.21 | | C |
| ANISOU | 1411 | CZ3 | TRP | A | 88 | 3580 | 6652 | 5045 | 974 | 782 | 851 | C |
| ATOM | 1413 | CH2 | TRP | A | 88 | -13.322 | 38.428 | 90.614 | 1.00 | 40.09 | | C |
| ANISOU | 1413 | CH2 | TRP | A | 88 | 3494 | 6805 | 4932 | 791 | 726 | 905 | C |
| ATOM | 1415 | CZ2 | TRP | A | 88 | -13.098 | 37.385 | 91.487 | 1.00 | 39.54 | | C |
| ANISOU | 1415 | CZ2 | TRP | A | 88 | 3494 | 6793 | 4737 | 636 | 801 | 835 | C |
| ATOM | 1417 | C | TRP | A | 88 | -9.483 | 42.190 | 94.903 | 1.00 | 36.45 | | C |

FIG. 18 (continued)

| | | | | | | | | | | | | |
|---|---|---|---|---|---|---|---|---|---|---|---|---|
| ANISOU | 1417 | C | TRP | A | 88 | 3816 | 5602 | 4433 | 1089 | 1182 | 296 | C |
| ATOM | 1418 | O | TRP | A | 88 | -10.014 | 43.085 | 94.261 | 1.00 | 33.89 | | O |
| ANISOU | 1418 | O | TRP | A | 88 | 3407 | 5200 | 4268 | 1247 | 1162 | 342 | O |
| ATOM | 1420 | N | THR | A | 89 | -8.753 | 42.427 | 95.994 | 1.00 | 35.46 | | N |
| ANISOU | 1420 | N | THR | A | 89 | 3844 | 5414 | 4214 | 1044 | 1269 | 158 | N |
| ATOM | 1421 | CA | THR | A | 89 | -8.412 | 43.800 | 96.407 | 1.00 | 38.05 | | C |
| ANISOU | 1421 | CA | THR | A | 89 | 4279 | 5555 | 4625 | 1165 | 1341 | 37 | C |
| ATOM | 1423 | CB | THR | A | 89 | -7.577 | 43.786 | 97.724 | 1.00 | 37.77 | | C |
| ANISOU | 1423 | CB | THR | A | 89 | 4417 | 5506 | 4428 | 1053 | 1426 | -120 | C |
| ATOM | 1425 | OG1 | THR | A | 89 | -8.433 | 43.412 | 98.797 | 1.00 | 39.86 | | O |
| ANISOU | 1425 | OG1 | THR | A | 89 | 4596 | 5935 | 4615 | 1042 | 1580 | -213 | O |
| ATOM | 1427 | CG2 | THR | A | 89 | -6.952 | 45.155 | 98.032 | 1.00 | 39.26 | | C |
| ANISOU | 1427 | CG2 | THR | A | 89 | 4760 | 5474 | 4683 | 1129 | 1471 | -248 | C |
| ATOM | 1431 | C | THR | A | 89 | -7.640 | 44.596 | 95.326 | 1.00 | 36.39 | | C |
| ANISOU | 1431 | C | THR | A | 89 | 4166 | 5145 | 4517 | 1210 | 1213 | 118 | C |
| ATOM | 1432 | O | THR | A | 89 | -7.857 | 45.781 | 95.154 | 1.00 | 35.42 | | O |
| ANISOU | 1432 | O | THR | A | 89 | 4054 | 4860 | 4544 | 1361 | 1242 | 90 | O |
| ATOM | 1434 | N | VAL | A | 90 | -6.742 | 43.926 | 94.607 | 1.00 | 36.12 | | N |
| ANISOU | 1434 | N | VAL | A | 90 | 4203 | 5120 | 4402 | 1075 | 1077 | 218 | N |
| ATOM | 1435 | CA | VAL | A | 90 | -5.989 | 44.539 | 93.523 | 1.00 | 36.31 | | C |
| ANISOU | 1435 | CA | VAL | A | 90 | 4311 | 4994 | 4493 | 1083 | 958 | 308 | C |
| ATOM | 1437 | CB | VAL | A | 90 | -4.743 | 43.682 | 93.123 | 1.00 | 33.77 | | C |
| ANISOU | 1437 | CB | VAL | A | 90 | 4090 | 4703 | 4039 | 904 | 855 | 355 | C |
| ATOM | 1439 | CG1 | VAL | A | 90 | -4.062 | 44.227 | 91.818 | 1.00 | 33.91 | | C |
| ANISOU | 1439 | CG1 | VAL | A | 90 | 4166 | 4606 | 4112 | 895 | 736 | 467 | C |
| ATOM | 1443 | CG2 | VAL | A | 90 | -3.772 | 43.620 | 94.264 | 1.00 | 32.32 | | C |
| ANISOU | 1443 | CG2 | VAL | A | 90 | 4045 | 4493 | 3744 | 809 | 906 | 226 | C |
| ATOM | 1447 | C | VAL | A | 90 | -6.930 | 44.820 | 92.336 | 1.00 | 37.86 | | C |
| ANISOU | 1447 | C | VAL | A | 90 | 4359 | 5200 | 4825 | 1198 | 883 | 458 | C |
| ATOM | 1448 | O | VAL | A | 90 | -6.987 | 45.943 | 91.848 | 1.00 | 39.28 | | O |
| ANISOU | 1448 | O | VAL | A | 90 | 4564 | 5218 | 5142 | 1317 | 858 | 498 | O |
| ATOM | 1450 | N | VAL | A | 91 | -7.722 | 43.825 | 91.937 | 1.00 | 38.11 | | N |
| ANISOU | 1450 | N | VAL | A | 91 | 4235 | 5421 | 4824 | 1161 | 846 | 542 | N |
| ATOM | 1451 | CA | VAL | A | 91 | -8.709 | 44.001 | 90.871 | 1.00 | 37.70 | | C |
| ANISOU | 1451 | CA | VAL | A | 91 | 4019 | 5421 | 4883 | 1255 | 763 | 689 | C |
| ATOM | 1453 | CB | VAL | A | 91 | -9.583 | 42.706 | 90.606 | 1.00 | 36.70 | | C |
| ANISOU | 1453 | CB | VAL | A | 91 | 3720 | 5536 | 4688 | 1166 | 730 | 756 | C |
| ATOM | 1455 | CG1 | VAL | A | 91 | -10.783 | 43.013 | 89.669 | 1.00 | 37.26 | | C |
| ANISOU | 1455 | CG1 | VAL | A | 91 | 3585 | 5687 | 4887 | 1278 | 649 | 901 | C |
| ATOM | 1459 | CG2 | VAL | A | 91 | -8.723 | 41.528 | 90.063 | 1.00 | 31.69 | | C |
| ANISOU | 1459 | CG2 | VAL | A | 91 | 3179 | 4966 | 3897 | 961 | 637 | 794 | C |
| ATOM | 1463 | C | VAL | A | 91 | -9.630 | 45.182 | 91.186 | 1.00 | 42.11 | | C |
| ANISOU | 1463 | C | VAL | A | 91 | 4481 | 5888 | 5630 | 1478 | 842 | 663 | C |
| ATOM | 1464 | O | VAL | A | 91 | -9.904 | 45.981 | 90.301 | 1.00 | 42.86 | | O |
| ANISOU | 1464 | O | VAL | A | 91 | 4539 | 5887 | 5859 | 1592 | 756 | 783 | O |
| ATOM | 1466 | N | ASN | A | 92 | -10.102 | 45.299 | 92.433 | 1.00 | 41.94 | | N |
| ANISOU | 1466 | N | ASN | A | 92 | 4421 | 5893 | 5620 | 1542 | 1008 | 507 | N |
| ATOM | 1467 | CA | ASN | A | 92 | -11.017 | 46.388 | 92.798 | 1.00 | 45.47 | | C |
| ANISOU | 1467 | CA | ASN | A | 92 | 4764 | 6252 | 6261 | 1772 | 1112 | 453 | C |
| ATOM | 1469 | CB | ASN | A | 92 | -11.642 | 46.146 | 94.167 | 1.00 | 47.13 | | C |
| ANISOU | 1469 | CB | ASN | A | 92 | 4899 | 6579 | 6430 | 1795 | 1311 | 274 | C |
| ATOM | 1472 | CG | ASN | A | 92 | -12.623 | 45.000 | 94.153 | 1.00 | 48.73 | | C |
| ANISOU | 1472 | CG | ASN | A | 92 | 4881 | 7060 | 6571 | 1727 | 1318 | 337 | C |
| ATOM | 1473 | OD1 | ASN | A | 92 | -13.247 | 44.726 | 93.130 | 1.00 | 50.39 | | O |
| ANISOU | 1473 | OD1 | ASN | A | 92 | 4933 | 7364 | 6850 | 1749 | 1195 | 503 | O |
| ATOM | 1474 | ND2 | ASN | A | 92 | -12.761 | 44.312 | 95.289 | 1.00 | 49.41 | | N |
| ANISOU | 1474 | ND2 | ASN | A | 92 | 4964 | 7291 | 6519 | 1624 | 1457 | 212 | N |
| ATOM | 1477 | C | ASN | A | 92 | -10.354 | 47.764 | 92.735 | 1.00 | 46.67 | | C |
| ANISOU | 1477 | C | ASN | A | 92 | 5088 | 6110 | 6534 | 1881 | 1113 | 413 | C |
| ATOM | 1478 | O | ASN | A | 92 | -10.917 | 48.694 | 92.164 | 1.00 | 47.73 | | O |
| ANISOU | 1478 | O | ASN | A | 92 | 5150 | 6118 | 6867 | 2066 | 1078 | 497 | O |
| ATOM | 1480 | N | SER | A | 93 | -9.152 | 47.880 | 93.294 | 1.00 | 46.31 | | N |
| ANISOU | 1480 | N | SER | A | 93 | 5268 | 5955 | 6374 | 1757 | 1142 | 298 | N |
| ATOM | 1481 | CA | SER | A | 93 | -8.383 | 49.115 | 93.197 | 1.00 | 48.88 | | C |
| ANISOU | 1481 | CA | SER | A | 93 | 5779 | 5999 | 6794 | 1810 | 1130 | 262 | C |
| ATOM | 1483 | CB | SER | A | 93 | -7.008 | 48.973 | 93.854 | 1.00 | 48.97 | | C |
| ANISOU | 1483 | CB | SER | A | 93 | 6013 | 5958 | 6636 | 1621 | 1148 | 139 | C |
| ATOM | 1486 | OG | SER | A | 93 | -6.323 | 50.223 | 93.856 | 1.00 | 52.31 | | O |
| ANISOU | 1486 | OG | SER | A | 93 | 6615 | 6106 | 7156 | 1658 | 1150 | 87 | O |
| ATOM | 1488 | C | SER | A | 93 | -8.215 | 49.513 | 91.743 | 1.00 | 49.95 | | C |
| ANISOU | 1488 | C | SER | A | 93 | 5918 | 6039 | 7021 | 1833 | 954 | 483 | C |
| ATOM | 1489 | O | SER | A | 93 | -8.478 | 50.658 | 91.376 | 1.00 | 51.74 | | O |
| ANISOU | 1489 | O | SER | A | 93 | 6163 | 6056 | 7438 | 1994 | 937 | 533 | O |
| ATOM | 1491 | N | ILE | A | 94 | -7.794 | 48.561 | 90.912 | 1.00 | 47.72 | | N |
| ANISOU | 1491 | N | ILE | A | 94 | 5622 | 5907 | 6603 | 1672 | 824 | 615 | N |
| ATOM | 1492 | CA | ILE | A | 94 | -7.625 | 48.813 | 89.483 | 1.00 | 48.30 | | C |
| ANISOU | 1492 | CA | ILE | A | 94 | 5699 | 5936 | 6718 | 1658 | 656 | 828 | C |
| ATOM | 1494 | CB | ILE | A | 94 | -7.089 | 47.550 | 88.721 | 1.00 | 46.53 | | C |
| ANISOU | 1494 | CB | ILE | A | 94 | 5468 | 5910 | 6300 | 1449 | 548 | 917 | C |

FIG. 18 (continued)

| | | | | | | | | | | | | | | |
|---|---|---|---|---|---|---|---|---|---|---|---|---|---|---|
| ATOM | 1496 | CG1 | ILE | A | 94 | -5.640 | 47.272 | 89.152 | 1.00 | 44.45 | | C |
| ANISOU | 1496 | CG1 | ILE | A | 94 | 5395 | 5600 | 5893 | 1275 | 572 | 810 | C |
| ATOM | 1499 | CD1 | ILE | A | 94 | -4.988 | 46.052 | 88.532 | 1.00 | 42.38 | | C |
| ANISOU | 1499 | CD1 | ILE | A | 94 | 5140 | 5502 | 5461 | 1087 | 493 | 862 | C |
| ATOM | 1503 | CG2 | ILE | A | 94 | -7.172 | 47.757 | 87.197 | 1.00 | 47.27 | | C |
| ANISOU | 1503 | CG2 | ILE | A | 94 | 5534 | 6009 | 6418 | 1436 | 381 | 1141 | C |
| ATOM | 1507 | C | ILE | A | 94 | -8.897 | 49.357 | 88.832 | 1.00 | 51.10 | | C |
| ANISOU | 1507 | C | ILE | A | 94 | 5871 | 6284 | 7261 | 1859 | 601 | 975 | C |
| ATOM | 1508 | O | ILE | A | 94 | -8.844 | 50.353 | 88.120 | 1.00 | 52.51 | | O |
| ANISOU | 1508 | O | ILE | A | 94 | 6101 | 6279 | 7572 | 1949 | 518 | 1100 | O |
| ATOM | 1510 | N | CYS | A | 95 | -10.034 | 48.712 | 89.072 | 1.00 | 51.34 | | N |
| ANISOU | 1510 | N | CYS | A | 95 | 5683 | 6517 | 7308 | 1924 | 640 | 971 | N |
| ATOM | 1511 | CA | CYS | A | 95 | -11.293 | 49.150 | 88.489 | 1.00 | 53.81 | | C |
| ANISOU | 1511 | CA | CYS | A | 95 | 5781 | 6860 | 7805 | 2117 | 581 | 1116 | C |
| ATOM | 1513 | CB | CYS | A | 95 | -12.411 | 48.139 | 88.772 | 1.00 | 53.69 | | C |
| ANISOU | 1513 | CB | CYS | A | 95 | 5514 | 7132 | 7753 | 2115 | 623 | 1103 | C |
| ATOM | 1516 | SG | CYS | A | 95 | -12.131 | 46.537 | 87.963 | 1.00 | 50.24 | | S |
| ANISOU | 1516 | SG | CYS | A | 95 | 5054 | 6966 | 7068 | 1833 | 488 | 1203 | S |
| ATOM | 1518 | C | CYS | A | 95 | -11.666 | 50.539 | 89.005 | 1.00 | 58.16 | | C |
| ANISOU | 1518 | C | CYS | A | 95 | 6346 | 7155 | 8597 | 2367 | 676 | 1050 | C |
| ATOM | 1519 | O | CYS | A | 95 | -12.103 | 51.382 | 88.233 | 1.00 | 58.50 | | O |
| ANISOU | 1519 | O | CYS | A | 95 | 6336 | 7070 | 8822 | 2523 | 575 | 1216 | O |
| ATOM | 1521 | N | ASN | A | 96 | -11.459 | 50.775 | 90.303 | 1.00 | 60.33 | | N |
| ANISOU | 1521 | N | ASN | A | 96 | 6705 | 7346 | 8870 | 2397 | 868 | 808 | N |
| ATOM | 1522 | CA | ASN | A | 96 | -11.687 | 52.096 | 90.909 | 1.00 | 64.36 | | C |
| ANISOU | 1522 | CA | ASN | A | 96 | 7271 | 7584 | 9600 | 2619 | 988 | 691 | C |
| ATOM | 1524 | CB | ASN | A | 96 | -11.307 | 52.094 | 92.408 | 1.00 | 64.57 | | C |
| ANISOU | 1524 | CB | ASN | A | 96 | 7418 | 7581 | 9537 | 2573 | 1204 | 392 | C |
| ATOM | 1527 | CG | ASN | A | 96 | -12.500 | 51.921 | 93.330 | 1.00 | 66.64 | | C |
| ANISOU | 1527 | CG | ASN | A | 96 | 7466 | 7988 | 9865 | 2722 | 1388 | 247 | C |
| ATOM | 1528 | OD1 | ASN | A | 96 | -12.789 | 50.816 | 93.802 | 1.00 | 65.86 | | O |
| ANISOU | 1528 | OD1 | ASN | A | 96 | 7260 | 8167 | 9599 | 2599 | 1444 | 198 | O |
| ATOM | 1529 | ND2 | ASN | A | 96 | -13.187 | 53.024 | 93.617 | 1.00 | 71.38 | | N |
| ANISOU | 1529 | ND2 | ASN | A | 96 | 8009 | 8397 | 10716 | 2986 | 1494 | 172 | N |
| ATOM | 1532 | C | ASN | A | 96 | -10.879 | 53.181 | 90.185 | 1.00 | 65.56 | | C |
| ANISOU | 1532 | C | ASN | A | 96 | 7631 | 7428 | 9851 | 2634 | 876 | 800 | C |
| ATOM | 1533 | O | ASN | A | 96 | -11.417 | 54.207 | 89.788 | 1.00 | 67.82 | | O |
| ANISOU | 1533 | O | ASN | A | 96 | 7878 | 7511 | 10378 | 2849 | 841 | 896 | O |
| ATOM | 1535 | N | THR | A | 97 | -9.587 | 52.919 | 90.014 | 1.00 | 64.06 | | N |
| ANISOU | 1535 | N | THR | A | 97 | 7654 | 7209 | 9478 | 2402 | 818 | 794 | N |
| ATOM | 1536 | CA | THR | A | 97 | -8.648 | 53.883 | 89.457 | 1.00 | 65.08 | | C |
| ANISOU | 1536 | CA | THR | A | 97 | 8004 | 7061 | 9662 | 2360 | 732 | 873 | C |
| ATOM | 1538 | CB | THR | A | 97 | -7.213 | 53.463 | 89.781 | 1.00 | 62.77 | | C |
| ANISOU | 1538 | CB | THR | A | 97 | 7919 | 6783 | 9146 | 2095 | 743 | 766 | C |
| ATOM | 1540 | OG1 | THR | A | 97 | -6.978 | 53.681 | 91.176 | 1.00 | 63.26 | | O |
| ANISOU | 1540 | OG1 | THR | A | 97 | 8076 | 6771 | 9187 | 2098 | 921 | 493 | O |
| ATOM | 1542 | CG2 | THR | A | 97 | -6.198 | 54.258 | 88.966 | 1.00 | 63.18 | | C |
| ANISOU | 1542 | CG2 | THR | A | 97 | 8172 | 6616 | 9219 | 1998 | 628 | 893 | C |
| ATOM | 1546 | C | THR | A | 97 | -8.789 | 54.095 | 87.950 | 1.00 | 66.52 | | C |
| ANISOU | 1546 | C | THR | A | 97 | 8143 | 7231 | 9900 | 2369 | 524 | 1178 | C |
| ATOM | 1547 | O | THR | A | 97 | -8.737 | 55.235 | 87.473 | 1.00 | 70.07 | | O |
| ANISOU | 1547 | O | THR | A | 97 | 8685 | 7411 | 10528 | 2477 | 462 | 1292 | O |
| ATOM | 1549 | N | THR | A | 98 | -8.980 | 53.015 | 87.204 | 1.00 | 64.38 | | N |
| ANISOU | 1549 | N | THR | A | 98 | 7741 | 7244 | 9476 | 2250 | 413 | 1314 | N |
| ATOM | 1550 | CA | THR | A | 98 | -9.003 | 53.084 | 85.739 | 1.00 | 64.71 | | C |
| ANISOU | 1550 | CA | THR | A | 98 | 7759 | 7322 | 9506 | 2204 | 209 | 1598 | C |
| ATOM | 1552 | CB | THR | A | 98 | -8.247 | 51.875 | 85.113 | 1.00 | 61.83 | | C |
| ANISOU | 1552 | CB | THR | A | 98 | 7427 | 7203 | 8862 | 1927 | 130 | 1639 | C |
| ATOM | 1554 | OG1 | THR | A | 98 | -8.883 | 50.648 | 85.496 | 1.00 | 60.42 | | O |
| ANISOU | 1554 | OG1 | THR | A | 98 | 7071 | 7306 | 8581 | 1892 | 176 | 1558 | O |
| ATOM | 1556 | CG2 | THR | A | 98 | -6.777 | 51.852 | 85.559 | 1.00 | 59.26 | | C |
| ANISOU | 1556 | CG2 | THR | A | 98 | 7334 | 6782 | 8401 | 1738 | 197 | 1494 | C |
| ATOM | 1560 | C | THR | A | 98 | -10.425 | 53.146 | 85.170 | 1.00 | 66.84 | | C |
| ANISOU | 1560 | C | THR | A | 98 | 7772 | 7696 | 9929 | 2399 | 118 | 1776 | C |
| ATOM | 1561 | O | THR | A | 98 | -10.620 | 53.449 | 83.992 | 1.00 | 67.52 | | O |
| ANISOU | 1561 | O | THR | A | 98 | 7829 | 7779 | 10046 | 2406 | -62 | 2032 | O |
| ATOM | 1563 | N | GLY | A | 99 | -11.420 | 52.856 | 86.002 | 1.00 | 67.98 | | N |
| ANISOU | 1563 | N | GLY | A | 99 | 7721 | 7949 | 10160 | 2548 | 238 | 1648 | N |
| ATOM | 1564 | CA | GLY | A | 99 | -12.791 | 52.709 | 85.519 | 1.00 | 69.72 | | C |
| ANISOU | 1564 | CA | GLY | A | 99 | 7651 | 8335 | 10504 | 2709 | 156 | 1805 | C |
| ATOM | 1567 | C | GLY | A | 99 | -13.000 | 51.466 | 84.659 | 1.00 | 67.84 | | C |
| ANISOU | 1567 | C | GLY | A | 99 | 7287 | 8434 | 10056 | 2512 | 15 | 1940 | C |
| ATOM | 1568 | O | GLY | A | 99 | -14.062 | 51.305 | 84.055 | 1.00 | 69.32 | | O |
| ANISOU | 1568 | O | GLY | A | 99 | 7236 | 8785 | 10316 | 2600 | -97 | 2106 | O |
| ATOM | 1570 | N | ALA | A | 100 | -12.006 | 50.571 | 84.613 | 1.00 | 64.70 | | N |
| ANISOU | 1570 | N | ALA | A | 100 | 7038 | 8141 | 9403 | 2248 | 22 | 1862 | N |
| ATOM | 1571 | CA | ALA | A | 100 | -12.150 | 49.314 | 83.878 | 1.00 | 62.86 | | C |
| ANISOU | 1571 | CA | ALA | A | 100 | 6709 | 8209 | 8965 | 2048 | -86 | 1946 | C |
| ATOM | 1573 | CB | ALA | A | 100 | -10.838 | 48.528 | 83.873 | 1.00 | 59.57 | | C |

FIG. 18 (continued)

| | | | | | | | | | | | | |
|---|---|---|---|---|---|---|---|---|---|---|---|---|
| ANISOU | 1573 | CB | ALA | A | 100 | 6501 | 7828 | 8306 | 1787 | -61 | 1841 | C |
| ATOM | 1577 | C | ALA | A | 100 | -13.299 | 48.489 | 84.473 | 1.00 | 63.88 | | C |
| ANISOU | 1577 | C | ALA | A | 100 | 6582 | 8577 | 9111 | 2096 | -14 | 1869 | C |
| ATOM | 1578 | O | ALA | A | 100 | -13.678 | 48.670 | 85.639 | 1.00 | 64.76 | | O |
| ANISOU | 1578 | O | ALA | A | 100 | 6635 | 8644 | 9325 | 2226 | 161 | 1695 | O |
| ATOM | 1580 | N | GLU | A | 101 | -13.882 | 47.618 | 83.653 | 1.00 | 65.18 | | N |
| ANISOU | 1580 | N | GLU | A | 101 | 6592 | 9003 | 9171 | 1981 | -146 | 1999 | N |
| ATOM | 1581 | CA | GLU | A | 101 | -15.026 | 46.804 | 84.075 | 1.00 | 66.61 | | C |
| ANISOU | 1581 | CA | GLU | A | 101 | 6512 | 9434 | 9364 | 1995 | -100 | 1957 | C |
| ATOM | 1583 | CB | GLU | A | 101 | -15.728 | 46.192 | 82.851 | 1.00 | 68.16 | | C |
| ANISOU | 1583 | CB | GLU | A | 101 | 6536 | 9880 | 9482 | 1887 | -306 | 2164 | C |
| ATOM | 1586 | CG | GLU | A | 101 | -17.031 | 45.440 | 83.166 | 1.00 | 70.09 | | C |
| ANISOU | 1586 | CG | GLU | A | 101 | 6476 | 10396 | 9760 | 1897 | -284 | 2153 | C |
| ATOM | 1589 | CD | GLU | A | 101 | -17.290 | 44.241 | 82.244 | 1.00 | 70.06 | | C |
| ANISOU | 1589 | CD | GLU | A | 101 | 6399 | 10668 | 9554 | 1641 | -435 | 2244 | C |
| ATOM | 1590 | OE1 | GLU | A | 101 | -16.319 | 43.538 | 81.865 | 1.00 | 68.48 | | O |
| ANISOU | 1590 | OE1 | GLU | A | 101 | 6411 | 10466 | 9142 | 1414 | -460 | 2195 | O |
| ATOM | 1591 | OE2 | GLU | A | 101 | -18.473 | 43.995 | 81.912 | 1.00 | 72.44 | | O |
| ANISOU | 1591 | OE2 | GLU | A | 101 | 6422 | 11189 | 9914 | 1665 | -525 | 2356 | O |
| ATOM | 1592 | C | GLU | A | 101 | -14.540 | 45.702 | 85.032 | 1.00 | 62.33 | | C |
| ANISOU | 1592 | C | GLU | A | 101 | 6051 | 8980 | 8651 | 1821 | 54 | 1736 | C |
| ATOM | 1593 | O | GLU | A | 101 | -13.541 | 45.042 | 84.753 | 1.00 | 59.26 | | O |
| ANISOU | 1593 | O | GLU | A | 101 | 5847 | 8597 | 8072 | 1614 | 26 | 1700 | O |
| ATOM | 1595 | N | LYS | A | 102 | -15.241 | 45.540 | 86.154 | 1.00 | 61.86 | | N |
| ANISOU | 1595 | N | LYS | A | 102 | 5852 | 8987 | 8665 | 1913 | 218 | 1596 | N |
| ATOM | 1596 | CA | LYS | A | 102 | -14.905 | 44.520 | 87.142 | 1.00 | 60.11 | | C |
| ANISOU | 1596 | CA | LYS | A | 102 | 5693 | 8856 | 8288 | 1755 | 361 | 1409 | C |
| ATOM | 1598 | CB | LYS | A | 102 | -15.591 | 44.769 | 88.496 | 1.00 | 62.51 | | C |
| ANISOU | 1598 | CB | LYS | A | 102 | 5878 | 9175 | 8698 | 1900 | 572 | 1246 | C |
| ATOM | 1601 | CG | LYS | A | 102 | -15.716 | 43.482 | 89.333 | 1.00 | 61.91 | | C |
| ANISOU | 1601 | CG | LYS | A | 102 | 5772 | 9295 | 8457 | 1715 | 681 | 1124 | C |
| ATOM | 1604 | CD | LYS | A | 102 | -15.694 | 43.711 | 90.840 | 1.00 | 63.25 | | C |
| ANISOU | 1604 | CD | LYS | A | 102 | 5981 | 9417 | 8632 | 1780 | 912 | 914 | C |
| ATOM | 1607 | CE | LYS | A | 102 | -15.557 | 42.378 | 91.593 | 1.00 | 62.12 | | C |
| ANISOU | 1607 | CE | LYS | A | 102 | 5871 | 9443 | 8288 | 1553 | 991 | 825 | C |
| ATOM | 1610 | NZ | LYS | A | 102 | -14.873 | 42.532 | 92.913 | 1.00 | 62.77 | | N |
| ANISOU | 1610 | NZ | LYS | A | 102 | 6132 | 9430 | 8289 | 1536 | 1163 | 633 | N |
| ATOM | 1614 | C | LYS | A | 102 | -15.302 | 43.140 | 86.636 | 1.00 | 56.47 | | C |
| ANISOU | 1614 | C | LYS | A | 102 | 5126 | 8658 | 7672 | 1540 | 275 | 1468 | C |
| ATOM | 1615 | O | LYS | A | 102 | -16.492 | 42.875 | 86.443 | 1.00 | 53.45 | | O |
| ANISOU | 1615 | O | LYS | A | 102 | 4485 | 8469 | 7353 | 1573 | 240 | 1545 | O |
| ATOM | 1617 | N | PRO | A | 103 | -14.310 | 42.235 | 86.489 | 1.00 | 50.83 | | N |
| ANISOU | 1617 | N | PRO | A | 103 | 4603 | 7947 | 6762 | 1318 | 253 | 1418 | N |
| ATOM | 1618 | CA | PRO | A | 103 | -14.623 | 40.928 | 85.922 | 1.00 | 49.41 | | C |
| ANISOU | 1618 | CA | PRO | A | 103 | 4353 | 7980 | 6439 | 1104 | 166 | 1464 | C |
| ATOM | 1620 | CB | PRO | A | 103 | -13.242 | 40.372 | 85.532 | 1.00 | 47.17 | | C |
| ANISOU | 1620 | CB | PRO | A | 103 | 4330 | 7604 | 5988 | 926 | 127 | 1421 | C |
| ATOM | 1623 | CG | PRO | A | 103 | -12.284 | 41.037 | 86.434 | 1.00 | 46.27 | | C |
| ANISOU | 1623 | CG | PRO | A | 103 | 4396 | 7281 | 5902 | 1010 | 249 | 1299 | C |
| ATOM | 1626 | CD | PRO | A | 103 | -12.894 | 42.356 | 86.873 | 1.00 | 48.65 | | C |
| ANISOU | 1626 | CD | PRO | A | 103 | 4603 | 7482 | 6399 | 1257 | 310 | 1309 | C |
| ATOM | 1629 | C | PRO | A | 103 | -15.368 | 40.024 | 86.922 | 1.00 | 49.00 | | C |
| ANISOU | 1629 | C | PRO | A | 103 | 4166 | 8093 | 6361 | 1037 | 292 | 1366 | C |
| ATOM | 1630 | O | PRO | A | 103 | -15.219 | 40.170 | 88.130 | 1.00 | 48.61 | | O |
| ANISOU | 1630 | O | PRO | A | 103 | 4159 | 7980 | 6329 | 1096 | 458 | 1229 | O |
| ATOM | 1631 | N | LYS | A | 104 | -16.182 | 39.116 | 86.401 | 1.00 | 49.20 | | N |
| ANISOU | 1631 | N | LYS | A | 104 | 4028 | 8334 | 6332 | 900 | 209 | 1439 | N |
| ATOM | 1632 | CA | LYS | A | 104 | -16.886 | 38.118 | 87.217 | 1.00 | 50.49 | | C |
| ANISOU | 1632 | CA | LYS | A | 104 | 4067 | 8668 | 6448 | 784 | 311 | 1368 | C |
| ATOM | 1634 | CB | LYS | A | 104 | -17.998 | 37.515 | 86.366 | 1.00 | 53.16 | | C |
| ANISOU | 1634 | CB | LYS | A | 104 | 4170 | 9247 | 6780 | 676 | 178 | 1493 | C |
| ATOM | 1637 | CG | LYS | A | 104 | -18.908 | 36.534 | 87.048 | 1.00 | 55.48 | | C |
| ANISOU | 1637 | CG | LYS | A | 104 | 4293 | 9744 | 7041 | 541 | 263 | 1452 | C |
| ATOM | 1640 | CD | LYS | A | 104 | -19.899 | 35.974 | 86.029 | 1.00 | 58.04 | | C |
| ANISOU | 1640 | CD | LYS | A | 104 | 4401 | 10302 | 7349 | 406 | 99 | 1584 | C |
| ATOM | 1643 | CE | LYS | A | 104 | -21.155 | 35.418 | 86.673 | 1.00 | 60.51 | | C |
| ANISOU | 1643 | CE | LYS | A | 104 | 4438 | 10853 | 7702 | 340 | 182 | 1578 | C |
| ATOM | 1646 | NZ | LYS | A | 104 | -22.257 | 35.323 | 85.673 | 1.00 | 64.09 | | N |
| ANISOU | 1646 | NZ | LYS | A | 104 | 4614 | 11541 | 8196 | 287 | 10 | 1729 | N |
| ATOM | 1650 | C | LYS | A | 104 | -15.933 | 37.006 | 87.711 | 1.00 | 47.06 | | C |
| ANISOU | 1650 | C | LYS | A | 104 | 3858 | 8179 | 5844 | 578 | 366 | 1259 | C |
| ATOM | 1651 | O | LYS | A | 104 | -16.153 | 36.382 | 88.751 | 1.00 | 49.72 | | O |
| ANISOU | 1651 | O | LYS | A | 104 | 4178 | 8575 | 6138 | 508 | 494 | 1173 | O |
| ATOM | 1653 | N | PHE | A | 105 | -14.893 | 36.751 | 86.935 | 1.00 | 42.65 | | N |
| ANISOU | 1653 | N | PHE | A | 105 | 3501 | 7513 | 5190 | 481 | 268 | 1272 | N |
| ATOM | 1654 | CA | PHE | A | 105 | -13.890 | 35.740 | 87.235 | 1.00 | 40.17 | | C |
| ANISOU | 1654 | CA | PHE | A | 105 | 3400 | 7124 | 4740 | 311 | 298 | 1183 | C |
| ATOM | 1656 | CB | PHE | A | 105 | -13.703 | 34.854 | 85.994 | 1.00 | 40.89 | | C |
| ANISOU | 1656 | CB | PHE | A | 105 | 3541 | 7271 | 4726 | 123 | 154 | 1235 | C |

FIG. 18 (continued)

```
ATOM   1665  C   PHE A 105    -12.563  36.439  87.558  1.00 35.91           C
ANISOU 1665  C   PHE A 105    3078   6367   4198    402    343   1114         C
ATOM   1666  O   PHE A 105    -12.258  37.492  86.991  1.00 33.69           O
ANISOU 1666  O   PHE A 105    2827   5992   3981    525    291   1164         O
ATOM   1668  N   LEU A 106    -11.760  35.817  88.409  1.00 32.84           N
ANISOU 1668  N   LEU A 106    2842   5903   3731    323    424   1015         N
ATOM   1669  CA  LEU A 106    -10.459  36.339  88.762  1.00 32.13           C
ANISOU 1669  CA  LEU A 106    2949   5632   3626    377    459    948         C
ATOM   1671  CB  LEU A 106     -9.894  35.594  89.964  1.00 32.75           C
ANISOU 1671  CB  LEU A 106    3139   5678   3627    296    553    854         C
ATOM   1674  CG  LEU A 106     -9.261  36.283  91.171  1.00 34.36           C
ANISOU 1674  CG  LEU A 106    3445   5778   3833    382    661    761         C
ATOM   1676  CD1 LEU A 106     -7.953  35.530  91.510  1.00 32.24           C
ANISOU 1676  CD1 LEU A 106    3361   5420   3467    273    645    717         C
ATOM   1680  CD2 LEU A 106     -9.055  37.780  91.096  1.00 32.13           C
ANISOU 1680  CD2 LEU A 106    3180   5382   3646    553    678    742         C
ATOM   1684  C   LEU A 106     -9.513  36.135  87.589  1.00 30.77           C
ANISOU 1684  C   LEU A 106    2902   5392   3396    299    346    982         C
ATOM   1685  O   LEU A 106     -9.188  34.998  87.270  1.00 30.51           O
ANISOU 1685  O   LEU A 106    2930   5386   3277    147    311    966         O
ATOM   1687  N   PRO A 107     -9.062  37.225  86.948  1.00 32.33           N
ANISOU 1687  N   PRO A 107    3146   5497   3641    397    298   1025         N
ATOM   1688  CA  PRO A 107     -8.127  37.067  85.825  1.00 31.83           C
ANISOU 1688  CA  PRO A 107    3201   5389   3506    310    209   1053         C
ATOM   1690  CB  PRO A 107     -8.328  38.358  85.029  1.00 34.03           C
ANISOU 1690  CB  PRO A 107    3444   5629   3857    424    138   1160         C
ATOM   1693  CG  PRO A 107     -8.730  39.359  86.027  1.00 35.91           C
ANISOU 1693  CG  PRO A 107    3635   5790   4221    597    225   1133         C
ATOM   1696  CD  PRO A 107     -9.352  38.648  87.217  1.00 34.58           C
ANISOU 1696  CD  PRO A 107    3386   5702   4049    585    331   1046         C
ATOM   1699  C   PRO A 107     -6.664  36.899  86.277  1.00 28.45           C
ANISOU 1699  C   PRO A 107    2954   4827   3028    273    258    959         C
ATOM   1700  O   PRO A 107     -6.371  36.844  87.473  1.00 28.40           O
ANISOU 1700  O   PRO A 107    2991   4769   3032    302    346    880         O
ATOM   1701  N   ASP A 108     -5.748  36.853  85.323  1.00 27.20           N
ANISOU 1701  N   ASP A 108    2892   4631   2813    207    201    971         N
ATOM   1702  CA  ASP A 108     -4.341  36.614  85.640  1.00 26.33           C
ANISOU 1702  CA  ASP A 108    2923   4417   2663    167    240    888         C
ATOM   1704  CB  ASP A 108     -3.734  35.677  84.599  1.00 23.93           C
ANISOU 1704  CB  ASP A 108    2674   4149   2270     35    195    871         C
ATOM   1707  CG  ASP A 108     -4.221  34.291  84.717  1.00 26.16           C
ANISOU 1707  CG  ASP A 108    2927   4500   2514    -63    197    834         C
ATOM   1708  OD1 ASP A 108     -4.249  33.741  85.868  1.00 26.57           O
ANISOU 1708  OD1 ASP A 108    2987   4522   2587    -56    254    786         O
ATOM   1709  OD2 ASP A 108     -4.545  33.726  83.651  1.00 27.02           O
ANISOU 1709  OD2 ASP A 108    3017   4689   2560   -162    139    851         O
ATOM   1710  C   ASP A 108     -3.498  37.909  85.733  1.00 26.79           C
ANISOU 1710  C   ASP A 108    3062   4350   2766    248    255    890         C
ATOM   1711  O   ASP A 108     -2.553  37.993  86.535  1.00 26.02           O
ANISOU 1711  O   ASP A 108    3050   4167   2668    253    307    814         O
ATOM   1713  N   LEU A 109     -3.810  38.862  84.857  1.00 27.82           N
ANISOU 1713  N   LEU A 109    3169   4473   2928    293    196    988         N
ATOM   1714  CA  LEU A 109     -3.083  40.134  84.726  1.00 29.24           C
ANISOU 1714  CA  LEU A 109    3434   4522   3154    348    195   1015         C
ATOM   1716  CB  LEU A 109     -2.064  40.082  83.584  1.00 31.81           C
ANISOU 1716  CB  LEU A 109    3841   4852   3393    237    149   1046         C
ATOM   1719  CG  LEU A 109     -0.867  39.152  83.518  1.00 32.41           C
ANISOU 1719  CG  LEU A 109    3986   4945   3385    125    183    950         C
ATOM   1721  CD1 LEU A 109      0.015  39.561  82.305  1.00 32.29           C
ANISOU 1721  CD1 LEU A 109    4035   4934   3301     39    151    999         C
ATOM   1725  CD2 LEU A 109     -0.053  39.162  84.846  1.00 31.02           C
ANISOU 1725  CD2 LEU A 109    3863   4676   3247    158    256    845         C
ATOM   1729  C   LEU A 109     -4.021  41.265  84.385  1.00 30.85           C
ANISOU 1729  C   LEU A 109    3572   4695   3456    466    151   1128         C
ATOM   1730  O   LEU A 109     -5.124  41.021  83.839  1.00 27.87           O
ANISOU 1730  O   LEU A 109    3072   4432   3085    481     90   1213         O
ATOM   1732  N   TYR A 110     -3.616  42.489  84.758  1.00 30.67           N
ANISOU 1732  N   TYR A 110    3622   4512   3518    553    178   1128         N
ATOM   1733  CA ATYR A 110     -4.206  43.703  84.170  0.50 32.97           C
ANISOU 1733  CA ATYR A 110    3890   4724   3915    661    117   1261         C
ATOM   1734  CA BTYR A 110     -4.201  43.708  84.188  0.50 32.99           C
ANISOU 1734  CA BTYR A 110    3893   4724   3918    662    119   1259         C
ATOM   1737  CB ATYR A 110     -4.671  44.737  85.201  0.50 34.78           C
ANISOU 1737  CB ATYR A 110    4112   4803   4299    832    192   1212         C
ATOM   1738  CB BTYR A 110     -4.611  44.725  85.254  0.50 34.74           C
ANISOU 1738  CB BTYR A 110    4114   4794   4291    829    197   1203         C
ATOM   1743  CG ATYR A 110     -5.385  45.901  84.549  0.50 36.87           C
ANISOU 1743  CG ATYR A 110    4336   4973   4700    966    119   1365         C
ATOM   1744  CG BTYR A 110     -5.274  45.929  84.645  0.50 36.87           C
```

FIG. 18 (continued)

```
ANISOU 1744  CG BTYR A 110    4351  4958  4698   963   130  1349       C
ATOM   1745  CD1ATYR A 110    -6.586  45.704  83.882  0.50 38.79       C
ANISOU 1745  CD1ATYR A 110    4413  5347  4977  1025    34  1496       C
ATOM   1746  CD1BTYR A 110    -6.556  45.838  84.124  0.50 38.83       C
ANISOU 1746  CD1BTYR A 110    4429  5319  5005  1048    58  1470       C
ATOM   1749  CE1ATYR A 110    -7.260  46.743  83.273  0.50 40.71       C
ANISOU 1749  CE1ATYR A 110    4604  5508  5357  1160   -51  1659       C
ATOM   1750  CE1BTYR A 110    -7.184  46.918  83.548  0.50 40.56       C
ANISOU 1750  CE1BTYR A 110    4604  5442  5365  1186   -21  1627       C
ATOM   1753  CZ ATYR A 110    -6.734  48.015  83.289  0.50 41.68       C
ANISOU 1753  CZ ATYR A 110    4859  5388  5588  1234   -48  1695       C
ATOM   1754  CZ BTYR A 110    -6.530  48.124  83.453  0.50 41.45       C
ANISOU 1754  CZ BTYR A 110    4865  5320  5563  1232   -27  1667       C
ATOM   1755  OH ATYR A 110    -7.432  49.037  82.677  0.50 43.79       O
ANISOU 1755  OH ATYR A 110    5077  5552  6010  1381  -143  1877       O
ATOM   1756  OH BTYR A 110    -7.164  49.201  82.880  0.50 43.77       O
ANISOU 1756  OH BTYR A 110    5124  5492  6016  1379  -114  1841       O
ATOM   1759  CE2ATYR A 110    -5.540  48.257  83.927  0.50 40.43       C
ANISOU 1759  CE2ATYR A 110    4877  5090  5393  1160    42  1557       C
ATOM   1760  CE2BTYR A 110    -5.258  48.255  83.940  0.50 40.21       C
ANISOU 1760  CE2BTYR A 110    4885  5048  5344  1129    48  1542       C
ATOM   1763  CD2ATYR A 110    -4.854  47.188  84.559  0.50 38.71       C
ANISOU 1763  CD2ATYR A 110    4694  4984  5032  1025   122  1392       C
ATOM   1764  CD2BTYR A 110    -4.616  47.149  84.539  0.50 38.21       C
ANISOU 1764  CD2BTYR A 110    4656  4915  4946   996   123  1383       C
ATOM   1767  C    TYR A 110    -3.199  44.383  83.263  1.00 33.50       C
ANISOU 1767  C    TYR A 110    4081  4703  3944   583    62  1340       C
ATOM   1768  O    TYR A 110    -2.030  44.522  83.616  1.00 33.42       O
ANISOU 1768  O    TYR A 110    4187  4610  3900   516   113  1257       O
ATOM   1770  N    ASP A 111    -3.680  44.813  82.107  1.00 35.03       N
ANISOU 1770  N    ASP A 111    4242  4930  4138   585   -47  1512       N
ATOM   1771  CA   ASP A 111    -2.878  45.530  81.116  1.00 37.42       C
ANISOU 1771  CA   ASP A 111    4658  5166  4395   500  -109  1626       C
ATOM   1773  CB   ASP A 111    -3.110  44.891  79.747  1.00 36.43       C
ANISOU 1773  CB   ASP A 111    4490  5232  4121   372  -213  1743       C
ATOM   1776  CG   ASP A 111    -2.240  45.510  78.621  1.00 38.67       C
ANISOU 1776  CG   ASP A 111    4892  5489  4311   245  -270  1865       C
ATOM   1777  OD1  ASP A 111    -1.670  46.632  78.776  1.00 37.15       O
ANISOU 1777  OD1  ASP A 111    4803  5110  4201   275  -258  1911       O
ATOM   1778  OD2  ASP A 111    -2.174  44.867  77.534  1.00 37.78       O
ANISOU 1778  OD2  ASP A 111    4771  5551  4033   101  -329  1918       O
ATOM   1779  C    ASP A 111    -3.303  47.013  81.087  1.00 39.95       C
ANISOU 1779  C    ASP A 111    5006  5293  4879   643  -152  1753       C
ATOM   1780  O    ASP A 111    -4.361  47.351  80.551  1.00 41.48       O
ANISOU 1780  O    ASP A 111    5102  5518  5142   738  -245  1905       O
ATOM   1782  N    TYR A 112    -2.506  47.883  81.706  1.00 41.76       N
ANISOU 1782  N    TYR A 112    5364  5318  5185   663   -87  1689       N
ATOM   1783  CA   TYR A 112    -2.855  49.309  81.799  1.00 44.65       C
ANISOU 1783  CA   TYR A 112    5782  5452  5733   805  -111  1785       C
ATOM   1785  CB   TYR A 112    -1.979  50.038  82.826  1.00 46.56       C
ANISOU 1785  CB   TYR A 112    6166  5477  6048   811    -6  1637       C
ATOM   1788  CG   TYR A 112    -2.186  49.620  84.277  1.00 46.28       C
ANISOU 1788  CG   TYR A 112    6091  5446  6049   889   120  1416       C
ATOM   1789  CD1  TYR A 112    -3.246  50.131  85.034  1.00 47.39       C
ANISOU 1789  CD1  TYR A 112    6162  5492  6354  1093   173  1371       C
ATOM   1791  CE1  TYR A 112    -3.423  49.747  86.370  1.00 47.32       C
ANISOU 1791  CE1  TYR A 112    6123  5508  6348  1143   300  1166       C
ATOM   1793  CZ   TYR A 112    -2.511  48.885  86.945  1.00 44.57       C
ANISOU 1793  CZ   TYR A 112    5824  5263  5847   991   352  1031       C
ATOM   1794  OH   TYR A 112    -2.620  48.473  88.235  1.00 45.33       O
ANISOU 1794  OH   TYR A 112    5905  5399  5918  1014   462   851       O
ATOM   1796  CE2  TYR A 112    -1.454  48.394  86.223  1.00 43.84       C
ANISOU 1796  CE2  TYR A 112    5792  5247  5620   812   293  1078       C
ATOM   1798  CD2  TYR A 112    -1.289  48.760  84.910  1.00 44.02       C
ANISOU 1798  CD2  TYR A 112    5838  5256  5633   760   190  1257       C
ATOM   1800  C    TYR A 112    -2.746  50.003  80.453  1.00 46.33       C
ANISOU 1800  C    TYR A 112    6052  5630  5923   744  -241  2021       C
ATOM   1801  O    TYR A 112    -3.324  51.072  80.245  1.00 49.10       O
ANISOU 1801  O    TYR A 112    6413  5813  6431   878  -304  2165       O
ATOM   1803  N    LYS A 113    -2.020  49.396  79.522  1.00 45.38       N
ANISOU 1803  N    LYS A 113    5968  5666  5607   544  -281  2067       N
ATOM   1804  CA   LYS A 113    -1.923  49.943  78.167  1.00 48.09       C
ANISOU 1804  CA   LYS A 113    6366  6023  5882   451  -406  2302       C
ATOM   1806  CB   LYS A 113    -0.706  49.372  77.435  1.00 47.46       C
ANISOU 1806  CB   LYS A 113    6369  6083  5582   205  -383  2274       C
ATOM   1809  CG   LYS A 113    -0.459  50.009  76.088  1.00 50.63       C
ANISOU 1809  CG   LYS A 113    6852  6500  5886    76  -493  2509       C
ATOM   1812  CD   LYS A 113     1.004  49.910  75.698  1.00 50.77       C
ANISOU 1812  CD   LYS A 113    6983  6560  5749   -146  -421  2453       C
```

FIG. 18 (continued)

| | | | | | | | | | | | | |
|---|---|---|---|---|---|---|---|---|---|---|---|---|
| ATOM | 1815 | CE | LYS | A | 113 | 1.322 | 50.701 | 74.424 | 1.00 | 53.31 | | C |
| ANISOU | 1815 | CE | LYS | A | 113 | 7407 | 6879 | 5969 | -294 | -516 | 2698 | C |
| ATOM | 1818 | NZ | LYS | A | 113 | 1.154 | 49.877 | 73.193 | 1.00 | 55.62 | | N |
| ANISOU | 1818 | NZ | LYS | A | 113 | 7653 | 7458 | 6021 | -447 | -578 | 2774 | N |
| ATOM | 1822 | C | LYS | A | 113 | -3.217 | 49.734 | 77.353 | 1.00 | 47.80 | | C |
| ANISOU | 1822 | C | LYS | A | 113 | 6190 | 6135 | 5839 | 519 | -544 | 2484 | C |
| ATOM | 1823 | O | LYS | A | 113 | -3.790 | 50.699 | 76.825 | 1.00 | 49.42 | | O |
| ANISOU | 1823 | O | LYS | A | 113 | 6398 | 6232 | 6149 | 610 | -658 | 2699 | O |
| ATOM | 1825 | N | GLU | A | 114 | -3.680 | 48.488 | 77.282 | 1.00 | 46.08 | | N |
| ANISOU | 1825 | N | GLU | A | 114 | 5847 | 6155 | 5507 | 474 | -542 | 2402 | N |
| ATOM | 1826 | CA | GLU | A | 114 | -4.890 | 48.134 | 76.549 | 1.00 | 46.36 | | C |
| ANISOU | 1826 | CA | GLU | A | 114 | 5732 | 6371 | 5513 | 506 | -675 | 2551 | C |
| ATOM | 1828 | CB | GLU | A | 114 | -4.813 | 46.699 | 76.030 | 1.00 | 45.98 | | C |
| ANISOU | 1828 | CB | GLU | A | 114 | 5633 | 6595 | 5241 | 324 | -674 | 2462 | C |
| ATOM | 1831 | CG | GLU | A | 114 | -3.627 | 46.385 | 75.131 | 1.00 | 46.29 | | C |
| ANISOU | 1831 | CG | GLU | A | 114 | 5809 | 6718 | 5061 | 90 | -661 | 2453 | C |
| ATOM | 1834 | CD | GLU | A | 114 | -3.669 | 47.049 | 73.763 | 1.00 | 49.91 | | C |
| ANISOU | 1834 | CD | GLU | A | 114 | 6322 | 7232 | 5409 | -13 | -808 | 2707 | C |
| ATOM | 1835 | OE1 | GLU | A | 114 | -4.740 | 47.488 | 73.282 | 1.00 | 53.52 | | O |
| ANISOU | 1835 | OE1 | GLU | A | 114 | 6688 | 7725 | 5920 | 71 | -958 | 2911 | O |
| ATOM | 1836 | OE2 | GLU | A | 114 | -2.601 | 47.126 | 73.133 | 1.00 | 51.33 | | O |
| ANISOU | 1836 | OE2 | GLU | A | 114 | 6631 | 7433 | 5438 | -188 | -777 | 2711 | O |
| ATOM | 1837 | C | GLU | A | 114 | -6.133 | 48.288 | 77.418 | 1.00 | 46.21 | | C |
| ANISOU | 1837 | C | GLU | A | 114 | 5549 | 6306 | 5701 | 741 | -665 | 2530 | C |
| ATOM | 1838 | O | GLU | A | 114 | -7.236 | 48.105 | 76.931 | 1.00 | 46.13 | | O |
| ANISOU | 1838 | O | GLU | A | 114 | 5384 | 6437 | 5707 | 794 | -778 | 2660 | O |
| ATOM | 1840 | N | ASN | A | 115 | -5.945 | 48.586 | 78.704 | 1.00 | 44.75 | | N |
| ANISOU | 1840 | N | ASN | A | 115 | 5393 | 5949 | 5663 | 866 | -525 | 2357 | N |
| ATOM | 1841 | CA | ASN | A | 115 | -7.042 | 48.746 | 79.651 | 1.00 | 45.53 | | C |
| ANISOU | 1841 | CA | ASN | A | 115 | 5341 | 6004 | 5953 | 1086 | -475 | 2299 | C |
| ATOM | 1843 | CB | ASN | A | 115 | -7.865 | 49.988 | 79.346 | 1.00 | 50.82 | | C |
| ANISOU | 1843 | CB | ASN | A | 115 | 5956 | 6520 | 6834 | 1288 | -573 | 2499 | C |
| ATOM | 1846 | CG | ASN | A | 115 | -7.014 | 51.233 | 79.254 | 1.00 | 52.61 | | C |
| ANISOU | 1846 | CG | ASN | A | 115 | 6387 | 6459 | 7145 | 1302 | -572 | 2563 | C |
| ATOM | 1847 | OD1 | ASN | A | 115 | -7.082 | 51.982 | 78.267 | 1.00 | 57.26 | | O |
| ANISOU | 1847 | OD1 | ASN | A | 115 | 7019 | 6979 | 7757 | 1300 | -714 | 2804 | O |
| ATOM | 1848 | ND2 | ASN | A | 115 | -6.187 | 51.458 | 80.270 | 1.00 | 52.51 | | N |
| ANISOU | 1848 | ND2 | ASN | A | 115 | 6505 | 6280 | 7167 | 1296 | -420 | 2357 | N |
| ATOM | 1851 | C | ASN | A | 115 | -7.945 | 47.555 | 79.677 | 1.00 | 43.56 | | C |
| ANISOU | 1851 | C | ASN | A | 115 | 4903 | 6015 | 5633 | 1062 | -488 | 2257 | C |
| ATOM | 1852 | O | ASN | A | 115 | -9.141 | 47.682 | 79.502 | 1.00 | 44.03 | | O |
| ANISOU | 1852 | O | ASN | A | 115 | 4783 | 6152 | 5794 | 1187 | -565 | 2370 | O |
| ATOM | 1854 | N | ARG | A | 116 | -7.364 | 46.391 | 79.907 | 1.00 | 41.20 | | N |
| ANISOU | 1854 | N | ARG | A | 116 | 4639 | 5845 | 5168 | 899 | -415 | 2097 | N |
| ATOM | 1855 | CA | ARG | A | 116 | -8.159 | 45.196 | 79.990 | 1.00 | 39.67 | | C |
| ANISOU | 1855 | CA | ARG | A | 116 | 4290 | 5878 | 4905 | 850 | -419 | 2044 | C |
| ATOM | 1857 | CB | ARG | A | 116 | -8.409 | 44.609 | 78.604 | 1.00 | 40.42 | | C |
| ANISOU | 1857 | CB | ARG | A | 116 | 4343 | 6182 | 4832 | 688 | -570 | 2185 | C |
| ATOM | 1860 | CG | ARG | A | 116 | -7.160 | 44.102 | 77.901 | 1.00 | 38.50 | | C |
| ANISOU | 1860 | CG | ARG | A | 116 | 4272 | 5974 | 4384 | 470 | -564 | 2138 | C |
| ATOM | 1863 | CD | ARG | A | 116 | -7.371 | 44.094 | 76.390 | 1.00 | 40.36 | | C |
| ANISOU | 1863 | CD | ARG | A | 116 | 4501 | 6364 | 4470 | 337 | -728 | 2326 | C |
| ATOM | 1866 | NE | ARG | A | 116 | -6.189 | 43.577 | 75.699 | 1.00 | 39.17 | | N |
| ANISOU | 1866 | NE | ARG | A | 116 | 4505 | 6265 | 4112 | 125 | -698 | 2260 | N |
| ATOM | 1868 | CZ | ARG | A | 116 | -5.933 | 43.726 | 74.402 | 1.00 | 40.64 | | C |
| ANISOU | 1868 | CZ | ARG | A | 116 | 4754 | 6554 | 4133 | -23 | -803 | 2397 | C |
| ATOM | 1869 | NH1 | ARG | A | 116 | -6.771 | 44.380 | 73.629 | 1.00 | 43.04 | | N |
| ANISOU | 1869 | NH1 | ARG | A | 116 | 4987 | 6917 | 4448 | 11 | -968 | 2632 | N |
| ATOM | 1872 | NH2 | ARG | A | 116 | -4.832 | 43.218 | 73.875 | 1.00 | 38.90 | | N |
| ANISOU | 1872 | NH2 | ARG | A | 116 | 4663 | 6386 | 3732 | -207 | -741 | 2302 | N |
| ATOM | 1875 | C | ARG | A | 116 | -7.438 | 44.231 | 80.858 | 1.00 | 35.53 | | C |
| ANISOU | 1875 | C | ARG | A | 116 | 3835 | 5372 | 4294 | 753 | -282 | 1823 | C |
| ATOM | 1876 | O | ARG | A | 116 | -6.227 | 44.307 | 81.050 | 1.00 | 34.06 | | O |
| ANISOU | 1876 | O | ARG | A | 116 | 3810 | 5080 | 4050 | 679 | -218 | 1736 | O |
| ATOM | 1878 | N | PHE | A | 117 | -8.225 | 43.349 | 81.424 | 1.00 | 34.44 | | N |
| ANISOU | 1878 | N | PHE | A | 117 | 3561 | 5367 | 4156 | 760 | -240 | 1744 | N |
| ATOM | 1879 | CA | PHE | A | 117 | -7.701 | 42.227 | 82.132 | 1.00 | 32.67 | | C |
| ANISOU | 1879 | CA | PHE | A | 117 | 3386 | 5191 | 3837 | 650 | -138 | 1568 | C |
| ATOM | 1881 | CB | PHE | A | 117 | -8.714 | 41.781 | 83.162 | 1.00 | 32.79 | | C |
| ANISOU | 1881 | CB | PHE | A | 117 | 3251 | 5280 | 3927 | 729 | -61 | 1494 | C |
| ATOM | 1884 | CG | PHE | A | 117 | -8.904 | 42.756 | 84.270 | 1.00 | 32.52 | | C |
| ANISOU | 1884 | CG | PHE | A | 117 | 3209 | 5097 | 4051 | 917 | 45 | 1432 | C |
| ATOM | 1885 | CD1 | PHE | A | 117 | -8.028 | 42.784 | 85.326 | 1.00 | 30.93 | | C |
| ANISOU | 1885 | CD1 | PHE | A | 117 | 3140 | 4776 | 3834 | 911 | 167 | 1277 | C |
| ATOM | 1887 | CE1 | PHE | A | 117 | -8.205 | 43.675 | 86.384 | 1.00 | 32.60 | | C |
| ANISOU | 1887 | CE1 | PHE | A | 117 | 3358 | 4855 | 4172 | 1067 | 276 | 1194 | C |
| ATOM | 1889 | CZ | PHE | A | 117 | -9.289 | 44.537 | 86.385 | 1.00 | 34.44 | | C |
| ANISOU | 1889 | CZ | PHE | A | 117 | 3454 | 5060 | 4572 | 1254 | 274 | 1263 | C |
| ATOM | 1891 | CE2 | PHE | A | 117 | -10.182 | 44.503 | 85.345 | 1.00 | 35.37 | | C |

FIG. 18 (continued)

| | | | | | | | | | | | | |
|---|---|---|---|---|---|---|---|---|---|---|---|---|
| ANISOU | 1891 | CE2 | PHE | A | 117 | 3417 | 5295 | 4725 | 1280 | 145 | 1434 | C |
| ATOM | 1893 | CD2 | PHE | A | 117 | -9.982 | 43.612 | 84.279 | 1.00 | 35.22 | | C |
| ANISOU | 1893 | CD2 | PHE | A | 117 | 3402 | 5425 | 4555 | 1099 | 24 | 1522 | C |
| ATOM | 1895 | C | PHE | A | 117 | -7.414 | 41.126 | 81.120 | 1.00 | 32.66 | | C |
| ANISOU | 1895 | C | PHE | A | 117 | 3410 | 5345 | 3654 | 446 | -210 | 1580 | C |
| ATOM | 1896 | O | PHE | A | 117 | -8.081 | 41.022 | 80.079 | 1.00 | 32.09 | | O |
| ANISOU | 1896 | O | PHE | A | 117 | 3256 | 5408 | 3530 | 393 | -333 | 1709 | O |
| ATOM | 1898 | N | ILE | A | 118 | -6.403 | 40.325 | 81.434 | 1.00 | 31.44 | | N |
| ANISOU | 1898 | N | ILE | A | 118 | 3371 | 5168 | 3406 | 335 | -133 | 1441 | N |
| ATOM | 1899 | CA | ILE | A | 118 | -5.980 | 39.234 | 80.577 | 1.00 | 31.47 | | C |
| ANISOU | 1899 | CA | ILE | A | 118 | 3422 | 5287 | 3250 | 150 | -168 | 1408 | C |
| ATOM | 1901 | CB | ILE | A | 118 | -4.493 | 39.371 | 80.168 | 1.00 | 30.83 | | C |
| ANISOU | 1901 | CB | ILE | A | 118 | 3503 | 5121 | 3089 | 70 | -135 | 1359 | C |
| ATOM | 1903 | CG1 | ILE | A | 118 | -4.226 | 40.699 | 79.447 | 1.00 | 32.53 | | C |
| ANISOU | 1903 | CG1 | ILE | A | 118 | 3769 | 5267 | 3323 | 108 | -199 | 1501 | C |
| ATOM | 1906 | CD1 | ILE | A | 118 | -2.657 | 40.972 | 79.171 | 1.00 | 31.41 | | C |
| ANISOU | 1906 | CD1 | ILE | A | 118 | 3782 | 5039 | 3114 | 23 | -146 | 1450 | C |
| ATOM | 1910 | CG2 | ILE | A | 118 | -4.038 | 38.175 | 79.305 | 1.00 | 32.99 | | C |
| ANISOU | 1910 | CG2 | ILE | A | 118 | 3822 | 5509 | 3203 | -111 | -146 | 1292 | C |
| ATOM | 1914 | C | ILE | A | 118 | -6.134 | 37.932 | 81.344 | 1.00 | 29.63 | | C |
| ANISOU | 1914 | C | ILE | A | 118 | 3162 | 5104 | 2992 | 89 | -97 | 1275 | C |
| ATOM | 1915 | O | ILE | A | 118 | -5.744 | 37.853 | 82.509 | 1.00 | 26.21 | | O |
| ANISOU | 1915 | O | ILE | A | 118 | 2766 | 4578 | 2616 | 148 | 1 | 1177 | O |
| ATOM | 1917 | N | GLU | A | 119 | -6.681 | 36.926 | 80.654 | 1.00 | 29.65 | | N |
| ANISOU | 1917 | N | GLU | A | 119 | 3112 | 5253 | 2901 | -43 | -155 | 1278 | N |
| ATOM | 1918 | CA | GLU | A | 119 | -6.774 | 35.552 | 81.133 | 1.00 | 29.48 | | C |
| ANISOU | 1918 | CA | GLU | A | 119 | 3090 | 5270 | 2839 | -143 | -105 | 1163 | C |
| ATOM | 1920 | CB | GLU | A | 119 | -8.222 | 35.052 | 81.015 | 1.00 | 31.71 | | C |
| ANISOU | 1920 | CB | GLU | A | 119 | 3210 | 5711 | 3126 | -189 | -166 | 1220 | C |
| ATOM | 1923 | CG | GLU | A | 119 | -8.436 | 33.597 | 81.435 | 1.00 | 31.96 | | C |
| ANISOU | 1923 | CG | GLU | A | 119 | 3247 | 5781 | 3117 | -321 | -125 | 1117 | C |
| ATOM | 1926 | CD | GLU | A | 119 | -8.043 | 33.329 | 82.887 | 1.00 | 32.35 | | C |
| ANISOU | 1926 | CD | GLU | A | 119 | 3340 | 5715 | 3236 | -254 | -4 | 1030 | C |
| ATOM | 1927 | OE1 | GLU | A | 119 | -8.187 | 34.216 | 83.759 | 1.00 | 33.88 | | O |
| ANISOU | 1927 | OE1 | GLU | A | 119 | 3491 | 5860 | 3522 | -105 | 50 | 1051 | O |
| ATOM | 1928 | OE2 | GLU | A | 119 | -7.595 | 32.211 | 83.151 | 1.00 | 30.56 | | O |
| ANISOU | 1928 | OE2 | GLU | A | 119 | 3197 | 5445 | 2970 | -354 | 36 | 940 | O |
| ATOM | 1929 | C | GLU | A | 119 | -5.811 | 34.655 | 80.343 | 1.00 | 26.83 | | C |
| ANISOU | 1929 | C | GLU | A | 119 | 2880 | 4935 | 2377 | -296 | -101 | 1075 | C |
| ATOM | 1930 | O | GLU | A | 119 | -5.953 | 34.464 | 79.128 | 1.00 | 28.62 | | O |
| ANISOU | 1930 | O | GLU | A | 119 | 3113 | 5266 | 2494 | -410 | -178 | 1111 | O |
| ATOM | 1932 | N | ILE | A | 120 | -4.822 | 34.124 | 81.058 | 1.00 | 28.08 | | N |
| ANISOU | 1932 | N | ILE | A | 120 | 3136 | 4980 | 2553 | -292 | -8 | 957 | N |
| ATOM | 1933 | CA | ILE | A | 120 | -3.814 | 33.237 | 80.515 | 1.00 | 27.71 | | C |
| ANISOU | 1933 | CA | ILE | A | 120 | 3198 | 4905 | 2424 | -401 | 24 | 849 | C |
| ATOM | 1935 | CB | ILE | A | 120 | -2.389 | 33.641 | 81.009 | 1.00 | 28.47 | | C |
| ANISOU | 1935 | CB | ILE | A | 120 | 3388 | 4869 | 2560 | -330 | 100 | 790 | C |
| ATOM | 1937 | CG1 | ILE | A | 120 | -2.046 | 35.036 | 80.470 | 1.00 | 27.40 | | C |
| ANISOU | 1937 | CG1 | ILE | A | 120 | 3266 | 4726 | 2418 | -280 | 70 | 882 | C |
| ATOM | 1940 | CD1 | ILE | A | 120 | -0.891 | 35.704 | 81.146 | 1.00 | 27.72 | | C |
| ANISOU | 1940 | CD1 | ILE | A | 120 | 3371 | 4644 | 2518 | -205 | 133 | 848 | C |
| ATOM | 1944 | CG2 | ILE | A | 120 | -1.303 | 32.614 | 80.540 | 1.00 | 27.82 | | C |
| ANISOU | 1944 | CG2 | ILE | A | 120 | 3395 | 4755 | 2421 | -419 | 151 | 663 | C |
| ATOM | 1948 | C | ILE | A | 120 | -4.133 | 31.745 | 80.753 | 1.00 | 28.03 | | C |
| ANISOU | 1948 | C | ILE | A | 120 | 3246 | 4954 | 2448 | -503 | 44 | 757 | C |
| ATOM | 1949 | O | ILE | A | 120 | -4.724 | 31.358 | 81.771 | 1.00 | 29.24 | | O |
| ANISOU | 1949 | O | ILE | A | 120 | 3352 | 5090 | 2669 | -474 | 68 | 757 | O |
| ATOM | 1951 | N | GLY | A | 121 | -3.818 | 30.928 | 79.751 | 1.00 | 27.10 | | N |
| ANISOU | 1951 | N | GLY | A | 121 | 3192 | 4871 | 2233 | -636 | 35 | 681 | N |
| ATOM | 1952 | CA | GLY | A | 121 | -3.902 | 29.491 | 79.865 | 1.00 | 27.84 | | C |
| ANISOU | 1952 | CA | GLY | A | 121 | 3330 | 4929 | 2320 | -740 | 62 | 573 | C |
| ATOM | 1955 | C | GLY | A | 121 | -2.786 | 28.821 | 79.079 | 1.00 | 27.26 | | C |
| ANISOU | 1955 | C | GLY | A | 121 | 3373 | 4801 | 2185 | -809 | 114 | 439 | C |
| ATOM | 1956 | O | GLY | A | 121 | -2.300 | 29.381 | 78.088 | 1.00 | 27.54 | | O |
| ANISOU | 1956 | O | GLY | A | 121 | 3435 | 4900 | 2130 | -839 | 107 | 439 | O |
| ATOM | 1958 | N | VAL | A | 122 | -2.370 | 27.641 | 79.561 | 1.00 | 27.39 | | N |
| ANISOU | 1958 | N | VAL | A | 122 | 3455 | 4694 | 2257 | -830 | 172 | 329 | N |
| ATOM | 1959 | CA | VAL | A | 122 | -1.303 | 26.829 | 78.953 | 1.00 | 27.56 | | C |
| ANISOU | 1959 | CA | VAL | A | 122 | 3579 | 4634 | 2259 | -872 | 242 | 176 | C |
| ATOM | 1961 | CB | VAL | A | 122 | -0.025 | 26.782 | 79.828 | 1.00 | 25.64 | | C |
| ANISOU | 1961 | CB | VAL | A | 122 | 3368 | 4238 | 2134 | -732 | 317 | 135 | C |
| ATOM | 1963 | CG1 | VAL | A | 122 | 1.083 | 26.017 | 79.107 | 1.00 | 26.86 | | C |
| ANISOU | 1963 | CG1 | VAL | A | 122 | 3600 | 4322 | 2282 | -756 | 398 | -26 | C |
| ATOM | 1967 | CG2 | VAL | A | 122 | 0.431 | 28.225 | 80.207 | 1.00 | 24.95 | | C |
| ANISOU | 1967 | CG2 | VAL | A | 122 | 3231 | 4187 | 2064 | -615 | 312 | 237 | C |
| ATOM | 1971 | C | VAL | A | 122 | -1.842 | 25.414 | 78.757 | 1.00 | 29.09 | | C |
| ANISOU | 1971 | C | VAL | A | 122 | 3828 | 4781 | 2446 | -1006 | 241 | 78 | C |
| ATOM | 1972 | O | VAL | A | 122 | -2.409 | 24.834 | 79.686 | 1.00 | 28.96 | | O |
| ANISOU | 1972 | O | VAL | A | 122 | 3798 | 4694 | 2511 | -1006 | 227 | 112 | O |

FIG. 18 (continued)

| | | | | | | | | | | | | |
|---|---|---|---|---|---|---|---|---|---|---|---|---|
| ATOM | 1974 | N | THR | A | 123 | -1.658 | 24.870 | 77.558 | 1.00 | 30.05 | | N |
| ANISOU | 1974 | N | THR | A | 123 | 4017 | 4938 | 2461 | -1132 | 260 | -48 | N |
| ATOM | 1975 | CA | THR | A | 123 | -2.205 | 23.567 | 77.197 | 1.00 | 31.81 | | C |
| ANISOU | 1975 | CA | THR | A | 123 | 4310 | 5117 | 2661 | -1288 | 256 | -161 | C |
| ATOM | 1977 | CB | THR | A | 123 | -3.425 | 23.724 | 76.240 | 1.00 | 33.44 | | C |
| ANISOU | 1977 | CB | THR | A | 123 | 4471 | 5528 | 2705 | -1472 | 156 | -119 | C |
| ATOM | 1979 | OG1 | THR | A | 123 | -4.011 | 22.445 | 75.971 | 1.00 | 34.29 | | O |
| ANISOU | 1979 | OG1 | THR | A | 123 | 4648 | 5587 | 2792 | -1647 | 146 | -232 | O |
| ATOM | 1981 | CG2 | THR | A | 123 | -3.031 | 24.400 | 74.907 | 1.00 | 32.87 | | C |
| ANISOU | 1981 | CG2 | THR | A | 123 | 4417 | 5611 | 2461 | -1533 | 151 | -148 | C |
| ATOM | 1985 | C | THR | A | 123 | -1.150 | 22.669 | 76.520 | 1.00 | 33.77 | | C |
| ANISOU | 1985 | C | THR | A | 123 | 4680 | 5245 | 2906 | -1316 | 360 | -371 | C |
| ATOM | 1986 | O | THR | A | 123 | -0.217 | 23.155 | 75.855 | 1.00 | 31.71 | | O |
| ANISOU | 1986 | O | THR | A | 123 | 4433 | 5028 | 2586 | -1275 | 422 | -432 | O |
| ATOM | 1988 | N | ARG | A | 124 | -1.336 | 21.364 | 76.708 | 1.00 | 34.06 | | N |
| ANISOU | 1988 | N | ARG | A | 124 | 4801 | 5128 | 3012 | -1389 | 384 | -479 | N |
| ATOM | 1989 | CA | ARG | A | 124 | -0.566 | 20.321 | 76.012 | 1.00 | 37.78 | | C |
| ANISOU | 1989 | CA | ARG | A | 124 | 5398 | 5465 | 3492 | -1434 | 485 | -705 | C |
| ATOM | 1991 | CB | ARG | A | 124 | -0.312 | 19.132 | 76.946 | 1.00 | 38.48 | | C |
| ANISOU | 1991 | CB | ARG | A | 124 | 5562 | 5281 | 3779 | -1373 | 521 | -753 | C |
| ATOM | 1994 | CG | ARG | A | 124 | 0.571 | 19.446 | 78.124 | 1.00 | 37.57 | | C |
| ANISOU | 1994 | CG | ARG | A | 124 | 5397 | 5046 | 3831 | -1149 | 545 | -655 | C |
| ATOM | 1997 | CD | ARG | A | 124 | 0.106 | 18.698 | 79.348 | 1.00 | 39.13 | | C |
| ANISOU | 1997 | CD | ARG | A | 124 | 5620 | 5076 | 4170 | -1134 | 500 | -560 | C |
| ATOM | 2000 | NE | ARG | A | 124 | -0.572 | 19.597 | 80.210 | 1.00 | 37.94 | | N |
| ANISOU | 2000 | NE | ARG | A | 124 | 5363 | 5055 | 3998 | -1103 | 424 | -360 | N |
| ATOM | 2002 | CZ | ARG | A | 124 | -1.193 | 19.304 | 81.339 | 1.00 | 36.52 | | C |
| ANISOU | 2002 | CZ | ARG | A | 124 | 5171 | 4817 | 3889 | -1109 | 376 | -232 | C |
| ATOM | 2003 | NH1 | ARG | A | 124 | -1.327 | 18.076 | 81.821 | 1.00 | 38.45 | | N |
| ANISOU | 2003 | NH1 | ARG | A | 124 | 5511 | 4863 | 4237 | -1163 | 378 | -254 | N |
| ATOM | 2006 | NH2 | ARG | A | 124 | -1.725 | 20.300 | 81.983 | 1.00 | 34.64 | | N |
| ANISOU | 2006 | NH2 | ARG | A | 124 | 4823 | 4726 | 3612 | -1067 | 330 | -79 | N |
| ATOM | 2009 | C | ARG | A | 124 | -1.320 | 19.788 | 74.813 | 1.00 | 39.67 | | C |
| ANISOU | 2009 | C | ARG | A | 124 | 5706 | 5809 | 3560 | -1673 | 460 | -826 | C |
| ATOM | 2010 | O | ARG | A | 124 | -0.813 | 18.916 | 74.136 | 1.00 | 41.12 | | O |
| ANISOU | 2010 | O | ARG | A | 124 | 6004 | 5890 | 3728 | -1737 | 549 | -1038 | O |
| ATOM | 2012 | N | ARG | A | 125 | -2.543 | 20.275 | 74.599 | 1.00 | 41.12 | | N |
| ANISOU | 2012 | N | ARG | A | 125 | 5813 | 6189 | 3623 | -1803 | 337 | -697 | N |
| ATOM | 2013 | CA | ARG | A | 125 | -3.411 | 19.830 | 73.500 | 1.00 | 45.63 | | C |
| ANISOU | 2013 | CA | ARG | A | 125 | 6429 | 6899 | 4012 | -2057 | 279 | -783 | C |
| ATOM | 2015 | CB | ARG | A | 125 | -4.786 | 19.447 | 74.053 | 1.00 | 46.29 | | C |
| ANISOU | 2015 | CB | ARG | A | 125 | 6452 | 7012 | 4123 | -2180 | 166 | -672 | C |
| ATOM | 2018 | CG | ARG | A | 125 | -4.743 | 18.383 | 75.153 | 1.00 | 48.85 | | C |
| ANISOU | 2018 | CG | ARG | A | 125 | 6842 | 7071 | 4649 | -2140 | 210 | -701 | C |
| ATOM | 2021 | CD | ARG | A | 125 | -4.514 | 16.986 | 74.587 | 1.00 | 55.08 | | C |
| ANISOU | 2021 | CD | ARG | A | 125 | 7810 | 7673 | 5444 | -2289 | 278 | -941 | C |
| ATOM | 2024 | NE | ARG | A | 125 | -4.604 | 15.981 | 75.651 | 1.00 | 57.60 | | N |
| ANISOU | 2024 | NE | ARG | A | 125 | 8195 | 7731 | 5960 | -2268 | 297 | -930 | N |
| ATOM | 2026 | CZ | ARG | A | 125 | -4.921 | 14.697 | 75.474 | 1.00 | 60.64 | | C |
| ANISOU | 2026 | CZ | ARG | A | 125 | 8718 | 7939 | 6381 | -2441 | 312 | -1072 | C |
| ATOM | 2027 | NH1 | ARG | A | 125 | -5.184 | 14.202 | 74.257 | 1.00 | 64.03 | | N |
| ANISOU | 2027 | NH1 | ARG | A | 125 | 9244 | 8427 | 6658 | -2659 | 316 | -1265 | N |
| ATOM | 2030 | NH2 | ARG | A | 125 | -4.967 | 13.896 | 76.532 | 1.00 | 60.93 | | N |
| ANISOU | 2030 | NH2 | ARG | A | 125 | 8811 | 7735 | 6604 | -2407 | 321 | -1020 | N |
| ATOM | 2033 | C | ARG | A | 125 | -3.538 | 20.948 | 72.446 | 1.00 | 45.79 | | C |
| ANISOU | 2033 | C | ARG | A | 125 | 6386 | 7194 | 3817 | -2118 | 221 | -714 | C |
| ATOM | 2034 | O | ARG | A | 125 | -2.938 | 22.006 | 72.589 | 1.00 | 44.62 | | O |
| ANISOU | 2034 | O | ARG | A | 125 | 6174 | 7099 | 3681 | -1964 | 237 | -608 | O |
| ATOM | 2036 | N | GLU | A | 126 | -4.333 | 20.715 | 71.403 | 1.00 | 48.29 | | N |
| ANISOU | 2036 | N | GLU | A | 126 | 6727 | 7684 | 3936 | -2356 | 143 | -762 | N |
| ATOM | 2037 | CA | GLU | A | 126 | -4.564 | 21.725 | 70.372 | 1.00 | 50.02 | | C |
| ANISOU | 2037 | CA | GLU | A | 126 | 6892 | 8177 | 3936 | -2439 | 61 | -668 | C |
| ATOM | 2039 | CB | GLU | A | 126 | -5.466 | 21.173 | 69.261 | 1.00 | 54.38 | | C |
| ANISOU | 2039 | CB | GLU | A | 126 | 7490 | 8908 | 4264 | -2738 | -31 | -751 | C |
| ATOM | 2042 | CG | GLU | A | 126 | -4.744 | 20.194 | 68.336 | 1.00 | 58.18 | | C |
| ANISOU | 2042 | CG | GLU | A | 126 | 8160 | 9318 | 4628 | -2882 | 99 | -1055 | C |
| ATOM | 2045 | CD | GLU | A | 126 | -5.599 | 19.708 | 67.177 | 1.00 | 62.53 | | C |
| ANISOU | 2045 | CD | GLU | A | 126 | 8770 | 10066 | 4921 | -3205 | 5 | -1150 | C |
| ATOM | 2046 | OE1 | GLU | A | 126 | -6.772 | 19.318 | 67.396 | 1.00 | 66.09 | | O |
| ANISOU | 2046 | OE1 | GLU | A | 126 | 9164 | 10569 | 5379 | -3346 | -126 | -1081 | O |
| ATOM | 2047 | OE2 | GLU | A | 126 | -5.090 | 19.700 | 66.029 | 1.00 | 67.00 | | O |
| ANISOU | 2047 | OE2 | GLU | A | 126 | 9440 | 10751 | 5266 | -3334 | 64 | -1302 | O |
| ATOM | 2048 | C | GLU | A | 126 | -5.161 | 22.998 | 70.981 | 1.00 | 46.88 | | C |
| ANISOU | 2048 | C | GLU | A | 126 | 6319 | 7899 | 3593 | -2304 | -56 | -382 | C |
| ATOM | 2049 | O | GLU | A | 126 | -6.163 | 22.923 | 71.687 | 1.00 | 45.32 | | O |
| ANISOU | 2049 | O | GLU | A | 126 | 6021 | 7714 | 3485 | -2307 | -144 | -263 | O |
| ATOM | 2051 | N | VAL | A | 127 | -4.539 | 24.151 | 70.693 | 1.00 | 44.69 | | N |
| ANISOU | 2051 | N | VAL | A | 127 | 6009 | 7705 | 3265 | -2193 | -48 | -282 | N |
| ATOM | 2052 | CA | VAL | A | 127 | -4.790 | 25.398 | 71.454 | 1.00 | 42.53 | | C |

FIG. 18 (continued)

| | | | | | | | | | | | | |
|---|---|---|---|---|---|---|---|---|---|---|---|---|
| ANISOU | 2052 | CA | VAL | A | 127 | 5597 | 7463 | 3102 | -2006 | -116 | -39 | C |
| ATOM | 2054 | CB | VAL | A | 127 | -3.921 | 26.626 | 70.971 | 1.00 | 42.31 | | C |
| ANISOU | 2054 | CB | VAL | A | 127 | 5571 | 7501 | 3003 | -1915 | -92 | 46 | C |
| ATOM | 2056 | CG1 | VAL | A | 127 | -2.595 | 26.651 | 71.664 | 1.00 | 41.52 | | C |
| ANISOU | 2056 | CG1 | VAL | A | 127 | 5521 | 7207 | 3049 | -1739 | 59 | -40 | C |
| ATOM | 2060 | CG2 | VAL | A | 127 | -3.786 | 26.676 | 69.432 | 1.00 | 42.52 | | C |
| ANISOU | 2060 | CG2 | VAL | A | 127 | 5675 | 7722 | 2759 | -2119 | -115 | -11 | C |
| ATOM | 2064 | C | VAL | A | 127 | -6.242 | 25.849 | 71.496 | 1.00 | 42.91 | | C |
| ANISOU | 2064 | C | VAL | A | 127 | 5496 | 7681 | 3126 | -2061 | -287 | 156 | C |
| ATOM | 2065 | O | VAL | A | 127 | -6.676 | 26.391 | 72.527 | 1.00 | 38.29 | | O |
| ANISOU | 2065 | O | VAL | A | 127 | 4794 | 7052 | 2703 | -1903 | -316 | 301 | O |
| ATOM | 2067 | N | HIS | A | 128 | -6.993 | 25.591 | 70.413 | 1.00 | 45.20 | | N |
| ANISOU | 2067 | N | HIS | A | 128 | 5785 | 8170 | 3219 | -2287 | -396 | 151 | N |
| ATOM | 2068 | CA | HIS | A | 128 | -8.389 | 26.051 | 70.311 | 1.00 | 47.61 | | C |
| ANISOU | 2068 | CA | HIS | A | 128 | 5922 | 8675 | 3492 | -2348 | -578 | 350 | C |
| ATOM | 2070 | CB | HIS | A | 128 | -8.966 | 25.920 | 68.878 | 1.00 | 52.22 | | C |
| ANISOU | 2070 | CB | HIS | A | 128 | 6522 | 9513 | 3806 | -2613 | -710 | 351 | C |
| ATOM | 2073 | CG | HIS | A | 128 | -9.092 | 24.509 | 68.389 | 1.00 | 55.29 | | C |
| ANISOU | 2073 | CG | HIS | A | 128 | 7034 | 9889 | 4084 | -2861 | -676 | 113 | C |
| ATOM | 2074 | ND1 | HIS | A | 128 | -8.044 | 23.833 | 67.803 | 1.00 | 57.20 | | N |
| ANISOU | 2074 | ND1 | HIS | A | 128 | 7474 | 10035 | 4225 | -2943 | -533 | -132 | N |
| ATOM | 2076 | CE1 | HIS | A | 128 | -8.436 | 22.616 | 67.473 | 1.00 | 58.85 | | C |
| ANISOU | 2076 | CE1 | HIS | A | 128 | 7770 | 10228 | 4362 | -3165 | -529 | -320 | C |
| ATOM | 2078 | NE2 | HIS | A | 128 | -9.708 | 22.485 | 67.803 | 1.00 | 59.70 | | N |
| ANISOU | 2078 | NE2 | HIS | A | 128 | 7737 | 10437 | 4509 | -3249 | -673 | -194 | N |
| ATOM | 2080 | CD2 | HIS | A | 128 | -10.145 | 23.657 | 68.374 | 1.00 | 57.87 | | C |
| ANISOU | 2080 | CD2 | HIS | A | 128 | 7316 | 10286 | 4387 | -3054 | -763 | 77 | C |
| ATOM | 2082 | C | HIS | A | 128 | -9.304 | 25.383 | 71.332 | 1.00 | 46.50 | | C |
| ANISOU | 2082 | C | HIS | A | 128 | 5685 | 8473 | 3511 | -2346 | -595 | 361 | C |
| ATOM | 2083 | O | HIS | A | 128 | -10.235 | 26.020 | 71.805 | 1.00 | 46.79 | | O |
| ANISOU | 2083 | O | HIS | A | 128 | 5542 | 8608 | 3630 | -2269 | -693 | 549 | O |
| ATOM | 2085 | N | ILE | A | 129 | -9.015 | 24.137 | 71.708 | 1.00 | 46.43 | | N |
| ANISOU | 2085 | N | ILE | A | 129 | 5791 | 8291 | 3558 | -2420 | -493 | 167 | N |
| ATOM | 2086 | CA | ILE | A | 129 | -9.842 | 23.417 | 72.690 | 1.00 | 45.59 | | C |
| ANISOU | 2086 | CA | ILE | A | 129 | 5613 | 8117 | 3593 | -2448 | -500 | 180 | C |
| ATOM | 2088 | CB | ILE | A | 129 | -9.346 | 21.959 | 72.928 | 1.00 | 46.37 | | C |
| ANISOU | 2088 | CB | ILE | A | 129 | 5890 | 7989 | 3741 | -2548 | -385 | -48 | C |
| ATOM | 2090 | CG1 | ILE | A | 129 | -9.480 | 21.130 | 71.650 | 1.00 | 49.20 | | C |
| ANISOU | 2090 | CG1 | ILE | A | 129 | 6368 | 8425 | 3898 | -2827 | -417 | -223 | C |
| ATOM | 2093 | CD1 | ILE | A | 129 | -8.604 | 19.886 | 71.593 | 1.00 | 50.17 | | C |
| ANISOU | 2093 | CD1 | ILE | A | 129 | 6709 | 8294 | 4059 | -2884 | -274 | -485 | C |
| ATOM | 2097 | CG2 | ILE | A | 129 | -10.130 | 21.287 | 74.078 | 1.00 | 46.25 | | C |
| ANISOU | 2097 | CG2 | ILE | A | 129 | 5806 | 7884 | 3881 | -2568 | -385 | -3 | C |
| ATOM | 2101 | C | ILE | A | 129 | -9.919 | 24.162 | 74.019 | 1.00 | 42.62 | | C |
| ANISOU | 2101 | C | ILE | A | 129 | 5112 | 7663 | 3417 | -2198 | -467 | 333 | C |
| ATOM | 2102 | O | ILE | A | 129 | -11.020 | 24.437 | 74.509 | 1.00 | 42.48 | | O |
| ANISOU | 2102 | O | ILE | A | 129 | 4919 | 7762 | 3459 | -2192 | -546 | 475 | O |
| ATOM | 2104 | N | TYR | A | 130 | -8.764 | 24.493 | 74.601 | 1.00 | 40.24 | | N |
| ANISOU | 2104 | N | TYR | A | 130 | 4893 | 7182 | 3216 | -2001 | -349 | 298 | N |
| ATOM | 2105 | CA | TYR | A | 130 | -8.722 | 25.192 | 75.890 | 1.00 | 38.32 | | C |
| ANISOU | 2105 | CA | TYR | A | 130 | 4559 | 6856 | 3146 | -1775 | -306 | 417 | C |
| ATOM | 2107 | CB | TYR | A | 130 | -7.328 | 25.056 | 76.582 | 1.00 | 36.58 | | C |
| ANISOU | 2107 | CB | TYR | A | 130 | 4470 | 6401 | 3029 | -1619 | -167 | 320 | C |
| ATOM | 2110 | CG | TYR | A | 130 | -7.282 | 25.441 | 78.057 | 1.00 | 35.93 | | C |
| ANISOU | 2110 | CG | TYR | A | 130 | 4325 | 6215 | 3112 | -1434 | -115 | 405 | C |
| ATOM | 2111 | CD1 | TYR | A | 130 | -8.351 | 25.148 | 78.925 | 1.00 | 36.07 | | C |
| ANISOU | 2111 | CD1 | TYR | A | 130 | 4237 | 6269 | 3201 | -1462 | -137 | 480 | C |
| ATOM | 2113 | CE1 | TYR | A | 130 | -8.300 | 25.494 | 80.279 | 1.00 | 33.86 | | C |
| ANISOU | 2113 | CE1 | TYR | A | 130 | 3911 | 5910 | 3045 | -1309 | -78 | 545 | C |
| ATOM | 2115 | CZ | TYR | A | 130 | -7.196 | 26.112 | 80.765 | 1.00 | 32.86 | | C |
| ANISOU | 2115 | CZ | TYR | A | 130 | 3846 | 5665 | 2974 | -1135 | -11 | 537 | C |
| ATOM | 2116 | OH | TYR | A | 130 | -7.169 | 26.413 | 82.116 | 1.00 | 33.26 | | O |
| ANISOU | 2116 | OH | TYR | A | 130 | 3862 | 5651 | 3124 | -1008 | 43 | 591 | O |
| ATOM | 2118 | CE2 | TYR | A | 130 | -6.101 | 26.403 | 79.926 | 1.00 | 32.09 | | C |
| ANISOU | 2118 | CE2 | TYR | A | 130 | 3845 | 5525 | 2823 | -1104 | 6 | 468 | C |
| ATOM | 2120 | CD2 | TYR | A | 130 | -6.136 | 26.053 | 78.614 | 1.00 | 32.96 | | C |
| ANISOU | 2120 | CD2 | TYR | A | 130 | 4000 | 5712 | 2810 | -1249 | -36 | 401 | C |
| ATOM | 2122 | C | TYR | A | 130 | -9.128 | 26.653 | 75.736 | 1.00 | 36.86 | | C |
| ANISOU | 2122 | C | TYR | A | 130 | 4229 | 6821 | 2955 | -1649 | -388 | 606 | C |
| ATOM | 2123 | O | TYR | A | 130 | -9.737 | 27.218 | 76.635 | 1.00 | 35.99 | | O |
| ANISOU | 2123 | O | TYR | A | 130 | 3983 | 6728 | 2963 | -1522 | -398 | 726 | O |
| ATOM | 2125 | N | TYR | A | 131 | -8.804 | 27.262 | 74.609 | 1.00 | 38.38 | | N |
| ANISOU | 2125 | N | TYR | A | 131 | 4454 | 7117 | 3012 | -1684 | -444 | 633 | N |
| ATOM | 2126 | CA | TYR | A | 131 | -9.315 | 28.599 | 74.318 | 1.00 | 40.22 | | C |
| ANISOU | 2126 | CA | TYR | A | 131 | 4554 | 7491 | 3238 | -1587 | -549 | 834 | C |
| ATOM | 2128 | CB | TYR | A | 131 | -8.871 | 29.095 | 72.931 | 1.00 | 42.14 | | C |
| ANISOU | 2128 | CB | TYR | A | 131 | 4870 | 7850 | 3291 | -1678 | -614 | 860 | C |
| ATOM | 2131 | CG | TYR | A | 131 | -9.357 | 30.506 | 72.685 | 1.00 | 42.83 | | C |
| ANISOU | 2131 | CG | TYR | A | 131 | 4831 | 8047 | 3395 | -1561 | -731 | 1093 | C |

FIG. 18 (continued)

| | | | | | | | | | | | | |
|---|---|---|---|---|---|---|---|---|---|---|---|---|
| ATOM | 2132 | CD1 | TYR | A | 131 | -8.554 | 31.597 | 72.981 | 1.00 | 41.19 | | C |
| ANISOU | 2132 | CD1 | TYR | A | 131 | 4660 | 7725 | 3265 | -1376 | -679 | 1164 | C |
| ATOM | 2134 | CE1 | TYR | A | 131 | -9.010 | 32.888 | 72.793 | 1.00 | 43.05 | | C |
| ANISOU | 2134 | CE1 | TYR | A | 131 | 4793 | 8023 | 3540 | -1259 | -785 | 1381 | C |
| ATOM | 2136 | CZ | TYR | A | 131 | -10.299 | 33.091 | 72.329 | 1.00 | 45.42 | | C |
| ANISOU | 2136 | CZ | TYR | A | 131 | 4929 | 8515 | 3811 | -1310 | -952 | 1538 | C |
| ATOM | 2137 | OH | TYR | A | 131 | -10.765 | 34.365 | 72.155 | 1.00 | 46.58 | | O |
| ANISOU | 2137 | OH | TYR | A | 131 | 4969 | 8704 | 4025 | -1172 | -1064 | 1764 | O |
| ATOM | 2139 | CE2 | TYR | A | 131 | -11.117 | 32.025 | 72.058 | 1.00 | 46.64 | | C |
| ANISOU | 2139 | CE2 | TYR | A | 131 | 5025 | 8813 | 3885 | -1496 | -1011 | 1474 | C |
| ATOM | 2141 | CD2 | TYR | A | 131 | -10.658 | 30.746 | 72.238 | 1.00 | 45.00 | | C |
| ANISOU | 2141 | CD2 | TYR | A | 131 | 4939 | 8530 | 3631 | -1629 | -899 | 1250 | C |
| ATOM | 2143 | C | TYR | A | 131 | -10.838 | 28.645 | 74.420 | 1.00 | 42.10 | | C |
| ANISOU | 2143 | C | TYR | A | 131 | 4591 | 7905 | 3502 | -1638 | -674 | 966 | C |
| ATOM | 2144 | O | TYR | A | 131 | -11.379 | 29.467 | 75.156 | 1.00 | 41.12 | | O |
| ANISOU | 2144 | O | TYR | A | 131 | 4318 | 7792 | 3513 | -1467 | -690 | 1102 | O |
| ATOM | 2146 | N | LEU | A | 132 | -11.514 | 27.743 | 73.703 | 1.00 | 44.84 | | N |
| ANISOU | 2146 | N | LEU | A | 132 | 4928 | 8387 | 3721 | -1877 | -755 | 913 | N |
| ATOM | 2147 | CA | LEU | A | 132 | -12.987 | 27.687 | 73.705 | 1.00 | 48.46 | | C |
| ANISOU | 2147 | CA | LEU | A | 132 | 5175 | 9046 | 4193 | -1961 | -885 | 1035 | C |
| ATOM | 2149 | CB | LEU | A | 132 | -13.494 | 26.706 | 72.642 | 1.00 | 51.39 | | C |
| ANISOU | 2149 | CB | LEU | A | 132 | 5581 | 9572 | 4372 | -2270 | -985 | 953 | C |
| ATOM | 2152 | CG | LEU | A | 132 | -13.257 | 27.196 | 71.219 | 1.00 | 53.77 | | C |
| ANISOU | 2152 | CG | LEU | A | 132 | 5940 | 10030 | 4461 | -2373 | -1098 | 998 | C |
| ATOM | 2154 | CD1 | LEU | A | 132 | -13.648 | 26.114 | 70.194 | 1.00 | 56.11 | | C |
| ANISOU | 2154 | CD1 | LEU | A | 132 | 6309 | 10468 | 4543 | -2707 | -1177 | 870 | C |
| ATOM | 2158 | CD2 | LEU | A | 132 | -14.022 | 28.498 | 70.954 | 1.00 | 55.16 | | C |
| ANISOU | 2158 | CD2 | LEU | A | 132 | 5908 | 10390 | 4659 | -2252 | -1257 | 1266 | C |
| ATOM | 2162 | C | LEU | A | 132 | -13.582 | 27.317 | 75.056 | 1.00 | 48.29 | | C |
| ANISOU | 2162 | C | LEU | A | 132 | 5042 | 8957 | 4349 | -1889 | -812 | 1038 | C |
| ATOM | 2163 | O | LEU | A | 132 | -14.611 | 27.888 | 75.468 | 1.00 | 48.07 | | O |
| ANISOU | 2163 | O | LEU | A | 132 | 4791 | 9058 | 4414 | -1807 | -874 | 1187 | O |
| ATOM | 2165 | N | GLU | A | 133 | -12.955 | 26.353 | 75.731 | 1.00 | 47.34 | | N |
| ANISOU | 2165 | N | GLU | A | 133 | 5071 | 8640 | 4276 | -1921 | -679 | 878 | N |
| ATOM | 2166 | CA | GLU | A | 133 | -13.354 | 26.018 | 77.101 | 1.00 | 48.96 | | C |
| ANISOU | 2166 | CA | GLU | A | 133 | 5202 | 8764 | 4637 | -1852 | -593 | 885 | C |
| ATOM | 2168 | CB | GLU | A | 133 | -12.405 | 24.967 | 77.683 | 1.00 | 49.11 | | C |
| ANISOU | 2168 | CB | GLU | A | 133 | 5431 | 8538 | 4691 | -1885 | -461 | 719 | C |
| ATOM | 2171 | CG | GLU | A | 133 | -12.731 | 24.509 | 79.087 | 1.00 | 50.08 | | C |
| ANISOU | 2171 | CG | GLU | A | 133 | 5512 | 8571 | 4946 | -1846 | -374 | 732 | C |
| ATOM | 2174 | CD | GLU | A | 133 | -11.711 | 23.502 | 79.628 | 1.00 | 50.60 | | C |
| ANISOU | 2174 | CD | GLU | A | 133 | 5793 | 8378 | 5054 | -1863 | -264 | 594 | C |
| ATOM | 2175 | OE1 | GLU | A | 133 | -11.265 | 22.635 | 78.831 | 1.00 | 53.37 | | O |
| ANISOU | 2175 | OE1 | GLU | A | 133 | 6297 | 8651 | 5330 | -2011 | -270 | 461 | O |
| ATOM | 2176 | OE2 | GLU | A | 133 | -11.357 | 23.589 | 80.835 | 1.00 | 49.10 | | O |
| ANISOU | 2176 | OE2 | GLU | A | 133 | 5620 | 8066 | 4971 | -1726 | -174 | 618 | O |
| ATOM | 2177 | C | GLU | A | 133 | -13.397 | 27.295 | 77.961 | 1.00 | 47.58 | | C |
| ANISOU | 2177 | C | GLU | A | 133 | 4902 | 8576 | 4599 | -1578 | -553 | 1014 | C |
| ATOM | 2178 | O | GLU | A | 133 | -14.422 | 27.610 | 78.561 | 1.00 | 49.05 | | O |
| ANISOU | 2178 | O | GLU | A | 133 | 4887 | 8877 | 4874 | -1527 | -571 | 1116 | O |
| ATOM | 2180 | N | LYS | A | 134 | -12.304 | 28.052 | 77.970 | 1.00 | 46.22 | | N |
| ANISOU | 2180 | N | LYS | A | 134 | 4843 | 8272 | 4445 | -1411 | -498 | 1004 | N |
| ATOM | 2181 | CA | LYS | A | 134 | -12.245 | 29.329 | 78.678 | 1.00 | 46.32 | | C |
| ANISOU | 2181 | CA | LYS | A | 134 | 4770 | 8250 | 4580 | -1162 | -462 | 1108 | C |
| ATOM | 2183 | CB | LYS | A | 134 | -10.828 | 29.918 | 78.629 | 1.00 | 44.96 | | C |
| ANISOU | 2183 | CB | LYS | A | 134 | 4769 | 7907 | 4406 | -1036 | -394 | 1060 | C |
| ATOM | 2186 | CG | LYS | A | 134 | -9.840 | 29.287 | 79.606 | 1.00 | 43.52 | | C |
| ANISOU | 2186 | CG | LYS | A | 134 | 4734 | 7522 | 4280 | -997 | -257 | 930 | C |
| ATOM | 2189 | CD | LYS | A | 134 | -8.647 | 30.241 | 79.840 | 1.00 | 42.71 | | C |
| ANISOU | 2189 | CD | LYS | A | 134 | 4726 | 7283 | 4218 | -825 | -196 | 926 | C |
| ATOM | 2192 | CE | LYS | A | 134 | -7.758 | 29.817 | 80.993 | 1.00 | 40.35 | | C |
| ANISOU | 2192 | CE | LYS | A | 134 | 4531 | 6805 | 3994 | -756 | -77 | 832 | C |
| ATOM | 2195 | NZ | LYS | A | 134 | -8.469 | 29.722 | 82.297 | 1.00 | 37.26 | | N |
| ANISOU | 2195 | NZ | LYS | A | 134 | 4050 | 6413 | 3694 | -699 | -27 | 861 | N |
| ATOM | 2199 | C | LYS | A | 134 | -13.222 | 30.382 | 78.163 | 1.00 | 49.37 | | C |
| ANISOU | 2199 | C | LYS | A | 134 | 4954 | 8819 | 4986 | -1088 | -587 | 1283 | C |
| ATOM | 2200 | O | LYS | A | 134 | -13.880 | 31.053 | 78.966 | 1.00 | 48.21 | | O |
| ANISOU | 2200 | O | LYS | A | 134 | 4645 | 8699 | 4973 | -930 | -561 | 1366 | O |
| ATOM | 2202 | N | ALA | A | 135 | -13.302 | 30.531 | 76.837 | 1.00 | 51.15 | | N |
| ANISOU | 2202 | N | ALA | A | 135 | 5188 | 9168 | 5078 | -1199 | -719 | 1338 | N |
| ATOM | 2203 | CA | ALA | A | 135 | -14.077 | 31.611 | 76.218 | 1.00 | 55.42 | | C |
| ANISOU | 2203 | CA | ALA | A | 135 | 5556 | 9868 | 5633 | -1117 | -861 | 1532 | C |
| ATOM | 2205 | CB | ALA | A | 135 | -13.682 | 31.781 | 74.761 | 1.00 | 54.66 | | C |
| ANISOU | 2205 | CB | ALA | A | 135 | 5558 | 9858 | 5351 | -1246 | -983 | 1574 | C |
| ATOM | 2209 | C | ALA | A | 135 | -15.598 | 31.419 | 76.343 | 1.00 | 59.22 | | C |
| ANISOU | 2209 | C | ALA | A | 135 | 5772 | 10560 | 6167 | -1168 | -953 | 1631 | C |
| ATOM | 2210 | O | ALA | A | 135 | -16.343 | 32.391 | 76.380 | 1.00 | 59.37 | | O |
| ANISOU | 2210 | O | ALA | A | 135 | 5595 | 10670 | 6291 | -1012 | -1027 | 1793 | O |
| ATOM | 2212 | N | ASN | A | 136 | -16.059 | 30.177 | 76.416 | 1.00 | 63.22 | | N |

FIG. 18 (continued)

| | | | | | | | | | | | |
|---|---|---|---|---|---|---|---|---|---|---|---|
| ANISOU | 2212 | N | ASN | A | 136 | 6267 | 11140 | 6614 | -1383 | -948 | 1535 | N |
| ATOM | 2213 | CA | ASN | A | 136 | -17.498 | 29.922 | 76.561 | 1.00 | 68.68 | | C |
| ANISOU | 2213 | CA | ASN | A | 136 | 6694 | 12050 | 7353 | -1460 | -1029 | 1622 | C |
| ATOM | 2215 | CB | ASN | A | 136 | -17.859 | 28.536 | 76.018 | 1.00 | 70.03 | | C |
| ANISOU | 2215 | CB | ASN | A | 136 | 6908 | 12323 | 7376 | -1788 | -1085 | 1523 | C |
| ATOM | 2218 | CG | ASN | A | 136 | -17.876 | 28.502 | 74.511 | 1.00 | 71.39 | | C |
| ANISOU | 2218 | CG | ASN | A | 136 | 7125 | 12646 | 7352 | -1968 | -1259 | 1559 | C |
| ATOM | 2219 | OD1 | ASN | A | 136 | -18.630 | 29.243 | 73.872 | 1.00 | 73.71 | | O |
| ANISOU | 2219 | OD1 | ASN | A | 136 | 7230 | 13145 | 7633 | -1939 | -1422 | 1738 | O |
| ATOM | 2220 | ND2 | ASN | A | 136 | -17.040 | 27.649 | 73.927 | 1.00 | 70.50 | | N |
| ANISOU | 2220 | ND2 | ASN | A | 136 | 7265 | 12439 | 7085 | -2153 | -1225 | 1391 | N |
| ATOM | 2223 | C | ASN | A | 136 | -18.020 | 30.096 | 77.990 | 1.00 | 71.44 | | C |
| ANISOU | 2223 | C | ASN | A | 136 | 6891 | 12363 | 7890 | -1300 | -897 | 1628 | C |
| ATOM | 2224 | O | ASN | A | 136 | -19.213 | 29.948 | 78.236 | 1.00 | 73.94 | | O |
| ANISOU | 2224 | O | ASN | A | 136 | 6961 | 12865 | 8266 | -1343 | -938 | 1699 | O |
| ATOM | 2226 | N | LYS | A | 137 | -17.123 | 30.393 | 78.925 | 1.00 | 73.18 | | N |
| ANISOU | 2226 | N | LYS | A | 137 | 7253 | 12359 | 8192 | -1130 | -738 | 1549 | N |
| ATOM | 2227 | CA | LYS | A | 137 | -17.507 | 30.883 | 80.249 | 1.00 | 75.80 | | C |
| ANISOU | 2227 | CA | LYS | A | 137 | 7455 | 12655 | 8690 | -937 | -608 | 1562 | C |
| ATOM | 2229 | CB | LYS | A | 137 | -16.696 | 30.175 | 81.342 | 1.00 | 74.26 | | C |
| ANISOU | 2229 | CB | LYS | A | 137 | 7450 | 12266 | 8501 | -956 | -437 | 1414 | C |
| ATOM | 2232 | CG | LYS | A | 137 | -17.202 | 28.767 | 81.693 | 1.00 | 75.54 | | C |
| ANISOU | 2232 | CG | LYS | A | 137 | 7603 | 12485 | 8612 | -1199 | -408 | 1346 | C |
| ATOM | 2235 | CD | LYS | A | 137 | -16.833 | 28.376 | 83.142 | 1.00 | 74.49 | | C |
| ANISOU | 2235 | CD | LYS | A | 137 | 7555 | 12211 | 8537 | -1156 | -233 | 1266 | C |
| ATOM | 2238 | CE | LYS | A | 137 | -17.685 | 27.210 | 83.679 | 1.00 | 75.65 | | C |
| ANISOU | 2238 | CE | LYS | A | 137 | 7621 | 12455 | 8669 | -1374 | -200 | 1251 | C |
| ATOM | 2241 | NZ | LYS | A | 137 | -17.634 | 27.093 | 85.172 | 1.00 | 75.06 | | N |
| ANISOU | 2241 | NZ | LYS | A | 137 | 7557 | 12311 | 8652 | -1310 | -35 | 1222 | N |
| ATOM | 2245 | C | LYS | A | 137 | -17.261 | 32.396 | 80.299 | 1.00 | 77.32 | | C |
| ANISOU | 2245 | C | LYS | A | 137 | 7610 | 12774 | 8995 | -653 | -607 | 1655 | C |
| ATOM | 2246 | O | LYS | A | 137 | -18.187 | 33.186 | 80.494 | 1.00 | 77.66 | | O |
| ANISOU | 2246 | O | LYS | A | 137 | 7416 | 12927 | 9165 | -500 | -634 | 1767 | O |
| ATOM | 2248 | N | ILE | A | 138 | -15.995 | 32.764 | 80.094 | 1.00 | 78.30 | | N |
| ANISOU | 2248 | N | ILE | A | 138 | 7968 | 12706 | 9077 | -591 | -576 | 1605 | N |
| ATOM | 2249 | CA | ILE | A | 138 | -15.515 | 34.154 | 80.084 | 1.00 | 79.99 | | C |
| ANISOU | 2249 | CA | ILE | A | 138 | 8211 | 12800 | 9380 | -354 | -572 | 1677 | C |
| ATOM | 2251 | CB | ILE | A | 138 | -13.967 | 34.188 | 79.899 | 1.00 | 77.72 | | C |
| ANISOU | 2251 | CB | ILE | A | 138 | 8210 | 12310 | 9012 | -365 | -519 | 1584 | C |
| ATOM | 2253 | CG1 | ILE | A | 138 | -13.276 | 33.618 | 81.140 | 1.00 | 76.00 | | C |
| ANISOU | 2253 | CG1 | ILE | A | 138 | 8118 | 11938 | 8821 | -354 | -348 | 1428 | C |
| ATOM | 2256 | CD1 | ILE | A | 138 | -11.880 | 33.167 | 80.884 | 1.00 | 74.39 | | C |
| ANISOU | 2256 | CD1 | ILE | A | 138 | 8159 | 11585 | 8519 | -432 | -309 | 1321 | C |
| ATOM | 2260 | CG2 | ILE | A | 138 | -13.472 | 35.598 | 79.615 | 1.00 | 77.65 | | C |
| ANISOU | 2260 | CG2 | ILE | A | 138 | 8245 | 12191 | 9069 | -176 | -547 | 1678 | C |
| ATOM | 2264 | C | ILE | A | 138 | -16.165 | 34.951 | 78.960 | 1.00 | 83.58 | | C |
| ANISOU | 2264 | C | ILE | A | 138 | 8524 | 13394 | 9838 | -314 | -754 | 1863 | C |
| ATOM | 2265 | O | ILE | A | 138 | -16.048 | 34.579 | 77.798 | 1.00 | 84.31 | | O |
| ANISOU | 2265 | O | ILE | A | 138 | 8676 | 13582 | 9777 | -487 | -885 | 1902 | O |
| ATOM | 2267 | N | LYS | A | 139 | -16.855 | 36.037 | 79.312 | 1.00 | 87.23 | | N |
| ANISOU | 2267 | N | LYS | A | 139 | 8802 | 13868 | 10475 | -85 | -762 | 1977 | N |
| ATOM | 2268 | CA | LYS | A | 139 | -17.618 | 36.834 | 78.342 | 1.00 | 91.40 | | C |
| ANISOU | 2268 | CA | LYS | A | 139 | 9156 | 14531 | 11042 | -16 | -950 | 2187 | C |
| ATOM | 2270 | CB | LYS | A | 139 | -19.097 | 36.422 | 78.370 | 1.00 | 94.18 | | C |
| ANISOU | 2270 | CB | LYS | A | 139 | 9193 | 15142 | 11448 | -63 | -1023 | 2262 | C |
| ATOM | 2273 | CG | LYS | A | 139 | -19.373 | 35.006 | 77.848 | 1.00 | 94.45 | | C |
| ANISOU | 2273 | CG | LYS | A | 139 | 9234 | 15358 | 11294 | -388 | -1091 | 2200 | C |
| ATOM | 2276 | CD | LYS | A | 139 | -20.717 | 34.467 | 78.340 | 1.00 | 96.28 | | C |
| ANISOU | 2276 | CD | LYS | A | 139 | 9169 | 15811 | 11603 | -443 | -1089 | 2218 | C |
| ATOM | 2279 | CE | LYS | A | 139 | -20.853 | 32.969 | 78.056 | 1.00 | 96.23 | | C |
| ANISOU | 2279 | CE | LYS | A | 139 | 9218 | 15924 | 11420 | -783 | -1114 | 2116 | C |
| ATOM | 2282 | NZ | LYS | A | 139 | -22.068 | 32.369 | 78.681 | 1.00 | 97.63 | | N |
| ANISOU | 2282 | NZ | LYS | A | 139 | 9126 | 16300 | 11669 | -865 | -1082 | 2116 | N |
| ATOM | 2286 | C | LYS | A | 139 | -17.476 | 38.346 | 78.595 | 1.00 | 92.86 | | C |
| ANISOU | 2286 | C | LYS | A | 139 | 9324 | 14549 | 11409 | 281 | -933 | 2285 | C |
| ATOM | 2287 | O | LYS | A | 139 | -18.387 | 38.990 | 79.127 | 1.00 | 95.32 | | O |
| ANISOU | 2287 | O | LYS | A | 139 | 9409 | 14893 | 11913 | 482 | -913 | 2353 | O |
| ATOM | 2289 | N | SER | A | 140 | -16.322 | 38.895 | 78.210 | 1.00 | 92.08 | | N |
| ANISOU | 2289 | N | SER | A | 140 | 9465 | 14266 | 11255 | 302 | -933 | 2286 | N |
| ATOM | 2290 | CA | SER | A | 140 | -16.079 | 40.341 | 78.252 | 1.00 | 92.86 | | C |
| ANISOU | 2290 | CA | SER | A | 140 | 9590 | 14182 | 11508 | 546 | -941 | 2394 | C |
| ATOM | 2292 | CB | SER | A | 140 | -15.804 | 40.810 | 79.686 | 1.00 | 91.69 | | C |
| ANISOU | 2292 | CB | SER | A | 140 | 9478 | 13834 | 11527 | 742 | -731 | 2248 | C |
| ATOM | 2295 | OG | SER | A | 140 | -15.576 | 42.212 | 79.720 | 1.00 | 92.19 | | O |
| ANISOU | 2295 | OG | SER | A | 140 | 9582 | 13697 | 11749 | 968 | -736 | 2339 | O |
| ATOM | 2297 | C | SER | A | 140 | -14.913 | 40.730 | 77.339 | 1.00 | 92.03 | | C |
| ANISOU | 2297 | C | SER | A | 140 | 9735 | 13963 | 11271 | 464 | -1008 | 2445 | C |
| ATOM | 2298 | O | SER | A | 140 | -14.881 | 41.832 | 76.788 | 1.00 | 93.16 | | O |
| ANISOU | 2298 | O | SER | A | 140 | 9887 | 14025 | 11483 | 585 | -1108 | 2617 | O |

FIG. 18 (continued)

| | | | | | | | | | | | | |
|---|---|---|---|---|---|---|---|---|---|---|---|---|
| ATOM | 2300 | N | THR | A | 143 | -12.500 | 40.872 | 79.269 | 1.00 | 47.17 | | N |
| ANISOU | 2300 | N | THR | A | 143 | 4479 | 7820 | 5623 | 542 | -627 | 2069 | N |
| ATOM | 2301 | CA | THR | A | 143 | -11.294 | 40.112 | 79.611 | 1.00 | 44.77 | | C |
| ANISOU | 2301 | CA | THR | A | 143 | 4379 | 7437 | 5195 | 405 | -515 | 1890 | C |
| ATOM | 2303 | CB | THR | A | 143 | -11.526 | 39.043 | 80.716 | 1.00 | 44.28 | | C |
| ANISOU | 2303 | CB | THR | A | 143 | 4273 | 7418 | 5133 | 360 | -386 | 1722 | C |
| ATOM | 2305 | OG1 | THR | A | 143 | -11.833 | 39.676 | 81.967 | 1.00 | 45.24 | | O |
| ANISOU | 2305 | OG1 | THR | A | 143 | 4332 | 7439 | 5419 | 551 | -265 | 1668 | O |
| ATOM | 2307 | CG2 | THR | A | 143 | -10.270 | 38.189 | 80.922 | 1.00 | 41.35 | | C |
| ANISOU | 2307 | CG2 | THR | A | 143 | 4104 | 6969 | 4637 | 218 | -301 | 1566 | C |
| ATOM | 2311 | C | THR | A | 143 | -10.760 | 39.434 | 78.348 | 1.00 | 43.76 | | C |
| ANISOU | 2311 | C | THR | A | 143 | 4355 | 7415 | 4857 | 181 | -612 | 1914 | C |
| ATOM | 2312 | O | THR | A | 143 | -11.485 | 38.717 | 77.670 | 1.00 | 46.32 | | O |
| ANISOU | 2312 | O | THR | A | 143 | 4580 | 7934 | 5087 | 49 | -711 | 1959 | O |
| ATOM | 2314 | N | HIS | A | 144 | -9.468 | 39.620 | 78.094 | 1.00 | 40.51 | | N |
| ANISOU | 2314 | N | HIS | A | 144 | 4144 | 6882 | 4368 | 127 | -569 | 1862 | N |
| ATOM | 2315 | CA | HIS | A | 144 | -8.793 | 39.135 | 76.900 | 1.00 | 39.05 | | C |
| ANISOU | 2315 | CA | HIS | A | 144 | 4077 | 6779 | 3981 | -73 | -631 | 1867 | C |
| ATOM | 2317 | CB | HIS | A | 144 | -7.682 | 40.134 | 76.579 | 1.00 | 40.22 | | C |
| ANISOU | 2317 | CB | HIS | A | 144 | 4381 | 6777 | 4122 | -41 | -615 | 1915 | C |
| ATOM | 2320 | CG | HIS | A | 144 | -7.268 | 40.159 | 75.143 | 1.00 | 40.58 | | C |
| ANISOU | 2320 | CG | HIS | A | 144 | 4511 | 6930 | 3976 | -210 | -714 | 2008 | C |
| ATOM | 2321 | ND1 | HIS | A | 144 | -7.949 | 40.869 | 74.181 | 1.00 | 43.03 | | N |
| ANISOU | 2321 | ND1 | HIS | A | 144 | 4759 | 7334 | 4255 | -213 | -879 | 2231 | N |
| ATOM | 2323 | CE1 | HIS | A | 144 | -7.348 | 40.713 | 73.015 | 1.00 | 42.66 | | C |
| ANISOU | 2323 | CE1 | HIS | A | 144 | 4823 | 7386 | 3999 | -400 | -929 | 2267 | C |
| ATOM | 2325 | NE2 | HIS | A | 144 | -6.293 | 39.936 | 73.191 | 1.00 | 40.23 | | N |
| ANISOU | 2325 | NE2 | HIS | A | 144 | 4637 | 7045 | 3604 | -504 | -790 | 2061 | N |
| ATOM | 2327 | CD2 | HIS | A | 144 | -6.205 | 39.601 | 74.520 | 1.00 | 39.11 | | C |
| ANISOU | 2327 | CD2 | HIS | A | 144 | 4467 | 6774 | 3617 | -381 | -664 | 1909 | C |
| ATOM | 2329 | C | HIS | A | 144 | -8.186 | 37.773 | 77.210 | 1.00 | 36.00 | | C |
| ANISOU | 2329 | C | HIS | A | 144 | 3774 | 6406 | 3496 | -215 | -527 | 1663 | C |
| ATOM | 2330 | O | HIS | A | 144 | -7.598 | 37.623 | 78.255 | 1.00 | 34.79 | | O |
| ANISOU | 2330 | O | HIS | A | 144 | 3679 | 6122 | 3419 | -149 | -401 | 1539 | O |
| ATOM | 2332 | N | ILE | A | 145 | -8.326 | 36.800 | 76.316 | 1.00 | 35.70 | | N |
| ANISOU | 2332 | N | ILE | A | 145 | 3747 | 6521 | 3295 | -410 | -585 | 1631 | N |
| ATOM | 2333 | CA | ILE | A | 145 | -7.771 | 35.438 | 76.499 | 1.00 | 34.71 | | C |
| ANISOU | 2333 | CA | ILE | A | 145 | 3712 | 6390 | 3087 | -548 | -493 | 1437 | C |
| ATOM | 2335 | CB | ILE | A | 145 | -8.802 | 34.311 | 76.153 | 1.00 | 35.82 | | C |
| ANISOU | 2335 | CB | ILE | A | 145 | 3758 | 6700 | 3151 | -704 | -560 | 1410 | C |
| ATOM | 2337 | CG1 | ILE | A | 145 | -10.039 | 34.391 | 77.054 | 1.00 | 37.69 | | C |
| ANISOU | 2337 | CG1 | ILE | A | 145 | 3806 | 6982 | 3533 | -601 | -574 | 1471 | C |
| ATOM | 2340 | CD1 | ILE | A | 145 | -11.292 | 33.742 | 76.458 | 1.00 | 39.09 | | C |
| ANISOU | 2340 | CD1 | ILE | A | 145 | 3836 | 7375 | 3642 | -748 | -695 | 1527 | C |
| ATOM | 2344 | CG2 | ILE | A | 145 | -8.195 | 32.911 | 76.264 | 1.00 | 34.65 | | C |
| ANISOU | 2344 | CG2 | ILE | A | 145 | 3726 | 6509 | 2930 | -847 | -468 | 1211 | C |
| ATOM | 2348 | C | ILE | A | 145 | -6.531 | 35.230 | 75.614 | 1.00 | 33.76 | | C |
| ANISOU | 2348 | C | ILE | A | 145 | 3760 | 6252 | 2816 | -672 | -461 | 1362 | C |
| ATOM | 2349 | O | ILE | A | 145 | -6.529 | 35.612 | 74.436 | 1.00 | 32.44 | | O |
| ANISOU | 2349 | O | ILE | A | 145 | 3618 | 6193 | 2516 | -766 | -553 | 1458 | O |
| ATOM | 2351 | N | HIS | A | 146 | -5.494 | 34.624 | 76.201 | 1.00 | 30.52 | | N |
| ANISOU | 2351 | N | HIS | A | 146 | 3454 | 5716 | 2425 | -672 | -329 | 1196 | N |
| ATOM | 2352 | CA | HIS | A | 146 | -4.276 | 34.273 | 75.492 | 1.00 | 30.69 | | C |
| ANISOU | 2352 | CA | HIS | A | 146 | 3614 | 5722 | 2326 | -777 | -267 | 1090 | C |
| ATOM | 2354 | CB | HIS | A | 146 | -3.179 | 35.304 | 75.787 | 1.00 | 30.54 | | C |
| ANISOU | 2354 | CB | HIS | A | 146 | 3662 | 5575 | 2366 | -672 | -205 | 1116 | C |
| ATOM | 2357 | CG | HIS | A | 146 | -2.031 | 35.272 | 74.836 | 1.00 | 29.21 | | C |
| ANISOU | 2357 | CG | HIS | A | 146 | 3603 | 5435 | 2061 | -785 | -157 | 1058 | C |
| ATOM | 2358 | ND1 | HIS | A | 146 | -1.281 | 36.388 | 74.554 | 1.00 | 31.04 | | N |
| ANISOU | 2358 | ND1 | HIS | A | 146 | 3885 | 5624 | 2284 | -759 | -149 | 1144 | N |
| ATOM | 2360 | CE1 | HIS | A | 146 | -0.332 | 36.074 | 73.687 | 1.00 | 32.01 | | C |
| ANISOU | 2360 | CE1 | HIS | A | 146 | 4089 | 5807 | 2265 | -888 | -88 | 1062 | C |
| ATOM | 2362 | NE2 | HIS | A | 146 | -0.453 | 34.797 | 73.384 | 1.00 | 33.21 | | N |
| ANISOU | 2362 | NE2 | HIS | A | 146 | 4252 | 6026 | 2340 | -986 | -55 | 914 | N |
| ATOM | 2364 | CD2 | HIS | A | 146 | -1.504 | 34.269 | 74.101 | 1.00 | 32.00 | | C |
| ANISOU | 2364 | CD2 | HIS | A | 146 | 4023 | 5854 | 2281 | -930 | -102 | 914 | C |
| ATOM | 2366 | C | HIS | A | 146 | -3.848 | 32.882 | 75.946 | 1.00 | 30.54 | | C |
| ANISOU | 2366 | C | HIS | A | 146 | 3649 | 5641 | 2314 | -836 | -168 | 895 | C |
| ATOM | 2367 | O | HIS | A | 146 | -3.496 | 32.666 | 77.106 | 1.00 | 28.95 | | O |
| ANISOU | 2367 | O | HIS | A | 146 | 3453 | 5307 | 2241 | -732 | -89 | 831 | O |
| ATOM | 2369 | N | ILE | A | 147 | -3.882 | 31.943 | 75.021 | 1.00 | 32.17 | | N |
| ANISOU | 2369 | N | ILE | A | 147 | 3904 | 5940 | 2380 | -1007 | -178 | 802 | N |
| ATOM | 2370 | CA | ILE | A | 147 | -3.512 | 30.560 | 75.304 | 1.00 | 32.34 | | C |
| ANISOU | 2370 | CA | ILE | A | 147 | 3990 | 5884 | 2412 | -1072 | -91 | 614 | C |
| ATOM | 2372 | CB | ILE | A | 147 | -4.612 | 29.532 | 74.812 | 1.00 | 32.68 | | C |
| ANISOU | 2372 | CB | ILE | A | 147 | 4007 | 6038 | 2372 | -1243 | -162 | 574 | C |
| ATOM | 2374 | CG1 | ILE | A | 147 | -6.003 | 29.856 | 75.380 | 1.00 | 32.46 | | C |
| ANISOU | 2374 | CG1 | ILE | A | 147 | 3827 | 6086 | 2420 | -1202 | -261 | 721 | C |
| ATOM | 2377 | CD1 | ILE | A | 147 | -6.156 | 29.828 | 76.943 | 1.00 | 30.54 | | C |

FIG. 18 (continued)

| | | | | | | | | | | | | |
|---|---|---|---|---|---|---|---|---|---|---|---|---|
| ANISOU | 2377 | CD1 | ILE | A | 147 | 3528 | 5710 | 2365 | -1048 | -198 | 732 | C |
| ATOM | 2381 | CG2 | ILE | A | 147 | -4.223 | 28.089 | 75.170 | 1.00 | 31.89 | | C |
| ANISOU | 2381 | CG2 | ILE | A | 147 | 3994 | 5813 | 2312 | -1303 | -68 | 381 | C |
| ATOM | 2385 | C | ILE | A | 147 | -2.186 | 30.252 | 74.627 | 1.00 | 31.80 | | C |
| ANISOU | 2385 | C | ILE | A | 147 | 4040 | 5781 | 2262 | -1126 | 8 | 474 | C |
| ATOM | 2386 | O | ILE | A | 147 | -1.951 | 30.674 | 73.488 | 1.00 | 33.41 | | O |
| ANISOU | 2386 | O | ILE | A | 147 | 4280 | 6103 | 2311 | -1224 | -16 | 497 | O |
| ATOM | 2388 | N | PHE | A | 148 | -1.310 | 29.550 | 75.353 | 1.00 | 31.13 | | N |
| ANISOU | 2388 | N | PHE | A | 148 | 4005 | 5540 | 2281 | -1059 | 119 | 339 | N |
| ATOM | 2389 | CA | PHE | A | 148 | -0.071 | 28.996 | 74.815 | 1.00 | 32.27 | | C |
| ANISOU | 2389 | CA | PHE | A | 148 | 4240 | 5640 | 2382 | -1097 | 232 | 172 | C |
| ATOM | 2391 | CB | PHE | A | 148 | 1.135 | 29.450 | 75.657 | 1.00 | 30.15 | | C |
| ANISOU | 2391 | CB | PHE | A | 148 | 3968 | 5243 | 2244 | -940 | 316 | 163 | C |
| ATOM | 2394 | CG | PHE | A | 148 | 1.391 | 30.945 | 75.660 | 1.00 | 29.42 | | C |
| ANISOU | 2394 | CG | PHE | A | 148 | 3841 | 5193 | 2145 | -877 | 283 | 312 | C |
| ATOM | 2395 | CD1 | PHE | A | 148 | 2.305 | 31.515 | 74.758 | 1.00 | 30.11 | | C |
| ANISOU | 2395 | CD1 | PHE | A | 148 | 3964 | 5350 | 2129 | -932 | 332 | 300 | C |
| ATOM | 2397 | CE1 | PHE | A | 148 | 2.549 | 32.872 | 74.735 | 1.00 | 29.73 | | C |
| ANISOU | 2397 | CE1 | PHE | A | 148 | 3900 | 5320 | 2077 | -893 | 300 | 444 | C |
| ATOM | 2399 | CZ | PHE | A | 148 | 1.916 | 33.700 | 75.690 | 1.00 | 30.26 | | C |
| ANISOU | 2399 | CZ | PHE | A | 148 | 3917 | 5317 | 2264 | -772 | 226 | 585 | C |
| ATOM | 2401 | CE2 | PHE | A | 148 | 1.030 | 33.149 | 76.615 | 1.00 | 27.15 | | C |
| ANISOU | 2401 | CE2 | PHE | A | 148 | 3478 | 4867 | 1970 | -705 | 192 | 582 | C |
| ATOM | 2403 | CD2 | PHE | A | 148 | 0.776 | 31.774 | 76.610 | 1.00 | 28.23 | | C |
| ANISOU | 2403 | CD2 | PHE | A | 148 | 3629 | 4999 | 2098 | -764 | 218 | 455 | C |
| ATOM | 2405 | C | PHE | A | 148 | -0.105 | 27.459 | 74.836 | 1.00 | 32.95 | | C |
| ANISOU | 2405 | C | PHE | A | 148 | 4387 | 5642 | 2490 | -1169 | 286 | -7 | C |
| ATOM | 2406 | O | PHE | A | 148 | -0.477 | 26.888 | 75.842 | 1.00 | 31.17 | | O |
| ANISOU | 2406 | O | PHE | A | 148 | 4145 | 5305 | 2395 | -1111 | 279 | -3 | O |
| ATOM | 2408 | N | SER | A | 149 | 0.364 | 26.784 | 73.776 | 1.00 | 36.22 | | N |
| ANISOU | 2408 | N | SER | A | 149 | 4882 | 6095 | 2784 | -1292 | 352 | -170 | N |
| ATOM | 2409 | CA | SER | A | 149 | 0.638 | 25.324 | 73.867 | 1.00 | 36.59 | | C |
| ANISOU | 2409 | CA | SER | A | 149 | 5008 | 6000 | 2894 | -1326 | 435 | -370 | C |
| ATOM | 2411 | CB | SER | A | 149 | 0.099 | 24.569 | 72.667 | 1.00 | 39.67 | | C |
| ANISOU | 2411 | CB | SER | A | 149 | 5474 | 6490 | 3107 | -1542 | 426 | -501 | C |
| ATOM | 2414 | OG | SER | A | 149 | 0.994 | 24.741 | 71.571 | 1.00 | 42.98 | | O |
| ANISOU | 2414 | OG | SER | A | 149 | 5948 | 7000 | 3383 | -1604 | 520 | -620 | O |
| ATOM | 2416 | C | SER | A | 149 | 2.134 | 25.043 | 73.982 | 1.00 | 37.30 | | C |
| ANISOU | 2416 | C | SER | A | 149 | 5130 | 5967 | 3074 | -1216 | 579 | -509 | C |
| ATOM | 2417 | O | SER | A | 149 | 2.952 | 25.850 | 73.547 | 1.00 | 38.59 | | O |
| ANISOU | 2417 | O | SER | A | 149 | 5272 | 6210 | 3179 | -1187 | 629 | -495 | O |
| ATOM | 2419 | N | PHE | A | 150 | 2.493 | 23.866 | 74.492 | 1.00 | 37.91 | | N |
| ANISOU | 2419 | N | PHE | A | 150 | 5256 | 5855 | 3293 | -1165 | 646 | -643 | N |
| ATOM | 2420 | CA | PHE | A | 150 | 3.916 | 23.485 | 74.625 | 1.00 | 38.73 | | C |
| ANISOU | 2420 | CA | PHE | A | 150 | 5370 | 5835 | 3513 | -1040 | 780 | -779 | C |
| ATOM | 2422 | CB | PHE | A | 150 | 4.054 | 22.174 | 75.416 | 1.00 | 37.56 | | C |
| ANISOU | 2422 | CB | PHE | A | 150 | 5270 | 5444 | 3558 | -965 | 811 | -870 | C |
| ATOM | 2425 | CG | PHE | A | 150 | 3.898 | 22.365 | 76.886 | 1.00 | 35.80 | | C |
| ANISOU | 2425 | CG | PHE | A | 150 | 4991 | 5116 | 3494 | -831 | 735 | -701 | C |
| ATOM | 2426 | CD1 | PHE | A | 150 | 5.006 | 22.554 | 77.715 | 1.00 | 34.57 | | C |
| ANISOU | 2426 | CD1 | PHE | A | 150 | 4780 | 4865 | 3490 | -652 | 773 | -671 | C |
| ATOM | 2428 | CE1 | PHE | A | 150 | 4.835 | 22.758 | 79.078 | 1.00 | 33.31 | | C |
| ANISOU | 2428 | CE1 | PHE | A | 150 | 4579 | 4631 | 3445 | -552 | 697 | -514 | C |
| ATOM | 2430 | CZ | PHE | A | 150 | 3.574 | 22.789 | 79.613 | 1.00 | 32.29 | | C |
| ANISOU | 2430 | CZ | PHE | A | 150 | 4457 | 4524 | 3287 | -621 | 602 | -395 | C |
| ATOM | 2432 | CE2 | PHE | A | 150 | 2.473 | 22.625 | 78.800 | 1.00 | 32.54 | | C |
| ANISOU | 2432 | CE2 | PHE | A | 150 | 4523 | 4653 | 3187 | -787 | 568 | -419 | C |
| ATOM | 2434 | CD2 | PHE | A | 150 | 2.631 | 22.427 | 77.448 | 1.00 | 34.29 | | C |
| ANISOU | 2434 | CD2 | PHE | A | 150 | 4791 | 4949 | 3287 | -895 | 624 | -565 | C |
| ATOM | 2436 | C | PHE | A | 150 | 4.699 | 23.386 | 73.301 | 1.00 | 41.53 | | C |
| ANISOU | 2436 | C | PHE | A | 150 | 5765 | 6286 | 3728 | -1124 | 905 | -961 | C |
| ATOM | 2437 | O | PHE | A | 150 | 5.942 | 23.490 | 73.300 | 1.00 | 41.64 | | O |
| ANISOU | 2437 | O | PHE | A | 150 | 5741 | 6267 | 3812 | -1017 | 1017 | -1038 | O |
| ATOM | 2439 | N | THR | A | 151 | 3.973 | 23.208 | 72.205 | 1.00 | 44.42 | | N |
| ANISOU | 2439 | N | THR | A | 151 | 6198 | 6787 | 3891 | -1321 | 883 | -1026 | N |
| ATOM | 2440 | CA | THR | A | 151 | 4.576 | 23.112 | 70.873 | 1.00 | 48.73 | | C |
| ANISOU | 2440 | CA | THR | A | 151 | 6799 | 7459 | 4257 | -1440 | 1002 | -1206 | C |
| ATOM | 2442 | CB | THR | A | 151 | 3.922 | 21.976 | 70.094 | 1.00 | 52.10 | | C |
| ANISOU | 2442 | CB | THR | A | 151 | 7346 | 7875 | 4576 | -1621 | 1020 | -1398 | C |
| ATOM | 2444 | OG1 | THR | A | 151 | 2.494 | 22.101 | 70.183 | 1.00 | 52.81 | | O |
| ANISOU | 2444 | OG1 | THR | A | 151 | 7436 | 8043 | 4586 | -1746 | 846 | -1249 | O |
| ATOM | 2446 | CG2 | THR | A | 151 | 4.351 | 20.621 | 70.688 | 1.00 | 53.45 | | C |
| ANISOU | 2446 | CG2 | THR | A | 151 | 7575 | 7762 | 4973 | -1516 | 1114 | -1581 | C |
| ATOM | 2450 | C | THR | A | 151 | 4.500 | 24.429 | 70.086 | 1.00 | 48.34 | | C |
| ANISOU | 2450 | C | THR | A | 151 | 6713 | 7663 | 3990 | -1538 | 954 | -1064 | C |
| ATOM | 2451 | O | THR | A | 151 | 4.640 | 24.454 | 68.877 | 1.00 | 50.49 | | O |
| ANISOU | 2451 | O | THR | A | 151 | 7042 | 8098 | 4045 | -1697 | 1013 | -1168 | O |
| ATOM | 2453 | N | GLY | A | 152 | 4.273 | 25.533 | 70.787 | 1.00 | 47.87 | | N |
| ANISOU | 2453 | N | GLY | A | 152 | 6569 | 7631 | 3988 | -1446 | 848 | -824 | N |

FIG. 18 (continued)

| | | | | | | | | | | | | |
|---|---|---|---|---|---|---|---|---|---|---|---|---|
| ATOM | 2454 | CA | GLY | A | 152 | 4.529 | 26.845 | 70.212 | 1.00 | 47.31 | | C |
| ANISOU | 2454 | CA | GLY | A | 152 | 6463 | 7739 | 3773 | -1491 | 824 | -682 | C |
| ATOM | 2457 | C | GLY | A | 152 | 3.358 | 27.530 | 69.553 | 1.00 | 46.47 | | C |
| ANISOU | 2457 | C | GLY | A | 152 | 6365 | 7816 | 3475 | -1640 | 668 | -511 | C |
| ATOM | 2458 | O | GLY | A | 152 | 3.507 | 28.654 | 69.075 | 1.00 | 45.72 | | O |
| ANISOU | 2458 | O | GLY | A | 152 | 6251 | 7855 | 3265 | -1679 | 631 | -364 | O |
| ATOM | 2460 | N | GLU | A | 153 | 2.189 | 26.897 | 69.512 | 1.00 | 46.87 | | N |
| ANISOU | 2460 | N | GLU | A | 153 | 6439 | 7878 | 3493 | -1729 | 569 | -513 | N |
| ATOM | 2461 | CA | GLU | A | 153 | 1.048 | 27.634 | 68.987 | 1.00 | 48.49 | | C |
| ANISOU | 2461 | CA | GLU | A | 153 | 6616 | 8265 | 3544 | -1846 | 398 | -316 | C |
| ATOM | 2463 | CB | GLU | A | 153 | 0.003 | 26.776 | 68.238 | 1.00 | 53.95 | | C |
| ANISOU | 2463 | CB | GLU | A | 153 | 7358 | 9064 | 4075 | -2055 | 322 | -397 | C |
| ATOM | 2466 | CG | GLU | A | 153 | -0.354 | 25.409 | 68.822 | 1.00 | 57.64 | | C |
| ANISOU | 2466 | CG | GLU | A | 153 | 7861 | 9364 | 4674 | -2057 | 355 | -564 | C |
| ATOM | 2469 | CD | GLU | A | 153 | 0.683 | 24.322 | 68.514 | 1.00 | 60.20 | | C |
| ANISOU | 2469 | CD | GLU | A | 153 | 8295 | 9565 | 5015 | -2072 | 545 | -861 | C |
| ATOM | 2470 | OE1 | GLU | A | 153 | 1.142 | 24.239 | 67.338 | 1.00 | 61.76 | | O |
| ANISOU | 2470 | OE1 | GLU | A | 153 | 8569 | 9898 | 5001 | -2218 | 625 | -999 | O |
| ATOM | 2471 | OE2 | GLU | A | 153 | 1.011 | 23.556 | 69.464 | 1.00 | 59.30 | | O |
| ANISOU | 2471 | OE2 | GLU | A | 153 | 8186 | 9218 | 5125 | -1936 | 614 | -949 | O |
| ATOM | 2472 | C | GLU | A | 153 | 0.445 | 28.520 | 70.088 | 1.00 | 44.10 | | C |
| ANISOU | 2472 | C | GLU | A | 153 | 5953 | 7643 | 3158 | -1684 | 280 | -79 | C |
| ATOM | 2473 | O | GLU | A | 153 | 0.711 | 28.350 | 71.287 | 1.00 | 40.32 | | O |
| ANISOU | 2473 | O | GLU | A | 153 | 5438 | 6986 | 2897 | -1516 | 319 | -86 | O |
| ATOM | 2475 | N | GLU | A | 154 | -0.295 | 29.520 | 69.631 | 1.00 | 41.23 | | N |
| ANISOU | 2475 | N | GLU | A | 154 | 5546 | 7432 | 2688 | -1735 | 140 | 131 | N |
| ATOM | 2476 | CA | GLU | A | 154 | -1.002 | 30.439 | 70.493 | 1.00 | 39.61 | | C |
| ANISOU | 2476 | CA | GLU | A | 154 | 5238 | 7186 | 2625 | -1593 | 26 | 353 | C |
| ATOM | 2478 | CB | GLU | A | 154 | -0.314 | 31.783 | 70.520 | 1.00 | 39.87 | | C |
| ANISOU | 2478 | CB | GLU | A | 154 | 5261 | 7210 | 2679 | -1501 | 32 | 498 | C |
| ATOM | 2481 | CG | GLU | A | 154 | 0.990 | 31.844 | 71.237 | 1.00 | 39.64 | | C |
| ANISOU | 2481 | CG | GLU | A | 154 | 5252 | 7025 | 2786 | -1373 | 177 | 402 | C |
| ATOM | 2484 | CD | GLU | A | 154 | 1.688 | 33.144 | 70.947 | 1.00 | 39.68 | | C |
| ANISOU | 2484 | CD | GLU | A | 154 | 5265 | 7056 | 2755 | -1354 | 181 | 535 | C |
| ATOM | 2485 | OE1 | GLU | A | 154 | 2.387 | 33.217 | 69.933 | 1.00 | 41.79 | | O |
| ANISOU | 2485 | OE1 | GLU | A | 154 | 5591 | 7434 | 2854 | -1482 | 245 | 486 | O |
| ATOM | 2486 | OE2 | GLU | A | 154 | 1.516 | 34.087 | 71.738 | 1.00 | 38.36 | | O |
| ANISOU | 2486 | OE2 | GLU | A | 154 | 5050 | 6797 | 2726 | -1219 | 127 | 684 | O |
| ATOM | 2487 | C | GLU | A | 154 | -2.345 | 30.710 | 69.899 | 1.00 | 40.55 | | C |
| ANISOU | 2487 | C | GLU | A | 154 | 5301 | 7479 | 2629 | -1702 | -149 | 508 | C |
| ATOM | 2488 | O | GLU | A | 154 | -2.493 | 30.712 | 68.693 | 1.00 | 38.34 | | O |
| ANISOU | 2488 | O | GLU | A | 154 | 5067 | 7376 | 2124 | -1883 | -199 | 514 | O |
| ATOM | 2490 | N | MET | A | 155 | -3.287 | 31.067 | 70.753 | 1.00 | 40.24 | | N |
| ANISOU | 2490 | N | MET | A | 155 | 5149 | 7400 | 2739 | -1586 | -244 | 650 | N |
| ATOM | 2491 | CA | MET | A | 155 | -4.554 | 31.620 | 70.291 | 1.00 | 41.74 | | C |
| ANISOU | 2491 | CA | MET | A | 155 | 5241 | 7756 | 2860 | -1640 | -426 | 850 | C |
| ATOM | 2493 | CB | MET | A | 155 | -5.611 | 30.528 | 70.200 | 1.00 | 44.38 | | C |
| ANISOU | 2493 | CB | MET | A | 155 | 5532 | 8176 | 3155 | -1776 | -492 | 779 | C |
| ATOM | 2496 | CG | MET | A | 155 | -6.897 | 30.974 | 69.543 | 1.00 | 47.07 | | C |
| ANISOU | 2496 | CG | MET | A | 155 | 5757 | 8732 | 3396 | -1867 | -692 | 974 | C |
| ATOM | 2499 | SD | MET | A | 155 | -7.967 | 29.595 | 69.230 | 1.00 | 50.35 | | S |
| ANISOU | 2499 | SD | MET | A | 155 | 6140 | 9272 | 3717 | -2094 | -762 | 857 | S |
| ATOM | 2500 | CE | MET | A | 155 | -9.417 | 30.460 | 68.602 | 1.00 | 50.87 | | C |
| ANISOU | 2500 | CE | MET | A | 155 | 6018 | 9602 | 3708 | -2143 | -1019 | 1149 | C |
| ATOM | 2504 | C | MET | A | 155 | -4.977 | 32.730 | 71.255 | 1.00 | 39.19 | | C |
| ANISOU | 2504 | C | MET | A | 155 | 4805 | 7347 | 2738 | -1422 | -479 | 1043 | C |
| ATOM | 2505 | O | MET | A | 155 | -4.970 | 32.547 | 72.475 | 1.00 | 35.53 | | O |
| ANISOU | 2505 | O | MET | A | 155 | 4302 | 6733 | 2463 | -1278 | -410 | 995 | O |
| ATOM | 2507 | N | ALA | A | 156 | -5.340 | 33.883 | 70.710 | 1.00 | 38.22 | | N |
| ANISOU | 2507 | N | ALA | A | 156 | 4637 | 7314 | 2570 | -1401 | -600 | 1259 | N |
| ATOM | 2508 | CA | ALA | A | 156 | -5.758 | 34.999 | 71.541 | 1.00 | 37.62 | | C |
| ANISOU | 2508 | CA | ALA | A | 156 | 4462 | 7142 | 2691 | -1188 | -647 | 1433 | C |
| ATOM | 2510 | CB | ALA | A | 156 | -4.647 | 36.006 | 71.686 | 1.00 | 36.51 | | C |
| ANISOU | 2510 | CB | ALA | A | 156 | 4408 | 6867 | 2599 | -1090 | -573 | 1475 | C |
| ATOM | 2514 | C | ALA | A | 156 | -6.986 | 35.671 | 70.974 | 1.00 | 40.19 | | C |
| ANISOU | 2514 | C | ALA | A | 156 | 4661 | 7620 | 2988 | -1194 | -840 | 1666 | C |
| ATOM | 2515 | O | ALA | A | 156 | -7.241 | 35.644 | 69.765 | 1.00 | 43.24 | | O |
| ANISOU | 2515 | O | ALA | A | 156 | 5067 | 8190 | 3171 | -1366 | -953 | 1743 | O |
| ATOM | 2517 | N | THR | A | 157 | -7.726 | 36.309 | 71.860 | 1.00 | 40.31 | | N |
| ANISOU | 2517 | N | THR | A | 157 | 4543 | 7562 | 3210 | -1000 | -877 | 1779 | N |
| ATOM | 2518 | CA | THR | A | 157 | -8.865 | 37.101 | 71.488 | 1.00 | 43.22 | | C |
| ANISOU | 2518 | CA | THR | A | 157 | 4765 | 8042 | 3614 | -943 | -1054 | 2017 | C |
| ATOM | 2520 | CB | THR | A | 157 | -9.466 | 37.790 | 72.733 | 1.00 | 42.78 | | C |
| ANISOU | 2520 | CB | THR | A | 157 | 4573 | 7850 | 3832 | -684 | -1028 | 2082 | C |
| ATOM | 2522 | OG1 | THR | A | 157 | -9.773 | 36.780 | 73.689 | 1.00 | 41.00 | | O |
| ANISOU | 2522 | OG1 | THR | A | 157 | 4291 | 7607 | 3681 | -681 | -927 | 1910 | O |
| ATOM | 2524 | CG2 | THR | A | 157 | -10.747 | 38.525 | 72.376 | 1.00 | 45.30 | | C |
| ANISOU | 2524 | CG2 | THR | A | 157 | 4703 | 8290 | 4220 | -602 | -1211 | 2323 | C |
| ATOM | 2528 | C | THR | A | 157 | -8.509 | 38.102 | 70.390 | 1.00 | 45.59 | | C |

FIG. 18 (continued)

```
ANISOU 2528 C   THR A 157     5140   8392   3792   -989  -1160   2208       C
ATOM   2529 O   THR A 157     -7.499  38.823  70.479  1.00 44.83          O
ANISOU 2529 O   THR A 157     5164   8145   3723   -928  -1081   2217       O
ATOM   2531 N   LYS A 158     -9.312  38.073  69.325  1.00 49.52          N
ANISOU 2531 N   LYS A 158     5570   9112   4134  -1127  -1343   2359       N
ATOM   2532 CA  LYS A 158     -9.192  38.990  68.178  1.00 52.94          C
ANISOU 2532 CA  LYS A 158     6057   9634   4422  -1198  -1486   2588       C
ATOM   2534 CB  LYS A 158     -9.389  40.445  68.636  1.00 55.48          C
ANISOU 2534 CB  LYS A 158     6322   9785   4974   -946  -1543   2813       C
ATOM   2537 CG  LYS A 158     -10.784  40.789  69.145  1.00 58.74          C
ANISOU 2537 CG  LYS A 158     6498  10225   5597   -762  -1666   2961       C
ATOM   2540 CD  LYS A 158     -10.771  42.198  69.769  1.00 59.82          C
ANISOU 2540 CD  LYS A 158     6611  10123   5994   -486  -1664   3120       C
ATOM   2543 CE  LYS A 158     -12.118  42.901  69.670  1.00 64.23          C
ANISOU 2543 CE  LYS A 158     6946  10746   6711   -323  -1856   3376       C
ATOM   2546 NZ  LYS A 158     -11.989  44.387  69.772  1.00 66.14          N
ANISOU 2546 NZ  LYS A 158     7220  10767   7145   -109  -1902   3585       N
ATOM   2550 C   LYS A 158     -7.859  38.873  67.419  1.00 50.94          C
ANISOU 2550 C   LYS A 158     6022   9386   3949  -1374  -1388   2490       C
ATOM   2551 O   LYS A 158     -7.491  39.781  66.663  1.00 50.57          O
ANISOU 2551 O   LYS A 158     6052   9357   3805  -1415  -1462   2675       O
ATOM   2553 N   ALA A 159     -7.151  37.759  67.618  1.00 47.86          N
ANISOU 2553 N   ALA A 159     5722   8978   3485  -1478  -1220   2208       N
ATOM   2554 CA  ALA A 159     -5.774  37.569  67.132  1.00 46.94          C
ANISOU 2554 CA  ALA A 159     5787   8837   3209  -1605  -1074   2063       C
ATOM   2556 CB  ALA A 159     -5.739  37.437  65.604  1.00 48.10          C
ANISOU 2556 CB  ALA A 159     6017   9234   3026  -1873  -1168   2124       C
ATOM   2560 C   ALA A 159     -4.797  38.658  67.612  1.00 45.61          C
ANISOU 2560 C   ALA A 159     5691   8464   3176  -1458   -984   2128       C
ATOM   2561 O   ALA A 159     -3.791  38.962  66.945  1.00 45.10          O
ANISOU 2561 O   ALA A 159     5754   8419   2962  -1572   -921   2124       O
ATOM   2563 N   ASP A 160     -5.090  39.217  68.780  1.00 43.97          N
ANISOU 2563 N   ASP A 160     5401   8065   3242  -1221   -970   2174       N
ATOM   2564 CA  ASP A 160     -4.322  40.294  69.378  1.00 43.28          C
ANISOU 2564 CA  ASP A 160     5371   7762   3310  -1072   -900   2235       C
ATOM   2566 CB  ASP A 160     -5.264  41.359  69.956  1.00 44.70          C
ANISOU 2566 CB  ASP A 160     5440   7828   3716   -854  -1015   2444       C
ATOM   2569 CG  ASP A 160     -4.530  42.536  70.623  1.00 44.17          C
ANISOU 2569 CG  ASP A 160     5446   7510   3825   -702   -945   2499       C
ATOM   2570 OD1 ASP A 160     -3.293  42.525  70.783  1.00 42.33          O
ANISOU 2570 OD1 ASP A 160     5332   7192   3558   -757   -807   2373       O
ATOM   2571 OD2 ASP A 160     -5.226  43.506  70.986  1.00 46.42          O
ANISOU 2571 OD2 ASP A 160     5662   7681   4293   -525  -1033   2670       O
ATOM   2572 C   ASP A 160     -3.526  39.628  70.468  1.00 40.52          C
ANISOU 2572 C   ASP A 160     5052   7267   3078  -1000   -707   1979       C
ATOM   2573 O   ASP A 160     -4.077  39.221  71.511  1.00 36.77          O
ANISOU 2573 O   ASP A 160     4486   6717   2770   -868   -676   1897       O
ATOM   2575 N   TYR A 161     -2.226  39.509  70.232  1.00 40.22          N
ANISOU 2575 N   TYR A 161     5131   7200   2949  -1091   -578   1861       N
ATOM   2576 CA  TYR A 161     -1.354  38.758  71.139  1.00 40.02          C
ANISOU 2576 CA  TYR A 161     5131   7060   3013  -1042   -405   1619       C
ATOM   2578 CB  TYR A 161     -0.285  38.045  70.300  1.00 41.77          C
ANISOU 2578 CB  TYR A 161     5447   7386   3037  -1226   -294   1460       C
ATOM   2581 CG  TYR A 161     -0.919  37.087  69.328  1.00 43.40          C
ANISOU 2581 CG  TYR A 161     5653   7794   3042  -1399   -349   1406       C
ATOM   2582 CD1 TYR A 161     -1.464  35.884  69.775  1.00 43.49          C
ANISOU 2582 CD1 TYR A 161     5617   7809   3097  -1394   -327   1247       C
ATOM   2584 CE1 TYR A 161     -2.070  35.009  68.893  1.00 45.61          C
ANISOU 2584 CE1 TYR A 161     5894   8255   3181  -1572   -382   1186       C
ATOM   2586 CZ  TYR A 161     -2.165  35.338  67.538  1.00 47.23          C
ANISOU 2586 CZ  TYR A 161     6151   8659   3136  -1758   -467   1289       C
ATOM   2587 OH  TYR A 161     -2.775  34.431  66.684  1.00 48.06          O
ANISOU 2587 OH  TYR A 161     6271   8949   3041  -1955   -524   1209       O
ATOM   2589 CE2 TYR A 161     -1.633  36.538  67.070  1.00 47.95          C
ANISOU 2589 CE2 TYR A 161     6288   8759   3170  -1764   -492   1466       C
ATOM   2591 CD2 TYR A 161     -1.023  37.405  67.971  1.00 46.55          C
ANISOU 2591 CD2 TYR A 161     6105   8382   3199  -1584   -433   1524       C
ATOM   2593 C   TYR A 161     -0.728  39.616  72.250  1.00 38.11          C
ANISOU 2593 C   TYR A 161     4902   6599   2977   -873   -333   1627       C
ATOM   2594 O   TYR A 161      0.113  39.136  73.011  1.00 35.34          O
ANISOU 2594 O   TYR A 161     4573   6156   2698   -834   -203   1453       O
ATOM   2596 N   THR A 162     -1.118  40.889  72.295  1.00 38.49          N
ANISOU 2596 N   THR A 162     4944   6565   3115   -782   -426   1832       N
ATOM   2597 CA  THR A 162     -0.718  41.825  73.356  1.00 37.10          C
ANISOU 2597 CA  THR A 162     4787   6169   3141   -622   -375   1848       C
ATOM   2599 CB  THR A 162     -1.166  41.328  74.752  1.00 34.17          C
ANISOU 2599 CB  THR A 162     4336   5702   2946   -463   -317   1716       C
ATOM   2601 OG1 THR A 162     -2.593  41.219  74.763  1.00 32.45          O
ANISOU 2601 OG1 THR A 162     4002   5554   2775   -392   -423   1807       O
```

FIG. 18 (continued)

| | | | | | | | | | | | | |
|---|---|---|---|---|---|---|---|---|---|---|---|---|
| ATOM | 2603 | CG2 | THR | A | 162 | -0.745 | 42.295 | 75.837 | 1.00 | 33.95 | | C |
| ANISOU | 2603 | CG2 | THR | A | 162 | 4340 | 5460 | 3101 | -319 | -263 | 1713 | C |
| ATOM | 2607 | C | THR | A | 162 | 0.779 | 42.166 | 73.336 | 1.00 | 36.45 | | C |
| ANISOU | 2607 | C | THR | A | 162 | 4809 | 6015 | 3025 | -697 | -263 | 1780 | C |
| ATOM | 2608 | O | THR | A | 162 | 1.138 | 43.298 | 73.036 | 1.00 | 33.73 | | O |
| ANISOU | 2608 | O | THR | A | 162 | 4531 | 5590 | 2694 | -712 | -295 | 1924 | O |
| ATOM | 2610 | N | LEU | A | 163 | 1.622 | 41.172 | 73.626 | 1.00 | 35.33 | | N |
| ANISOU | 2610 | N | LEU | A | 163 | 4674 | 5904 | 2847 | -747 | -137 | 1568 | N |
| ATOM | 2611 | CA | LEU | A | 163 | 3.071 | 41.334 | 73.668 | 1.00 | 35.43 | | C |
| ANISOU | 2611 | CA | LEU | A | 163 | 4749 | 5875 | 2838 | -814 | -21 | 1480 | C |
| ATOM | 2613 | CB | LEU | A | 163 | 3.703 | 40.158 | 74.403 | 1.00 | 33.67 | | C |
| ANISOU | 2613 | CB | LEU | A | 163 | 4490 | 5644 | 2657 | -786 | 98 | 1249 | C |
| ATOM | 2616 | CG | LEU | A | 163 | 3.261 | 39.915 | 75.832 | 1.00 | 31.31 | | C |
| ANISOU | 2616 | CG | LEU | A | 163 | 4140 | 5216 | 2540 | -619 | 104 | 1181 | C |
| ATOM | 2618 | CD1 | LEU | A | 163 | 3.732 | 38.518 | 76.281 | 1.00 | 30.01 | | C |
| ANISOU | 2618 | CD1 | LEU | A | 163 | 3945 | 5075 | 2381 | -619 | 195 | 980 | C |
| ATOM | 2622 | CD2 | LEU | A | 163 | 3.783 | 41.012 | 76.718 | 1.00 | 32.37 | | C |
| ANISOU | 2622 | CD2 | LEU | A | 163 | 4304 | 5187 | 2810 | -535 | 122 | 1220 | C |
| ATOM | 2626 | C | LEU | A | 163 | 3.696 | 41.371 | 72.298 | 1.00 | 37.64 | | C |
| ANISOU | 2626 | C | LEU | A | 163 | 5088 | 6309 | 2904 | -1011 | -3 | 1519 | C |
| ATOM | 2627 | O | LEU | A | 163 | 3.105 | 40.935 | 71.301 | 1.00 | 36.46 | | O |
| ANISOU | 2627 | O | LEU | A | 163 | 4940 | 6322 | 2590 | -1117 | -63 | 1561 | O |
| ATOM | 2629 | N | ASP | A | 164 | 4.925 | 41.862 | 72.264 | 1.00 | 40.18 | | N |
| ANISOU | 2629 | N | ASP | A | 164 | 5456 | 6594 | 3216 | -1077 | 86 | 1496 | N |
| ATOM | 2630 | CA | ASP | A | 164 | 5.705 | 41.777 | 71.052 | 1.00 | 43.07 | | C |
| ANISOU | 2630 | CA | ASP | A | 164 | 5869 | 7124 | 3372 | -1276 | 146 | 1492 | C |
| ATOM | 2632 | CB | ASP | A | 164 | 6.867 | 42.797 | 71.028 | 1.00 | 46.28 | | C |
| ANISOU | 2632 | CB | ASP | A | 164 | 6325 | 7466 | 3792 | -1351 | 207 | 1554 | C |
| ATOM | 2635 | CG | ASP | A | 164 | 7.964 | 42.496 | 72.036 | 1.00 | 45.91 | | C |
| ANISOU | 2635 | CG | ASP | A | 164 | 6229 | 7334 | 3881 | -1288 | 334 | 1371 | C |
| ATOM | 2636 | OD1 | ASP | A | 164 | 7.985 | 41.417 | 72.645 | 1.00 | 45.65 | | O |
| ANISOU | 2636 | OD1 | ASP | A | 164 | 6129 | 7303 | 3912 | -1198 | 389 | 1191 | O |
| ATOM | 2637 | OD2 | ASP | A | 164 | 8.829 | 43.371 | 72.219 | 1.00 | 49.97 | | O |
| ANISOU | 2637 | OD2 | ASP | A | 164 | 6770 | 7776 | 4438 | -1339 | 369 | 1421 | O |
| ATOM | 2638 | C | ASP | A | 164 | 6.192 | 40.346 | 70.805 | 1.00 | 42.50 | | C |
| ANISOU | 2638 | C | ASP | A | 164 | 5759 | 7181 | 3208 | -1334 | 269 | 1252 | C |
| ATOM | 2639 | O | ASP | A | 164 | 6.177 | 39.470 | 71.703 | 1.00 | 37.45 | | O |
| ANISOU | 2639 | O | ASP | A | 164 | 5062 | 6471 | 2695 | -1215 | 317 | 1090 | O |
| ATOM | 2641 | N | GLU | A | 165 | 6.661 | 40.166 | 69.577 | 1.00 | 44.17 | | N |
| ANISOU | 2641 | N | GLU | A | 165 | 6010 | 7574 | 3197 | -1521 | 324 | 1236 | N |
| ATOM | 2642 | CA | GLU | A | 165 | 7.064 | 38.888 | 69.014 | 1.00 | 47.25 | | C |
| ANISOU | 2642 | CA | GLU | A | 165 | 6386 | 8108 | 3459 | -1608 | 445 | 1013 | C |
| ATOM | 2644 | CB | GLU | A | 165 | 7.532 | 39.110 | 67.558 | 1.00 | 49.74 | | C |
| ANISOU | 2644 | CB | GLU | A | 165 | 6765 | 8636 | 3498 | -1842 | 494 | 1051 | C |
| ATOM | 2647 | CG | GLU | A | 165 | 7.649 | 37.866 | 66.690 | 1.00 | 52.86 | | C |
| ANISOU | 2647 | CG | GLU | A | 165 | 7172 | 9211 | 3703 | -1965 | 599 | 837 | C |
| ATOM | 2650 | CD | GLU | A | 165 | 8.409 | 38.116 | 65.369 | 1.00 | 55.85 | | C |
| ANISOU | 2650 | CD | GLU | A | 165 | 7607 | 9807 | 3805 | -2202 | 699 | 836 | C |
| ATOM | 2651 | OE1 | GLU | A | 165 | 9.198 | 39.082 | 65.276 | 1.00 | 55.86 | | O |
| ANISOU | 2651 | OE1 | GLU | A | 165 | 7617 | 9809 | 3799 | -2261 | 738 | 951 | O |
| ATOM | 2652 | OE2 | GLU | A | 165 | 8.229 | 37.333 | 64.418 | 1.00 | 61.51 | | O |
| ANISOU | 2652 | OE2 | GLU | A | 165 | 8365 | 10703 | 4304 | -2345 | 747 | 712 | O |
| ATOM | 2653 | C | GLU | A | 165 | 8.167 | 38.270 | 69.848 | 1.00 | 45.25 | | C |
| ANISOU | 2653 | C | GLU | A | 165 | 6068 | 7772 | 3354 | -1516 | 596 | 803 | C |
| ATOM | 2654 | O | GLU | A | 165 | 8.147 | 37.070 | 70.107 | 1.00 | 43.06 | | O |
| ANISOU | 2654 | O | GLU | A | 165 | 5754 | 7489 | 3118 | -1459 | 659 | 612 | O |
| ATOM | 2656 | N | GLU | A | 166 | 9.093 | 39.112 | 70.305 | 1.00 | 46.32 | | N |
| ANISOU | 2656 | N | GLU | A | 166 | 6188 | 7832 | 3581 | -1500 | 640 | 852 | N |
| ATOM | 2657 | CA | GLU | A | 166 | 10.241 | 38.669 | 71.095 | 1.00 | 46.57 | | C |
| ANISOU | 2657 | CA | GLU | A | 166 | 6138 | 7802 | 3754 | -1421 | 767 | 682 | C |
| ATOM | 2659 | CB | GLU | A | 166 | 11.304 | 39.774 | 71.206 | 1.00 | 48.03 | | C |
| ANISOU | 2659 | CB | GLU | A | 166 | 6313 | 7966 | 3968 | -1486 | 811 | 765 | C |
| ATOM | 2662 | CG | GLU | A | 166 | 12.059 | 40.029 | 69.890 | 1.00 | 53.22 | | C |
| ANISOU | 2662 | CG | GLU | A | 166 | 6992 | 8820 | 4408 | -1702 | 913 | 775 | C |
| ATOM | 2665 | CD | GLU | A | 166 | 12.915 | 41.310 | 69.882 | 1.00 | 54.66 | | C |
| ANISOU | 2665 | CD | GLU | A | 166 | 7187 | 8983 | 4598 | -1808 | 929 | 912 | C |
| ATOM | 2666 | OE1 | GLU | A | 166 | 12.529 | 42.324 | 70.534 | 1.00 | 54.98 | | O |
| ANISOU | 2666 | OE1 | GLU | A | 166 | 7278 | 8855 | 4757 | -1752 | 809 | 1078 | O |
| ATOM | 2667 | OE2 | GLU | A | 166 | 13.970 | 41.297 | 69.184 | 1.00 | 58.48 | | O |
| ANISOU | 2667 | OE2 | GLU | A | 166 | 7631 | 9623 | 4966 | -1958 | 1070 | 848 | O |
| ATOM | 2668 | C | GLU | A | 166 | 9.869 | 38.162 | 72.485 | 1.00 | 42.12 | | C |
| ANISOU | 2668 | C | GLU | A | 166 | 5526 | 7068 | 3409 | -1220 | 724 | 617 | C |
| ATOM | 2669 | O | GLU | A | 166 | 10.371 | 37.109 | 72.904 | 1.00 | 39.73 | | O |
| ANISOU | 2669 | O | GLU | A | 166 | 5161 | 6750 | 3183 | -1149 | 811 | 436 | O |
| ATOM | 2671 | N | SER | A | 167 | 9.039 | 38.898 | 73.231 | 1.00 | 41.10 | | N |
| ANISOU | 2671 | N | SER | A | 167 | 5423 | 6808 | 3385 | -1126 | 599 | 761 | N |
| ATOM | 2672 | CA | SER | A | 167 | 8.586 | 38.393 | 74.541 | 1.00 | 38.85 | | C |
| ANISOU | 2672 | CA | SER | A | 167 | 5098 | 6385 | 3278 | -954 | 562 | 701 | C |
| ATOM | 2674 | CB | SER | A | 167 | 7.831 | 39.471 | 75.358 | 1.00 | 40.37 | | C |

FIG. 18 (continued)

| | | | | | | | | | | | | |
|---|---|---|---|---|---|---|---|---|---|---|---|---|
| ANISOU | 2674 | CB | SER | A | 167 | 5318 | 6437 | 3583 | -860 | 450 | 856 | C |
| ATOM | 2677 | OG | SER | A | 167 | 8.449 | 40.743 | 75.221 | 1.00 | 43.59 | | O |
| ANISOU | 2677 | OG | SER | A | 167 | 5767 | 6803 | 3992 | -923 | 446 | 968 | O |
| ATOM | 2679 | C | SER | A | 167 | 7.731 | 37.114 | 74.405 | 1.00 | 36.14 | | C |
| ANISOU | 2679 | C | SER | A | 167 | 4744 | 6081 | 2906 | -925 | 550 | 604 | C |
| ATOM | 2680 | O | SER | A | 167 | 7.811 | 36.202 | 75.237 | 1.00 | 33.55 | | O |
| ANISOU | 2680 | O | SER | A | 167 | 4376 | 5681 | 2690 | -825 | 581 | 484 | O |
| ATOM | 2682 | N | ARG | A | 168 | 6.888 | 37.053 | 73.383 | 1.00 | 37.12 | | N |
| ANISOU | 2682 | N | ARG | A | 168 | 4909 | 6316 | 2879 | -1021 | 494 | 666 | N |
| ATOM | 2683 | CA | ARG | A | 168 | 6.145 | 35.834 | 73.118 | 1.00 | 39.36 | | C |
| ANISOU | 2683 | CA | ARG | A | 168 | 5191 | 6651 | 3114 | -1036 | 486 | 562 | C |
| ATOM | 2685 | CB | ARG | A | 168 | 5.185 | 36.032 | 71.950 | 1.00 | 43.65 | | C |
| ANISOU | 2685 | CB | ARG | A | 168 | 5777 | 7339 | 3470 | -1167 | 393 | 670 | C |
| ATOM | 2688 | CG | ARG | A | 168 | 4.008 | 36.898 | 72.338 | 1.00 | 44.92 | | C |
| ANISOU | 2688 | CG | ARG | A | 168 | 5921 | 7449 | 3698 | -1092 | 240 | 875 | C |
| ATOM | 2691 | CD | ARG | A | 168 | 2.872 | 36.651 | 71.426 | 1.00 | 48.22 | | C |
| ANISOU | 2691 | CD | ARG | A | 168 | 6345 | 8008 | 3968 | -1193 | 132 | 949 | C |
| ATOM | 2694 | NE | ARG | A | 168 | 2.961 | 37.416 | 70.218 | 1.00 | 50.50 | | N |
| ANISOU | 2694 | NE | ARG | A | 168 | 6688 | 8431 | 4070 | -1338 | 83 | 1089 | N |
| ATOM | 2696 | CZ | ARG | A | 168 | 2.692 | 36.960 | 68.988 | 1.00 | 53.49 | | C |
| ANISOU | 2696 | CZ | ARG | A | 168 | 7106 | 9001 | 4216 | -1519 | 59 | 1073 | C |
| ATOM | 2697 | NH1 | ARG | A | 168 | 2.264 | 35.719 | 68.755 | 1.00 | 54.74 | | N |
| ANISOU | 2697 | NH1 | ARG | A | 168 | 7261 | 9233 | 4306 | -1581 | 78 | 911 | N |
| ATOM | 2700 | NH2 | ARG | A | 168 | 2.826 | 37.774 | 67.969 | 1.00 | 53.68 | | N |
| ANISOU | 2700 | NH2 | ARG | A | 168 | 7185 | 9145 | 4066 | -1653 | 9 | 1229 | N |
| ATOM | 2703 | C | ARG | A | 168 | 7.082 | 34.649 | 72.861 | 1.00 | 39.34 | | C |
| ANISOU | 2703 | C | ARG | A | 168 | 5175 | 6681 | 3091 | -1066 | 629 | 337 | C |
| ATOM | 2704 | O | ARG | A | 168 | 6.890 | 33.562 | 73.421 | 1.00 | 39.19 | | O |
| ANISOU | 2704 | O | ARG | A | 168 | 5138 | 6588 | 3164 | -993 | 651 | 213 | O |
| ATOM | 2706 | N | ALA | A | 169 | 8.107 | 34.873 | 72.049 | 1.00 | 38.86 | | N |
| ANISOU | 2706 | N | ALA | A | 169 | 5122 | 6722 | 2923 | -1169 | 732 | 287 | N |
| ATOM | 2707 | CA | ALA | A | 169 | 9.109 | 33.847 | 71.764 | 1.00 | 39.70 | | C |
| ANISOU | 2707 | CA | ALA | A | 169 | 5198 | 6862 | 3025 | -1182 | 891 | 64 | C |
| ATOM | 2709 | CB | ALA | A | 169 | 10.123 | 34.347 | 70.732 | 1.00 | 40.38 | | C |
| ANISOU | 2709 | CB | ALA | A | 169 | 5283 | 7101 | 2957 | -1325 | 1004 | 43 | C |
| ATOM | 2713 | C | ALA | A | 169 | 9.829 | 33.355 | 73.024 | 1.00 | 37.99 | | C |
| ANISOU | 2713 | C | ALA | A | 169 | 4904 | 6492 | 3039 | -1012 | 938 | -27 | C |
| ATOM | 2714 | O | ALA | A | 169 | 10.196 | 32.192 | 73.085 | 1.00 | 37.56 | | O |
| ANISOU | 2714 | O | ALA | A | 169 | 4826 | 6401 | 3043 | -964 | 1024 | -205 | O |
| ATOM | 2716 | N | ARG | A | 170 | 10.015 | 34.220 | 74.022 | 1.00 | 38.51 | | N |
| ANISOU | 2716 | N | ARG | A | 170 | 4937 | 6464 | 3232 | -924 | 876 | 94 | N |
| ATOM | 2717 | CA | ARG | A | 170 | 10.674 | 33.804 | 75.257 | 1.00 | 40.21 | | C |
| ANISOU | 2717 | CA | ARG | A | 170 | 5080 | 6553 | 3646 | -778 | 898 | 30 | C |
| ATOM | 2719 | CB | ARG | A | 170 | 11.046 | 35.009 | 76.134 | 1.00 | 42.67 | | C |
| ANISOU | 2719 | CB | ARG | A | 170 | 5368 | 6802 | 4045 | -737 | 841 | 160 | C |
| ATOM | 2722 | CG | ARG | A | 170 | 12.023 | 35.936 | 75.426 | 1.00 | 48.08 | | C |
| ANISOU | 2722 | CG | ARG | A | 170 | 6034 | 7588 | 4647 | -855 | 906 | 197 | C |
| ATOM | 2725 | CD | ARG | A | 170 | 12.687 | 36.967 | 76.331 | 1.00 | 50.23 | | C |
| ANISOU | 2725 | CD | ARG | A | 170 | 6272 | 7789 | 5024 | -829 | 873 | 281 | C |
| ATOM | 2728 | NE | ARG | A | 170 | 11.893 | 38.200 | 76.458 | 1.00 | 53.38 | | N |
| ANISOU | 2728 | NE | ARG | A | 170 | 6758 | 8124 | 5400 | -857 | 765 | 456 | N |
| ATOM | 2730 | CZ | ARG | A | 170 | 11.189 | 38.536 | 77.537 | 1.00 | 53.20 | | C |
| ANISOU | 2730 | CZ | ARG | A | 170 | 6763 | 7968 | 5483 | -751 | 671 | 518 | C |
| ATOM | 2731 | NH1 | ARG | A | 170 | 11.163 | 37.734 | 78.607 | 1.00 | 54.69 | | N |
| ANISOU | 2731 | NH1 | ARG | A | 170 | 6908 | 8086 | 5787 | -629 | 662 | 436 | N |
| ATOM | 2734 | NH2 | ARG | A | 170 | 10.507 | 39.684 | 77.555 | 1.00 | 52.77 | | N |
| ANISOU | 2734 | NH2 | ARG | A | 170 | 6783 | 7848 | 5420 | -767 | 590 | 666 | N |
| ATOM | 2737 | C | ARG | A | 170 | 9.835 | 32.794 | 76.054 | 1.00 | 36.27 | | C |
| ANISOU | 2737 | C | ARG | A | 170 | 4595 | 5938 | 3249 | -672 | 841 | -12 | C |
| ATOM | 2738 | O | ARG | A | 170 | 10.387 | 31.866 | 76.670 | 1.00 | 33.96 | | O |
| ANISOU | 2738 | O | ARG | A | 170 | 4256 | 5563 | 3083 | -575 | 887 | -121 | O |
| ATOM | 2740 | N | ILE | A | 171 | 8.516 | 32.995 | 76.040 | 1.00 | 31.19 | | N |
| ANISOU | 2740 | N | ILE | A | 171 | 4006 | 5289 | 2554 | -692 | 737 | 89 | N |
| ATOM | 2741 | CA | ILE | A | 171 | 7.574 | 32.081 | 76.684 | 1.00 | 31.00 | | C |
| ANISOU | 2741 | CA | ILE | A | 171 | 3997 | 5181 | 2602 | -629 | 683 | 64 | C |
| ATOM | 2743 | CB | ILE | A | 171 | 6.140 | 32.692 | 76.755 | 1.00 | 28.12 | | C |
| ANISOU | 2743 | CB | ILE | A | 171 | 3658 | 4835 | 2192 | -647 | 561 | 215 | C |
| ATOM | 2745 | CG1 | ILE | A | 171 | 6.175 | 33.903 | 77.699 | 1.00 | 27.38 | | C |
| ANISOU | 2745 | CG1 | ILE | A | 171 | 3543 | 4674 | 2187 | -562 | 508 | 346 | C |
| ATOM | 2748 | CD1 | ILE | A | 171 | 4.932 | 34.839 | 77.667 | 1.00 | 28.27 | | C |
| ANISOU | 2748 | CD1 | ILE | A | 171 | 3665 | 4804 | 2271 | -560 | 402 | 508 | C |
| ATOM | 2752 | CG2 | ILE | A | 171 | 5.108 | 31.621 | 77.164 | 1.00 | 27.54 | | C |
| ANISOU | 2752 | CG2 | ILE | A | 171 | 3593 | 4714 | 2158 | -629 | 519 | 177 | C |
| ATOM | 2756 | C | ILE | A | 171 | 7.575 | 30.743 | 75.950 | 1.00 | 29.83 | | C |
| ANISOU | 2756 | C | ILE | A | 171 | 3877 | 5051 | 2405 | -683 | 754 | -103 | C |
| ATOM | 2757 | O | ILE | A | 171 | 7.767 | 29.705 | 76.579 | 1.00 | 27.63 | | O |
| ANISOU | 2757 | O | ILE | A | 171 | 3589 | 4660 | 2248 | -603 | 783 | -199 | O |
| ATOM | 2759 | N | LYS | A | 172 | 7.434 | 30.805 | 74.624 | 1.00 | 30.83 | | N |
| ANISOU | 2759 | N | LYS | A | 172 | 4046 | 5316 | 2354 | -824 | 785 | -138 | N |

FIG. 18 (continued)

| | | | | | | | | | | | | |
|---|---|---|---|---|---|---|---|---|---|---|---|---|
| ATOM | 2760 | CA | LYS | A | 172 | 7.447 | 29.636 | 73.770 | 1.00 | 34.56 | | C |
| ANISOU | 2760 | CA | LYS | A | 172 | 4562 | 5821 | 2748 | -905 | 865 | -320 | C |
| ATOM | 2762 | CB | LYS | A | 172 | 7.298 | 30.039 | 72.294 | 1.00 | 37.24 | | C |
| ANISOU | 2762 | CB | LYS | A | 172 | 4951 | 6353 | 2844 | -1088 | 885 | -322 | C |
| ATOM | 2765 | CG | LYS | A | 172 | 5.875 | 30.464 | 71.966 | 1.00 | 38.58 | | C |
| ANISOU | 2765 | CG | LYS | A | 172 | 5158 | 6603 | 2898 | -1178 | 734 | -169 | C |
| ATOM | 2768 | CD | LYS | A | 172 | 5.687 | 30.824 | 70.514 | 1.00 | 41.54 | | C |
| ANISOU | 2768 | CD | LYS | A | 172 | 5588 | 7181 | 3016 | -1371 | 730 | -150 | C |
| ATOM | 2771 | CE | LYS | A | 172 | 5.782 | 32.312 | 70.251 | 1.00 | 42.73 | | C |
| ANISOU | 2771 | CE | LYS | A | 172 | 5728 | 7415 | 3095 | -1402 | 665 | 64 | C |
| ATOM | 2774 | NZ | LYS | A | 172 | 5.290 | 32.666 | 68.884 | 1.00 | 46.85 | | N |
| ANISOU | 2774 | NZ | LYS | A | 172 | 6310 | 8141 | 3351 | -1602 | 611 | 137 | N |
| ATOM | 2778 | C | LYS | A | 172 | 8.699 | 28.797 | 73.946 | 1.00 | 34.84 | | C |
| ANISOU | 2778 | C | LYS | A | 172 | 4560 | 5778 | 2902 | -821 | 1005 | -501 | C |
| ATOM | 2779 | O | LYS | A | 172 | 8.638 | 27.576 | 73.891 | 1.00 | 35.70 | | O |
| ANISOU | 2779 | O | LYS | A | 172 | 4700 | 5802 | 3061 | -804 | 1056 | -654 | O |
| ATOM | 2781 | N | THR | A | 173 | 9.828 | 29.467 | 74.140 | 1.00 | 36.99 | | N |
| ANISOU | 2781 | N | THR | A | 173 | 4757 | 6073 | 3223 | -770 | 1065 | -481 | N |
| ATOM | 2782 | CA | THR | A | 173 | 11.119 | 28.808 | 74.249 | 1.00 | 38.96 | | C |
| ANISOU | 2782 | CA | THR | A | 173 | 4934 | 6278 | 3592 | -682 | 1199 | -640 | C |
| ATOM | 2784 | CB | THR | A | 173 | 12.268 | 29.849 | 74.110 | 1.00 | 39.55 | | C |
| ANISOU | 2784 | CB | THR | A | 173 | 4919 | 6457 | 3650 | -698 | 1261 | -593 | C |
| ATOM | 2786 | OG1 | THR | A | 173 | 12.366 | 30.218 | 72.727 | 1.00 | 42.37 | | O |
| ANISOU | 2786 | OG1 | THR | A | 173 | 5314 | 6996 | 3789 | -869 | 1342 | -634 | O |
| ATOM | 2788 | CG2 | THR | A | 173 | 13.623 | 29.314 | 74.605 | 1.00 | 40.94 | | C |
| ANISOU | 2788 | CG2 | THR | A | 173 | 4971 | 6579 | 4008 | -566 | 1365 | -710 | C |
| ATOM | 2792 | C | THR | A | 173 | 11.169 | 28.027 | 75.549 | 1.00 | 37.48 | | C |
| ANISOU | 2792 | C | THR | A | 173 | 4715 | 5897 | 3629 | -514 | 1153 | -646 | C |
| ATOM | 2793 | O | THR | A | 173 | 11.562 | 26.868 | 75.582 | 1.00 | 39.51 | | O |
| ANISOU | 2793 | O | THR | A | 173 | 4965 | 6054 | 3993 | -442 | 1228 | -798 | O |
| ATOM | 2795 | N | ARG | A | 174 | 10.729 | 28.673 | 76.607 | 1.00 | 36.00 | | N |
| ANISOU | 2795 | N | ARG | A | 174 | 4518 | 5655 | 3507 | -458 | 1030 | -477 | N |
| ATOM | 2796 | CA | ARG | A | 174 | 10.703 | 28.069 | 77.914 | 1.00 | 34.90 | | C |
| ANISOU | 2796 | CA | ARG | A | 174 | 4357 | 5355 | 3547 | -321 | 969 | -447 | C |
| ATOM | 2798 | CB | ARG | A | 174 | 10.300 | 29.141 | 78.927 | 1.00 | 35.07 | | C |
| ANISOU | 2798 | CB | ARG | A | 174 | 4369 | 5371 | 3587 | -294 | 853 | -264 | C |
| ATOM | 2801 | CG | ARG | A | 174 | 10.147 | 28.685 | 80.368 | 1.00 | 34.54 | | C |
| ANISOU | 2801 | CG | ARG | A | 174 | 4292 | 5168 | 3665 | -179 | 776 | -205 | C |
| ATOM | 2804 | CD | ARG | A | 174 | 11.430 | 28.023 | 80.900 | 1.00 | 36.35 | | C |
| ANISOU | 2804 | CD | ARG | A | 174 | 4438 | 5324 | 4051 | -63 | 819 | -272 | C |
| ATOM | 2807 | NE | ARG | A | 174 | 11.194 | 27.511 | 82.242 | 1.00 | 35.96 | | N |
| ANISOU | 2807 | NE | ARG | A | 174 | 4396 | 5149 | 4116 | 28 | 730 | -196 | N |
| ATOM | 2809 | CZ | ARG | A | 174 | 11.848 | 26.497 | 82.805 | 1.00 | 38.27 | | C |
| ANISOU | 2809 | CZ | ARG | A | 174 | 4652 | 5329 | 4561 | 136 | 732 | -233 | C |
| ATOM | 2810 | NH1 | ARG | A | 174 | 12.813 | 25.823 | 82.159 | 1.00 | 39.26 | | N |
| ANISOU | 2810 | NH1 | ARG | A | 174 | 4715 | 5432 | 4768 | 192 | 830 | -366 | N |
| ATOM | 2813 | NH2 | ARG | A | 174 | 11.506 | 26.131 | 84.034 | 1.00 | 38.45 | | N |
| ANISOU | 2813 | NH2 | ARG | A | 174 | 4699 | 5254 | 4655 | 191 | 636 | -133 | N |
| ATOM | 2816 | C | ARG | A | 174 | 9.786 | 26.822 | 77.956 | 1.00 | 34.44 | | C |
| ANISOU | 2816 | C | ARG | A | 174 | 4381 | 5185 | 3518 | -325 | 947 | -513 | C |
| ATOM | 2817 | O | ARG | A | 174 | 10.179 | 25.794 | 78.503 | 1.00 | 33.35 | | O |
| ANISOU | 2817 | O | ARG | A | 174 | 4234 | 4905 | 3531 | -224 | 968 | -583 | O |
| ATOM | 2819 | N | LEU | A | 175 | 8.607 | 26.914 | 77.331 | 1.00 | 32.55 | | N |
| ANISOU | 2819 | N | LEU | A | 175 | 4219 | 5013 | 3137 | -448 | 901 | -487 | N |
| ATOM | 2820 | CA | LEU | A | 175 | 7.682 | 25.785 | 77.183 | 1.00 | 34.42 | | C |
| ANISOU | 2820 | CA | LEU | A | 175 | 4537 | 5171 | 3371 | -499 | 882 | -557 | C |
| ATOM | 2822 | CB | LEU | A | 175 | 6.355 | 26.237 | 76.518 | 1.00 | 32.72 | | C |
| ANISOU | 2822 | CB | LEU | A | 175 | 4370 | 5083 | 2978 | -650 | 802 | -481 | C |
| ATOM | 2825 | CG | LEU | A | 175 | 5.480 | 27.172 | 77.368 | 1.00 | 30.89 | | C |
| ANISOU | 2825 | CG | LEU | A | 175 | 4105 | 4876 | 2756 | -621 | 679 | -278 | C |
| ATOM | 2827 | CD1 | LEU | A | 175 | 4.195 | 27.605 | 76.636 | 1.00 | 30.17 | | C |
| ANISOU | 2827 | CD1 | LEU | A | 175 | 4035 | 4921 | 2509 | -754 | 596 | -197 | C |
| ATOM | 2831 | CD2 | LEU | A | 175 | 5.099 | 26.510 | 78.703 | 1.00 | 27.44 | | C |
| ANISOU | 2831 | CD2 | LEU | A | 175 | 3667 | 4289 | 2471 | -532 | 630 | -235 | C |
| ATOM | 2835 | C | LEU | A | 175 | 8.305 | 24.606 | 76.412 | 1.00 | 36.46 | | C |
| ANISOU | 2835 | C | LEU | A | 175 | 4832 | 5367 | 3655 | -509 | 1009 | -780 | C |
| ATOM | 2836 | O | LEU | A | 175 | 8.148 | 23.455 | 76.805 | 1.00 | 34.73 | | O |
| ANISOU | 2836 | O | LEU | A | 175 | 4659 | 4982 | 3556 | -465 | 1014 | -854 | O |
| ATOM | 2838 | N | PHE | A | 176 | 9.017 | 24.912 | 75.327 | 1.00 | 38.45 | | N |
| ANISOU | 2838 | N | PHE | A | 176 | 5066 | 5746 | 3796 | -569 | 1118 | -887 | N |
| ATOM | 2839 | CA | PHE | A | 176 | 9.703 | 23.895 | 74.505 | 1.00 | 40.84 | | C |
| ANISOU | 2839 | CA | PHE | A | 176 | 5396 | 6010 | 4113 | -575 | 1271 | -1129 | C |
| ATOM | 2841 | CB | PHE | A | 176 | 10.338 | 24.546 | 73.254 | 1.00 | 44.17 | | C |
| ANISOU | 2841 | CB | PHE | A | 176 | 5794 | 6641 | 4348 | -683 | 1387 | -1212 | C |
| ATOM | 2844 | CG | PHE | A | 176 | 11.020 | 23.572 | 72.322 | 1.00 | 47.03 | | C |
| ANISOU | 2844 | CG | PHE | A | 176 | 6181 | 6990 | 4696 | -702 | 1570 | -1485 | C |
| ATOM | 2845 | CD1 | PHE | A | 176 | 10.377 | 23.114 | 71.177 | 1.00 | 50.11 | | C |
| ANISOU | 2845 | CD1 | PHE | A | 176 | 6691 | 7462 | 4887 | -883 | 1614 | -1627 | C |
| ATOM | 2847 | CE1 | PHE | A | 176 | 10.998 | 22.214 | 70.301 | 1.00 | 52.41 | | C |

FIG. 18 (continued)

| | | | | | | | | | | | | | |
|---|---|---|---|---|---|---|---|---|---|---|---|---|---|
| ANISOU | 2847 | CE1 | PHE | A | 176 | 7018 | 7740 | 5156 | -906 | 1801 | -1910 | | C |
| ATOM | 2849 | CZ | PHE | A | 176 | 12.282 | 21.758 | 70.574 | 1.00 | 53.39 | | | C |
| ANISOU | 2849 | CZ | PHE | A | 176 | 7040 | 7763 | 5484 | -724 | 1948 | -2044 | | C |
| ATOM | 2851 | CE2 | PHE | A | 176 | 12.941 | 22.202 | 71.713 | 1.00 | 51.95 | | | C |
| ANISOU | 2851 | CE2 | PHE | A | 176 | 6720 | 7507 | 5510 | -538 | 1889 | -1884 | | C |
| ATOM | 2853 | CD2 | PHE | A | 176 | 12.307 | 23.120 | 72.580 | 1.00 | 49.32 | | | C |
| ANISOU | 2853 | CD2 | PHE | A | 176 | 6371 | 7195 | 5172 | -539 | 1699 | -1608 | | C |
| ATOM | 2855 | C | PHE | A | 176 | 10.768 | 23.186 | 75.349 | 1.00 | 39.76 | | | C |
| ANISOU | 2855 | C | PHE | A | 176 | 5184 | 5693 | 4229 | -375 | 1327 | -1191 | | C |
| ATOM | 2856 | O | PHE | A | 176 | 10.893 | 21.982 | 75.299 | 1.00 | 39.32 | | | O |
| ANISOU | 2856 | O | PHE | A | 176 | 5175 | 5477 | 4286 | -323 | 1390 | -1343 | | O |
| ATOM | 2858 | N | THR | A | 177 | 11.508 | 23.951 | 76.141 | 1.00 | 37.82 | | | N |
| ANISOU | 2858 | N | THR | A | 177 | 4824 | 5469 | 4075 | -266 | 1294 | -1065 | | N |
| ATOM | 2859 | CA | THR | A | 177 | 12.524 | 23.395 | 77.010 | 1.00 | 39.17 | | | C |
| ANISOU | 2859 | CA | THR | A | 177 | 4903 | 5498 | 4484 | -76 | 1317 | -1085 | | C |
| ATOM | 2861 | CB | THR | A | 177 | 13.366 | 24.498 | 77.691 | 1.00 | 39.85 | | | C |
| ANISOU | 2861 | CB | THR | A | 177 | 4854 | 5676 | 4612 | -9 | 1277 | -945 | | C |
| ATOM | 2863 | OG1 | THR | A | 177 | 13.971 | 25.335 | 76.693 | 1.00 | 41.61 | | | O |
| ANISOU | 2863 | OG1 | THR | A | 177 | 5021 | 6096 | 4694 | -103 | 1380 | -997 | | O |
| ATOM | 2865 | CG2 | THR | A | 177 | 14.476 | 23.879 | 78.544 | 1.00 | 41.92 | | | C |
| ANISOU | 2865 | CG2 | THR | A | 177 | 4999 | 5812 | 5117 | 184 | 1288 | -962 | | C |
| ATOM | 2869 | C | THR | A | 177 | 11.904 | 22.463 | 78.066 | 1.00 | 38.20 | | | C |
| ANISOU | 2869 | C | THR | A | 177 | 4844 | 5155 | 4514 | 5 | 1213 | -1021 | | C |
| ATOM | 2870 | O | THR | A | 177 | 12.417 | 21.383 | 78.310 | 1.00 | 40.54 | | | O |
| ANISOU | 2870 | O | THR | A | 177 | 5136 | 5277 | 4991 | 125 | 1258 | -1116 | | O |
| ATOM | 2872 | N | ILE | A | 178 | 10.789 | 22.860 | 78.667 | 1.00 | 35.86 | | | N |
| ANISOU | 2872 | N | ILE | A | 178 | 4609 | 4867 | 4149 | -62 | 1080 | -859 | | N |
| ATOM | 2873 | CA | ILE | A | 178 | 10.134 | 22.032 | 79.692 | 1.00 | 35.33 | | | C |
| ANISOU | 2873 | CA | ILE | A | 178 | 4606 | 4616 | 4202 | -15 | 983 | -780 | | C |
| ATOM | 2875 | CB | ILE | A | 178 | 8.909 | 22.747 | 80.325 | 1.00 | 33.49 | | | C |
| ANISOU | 2875 | CB | ILE | A | 178 | 4408 | 4451 | 3865 | -101 | 854 | -596 | | C |
| ATOM | 2877 | CG1 | ILE | A | 178 | 9.349 | 23.956 | 81.173 | 1.00 | 31.94 | | | C |
| ANISOU | 2877 | CG1 | ILE | A | 178 | 4120 | 4346 | 3671 | -37 | 792 | -442 | | C |
| ATOM | 2880 | CD1 | ILE | A | 178 | 8.219 | 24.945 | 81.388 | 1.00 | 29.60 | | | C |
| ANISOU | 2880 | CD1 | ILE | A | 178 | 3846 | 4161 | 3241 | -128 | 709 | -307 | | C |
| ATOM | 2884 | CG2 | ILE | A | 178 | 8.070 | 21.804 | 81.184 | 1.00 | 31.69 | | | C |
| ANISOU | 2884 | CG2 | ILE | A | 178 | 4260 | 4060 | 3722 | -102 | 775 | -532 | | C |
| ATOM | 2888 | C | ILE | A | 178 | 9.724 | 20.699 | 79.073 | 1.00 | 37.25 | | | C |
| ANISOU | 2888 | C | ILE | A | 178 | 4960 | 4712 | 4479 | -62 | 1043 | -945 | | C |
| ATOM | 2889 | O | ILE | A | 178 | 10.056 | 19.632 | 79.614 | 1.00 | 36.51 | | | O |
| ANISOU | 2889 | O | ILE | A | 178 | 4891 | 4406 | 4575 | 47 | 1046 | -979 | | O |
| ATOM | 2891 | N | ARG | A | 179 | 9.018 | 20.778 | 77.939 | 1.00 | 37.75 | | | N |
| ANISOU | 2891 | N | ARG | A | 179 | 5097 | 4887 | 4359 | -229 | 1083 | -1041 | | N |
| ATOM | 2892 | CA | ARG | A | 179 | 8.543 | 19.597 | 77.222 | 1.00 | 41.26 | | | C |
| ANISOU | 2892 | CA | ARG | A | 179 | 5665 | 5216 | 4796 | -318 | 1141 | -1220 | | C |
| ATOM | 2894 | CB | ARG | A | 179 | 7.807 | 20.015 | 75.936 | 1.00 | 41.55 | | | C |
| ANISOU | 2894 | CB | ARG | A | 179 | 5759 | 5453 | 4575 | -528 | 1165 | -1296 | | C |
| ATOM | 2897 | CG | ARG | A | 179 | 7.507 | 18.863 | 74.946 | 1.00 | 44.76 | | | C |
| ANISOU | 2897 | CG | ARG | A | 179 | 6296 | 5777 | 4935 | -648 | 1253 | -1536 | | C |
| ATOM | 2900 | CD | ARG | A | 179 | 6.521 | 19.325 | 73.893 | 1.00 | 46.07 | | | C |
| ANISOU | 2900 | CD | ARG | A | 179 | 6518 | 6161 | 4825 | -883 | 1218 | -1549 | | C |
| ATOM | 2903 | NE | ARG | A | 179 | 6.174 | 18.296 | 72.922 | 1.00 | 49.10 | | | N |
| ANISOU | 2903 | NE | ARG | A | 179 | 7036 | 6492 | 5127 | -1034 | 1292 | -1784 | | N |
| ATOM | 2905 | CZ | ARG | A | 179 | 6.865 | 18.026 | 71.818 | 1.00 | 53.12 | | | C |
| ANISOU | 2905 | CZ | ARG | A | 179 | 7583 | 7055 | 5546 | -1079 | 1451 | -2022 | | C |
| ATOM | 2906 | NH1 | ARG | A | 179 | 7.983 | 18.700 | 71.519 | 1.00 | 53.77 | | | N |
| ANISOU | 2906 | NH1 | ARG | A | 179 | 7565 | 7253 | 5613 | -984 | 1559 | -2051 | | N |
| ATOM | 2909 | NH2 | ARG | A | 179 | 6.439 | 17.065 | 71.007 | 1.00 | 55.06 | | | N |
| ANISOU | 2909 | NH2 | ARG | A | 179 | 7968 | 7241 | 5710 | -1234 | 1510 | -2243 | | N |
| ATOM | 2912 | C | ARG | A | 179 | 9.678 | 18.646 | 76.870 | 1.00 | 44.09 | | | C |
| ANISOU | 2912 | C | ARG | A | 179 | 6017 | 5419 | 5316 | -193 | 1284 | -1429 | | C |
| ATOM | 2913 | O | ARG | A | 179 | 9.566 | 17.437 | 77.061 | 1.00 | 43.91 | | | O |
| ANISOU | 2913 | O | ARG | A | 179 | 6082 | 5162 | 5438 | -156 | 1300 | -1518 | | O |
| ATOM | 2915 | N | GLN | A | 180 | 10.745 | 19.219 | 76.312 | 1.00 | 46.17 | | | N |
| ANISOU | 2915 | N | GLN | A | 180 | 6175 | 5815 | 5552 | -137 | 1395 | -1509 | | N |
| ATOM | 2916 | CA | GLN | A | 180 | 11.948 | 18.504 | 75.932 | 1.00 | 49.44 | | | C |
| ANISOU | 2916 | CA | GLN | A | 180 | 6537 | 6127 | 6119 | 1 | 1553 | -1712 | | C |
| ATOM | 2918 | CB | GLN | A | 180 | 12.959 | 19.529 | 75.417 | 1.00 | 51.72 | | | C |
| ANISOU | 2918 | CB | GLN | A | 180 | 6680 | 6647 | 6325 | 20 | 1648 | -1732 | | C |
| ATOM | 2921 | CG | GLN | A | 180 | 14.378 | 19.045 | 75.281 | 1.00 | 56.26 | | | C |
| ANISOU | 2921 | CG | GLN | A | 180 | 7128 | 7159 | 7089 | 201 | 1802 | -1891 | | C |
| ATOM | 2924 | CD | GLN | A | 180 | 14.697 | 18.698 | 73.875 | 1.00 | 61.33 | | | C |
| ANISOU | 2924 | CD | GLN | A | 180 | 7804 | 7884 | 7613 | 117 | 2007 | -2170 | | C |
| ATOM | 2925 | OE1 | GLN | A | 180 | 15.466 | 19.410 | 73.214 | 1.00 | 64.33 | | | O |
| ANISOU | 2925 | OE1 | GLN | A | 180 | 8075 | 8479 | 7888 | 86 | 2124 | -2230 | | O |
| ATOM | 2926 | NE2 | GLN | A | 180 | 14.085 | 17.617 | 73.371 | 1.00 | 64.71 | | | N |
| ANISOU | 2926 | NE2 | GLN | A | 180 | 8394 | 8154 | 8039 | 55 | 2058 | -2351 | | N |
| ATOM | 2929 | C | GLN | A | 180 | 12.554 | 17.700 | 77.092 | 1.00 | 49.59 | | | C |
| ANISOU | 2929 | C | GLN | A | 180 | 6509 | 5891 | 6442 | 223 | 1509 | -1651 | | C |

FIG. 18 (continued)

| | | | | | | | | | | | | |
|---|---|---|---|---|---|---|---|---|---|---|---|---|
| ATOM | 2930 | O | GLN | A | 180 | 12.852 | 16.499 | 76.949 | 1.00 | 50.00 | | O |
| ANISOU | 2930 | O | GLN | A | 180 | 6616 | 5717 | 6666 | 313 | 1588 | -1813 | O |
| ATOM | 2932 | N | GLU | A | 181 | 12.756 | 18.386 | 78.215 | 1.00 | 47.98 | | N |
| ANISOU | 2932 | N | GLU | A | 181 | 6207 | 5723 | 6299 | 308 | 1382 | -1421 | N |
| ATOM | 2933 | CA | GLU | A | 181 | 13.348 | 17.801 | 79.416 | 1.00 | 49.22 | | C |
| ANISOU | 2933 | CA | GLU | A | 181 | 6305 | 5682 | 6715 | 506 | 1306 | -1312 | C |
| ATOM | 2935 | CB | GLU | A | 181 | 13.647 | 18.886 | 80.455 | 1.00 | 49.52 | | C |
| ANISOU | 2935 | CB | GLU | A | 181 | 6222 | 5853 | 6740 | 552 | 1180 | -1077 | C |
| ATOM | 2938 | CG | GLU | A | 181 | 14.749 | 19.866 | 80.026 | 1.00 | 51.92 | | C |
| ANISOU | 2938 | CG | GLU | A | 181 | 6357 | 6370 | 7002 | 586 | 1262 | -1114 | C |
| ATOM | 2941 | CD | GLU | A | 181 | 16.073 | 19.198 | 79.797 | 1.00 | 56.38 | | C |
| ANISOU | 2941 | CD | GLU | A | 181 | 6790 | 6856 | 7777 | 769 | 1381 | -1257 | C |
| ATOM | 2942 | OE1 | GLU | A | 181 | 16.359 | 18.216 | 80.537 | 1.00 | 59.61 | | O |
| ANISOU | 2942 | OE1 | GLU | A | 181 | 7194 | 7038 | 8418 | 930 | 1329 | -1224 | O |
| ATOM | 2943 | OE2 | GLU | A | 181 | 16.819 | 19.639 | 78.873 | 1.00 | 59.10 | | O |
| ANISOU | 2943 | OE2 | GLU | A | 181 | 7033 | 7365 | 8059 | 752 | 1528 | -1397 | O |
| ATOM | 2944 | C | GLU | A | 181 | 12.446 | 16.741 | 80.035 | 1.00 | 48.20 | | C |
| ANISOU | 2944 | C | GLU | A | 181 | 6329 | 5306 | 6680 | 489 | 1213 | -1255 | C |
| ATOM | 2945 | O | GLU | A | 181 | 12.934 | 15.729 | 80.530 | 1.00 | 48.46 | | O |
| ANISOU | 2945 | O | GLU | A | 181 | 6368 | 5095 | 6949 | 642 | 1209 | -1268 | O |
| ATOM | 2947 | N | MET | A | 182 | 11.135 | 16.970 | 80.005 | 1.00 | 45.43 | | N |
| ANISOU | 2947 | N | MET | A | 182 | 6093 | 5014 | 6153 | 301 | 1137 | -1183 | N |
| ATOM | 2948 | CA | MET | A | 182 | 10.182 | 15.936 | 80.436 | 1.00 | 44.59 | | C |
| ANISOU | 2948 | CA | MET | A | 182 | 6139 | 4692 | 6111 | 238 | 1065 | -1148 | C |
| ATOM | 2950 | CB | MET | A | 182 | 8.741 | 16.443 | 80.362 | 1.00 | 41.86 | | C |
| ANISOU | 2950 | CB | MET | A | 182 | 5870 | 4489 | 5545 | 20 | 983 | -1056 | C |
| ATOM | 2953 | CG | MET | A | 182 | 8.296 | 17.263 | 81.557 | 1.00 | 39.33 | | C |
| ANISOU | 2953 | CG | MET | A | 182 | 5494 | 4268 | 5183 | 22 | 843 | -796 | C |
| ATOM | 2956 | SD | MET | A | 182 | 6.582 | 17.682 | 81.277 | 1.00 | 38.52 | | S |
| ANISOU | 2956 | SD | MET | A | 182 | 5463 | 4318 | 4853 | -220 | 775 | -732 | S |
| ATOM | 2957 | CE | MET | A | 182 | 6.295 | 18.790 | 82.676 | 1.00 | 34.74 | | C |
| ANISOU | 2957 | CE | MET | A | 182 | 4894 | 3966 | 4339 | -175 | 651 | -463 | C |
| ATOM | 2961 | C | MET | A | 182 | 10.337 | 14.692 | 79.564 | 1.00 | 47.22 | | C |
| ANISOU | 2961 | C | MET | A | 182 | 6581 | 4817 | 6544 | 240 | 1191 | -1400 | C |
| ATOM | 2962 | O | MET | A | 182 | 10.392 | 13.573 | 80.082 | 1.00 | 49.49 | | O |
| ANISOU | 2962 | O | MET | A | 182 | 6946 | 4819 | 7038 | 323 | 1167 | -1398 | O |
| ATOM | 2964 | N | ALA | A | 183 | 10.381 | 14.885 | 78.243 | 1.00 | 47.79 | | N |
| ANISOU | 2964 | N | ALA | A | 183 | 6669 | 5025 | 6463 | 138 | 1324 | -1616 | N |
| ATOM | 2965 | CA | ALA | A | 183 | 10.523 | 13.769 | 77.296 | 1.00 | 51.59 | | C |
| ANISOU | 2965 | CA | ALA | A | 183 | 7264 | 5331 | 7006 | 118 | 1468 | -1899 | C |
| ATOM | 2967 | CB | ALA | A | 183 | 10.467 | 14.262 | 75.852 | 1.00 | 51.38 | | C |
| ANISOU | 2967 | CB | ALA | A | 183 | 7249 | 5543 | 6729 | -41 | 1599 | -2105 | C |
| ATOM | 2971 | C | ALA | A | 183 | 11.810 | 12.996 | 77.527 | 1.00 | 54.11 | | C |
| ANISOU | 2971 | C | ALA | A | 183 | 7516 | 5424 | 7621 | 378 | 1562 | -2001 | C |
| ATOM | 2972 | O | ALA | A | 183 | 11.826 | 11.759 | 77.463 | 1.00 | 56.96 | | O |
| ANISOU | 2972 | O | ALA | A | 183 | 7993 | 5486 | 8164 | 431 | 1611 | -2136 | O |
| ATOM | 2974 | N | ASN | A | 184 | 12.892 | 13.723 | 77.793 | 1.00 | 54.11 | | N |
| ANISOU | 2974 | N | ASN | A | 184 | 7321 | 5559 | 7680 | 539 | 1585 | -1937 | N |
| ATOM | 2975 | CA | ASN | A | 184 | 14.171 | 13.091 | 78.137 | 1.00 | 56.95 | | C |
| ANISOU | 2975 | CA | ASN | A | 184 | 7566 | 5733 | 8339 | 811 | 1652 | -1993 | C |
| ATOM | 2977 | CB | ASN | A | 184 | 15.254 | 14.141 | 78.380 | 1.00 | 57.02 | | C |
| ANISOU | 2977 | CB | ASN | A | 184 | 7338 | 5975 | 8353 | 932 | 1661 | -1901 | C |
| ATOM | 2980 | CG | ASN | A | 184 | 15.743 | 14.801 | 77.084 | 1.00 | 58.55 | | C |
| ANISOU | 2980 | CG | ASN | A | 184 | 7453 | 6429 | 8362 | 851 | 1849 | -2113 | C |
| ATOM | 2981 | OD1 | ASN | A | 184 | 15.387 | 14.378 | 75.979 | 1.00 | 59.33 | | O |
| ANISOU | 2981 | OD1 | ASN | A | 184 | 7673 | 6525 | 8346 | 729 | 1986 | -2352 | O |
| ATOM | 2982 | ND2 | ASN | A | 184 | 16.555 | 15.853 | 77.223 | 1.00 | 57.58 | | N |
| ANISOU | 2982 | ND2 | ASN | A | 184 | 7136 | 6541 | 8199 | 900 | 1853 | -2022 | N |
| ATOM | 2985 | C | ASN | A | 184 | 14.067 | 12.159 | 79.348 | 1.00 | 57.31 | | C |
| ANISOU | 2985 | C | ASN | A | 184 | 7670 | 5460 | 8645 | 945 | 1512 | -1824 | C |
| ATOM | 2986 | O | ASN | A | 184 | 14.697 | 11.100 | 79.372 | 1.00 | 58.93 | | O |
| ANISOU | 2986 | O | ASN | A | 184 | 7886 | 5387 | 9117 | 1125 | 1577 | -1935 | O |
| ATOM | 2988 | N | ARG | A | 185 | 13.259 | 12.541 | 80.330 | 1.00 | 54.36 | | N |
| ANISOU | 2988 | N | ARG | A | 185 | 7340 | 5124 | 8192 | 854 | 1326 | -1557 | N |
| ATOM | 2989 | CA | ARG | A | 185 | 13.071 | 11.729 | 81.535 | 1.00 | 55.58 | | C |
| ANISOU | 2989 | CA | ARG | A | 185 | 7561 | 5007 | 8550 | 943 | 1179 | -1360 | C |
| ATOM | 2991 | CB | ARG | A | 185 | 12.810 | 12.642 | 82.739 | 1.00 | 53.50 | | C |
| ANISOU | 2991 | CB | ARG | A | 185 | 7223 | 4912 | 8192 | 917 | 998 | -1050 | C |
| ATOM | 2994 | CG | ARG | A | 185 | 13.948 | 13.615 | 83.044 | 1.00 | 54.02 | | C |
| ANISOU | 2994 | CG | ARG | A | 185 | 7063 | 5187 | 8274 | 1060 | 990 | -975 | C |
| ATOM | 3002 | C | ARG | A | 185 | 11.941 | 10.700 | 81.423 | 1.00 | 55.51 | | C |
| ANISOU | 3002 | C | ARG | A | 185 | 7787 | 4759 | 8544 | 788 | 1157 | -1406 | C |
| ATOM | 3003 | O | ARG | A | 185 | 11.687 | 9.956 | 82.380 | 1.00 | 56.48 | | O |
| ANISOU | 3003 | O | ARG | A | 185 | 7994 | 4641 | 8825 | 830 | 1037 | -1237 | O |
| ATOM | 3005 | N | GLY | A | 186 | 11.274 | 10.646 | 80.270 | 1.00 | 54.79 | | N |
| ANISOU | 3005 | N | GLY | A | 186 | 7805 | 4738 | 8276 | 596 | 1264 | -1625 | N |
| ATOM | 3006 | CA | GLY | A | 186 | 10.128 | 9.750 | 80.066 | 1.00 | 55.10 | | C |
| ANISOU | 3006 | CA | GLY | A | 186 | 8063 | 4588 | 8284 | 402 | 1242 | -1684 | C |
| ATOM | 3009 | C | GLY | A | 186 | 8.829 | 10.193 | 80.724 | 1.00 | 52.34 | | C |

FIG. 18 (continued)

| | | | | | | | | | | | | |
|---|---|---|---|---|---|---|---|---|---|---|---|---|
| ANISOU | 3009 | C | GLY | A | 186 | 7768 | 4366 | 7751 | 192 | 1084 | -1452 | C |
| ATOM | 3010 | O | GLY | A | 186 | 7.959 | 9.370 | 81.000 | 1.00 | 52.52 | | O |
| ANISOU | 3010 | O | GLY | A | 186 | 7949 | 4196 | 7809 | 61 | 1023 | -1413 | O |
| ATOM | 3012 | N | LEU | A | 187 | 8.683 | 11.500 | 80.952 | 1.00 | 49.24 | | N |
| ANISOU | 3012 | N | LEU | A | 187 | 7244 | 4298 | 7167 | 153 | 1026 | -1307 | N |
| ATOM | 3013 | CA | LEU | A | 187 | 7.541 | 12.050 | 81.698 | 1.00 | 46.49 | | C |
| ANISOU | 3013 | CA | LEU | A | 187 | 6909 | 4092 | 6662 | -6 | 885 | -1077 | C |
| ATOM | 3015 | CB | LEU | A | 187 | 8.039 | 13.038 | 82.760 | 1.00 | 44.65 | | C |
| ANISOU | 3015 | CB | LEU | A | 187 | 6522 | 4015 | 6429 | 124 | 792 | -843 | C |
| ATOM | 3018 | CG | LEU | A | 187 | 9.035 | 12.558 | 83.827 | 1.00 | 46.15 | | C |
| ANISOU | 3018 | CG | LEU | A | 187 | 6662 | 4008 | 6865 | 349 | 732 | -709 | C |
| ATOM | 3020 | CD1 | LEU | A | 187 | 9.632 | 13.743 | 84.570 | 1.00 | 43.03 | | C |
| ANISOU | 3020 | CD1 | LEU | A | 187 | 6098 | 3838 | 6415 | 447 | 664 | -540 | C |
| ATOM | 3024 | CD2 | LEU | A | 187 | 8.410 | 11.582 | 84.801 | 1.00 | 48.01 | | C |
| ANISOU | 3024 | CD2 | LEU | A | 187 | 7031 | 3999 | 7212 | 306 | 621 | -544 | C |
| ATOM | 3028 | C | LEU | A | 187 | 6.498 | 12.766 | 80.820 | 1.00 | 44.89 | | C |
| ANISOU | 3028 | C | LEU | A | 187 | 6721 | 4158 | 6177 | -242 | 898 | -1141 | C |
| ATOM | 3029 | O | LEU | A | 187 | 5.380 | 13.037 | 81.270 | 1.00 | 41.95 | | O |
| ANISOU | 3029 | O | LEU | A | 187 | 6371 | 3883 | 5685 | -396 | 798 | -990 | O |
| ATOM | 3031 | N | TRP | A | 188 | 6.864 | 13.114 | 79.591 | 1.00 | 45.45 | | N |
| ANISOU | 3031 | N | TRP | A | 188 | 6766 | 4367 | 6135 | -271 | 1017 | -1350 | N |
| ATOM | 3032 | CA | TRP | A | 188 | 5.980 | 13.895 | 78.734 | 1.00 | 44.47 | | C |
| ANISOU | 3032 | CA | TRP | A | 188 | 6639 | 4521 | 5736 | -481 | 1013 | -1385 | C |
| ATOM | 3034 | CB | TRP | A | 188 | 6.699 | 14.334 | 77.466 | 1.00 | 45.78 | | C |
| ANISOU | 3034 | CB | TRP | A | 188 | 6762 | 4843 | 5788 | -477 | 1152 | -1597 | C |
| ATOM | 3037 | CG | TRP | A | 188 | 5.769 | 15.034 | 76.523 | 1.00 | 44.93 | | C |
| ANISOU | 3037 | CG | TRP | A | 188 | 6669 | 5008 | 5395 | -706 | 1133 | -1622 | C |
| ATOM | 3038 | CD1 | TRP | A | 188 | 5.248 | 14.534 | 75.359 | 1.00 | 46.99 | | C |
| ANISOU | 3038 | CD1 | TRP | A | 188 | 7044 | 5299 | 5509 | -902 | 1192 | -1829 | C |
| ATOM | 3040 | NE1 | TRP | A | 188 | 4.415 | 15.454 | 74.784 | 1.00 | 45.62 | | N |
| ANISOU | 3040 | NE1 | TRP | A | 188 | 6836 | 5417 | 5079 | -1079 | 1124 | -1754 | N |
| ATOM | 3042 | CE2 | TRP | A | 188 | 4.377 | 16.573 | 75.574 | 1.00 | 43.20 | | C |
| ANISOU | 3042 | CE2 | TRP | A | 188 | 6397 | 5251 | 4765 | -989 | 1031 | -1507 | C |
| ATOM | 3043 | CD2 | TRP | A | 188 | 5.226 | 16.343 | 76.675 | 1.00 | 42.24 | | C |
| ANISOU | 3043 | CD2 | TRP | A | 188 | 6227 | 4940 | 4881 | -765 | 1037 | -1429 | C |
| ATOM | 3044 | CE3 | TRP | A | 188 | 5.363 | 17.345 | 77.641 | 1.00 | 40.40 | | C |
| ANISOU | 3044 | CE3 | TRP | A | 188 | 5872 | 4804 | 4673 | -653 | 954 | -1200 | C |
| ATOM | 3046 | CZ3 | TRP | A | 188 | 4.680 | 18.540 | 77.474 | 1.00 | 38.46 | | C |
| ANISOU | 3046 | CZ3 | TRP | A | 188 | 5560 | 4812 | 4242 | -745 | 880 | -1066 | C |
| ATOM | 3048 | CH2 | TRP | A | 188 | 3.850 | 18.741 | 76.371 | 1.00 | 39.59 | | C |
| ANISOU | 3048 | CH2 | TRP | A | 188 | 5744 | 5128 | 4173 | -946 | 871 | -1131 | C |
| ATOM | 3050 | CZ2 | TRP | A | 188 | 3.683 | 17.774 | 75.405 | 1.00 | 42.11 | | C |
| ANISOU | 3050 | CZ2 | TRP | A | 188 | 6179 | 5384 | 4437 | -1080 | 939 | -1348 | C |
| ATOM | 3052 | C | TRP | A | 188 | 4.664 | 13.194 | 78.345 | 1.00 | 44.65 | | C |
| ANISOU | 3052 | C | TRP | A | 188 | 6807 | 4496 | 5663 | -728 | 973 | -1439 | C |
| ATOM | 3053 | O | TRP | A | 188 | 3.612 | 13.802 | 78.419 | 1.00 | 42.57 | | O |
| ANISOU | 3053 | O | TRP | A | 188 | 6515 | 4427 | 5233 | -881 | 880 | -1311 | O |
| ATOM | 3055 | N | ASP | A | 189 | 4.712 | 11.940 | 77.920 | 1.00 | 48.60 | | N |
| ANISOU | 3055 | N | ASP | A | 189 | 7453 | 4739 | 6272 | -769 | 1041 | -1631 | N |
| ATOM | 3056 | CA | ASP | A | 189 | 3.477 | 11.243 | 77.497 | 1.00 | 50.57 | | C |
| ANISOU | 3056 | CA | ASP | A | 189 | 7846 | 4943 | 6425 | -1033 | 1002 | -1700 | C |
| ATOM | 3058 | CB | ASP | A | 189 | 3.764 | 9.815 | 77.034 | 1.00 | 55.47 | | C |
| ANISOU | 3058 | CB | ASP | A | 189 | 8646 | 5228 | 7204 | -1049 | 1100 | -1946 | C |
| ATOM | 3061 | CG | ASP | A | 189 | 4.463 | 9.759 | 75.690 | 1.00 | 58.87 | | C |
| ANISOU | 3061 | CG | ASP | A | 189 | 9104 | 5709 | 7555 | -1046 | 1268 | -2257 | C |
| ATOM | 3062 | OD1 | ASP | A | 189 | 4.806 | 10.833 | 75.152 | 1.00 | 59.44 | | O |
| ANISOU | 3062 | OD1 | ASP | A | 189 | 9052 | 6079 | 7454 | -1026 | 1304 | -2261 | O |
| ATOM | 3063 | OD2 | ASP | A | 189 | 4.667 | 8.636 | 75.179 | 1.00 | 62.94 | | O |
| ANISOU | 3063 | OD2 | ASP | A | 189 | 9773 | 5962 | 8180 | -1071 | 1369 | -2501 | O |
| ATOM | 3064 | C | ASP | A | 189 | 2.398 | 11.191 | 78.585 | 1.00 | 49.31 | | C |
| ANISOU | 3064 | C | ASP | A | 189 | 7689 | 4772 | 6275 | -1133 | 852 | -1445 | C |
| ATOM | 3065 | O | ASP | A | 189 | 1.232 | 11.404 | 78.287 | 1.00 | 49.37 | | O |
| ANISOU | 3065 | O | ASP | A | 189 | 7703 | 4950 | 6106 | -1358 | 786 | -1409 | O |
| ATOM | 3067 | N | SER | A | 190 | 2.785 | 10.895 | 79.824 | 1.00 | 48.53 | | N |
| ANISOU | 3067 | N | SER | A | 190 | 7579 | 4486 | 6375 | -974 | 801 | -1270 | N |
| ATOM | 3068 | CA | SER | A | 190 | 1.848 | 10.916 | 80.959 | 1.00 | 48.25 | | C |
| ANISOU | 3068 | CA | SER | A | 190 | 7533 | 4463 | 6335 | -1060 | 673 | -1016 | C |
| ATOM | 3070 | CB | SER | A | 190 | 2.517 | 10.347 | 82.222 | 1.00 | 49.23 | | C |
| ANISOU | 3070 | CB | SER | A | 190 | 7682 | 4326 | 6696 | -876 | 631 | -857 | C |
| ATOM | 3073 | OG | SER | A | 190 | 1.711 | 10.528 | 83.387 | 1.00 | 48.88 | | O |
| ANISOU | 3073 | OG | SER | A | 190 | 7612 | 4342 | 6619 | -952 | 518 | -598 | O |
| ATOM | 3075 | C | SER | A | 190 | 1.315 | 12.327 | 81.225 | 1.00 | 44.94 | | C |
| ANISOU | 3075 | C | SER | A | 190 | 6950 | 4398 | 5725 | -1086 | 607 | -846 | C |
| ATOM | 3076 | O | SER | A | 190 | 0.111 | 12.519 | 81.441 | 1.00 | 44.25 | | O |
| ANISOU | 3076 | O | SER | A | 190 | 6844 | 4449 | 5519 | -1266 | 532 | -736 | O |
| ATOM | 3078 | N | PHE | A | 191 | 2.217 | 13.306 | 81.218 | 1.00 | 43.17 | | N |
| ANISOU | 3078 | N | PHE | A | 191 | 6604 | 4314 | 5483 | -906 | 638 | -827 | N |
| ATOM | 3079 | CA | PHE | A | 191 | 1.853 | 14.718 | 81.396 | 1.00 | 40.71 | | C |
| ANISOU | 3079 | CA | PHE | A | 191 | 6147 | 4312 | 5008 | -907 | 588 | -686 | C |

FIG. 18 (continued)

| | | | | | | | | | | | | |
|---|---|---|---|---|---|---|---|---|---|---|---|---|
| ATOM | 3081 | CB | PHE | A | 191 | 3.119 | 15.594 | 81.407 | 1.00 | 38.24 | | C |
| ANISOU | 3081 | CB | PHE | A | 191 | 5727 | 4078 | 4725 | -697 | 635 | -689 | C |
| ATOM | 3084 | CG | PHE | A | 191 | 2.866 | 17.052 | 81.698 | 1.00 | 35.68 | | C |
| ANISOU | 3084 | CG | PHE | A | 191 | 5270 | 4022 | 4264 | -679 | 586 | -542 | C |
| ATOM | 3085 | CD1 | PHE | A | 191 | 2.311 | 17.456 | 82.905 | 1.00 | 34.06 | | C |
| ANISOU | 3085 | CD1 | PHE | A | 191 | 5018 | 3864 | 4062 | -668 | 501 | -336 | C |
| ATOM | 3087 | CE1 | PHE | A | 191 | 2.097 | 18.819 | 83.166 | 1.00 | 32.92 | | C |
| ANISOU | 3087 | CE1 | PHE | A | 191 | 4759 | 3942 | 3806 | -639 | 468 | -222 | C |
| ATOM | 3089 | CZ | PHE | A | 191 | 2.457 | 19.786 | 82.206 | 1.00 | 32.71 | | C |
| ANISOU | 3089 | CZ | PHE | A | 191 | 4670 | 4085 | 3672 | -625 | 507 | -292 | C |
| ATOM | 3091 | CE2 | PHE | A | 191 | 2.994 | 19.387 | 81.007 | 1.00 | 32.51 | | C |
| ANISOU | 3091 | CE2 | PHE | A | 191 | 4690 | 4034 | 3627 | -652 | 586 | -478 | C |
| ATOM | 3093 | CD2 | PHE | A | 191 | 3.198 | 18.026 | 80.757 | 1.00 | 35.19 | | C |
| ANISOU | 3093 | CD2 | PHE | A | 191 | 5139 | 4160 | 4072 | -675 | 632 | -614 | C |
| ATOM | 3095 | C | PHE | A | 191 | 0.877 | 15.169 | 80.301 | 1.00 | 42.50 | | C |
| ANISOU | 3095 | C | PHE | A | 191 | 6360 | 4770 | 5020 | -1111 | 581 | -761 | C |
| ATOM | 3096 | O | PHE | A | 191 | -0.138 | 15.801 | 80.588 | 1.00 | 41.37 | | O |
| ANISOU | 3096 | O | PHE | A | 191 | 6143 | 4813 | 4764 | -1209 | 504 | -620 | O |
| ATOM | 3098 | N | ARG | A | 192 | 1.158 | 14.841 | 79.048 | 1.00 | 45.60 | | N |
| ANISOU | 3098 | N | ARG | A | 192 | 6817 | 5160 | 5350 | -1178 | 660 | -982 | N |
| ATOM | 3099 | CA | ARG | A | 192 | 0.195 | 15.172 | 77.984 | 1.00 | 48.27 | | C |
| ANISOU | 3099 | CA | ARG | A | 192 | 7153 | 5722 | 5467 | -1397 | 634 | -1045 | C |
| ATOM | 3101 | CB | ARG | A | 192 | 0.741 | 14.867 | 76.597 | 1.00 | 51.08 | | C |
| ANISOU | 3101 | CB | ARG | A | 192 | 7587 | 6087 | 5736 | -1457 | 739 | -1305 | C |
| ATOM | 3104 | CG | ARG | A | 192 | -0.164 | 15.418 | 75.522 | 1.00 | 53.54 | | C |
| ANISOU | 3104 | CG | ARG | A | 192 | 7876 | 6679 | 5789 | -1676 | 691 | -1333 | C |
| ATOM | 3107 | CD | ARG | A | 192 | 0.193 | 14.933 | 74.166 | 1.00 | 57.85 | | C |
| ANISOU | 3107 | CD | ARG | A | 192 | 8529 | 7233 | 6217 | -1792 | 791 | -1603 | C |
| ATOM | 3110 | NE | ARG | A | 192 | -0.439 | 15.765 | 73.145 | 1.00 | 60.47 | | N |
| ANISOU | 3110 | NE | ARG | A | 192 | 8811 | 7887 | 6278 | -1965 | 735 | -1587 | N |
| ATOM | 3112 | CZ | ARG | A | 192 | -1.623 | 15.529 | 72.563 | 1.00 | 63.32 | | C |
| ANISOU | 3112 | CZ | ARG | A | 192 | 9204 | 8378 | 6475 | -2222 | 643 | -1600 | C |
| ATOM | 3113 | NH1 | ARG | A | 192 | -2.357 | 14.473 | 72.896 | 1.00 | 66.11 | | N |
| ANISOU | 3113 | NH1 | ARG | A | 192 | 9645 | 8568 | 6906 | -2358 | 603 | -1638 | N |
| ATOM | 3116 | NH2 | ARG | A | 192 | -2.078 | 16.366 | 71.619 | 1.00 | 62.99 | | N |
| ANISOU | 3116 | NH2 | ARG | A | 192 | 9104 | 8641 | 6186 | -2357 | 581 | -1564 | N |
| ATOM | 3119 | C | ARG | A | 192 | -1.151 | 14.458 | 78.151 | 1.00 | 49.10 | | C |
| ANISOU | 3119 | C | ARG | A | 192 | 7317 | 5799 | 5541 | -1621 | 552 | -1003 | C |
| ATOM | 3120 | O | ARG | A | 192 | -2.203 | 15.089 | 78.070 | 1.00 | 48.14 | | O |
| ANISOU | 3120 | O | ARG | A | 192 | 7106 | 5908 | 5278 | -1749 | 467 | -888 | O |
| ATOM | 3122 | N | GLN | A | 193 | -1.116 | 13.153 | 78.384 | 1.00 | 52.50 | | N |
| ANISOU | 3122 | N | GLN | A | 193 | 7889 | 5944 | 6113 | -1668 | 578 | -1090 | N |
| ATOM | 3123 | CA | GLN | A | 193 | -2.357 | 12.381 | 78.480 | 1.00 | 55.90 | | C |
| ANISOU | 3123 | CA | GLN | A | 193 | 8389 | 6333 | 6518 | -1912 | 508 | -1066 | C |
| ATOM | 3125 | CB | GLN | A | 193 | -2.068 | 10.880 | 78.544 | 1.00 | 59.49 | | C |
| ANISOU | 3125 | CB | GLN | A | 193 | 9039 | 6418 | 7148 | -1952 | 559 | -1208 | C |
| ATOM | 3128 | CG | GLN | A | 193 | -1.476 | 10.314 | 77.278 | 1.00 | 62.20 | | C |
| ANISOU | 3128 | CG | GLN | A | 193 | 9506 | 6661 | 7465 | -1991 | 668 | -1513 | C |
| ATOM | 3131 | CD | GLN | A | 193 | -1.068 | 8.852 | 77.434 | 1.00 | 66.43 | | C |
| ANISOU | 3131 | CD | GLN | A | 193 | 10238 | 6780 | 8222 | -1981 | 730 | -1655 | C |
| ATOM | 3132 | OE1 | GLN | A | 193 | -0.807 | 8.378 | 78.550 | 1.00 | 68.34 | | O |
| ANISOU | 3132 | OE1 | GLN | A | 193 | 10508 | 6787 | 8670 | -1857 | 701 | -1508 | O |
| ATOM | 3133 | NE2 | GLN | A | 193 | -1.015 | 8.127 | 76.312 | 1.00 | 69.74 | | N |
| ANISOU | 3133 | NE2 | GLN | A | 193 | 10803 | 7099 | 8596 | -2118 | 814 | -1943 | N |
| ATOM | 3136 | C | GLN | A | 193 | -3.238 | 12.794 | 79.662 | 1.00 | 54.27 | | C |
| ANISOU | 3136 | C | GLN | A | 193 | 8074 | 6229 | 6318 | -1934 | 408 | -800 | C |
| ATOM | 3137 | O | GLN | A | 193 | -4.470 | 12.702 | 79.577 | 1.00 | 55.17 | | O |
| ANISOU | 3137 | O | GLN | A | 193 | 8157 | 6473 | 6332 | -2152 | 337 | -745 | O |
| ATOM | 3139 | N | SER | A | 194 | -2.630 | 13.254 | 80.752 | 1.00 | 52.51 | | N |
| ANISOU | 3139 | N | SER | A | 194 | 7785 | 5965 | 6201 | -1721 | 406 | -643 | N |
| ATOM | 3140 | CA | SER | A | 194 | -3.415 | 13.610 | 81.935 | 1.00 | 51.86 | | C |
| ANISOU | 3140 | CA | SER | A | 194 | 7610 | 5975 | 6118 | -1741 | 333 | -408 | C |
| ATOM | 3142 | CB | SER | A | 194 | -2.542 | 13.653 | 83.206 | 1.00 | 50.85 | | C |
| ANISOU | 3142 | CB | SER | A | 194 | 7481 | 5700 | 6140 | -1524 | 338 | -271 | C |
| ATOM | 3145 | OG | SER | A | 194 | -1.712 | 14.792 | 83.251 | 1.00 | 51.85 | | O |
| ANISOU | 3145 | OG | SER | A | 194 | 7500 | 5959 | 6240 | -1323 | 360 | -246 | O |
| ATOM | 3147 | C | SER | A | 194 | -4.268 | 14.895 | 81.764 | 1.00 | 49.77 | | C |
| ANISOU | 3147 | C | SER | A | 194 | 7167 | 6061 | 5682 | -1784 | 282 | -305 | C |
| ATOM | 3148 | O | SER | A | 194 | -5.159 | 15.139 | 82.563 | 1.00 | 49.24 | | O |
| ANISOU | 3148 | O | SER | A | 194 | 7014 | 6103 | 5593 | -1844 | 233 | -143 | O |
| ATOM | 3150 | N | GLU | A | 195 | -4.049 | 15.683 | 80.710 | 1.00 | 48.38 | | N |
| ANISOU | 3150 | N | GLU | A | 195 | 6936 | 6062 | 5386 | -1763 | 296 | -394 | N |
| ATOM | 3151 | CA | GLU | A | 195 | -4.897 | 16.859 | 80.479 | 1.00 | 48.67 | | C |
| ANISOU | 3151 | CA | GLU | A | 195 | 6809 | 6406 | 5277 | -1801 | 235 | -286 | C |
| ATOM | 3153 | CB | GLU | A | 195 | -4.323 | 17.786 | 79.394 | 1.00 | 46.71 | | C |
| ANISOU | 3153 | CB | GLU | A | 195 | 6522 | 6311 | 4915 | -1734 | 254 | -364 | C |
| ATOM | 3156 | CG | GLU | A | 195 | -5.043 | 19.143 | 79.364 | 1.00 | 44.13 | | C |
| ANISOU | 3156 | CG | GLU | A | 195 | 6022 | 6262 | 4482 | -1711 | 185 | -211 | C |
| ATOM | 3159 | CD | GLU | A | 195 | -4.361 | 20.182 | 78.516 | 1.00 | 42.87 | | C |

FIG. 18 (continued)

| | | | | | | | | | | | | |
|---|---|---|---|---|---|---|---|---|---|---|---|---|
| ANISOU | 3159 | CD | GLU | A | 195 | 5830 | 6230 | 4230 | -1619 | 201 | -239 | C |
| ATOM | 3160 | OE1 | GLU | A | 195 | -5.036 | 21.165 | 78.156 | 1.00 | 41.99 | | O |
| ANISOU | 3160 | OE1 | GLU | A | 195 | 5601 | 6338 | 4017 | -1640 | 132 | -135 | O |
| ATOM | 3161 | OE2 | GLU | A | 195 | -3.159 | 20.038 | 78.218 | 1.00 | 41.40 | | O |
| ANISOU | 3161 | OE2 | GLU | A | 195 | 5725 | 5926 | 4077 | -1525 | 282 | -356 | O |
| ATOM | 3162 | C | GLU | A | 195 | -6.372 | 16.502 | 80.175 | 1.00 | 52.44 | | C |
| ANISOU | 3162 | C | GLU | A | 195 | 7241 | 7021 | 5661 | -2055 | 159 | -256 | C |
| ATOM | 3163 | O | GLU | A | 195 | -7.289 | 17.144 | 80.698 | 1.00 | 54.84 | | O |
| ANISOU | 3163 | O | GLU | A | 195 | 7396 | 7511 | 5931 | -2074 | 106 | -99 | O |
| ATOM | 3165 | N | ARG | A | 196 | -6.603 | 15.483 | 79.357 | 1.00 | 56.00 | | N |
| ANISOU | 3165 | N | ARG | A | 196 | 7812 | 7385 | 6079 | -2252 | 159 | -412 | N |
| ATOM | 3166 | CA | ARG | A | 196 | -7.964 | 14.971 | 79.122 | 1.00 | 57.53 | | C |
| ANISOU | 3166 | CA | ARG | A | 196 | 7974 | 7688 | 6197 | -2524 | 82 | -392 | C |
| ATOM | 3168 | CB | ARG | A | 196 | -7.972 | 13.965 | 77.970 | 1.00 | 59.65 | | C |
| ANISOU | 3168 | CB | ARG | A | 196 | 8403 | 7861 | 6402 | -2736 | 92 | -616 | C |
| ATOM | 3177 | C | ARG | A | 196 | -8.519 | 14.303 | 80.388 | 1.00 | 59.33 | | C |
| ANISOU | 3177 | C | ARG | A | 196 | 8207 | 7792 | 6544 | -2580 | 74 | -263 | C |
| ATOM | 3178 | O | ARG | A | 196 | -9.540 | 13.602 | 80.343 | 1.00 | 61.95 | | O |
| ANISOU | 3178 | O | ARG | A | 196 | 8541 | 8148 | 6848 | -2824 | 26 | -255 | O |
| ATOM | 3180 | MN | MN | A | 301 | -5.664 | 32.633 | 87.064 | 0.80 | 34.83 | | MN |
| ANISOU | 3180 | MN | MN | A | 301 | 3930 | 5661 | 3642 | -113 | 299 | 788 | MN |
| ATOM | 3181 | MN | MN | A | 302 | -5.252 | 31.856 | 83.885 | 0.40 | 49.14 | | MN |
| ANISOU | 3181 | MN | MN | A | 302 | 5797 | 7549 | 5325 | -314 | 144 | 793 | MN |
| ATOM | 3182 | OH2 | HOH | A | 303 | -5.570 | 34.267 | 88.637 | 1.00 | 24.91 | | O |
| ANISOU | 3182 | OH2 | HOH | A | 303 | 2668 | 4340 | 2457 | 80 | 399 | 768 | O |
| ATOM | 3185 | OH2 | HOH | A | 304 | -7.572 | 33.669 | 86.032 | 1.00 | 27.37 | | O |
| ANISOU | 3185 | OH2 | HOH | A | 304 | 2755 | 4903 | 2743 | -56 | 224 | 918 | O |
| ATOM | 3188 | OH2 | HOH | A | 305 | -2.907 | 27.064 | 82.458 | 1.00 | 25.70 | | O |
| ANISOU | 3188 | OH2 | HOH | A | 305 | 3196 | 4310 | 2258 | -693 | 208 | 413 | O |
| ATOM | 3191 | OH2 | HOH | A | 306 | -5.371 | 27.889 | 82.733 | 1.00 | 31.80 | | O |
| ANISOU | 3191 | OH2 | HOH | A | 306 | 3751 | 5326 | 3006 | -734 | 120 | 593 | O |
| ATOM | 3194 | S | SO4 | A | 401 | -11.964 | 32.190 | 89.101 | 0.50 | 36.98 | | S |
| ANISOU | 3194 | S | SO4 | A | 401 | 3446 | 6573 | 4031 | -164 | 444 | 963 | S |
| ATOM | 3195 | O1 | SO4 | A | 401 | -10.789 | 32.730 | 88.403 | 0.50 | 34.42 | | O |
| ANISOU | 3195 | O1 | SO4 | A | 401 | 3270 | 6104 | 3703 | -98 | 384 | 947 | O |
| ATOM | 3196 | O2 | SO4 | A | 401 | -12.755 | 33.239 | 89.799 | 0.50 | 30.74 | | O |
| ANISOU | 3196 | O2 | SO4 | A | 401 | 2502 | 5854 | 3324 | -4 | 534 | 964 | O |
| ATOM | 3197 | O3 | SO4 | A | 401 | -11.370 | 31.165 | 89.966 | 0.50 | 32.74 | | O |
| ANISOU | 3197 | O3 | SO4 | A | 401 | 3050 | 5967 | 3423 | -280 | 498 | 914 | O |
| ATOM | 3198 | O4 | SO4 | A | 401 | -12.852 | 31.537 | 88.124 | 0.50 | 35.27 | | O |
| ANISOU | 3198 | O4 | SO4 | A | 401 | 3107 | 6495 | 3800 | -295 | 348 | 1026 | O |
| ATOM | 3199 | S | SO4 | A | 402 | 2.793 | 15.687 | 71.380 | 0.40 | 56.51 | | S |
| ANISOU | 3199 | S | SO4 | A | 402 | 8387 | 7320 | 5763 | -1716 | 1152 | -2099 | S |
| ATOM | 3200 | O1 | SO4 | A | 402 | 2.962 | 16.829 | 72.269 | 0.40 | 53.07 | | O |
| ANISOU | 3200 | O1 | SO4 | A | 402 | 7795 | 6981 | 5387 | -1552 | 1071 | -1827 | O |
| ATOM | 3201 | O2 | SO4 | A | 402 | 3.511 | 14.517 | 71.878 | 0.40 | 57.16 | | O |
| ANISOU | 3201 | O2 | SO4 | A | 402 | 8549 | 7061 | 6110 | -1569 | 1257 | -2251 | O |
| ATOM | 3202 | O3 | SO4 | A | 402 | 3.318 | 16.051 | 70.066 | 0.40 | 58.13 | | O |
| ANISOU | 3202 | O3 | SO4 | A | 402 | 8613 | 7726 | 5749 | -1807 | 1265 | -2275 | O |
| ATOM | 3203 | O4 | SO4 | A | 402 | 1.386 | 15.341 | 71.249 | 0.40 | 57.55 | | O |
| ANISOU | 3203 | O4 | SO4 | A | 402 | 8579 | 7504 | 5783 | -1952 | 1020 | -2053 | O |
| ATOM | 3204 | N | ALA | B | 0 | 30.545 | 47.206 | 81.073 | 1.00 | 41.02 | | N |
| ANISOU | 3204 | N | ALA | B | 0 | 6001 | 6061 | 3524 | -510 | 1990 | 853 | N |
| ATOM | 3205 | CA | ALA | B | 0 | 31.428 | 47.994 | 81.988 | 1.00 | 40.58 | | C |
| ANISOU | 3205 | CA | ALA | B | 0 | 5759 | 5926 | 3732 | -576 | 2050 | 836 | C |
| ATOM | 3207 | CB | ALA | B | 0 | 31.363 | 49.490 | 81.648 | 1.00 | 42.81 | | C |
| ANISOU | 3207 | CB | ALA | B | 0 | 6065 | 6102 | 4100 | -693 | 2112 | 1036 | C |
| ATOM | 3211 | C | ALA | B | 0 | 31.029 | 47.753 | 83.452 | 1.00 | 37.95 | | C |
| ANISOU | 3211 | C | ALA | B | 0 | 5341 | 5503 | 3573 | -526 | 1882 | 707 | C |
| ATOM | 3212 | O | ALA | B | 0 | 31.871 | 47.587 | 84.306 | 1.00 | 37.38 | | O |
| ANISOU | 3212 | O | ALA | B | 0 | 5108 | 5449 | 3647 | -527 | 1904 | 592 | O |
| ATOM | 3216 | N | MET | B | 1 | 29.735 | 47.725 | 83.729 | 1.00 | 37.46 | | N |
| ANISOU | 3216 | N | MET | B | 1 | 5382 | 5367 | 3486 | -481 | 1716 | 732 | N |
| ATOM | 3217 | CA | MET | B | 1 | 29.291 | 47.458 | 85.101 | 1.00 | 37.00 | | C |
| ANISOU | 3217 | CA | MET | B | 1 | 5255 | 5235 | 3567 | -432 | 1568 | 614 | C |
| ATOM | 3219 | CB | MET | B | 1 | 27.811 | 47.796 | 85.318 | 1.00 | 35.58 | | C |
| ANISOU | 3219 | CB | MET | B | 1 | 5173 | 4964 | 3383 | -403 | 1413 | 689 | C |
| ATOM | 3222 | CG | MET | B | 1 | 27.303 | 47.444 | 86.759 | 1.00 | 32.62 | | C |
| ANISOU | 3222 | CG | MET | B | 1 | 4732 | 4530 | 3131 | -348 | 1274 | 564 | C |
| ATOM | 3225 | SD | MET | B | 1 | 28.149 | 48.373 | 88.055 | 1.00 | 32.96 | | S |
| ANISOU | 3225 | SD | MET | B | 1 | 4614 | 4483 | 3425 | -416 | 1307 | 485 | S |
| ATOM | 3226 | CE | MET | B | 1 | 27.121 | 49.874 | 88.115 | 1.00 | 32.54 | | C |
| ANISOU | 3226 | CE | MET | B | 1 | 4636 | 4242 | 3485 | -453 | 1277 | 626 | C |
| ATOM | 3230 | C | MET | B | 1 | 29.562 | 46.026 | 85.505 | 1.00 | 36.22 | | C |
| ANISOU | 3230 | C | MET | B | 1 | 5127 | 5223 | 3414 | -335 | 1536 | 452 | C |
| ATOM | 3231 | O | MET | B | 1 | 29.978 | 45.782 | 86.614 | 1.00 | 34.28 | | O |
| ANISOU | 3231 | O | MET | B | 1 | 4759 | 4969 | 3299 | -306 | 1496 | 345 | O |
| ATOM | 3233 | N | GLU | B | 2 | 29.387 | 45.080 | 84.584 | 1.00 | 37.89 | | N |
| ANISOU | 3233 | N | GLU | B | 2 | 5455 | 5516 | 3426 | -286 | 1565 | 432 | N |

FIG. 18 (continued)

| | | | | | | | | | | | | |
|---|---|---|---|---|---|---|---|---|---|---|---|---|
| ATOM | 3234 | CA | GLU | B | 2 | 29.663 | 43.696 | 84.897 | 1.00 | 38.86 | | C |
| ANISOU | 3234 | CA | GLU | B | 2 | 5575 | 5684 | 3506 | -187 | 1559 | 282 | C |
| ATOM | 3236 | CB | GLU | B | 2 | 29.228 | 42.785 | 83.753 | 1.00 | 41.78 | | C |
| ANISOU | 3236 | CB | GLU | B | 2 | 6125 | 6112 | 3637 | -161 | 1585 | 257 | C |
| ATOM | 3239 | CG | GLU | B | 2 | 29.125 | 41.350 | 84.174 | 1.00 | 42.11 | | C |
| ANISOU | 3239 | CG | GLU | B | 2 | 6213 | 6137 | 3650 | -62 | 1547 | 105 | C |
| ATOM | 3242 | CD | GLU | B | 2 | 28.871 | 40.406 | 83.023 | 1.00 | 43.51 | | C |
| ANISOU | 3242 | CD | GLU | B | 2 | 6577 | 6362 | 3593 | -53 | 1601 | 41 | C |
| ATOM | 3243 | OE1 | GLU | B | 2 | 28.395 | 40.850 | 81.959 | 1.00 | 45.80 | | O |
| ANISOU | 3243 | OE1 | GLU | B | 2 | 6978 | 6713 | 3711 | -132 | 1606 | 125 | O |
| ATOM | 3244 | OE2 | GLU | B | 2 | 29.137 | 39.209 | 83.208 | 1.00 | 44.32 | | O |
| ANISOU | 3244 | OE2 | GLU | B | 2 | 6722 | 6436 | 3681 | 35 | 1638 | -94 | O |
| ATOM | 3245 | C | GLU | B | 2 | 31.147 | 43.498 | 85.219 | 1.00 | 39.59 | | C |
| ANISOU | 3245 | C | GLU | B | 2 | 5498 | 5844 | 3701 | -153 | 1694 | 209 | C |
| ATOM | 3246 | O | GLU | B | 2 | 31.481 | 42.792 | 86.179 | 1.00 | 37.45 | | O |
| ANISOU | 3246 | O | GLU | B | 2 | 5134 | 5574 | 3520 | -68 | 1649 | 107 | O |
| ATOM | 3248 | N | ASP | B | 3 | 32.017 | 44.109 | 84.418 | 1.00 | 40.30 | | N |
| ANISOU | 3248 | N | ASP | B | 3 | 5537 | 6002 | 3773 | -218 | 1859 | 276 | N |
| ATOM | 3249 | CA | ASP | B | 3 | 33.471 | 44.118 | 84.665 | 1.00 | 42.09 | | C |
| ANISOU | 3249 | CA | ASP | B | 3 | 5560 | 6319 | 4113 | -210 | 1998 | 230 | C |
| ATOM | 3251 | CB | ASP | B | 3 | 34.232 | 44.908 | 83.568 | 1.00 | 44.99 | | C |
| ANISOU | 3251 | CB | ASP | B | 3 | 5901 | 6760 | 4433 | -313 | 2195 | 336 | C |
| ATOM | 3254 | CG | ASP | B | 3 | 34.316 | 44.158 | 82.263 | 1.00 | 48.10 | | C |
| ANISOU | 3254 | CG | ASP | B | 3 | 6438 | 7245 | 4594 | -255 | 2332 | 330 | C |
| ATOM | 3255 | OD1 | ASP | B | 3 | 34.202 | 42.919 | 82.309 | 1.00 | 49.35 | | O |
| ANISOU | 3255 | OD1 | ASP | B | 3 | 6660 | 7418 | 4672 | -125 | 2314 | 207 | O |
| ATOM | 3256 | OD2 | ASP | B | 3 | 34.503 | 44.801 | 81.195 | 1.00 | 51.10 | | O |
| ANISOU | 3256 | OD2 | ASP | B | 3 | 6877 | 7675 | 4865 | -343 | 2465 | 447 | O |
| ATOM | 3257 | C | ASP | B | 3 | 33.780 | 44.747 | 85.998 | 1.00 | 39.27 | | C |
| ANISOU | 3257 | C | ASP | B | 3 | 5020 | 5926 | 3976 | -256 | 1907 | 203 | C |
| ATOM | 3258 | O | ASP | B | 3 | 34.567 | 44.228 | 86.765 | 1.00 | 39.79 | | O |
| ANISOU | 3258 | O | ASP | B | 3 | 4920 | 6063 | 4133 | -188 | 1906 | 115 | O |
| ATOM | 3260 | N | PHE | B | 4 | 33.175 | 45.889 | 86.273 | 1.00 | 38.41 | | N |
| ANISOU | 3260 | N | PHE | B | 4 | 4939 | 5709 | 3946 | -370 | 1834 | 279 | N |
| ATOM | 3261 | CA | PHE | B | 4 | 33.352 | 46.499 | 87.570 | 1.00 | 37.36 | | C |
| ANISOU | 3261 | CA | PHE | B | 4 | 4664 | 5529 | 4002 | -427 | 1741 | 227 | C |
| ATOM | 3263 | CB | PHE | B | 4 | 32.513 | 47.757 | 87.681 | 1.00 | 37.89 | | C |
| ANISOU | 3263 | CB | PHE | B | 4 | 4818 | 5438 | 4139 | -535 | 1686 | 314 | C |
| ATOM | 3266 | CG | PHE | B | 4 | 32.526 | 48.332 | 89.036 | 1.00 | 37.33 | | C |
| ANISOU | 3266 | CG | PHE | B | 4 | 4642 | 5302 | 4238 | -590 | 1586 | 232 | C |
| ATOM | 3267 | CD1 | PHE | B | 4 | 33.610 | 49.072 | 89.467 | 1.00 | 40.07 | | C |
| ANISOU | 3267 | CD1 | PHE | B | 4 | 4815 | 5679 | 4732 | -723 | 1652 | 190 | C |
| ATOM | 3269 | CE1 | PHE | B | 4 | 33.651 | 49.563 | 90.747 | 1.00 | 38.64 | | C |
| ANISOU | 3269 | CE1 | PHE | B | 4 | 4543 | 5456 | 4684 | -786 | 1553 | 86 | C |
| ATOM | 3271 | CZ | PHE | B | 4 | 32.623 | 49.335 | 91.586 | 1.00 | 36.89 | | C |
| ANISOU | 3271 | CZ | PHE | B | 4 | 4405 | 5163 | 4448 | -706 | 1406 | 35 | C |
| ATOM | 3273 | CE2 | PHE | B | 4 | 31.542 | 48.589 | 91.186 | 1.00 | 35.90 | | C |
| ANISOU | 3273 | CE2 | PHE | B | 4 | 4437 | 5009 | 4193 | -569 | 1347 | 88 | C |
| ATOM | 3275 | CD2 | PHE | B | 4 | 31.493 | 48.083 | 89.925 | 1.00 | 36.44 | | C |
| ANISOU | 3275 | CD2 | PHE | B | 4 | 4596 | 5120 | 4131 | -519 | 1428 | 180 | C |
| ATOM | 3277 | C | PHE | B | 4 | 33.012 | 45.566 | 88.754 | 1.00 | 35.96 | | C |
| ANISOU | 3277 | C | PHE | B | 4 | 4455 | 5361 | 3848 | -306 | 1588 | 111 | C |
| ATOM | 3278 | O | PHE | B | 4 | 33.776 | 45.459 | 89.716 | 1.00 | 33.47 | | O |
| ANISOU | 3278 | O | PHE | B | 4 | 3960 | 5118 | 3638 | -298 | 1558 | 31 | O |
| ATOM | 3280 | N | VAL | B | 5 | 31.852 | 44.923 | 88.690 | 1.00 | 33.91 | | N |
| ANISOU | 3280 | N | VAL | B | 5 | 4363 | 5038 | 3484 | -225 | 1489 | 112 | N |
| ATOM | 3281 | CA | VAL | B | 5 | 31.415 | 44.050 | 89.769 | 1.00 | 33.64 | | C |
| ANISOU | 3281 | CA | VAL | B | 5 | 4322 | 4996 | 3464 | -122 | 1355 | 26 | C |
| ATOM | 3283 | CB | VAL | B | 5 | 30.007 | 43.451 | 89.488 | 1.00 | 32.36 | | C |
| ANISOU | 3283 | CB | VAL | B | 5 | 4358 | 4757 | 3182 | -73 | 1261 | 47 | C |
| ATOM | 3285 | CG1 | VAL | B | 5 | 29.671 | 42.326 | 90.530 | 1.00 | 29.96 | | C |
| ANISOU | 3285 | CG1 | VAL | B | 5 | 4053 | 4447 | 2883 | 38 | 1153 | -35 | C |
| ATOM | 3289 | CG2 | VAL | B | 5 | 28.911 | 44.566 | 89.475 | 1.00 | 31.11 | | C |
| ANISOU | 3289 | CG2 | VAL | B | 5 | 4274 | 4496 | 3051 | -158 | 1187 | 134 | C |
| ATOM | 3293 | C | VAL | B | 5 | 32.422 | 42.911 | 89.987 | 1.00 | 34.46 | | C |
| ANISOU | 3293 | C | VAL | B | 5 | 4320 | 5211 | 3562 | 1 | 1408 | -49 | C |
| ATOM | 3294 | O | VAL | B | 5 | 32.836 | 42.648 | 91.114 | 1.00 | 34.18 | | O |
| ANISOU | 3294 | O | VAL | B | 5 | 4151 | 5225 | 3611 | 51 | 1336 | -106 | O |
| ATOM | 3296 | N | ARG | B | 6 | 32.815 | 42.265 | 88.900 | 1.00 | 37.40 | | N |
| ANISOU | 3296 | N | ARG | B | 6 | 4754 | 5629 | 3829 | 57 | 1537 | -45 | N |
| ATOM | 3297 | CA | ARG | B | 6 | 33.742 | 41.126 | 88.948 | 1.00 | 40.63 | | C |
| ANISOU | 3297 | CA | ARG | B | 6 | 5081 | 6123 | 4233 | 207 | 1618 | -110 | C |
| ATOM | 3299 | CB | ARG | B | 6 | 33.852 | 40.472 | 87.568 | 1.00 | 41.27 | | C |
| ANISOU | 3299 | CB | ARG | B | 6 | 5304 | 6216 | 4161 | 256 | 1772 | -117 | C |
| ATOM | 3302 | CG | ARG | B | 6 | 32.539 | 39.829 | 87.131 | 1.00 | 40.52 | | C |
| ANISOU | 3302 | CG | ARG | B | 6 | 5465 | 6010 | 3922 | 266 | 1694 | -134 | C |
| ATOM | 3305 | CD | ARG | B | 6 | 32.676 | 39.065 | 85.841 | 1.00 | 42.28 | | C |
| ANISOU | 3305 | CD | ARG | B | 6 | 5841 | 6251 | 3974 | 313 | 1840 | -177 | C |
| ATOM | 3308 | NE | ARG | B | 6 | 31.352 | 38.625 | 85.396 | 1.00 | 42.64 | | N |

FIG. 18 (continued)

| | | | | | | | | | | | | |
|---|---|---|---|---|---|---|---|---|---|---|---|---|
| ANISOU | 3308 | NE | ARG | B | 6 | 6120 | 6209 | 3873 | 271 | 1743 | -195 | N |
| ATOM | 3310 | CZ | ARG | B | 6 | 30.645 | 37.624 | 85.950 | 1.00 | 40.99 | | C |
| ANISOU | 3310 | CZ | ARG | B | 6 | 6013 | 5902 | 3661 | 332 | 1642 | -263 | C |
| ATOM | 3311 | NH1 | ARG | B | 6 | 31.125 | 36.898 | 86.949 | 1.00 | 39.93 | | N |
| ANISOU | 3311 | NH1 | ARG | B | 6 | 5789 | 5734 | 3649 | 461 | 1630 | -310 | N |
| ATOM | 3314 | NH2 | ARG | B | 6 | 29.457 | 37.322 | 85.467 | 1.00 | 40.90 | | N |
| ANISOU | 3314 | NH2 | ARG | B | 6 | 6191 | 5835 | 3515 | 260 | 1554 | -277 | N |
| ATOM | 3317 | C | ARG | B | 6 | 35.130 | 41.498 | 89.464 | 1.00 | 43.15 | | C |
| ANISOU | 3317 | C | ARG | B | 6 | 5129 | 6582 | 4686 | 203 | 1679 | -121 | C |
| ATOM | 3318 | O | ARG | B | 6 | 35.805 | 40.678 | 90.071 | 1.00 | 44.22 | | O |
| ANISOU | 3318 | O | ARG | B | 6 | 5139 | 6794 | 4868 | 342 | 1676 | -163 | O |
| ATOM | 3320 | N | GLN | B | 7 | 35.559 | 42.731 | 89.213 | 1.00 | 45.76 | | N |
| ANISOU | 3320 | N | GLN | B | 7 | 5360 | 6945 | 5082 | 41 | 1735 | -73 | N |
| ATOM | 3321 | CA | GLN | B | 7 | 36.863 | 43.186 | 89.684 | 1.00 | 48.73 | | C |
| ANISOU | 3321 | CA | GLN | B | 7 | 5458 | 7467 | 5590 | -8 | 1787 | -88 | C |
| ATOM | 3323 | CB | GLN | B | 7 | 37.416 | 44.290 | 88.759 | 1.00 | 51.46 | | C |
| ANISOU | 3323 | CB | GLN | B | 7 | 5753 | 7840 | 5962 | -181 | 1942 | -19 | C |
| ATOM | 3326 | CG | GLN | B | 7 | 37.826 | 43.754 | 87.366 | 1.00 | 55.42 | | C |
| ANISOU | 3326 | CG | GLN | B | 7 | 6321 | 8400 | 6335 | -113 | 2147 | 17 | C |
| ATOM | 3329 | CD | GLN | B | 7 | 38.347 | 44.835 | 86.404 | 1.00 | 58.50 | | C |
| ANISOU | 3329 | CD | GLN | B | 7 | 6674 | 8822 | 6731 | -288 | 2317 | 111 | C |
| ATOM | 3330 | OE1 | GLN | B | 7 | 38.573 | 45.988 | 86.803 | 1.00 | 61.77 | | O |
| ANISOU | 3330 | OE1 | GLN | B | 7 | 6983 | 9210 | 7276 | -468 | 2296 | 145 | O |
| ATOM | 3331 | NE2 | GLN | B | 7 | 38.559 | 44.455 | 85.132 | 1.00 | 60.60 | | N |
| ANISOU | 3331 | NE2 | GLN | B | 7 | 7035 | 9140 | 6850 | -242 | 2499 | 149 | N |
| ATOM | 3334 | C | GLN | B | 7 | 36.806 | 43.649 | 91.131 | 1.00 | 45.96 | | C |
| ANISOU | 3334 | C | GLN | B | 7 | 4982 | 7126 | 5355 | -65 | 1614 | -135 | C |
| ATOM | 3335 | O | GLN | B | 7 | 37.775 | 43.527 | 91.855 | 1.00 | 46.60 | | O |
| ANISOU | 3335 | O | GLN | B | 7 | 4828 | 7358 | 5520 | -41 | 1592 | -173 | O |
| ATOM | 3337 | N | CYS | B | 8 | 35.671 | 44.178 | 91.562 | 1.00 | 43.23 | | N |
| ANISOU | 3337 | N | CYS | B | 8 | 4785 | 6636 | 5005 | -136 | 1491 | -133 | N |
| ATOM | 3338 | CA | CYS | B | 8 | 35.619 | 44.884 | 92.838 | 1.00 | 43.38 | | C |
| ANISOU | 3338 | CA | CYS | B | 8 | 4702 | 6655 | 5124 | -231 | 1355 | -190 | C |
| ATOM | 3340 | CB | CYS | B | 8 | 35.080 | 46.299 | 92.585 | 1.00 | 45.86 | | C |
| ANISOU | 3340 | CB | CYS | B | 8 | 5107 | 6822 | 5497 | -422 | 1372 | -157 | C |
| ATOM | 3343 | SG | CYS | B | 8 | 36.218 | 47.318 | 91.523 | 1.00 | 54.05 | | S |
| ANISOU | 3343 | SG | CYS | B | 8 | 6025 | 7900 | 6610 | -604 | 1573 | -93 | S |
| ATOM | 3345 | C | CYS | B | 8 | 34.915 | 44.201 | 94.029 | 1.00 | 39.48 | | C |
| ANISOU | 3345 | C | CYS | B | 8 | 4254 | 6147 | 4601 | -120 | 1185 | -240 | C |
| ATOM | 3346 | O | CYS | B | 8 | 35.067 | 44.633 | 95.152 | 1.00 | 39.97 | | O |
| ANISOU | 3346 | O | CYS | B | 8 | 4207 | 6258 | 4722 | -180 | 1079 | -302 | O |
| ATOM | 3348 | N | PHE | B | 9 | 34.168 | 43.133 | 93.793 | 1.00 | 36.84 | | N |
| ANISOU | 3348 | N | PHE | B | 9 | 4080 | 5750 | 4166 | 29 | 1164 | -218 | N |
| ATOM | 3349 | CA | PHE | B | 9 | 33.641 | 42.271 | 94.879 | 1.00 | 33.08 | | C |
| ANISOU | 3349 | CA | PHE | B | 9 | 3636 | 5274 | 3657 | 151 | 1029 | -247 | C |
| ATOM | 3351 | CB | PHE | B | 9 | 32.158 | 41.998 | 94.695 | 1.00 | 28.59 | | C |
| ANISOU | 3351 | CB | PHE | B | 9 | 3304 | 4548 | 3012 | 168 | 975 | -222 | C |
| ATOM | 3354 | CG | PHE | B | 9 | 31.301 | 43.209 | 94.868 | 1.00 | 28.22 | | C |
| ANISOU | 3354 | CG | PHE | B | 9 | 3322 | 4401 | 3001 | 28 | 925 | -217 | C |
| ATOM | 3355 | CD1 | PHE | B | 9 | 30.925 | 43.619 | 96.134 | 1.00 | 28.05 | | C |
| ANISOU | 3355 | CD1 | PHE | B | 9 | 3261 | 4378 | 3018 | -4 | 812 | -267 | C |
| ATOM | 3357 | CE1 | PHE | B | 9 | 30.099 | 44.794 | 96.310 | 1.00 | 27.48 | | C |
| ANISOU | 3357 | CE1 | PHE | B | 9 | 3258 | 4190 | 2994 | -117 | 787 | -272 | C |
| ATOM | 3359 | CZ | PHE | B | 9 | 29.713 | 45.518 | 95.217 | 1.00 | 25.04 | | C |
| ANISOU | 3359 | CZ | PHE | B | 9 | 3043 | 3773 | 2698 | -187 | 865 | -202 | C |
| ATOM | 3361 | CE2 | PHE | B | 9 | 30.126 | 45.118 | 93.929 | 1.00 | 28.18 | | C |
| ANISOU | 3361 | CE2 | PHE | B | 9 | 3474 | 4193 | 3039 | -166 | 967 | -137 | C |
| ATOM | 3363 | CD2 | PHE | B | 9 | 30.918 | 43.980 | 93.763 | 1.00 | 27.30 | | C |
| ANISOU | 3363 | CD2 | PHE | B | 9 | 3303 | 4193 | 2876 | -64 | 1003 | -157 | C |
| ATOM | 3365 | C | PHE | B | 9 | 34.383 | 40.930 | 94.845 | 1.00 | 32.66 | | C |
| ANISOU | 3365 | C | PHE | B | 9 | 3519 | 5315 | 3577 | 343 | 1072 | -240 | C |
| ATOM | 3366 | O | PHE | B | 9 | 34.707 | 40.447 | 93.789 | 1.00 | 32.02 | | O |
| ANISOU | 3366 | O | PHE | B | 9 | 3484 | 5225 | 3459 | 403 | 1202 | -221 | O |
| ATOM | 3368 | N | ASN | B | 10 | 34.626 | 40.341 | 96.006 | 1.00 | 33.06 | | N |
| ANISOU | 3368 | N | ASN | B | 10 | 3472 | 5451 | 3639 | 446 | 967 | -252 | N |
| ATOM | 3369 | CA | ASN | B | 10 | 35.328 | 39.084 | 96.084 | 1.00 | 35.34 | | C |
| ANISOU | 3369 | CA | ASN | B | 10 | 3696 | 5813 | 3919 | 655 | 1006 | -225 | C |
| ATOM | 3371 | CB | ASN | B | 10 | 35.822 | 38.836 | 97.517 | 1.00 | 38.44 | | C |
| ANISOU | 3371 | CB | ASN | B | 10 | 3911 | 6359 | 4335 | 731 | 869 | -219 | C |
| ATOM | 3374 | CG | ASN | B | 10 | 34.775 | 38.280 | 98.415 | 1.00 | 38.01 | | C |
| ANISOU | 3374 | CG | ASN | B | 10 | 4010 | 6215 | 4218 | 789 | 748 | -200 | C |
| ATOM | 3375 | OD1 | ASN | B | 10 | 34.098 | 37.315 | 98.066 | 1.00 | 40.91 | | O |
| ANISOU | 3375 | OD1 | ASN | B | 10 | 4569 | 6435 | 4540 | 894 | 784 | -168 | O |
| ATOM | 3376 | ND2 | ASN | B | 10 | 34.641 | 38.853 | 99.598 | 1.00 | 40.92 | | N |
| ANISOU | 3376 | ND2 | ASN | B | 10 | 4296 | 6674 | 4577 | 712 | 610 | -226 | N |
| ATOM | 3379 | C | ASN | B | 10 | 34.527 | 37.903 | 95.443 | 1.00 | 34.34 | | C |
| ANISOU | 3379 | C | ASN | B | 10 | 3818 | 5516 | 3714 | 782 | 1061 | -206 | C |
| ATOM | 3380 | O | ASN | B | 10 | 33.291 | 37.967 | 95.329 | 1.00 | 29.30 | | O |
| ANISOU | 3380 | O | ASN | B | 10 | 3380 | 4734 | 3020 | 711 | 1011 | -209 | O |

FIG. 18 (continued)

| | | | | | | | | | | | | |
|---|---|---|---|---|---|---|---|---|---|---|---|---|
| ATOM | 3382 | N | PRO | B | 11 | 35.239 | 36.878 | 94.946 | 1.00 | 34.64 | | N |
| ANISOU | 3382 | N | PRO | B | 11 | 3841 | 5570 | 3753 | 958 | 1177 | -194 | N |
| ATOM | 3383 | CA | PRO | B | 11 | 34.588 | 35.873 | 94.086 | 1.00 | 34.58 | | C |
| ANISOU | 3383 | CA | PRO | B | 11 | 4084 | 5386 | 3669 | 1039 | 1265 | -207 | C |
| ATOM | 3385 | CB | PRO | B | 11 | 35.728 | 34.898 | 93.726 | 1.00 | 36.61 | | C |
| ANISOU | 3385 | CB | PRO | B | 11 | 4256 | 5693 | 3960 | 1255 | 1410 | -203 | C |
| ATOM | 3388 | CG | PRO | B | 11 | 36.987 | 35.612 | 94.040 | 1.00 | 39.44 | | C |
| ANISOU | 3388 | CG | PRO | B | 11 | 4300 | 6279 | 4405 | 1248 | 1423 | -182 | C |
| ATOM | 3391 | CD | PRO | B | 11 | 36.678 | 36.602 | 95.127 | 1.00 | 38.15 | | C |
| ANISOU | 3391 | CD | PRO | B | 11 | 4032 | 6195 | 4269 | 1092 | 1240 | -173 | C |
| ATOM | 3394 | C | PRO | B | 11 | 33.395 | 35.119 | 94.720 | 1.00 | 31.75 | | C |
| ANISOU | 3394 | C | PRO | B | 11 | 3923 | 4875 | 3266 | 1071 | 1156 | -195 | C |
| ATOM | 3395 | O | PRO | B | 11 | 32.458 | 34.773 | 93.990 | 1.00 | 28.80 | | O |
| ANISOU | 3395 | O | PRO | B | 11 | 3774 | 4351 | 2818 | 1018 | 1184 | -223 | O |
| ATOM | 3396 | N | MET | B | 12 | 33.379 | 34.922 | 96.035 | 1.00 | 31.80 | | N |
| ANISOU | 3396 | N | MET | B | 12 | 3846 | 4932 | 3306 | 1133 | 1031 | -151 | N |
| ATOM | 3397 | CA | MET | B | 12 | 32.244 | 34.226 | 96.628 | 1.00 | 33.60 | | C |
| ANISOU | 3397 | CA | MET | B | 12 | 4256 | 5019 | 3491 | 1149 | 947 | -127 | C |
| ATOM | 3399 | CB | MET | B | 12 | 32.514 | 33.623 | 98.013 | 1.00 | 39.81 | | C |
| ANISOU | 3399 | CB | MET | B | 12 | 4954 | 5870 | 4300 | 1289 | 852 | -53 | C |
| ATOM | 3402 | CG | MET | B | 12 | 32.544 | 34.559 | 99.206 | 1.00 | 42.14 | | C |
| ANISOU | 3402 | CG | MET | B | 12 | 5086 | 6331 | 4595 | 1202 | 705 | -42 | C |
| ATOM | 3405 | SD | MET | B | 12 | 34.218 | 35.131 | 99.294 | 1.00 | 52.60 | | S |
| ANISOU | 3405 | SD | MET | B | 12 | 6093 | 7905 | 5987 | 1247 | 723 | -48 | S |
| ATOM | 3406 | CE | MET | B | 12 | 34.264 | 36.022 | 100.867 | 1.00 | 49.81 | | C |
| ANISOU | 3406 | CE | MET | B | 12 | 5568 | 7751 | 5608 | 1147 | 531 | -54 | C |
| ATOM | 3410 | C | MET | B | 12 | 30.990 | 35.071 | 96.646 | 1.00 | 29.79 | | C |
| ANISOU | 3410 | C | MET | B | 12 | 3875 | 4478 | 2965 | 952 | 860 | -148 | C |
| ATOM | 3411 | O | MET | B | 12 | 29.907 | 34.530 | 96.495 | 1.00 | 25.54 | | O |
| ANISOU | 3411 | O | MET | B | 12 | 3526 | 3799 | 2378 | 921 | 841 | -147 | O |
| ATOM | 3413 | N | ILE | B | 13 | 31.154 | 36.390 | 96.829 | 1.00 | 28.15 | | N |
| ANISOU | 3413 | N | ILE | B | 13 | 3534 | 4376 | 2785 | 820 | 814 | -167 | N |
| ATOM | 3414 | CA | ILE | B | 13 | 30.055 | 37.330 | 96.794 | 1.00 | 27.44 | | C |
| ANISOU | 3414 | CA | ILE | B | 13 | 3522 | 4230 | 2675 | 655 | 751 | -180 | C |
| ATOM | 3416 | CB | ILE | B | 13 | 30.480 | 38.801 | 97.144 | 1.00 | 27.48 | | C |
| ANISOU | 3416 | CB | ILE | B | 13 | 3366 | 4337 | 2737 | 527 | 717 | -208 | C |
| ATOM | 3418 | CG1 | ILE | B | 13 | 31.003 | 38.905 | 98.591 | 1.00 | 29.24 | | C |
| ANISOU | 3418 | CG1 | ILE | B | 13 | 3430 | 4695 | 2986 | 561 | 617 | -220 | C |
| ATOM | 3421 | CD1 | ILE | B | 13 | 30.032 | 38.569 | 99.626 | 1.00 | 29.19 | | C |
| ANISOU | 3421 | CD1 | ILE | B | 13 | 3506 | 4653 | 2932 | 582 | 515 | -204 | C |
| ATOM | 3425 | CG2 | ILE | B | 13 | 29.323 | 39.796 | 96.867 | 1.00 | 25.15 | | C |
| ANISOU | 3425 | CG2 | ILE | B | 13 | 3174 | 3947 | 2436 | 381 | 687 | -211 | C |
| ATOM | 3429 | C | ILE | B | 13 | 29.457 | 37.304 | 95.406 | 1.00 | 24.23 | | C |
| ANISOU | 3429 | C | ILE | B | 13 | 3277 | 3715 | 2213 | 589 | 829 | -189 | C |
| ATOM | 3430 | O | ILE | B | 13 | 28.243 | 37.238 | 95.266 | 1.00 | 22.87 | | O |
| ANISOU | 3430 | O | ILE | B | 13 | 3246 | 3450 | 1994 | 524 | 779 | -179 | O |
| ATOM | 3432 | N | VAL | B | 14 | 30.316 | 37.383 | 94.402 | 1.00 | 26.14 | | N |
| ANISOU | 3432 | N | VAL | B | 14 | 3485 | 3995 | 2453 | 601 | 948 | -204 | N |
| ATOM | 3433 | CA | VAL | B | 14 | 29.891 | 37.398 | 93.011 | 1.00 | 26.67 | | C |
| ANISOU | 3433 | CA | VAL | B | 14 | 3702 | 3995 | 2438 | 537 | 1030 | -212 | C |
| ATOM | 3435 | CB | VAL | B | 14 | 31.100 | 37.672 | 92.063 | 1.00 | 28.89 | | C |
| ANISOU | 3435 | CB | VAL | B | 14 | 3894 | 4361 | 2721 | 551 | 1181 | -223 | C |
| ATOM | 3437 | CG1 | VAL | B | 14 | 30.706 | 37.478 | 90.624 | 1.00 | 28.17 | | C |
| ANISOU | 3437 | CG1 | VAL | B | 14 | 3980 | 4217 | 2508 | 505 | 1274 | -237 | C |
| ATOM | 3441 | CG2 | VAL | B | 14 | 31.639 | 39.109 | 92.329 | 1.00 | 27.45 | | C |
| ANISOU | 3441 | CG2 | VAL | B | 14 | 3532 | 4274 | 2623 | 435 | 1170 | -197 | C |
| ATOM | 3445 | C | VAL | B | 14 | 29.148 | 36.116 | 92.618 | 1.00 | 26.80 | | C |
| ANISOU | 3445 | C | VAL | B | 14 | 3923 | 3888 | 2372 | 591 | 1040 | -238 | C |
| ATOM | 3446 | O | VAL | B | 14 | 28.138 | 36.154 | 91.892 | 1.00 | 25.35 | | O |
| ANISOU | 3446 | O | VAL | B | 14 | 3890 | 3640 | 2101 | 492 | 1017 | -242 | O |
| ATOM | 3448 | N | GLU | B | 15 | 29.667 | 34.994 | 93.096 | 1.00 | 28.12 | | N |
| ANISOU | 3448 | N | GLU | B | 15 | 4090 | 4025 | 2568 | 743 | 1073 | -252 | N |
| ATOM | 3449 | CA | GLU | B | 15 | 29.098 | 33.685 | 92.858 | 1.00 | 31.11 | | C |
| ANISOU | 3449 | CA | GLU | B | 15 | 4669 | 4257 | 2896 | 799 | 1099 | -284 | C |
| ATOM | 3451 | CB | GLU | B | 15 | 30.059 | 32.650 | 93.465 | 1.00 | 34.20 | | C |
| ANISOU | 3451 | CB | GLU | B | 15 | 5007 | 4629 | 3358 | 1008 | 1162 | -273 | C |
| ATOM | 3454 | CG | GLU | B | 15 | 29.699 | 31.204 | 93.369 | 1.00 | 36.94 | | C |
| ANISOU | 3454 | CG | GLU | B | 15 | 5557 | 4790 | 3689 | 1099 | 1215 | -301 | C |
| ATOM | 3457 | CD | GLU | B | 15 | 30.731 | 30.332 | 94.062 | 1.00 | 39.17 | | C |
| ANISOU | 3457 | CD | GLU | B | 15 | 5758 | 5063 | 4062 | 1337 | 1276 | -254 | C |
| ATOM | 3458 | OE1 | GLU | B | 15 | 31.943 | 30.529 | 93.807 | 1.00 | 40.20 | | O |
| ANISOU | 3458 | OE1 | GLU | B | 15 | 5728 | 5311 | 4234 | 1451 | 1369 | -254 | O |
| ATOM | 3459 | OE2 | GLU | B | 15 | 30.314 | 29.454 | 94.839 | 1.00 | 42.53 | | O |
| ANISOU | 3459 | OE2 | GLU | B | 15 | 6275 | 5369 | 4517 | 1409 | 1236 | -205 | O |
| ATOM | 3460 | C | GLU | B | 15 | 27.689 | 33.569 | 93.473 | 1.00 | 28.14 | | C |
| ANISOU | 3460 | C | GLU | B | 15 | 4394 | 3800 | 2500 | 703 | 965 | -259 | C |
| ATOM | 3461 | O | GLU | B | 15 | 26.787 | 33.006 | 92.883 | 1.00 | 28.24 | | O |
| ANISOU | 3461 | O | GLU | B | 15 | 4583 | 3707 | 2439 | 629 | 962 | -293 | O |
| ATOM | 3463 | N | LEU | B | 16 | 27.526 | 34.072 | 94.684 | 1.00 | 27.06 | | N |

FIG. 18 (continued)

| | | | | | | | | | | | | |
|---|---|---|---|---|---|---|---|---|---|---|---|---|
| ANISOU | 3463 | N | LEU | B | 16 | 4135 | 3723 | 2422 | 700 | 861 | -205 | N |
| ATOM | 3464 | CA | LEU | B | 16 | 26.236 | 34.026 | 95.390 | 1.00 | 26.08 | | C |
| ANISOU | 3464 | CA | LEU | B | 16 | 4076 | 3547 | 2286 | 620 | 749 | -173 | C |
| ATOM | 3466 | CB | LEU | B | 16 | 26.394 | 34.430 | 96.856 | 1.00 | 25.85 | | C |
| ANISOU | 3466 | CB | LEU | B | 16 | 3903 | 3605 | 2313 | 662 | 664 | -124 | C |
| ATOM | 3469 | CG | LEU | B | 16 | 27.145 | 33.443 | 97.753 | 1.00 | 27.01 | | C |
| ANISOU | 3469 | CG | LEU | B | 16 | 4015 | 3755 | 2491 | 830 | 675 | -83 | C |
| ATOM | 3471 | CD1 | LEU | B | 16 | 27.489 | 34.066 | 99.121 | 1.00 | 26.92 | | C |
| ANISOU | 3471 | CD1 | LEU | B | 16 | 3834 | 3892 | 2503 | 856 | 582 | -45 | C |
| ATOM | 3475 | CD2 | LEU | B | 16 | 26.331 | 32.155 | 97.958 | 1.00 | 27.65 | | C |
| ANISOU | 3475 | CD2 | LEU | B | 16 | 4277 | 3677 | 2552 | 856 | 680 | -51 | C |
| ATOM | 3479 | C | LEU | B | 16 | 25.224 | 34.929 | 94.735 | 1.00 | 25.26 | | C |
| ANISOU | 3479 | C | LEU | B | 16 | 4009 | 3453 | 2135 | 459 | 700 | -174 | C |
| ATOM | 3480 | O | LEU | B | 16 | 24.072 | 34.569 | 94.631 | 1.00 | 24.70 | | O |
| ANISOU | 3480 | O | LEU | B | 16 | 4045 | 3317 | 2022 | 380 | 649 | -168 | O |
| ATOM | 3482 | N | ALA | B | 17 | 25.667 | 36.101 | 94.260 | 1.00 | 24.30 | | N |
| ANISOU | 3482 | N | ALA | B | 17 | 3793 | 3416 | 2026 | 411 | 720 | -172 | N |
| ATOM | 3483 | CA | ALA | B | 17 | 24.825 | 37.011 | 93.474 | 1.00 | 22.70 | | C |
| ANISOU | 3483 | CA | ALA | B | 17 | 3626 | 3221 | 1778 | 284 | 688 | -148 | C |
| ATOM | 3485 | CB | ALA | B | 17 | 25.574 | 38.297 | 93.204 | 1.00 | 20.87 | | C |
| ANISOU | 3485 | CB | ALA | B | 17 | 3276 | 3061 | 1592 | 253 | 730 | -129 | C |
| ATOM | 3489 | C | ALA | B | 17 | 24.357 | 36.403 | 92.171 | 1.00 | 25.31 | | C |
| ANISOU | 3489 | C | ALA | B | 17 | 4116 | 3507 | 1992 | 231 | 723 | -174 | C |
| ATOM | 3490 | O | ALA | B | 17 | 23.205 | 36.543 | 91.805 | 1.00 | 25.44 | | O |
| ANISOU | 3490 | O | ALA | B | 17 | 4200 | 3515 | 1952 | 135 | 651 | -148 | O |
| ATOM | 3492 | N | GLU | B | 18 | 25.256 | 35.750 | 91.446 | 1.00 | 26.71 | | N |
| ANISOU | 3492 | N | GLU | B | 18 | 4349 | 3674 | 2127 | 291 | 836 | -229 | N |
| ATOM | 3493 | CA | GLU | B | 18 | 24.860 | 35.063 | 90.225 | 1.00 | 28.33 | | C |
| ANISOU | 3493 | CA | GLU | B | 18 | 4730 | 3837 | 2198 | 236 | 879 | -284 | C |
| ATOM | 3495 | CB | GLU | B | 18 | 26.090 | 34.473 | 89.515 | 1.00 | 30.71 | | C |
| ANISOU | 3495 | CB | GLU | B | 18 | 5069 | 4134 | 2467 | 334 | 1040 | -354 | C |
| ATOM | 3498 | CG | GLU | B | 18 | 26.982 | 35.534 | 88.920 | 1.00 | 33.41 | | C |
| ANISOU | 3498 | CG | GLU | B | 18 | 5298 | 4592 | 2806 | 329 | 1121 | -319 | C |
| ATOM | 3501 | CD | GLU | B | 18 | 28.150 | 34.971 | 88.100 | 1.00 | 37.31 | | C |
| ANISOU | 3501 | CD | GLU | B | 18 | 5821 | 5103 | 3252 | 423 | 1302 | -388 | C |
| ATOM | 3502 | OE1 | GLU | B | 18 | 29.145 | 34.446 | 88.670 | 1.00 | 42.58 | | O |
| ANISOU | 3502 | OE1 | GLU | B | 18 | 6397 | 5764 | 4019 | 570 | 1379 | -410 | O |
| ATOM | 3503 | OE2 | GLU | B | 18 | 28.034 | 35.042 | 86.873 | 1.00 | 41.56 | | O |
| ANISOU | 3503 | OE2 | GLU | B | 18 | 6472 | 5673 | 3645 | 355 | 1369 | -417 | O |
| ATOM | 3504 | C | GLU | B | 18 | 23.799 | 33.990 | 90.497 | 1.00 | 27.83 | | C |
| ANISOU | 3504 | C | GLU | B | 18 | 4801 | 3669 | 2105 | 191 | 810 | -318 | C |
| ATOM | 3505 | O | GLU | B | 18 | 22.815 | 33.879 | 89.752 | 1.00 | 26.05 | | O |
| ANISOU | 3505 | O | GLU | B | 18 | 4681 | 3445 | 1772 | 66 | 754 | -334 | O |
| ATOM | 3507 | N | LYS | B | 19 | 23.994 | 33.233 | 91.568 | 1.00 | 30.12 | | N |
| ANISOU | 3507 | N | LYS | B | 19 | 5077 | 3881 | 2485 | 284 | 809 | -318 | N |
| ATOM | 3508 | CA | LYS | B | 19 | 23.063 | 32.171 | 91.979 | 1.00 | 32.75 | | C |
| ANISOU | 3508 | CA | LYS | B | 19 | 5534 | 4096 | 2815 | 239 | 762 | -336 | C |
| ATOM | 3510 | CB | LYS | B | 19 | 23.664 | 31.317 | 93.109 | 1.00 | 34.77 | | C |
| ANISOU | 3510 | CB | LYS | B | 19 | 5776 | 4264 | 3172 | 389 | 800 | -313 | C |
| ATOM | 3513 | CG | LYS | B | 19 | 22.661 | 30.498 | 93.921 | 1.00 | 36.61 | | C |
| ANISOU | 3513 | CG | LYS | B | 19 | 6089 | 4389 | 3432 | 338 | 739 | -282 | C |
| ATOM | 3516 | CD | LYS | B | 19 | 23.353 | 29.669 | 95.023 | 1.00 | 39.72 | | C |
| ANISOU | 3516 | CD | LYS | B | 19 | 6474 | 4701 | 3915 | 509 | 784 | -229 | C |
| ATOM | 3519 | CE | LYS | B | 19 | 22.500 | 29.474 | 96.305 | 1.00 | 39.85 | | C |
| ANISOU | 3519 | CE | LYS | B | 19 | 6467 | 4703 | 3971 | 476 | 700 | -136 | C |
| ATOM | 3522 | NZ | LYS | B | 19 | 23.108 | 30.230 | 97.483 | 1.00 | 40.11 | | N |
| ANISOU | 3522 | NZ | LYS | B | 19 | 6308 | 4882 | 4049 | 587 | 651 | -54 | N |
| ATOM | 3526 | C | LYS | B | 19 | 21.704 | 32.745 | 92.373 | 1.00 | 30.26 | | C |
| ANISOU | 3526 | C | LYS | B | 19 | 5172 | 3828 | 2496 | 107 | 625 | -273 | C |
| ATOM | 3527 | O | LYS | B | 19 | 20.703 | 32.174 | 92.016 | 1.00 | 30.79 | | O |
| ANISOU | 3527 | O | LYS | B | 19 | 5347 | 3848 | 2504 | -12 | 578 | -300 | O |
| ATOM | 3529 | N | ALA | B | 20 | 21.673 | 33.865 | 93.092 | 1.00 | 28.47 | | N |
| ANISOU | 3529 | N | ALA | B | 20 | 4785 | 3698 | 2336 | 125 | 568 | -198 | N |
| ATOM | 3530 | CA | ALA | B | 20 | 20.406 | 34.544 | 93.429 | 1.00 | 26.68 | | C |
| ANISOU | 3530 | CA | ALA | B | 20 | 4497 | 3525 | 2115 | 26 | 458 | -136 | C |
| ATOM | 3532 | CB | ALA | B | 20 | 20.629 | 35.736 | 94.379 | 1.00 | 25.75 | | C |
| ANISOU | 3532 | CB | ALA | B | 20 | 4216 | 3482 | 2088 | 79 | 431 | -79 | C |
| ATOM | 3536 | C | ALA | B | 20 | 19.664 | 34.987 | 92.152 | 1.00 | 26.58 | | C |
| ANISOU | 3536 | C | ALA | B | 20 | 4529 | 3570 | 1999 | -95 | 415 | -130 | C |
| ATOM | 3537 | O | ALA | B | 20 | 18.484 | 34.703 | 91.991 | 1.00 | 24.40 | | O |
| ANISOU | 3537 | O | ALA | B | 20 | 4285 | 3304 | 1680 | -203 | 336 | -116 | O |
| ATOM | 3539 | N | MET | B | 21 | 20.375 | 35.627 | 91.218 | 1.00 | 27.49 | | N |
| ANISOU | 3539 | N | MET | B | 21 | 4642 | 3737 | 2064 | -81 | 468 | -134 | N |
| ATOM | 3540 | CA | MET | B | 21 | 19.752 | 36.094 | 89.995 | 1.00 | 29.79 | | C |
| ANISOU | 3540 | CA | MET | B | 21 | 4977 | 4106 | 2236 | -182 | 426 | -105 | C |
| ATOM | 3542 | CB | MET | B | 21 | 20.749 | 36.872 | 89.115 | 1.00 | 30.08 | | C |
| ANISOU | 3542 | CB | MET | B | 21 | 5004 | 4196 | 2228 | -147 | 513 | -89 | C |
| ATOM | 3545 | CG | MET | B | 21 | 21.017 | 38.237 | 89.737 | 1.00 | 29.83 | | C |
| ANISOU | 3545 | CG | MET | B | 21 | 4820 | 4193 | 2321 | -100 | 510 | 2 | C |

FIG. 18 (continued)

```
ATOM    3548  SD   MET B  21      21.889  39.420  88.725  1.00 30.90           S
ANISOU  3548  SD   MET B  21    4930   4388   2424   -102    600     66        S
ATOM    3549  CE   MET B  21      20.530  40.208  87.807  1.00 28.12           C
ANISOU  3549  CE   MET B  21    4604   4111   1968   -189    491    198        C
ATOM    3553  C    MET B  21      19.112  34.930  89.221  1.00 29.38           C
ANISOU  3553  C    MET B  21    5083   4027   2053   -289    400   -187        C
ATOM    3554  O    MET B  21      18.001  35.077  88.709  1.00 29.49           O
ANISOU  3554  O    MET B  21    5103   4118   1985   -406    296   -151        O
ATOM    3556  N    LYS B  22      19.832  33.806  89.161  1.00 28.41           N
ANISOU  3556  N    LYS B  22    5081   3797   1917   -247    497   -295        N
ATOM    3557  CA   LYS B  22      19.403  32.585  88.492  1.00 33.43           C
ANISOU  3557  CA   LYS B  22    5899   4360   2444   -348    504   -409        C
ATOM    3559  CB   LYS B  22      20.562  31.574  88.519  1.00 36.47           C
ANISOU  3559  CB   LYS B  22    6398   4602   2856   -230    659   -515        C
ATOM    3562  CG   LYS B  22      20.479  30.431  87.527  1.00 41.20           C
ANISOU  3562  CG   LYS B  22    7223   5109   3323   -314    721   -669        C
ATOM    3565  CD   LYS B  22      21.222  29.178  88.078  1.00 42.96           C
ANISOU  3565  CD   LYS B  22    7559   5120   3646   -187    854   -748        C
ATOM    3568  CE   LYS B  22      21.658  28.206  86.996  1.00 45.33           C
ANISOU  3568  CE   LYS B  22    8084   5311   3829   -199    988   -922        C
ATOM    3571  NZ   LYS B  22      22.959  27.517  87.351  1.00 47.57           N
ANISOU  3571  NZ   LYS B  22    8403   5449   4222     29   1168   -959        N
ATOM    3575  C    LYS B  22      18.159  31.975  89.160  1.00 31.96           C
ANISOU  3575  C    LYS B  22    5719   4127   2298   -460    400   -398        C
ATOM    3576  O    LYS B  22      17.194  31.606  88.496  1.00 33.06           O
ANISOU  3576  O    LYS B  22    5930   4303   2329   -625    320   -439        O
ATOM    3578  N    GLU B  23      18.202  31.866  90.477  1.00 31.02           N
ANISOU  3578  N    GLU B  23    5519   3942   2325   -378    403   -343        N
ATOM    3579  CA   GLU B  23      17.102  31.345  91.280  1.00 33.52           C
ANISOU  3579  CA   GLU B  23    5820   4218   2696   -469    328   -311        C
ATOM    3581  CB   GLU B  23      17.454  31.384  92.785  1.00 33.98           C
ANISOU  3581  CB   GLU B  23    5784   4229   2899   -337    356   -236        C
ATOM    3584  CG   GLU B  23      18.302  30.253  93.299  1.00 37.63           C
ANISOU  3584  CG   GLU B  23    6359   4522   3416   -230    461   -277        C
ATOM    3587  CD   GLU B  23      18.011  29.938  94.768  1.00 36.25           C
ANISOU  3587  CD   GLU B  23    6128   4304   3340   -182    448   -189        C
ATOM    3588  OE1  GLU B  23      17.891  30.865  95.593  1.00 37.22           O
ANISOU  3588  OE1  GLU B  23    6091   4543   3507   -134    400   -109        O
ATOM    3589  OE2  GLU B  23      17.886  28.747  95.092  1.00 41.74           O
ANISOU  3589  OE2  GLU B  23    6953   4842   4064   -198    495   -202        O
ATOM    3590  C    GLU B  23      15.828  32.167  91.158  1.00 32.37           C
ANISOU  3590  C    GLU B  23    5547   4228   2523   -587    193   -227        C
ATOM    3591  O    GLU B  23      14.753  31.674  91.504  1.00 31.41           O
ANISOU  3591  O    GLU B  23    5415   4104   2416   -709    126   -213        O
ATOM    3593  N    TYR B  24      15.949  33.430  90.750  1.00 30.92           N
ANISOU  3593  N    TYR B  24    5256   4175   2319   -541    162   -157        N
ATOM    3594  CA   TYR B  24      14.799  34.330  90.750  1.00 30.96           C
ANISOU  3594  CA   TYR B  24    5116   4320   2326   -601     45    -50        C
ATOM    3596  CB   TYR B  24      15.048  35.537  91.694  1.00 28.69           C
ANISOU  3596  CB   TYR B  24    4672   4060   2168   -462     62     46        C
ATOM    3599  CG   TYR B  24      14.882  35.230  93.157  1.00 27.95           C
ANISOU  3599  CG   TYR B  24    4519   3906   2193   -414     82     59        C
ATOM    3600  CD1  TYR B  24      13.609  35.203  93.749  1.00 29.90           C
ANISOU  3600  CD1  TYR B  24    4673   4209   2478   -482     14    119        C
ATOM    3602  CE1  TYR B  24      13.448  34.924  95.085  1.00 28.57           C
ANISOU  3602  CE1  TYR B  24    4458   4000   2396   -440     45    137        C
ATOM    3604  CZ   TYR B  24      14.566  34.630  95.855  1.00 27.36           C
ANISOU  3604  CZ   TYR B  24    4355   3757   2285   -328    126    101        C
ATOM    3605  OH   TYR B  24      14.451  34.383  97.162  1.00 26.40           O
ANISOU  3605  OH   TYR B  24    4194   3617   2220   -282    152    131        O
ATOM    3607  CE2  TYR B  24      15.840  34.660  95.305  1.00 27.94           C
ANISOU  3607  CE2  TYR B  24    4500   3783   2334   -253    182     45        C
ATOM    3609  CD2  TYR B  24      15.981  34.937  93.956  1.00 27.00           C
ANISOU  3609  CD2  TYR B  24    4427   3695   2135   -300    169     21        C
ATOM    3611  C    TYR B  24      14.393  34.738  89.338  1.00 33.00           C
ANISOU  3611  C    TYR B  24    5398   4710   2430   -693    -27    -35        C
ATOM    3612  O    TYR B  24      13.526  35.603  89.142  1.00 35.84           O
ANISOU  3612  O    TYR B  24    5632   5204   2781   -716   -125     77        O
ATOM    3614  N    GLY B  25      14.990  34.088  88.341  1.00 33.77           N
ANISOU  3614  N    GLY B  25    5660   4776   2395   -740     23   -144        N
ATOM    3615  CA   GLY B  25      14.696  34.383  86.967  1.00 35.16           C
ANISOU  3615  CA   GLY B  25    5882   5091   2385   -833    -39   -139        C
ATOM    3618  C    GLY B  25      15.161  35.723  86.419  1.00 35.00           C
ANISOU  3618  C    GLY B  25    5791   5172   2336   -737    -25    -21        C
ATOM    3619  O    GLY B  25      14.664  36.158  85.377  1.00 36.80           O
ANISOU  3619  O    GLY B  25    6021   5552   2410   -808   -107     40        O
ATOM    3621  N   AGLU B  26      16.129  36.354  87.086  0.30 33.17           N
ANISOU  3621  N   AGLU B  26    5500   4861   2241   -587     79     15        N
ATOM    3622  N   BGLU B  26      16.126  36.363  87.071  0.70 32.54           N
```

FIG. 18 (continued)

| | | | | | | | | | | | | |
|---|---|---|---|---|---|---|---|---|---|---|---|---|
| ANISOU | 3622 | N | BGLU | B | 26 | 5421 | 4783 | 2160 | -588 | 78 | 16 | N |
| ATOM | 3623 | CA | AGLU | B | 26 | 16.717 | 37.623 | 86.620 | 0.30 | 33.22 | | C |
| ANISOU | 3623 | CA | AGLU | B | 26 | 5452 | 4926 | 2245 | -507 | 122 | 122 | C |
| ATOM | 3624 | CA | BGLU | B | 26 | 16.666 | 37.642 | 86.568 | 0.70 | 32.82 | | C |
| ANISOU | 3624 | CA | BGLU | B | 26 | 5401 | 4882 | 2187 | -512 | 116 | 126 | C |
| ATOM | 3627 | CB | AGLU | B | 26 | 17.238 | 38.438 | 87.809 | 0.30 | 31.33 | | C |
| ANISOU | 3627 | CB | AGLU | B | 26 | 5085 | 4605 | 2212 | -381 | 178 | 176 | C |
| ATOM | 3628 | CB | BGLU | B | 26 | 16.975 | 38.584 | 87.732 | 0.70 | 31.72 | | C |
| ANISOU | 3628 | CB | BGLU | B | 26 | 5121 | 4678 | 2254 | -392 | 152 | 202 | C |
| ATOM | 3633 | CG | AGLU | B | 26 | 16.240 | 38.660 | 88.944 | 0.30 | 30.62 | | C |
| ANISOU | 3633 | CG | AGLU | B | 26 | 4872 | 4506 | 2255 | -369 | 95 | 230 | C |
| ATOM | 3634 | CG | BGLU | B | 26 | 15.893 | 38.642 | 88.802 | 0.70 | 32.48 | | C |
| ANISOU | 3634 | CG | BGLU | B | 26 | 5103 | 4770 | 2468 | -393 | 62 | 247 | C |
| ATOM | 3639 | CD | AGLU | B | 26 | 15.230 | 39.751 | 88.655 | 0.30 | 30.01 | | C |
| ANISOU | 3639 | CD | AGLU | B | 26 | 4690 | 4529 | 2185 | -369 | 3 | 383 | C |
| ATOM | 3640 | CD | BGLU | B | 26 | 14.865 | 39.690 | 88.523 | 0.70 | 31.84 | | C |
| ANISOU | 3640 | CD | BGLU | B | 26 | 4914 | 4793 | 2393 | -393 | -33 | 399 | C |
| ATOM | 3641 | OE1 | AGLU | B | 26 | 14.098 | 39.647 | 89.160 | 0.30 | 29.09 | | O |
| ANISOU | 3641 | OE1 | AGLU | B | 26 | 4486 | 4456 | 2110 | -397 | -86 | 423 | O |
| ATOM | 3642 | OE1 | BGLU | B | 26 | 14.433 | 39.803 | 87.366 | 0.70 | 33.57 | | O |
| ANISOU | 3642 | OE1 | BGLU | B | 26 | 5167 | 5127 | 2462 | -458 | -100 | 458 | O |
| ATOM | 3643 | OE2 | AGLU | B | 26 | 15.569 | 40.713 | 87.943 | 0.30 | 28.06 | | O |
| ANISOU | 3643 | OE2 | AGLU | B | 26 | 4439 | 4314 | 1907 | -333 | 29 | 475 | O |
| ATOM | 3644 | OE2 | BGLU | B | 26 | 14.496 | 40.396 | 89.471 | 0.70 | 27.95 | | O |
| ANISOU | 3644 | OE2 | BGLU | B | 26 | 4302 | 4270 | 2048 | -320 | -37 | 461 | O |
| ATOM | 3645 | C | AGLU | B | 26 | 17.892 | 37.370 | 85.674 | 0.30 | 34.43 | | C |
| ANISOU | 3645 | C | AGLU | B | 26 | 5734 | 5071 | 2278 | -493 | 247 | 44 | C |
| ATOM | 3646 | C | BGLU | B | 26 | 17.943 | 37.463 | 85.740 | 0.70 | 33.50 | | C |
| ANISOU | 3646 | C | BGLU | B | 26 | 5604 | 4950 | 2175 | -482 | 252 | 53 | C |
| ATOM | 3647 | O | AGLU | B | 26 | 18.668 | 36.436 | 85.883 | 0.30 | 34.39 | | O |
| ANISOU | 3647 | O | AGLU | B | 26 | 5814 | 4965 | 2288 | -462 | 346 | -87 | O |
| ATOM | 3648 | O | BGLU | B | 26 | 18.846 | 36.712 | 86.102 | 0.70 | 32.02 | | O |
| ANISOU | 3648 | O | BGLU | B | 26 | 5476 | 4657 | 2035 | -429 | 360 | -62 | O |
| ATOM | 3651 | N | ASP | B | 27 | 18.032 | 38.207 | 84.645 | 1.00 | 36.87 | | N |
| ANISOU | 3651 | N | ASP | B | 27 | 6053 | 5487 | 2469 | -503 | 254 | 138 | N |
| ATOM | 3652 | CA | ASP | B | 27 | 19.139 | 38.102 | 83.704 | 1.00 | 36.99 | | C |
| ANISOU | 3652 | CA | ASP | B | 27 | 6176 | 5520 | 2359 | -488 | 391 | 83 | C |
| ATOM | 3654 | CB | ASP | B | 27 | 18.570 | 38.266 | 82.298 | 1.00 | 41.40 | | C |
| ANISOU | 3654 | CB | ASP | B | 27 | 6822 | 6244 | 2662 | -590 | 323 | 136 | C |
| ATOM | 3657 | CG | ASP | B | 27 | 19.625 | 38.168 | 81.202 | 1.00 | 43.86 | | C |
| ANISOU | 3657 | CG | ASP | B | 27 | 7260 | 6603 | 2802 | -587 | 474 | 83 | C |
| ATOM | 3658 | OD1 | ASP | B | 27 | 20.845 | 38.048 | 81.499 | 1.00 | 44.98 | | O |
| ANISOU | 3658 | OD1 | ASP | B | 27 | 7399 | 6652 | 3040 | -497 | 641 | 16 | O |
| ATOM | 3659 | OD2 | ASP | B | 27 | 19.202 | 38.209 | 80.032 | 1.00 | 46.91 | | O |
| ANISOU | 3659 | OD2 | ASP | B | 27 | 7738 | 7141 | 2943 | -675 | 423 | 112 | O |
| ATOM | 3660 | C | ASP | B | 27 | 20.199 | 39.183 | 84.033 | 1.00 | 36.42 | | C |
| ANISOU | 3660 | C | ASP | B | 27 | 6005 | 5408 | 2427 | -383 | 508 | 170 | C |
| ATOM | 3661 | O | ASP | B | 27 | 19.948 | 40.372 | 83.831 | 1.00 | 35.43 | | O |
| ANISOU | 3661 | O | ASP | B | 27 | 5808 | 5330 | 2325 | -374 | 478 | 329 | O |
| ATOM | 3663 | N | LEU | B | 28 | 21.371 | 38.769 | 84.537 | 1.00 | 35.13 | | N |
| ANISOU | 3663 | N | LEU | B | 28 | 5833 | 5154 | 2360 | -305 | 642 | 71 | N |
| ATOM | 3664 | CA | LEU | B | 28 | 22.454 | 39.721 | 84.869 | 1.00 | 36.12 | | C |
| ANISOU | 3664 | CA | LEU | B | 28 | 5849 | 5256 | 2621 | -233 | 753 | 132 | C |
| ATOM | 3666 | CB | LEU | B | 28 | 23.610 | 39.043 | 85.647 | 1.00 | 36.23 | | C |
| ANISOU | 3666 | CB | LEU | B | 28 | 5818 | 5192 | 2754 | -142 | 863 | 12 | C |
| ATOM | 3669 | CG | LEU | B | 28 | 24.721 | 38.215 | 85.023 | 1.00 | 38.84 | | C |
| ANISOU | 3669 | CG | LEU | B | 28 | 6222 | 5530 | 3005 | -93 | 1022 | -99 | C |
| ATOM | 3671 | CD1 | LEU | B | 28 | 25.661 | 39.074 | 84.192 | 1.00 | 40.58 | | C |
| ANISOU | 3671 | CD1 | LEU | B | 28 | 6405 | 5832 | 3180 | -98 | 1157 | -32 | C |
| ATOM | 3675 | CD2 | LEU | B | 28 | 25.498 | 37.545 | 86.112 | 1.00 | 38.02 | | C |
| ANISOU | 3675 | CD2 | LEU | B | 28 | 6042 | 5348 | 3057 | 19 | 1072 | -180 | C |
| ATOM | 3679 | C | LEU | B | 28 | 22.973 | 40.537 | 83.685 | 1.00 | 37.83 | | C |
| ANISOU | 3679 | C | LEU | B | 28 | 6096 | 5560 | 2719 | -261 | 844 | 227 | C |
| ATOM | 3680 | O | LEU | B | 28 | 23.392 | 41.680 | 83.866 | 1.00 | 36.71 | | O |
| ANISOU | 3680 | O | LEU | B | 28 | 5859 | 5401 | 2688 | -246 | 889 | 337 | O |
| ATOM | 3682 | N | LYS | B | 29 | 22.932 | 39.965 | 82.478 | 1.00 | 40.35 | | N |
| ANISOU | 3682 | N | LYS | B | 29 | 6558 | 5966 | 2806 | -313 | 877 | 183 | N |
| ATOM | 3683 | CA | LYS | B | 29 | 23.401 | 40.659 | 81.287 | 1.00 | 41.88 | | C |
| ANISOU | 3683 | CA | LYS | B | 29 | 6799 | 6264 | 2849 | -344 | 973 | 282 | C |
| ATOM | 3685 | CB | LYS | B | 29 | 23.455 | 39.683 | 80.110 | 1.00 | 46.09 | | C |
| ANISOU | 3685 | CB | LYS | B | 29 | 7512 | 6892 | 3109 | -395 | 1025 | 165 | C |
| ATOM | 3688 | CG | LYS | B | 29 | 24.574 | 38.662 | 80.238 | 1.00 | 47.10 | | C |
| ANISOU | 3688 | CG | LYS | B | 29 | 7680 | 6955 | 3263 | -324 | 1195 | -22 | C |
| ATOM | 3691 | CD | LYS | B | 29 | 25.883 | 39.273 | 79.770 | 1.00 | 50.02 | | C |
| ANISOU | 3691 | CD | LYS | B | 29 | 7994 | 7373 | 3638 | -280 | 1398 | 28 | C |
| ATOM | 3694 | CE | LYS | B | 29 | 27.105 | 38.455 | 80.189 | 1.00 | 49.98 | | C |
| ANISOU | 3694 | CE | LYS | B | 29 | 7948 | 7302 | 3739 | -169 | 1569 | -123 | C |
| ATOM | 3697 | NZ | LYS | B | 29 | 28.321 | 39.114 | 79.626 | 1.00 | 52.57 | | N |
| ANISOU | 3697 | NZ | LYS | B | 29 | 8202 | 7714 | 4060 | -146 | 1769 | -60 | N |

FIG. 18 (continued)

| | | | | | | | | | | | | |
|---|---|---|---|---|---|---|---|---|---|---|---|---|
| ATOM | 3701 | C | LYS | B | 29 | 22.517 | 41.854 | 80.928 | 1.00 | 42.35 | | C |
| ANISOU | 3701 | C | LYS | B | 29 | 6828 | 6385 | 2880 | -384 | 863 | 495 | C |
| ATOM | 3702 | O | LYS | B | 29 | 22.960 | 42.828 | 80.297 | 1.00 | 41.87 | | O |
| ANISOU | 3702 | O | LYS | B | 29 | 6760 | 6364 | 2784 | -391 | 946 | 640 | O |
| ATOM | 3704 | N | ILE | B | 30 | 21.254 | 41.782 | 81.310 | 1.00 | 41.10 | | N |
| ANISOU | 3704 | N | ILE | B | 30 | 6647 | 6231 | 2737 | -406 | 683 | 529 | N |
| ATOM | 3705 | CA | ILE | B | 30 | 20.340 | 42.884 | 81.060 | 1.00 | 42.98 | | C |
| ANISOU | 3705 | CA | ILE | B | 30 | 6836 | 6522 | 2973 | -411 | 572 | 743 | C |
| ATOM | 3707 | CB | ILE | B | 30 | 18.987 | 42.352 | 80.635 | 1.00 | 44.63 | | C |
| ANISOU | 3707 | CB | ILE | B | 30 | 7084 | 6857 | 3017 | -477 | 385 | 753 | C |
| ATOM | 3709 | CG1 | ILE | B | 30 | 19.121 | 41.661 | 79.281 | 1.00 | 47.58 | | C |
| ANISOU | 3709 | CG1 | ILE | B | 30 | 7618 | 7384 | 3074 | -566 | 404 | 688 | C |
| ATOM | 3712 | CD1 | ILE | B | 30 | 19.201 | 42.636 | 78.112 | 1.00 | 51.53 | | C |
| ANISOU | 3712 | CD1 | ILE | B | 30 | 8161 | 8019 | 3397 | -573 | 428 | 895 | C |
| ATOM | 3716 | CG2 | ILE | B | 30 | 17.978 | 43.488 | 80.542 | 1.00 | 47.42 | | C |
| ANISOU | 3716 | CG2 | ILE | B | 30 | 7347 | 7264 | 3405 | -446 | 262 | 991 | C |
| ATOM | 3720 | C | ILE | B | 30 | 20.240 | 43.761 | 82.313 | 1.00 | 40.03 | | C |
| ANISOU | 3720 | C | ILE | B | 30 | 6316 | 6006 | 2887 | -339 | 558 | 811 | C |
| ATOM | 3721 | O | ILE | B | 30 | 20.211 | 44.985 | 82.240 | 1.00 | 39.57 | | O |
| ANISOU | 3721 | O | ILE | B | 30 | 6211 | 5912 | 2913 | -308 | 580 | 983 | O |
| ATOM | 3723 | N | GLU | B | 31 | 20.236 | 43.125 | 83.469 | 1.00 | 37.28 | | N |
| ANISOU | 3723 | N | GLU | B | 31 | 5911 | 5568 | 2687 | -312 | 536 | 670 | N |
| ATOM | 3724 | CA | GLU | B | 31 | 20.084 | 43.823 | 84.742 | 1.00 | 36.49 | | C |
| ANISOU | 3724 | CA | GLU | B | 31 | 5685 | 5347 | 2833 | -252 | 518 | 698 | C |
| ATOM | 3726 | CB | GLU | B | 31 | 18.971 | 43.132 | 85.540 | 1.00 | 36.84 | | C |
| ANISOU | 3726 | CB | GLU | B | 31 | 5690 | 5393 | 2916 | -251 | 381 | 639 | C |
| ATOM | 3729 | CG | GLU | B | 31 | 17.579 | 43.387 | 84.963 | 1.00 | 40.94 | | C |
| ANISOU | 3729 | CG | GLU | B | 31 | 6199 | 6022 | 3337 | -277 | 235 | 773 | C |
| ATOM | 3732 | CD | GLU | B | 31 | 16.488 | 43.046 | 85.962 | 1.00 | 43.02 | | C |
| ANISOU | 3732 | CD | GLU | B | 31 | 6370 | 6273 | 3701 | -267 | 122 | 747 | C |
| ATOM | 3733 | OE1 | GLU | B | 31 | 15.912 | 43.985 | 86.586 | 1.00 | 45.26 | | O |
| ANISOU | 3733 | OE1 | GLU | B | 31 | 6549 | 6514 | 4135 | -196 | 95 | 853 | O |
| ATOM | 3734 | OE2 | GLU | B | 31 | 16.233 | 41.826 | 86.151 | 1.00 | 46.30 | | O |
| ANISOU | 3734 | OE2 | GLU | B | 31 | 6826 | 6712 | 4055 | -330 | 78 | 616 | O |
| ATOM | 3735 | C | GLU | B | 31 | 21.404 | 43.896 | 85.527 | 1.00 | 33.41 | | C |
| ANISOU | 3735 | C | GLU | B | 31 | 5238 | 4858 | 2598 | -219 | 650 | 597 | C |
| ATOM | 3736 | O | GLU | B | 31 | 21.542 | 43.344 | 86.624 | 1.00 | 29.97 | | O |
| ANISOU | 3736 | O | GLU | B | 31 | 4748 | 4365 | 2274 | -187 | 635 | 479 | O |
| ATOM | 3738 | N | THR | B | 32 | 22.368 | 44.598 | 84.954 | 1.00 | 33.44 | | N |
| ANISOU | 3738 | N | THR | B | 32 | 5244 | 4858 | 2602 | -232 | 778 | 655 | N |
| ATOM | 3739 | CA | THR | B | 32 | 23.717 | 44.684 | 85.512 | 1.00 | 32.47 | | C |
| ANISOU | 3739 | CA | THR | B | 32 | 5047 | 4682 | 2607 | -221 | 907 | 567 | C |
| ATOM | 3741 | CB | THR | B | 32 | 24.764 | 45.059 | 84.395 | 1.00 | 35.41 | | C |
| ANISOU | 3741 | CB | THR | B | 32 | 5454 | 5111 | 2889 | -262 | 1066 | 625 | C |
| ATOM | 3743 | OG1 | THR | B | 32 | 24.569 | 46.416 | 83.943 | 1.00 | 37.88 | | O |
| ANISOU | 3743 | OG1 | THR | B | 32 | 5769 | 5383 | 3239 | -297 | 1092 | 811 | O |
| ATOM | 3745 | CG2 | THR | B | 32 | 24.616 | 44.137 | 83.217 | 1.00 | 34.87 | | C |
| ANISOU | 3745 | CG2 | THR | B | 32 | 5519 | 5163 | 2568 | -277 | 1078 | 597 | C |
| ATOM | 3749 | C | THR | B | 32 | 23.821 | 45.628 | 86.702 | 1.00 | 30.07 | | C |
| ANISOU | 3749 | C | THR | B | 32 | 4627 | 4264 | 2533 | -208 | 900 | 576 | C |
| ATOM | 3750 | O | THR | B | 32 | 24.624 | 45.388 | 87.618 | 1.00 | 27.93 | | O |
| ANISOU | 3750 | O | THR | B | 32 | 4269 | 3967 | 2375 | -193 | 937 | 459 | O |
| ATOM | 3752 | N | ASN | B | 33 | 23.025 | 46.693 | 86.733 | 1.00 | 31.16 | | N |
| ANISOU | 3752 | N | ASN | B | 33 | 4763 | 4337 | 2741 | -207 | 853 | 708 | N |
| ATOM | 3753 | CA | ASN | B | 33 | 22.964 | 47.526 | 87.946 | 1.00 | 29.31 | | C |
| ANISOU | 3753 | CA | ASN | B | 33 | 4440 | 3977 | 2718 | -192 | 845 | 684 | C |
| ATOM | 3755 | CB | ASN | B | 33 | 22.144 | 48.805 | 87.719 | 1.00 | 31.15 | | C |
| ANISOU | 3755 | CB | ASN | B | 33 | 4695 | 4115 | 3026 | -175 | 831 | 855 | C |
| ATOM | 3758 | CG | ASN | B | 33 | 22.885 | 49.832 | 86.866 | 1.00 | 33.74 | | C |
| ANISOU | 3758 | CG | ASN | B | 33 | 5058 | 4385 | 3375 | -231 | 960 | 985 | C |
| ATOM | 3759 | OD1 | ASN | B | 33 | 24.099 | 49.916 | 86.933 | 1.00 | 34.77 | | O |
| ANISOU | 3759 | OD1 | ASN | B | 33 | 5150 | 4506 | 3554 | -298 | 1070 | 913 | O |
| ATOM | 3760 | ND2 | ASN | B | 33 | 22.161 | 50.584 | 86.044 | 1.00 | 34.09 | | N |
| ANISOU | 3760 | ND2 | ASN | B | 33 | 5167 | 4405 | 3380 | -205 | 948 | 1188 | N |
| ATOM | 3763 | C | ASN | B | 33 | 22.405 | 46.720 | 89.108 | 1.00 | 26.85 | | C |
| ANISOU | 3763 | C | ASN | B | 33 | 4085 | 3673 | 2445 | -145 | 743 | 560 | C |
| ATOM | 3764 | O | ASN | B | 33 | 22.870 | 46.817 | 90.232 | 1.00 | 24.57 | | O |
| ANISOU | 3764 | O | ASN | B | 33 | 3719 | 3337 | 2279 | -139 | 755 | 455 | O |
| ATOM | 3766 | N | LYS | B | 34 | 21.389 | 45.911 | 88.846 | 1.00 | 27.76 | | N |
| ANISOU | 3766 | N | LYS | B | 34 | 4247 | 3857 | 2443 | -122 | 641 | 573 | N |
| ATOM | 3767 | CA | LYS | B | 34 | 20.822 | 45.038 | 89.879 | 1.00 | 26.52 | | C |
| ANISOU | 3767 | CA | LYS | B | 34 | 4058 | 3709 | 2309 | -90 | 557 | 471 | C |
| ATOM | 3769 | CB | LYS | B | 34 | 19.563 | 44.325 | 89.356 | 1.00 | 27.01 | | C |
| ANISOU | 3769 | CB | LYS | B | 34 | 4170 | 3850 | 2243 | -99 | 445 | 516 | C |
| ATOM | 3772 | CG | LYS | B | 34 | 18.750 | 43.591 | 90.443 | 1.00 | 26.49 | | C |
| ANISOU | 3772 | CG | LYS | B | 34 | 4062 | 3784 | 2219 | -80 | 362 | 446 | C |
| ATOM | 3775 | CD | LYS | B | 34 | 17.485 | 42.916 | 89.872 | 1.00 | 27.43 | | C |
| ANISOU | 3775 | CD | LYS | B | 34 | 4212 | 3992 | 2217 | -122 | 250 | 492 | C |
| ATOM | 3778 | CE | LYS | B | 34 | 16.342 | 43.902 | 89.600 | 1.00 | 28.72 | | C |

FIG. 18 (continued)

| | | | | | | | | | | | | | |
|---|---|---|---|---|---|---|---|---|---|---|---|---|---|
| ANISOU | 3778 | CE | LYS | B | 34 | 4313 | 4190 | 2408 | -96 | 180 | 649 | C |
| ATOM | 3781 | NZ | LYS | B | 34 | 15.074 | 43.223 | 89.165 | 1.00 | 28.25 | | N |
| ANISOU | 3781 | NZ | LYS | B | 34 | 4242 | 4252 | 2238 | -149 | 53 | 690 | N |
| ATOM | 3785 | C | LYS | B | 34 | 21.853 | 44.027 | 90.389 | 1.00 | 25.22 | | C |
| ANISOU | 3785 | C | LYS | B | 34 | 3880 | 3564 | 2139 | -82 | 601 | 325 | C |
| ATOM | 3786 | O | LYS | B | 34 | 21.907 | 43.777 | 91.566 | 1.00 | 23.46 | | O |
| ANISOU | 3786 | O | LYS | B | 34 | 3598 | 3317 | 1998 | -51 | 575 | 247 | O |
| ATOM | 3788 | N | PHE | B | 35 | 22.660 | 43.472 | 89.480 | 1.00 | 25.90 | | N |
| ANISOU | 3788 | N | PHE | B | 35 | 4021 | 3700 | 2121 | -99 | 673 | 301 | N |
| ATOM | 3789 | CA | PHE | B | 35 | 23.767 | 42.579 | 89.811 | 1.00 | 26.10 | | C |
| ANISOU | 3789 | CA | PHE | B | 35 | 4023 | 3743 | 2148 | -64 | 739 | 184 | C |
| ATOM | 3791 | CB | PHE | B | 35 | 24.523 | 42.209 | 88.494 | 1.00 | 28.93 | | C |
| ANISOU | 3791 | CB | PHE | B | 35 | 4455 | 4160 | 2376 | -80 | 846 | 182 | C |
| ATOM | 3794 | CG | PHE | B | 35 | 25.685 | 41.258 | 88.657 | 1.00 | 28.42 | | C |
| ANISOU | 3794 | CG | PHE | B | 35 | 4365 | 4119 | 2313 | -18 | 937 | 73 | C |
| ATOM | 3795 | CD1 | PHE | B | 35 | 25.664 | 40.230 | 89.597 | 1.00 | 27.98 | | C |
| ANISOU | 3795 | CD1 | PHE | B | 35 | 4300 | 4034 | 2298 | 53 | 893 | -12 | C |
| ATOM | 3797 | CE1 | PHE | B | 35 | 26.763 | 39.332 | 89.700 | 1.00 | 29.36 | | C |
| ANISOU | 3797 | CE1 | PHE | B | 35 | 4448 | 4226 | 2481 | 141 | 985 | -91 | C |
| ATOM | 3799 | CZ | PHE | B | 35 | 27.842 | 39.463 | 88.855 | 1.00 | 29.50 | | C |
| ANISOU | 3799 | CZ | PHE | B | 35 | 4440 | 4303 | 2466 | 153 | 1125 | -99 | C |
| ATOM | 3801 | CE2 | PHE | B | 35 | 27.833 | 40.476 | 87.882 | 1.00 | 31.96 | | C |
| ANISOU | 3801 | CE2 | PHE | B | 35 | 4768 | 4652 | 2722 | 61 | 1176 | -19 | C |
| ATOM | 3803 | CD2 | PHE | B | 35 | 26.767 | 41.349 | 87.796 | 1.00 | 30.61 | | C |
| ANISOU | 3803 | CD2 | PHE | B | 35 | 4635 | 4452 | 2544 | -20 | 1078 | 71 | C |
| ATOM | 3805 | C | PHE | B | 35 | 24.677 | 43.248 | 90.851 | 1.00 | 24.47 | | C |
| ANISOU | 3805 | C | PHE | B | 35 | 3684 | 3513 | 2099 | -52 | 778 | 143 | C |
| ATOM | 3806 | O | PHE | B | 35 | 24.954 | 42.650 | 91.882 | 1.00 | 24.51 | | O |
| ANISOU | 3806 | O | PHE | B | 35 | 3634 | 3525 | 2154 | -3 | 749 | 62 | O |
| ATOM | 3808 | N | ALA | B | 36 | 25.089 | 44.493 | 90.605 | 1.00 | 24.46 | | N |
| ANISOU | 3808 | N | ALA | B | 36 | 3638 | 3483 | 2173 | -106 | 839 | 202 | N |
| ATOM | 3809 | CA | ALA | B | 36 | 25.924 | 45.261 | 91.534 | 1.00 | 25.05 | | C |
| ANISOU | 3809 | CA | ALA | B | 36 | 3589 | 3533 | 2396 | -134 | 872 | 150 | C |
| ATOM | 3811 | CB | ALA | B | 36 | 26.291 | 46.642 | 90.923 | 1.00 | 23.46 | | C |
| ANISOU | 3811 | CB | ALA | B | 36 | 3378 | 3269 | 2265 | -222 | 961 | 236 | C |
| ATOM | 3815 | C | ALA | B | 36 | 25.228 | 45.461 | 92.905 | 1.00 | 22.43 | | C |
| ANISOU | 3815 | C | ALA | B | 36 | 3219 | 3155 | 2148 | -111 | 775 | 97 | C |
| ATOM | 3816 | O | ALA | B | 36 | 25.873 | 45.425 | 93.950 | 1.00 | 24.37 | | O |
| ANISOU | 3816 | O | ALA | B | 36 | 3368 | 3430 | 2460 | -109 | 763 | 4 | O |
| ATOM | 3818 | N | ALA | B | 37 | 23.934 | 45.720 | 92.868 | 1.00 | 21.52 | | N |
| ANISOU | 3818 | N | ALA | B | 37 | 3169 | 2986 | 2022 | -96 | 712 | 162 | N |
| ATOM | 3819 | CA | ALA | B | 37 | 23.120 | 45.929 | 94.078 | 1.00 | 22.35 | | C |
| ANISOU | 3819 | CA | ALA | B | 37 | 3246 | 3053 | 2194 | -65 | 640 | 122 | C |
| ATOM | 3821 | CB | ALA | B | 37 | 21.707 | 46.485 | 93.715 | 1.00 | 21.43 | | C |
| ANISOU | 3821 | CB | ALA | B | 37 | 3182 | 2878 | 2081 | -44 | 598 | 232 | C |
| ATOM | 3825 | C | ALA | B | 37 | 23.007 | 44.658 | 94.920 | 1.00 | 20.09 | | C |
| ANISOU | 3825 | C | ALA | B | 37 | 2945 | 2835 | 1851 | -11 | 575 | 44 | C |
| ATOM | 3826 | O | ALA | B | 37 | 23.055 | 44.726 | 96.146 | 1.00 | 21.87 | | O |
| ANISOU | 3826 | O | ALA | B | 37 | 3113 | 3070 | 2125 | 5 | 545 | -29 | O |
| ATOM | 3828 | N | ILE | B | 38 | 22.814 | 43.511 | 94.268 | 1.00 | 21.22 | | N |
| ANISOU | 3828 | N | ILE | B | 38 | 3155 | 3021 | 1885 | 12 | 558 | 62 | N |
| ATOM | 3829 | CA | ILE | B | 38 | 22.763 | 42.239 | 94.967 | 1.00 | 21.48 | | C |
| ANISOU | 3829 | CA | ILE | B | 38 | 3198 | 3090 | 1875 | 64 | 516 | 6 | C |
| ATOM | 3831 | CB | ILE | B | 38 | 22.430 | 41.050 | 94.030 | 1.00 | 22.50 | | C |
| ANISOU | 3831 | CB | ILE | B | 38 | 3435 | 3225 | 1888 | 67 | 511 | 21 | C |
| ATOM | 3833 | CG1 | ILE | B | 38 | 21.030 | 41.193 | 93.461 | 1.00 | 22.36 | | C |
| ANISOU | 3833 | CG1 | ILE | B | 38 | 3476 | 3199 | 1820 | 20 | 447 | 93 | C |
| ATOM | 3836 | CD1 | ILE | B | 38 | 20.780 | 40.294 | 92.238 | 1.00 | 21.55 | | C |
| ANISOU | 3836 | CD1 | ILE | B | 38 | 3490 | 3117 | 1583 | -20 | 445 | 97 | C |
| ATOM | 3840 | CG2 | ILE | B | 38 | 22.496 | 39.705 | 94.837 | 1.00 | 22.18 | | C |
| ANISOU | 3840 | CG2 | ILE | B | 38 | 3417 | 3183 | 1826 | 125 | 488 | -32 | C |
| ATOM | 3844 | C | ILE | B | 38 | 24.104 | 41.971 | 95.631 | 1.00 | 21.30 | | C |
| ANISOU | 3844 | C | ILE | B | 38 | 3090 | 3115 | 1887 | 101 | 551 | -68 | C |
| ATOM | 3845 | O | ILE | B | 38 | 24.156 | 41.611 | 96.815 | 1.00 | 22.38 | | O |
| ANISOU | 3845 | O | ILE | B | 38 | 3180 | 3283 | 2040 | 142 | 506 | -110 | O |
| ATOM | 3847 | N | CYS | B | 39 | 25.192 | 42.180 | 94.895 | 1.00 | 21.34 | | N |
| ANISOU | 3847 | N | CYS | B | 39 | 3063 | 3148 | 1899 | 86 | 631 | -73 | N |
| ATOM | 3848 | CA | CYS | B | 39 | 26.553 | 42.042 | 95.486 | 1.00 | 22.77 | | C |
| ANISOU | 3848 | CA | CYS | B | 39 | 3120 | 3406 | 2125 | 118 | 663 | -134 | C |
| ATOM | 3850 | CB | CYS | B | 39 | 27.656 | 42.325 | 94.463 | 1.00 | 22.18 | | C |
| ANISOU | 3850 | CB | CYS | B | 39 | 3001 | 3368 | 2057 | 90 | 773 | -125 | C |
| ATOM | 3853 | SG | CYS | B | 39 | 27.814 | 41.093 | 93.202 | 1.00 | 24.03 | | S |
| ANISOU | 3853 | SG | CYS | B | 39 | 3349 | 3606 | 2176 | 158 | 851 | -110 | S |
| ATOM | 3855 | C | CYS | B | 39 | 26.752 | 42.937 | 96.712 | 1.00 | 21.39 | | C |
| ANISOU | 3855 | C | CYS | B | 39 | 2837 | 3256 | 2034 | 77 | 617 | -187 | C |
| ATOM | 3856 | O | CYS | B | 39 | 27.299 | 42.498 | 97.740 | 1.00 | 21.55 | | O |
| ANISOU | 3856 | O | CYS | B | 39 | 2771 | 3360 | 2056 | 126 | 573 | -236 | O |
| ATOM | 3858 | N | THR | B | 40 | 26.288 | 44.174 | 96.606 | 1.00 | 22.76 | | N |
| ANISOU | 3858 | N | THR | B | 40 | 3024 | 3355 | 2268 | -7 | 627 | -175 | N |

FIG. 18 (continued)

| | | | | | | | | | | | | |
|---|---|---|---|---|---|---|---|---|---|---|---|---|
| ATOM | 3859 | CA | THR | B | 40 | 26.420 | 45.115 | 97.673 | 1.00 | 23.17 | | C |
| ANISOU | 3859 | CA | THR | B | 40 | 3002 | 3403 | 2398 | -63 | 600 | -248 | C |
| ATOM | 3861 | CB | THR | B | 40 | 25.994 | 46.537 | 97.252 | 1.00 | 24.77 | | C |
| ANISOU | 3861 | CB | THR | B | 40 | 3246 | 3476 | 2689 | -151 | 651 | -221 | C |
| ATOM | 3863 | OG1 | THR | B | 40 | 26.824 | 46.992 | 96.160 | 1.00 | 26.01 | | O |
| ANISOU | 3863 | OG1 | THR | B | 40 | 3386 | 3619 | 2879 | -217 | 743 | -174 | O |
| ATOM | 3865 | CG2 | THR | B | 40 | 26.191 | 47.493 | 98.412 | 1.00 | 25.21 | | C |
| ANISOU | 3865 | CG2 | THR | B | 40 | 3243 | 3509 | 2828 | -220 | 636 | -333 | C |
| ATOM | 3869 | C | THR | B | 40 | 25.640 | 44.676 | 98.893 | 1.00 | 23.02 | | C |
| ANISOU | 3869 | C | THR | B | 40 | 2998 | 3408 | 2341 | -7 | 515 | -286 | C |
| ATOM | 3870 | O | THR | B | 40 | 26.167 | 44.708 | 100.001 | 1.00 | 22.97 | | O |
| ANISOU | 3870 | O | THR | B | 40 | 2908 | 3487 | 2334 | -11 | 473 | -368 | O |
| ATOM | 3872 | N | HIS | B | 41 | 24.390 | 44.277 | 98.686 | 1.00 | 23.44 | | N |
| ANISOU | 3872 | N | HIS | B | 41 | 3149 | 3406 | 2352 | 37 | 490 | -223 | N |
| ATOM | 3873 | CA | HIS | B | 41 | 23.527 | 43.861 | 99.758 | 1.00 | 20.90 | | C |
| ANISOU | 3873 | CA | HIS | B | 41 | 2844 | 3106 | 1992 | 83 | 429 | -241 | C |
| ATOM | 3875 | CB | HIS | B | 41 | 22.120 | 43.518 | 99.235 | 1.00 | 21.24 | | C |
| ANISOU | 3875 | CB | HIS | B | 41 | 2976 | 3091 | 2005 | 105 | 413 | -155 | C |
| ATOM | 3878 | CG | HIS | B | 41 | 21.201 | 43.015 | 100.313 | 1.00 | 20.44 | | C |
| ANISOU | 3878 | CG | HIS | B | 41 | 2881 | 3020 | 1865 | 144 | 367 | -160 | C |
| ATOM | 3879 | ND1 | HIS | B | 41 | 20.906 | 41.679 | 100.471 | 1.00 | 19.10 | | N |
| ANISOU | 3879 | ND1 | HIS | B | 41 | 2752 | 2884 | 1620 | 182 | 335 | -124 | N |
| ATOM | 3881 | CE1 | HIS | B | 41 | 20.083 | 41.531 | 101.498 | 1.00 | 20.87 | | C |
| ANISOU | 3881 | CE1 | HIS | B | 41 | 2971 | 3137 | 1823 | 200 | 312 | -124 | C |
| ATOM | 3883 | NE2 | HIS | B | 41 | 19.861 | 42.718 | 102.034 | 1.00 | 22.44 | | N |
| ANISOU | 3883 | NE2 | HIS | B | 41 | 3126 | 3326 | 2073 | 186 | 331 | -176 | N |
| ATOM | 3885 | CD2 | HIS | B | 41 | 20.543 | 43.668 | 101.299 | 1.00 | 19.96 | | C |
| ANISOU | 3885 | CD2 | HIS | B | 41 | 2796 | 2958 | 1828 | 147 | 364 | -200 | C |
| ATOM | 3887 | C | HIS | B | 41 | 24.142 | 42.675 | 100.481 | 1.00 | 21.61 | | C |
| ANISOU | 3887 | C | HIS | B | 41 | 2897 | 3301 | 2012 | 150 | 388 | -261 | C |
| ATOM | 3888 | O | HIS | B | 41 | 24.244 | 42.672 | 101.709 | 1.00 | 20.41 | | O |
| ANISOU | 3888 | O | HIS | B | 41 | 2698 | 3223 | 1836 | 165 | 344 | -314 | O |
| ATOM | 3890 | N | LEU | B | 42 | 24.576 | 41.673 | 99.715 | 1.00 | 22.28 | | N |
| ANISOU | 3890 | N | LEU | B | 42 | 3013 | 3393 | 2061 | 197 | 408 | -216 | N |
| ATOM | 3891 | CA | LEU | B | 42 | 25.241 | 40.494 | 100.292 | 1.00 | 23.85 | | C |
| ANISOU | 3891 | CA | LEU | B | 42 | 3184 | 3669 | 2210 | 290 | 385 | -212 | C |
| ATOM | 3893 | CB | LEU | B | 42 | 25.685 | 39.527 | 99.172 | 1.00 | 24.81 | | C |
| ANISOU | 3893 | CB | LEU | B | 42 | 3363 | 3753 | 2310 | 343 | 443 | -174 | C |
| ATOM | 3896 | CG | LEU | B | 42 | 24.604 | 38.665 | 98.542 | 1.00 | 24.63 | | C |
| ANISOU | 3896 | CG | LEU | B | 42 | 3490 | 3631 | 2236 | 345 | 446 | -128 | C |
| ATOM | 3898 | CD1 | LEU | B | 42 | 25.106 | 38.215 | 97.167 | 1.00 | 24.92 | | C |
| ANISOU | 3898 | CD1 | LEU | B | 42 | 3590 | 3629 | 2249 | 354 | 524 | -128 | C |
| ATOM | 3902 | CD2 | LEU | B | 42 | 24.254 | 37.472 | 99.495 | 1.00 | 24.51 | | C |
| ANISOU | 3902 | CD2 | LEU | B | 42 | 3521 | 3608 | 2182 | 421 | 408 | -97 | C |
| ATOM | 3906 | C | LEU | B | 42 | 26.459 | 40.870 | 101.148 | 1.00 | 24.94 | | C |
| ANISOU | 3906 | C | LEU | B | 42 | 3174 | 3935 | 2366 | 296 | 360 | -272 | C |
| ATOM | 3907 | O | LEU | B | 42 | 26.626 | 40.414 | 102.313 | 1.00 | 25.35 | | O |
| ANISOU | 3907 | O | LEU | B | 42 | 3181 | 4084 | 2368 | 353 | 297 | -278 | O |
| ATOM | 3909 | N | GLU | B | 43 | 27.303 | 41.735 | 100.590 | 1.00 | 26.12 | | N |
| ANISOU | 3909 | N | GLU | B | 43 | 3241 | 4103 | 2579 | 225 | 404 | -312 | N |
| ATOM | 3910 | CA | GLU | B | 43 | 28.505 | 42.137 | 101.284 | 1.00 | 29.48 | | C |
| ANISOU | 3910 | CA | GLU | B | 43 | 3505 | 4669 | 3029 | 200 | 377 | -376 | C |
| ATOM | 3912 | CB | GLU | B | 43 | 29.411 | 42.989 | 100.409 | 1.00 | 32.32 | | C |
| ANISOU | 3912 | CB | GLU | B | 43 | 3780 | 5030 | 3471 | 104 | 452 | -402 | C |
| ATOM | 3915 | CG | GLU | B | 43 | 30.680 | 43.340 | 101.172 | 1.00 | 36.01 | | C |
| ANISOU | 3915 | CG | GLU | B | 43 | 4049 | 5670 | 3962 | 59 | 411 | -475 | C |
| ATOM | 3918 | CD | GLU | B | 43 | 31.837 | 43.781 | 100.311 | 1.00 | 38.91 | | C |
| ANISOU | 3918 | CD | GLU | B | 43 | 4291 | 6085 | 4408 | -10 | 496 | -479 | C |
| ATOM | 3919 | OE1 | GLU | B | 43 | 32.981 | 43.738 | 100.798 | 1.00 | 43.95 | | O |
| ANISOU | 3919 | OE1 | GLU | B | 43 | 4736 | 6901 | 5060 | -18 | 462 | -515 | O |
| ATOM | 3920 | OE2 | GLU | B | 43 | 31.612 | 44.203 | 99.167 | 1.00 | 41.61 | | O |
| ANISOU | 3920 | OE2 | GLU | B | 43 | 4714 | 6304 | 4790 | -63 | 594 | -439 | O |
| ATOM | 3921 | C | GLU | B | 43 | 28.230 | 42.883 | 102.586 | 1.00 | 27.69 | | C |
| ANISOU | 3921 | C | GLU | B | 43 | 3240 | 4496 | 2784 | 136 | 303 | -461 | C |
| ATOM | 3922 | O | GLU | B | 43 | 28.881 | 42.607 | 103.606 | 1.00 | 26.60 | | O |
| ANISOU | 3922 | O | GLU | B | 43 | 2997 | 4516 | 2594 | 166 | 230 | -495 | O |
| ATOM | 3924 | N | VAL | B | 44 | 27.271 | 43.801 | 102.554 | 1.00 | 27.27 | | N |
| ANISOU | 3924 | N | VAL | B | 44 | 3272 | 4321 | 2767 | 58 | 325 | -493 | N |
| ATOM | 3925 | CA | VAL | B | 44 | 26.817 | 44.491 | 103.772 | 1.00 | 26.34 | | C |
| ANISOU | 3925 | CA | VAL | B | 44 | 3155 | 4228 | 2625 | 8 | 280 | -588 | C |
| ATOM | 3927 | CB | VAL | B | 44 | 25.792 | 45.611 | 103.447 | 1.00 | 26.31 | | C |
| ANISOU | 3927 | CB | VAL | B | 44 | 3248 | 4050 | 2699 | -58 | 340 | -611 | C |
| ATOM | 3929 | CG1 | VAL | B | 44 | 25.160 | 46.169 | 104.700 | 1.00 | 27.05 | | C |
| ANISOU | 3929 | CG1 | VAL | B | 44 | 3365 | 4155 | 2757 | -79 | 317 | -713 | C |
| ATOM | 3933 | CG2 | VAL | B | 44 | 26.501 | 46.737 | 102.639 | 1.00 | 25.52 | | C |
| ANISOU | 3933 | CG2 | VAL | B | 44 | 3113 | 3864 | 2718 | -177 | 410 | -646 | C |
| ATOM | 3937 | C | VAL | B | 44 | 26.316 | 43.494 | 104.850 | 1.00 | 26.50 | | C |
| ANISOU | 3937 | C | VAL | B | 44 | 3200 | 4345 | 2524 | 109 | 210 | -558 | C |
| ATOM | 3938 | O | VAL | B | 44 | 26.734 | 43.601 | 105.997 | 1.00 | 27.73 | | O |

FIG. 18 (continued)

| | | | | | | | | | | | | |
|---|---|---|---|---|---|---|---|---|---|---|---|---|
| ANISOU | 3938 | O | VAL | B | 44 | 3286 | 4641 | 2608 | 96 | 145 | -631 | O |
| ATOM | 3940 | N | CYS | B | 45 | 25.469 | 42.534 | 104.482 | 1.00 | 24.68 | | N |
| ANISOU | 3940 | N | CYS | B | 45 | 3067 | 4048 | 2261 | 196 | 222 | -450 | N |
| ATOM | 3941 | CA | CYS | B | 45 | 24.944 | 41.532 | 105.429 | 1.00 | 25.23 | | C |
| ANISOU | 3941 | CA | CYS | B | 45 | 3176 | 4186 | 2225 | 283 | 175 | -396 | C |
| ATOM | 3943 | CB | CYS | B | 45 | 23.918 | 40.606 | 104.745 | 1.00 | 23.40 | | C |
| ANISOU | 3943 | CB | CYS | B | 45 | 3063 | 3836 | 1992 | 333 | 208 | -285 | C |
| ATOM | 3946 | SG | CYS | B | 45 | 22.450 | 41.442 | 104.280 | 1.00 | 23.77 | | S |
| ANISOU | 3946 | SG | CYS | B | 45 | 3183 | 3753 | 2094 | 265 | 252 | -289 | S |
| ATOM | 3948 | C | CYS | B | 45 | 26.053 | 40.720 | 106.105 | 1.00 | 26.80 | | C |
| ANISOU | 3948 | C | CYS | B | 45 | 3283 | 4549 | 2351 | 364 | 112 | -370 | C |
| ATOM | 3949 | O | CYS | B | 45 | 26.032 | 40.491 | 107.330 | 1.00 | 27.96 | | O |
| ANISOU | 3949 | O | CYS | B | 45 | 3407 | 4823 | 2392 | 395 | 50 | -375 | O |
| ATOM | 3951 | N | PHE | B | 46 | 27.051 | 40.338 | 105.321 | 1.00 | 28.92 | | N |
| ANISOU | 3951 | N | PHE | B | 46 | 3490 | 4830 | 2669 | 403 | 130 | -338 | N |
| ATOM | 3952 | CA | PHE | B | 46 | 28.196 | 39.589 | 105.816 | 1.00 | 31.01 | | C |
| ANISOU | 3952 | CA | PHE | B | 46 | 3640 | 5255 | 2888 | 505 | 77 | -296 | C |
| ATOM | 3954 | CB | PHE | B | 46 | 29.016 | 38.983 | 104.664 | 1.00 | 33.37 | | C |
| ANISOU | 3954 | CB | PHE | B | 46 | 3906 | 5513 | 3260 | 579 | 142 | -241 | C |
| ATOM | 3957 | CG | PHE | B | 46 | 28.272 | 37.984 | 103.857 | 1.00 | 32.96 | | C |
| ANISOU | 3957 | CG | PHE | B | 46 | 4019 | 5288 | 3217 | 651 | 209 | -157 | C |
| ATOM | 3958 | CD1 | PHE | B | 46 | 27.389 | 37.089 | 104.455 | 1.00 | 35.96 | | C |
| ANISOU | 3958 | CD1 | PHE | B | 46 | 4518 | 5614 | 3533 | 715 | 188 | -81 | C |
| ATOM | 3960 | CE1 | PHE | B | 46 | 26.685 | 36.153 | 103.694 | 1.00 | 35.91 | | C |
| ANISOU | 3960 | CE1 | PHE | B | 46 | 4667 | 5437 | 3539 | 750 | 250 | -20 | C |
| ATOM | 3962 | CZ | PHE | B | 46 | 26.871 | 36.104 | 102.325 | 1.00 | 33.96 | | C |
| ANISOU | 3962 | CZ | PHE | B | 46 | 4465 | 5088 | 3349 | 732 | 329 | -43 | C |
| ATOM | 3964 | CE2 | PHE | B | 46 | 27.758 | 36.987 | 101.724 | 1.00 | 33.75 | | C |
| ANISOU | 3964 | CE2 | PHE | B | 46 | 4324 | 5128 | 3374 | 686 | 357 | -105 | C |
| ATOM | 3966 | CD2 | PHE | B | 46 | 28.441 | 37.924 | 102.489 | 1.00 | 32.82 | | C |
| ANISOU | 3966 | CD2 | PHE | B | 46 | 4044 | 5164 | 3264 | 640 | 300 | -158 | C |
| ATOM | 3968 | C | PHE | B | 46 | 29.095 | 40.417 | 106.695 | 1.00 | 32.25 | | C |
| ANISOU | 3968 | C | PHE | B | 46 | 3635 | 5606 | 3013 | 433 | -1 | -396 | C |
| ATOM | 3969 | O | PHE | B | 46 | 29.625 | 39.892 | 107.688 | 1.00 | 34.68 | | O |
| ANISOU | 3969 | O | PHE | B | 46 | 3859 | 6096 | 3223 | 510 | -88 | -361 | O |
| ATOM | 3971 | N | MET | B | 47 | 29.297 | 41.687 | 106.346 | 1.00 | 31.64 | | N |
| ANISOU | 3971 | N | MET | B | 47 | 3512 | 5498 | 3012 | 280 | 27 | -515 | N |
| ATOM | 3972 | CA | MET | B | 47 | 30.099 | 42.581 | 107.194 | 1.00 | 34.75 | | C |
| ANISOU | 3972 | CA | MET | B | 47 | 3762 | 6063 | 3379 | 166 | -47 | -644 | C |
| ATOM | 3974 | CB | MET | B | 47 | 30.363 | 43.935 | 106.538 | 1.00 | 36.29 | | C |
| ANISOU | 3974 | CB | MET | B | 47 | 3928 | 6162 | 3699 | -13 | 17 | -760 | C |
| ATOM | 3977 | CG | MET | B | 47 | 31.330 | 43.964 | 105.357 | 1.00 | 38.47 | | C |
| ANISOU | 3977 | CG | MET | B | 47 | 4104 | 6426 | 4088 | -32 | 84 | -721 | C |
| ATOM | 3980 | SD | MET | B | 47 | 31.556 | 45.695 | 104.812 | 1.00 | 39.73 | | S |
| ANISOU | 3980 | SD | MET | B | 47 | 4248 | 6459 | 4387 | -272 | 163 | -853 | S |
| ATOM | 3981 | CE | MET | B | 47 | 32.534 | 46.256 | 106.199 | 1.00 | 39.22 | | C |
| ANISOU | 3981 | CE | MET | B | 47 | 3998 | 6644 | 4260 | -406 | 36 | -1014 | C |
| ATOM | 3985 | C | MET | B | 47 | 29.343 | 42.864 | 108.500 | 1.00 | 34.90 | | C |
| ANISOU | 3985 | C | MET | B | 47 | 3845 | 6141 | 3273 | 135 | -108 | -715 | C |
| ATOM | 3986 | O | MET | B | 47 | 29.933 | 42.859 | 109.568 | 1.00 | 34.54 | | O |
| ANISOU | 3986 | O | MET | B | 47 | 3698 | 6311 | 3114 | 124 | -210 | -764 | O |
| ATOM | 3988 | N | TYR | B | 48 | 28.041 | 43.132 | 108.392 | 1.00 | 31.59 | | N |
| ANISOU | 3988 | N | TYR | B | 48 | 3587 | 5547 | 2869 | 123 | -43 | -719 | N |
| ATOM | 3989 | CA | TYR | B | 48 | 27.202 | 43.382 | 109.581 | 1.00 | 32.21 | | C |
| ANISOU | 3989 | CA | TYR | B | 48 | 3738 | 5671 | 2830 | 107 | -69 | -785 | C |
| ATOM | 3991 | CB | TYR | B | 48 | 25.766 | 43.625 | 109.109 | 1.00 | 28.63 | | C |
| ANISOU | 3991 | CB | TYR | B | 48 | 3434 | 5003 | 2440 | 113 | 28 | -759 | C |
| ATOM | 3994 | CG | TYR | B | 48 | 24.832 | 44.342 | 110.046 | 1.00 | 30.09 | | C |
| ANISOU | 3994 | CG | TYR | B | 48 | 3692 | 5178 | 2564 | 70 | 55 | -865 | C |
| ATOM | 3995 | CD1 | TYR | B | 48 | 24.364 | 45.635 | 109.750 | 1.00 | 30.52 | | C |
| ANISOU | 3995 | CD1 | TYR | B | 48 | 3795 | 5073 | 2729 | -22 | 135 | -983 | C |
| ATOM | 3997 | CE1 | TYR | B | 48 | 23.461 | 46.285 | 110.601 | 1.00 | 30.00 | | C |
| ANISOU | 3997 | CE1 | TYR | B | 48 | 3802 | 4983 | 2615 | -39 | 183 | -1087 | C |
| ATOM | 3999 | CZ | TYR | B | 48 | 22.993 | 45.618 | 111.733 | 1.00 | 30.27 | | C |
| ANISOU | 3999 | CZ | TYR | B | 48 | 3858 | 5169 | 2473 | 26 | 153 | -1067 | C |
| ATOM | 4000 | OH | TYR | B | 48 | 22.076 | 46.211 | 112.569 | 1.00 | 29.68 | | O |
| ANISOU | 4000 | OH | TYR | B | 48 | 3853 | 5083 | 2339 | 21 | 221 | -1170 | O |
| ATOM | 4002 | CE2 | TYR | B | 48 | 23.403 | 44.329 | 112.004 | 1.00 | 29.42 | | C |
| ANISOU | 4002 | CE2 | TYR | B | 48 | 3711 | 5216 | 2252 | 108 | 71 | -931 | C |
| ATOM | 4004 | CD2 | TYR | B | 48 | 24.316 | 43.702 | 111.171 | 1.00 | 29.28 | | C |
| ANISOU | 4004 | CD2 | TYR | B | 48 | 3624 | 5204 | 2298 | 136 | 22 | -832 | C |
| ATOM | 4006 | C | TYR | B | 48 | 27.235 | 42.205 | 110.581 | 1.00 | 32.87 | | C |
| ANISOU | 4006 | C | TYR | B | 48 | 3812 | 5933 | 2745 | 234 | -150 | -679 | C |
| ATOM | 4007 | O | TYR | B | 48 | 27.314 | 42.420 | 111.803 | 1.00 | 29.07 | | O |
| ANISOU | 4007 | O | TYR | B | 48 | 3304 | 5625 | 2116 | 207 | -219 | -753 | O |
| ATOM | 4009 | N | SER | B | 49 | 27.151 | 40.982 | 110.063 | 1.00 | 31.27 | | N |
| ANISOU | 4009 | N | SER | B | 49 | 3645 | 5679 | 2558 | 369 | -134 | -508 | N |
| ATOM | 4010 | CA | SER | B | 49 | 27.164 | 39.775 | 110.895 | 1.00 | 36.06 | | C |
| ANISOU | 4010 | CA | SER | B | 49 | 4263 | 6409 | 3029 | 506 | -191 | -370 | C |

FIG. 18 (continued)

| | | | | | | | | | | | | |
|---|---|---|---|---|---|---|---|---|---|---|---|---|
| ATOM | 4012 | CB | SER | B | 49 | 26.385 | 38.666 | 110.210 | 1.00 | 34.87 | | C |
| ANISOU | 4012 | CB | SER | B | 49 | 4244 | 6076 | 2931 | 605 | -118 | -216 | C |
| ATOM | 4015 | OG | SER | B | 49 | 27.043 | 38.297 | 109.023 | 1.00 | 36.13 | | O |
| ANISOU | 4015 | OG | SER | B | 49 | 4373 | 6142 | 3212 | 649 | -80 | -174 | O |
| ATOM | 4017 | C | SER | B | 49 | 28.558 | 39.231 | 111.254 | 1.00 | 37.15 | | C |
| ANISOU | 4017 | C | SER | B | 49 | 4243 | 6760 | 3113 | 593 | -290 | -312 | C |
| ATOM | 4018 | O | SER | B | 49 | 28.651 | 38.196 | 111.906 | 1.00 | 39.73 | | O |
| ANISOU | 4018 | O | SER | B | 49 | 4578 | 7184 | 3334 | 730 | -337 | -169 | O |
| ATOM | 4020 | N | ASP | B | 50 | 29.617 | 39.933 | 110.845 | 1.00 | 39.83 | | N |
| ANISOU | 4020 | N | ASP | B | 50 | 4430 | 7176 | 3527 | 516 | -316 | -409 | N |
| ATOM | 4021 | CA | ASP | B | 50 | 31.005 | 39.514 | 111.078 | 1.00 | 43.28 | | C |
| ANISOU | 4021 | CA | ASP | B | 50 | 4670 | 7838 | 3935 | 594 | -409 | -357 | C |
| ATOM | 4023 | CB | ASP | B | 50 | 31.381 | 39.660 | 112.568 | 1.00 | 46.67 | | C |
| ANISOU | 4023 | CB | ASP | B | 50 | 5005 | 8562 | 4165 | 577 | -554 | -393 | C |
| ATOM | 4026 | CG | ASP | B | 50 | 32.881 | 39.532 | 112.818 | 1.00 | 49.34 | | C |
| ANISOU | 4026 | CG | ASP | B | 50 | 5090 | 9181 | 4478 | 616 | -672 | -371 | C |
| ATOM | 4027 | OD1 | ASP | B | 50 | 33.694 | 39.771 | 111.892 | 1.00 | 47.13 | | O |
| ANISOU | 4027 | OD1 | ASP | B | 50 | 4680 | 8878 | 4350 | 588 | -634 | -396 | O |
| ATOM | 4028 | OD2 | ASP | B | 50 | 33.240 | 39.181 | 113.968 | 1.00 | 51.65 | | O |
| ANISOU | 4028 | OD2 | ASP | B | 50 | 5302 | 9737 | 4587 | 677 | -805 | -317 | O |
| ATOM | 4029 | C | ASP | B | 50 | 31.249 | 38.089 | 110.581 | 1.00 | 44.85 | | C |
| ANISOU | 4029 | C | ASP | B | 50 | 4889 | 7977 | 4173 | 811 | -373 | -155 | C |
| ATOM | 4030 | O | ASP | B | 50 | 31.951 | 37.289 | 111.208 | 1.00 | 43.12 | | O |
| ANISOU | 4030 | O | ASP | B | 50 | 4572 | 7938 | 3873 | 960 | -454 | -32 | O |
| ATOM | 4032 | N | PHE | B | 51 | 30.683 | 37.799 | 109.410 | 1.00 | 44.63 | | N |
| ANISOU | 4032 | N | PHE | B | 51 | 4993 | 7691 | 4273 | 828 | -249 | -123 | N |
| ATOM | 4033 | CA | PHE | B | 51 | 30.847 | 36.508 | 108.791 | 1.00 | 45.00 | | C |
| ANISOU | 4033 | CA | PHE | B | 51 | 5094 | 7629 | 4374 | 1011 | -187 | 32 | C |
| ATOM | 4035 | CB | PHE | B | 51 | 29.888 | 36.379 | 107.603 | 1.00 | 45.25 | | C |
| ANISOU | 4035 | CB | PHE | B | 51 | 5311 | 7375 | 4506 | 967 | -61 | 22 | C |
| ATOM | 4038 | CG | PHE | B | 51 | 29.946 | 35.053 | 106.959 | 1.00 | 45.85 | | C |
| ANISOU | 4038 | CG | PHE | B | 51 | 5483 | 7308 | 4632 | 1130 | 15 | 149 | C |
| ATOM | 4039 | CD1 | PHE | B | 51 | 29.601 | 33.927 | 107.679 | 1.00 | 47.06 | | C |
| ANISOU | 4039 | CD1 | PHE | B | 51 | 5730 | 7436 | 4717 | 1264 | -1 | 291 | C |
| ATOM | 4041 | CE1 | PHE | B | 51 | 29.666 | 32.689 | 107.107 | 1.00 | 48.15 | | C |
| ANISOU | 4041 | CE1 | PHE | B | 51 | 5975 | 7407 | 4912 | 1412 | 82 | 399 | C |
| ATOM | 4043 | CZ | PHE | B | 51 | 30.075 | 32.551 | 105.788 | 1.00 | 48.07 | | C |
| ANISOU | 4043 | CZ | PHE | B | 51 | 5980 | 7271 | 5013 | 1431 | 184 | 351 | C |
| ATOM | 4045 | CE2 | PHE | B | 51 | 30.441 | 33.670 | 105.048 | 1.00 | 47.64 | | C |
| ANISOU | 4045 | CE2 | PHE | B | 51 | 5822 | 7269 | 5010 | 1301 | 200 | 219 | C |
| ATOM | 4047 | CD2 | PHE | B | 51 | 30.391 | 34.914 | 105.643 | 1.00 | 46.70 | | C |
| ANISOU | 4047 | CD2 | PHE | B | 51 | 5593 | 7301 | 4849 | 1151 | 115 | 127 | C |
| ATOM | 4049 | C | PHE | B | 51 | 32.293 | 36.312 | 108.317 | 1.00 | 46.48 | | C |
| ANISOU | 4049 | C | PHE | B | 51 | 5083 | 7942 | 4635 | 1103 | -191 | 58 | C |
| ATOM | 4050 | O | PHE | B | 51 | 32.946 | 37.249 | 107.821 | 1.00 | 46.16 | | O |
| ANISOU | 4050 | O | PHE | B | 51 | 4908 | 7965 | 4668 | 981 | -182 | -57 | O |
| ATOM | 4052 | N | HIS | B | 52 | 32.787 | 35.091 | 108.460 | 1.00 | 46.77 | | N |
| ANISOU | 4052 | N | HIS | B | 52 | 5101 | 8007 | 4664 | 1322 | -192 | 217 | N |
| ATOM | 4053 | CA | HIS | B | 52 | 34.153 | 34.786 | 108.050 | 1.00 | 48.08 | | C |
| ANISOU | 4053 | CA | HIS | B | 52 | 5061 | 8301 | 4904 | 1452 | -183 | 263 | C |
| ATOM | 4055 | CB | HIS | B | 52 | 34.937 | 34.229 | 109.221 | 1.00 | 50.74 | | C |
| ANISOU | 4055 | CB | HIS | B | 52 | 5234 | 8907 | 5138 | 1615 | -316 | 394 | C |
| ATOM | 4058 | CG | HIS | B | 52 | 35.348 | 35.279 | 110.199 | 1.00 | 52.83 | | C |
| ANISOU | 4058 | CG | HIS | B | 52 | 5314 | 9468 | 5290 | 1457 | -473 | 288 | C |
| ATOM | 4059 | ND1 | HIS | B | 52 | 36.471 | 36.059 | 110.024 | 1.00 | 55.70 | | N |
| ANISOU | 4059 | ND1 | HIS | B | 52 | 5414 | 10046 | 5704 | 1365 | -522 | 192 | N |
| ATOM | 4061 | CE1 | HIS | B | 52 | 36.584 | 36.898 | 111.037 | 1.00 | 56.42 | | C |
| ANISOU | 4061 | CE1 | HIS | B | 52 | 5403 | 10368 | 5666 | 1206 | -666 | 88 | C |
| ATOM | 4063 | NE2 | HIS | B | 52 | 35.569 | 36.695 | 111.857 | 1.00 | 56.19 | | N |
| ANISOU | 4063 | NE2 | HIS | B | 52 | 5566 | 10287 | 5498 | 1206 | -704 | 115 | N |
| ATOM | 4065 | CD2 | HIS | B | 52 | 34.782 | 35.686 | 111.358 | 1.00 | 53.30 | | C |
| ANISOU | 4065 | CD2 | HIS | B | 52 | 5421 | 9647 | 5184 | 1359 | -584 | 249 | C |
| ATOM | 4067 | C | HIS | B | 52 | 34.185 | 33.847 | 106.839 | 1.00 | 46.07 | | C |
| ANISOU | 4067 | C | HIS | B | 52 | 4920 | 7812 | 4770 | 1595 | -26 | 330 | C |
| ATOM | 4068 | O | HIS | B | 52 | 33.668 | 32.724 | 106.880 | 1.00 | 43.63 | | O |
| ANISOU | 4068 | O | HIS | B | 52 | 4785 | 7337 | 4453 | 1740 | 23 | 449 | O |
| ATOM | 4070 | N | PHE | B | 53 | 34.808 | 34.342 | 105.771 | 1.00 | 44.86 | | N |
| ANISOU | 4070 | N | PHE | B | 53 | 4673 | 7648 | 4724 | 1538 | 61 | 245 | N |
| ATOM | 4071 | CA | PHE | B | 53 | 34.852 | 33.648 | 104.485 | 1.00 | 43.72 | | C |
| ANISOU | 4071 | CA | PHE | B | 53 | 4641 | 7293 | 4679 | 1637 | 227 | 262 | C |
| ATOM | 4073 | CB | PHE | B | 53 | 35.270 | 34.663 | 103.414 | 1.00 | 44.31 | | C |
| ANISOU | 4073 | CB | PHE | B | 53 | 4626 | 7379 | 4830 | 1477 | 307 | 136 | C |
| ATOM | 4076 | CG | PHE | B | 53 | 34.264 | 35.775 | 103.204 | 1.00 | 42.26 | | C |
| ANISOU | 4076 | CG | PHE | B | 53 | 4487 | 7018 | 4550 | 1226 | 294 | 20 | C |
| ATOM | 4082 | C | PHE | B | 53 | 35.772 | 32.390 | 104.458 | 1.00 | 47.45 | | C |
| ANISOU | 4082 | C | PHE | B | 53 | 5040 | 7791 | 5198 | 1930 | 281 | 403 | C |
| ATOM | 4083 | O | PHE | B | 53 | 35.770 | 31.630 | 103.471 | 1.00 | 46.83 | | O |
| ANISOU | 4083 | O | PHE | B | 53 | 5089 | 7511 | 5191 | 2041 | 433 | 415 | O |
| ATOM | 4085 | N | ILE | B | 54 | 36.560 | 32.171 | 105.521 | 1.00 | 48.19 | | N |

FIG. 18 (continued)

| | | | | | | | | | | | | |
|---|---|---|---|---|---|---|---|---|---|---|---|---|
| ANISOU | 4085 | N | ILE | B | 54 | 4929 | 8132 | 5247 | 2064 | 160 | 507 | N |
| ATOM | 4086 | CA | ILE | B | 54 | 37.402 | 30.960 | 105.654 | 1.00 | 49.38 | | C |
| ANISOU | 4086 | CA | ILE | B | 54 | 5001 | 8317 | 5445 | 2379 | 198 | 674 | C |
| ATOM | 4088 | CB | ILE | B | 54 | 38.908 | 31.260 | 105.434 | 1.00 | 51.56 | | C |
| ANISOU | 4088 | CB | ILE | B | 54 | 4929 | 8868 | 5795 | 2467 | 198 | 678 | C |
| ATOM | 4090 | CG1 | ILE | B | 54 | 39.164 | 31.784 | 104.017 | 1.00 | 50.05 | | C |
| ANISOU | 4090 | CG1 | ILE | B | 54 | 4727 | 8581 | 5709 | 2355 | 364 | 538 | C |
| ATOM | 4093 | CD1 | ILE | B | 54 | 40.550 | 32.357 | 103.863 | 1.00 | 52.59 | | C |
| ANISOU | 4093 | CD1 | ILE | B | 54 | 4682 | 9204 | 6097 | 2360 | 356 | 519 | C |
| ATOM | 4097 | CG2 | ILE | B | 54 | 39.794 | 30.018 | 105.738 | 1.00 | 51.38 | | C |
| ANISOU | 4097 | CG2 | ILE | B | 54 | 4791 | 8912 | 5820 | 2832 | 222 | 878 | C |
| ATOM | 4101 | C | ILE | B | 54 | 37.202 | 30.389 | 107.057 | 1.00 | 50.51 | | C |
| ANISOU | 4101 | C | ILE | B | 54 | 5154 | 8566 | 5473 | 2501 | 54 | 834 | C |
| ATOM | 4102 | O | ILE | B | 54 | 37.094 | 31.135 | 108.030 | 1.00 | 52.87 | | O |
| ANISOU | 4102 | O | ILE | B | 54 | 5353 | 9083 | 5652 | 2362 | -107 | 804 | O |
| ATOM | 4104 | N | ASN | B | 55 | 37.156 | 29.070 | 107.156 | 1.00 | 50.54 | | N |
| ANISOU | 4104 | N | ASN | B | 55 | 5289 | 8408 | 5507 | 2757 | 122 | 1004 | N |
| ATOM | 4105 | CA | ASN | B | 55 | 36.907 | 28.414 | 108.422 | 1.00 | 50.76 | | C |
| ANISOU | 4105 | CA | ASN | B | 55 | 5363 | 8501 | 5424 | 2888 | 9 | 1190 | C |
| ATOM | 4107 | CB | ASN | B | 55 | 36.137 | 27.084 | 108.209 | 1.00 | 51.76 | | C |
| ANISOU | 4107 | CB | ASN | B | 55 | 5809 | 8257 | 5599 | 3040 | 144 | 1314 | C |
| ATOM | 4110 | CG | ASN | B | 55 | 36.997 | 25.952 | 107.633 | 1.00 | 55.76 | | C |
| ANISOU | 4110 | CG | ASN | B | 55 | 6303 | 8634 | 6251 | 3362 | 286 | 1437 | C |
| ATOM | 4111 | OD1 | ASN | B | 55 | 38.159 | 26.139 | 107.290 | 1.00 | 56.74 | | O |
| ANISOU | 4111 | OD1 | ASN | B | 55 | 6169 | 8944 | 6445 | 3485 | 299 | 1430 | O |
| ATOM | 4112 | ND2 | ASN | B | 55 | 36.418 | 24.749 | 107.565 | 1.00 | 57.44 | | N |
| ANISOU | 4112 | ND2 | ASN | B | 55 | 6796 | 8518 | 6512 | 3504 | 401 | 1554 | N |
| ATOM | 4115 | C | ASN | B | 55 | 38.201 | 28.250 | 109.237 | 1.00 | 51.28 | | C |
| ANISOU | 4115 | C | ASN | B | 55 | 5109 | 8922 | 5454 | 3102 | -120 | 1343 | C |
| ATOM | 4116 | O | ASN | B | 55 | 39.325 | 28.594 | 108.782 | 1.00 | 49.85 | | O |
| ANISOU | 4116 | O | ASN | B | 55 | 4654 | 8931 | 5355 | 3155 | -111 | 1302 | O |
| ATOM | 4118 | N | GLU | B | 56 | 38.058 | 27.719 | 110.440 | 1.00 | 50.28 | | N |
| ANISOU | 4118 | N | GLU | B | 56 | 5001 | 8904 | 5199 | 3225 | -240 | 1531 | N |
| ATOM | 4119 | CA | GLU | B | 56 | 39.224 | 27.562 | 111.292 | 1.00 | 52.93 | | C |
| ANISOU | 4119 | CA | GLU | B | 56 | 5028 | 9611 | 5472 | 3428 | -391 | 1696 | C |
| ATOM | 4121 | CB | GLU | B | 56 | 38.815 | 27.363 | 112.766 | 1.00 | 56.23 | | C |
| ANISOU | 4121 | CB | GLU | B | 56 | 5488 | 10206 | 5672 | 3452 | -565 | 1857 | C |
| ATOM | 4124 | CG | GLU | B | 56 | 38.173 | 28.628 | 113.412 | 1.00 | 56.41 | | C |
| ANISOU | 4124 | CG | GLU | B | 56 | 5508 | 10409 | 5515 | 3102 | -704 | 1662 | C |
| ATOM | 4127 | CD | GLU | B | 56 | 39.157 | 29.818 | 113.667 | 1.00 | 59.35 | | C |
| ANISOU | 4127 | CD | GLU | B | 56 | 5523 | 11196 | 5830 | 2943 | -867 | 1510 | C |
| ATOM | 4128 | OE1 | GLU | B | 56 | 40.400 | 29.641 | 113.685 | 1.00 | 61.99 | | O |
| ANISOU | 4128 | OE1 | GLU | B | 56 | 5555 | 11789 | 6209 | 3116 | -932 | 1603 | O |
| ATOM | 4129 | OE2 | GLU | B | 56 | 38.659 | 30.954 | 113.872 | 1.00 | 60.51 | | O |
| ANISOU | 4129 | OE2 | GLU | B | 56 | 5691 | 11411 | 5890 | 2635 | -928 | 1292 | O |
| ATOM | 4130 | C | GLU | B | 56 | 40.160 | 26.442 | 110.778 | 1.00 | 52.13 | | C |
| ANISOU | 4130 | C | GLU | B | 56 | 4844 | 9430 | 5533 | 3799 | -269 | 1875 | C |
| ATOM | 4131 | O | GLU | B | 56 | 41.328 | 26.386 | 111.142 | 1.00 | 51.84 | | O |
| ANISOU | 4131 | O | GLU | B | 56 | 4486 | 9712 | 5500 | 3984 | -363 | 1990 | O |
| ATOM | 4133 | N | GLN | B | 57 | 39.651 | 25.564 | 109.920 | 1.00 | 48.47 | | N |
| ANISOU | 4133 | N | GLN | B | 57 | 4664 | 8546 | 5207 | 3907 | -55 | 1889 | N |
| ATOM | 4134 | CA | GLN | B | 57 | 40.466 | 24.495 | 109.357 | 1.00 | 49.92 | | C |
| ANISOU | 4134 | CA | GLN | B | 57 | 4811 | 8598 | 5559 | 4262 | 98 | 2031 | C |
| ATOM | 4136 | CB | GLN | B | 57 | 39.612 | 23.251 | 109.149 | 1.00 | 51.22 | | C |
| ANISOU | 4136 | CB | GLN | B | 57 | 5370 | 8301 | 5791 | 4399 | 264 | 2138 | C |
| ATOM | 4139 | CG | GLN | B | 57 | 39.048 | 22.666 | 110.451 | 1.00 | 54.11 | | C |
| ANISOU | 4139 | CG | GLN | B | 57 | 5867 | 8673 | 6018 | 4478 | 146 | 2375 | C |
| ATOM | 4142 | CD | GLN | B | 57 | 37.719 | 23.251 | 110.886 | 1.00 | 50.52 | | C |
| ANISOU | 4142 | CD | GLN | B | 57 | 5621 | 8161 | 5414 | 4137 | 72 | 2265 | C |
| ATOM | 4143 | OE1 | GLN | B | 57 | 37.100 | 24.078 | 110.209 | 1.00 | 52.78 | | O |
| ANISOU | 4143 | OE1 | GLN | B | 57 | 5979 | 8370 | 5707 | 3839 | 107 | 2013 | O |
| ATOM | 4144 | NE2 | GLN | B | 57 | 37.280 | 22.832 | 112.051 | 1.00 | 55.51 | | N |
| ANISOU | 4144 | NE2 | GLN | B | 57 | 6340 | 8846 | 5905 | 4191 | -28 | 2468 | N |
| ATOM | 4147 | C | GLN | B | 57 | 41.155 | 24.919 | 108.052 | 1.00 | 47.25 | | C |
| ANISOU | 4147 | C | GLN | B | 57 | 4331 | 8248 | 5373 | 4232 | 246 | 1845 | C |
| ATOM | 4148 | O | GLN | B | 57 | 41.773 | 24.103 | 107.384 | 1.00 | 49.15 | | O |
| ANISOU | 4148 | O | GLN | B | 57 | 4565 | 8345 | 5766 | 4506 | 417 | 1912 | O |
| ATOM | 4150 | N | GLY | B | 58 | 41.029 | 26.198 | 107.718 | 1.00 | 47.25 | | N |
| ANISOU | 4150 | N | GLY | B | 58 | 4231 | 8392 | 5329 | 3902 | 190 | 1619 | N |
| ATOM | 4151 | CA | GLY | B | 58 | 41.736 | 26.821 | 106.619 | 1.00 | 48.48 | | C |
| ANISOU | 4151 | CA | GLY | B | 58 | 4209 | 8615 | 5597 | 3827 | 301 | 1453 | C |
| ATOM | 4154 | C | GLY | B | 58 | 41.100 | 26.640 | 105.256 | 1.00 | 47.34 | | C |
| ANISOU | 4154 | C | GLY | B | 58 | 4355 | 8087 | 5547 | 3741 | 532 | 1294 | C |
| ATOM | 4155 | O | GLY | B | 58 | 41.795 | 26.732 | 104.254 | 1.00 | 47.90 | | O |
| ANISOU | 4155 | O | GLY | B | 58 | 4313 | 8161 | 5725 | 3791 | 682 | 1212 | O |
| ATOM | 4157 | N | GLU | B | 59 | 39.790 | 26.392 | 105.224 | 1.00 | 48.54 | | N |
| ANISOU | 4157 | N | GLU | B | 59 | 4863 | 7933 | 5646 | 3605 | 558 | 1251 | N |
| ATOM | 4158 | CA | GLU | B | 59 | 39.046 | 26.171 | 103.981 | 1.00 | 50.56 | | C |
| ANISOU | 4158 | CA | GLU | B | 59 | 5418 | 7831 | 5962 | 3502 | 751 | 1100 | C |

FIG. 18 (continued)

| | | | | | | | | | | | | |
|---|---|---|---|---|---|---|---|---|---|---|---|---|
| ATOM | 4160 | CB | GLU | B | 59 | 38.381 | 24.804 | 103.980 | 1.00 | 51.10 | | C |
| ANISOU | 4160 | CB | GLU | B | 59 | 5816 | 7531 | 6068 | 3675 | 863 | 1204 | C |
| ATOM | 4163 | CG | GLU | B | 59 | 39.263 | 23.653 | 104.251 | 1.00 | 55.45 | | C |
| ANISOU | 4163 | CG | GLU | B | 59 | 6302 | 8051 | 6716 | 4070 | 939 | 1403 | C |
| ATOM | 4166 | CD | GLU | B | 59 | 38.662 | 22.354 | 103.780 | 1.00 | 56.51 | | C |
| ANISOU | 4166 | CD | GLU | B | 59 | 6805 | 7734 | 6932 | 4209 | 1127 | 1436 | C |
| ATOM | 4167 | OE1 | GLU | B | 59 | 38.838 | 21.301 | 104.441 | 1.00 | 57.39 | | O |
| ANISOU | 4167 | OE1 | GLU | B | 59 | 6985 | 7733 | 7089 | 4487 | 1146 | 1652 | O |
| ATOM | 4168 | OE2 | GLU | B | 59 | 38.024 | 22.401 | 102.716 | 1.00 | 56.70 | | O |
| ANISOU | 4168 | OE2 | GLU | B | 59 | 7055 | 7515 | 6973 | 4032 | 1260 | 1242 | O |
| ATOM | 4169 | C | GLU | B | 59 | 37.935 | 27.164 | 103.754 | 1.00 | 50.90 | | C |
| ANISOU | 4169 | C | GLU | B | 59 | 5607 | 7815 | 5919 | 3133 | 695 | 927 | C |
| ATOM | 4170 | O | GLU | B | 59 | 37.332 | 27.698 | 104.699 | 1.00 | 50.93 | | O |
| ANISOU | 4170 | O | GLU | B | 59 | 5610 | 7928 | 5812 | 2977 | 529 | 942 | O |
| ATOM | 4172 | N | SER | B | 60 | 37.615 | 27.388 | 102.488 | 1.00 | 54.45 | | N |
| ANISOU | 4172 | N | SER | B | 60 | 6195 | 8083 | 6410 | 3002 | 842 | 765 | N |
| ATOM | 4173 | CA | SER | B | 60 | 36.305 | 27.976 | 102.134 | 1.00 | 55.07 | | C |
| ANISOU | 4173 | CA | SER | B | 60 | 6501 | 8004 | 6419 | 2703 | 822 | 632 | C |
| ATOM | 4175 | CB | SER | B | 60 | 36.214 | 28.258 | 100.641 | 1.00 | 54.14 | | C |
| ANISOU | 4175 | CB | SER | B | 60 | 6483 | 7751 | 6337 | 2589 | 982 | 469 | C |
| ATOM | 4178 | OG | SER | B | 60 | 36.515 | 27.089 | 99.884 | 1.00 | 57.54 | | O |
| ANISOU | 4178 | OG | SER | B | 60 | 7059 | 7964 | 6841 | 2803 | 1171 | 479 | O |
| ATOM | 4180 | C | SER | B | 60 | 35.166 | 27.027 | 102.563 | 1.00 | 56.79 | | C |
| ANISOU | 4180 | C | SER | B | 60 | 7021 | 7952 | 6604 | 2722 | 821 | 707 | C |
| ATOM | 4181 | O | SER | B | 60 | 35.277 | 25.799 | 102.436 | 1.00 | 59.14 | | O |
| ANISOU | 4181 | O | SER | B | 60 | 7464 | 8041 | 6965 | 2938 | 933 | 794 | O |
| ATOM | 4183 | N | ILE | B | 61 | 34.082 | 27.602 | 103.087 | 1.00 | 57.68 | | N |
| ANISOU | 4183 | N | ILE | B | 61 | 7225 | 8065 | 6627 | 2497 | 706 | 675 | N |
| ATOM | 4184 | CA | ILE | B | 61 | 32.922 | 26.831 | 103.561 | 1.00 | 58.00 | | C |
| ANISOU | 4184 | CA | ILE | B | 61 | 7526 | 7883 | 6630 | 2469 | 699 | 748 | C |
| ATOM | 4186 | CB | ILE | B | 61 | 32.813 | 26.891 | 105.104 | 1.00 | 59.32 | | C |
| ANISOU | 4186 | CB | ILE | B | 61 | 7603 | 8232 | 6705 | 2505 | 538 | 896 | C |
| ATOM | 4188 | CG1 | ILE | B | 61 | 33.040 | 28.339 | 105.593 | 1.00 | 58.58 | | C |
| ANISOU | 4188 | CG1 | ILE | B | 61 | 7273 | 8454 | 6531 | 2333 | 391 | 809 | C |
| ATOM | 4191 | CD1 | ILE | B | 61 | 32.517 | 28.601 | 106.991 | 1.00 | 58.25 | | C |
| ANISOU | 4191 | CD1 | ILE | B | 61 | 7211 | 8564 | 6357 | 2273 | 241 | 889 | C |
| ATOM | 4195 | CG2 | ILE | B | 61 | 33.772 | 25.912 | 105.736 | 1.00 | 61.56 | | C |
| ANISOU | 4195 | CG2 | ILE | B | 61 | 7802 | 8566 | 7022 | 2821 | 543 | 1094 | C |
| ATOM | 4199 | C | ILE | B | 61 | 31.574 | 27.301 | 102.960 | 1.00 | 56.45 | | C |
| ANISOU | 4199 | C | ILE | B | 61 | 7524 | 7531 | 6394 | 2187 | 709 | 611 | C |
| ATOM | 4200 | O | ILE | B | 61 | 30.516 | 26.955 | 103.489 | 1.00 | 55.75 | | O |
| ANISOU | 4200 | O | ILE | B | 61 | 7598 | 7324 | 6260 | 2104 | 674 | 660 | O |
| ATOM | 4202 | N | VAL | B | 62 | 31.625 | 28.052 | 101.855 | 1.00 | 55.33 | | N |
| ANISOU | 4202 | N | VAL | B | 62 | 7358 | 7398 | 6267 | 2050 | 762 | 457 | N |
| ATOM | 4203 | CA | VAL | B | 62 | 30.434 | 28.627 | 101.176 | 1.00 | 54.73 | | C |
| ANISOU | 4203 | CA | VAL | B | 62 | 7429 | 7216 | 6150 | 1793 | 760 | 336 | C |
| ATOM | 4205 | CB | VAL | B | 62 | 30.808 | 29.129 | 99.716 | 1.00 | 54.39 | | C |
| ANISOU | 4205 | CB | VAL | B | 62 | 7378 | 7160 | 6129 | 1722 | 865 | 198 | C |
| ATOM | 4207 | CG1 | VAL | B | 62 | 29.557 | 29.396 | 98.870 | 1.00 | 51.54 | | C |
| ANISOU | 4207 | CG1 | VAL | B | 62 | 7206 | 6658 | 5718 | 1499 | 876 | 99 | C |
| ATOM | 4211 | CG2 | VAL | B | 62 | 31.707 | 30.395 | 99.770 | 1.00 | 53.58 | | C |
| ANISOU | 4211 | CG2 | VAL | B | 62 | 7004 | 7319 | 6033 | 1679 | 815 | 162 | C |
| ATOM | 4215 | C | VAL | B | 62 | 29.158 | 27.726 | 101.103 | 1.00 | 55.20 | | C |
| ANISOU | 4215 | C | VAL | B | 62 | 7765 | 7014 | 6194 | 1719 | 793 | 352 | C |
| ATOM | 4216 | O | VAL | B | 62 | 28.047 | 28.246 | 101.057 | 1.00 | 52.37 | | O |
| ANISOU | 4216 | O | VAL | B | 62 | 7474 | 6636 | 5788 | 1514 | 737 | 303 | O |
| ATOM | 4218 | N | VAL | B | 63 | 29.310 | 26.397 | 101.079 | 1.00 | 58.13 | | N |
| ANISOU | 4218 | N | VAL | B | 63 | 8289 | 7182 | 6616 | 1881 | 890 | 420 | N |
| ATOM | 4219 | CA | VAL | B | 63 | 28.137 | 25.480 | 101.040 | 1.00 | 59.00 | | C |
| ANISOU | 4219 | CA | VAL | B | 63 | 8664 | 7028 | 6725 | 1789 | 928 | 435 | C |
| ATOM | 4221 | CB | VAL | B | 63 | 28.440 | 24.166 | 100.258 | 1.00 | 61.81 | | C |
| ANISOU | 4221 | CB | VAL | B | 63 | 9230 | 7097 | 7157 | 1924 | 1098 | 409 | C |
| ATOM | 4223 | CG1 | VAL | B | 63 | 27.189 | 23.282 | 100.106 | 1.00 | 61.42 | | C |
| ANISOU | 4223 | CG1 | VAL | B | 63 | 9461 | 6765 | 7110 | 1773 | 1140 | 393 | C |
| ATOM | 4227 | CG2 | VAL | B | 63 | 28.974 | 24.520 | 98.890 | 1.00 | 62.15 | | C |
| ANISOU | 4227 | CG2 | VAL | B | 63 | 9261 | 7151 | 7202 | 1905 | 1193 | 244 | C |
| ATOM | 4231 | C | VAL | B | 63 | 27.541 | 25.182 | 102.440 | 1.00 | 58.62 | | C |
| ANISOU | 4231 | C | VAL | B | 63 | 8630 | 6999 | 6644 | 1795 | 839 | 594 | C |
| ATOM | 4232 | O | VAL | B | 63 | 26.523 | 24.504 | 102.541 | 1.00 | 57.30 | | O |
| ANISOU | 4232 | O | VAL | B | 63 | 8657 | 6637 | 6476 | 1693 | 865 | 622 | O |
| ATOM | 4234 | N | GLU | B | 64 | 28.139 | 25.717 | 103.503 | 1.00 | 59.48 | | N |
| ANISOU | 4234 | N | GLU | B | 64 | 8534 | 7356 | 6712 | 1890 | 735 | 692 | N |
| ATOM | 4235 | CA | GLU | B | 64 | 27.464 | 25.734 | 104.809 | 1.00 | 61.04 | | C |
| ANISOU | 4235 | CA | GLU | B | 64 | 8728 | 7631 | 6832 | 1848 | 638 | 817 | C |
| ATOM | 4237 | CB | GLU | B | 64 | 28.368 | 26.319 | 105.881 | 1.00 | 62.22 | | C |
| ANISOU | 4237 | CB | GLU | B | 64 | 8638 | 8085 | 6918 | 1971 | 522 | 903 | C |
| ATOM | 4240 | CG | GLU | B | 64 | 29.440 | 25.345 | 106.325 | 1.00 | 65.67 | | C |
| ANISOU | 4240 | CG | GLU | B | 64 | 9038 | 8518 | 7394 | 2265 | 551 | 1071 | C |
| ATOM | 4243 | CD | GLU | B | 64 | 30.084 | 25.744 | 107.625 | 1.00 | 67.47 | | C |

FIG. 18 (continued)

| | | | | | | | | | | | | |
|---|---|---|---|---|---|---|---|---|---|---|---|---|
| ANISOU | 4243 | CD | GLU | B | 64 | 9055 | 9060 | 7521 | 2369 | 409 | 1194 | C |
| ATOM | 4244 | OE1 | GLU | B | 64 | 29.346 | 26.162 | 108.551 | 1.00 | 69.21 | | O |
| ANISOU | 4244 | OE1 | GLU | B | 64 | 9279 | 9393 | 7624 | 2244 | 317 | 1225 | O |
| ATOM | 4245 | OE2 | GLU | B | 64 | 31.322 | 25.621 | 107.738 | 1.00 | 70.50 | | O |
| ANISOU | 4245 | OE2 | GLU | B | 64 | 9262 | 9592 | 7933 | 2576 | 388 | 1260 | O |
| ATOM | 4246 | C | GLU | B | 64 | 26.147 | 26.500 | 104.770 | 1.00 | 59.40 | | C |
| ANISOU | 4246 | C | GLU | B | 64 | 8560 | 7442 | 6567 | 1578 | 585 | 727 | C |
| ATOM | 4247 | O | GLU | B | 64 | 25.245 | 26.239 | 105.554 | 1.00 | 60.15 | | O |
| ANISOU | 4247 | O | GLU | B | 64 | 8732 | 7509 | 6616 | 1505 | 559 | 812 | O |
| ATOM | 4249 | N | LEU | B | 65 | 26.046 | 27.440 | 103.844 | 1.00 | 57.94 | | N |
| ANISOU | 4249 | N | LEU | B | 65 | 8317 | 7309 | 6389 | 1441 | 579 | 569 | N |
| ATOM | 4250 | CA | LEU | B | 65 | 24.883 | 28.281 | 103.731 | 1.00 | 58.05 | | C |
| ANISOU | 4250 | CA | LEU | B | 65 | 8337 | 7359 | 6360 | 1215 | 528 | 491 | C |
| ATOM | 4252 | CB | LEU | B | 65 | 25.287 | 29.601 | 103.030 | 1.00 | 57.54 | | C |
| ANISOU | 4252 | CB | LEU | B | 65 | 8127 | 7439 | 6298 | 1138 | 498 | 359 | C |
| ATOM | 4255 | CG | LEU | B | 65 | 26.193 | 30.512 | 103.902 | 1.00 | 57.38 | | C |
| ANISOU | 4255 | CG | LEU | B | 65 | 7887 | 7671 | 6246 | 1204 | 414 | 369 | C |
| ATOM | 4257 | CD1 | LEU | B | 65 | 27.502 | 30.917 | 103.190 | 1.00 | 58.51 | | C |
| ANISOU | 4257 | CD1 | LEU | B | 65 | 7894 | 7899 | 6439 | 1282 | 445 | 306 | C |
| ATOM | 4261 | CD2 | LEU | B | 65 | 25.443 | 31.740 | 104.392 | 1.00 | 54.74 | | C |
| ANISOU | 4261 | CD2 | LEU | B | 65 | 7478 | 7460 | 5861 | 1045 | 336 | 310 | C |
| ATOM | 4265 | C | LEU | B | 65 | 23.682 | 27.567 | 103.051 | 1.00 | 57.91 | | C |
| ANISOU | 4265 | C | LEU | B | 65 | 8528 | 7110 | 6363 | 1068 | 589 | 462 | C |
| ATOM | 4266 | O | LEU | B | 65 | 22.535 | 27.878 | 103.349 | 1.00 | 53.99 | | O |
| ANISOU | 4266 | O | LEU | B | 65 | 8050 | 6632 | 5833 | 910 | 547 | 464 | O |
| ATOM | 4268 | N | ASP | B | 66 | 23.932 | 26.601 | 102.166 | 1.00 | 60.65 | | N |
| ANISOU | 4268 | N | ASP | B | 66 | 9029 | 7248 | 6765 | 1115 | 689 | 429 | N |
| ATOM | 4269 | CA | ASP | B | 66 | 22.831 | 25.817 | 101.547 | 1.00 | 62.08 | | C |
| ANISOU | 4269 | CA | ASP | B | 66 | 9420 | 7206 | 6962 | 955 | 742 | 388 | C |
| ATOM | 4271 | CB | ASP | B | 66 | 23.014 | 25.674 | 100.025 | 1.00 | 62.50 | | C |
| ANISOU | 4271 | CB | ASP | B | 66 | 9574 | 7146 | 7028 | 902 | 815 | 234 | C |
| ATOM | 4274 | CG | ASP | B | 66 | 22.462 | 26.869 | 99.260 | 1.00 | 60.91 | | C |
| ANISOU | 4274 | CG | ASP | B | 66 | 9283 | 7090 | 6769 | 724 | 745 | 126 | C |
| ATOM | 4275 | OD1 | ASP | B | 66 | 22.224 | 27.904 | 99.925 | 1.00 | 56.07 | | O |
| ANISOU | 4275 | OD1 | ASP | B | 66 | 8507 | 6667 | 6131 | 688 | 654 | 165 | O |
| ATOM | 4276 | OD2 | ASP | B | 66 | 22.273 | 26.767 | 98.012 | 1.00 | 61.24 | | O |
| ANISOU | 4276 | OD2 | ASP | B | 66 | 9426 | 7057 | 6785 | 626 | 786 | 7 | O |
| ATOM | 4277 | C | ASP | B | 66 | 22.675 | 24.434 | 102.159 | 1.00 | 65.38 | | C |
| ANISOU | 4277 | C | ASP | B | 66 | 10009 | 7409 | 7425 | 1030 | 812 | 511 | C |
| ATOM | 4278 | O | ASP | B | 66 | 21.699 | 23.736 | 101.864 | 1.00 | 67.46 | | O |
| ANISOU | 4278 | O | ASP | B | 66 | 10444 | 7484 | 7706 | 873 | 852 | 492 | O |
| ATOM | 4280 | N | ASP | B | 67 | 23.620 | 24.049 | 103.015 | 1.00 | 66.80 | | N |
| ANISOU | 4280 | N | ASP | B | 67 | 10138 | 7621 | 7623 | 1261 | 824 | 646 | N |
| ATOM | 4281 | CA | ASP | B | 67 | 23.653 | 22.714 | 103.595 | 1.00 | 69.19 | | C |
| ANISOU | 4281 | CA | ASP | B | 67 | 10607 | 7704 | 7978 | 1380 | 905 | 795 | C |
| ATOM | 4283 | CB | ASP | B | 67 | 24.459 | 21.787 | 102.658 | 1.00 | 71.61 | | C |
| ANISOU | 4283 | CB | ASP | B | 67 | 11060 | 7771 | 8379 | 1531 | 1043 | 737 | C |
| ATOM | 4286 | CG | ASP | B | 67 | 24.070 | 20.315 | 102.775 | 1.00 | 74.64 | | C |
| ANISOU | 4286 | CG | ASP | B | 67 | 11713 | 7804 | 8844 | 1554 | 1164 | 821 | C |
| ATOM | 4287 | OD1 | ASP | B | 67 | 23.354 | 19.941 | 103.738 | 1.00 | 75.68 | | O |
| ANISOU | 4287 | OD1 | ASP | B | 67 | 11899 | 7895 | 8962 | 1493 | 1141 | 971 | O |
| ATOM | 4288 | OD2 | ASP | B | 67 | 24.495 | 19.529 | 101.889 | 1.00 | 76.89 | | O |
| ANISOU | 4288 | OD2 | ASP | B | 67 | 12163 | 7843 | 9208 | 1631 | 1296 | 732 | O |
| ATOM | 4289 | C | ASP | B | 67 | 24.289 | 22.830 | 104.989 | 1.00 | 70.12 | | C |
| ANISOU | 4289 | C | ASP | B | 67 | 10581 | 8011 | 8050 | 1572 | 836 | 986 | C |
| ATOM | 4290 | O | ASP | B | 67 | 25.330 | 22.224 | 105.263 | 1.00 | 71.65 | | O |
| ANISOU | 4290 | O | ASP | B | 67 | 10765 | 8172 | 8286 | 1824 | 878 | 1094 | O |
| ATOM | 4292 | N | PRO | B | 68 | 23.662 | 23.620 | 105.882 | 1.00 | 69.81 | | N |
| ANISOU | 4292 | N | PRO | B | 68 | 10425 | 8187 | 7914 | 1460 | 732 | 1027 | N |
| ATOM | 4293 | CA | PRO | B | 68 | 24.272 | 23.953 | 107.175 | 1.00 | 71.20 | | C |
| ANISOU | 4293 | CA | PRO | B | 68 | 10443 | 8607 | 8003 | 1611 | 643 | 1171 | C |
| ATOM | 4295 | CB | PRO | B | 68 | 23.243 | 24.893 | 107.835 | 1.00 | 69.68 | | C |
| ANISOU | 4295 | CB | PRO | B | 68 | 10170 | 8599 | 7706 | 1412 | 560 | 1142 | C |
| ATOM | 4298 | CG | PRO | B | 68 | 21.951 | 24.585 | 107.170 | 1.00 | 69.29 | | C |
| ANISOU | 4298 | CG | PRO | B | 68 | 10273 | 8348 | 7705 | 1189 | 623 | 1074 | C |
| ATOM | 4301 | CD | PRO | B | 68 | 22.327 | 24.224 | 105.740 | 1.00 | 68.95 | | C |
| ANISOU | 4301 | CD | PRO | B | 68 | 10323 | 8110 | 7764 | 1191 | 694 | 941 | C |
| ATOM | 4304 | C | PRO | B | 68 | 24.537 | 22.753 | 108.082 | 1.00 | 74.71 | | C |
| ANISOU | 4304 | C | PRO | B | 68 | 10995 | 8938 | 8452 | 1798 | 689 | 1408 | C |
| ATOM | 4305 | O | PRO | B | 68 | 23.866 | 21.719 | 107.981 | 1.00 | 75.25 | | O |
| ANISOU | 4305 | O | PRO | B | 68 | 11282 | 8728 | 8583 | 1749 | 788 | 1478 | O |
| ATOM | 4306 | N | ASN | B | 69 | 25.540 | 22.917 | 108.940 | 1.00 | 76.79 | | N |
| ANISOU | 4306 | N | ASN | B | 69 | 11103 | 9425 | 8651 | 2007 | 612 | 1531 | N |
| ATOM | 4307 | CA | ASN | B | 69 | 25.799 | 22.019 | 110.069 | 1.00 | 80.02 | | C |
| ANISOU | 4307 | CA | ASN | B | 69 | 11566 | 9823 | 9015 | 2197 | 615 | 1795 | C |
| ATOM | 4309 | CB | ASN | B | 69 | 27.314 | 21.958 | 110.358 | 1.00 | 82.66 | | C |
| ANISOU | 4309 | CB | ASN | B | 69 | 11727 | 10333 | 9348 | 2494 | 560 | 1894 | C |
| ATOM | 4312 | CG | ASN | B | 69 | 28.010 | 23.312 | 110.167 | 1.00 | 81.51 | | C |
| ANISOU | 4312 | CG | ASN | B | 69 | 11309 | 10514 | 9148 | 2452 | 441 | 1721 | C |

FIG. 18 (continued)

| | | | | | | | | | | | | |
|---|---|---|---|---|---|---|---|---|---|---|---|---|
| ATOM | 4313 | OD1 | ASN | B | 69 | 28.846 | 23.460 | 109.272 | 1.00 | 81.67 | | O |
| ANISOU | 4313 | OD1 | ASN | B | 69 | 11243 | 10524 | 9265 | 2534 | 474 | 1615 | O |
| ATOM | 4314 | ND2 | ASN | B | 69 | 27.645 | 24.306 | 110.988 | 1.00 | 79.62 | | N |
| ANISOU | 4314 | ND2 | ASN | B | 69 | 10945 | 10552 | 8757 | 2313 | 318 | 1683 | N |
| ATOM | 4317 | C | ASN | B | 69 | 24.985 | 22.568 | 111.244 | 1.00 | 78.84 | | C |
| ANISOU | 4317 | C | ASN | B | 69 | 11368 | 9889 | 8700 | 2061 | 529 | 1864 | C |
| ATOM | 4318 | O | ASN | B | 69 | 23.934 | 23.173 | 111.010 | 1.00 | 77.42 | | O |
| ANISOU | 4318 | O | ASN | B | 69 | 11207 | 9711 | 8499 | 1815 | 529 | 1728 | O |
| ATOM | 4320 | N | ALA | B | 70 | 25.436 | 22.365 | 112.486 | 1.00 | 79.88 | | N |
| ANISOU | 4320 | N | ALA | B | 70 | 11436 | 10210 | 8705 | 2222 | 460 | 2073 | N |
| ATOM | 4321 | CA | ALA | B | 70 | 24.869 | 23.087 | 113.638 | 1.00 | 78.65 | | C |
| ANISOU | 4321 | CA | ALA | B | 70 | 11197 | 10334 | 8352 | 2109 | 367 | 2105 | C |
| ATOM | 4323 | CB | ALA | B | 70 | 25.785 | 22.957 | 114.847 | 1.00 | 80.90 | | C |
| ANISOU | 4323 | CB | ALA | B | 70 | 11365 | 10892 | 8481 | 2332 | 261 | 2311 | C |
| ATOM | 4327 | C | ALA | B | 70 | 24.614 | 24.578 | 113.306 | 1.00 | 75.70 | | C |
| ANISOU | 4327 | C | ALA | B | 70 | 10661 | 10165 | 7936 | 1911 | 290 | 1838 | C |
| ATOM | 4328 | O | ALA | B | 70 | 25.434 | 25.230 | 112.636 | 1.00 | 74.53 | | O |
| ANISOU | 4328 | O | ALA | B | 70 | 10371 | 10103 | 7844 | 1943 | 241 | 1687 | O |
| ATOM | 4330 | N | LEU | B | 71 | 23.478 | 25.109 | 113.759 | 1.00 | 73.85 | | N |
| ANISOU | 4330 | N | LEU | B | 71 | 10450 | 9998 | 7613 | 1712 | 293 | 1787 | N |
| ATOM | 4331 | CA | LEU | B | 71 | 23.069 | 26.475 | 113.376 | 1.00 | 70.57 | | C |
| ANISOU | 4331 | CA | LEU | B | 71 | 9914 | 9714 | 7185 | 1526 | 248 | 1542 | C |
| ATOM | 4333 | CB | LEU | B | 71 | 21.548 | 26.551 | 113.107 | 1.00 | 69.02 | | C |
| ANISOU | 4333 | CB | LEU | B | 71 | 9823 | 9378 | 7024 | 1303 | 332 | 1484 | C |
| ATOM | 4336 | CG | LEU | B | 71 | 21.153 | 26.202 | 111.663 | 1.00 | 67.43 | | C |
| ANISOU | 4336 | CG | LEU | B | 71 | 9720 | 8893 | 7007 | 1206 | 410 | 1381 | C |
| ATOM | 4338 | CD1 | LEU | B | 71 | 19.717 | 25.739 | 111.581 | 1.00 | 67.12 | | C |
| ANISOU | 4338 | CD1 | LEU | B | 71 | 9809 | 8693 | 7002 | 1020 | 497 | 1414 | C |
| ATOM | 4342 | CD2 | LEU | B | 71 | 21.401 | 27.385 | 110.725 | 1.00 | 64.97 | | C |
| ANISOU | 4342 | CD2 | LEU | B | 71 | 9281 | 8654 | 6750 | 1130 | 361 | 1153 | C |
| ATOM | 4346 | C | LEU | B | 71 | 23.510 | 27.557 | 114.379 | 1.00 | 69.92 | | C |
| ANISOU | 4346 | C | LEU | B | 71 | 9654 | 9989 | 6922 | 1533 | 125 | 1484 | C |
| ATOM | 4347 | O | LEU | B | 71 | 24.238 | 28.486 | 113.998 | 1.00 | 69.86 | | O |
| ANISOU | 4347 | O | LEU | B | 71 | 9495 | 10114 | 6934 | 1525 | 52 | 1321 | O |
| ATOM | 4349 | N | LEU | B | 72 | 23.093 | 27.421 | 115.638 | 1.00 | 69.38 | | N |
| ANISOU | 4349 | N | LEU | B | 72 | 9611 | 10074 | 6674 | 1538 | 109 | 1614 | N |
| ATOM | 4350 | CA | LEU | B | 72 | 23.277 | 28.466 | 116.655 | 1.00 | 69.10 | | C |
| ANISOU | 4350 | CA | LEU | B | 72 | 9440 | 10375 | 6438 | 1503 | 7 | 1530 | C |
| ATOM | 4352 | CB | LEU | B | 72 | 22.355 | 28.230 | 117.876 | 1.00 | 70.15 | | C |
| ANISOU | 4352 | CB | LEU | B | 72 | 9659 | 10613 | 6380 | 1458 | 48 | 1661 | C |
| ATOM | 4355 | CG | LEU | B | 72 | 20.927 | 27.673 | 117.739 | 1.00 | 69.69 | | C |
| ANISOU | 4355 | CG | LEU | B | 72 | 9757 | 10336 | 6385 | 1329 | 195 | 1732 | C |
| ATOM | 4357 | CD1 | LEU | B | 72 | 20.314 | 27.486 | 119.137 | 1.00 | 70.96 | | C |
| ANISOU | 4357 | CD1 | LEU | B | 72 | 9968 | 10679 | 6315 | 1318 | 226 | 1883 | C |
| ATOM | 4361 | CD2 | LEU | B | 72 | 20.007 | 28.534 | 116.869 | 1.00 | 66.94 | | C |
| ANISOU | 4361 | CD2 | LEU | B | 72 | 9382 | 9885 | 6166 | 1136 | 250 | 1506 | C |
| ATOM | 4365 | C | LEU | B | 72 | 24.736 | 28.540 | 117.124 | 1.00 | 69.61 | | C |
| ANISOU | 4365 | C | LEU | B | 72 | 9356 | 10682 | 6411 | 1674 | -130 | 1578 | C |
| ATOM | 4366 | O | LEU | B | 72 | 25.078 | 28.083 | 118.225 | 1.00 | 71.28 | | O |
| ANISOU | 4366 | O | LEU | B | 72 | 9561 | 11081 | 6441 | 1794 | -191 | 1761 | O |
| ATOM | 4368 | N | LYS | B | 73 | 25.593 | 29.129 | 116.291 | 1.00 | 66.79 | | N |
| ANISOU | 4368 | N | LYS | B | 73 | 8865 | 10339 | 6171 | 1681 | -180 | 1421 | N |
| ATOM | 4369 | CA | LYS | B | 73 | 27.027 | 29.203 | 116.570 | 1.00 | 66.88 | | C |
| ANISOU | 4369 | CA | LYS | B | 73 | 8698 | 10582 | 6131 | 1833 | -308 | 1456 | C |
| ATOM | 4371 | CB | LYS | B | 73 | 27.824 | 28.859 | 115.307 | 1.00 | 66.45 | | C |
| ANISOU | 4371 | CB | LYS | B | 73 | 8599 | 10349 | 6298 | 1931 | -268 | 1432 | C |
| ATOM | 4374 | CG | LYS | B | 73 | 27.549 | 27.473 | 114.714 | 1.00 | 66.74 | | C |
| ANISOU | 4374 | CG | LYS | B | 73 | 8823 | 10055 | 6479 | 2057 | -137 | 1607 | C |
| ATOM | 4377 | CD | LYS | B | 73 | 28.340 | 26.387 | 115.382 | 1.00 | 69.96 | | C |
| ANISOU | 4377 | CD | LYS | B | 73 | 9225 | 10520 | 6837 | 2322 | -170 | 1878 | C |
| ATOM | 4380 | CE | LYS | B | 73 | 28.325 | 25.100 | 114.562 | 1.00 | 70.69 | | C |
| ANISOU | 4380 | CE | LYS | B | 73 | 9492 | 10244 | 7121 | 2463 | -25 | 2006 | C |
| ATOM | 4383 | NZ | LYS | B | 73 | 28.640 | 23.897 | 115.411 | 1.00 | 74.43 | | N |
| ANISOU | 4383 | NZ | LYS | B | 73 | 10044 | 10699 | 7538 | 2704 | -21 | 2324 | N |
| ATOM | 4387 | C | LYS | B | 73 | 27.467 | 30.587 | 117.085 | 1.00 | 64.84 | | C |
| ANISOU | 4387 | C | LYS | B | 73 | 8258 | 10637 | 5741 | 1712 | -434 | 1248 | C |
| ATOM | 4388 | O | LYS | B | 73 | 28.325 | 30.681 | 117.971 | 1.00 | 65.17 | | O |
| ANISOU | 4388 | O | LYS | B | 73 | 8164 | 10981 | 5617 | 1796 | -569 | 1305 | O |
| ATOM | 4390 | N | HIS | B | 74 | 26.892 | 31.649 | 116.519 | 1.00 | 59.12 | | N |
| ANISOU | 4390 | N | HIS | B | 74 | 7534 | 9837 | 5092 | 1516 | -390 | 1011 | N |
| ATOM | 4391 | CA | HIS | B | 74 | 27.396 | 33.009 | 116.740 | 1.00 | 56.19 | | C |
| ANISOU | 4391 | CA | HIS | B | 74 | 7004 | 9687 | 4658 | 1387 | -484 | 782 | C |
| ATOM | 4393 | CB | HIS | B | 74 | 28.065 | 33.519 | 115.445 | 1.00 | 55.89 | | C |
| ANISOU | 4393 | CB | HIS | B | 74 | 6865 | 9535 | 4834 | 1347 | -466 | 643 | C |
| ATOM | 4396 | CG | HIS | B | 74 | 28.983 | 32.523 | 114.783 | 1.00 | 56.90 | | C |
| ANISOU | 4396 | CG | HIS | B | 74 | 6945 | 9589 | 5085 | 1538 | -458 | 795 | C |
| ATOM | 4397 | ND1 | HIS | B | 74 | 30.004 | 31.879 | 115.454 | 1.00 | 60.03 | | N |
| ANISOU | 4397 | ND1 | HIS | B | 74 | 7222 | 10196 | 5389 | 1723 | -560 | 960 | N |
| ATOM | 4399 | CE1 | HIS | B | 74 | 30.646 | 31.080 | 114.618 | 1.00 | 60.63 | | C |

FIG. 18 (continued)

| | | | | | | | | | | | | |
|---|---|---|---|---|---|---|---|---|---|---|---|---|
| ANISOU | 4399 | CE1 | HIS | B | 74 | 7279 | 10133 | 5625 | 1886 | -505 | 1063 | C |
| ATOM | 4401 | NE2 | HIS | B | 74 | 30.092 | 31.193 | 113.423 | 1.00 | 58.32 | | N |
| ANISOU | 4401 | NE2 | HIS | B | 74 | 7096 | 9556 | 5507 | 1795 | -376 | 957 | N |
| ATOM | 4403 | CD2 | HIS | B | 74 | 29.053 | 32.092 | 113.498 | 1.00 | 57.11 | | C |
| ANISOU | 4403 | CD2 | HIS | B | 74 | 7022 | 9361 | 5315 | 1579 | -354 | 800 | C |
| ATOM | 4405 | C | HIS | B | 74 | 26.265 | 33.947 | 117.197 | 1.00 | 53.91 | | C |
| ANISOU | 4405 | C | HIS | B | 74 | 6792 | 9408 | 4283 | 1203 | -437 | 619 | C |
| ATOM | 4406 | O | HIS | B | 74 | 25.120 | 33.514 | 117.278 | 1.00 | 56.23 | | O |
| ANISOU | 4406 | O | HIS | B | 74 | 7236 | 9553 | 4575 | 1182 | -334 | 695 | O |
| ATOM | 4408 | N | ARG | B | 75 | 26.566 | 35.217 | 117.491 | 1.00 | 50.06 | | N |
| ANISOU | 4408 | N | ARG | B | 75 | 6201 | 9086 | 3734 | 1069 | -501 | 394 | N |
| ATOM | 4409 | CA | ARG | B | 75 | 25.518 | 36.201 | 117.841 | 1.00 | 47.87 | | C |
| ANISOU | 4409 | CA | ARG | B | 75 | 5998 | 8788 | 3403 | 910 | -434 | 216 | C |
| ATOM | 4411 | CB | ARG | B | 75 | 26.106 | 37.580 | 118.133 | 1.00 | 48.18 | | C |
| ANISOU | 4411 | CB | ARG | B | 75 | 5922 | 8993 | 3389 | 769 | -509 | -43 | C |
| ATOM | 4414 | CG | ARG | B | 75 | 25.055 | 38.694 | 117.966 | 1.00 | 46.43 | | C |
| ANISOU | 4414 | CG | ARG | B | 75 | 5785 | 8627 | 3230 | 620 | -396 | -248 | C |
| ATOM | 4417 | CD | ARG | B | 75 | 25.462 | 39.994 | 118.570 | 1.00 | 47.49 | | C |
| ANISOU | 4417 | CD | ARG | B | 75 | 5855 | 8921 | 3268 | 477 | -452 | -506 | C |
| ATOM | 4420 | NE | ARG | B | 75 | 24.409 | 41.000 | 118.419 | 1.00 | 45.25 | | N |
| ANISOU | 4420 | NE | ARG | B | 75 | 5667 | 8468 | 3059 | 370 | -321 | -682 | N |
| ATOM | 4422 | CZ | ARG | B | 75 | 24.546 | 42.266 | 118.793 | 1.00 | 45.70 | | C |
| ANISOU | 4422 | CZ | ARG | B | 75 | 5711 | 8572 | 3081 | 232 | -322 | -939 | C |
| ATOM | 4423 | NH1 | ARG | B | 75 | 25.679 | 42.674 | 119.344 | 1.00 | 49.27 | | N |
| ANISOU | 4423 | NH1 | ARG | B | 75 | 6055 | 9252 | 3414 | 155 | -457 | -1060 | N |
| ATOM | 4426 | NH2 | ARG | B | 75 | 23.554 | 43.124 | 118.631 | 1.00 | 43.74 | | N |
| ANISOU | 4426 | NH2 | ARG | B | 75 | 5555 | 8145 | 2920 | 169 | -186 | -1076 | N |
| ATOM | 4429 | C | ARG | B | 75 | 24.428 | 36.435 | 116.776 | 1.00 | 42.11 | | C |
| ANISOU | 4429 | C | ARG | B | 75 | 5371 | 7750 | 2880 | 834 | -290 | 160 | C |
| ATOM | 4430 | O | ARG | B | 75 | 23.306 | 36.795 | 117.118 | 1.00 | 38.43 | | O |
| ANISOU | 4430 | O | ARG | B | 75 | 4990 | 7239 | 2371 | 763 | -205 | 108 | O |
| ATOM | 4432 | N | PHE | B | 76 | 24.807 | 36.361 | 115.504 | 1.00 | 38.98 | | N |
| ANISOU | 4432 | N | PHE | B | 76 | 4946 | 7172 | 2692 | 843 | -266 | 153 | N |
| ATOM | 4433 | CA | PHE | B | 76 | 23.886 | 36.475 | 114.393 | 1.00 | 37.35 | | C |
| ANISOU | 4433 | CA | PHE | B | 76 | 4825 | 6697 | 2669 | 782 | -153 | 125 | C |
| ATOM | 4435 | CB | PHE | B | 76 | 24.377 | 37.535 | 113.387 | 1.00 | 37.26 | | C |
| ANISOU | 4435 | CB | PHE | B | 76 | 4736 | 6610 | 2813 | 692 | -151 | -46 | C |
| ATOM | 4438 | CG | PHE | B | 76 | 24.342 | 38.944 | 113.927 | 1.00 | 37.60 | | C |
| ANISOU | 4438 | CG | PHE | B | 76 | 4730 | 6751 | 2805 | 566 | -167 | -255 | C |
| ATOM | 4439 | CD1 | PHE | B | 76 | 23.126 | 39.614 | 114.070 | 1.00 | 37.76 | | C |
| ANISOU | 4439 | CD1 | PHE | B | 76 | 4831 | 6681 | 2834 | 491 | -79 | -338 | C |
| ATOM | 4441 | CE1 | PHE | B | 76 | 23.074 | 40.916 | 114.603 | 1.00 | 37.63 | | C |
| ANISOU | 4441 | CE1 | PHE | B | 76 | 4793 | 6727 | 2778 | 387 | -72 | -544 | C |
| ATOM | 4443 | CZ | PHE | B | 76 | 24.266 | 41.569 | 114.985 | 1.00 | 39.10 | | C |
| ANISOU | 4443 | CZ | PHE | B | 76 | 4875 | 7071 | 2909 | 323 | -167 | -681 | C |
| ATOM | 4445 | CE2 | PHE | B | 76 | 25.495 | 40.917 | 114.817 | 1.00 | 39.93 | | C |
| ANISOU | 4445 | CE2 | PHE | B | 76 | 4871 | 7294 | 3005 | 381 | -270 | -592 | C |
| ATOM | 4447 | CD2 | PHE | B | 76 | 25.524 | 39.600 | 114.302 | 1.00 | 39.05 | | C |
| ANISOU | 4447 | CD2 | PHE | B | 76 | 4783 | 7116 | 2937 | 519 | -264 | -374 | C |
| ATOM | 4449 | C | PHE | B | 76 | 23.795 | 35.129 | 113.697 | 1.00 | 37.37 | | C |
| ANISOU | 4449 | C | PHE | B | 76 | 4910 | 6525 | 2765 | 886 | -108 | 315 | C |
| ATOM | 4450 | O | PHE | B | 76 | 24.806 | 34.458 | 113.536 | 1.00 | 39.81 | | O |
| ANISOU | 4450 | O | PHE | B | 76 | 5169 | 6867 | 3090 | 1002 | -156 | 407 | O |
| ATOM | 4452 | N | GLU | B | 77 | 22.583 | 34.733 | 113.301 | 1.00 | 37.63 | | N |
| ANISOU | 4452 | N | GLU | B | 77 | 5062 | 6375 | 2861 | 843 | -11 | 368 | N |
| ATOM | 4453 | CA | GLU | B | 77 | 22.369 | 33.693 | 112.286 | 1.00 | 35.36 | | C |
| ANISOU | 4453 | CA | GLU | B | 77 | 4868 | 5861 | 2706 | 881 | 49 | 478 | C |
| ATOM | 4455 | CB | GLU | B | 77 | 21.067 | 32.902 | 112.549 | 1.00 | 37.09 | | C |
| ANISOU | 4455 | CB | GLU | B | 77 | 5217 | 5969 | 2908 | 845 | 130 | 599 | C |
| ATOM | 4458 | CG | GLU | B | 77 | 21.069 | 31.461 | 112.001 | 1.00 | 38.39 | | C |
| ANISOU | 4458 | CG | GLU | B | 77 | 5502 | 5932 | 3150 | 911 | 179 | 756 | C |
| ATOM | 4461 | CD | GLU | B | 77 | 22.079 | 30.535 | 112.737 | 1.00 | 41.58 | | C |
| ANISOU | 4461 | CD | GLU | B | 77 | 5914 | 6410 | 3474 | 1088 | 137 | 920 | C |
| ATOM | 4462 | OE1 | GLU | B | 77 | 22.060 | 30.482 | 113.994 | 1.00 | 41.91 | | O |
| ANISOU | 4462 | OE1 | GLU | B | 77 | 5941 | 6630 | 3352 | 1130 | 103 | 1007 | O |
| ATOM | 4463 | OE2 | GLU | B | 77 | 22.893 | 29.858 | 112.064 | 1.00 | 42.31 | | O |
| ANISOU | 4463 | OE2 | GLU | B | 77 | 6025 | 6390 | 3659 | 1197 | 143 | 968 | O |
| ATOM | 4464 | C | GLU | B | 77 | 22.242 | 34.442 | 110.974 | 1.00 | 32.33 | | C |
| ANISOU | 4464 | C | GLU | B | 77 | 4463 | 5343 | 2477 | 791 | 80 | 342 | C |
| ATOM | 4465 | O | GLU | B | 77 | 21.543 | 35.442 | 110.918 | 1.00 | 27.76 | | O |
| ANISOU | 4465 | O | GLU | B | 77 | 3864 | 4767 | 1915 | 686 | 101 | 230 | O |
| ATOM | 4467 | N | ILE | B | 78 | 22.914 | 33.977 | 109.927 | 1.00 | 31.10 | | N |
| ANISOU | 4467 | N | ILE | B | 78 | 4315 | 5073 | 2429 | 840 | 92 | 358 | N |
| ATOM | 4468 | CA | ILE | B | 78 | 22.853 | 34.671 | 108.634 | 1.00 | 31.78 | | C |
| ANISOU | 4468 | CA | ILE | B | 78 | 4387 | 5047 | 2639 | 756 | 123 | 245 | C |
| ATOM | 4470 | CB | ILE | B | 78 | 24.206 | 34.667 | 107.852 | 1.00 | 35.29 | | C |
| ANISOU | 4470 | CB | ILE | B | 78 | 4756 | 5499 | 3154 | 823 | 112 | 213 | C |
| ATOM | 4472 | CG1 | ILE | B | 78 | 25.361 | 34.908 | 108.809 | 1.00 | 38.71 | | C |
| ANISOU | 4472 | CG1 | ILE | B | 78 | 5049 | 6151 | 3508 | 899 | 30 | 210 | C |

FIG. 18 (continued)

| | | | | | | | | | | | | |
|---|---|---|---|---|---|---|---|---|---|---|---|---|
| ATOM | 4475 | CD1 | ILE | B | 78 | 26.674 | 35.168 | 108.116 | 1.00 | 40.34 | | C |
| ANISOU | 4475 | CD1 | ILE | B | 78 | 5131 | 6408 | 3789 | 939 | 19 | 161 | C |
| ATOM | 4479 | CG2 | ILE | B | 78 | 24.181 | 35.757 | 106.725 | 1.00 | 33.14 | | C |
| ANISOU | 4479 | CG2 | ILE | B | 78 | 4448 | 5166 | 2978 | 713 | 140 | 86 | C |
| ATOM | 4483 | C | ILE | B | 78 | 21.787 | 33.923 | 107.872 | 1.00 | 29.58 | | C |
| ANISOU | 4483 | C | ILE | B | 78 | 4242 | 4574 | 2422 | 706 | 191 | 302 | C |
| ATOM | 4484 | O | ILE | B | 78 | 21.746 | 32.688 | 107.905 | 1.00 | 27.81 | | O |
| ANISOU | 4484 | O | ILE | B | 78 | 4116 | 4255 | 2197 | 769 | 220 | 416 | O |
| ATOM | 4486 | N | ILE | B | 79 | 20.875 | 34.670 | 107.262 | 1.00 | 27.98 | | N |
| ANISOU | 4486 | N | ILE | B | 79 | 4045 | 4316 | 2271 | 590 | 214 | 230 | N |
| ATOM | 4487 | CA | ILE | B | 79 | 19.798 | 34.091 | 106.462 | 1.00 | 26.94 | | C |
| ANISOU | 4487 | CA | ILE | B | 79 | 4013 | 4033 | 2191 | 512 | 259 | 268 | C |
| ATOM | 4489 | CB | ILE | B | 79 | 18.376 | 34.604 | 106.919 | 1.00 | 25.79 | | C |
| ANISOU | 4489 | CB | ILE | B | 79 | 3849 | 3921 | 2027 | 416 | 275 | 268 | C |
| ATOM | 4491 | CG1 | ILE | B | 79 | 18.045 | 34.180 | 108.361 | 1.00 | 26.42 | | C |
| ANISOU | 4491 | CG1 | ILE | B | 79 | 3937 | 4096 | 2006 | 449 | 285 | 348 | C |
| ATOM | 4494 | CD1 | ILE | B | 79 | 16.999 | 35.127 | 109.046 | 1.00 | 25.22 | | C |
| ANISOU | 4494 | CD1 | ILE | B | 79 | 3719 | 4043 | 1820 | 390 | 310 | 305 | C |
| ATOM | 4498 | CG2 | ILE | B | 79 | 17.290 | 34.108 | 105.939 | 1.00 | 26.51 | | C |
| ANISOU | 4498 | CG2 | ILE | B | 79 | 4008 | 3885 | 2178 | 312 | 301 | 298 | C |
| ATOM | 4502 | C | ILE | B | 79 | 20.023 | 34.426 | 104.994 | 1.00 | 27.33 | | C |
| ANISOU | 4502 | C | ILE | B | 79 | 4071 | 3992 | 2321 | 468 | 270 | 198 | C |
| ATOM | 4503 | O | ILE | B | 79 | 19.865 | 33.560 | 104.100 | 1.00 | 26.19 | | O |
| ANISOU | 4503 | O | ILE | B | 79 | 4027 | 3717 | 2208 | 447 | 301 | 221 | O |
| ATOM | 4505 | N | GLU | B | 80 | 20.406 | 35.675 | 104.742 | 1.00 | 29.29 | | N |
| ANISOU | 4505 | N | GLU | B | 80 | 4227 | 4307 | 2597 | 447 | 253 | 109 | N |
| ATOM | 4506 | CA | GLU | B | 80 | 20.898 | 36.096 | 103.409 | 1.00 | 28.85 | | C |
| ANISOU | 4506 | CA | GLU | B | 80 | 4167 | 4193 | 2602 | 420 | 269 | 55 | C |
| ATOM | 4508 | CB | GLU | B | 80 | 21.287 | 37.588 | 103.422 | 1.00 | 30.90 | | C |
| ANISOU | 4508 | CB | GLU | B | 80 | 4322 | 4524 | 2896 | 388 | 258 | -29 | C |
| ATOM | 4511 | CG | GLU | B | 80 | 21.491 | 38.175 | 102.037 | 1.00 | 32.87 | | C |
| ANISOU | 4511 | CG | GLU | B | 80 | 4576 | 4710 | 3202 | 339 | 286 | -59 | C |
| ATOM | 4514 | CD | GLU | B | 80 | 20.292 | 37.922 | 101.133 | 1.00 | 35.53 | | C |
| ANISOU | 4514 | CD | GLU | B | 80 | 4995 | 4963 | 3540 | 272 | 292 | -17 | C |
| ATOM | 4515 | OE1 | GLU | B | 80 | 19.274 | 38.611 | 101.272 | 1.00 | 37.27 | | O |
| ANISOU | 4515 | OE1 | GLU | B | 80 | 5192 | 5190 | 3779 | 225 | 279 | -7 | O |
| ATOM | 4516 | OE2 | GLU | B | 80 | 20.327 | 36.984 | 100.301 | 1.00 | 39.98 | | O |
| ANISOU | 4516 | OE2 | GLU | B | 80 | 5647 | 5461 | 4084 | 267 | 309 | 4 | O |
| ATOM | 4517 | C | GLU | B | 80 | 22.088 | 35.277 | 102.879 | 1.00 | 29.42 | | C |
| ANISOU | 4517 | C | GLU | B | 80 | 4266 | 4229 | 2684 | 507 | 295 | 64 | C |
| ATOM | 4518 | O | GLU | B | 80 | 22.987 | 34.856 | 103.622 | 1.00 | 28.81 | | O |
| ANISOU | 4518 | O | GLU | B | 80 | 4145 | 4220 | 2584 | 611 | 282 | 92 | O |
| ATOM | 4520 | N | GLY | B | 81 | 22.114 | 35.085 | 101.565 | 1.00 | 27.54 | | N |
| ANISOU | 4520 | N | GLY | B | 81 | 4092 | 3898 | 2473 | 474 | 334 | 42 | N |
| ATOM | 4521 | CA | GLY | B | 81 | 23.166 | 34.335 | 100.950 | 1.00 | 30.59 | | C |
| ANISOU | 4521 | CA | GLY | B | 81 | 4511 | 4239 | 2871 | 562 | 385 | 37 | C |
| ATOM | 4524 | C | GLY | B | 81 | 22.833 | 32.850 | 100.752 | 1.00 | 32.68 | | C |
| ANISOU | 4524 | C | GLY | B | 81 | 4931 | 4360 | 3125 | 595 | 426 | 82 | C |
| ATOM | 4525 | O | GLY | B | 81 | 23.604 | 32.156 | 100.131 | 1.00 | 34.42 | | O |
| ANISOU | 4525 | O | GLY | B | 81 | 5205 | 4511 | 3361 | 676 | 489 | 68 | O |
| ATOM | 4527 | N | ARG | B | 82 | 21.706 | 32.359 | 101.288 | 1.00 | 32.98 | | N |
| ANISOU | 4527 | N | ARG | B | 82 | 5042 | 4345 | 3143 | 533 | 404 | 133 | N |
| ATOM | 4528 | CA | ARG | B | 82 | 21.338 | 30.943 | 101.143 | 1.00 | 32.42 | | C |
| ANISOU | 4528 | CA | ARG | B | 82 | 5133 | 4110 | 3074 | 536 | 451 | 174 | C |
| ATOM | 4530 | CB | ARG | B | 82 | 20.702 | 30.414 | 102.404 | 1.00 | 29.87 | | C |
| ANISOU | 4530 | CB | ARG | B | 82 | 4830 | 3785 | 2733 | 541 | 433 | 275 | C |
| ATOM | 4533 | CG | ARG | B | 82 | 21.498 | 30.675 | 103.639 | 1.00 | 29.18 | | C |
| ANISOU | 4533 | CG | ARG | B | 82 | 4633 | 3836 | 2618 | 675 | 400 | 336 | C |
| ATOM | 4536 | CD | ARG | B | 82 | 20.807 | 30.116 | 104.832 | 1.00 | 28.35 | | C |
| ANISOU | 4536 | CD | ARG | B | 82 | 4567 | 3736 | 2471 | 673 | 393 | 448 | C |
| ATOM | 4539 | NE | ARG | B | 82 | 21.564 | 30.347 | 106.070 | 1.00 | 29.38 | | N |
| ANISOU | 4539 | NE | ARG | B | 82 | 4594 | 4029 | 2539 | 799 | 349 | 511 | N |
| ATOM | 4541 | CZ | ARG | B | 82 | 22.390 | 29.455 | 106.632 | 1.00 | 30.89 | | C |
| ANISOU | 4541 | CZ | ARG | B | 82 | 4812 | 4206 | 2716 | 961 | 360 | 620 | C |
| ATOM | 4542 | NH1 | ARG | B | 82 | 22.567 | 28.244 | 106.114 | 1.00 | 30.04 | | N |
| ANISOU | 4542 | NH1 | ARG | B | 82 | 4848 | 3895 | 2670 | 1027 | 433 | 676 | N |
| ATOM | 4545 | NH2 | ARG | B | 82 | 23.006 | 29.763 | 107.750 | 1.00 | 30.51 | | N |
| ANISOU | 4545 | NH2 | ARG | B | 82 | 4655 | 4350 | 2589 | 1058 | 297 | 675 | N |
| ATOM | 4548 | C | ARG | B | 82 | 20.357 | 30.764 | 99.979 | 1.00 | 33.27 | | C |
| ANISOU | 4548 | C | ARG | B | 82 | 5347 | 4121 | 3172 | 378 | 460 | 117 | C |
| ATOM | 4549 | O | ARG | B | 82 | 19.676 | 31.671 | 99.603 | 1.00 | 35.45 | | O |
| ANISOU | 4549 | O | ARG | B | 82 | 5560 | 4474 | 3434 | 273 | 413 | 89 | O |
| ATOM | 4551 | N | ASP | B | 83 | 20.264 | 29.573 | 99.435 | 1.00 | 35.12 | | N |
| ANISOU | 4551 | N | ASP | B | 83 | 5745 | 4186 | 3411 | 361 | 518 | 101 | N |
| ATOM | 4552 | CA | ASP | B | 83 | 19.245 | 29.316 | 98.448 | 1.00 | 37.88 | | C |
| ANISOU | 4552 | CA | ASP | B | 83 | 6197 | 4465 | 3733 | 183 | 509 | 41 | C |
| ATOM | 4554 | CB | ASP | B | 83 | 19.463 | 27.989 | 97.671 | 1.00 | 42.20 | | C |
| ANISOU | 4554 | CB | ASP | B | 83 | 6951 | 4802 | 4281 | 173 | 595 | -22 | C |
| ATOM | 4557 | CG | ASP | B | 83 | 19.028 | 26.734 | 98.406 | 1.00 | 47.54 | | C |

FIG. 18 (continued)

| | | | | | | | | | | | | |
|---|---|---|---|---|---|---|---|---|---|---|---|---|
| ANISOU | 4557 | CG | ASP | B | 83 | 7759 | 5304 | 5000 | 160 | 637 | 44 | C |
| ATOM | 4558 | OD1 | ASP | B | 83 | 18.333 | 26.787 | 99.441 | 1.00 | 51.95 | | O |
| ANISOU | 4558 | OD1 | ASP | B | 83 | 8258 | 5910 | 5572 | 120 | 596 | 144 | O |
| ATOM | 4559 | OD2 | ASP | B | 83 | 19.373 | 25.628 | 97.893 | 1.00 | 54.28 | | O |
| ANISOU | 4559 | OD2 | ASP | B | 83 | 8796 | 5951 | 5875 | 185 | 729 | -8 | O |
| ATOM | 4560 | C | ASP | B | 83 | 17.922 | 29.473 | 99.156 | 1.00 | 35.51 | | C |
| ANISOU | 4560 | C | ASP | B | 83 | 5847 | 4213 | 3431 | 57 | 447 | 106 | C |
| ATOM | 4561 | O | ASP | B | 83 | 17.814 | 29.259 | 100.354 | 1.00 | 35.66 | | O |
| ANISOU | 4561 | O | ASP | B | 83 | 5834 | 4247 | 3468 | 109 | 449 | 194 | O |
| ATOM | 4563 | N | ARG | B | 84 | 16.925 | 29.916 | 98.418 | 1.00 | 33.93 | | N |
| ANISOU | 4563 | N | ARG | B | 84 | 5624 | 4067 | 3201 | -102 | 392 | 69 | N |
| ATOM | 4564 | CA | ARG | B | 84 | 15.655 | 30.245 | 99.005 | 1.00 | 32.89 | | C |
| ANISOU | 4564 | CA | ARG | B | 84 | 5401 | 4019 | 3075 | -213 | 337 | 131 | C |
| ATOM | 4566 | CB | ARG | B | 84 | 14.625 | 30.539 | 97.920 | 1.00 | 31.07 | | C |
| ANISOU | 4566 | CB | ARG | B | 84 | 5153 | 3844 | 2807 | -386 | 271 | 90 | C |
| ATOM | 4569 | CG | ARG | B | 84 | 13.327 | 31.114 | 98.496 | 1.00 | 31.11 | | C |
| ANISOU | 4569 | CG | ARG | B | 84 | 5010 | 3979 | 2832 | -472 | 215 | 164 | C |
| ATOM | 4572 | CD | ARG | B | 84 | 12.359 | 31.694 | 97.449 | 1.00 | 30.12 | | C |
| ANISOU | 4572 | CD | ARG | B | 84 | 4808 | 3967 | 2670 | -604 | 128 | 151 | C |
| ATOM | 4575 | NE | ARG | B | 84 | 11.197 | 32.154 | 98.204 | 1.00 | 28.49 | | N |
| ANISOU | 4575 | NE | ARG | B | 84 | 4442 | 3880 | 2504 | -648 | 98 | 235 | N |
| ATOM | 4577 | CZ | ARG | B | 84 | 11.056 | 33.372 | 98.705 | 1.00 | 27.45 | | C |
| ANISOU | 4577 | CZ | ARG | B | 84 | 4160 | 3864 | 2407 | -545 | 91 | 281 | C |
| ATOM | 4578 | NH1 | ARG | B | 84 | 11.969 | 34.330 | 98.466 | 1.00 | 26.51 | | N |
| ANISOU | 4578 | NH1 | ARG | B | 84 | 4026 | 3758 | 2290 | -417 | 98 | 254 | N |
| ATOM | 4581 | NH2 | ARG | B | 84 | 9.974 | 33.649 | 99.421 | 1.00 | 27.10 | | N |
| ANISOU | 4581 | NH2 | ARG | B | 84 | 3979 | 3918 | 2399 | -578 | 87 | 351 | N |
| ATOM | 4584 | C | ARG | B | 84 | 15.118 | 29.173 | 99.942 | 1.00 | 33.03 | | C |
| ANISOU | 4584 | C | ARG | B | 84 | 5489 | 3941 | 3119 | -255 | 373 | 206 | C |
| ATOM | 4585 | O | ARG | B | 84 | 14.567 | 29.488 | 100.994 | 1.00 | 33.41 | | O |
| ANISOU | 4585 | O | ARG | B | 84 | 5440 | 4079 | 3177 | -251 | 363 | 286 | O |
| ATOM | 4587 | N | THR | B | 85 | 15.231 | 27.910 | 99.533 | 1.00 | 34.44 | | N |
| ANISOU | 4587 | N | THR | B | 85 | 5848 | 3930 | 3309 | -303 | 428 | 176 | N |
| ATOM | 4588 | CA | THR | B | 85 | 14.681 | 26.809 | 100.322 | 1.00 | 36.80 | | C |
| ANISOU | 4588 | CA | THR | B | 85 | 6241 | 4100 | 3643 | -367 | 477 | 257 | C |
| ATOM | 4590 | CB | THR | B | 85 | 14.588 | 25.466 | 99.524 | 1.00 | 40.03 | | C |
| ANISOU | 4590 | CB | THR | B | 85 | 6875 | 4264 | 4071 | -482 | 537 | 185 | C |
| ATOM | 4592 | OG1 | THR | B | 85 | 15.904 | 24.963 | 99.253 | 1.00 | 43.43 | | O |
| ANISOU | 4592 | OG1 | THR | B | 85 | 7430 | 4553 | 4519 | -300 | 616 | 147 | O |
| ATOM | 4594 | CG2 | THR | B | 85 | 13.845 | 25.686 | 98.193 | 1.00 | 38.84 | | C |
| ANISOU | 4594 | CG2 | THR | B | 85 | 6729 | 4161 | 3868 | -687 | 470 | 60 | C |
| ATOM | 4598 | C | THR | B | 85 | 15.454 | 26.648 | 101.624 | 1.00 | 34.91 | | C |
| ANISOU | 4598 | C | THR | B | 85 | 5986 | 3858 | 3419 | -173 | 522 | 371 | C |
| ATOM | 4599 | O | THR | B | 85 | 14.851 | 26.478 | 102.674 | 1.00 | 36.90 | | O |
| ANISOU | 4599 | O | THR | B | 85 | 6204 | 4144 | 3672 | -200 | 533 | 480 | O |
| ATOM | 4601 | N | MET | B | 86 | 16.778 | 26.734 | 101.561 | 1.00 | 34.77 | | N |
| ANISOU | 4601 | N | MET | B | 86 | 5980 | 3827 | 3403 | 20 | 547 | 353 | N |
| ATOM | 4602 | CA | MET | B | 86 | 17.594 | 26.614 | 102.764 | 1.00 | 35.89 | | C |
| ANISOU | 4602 | CA | MET | B | 86 | 6087 | 4006 | 3544 | 213 | 568 | 465 | C |
| ATOM | 4604 | CB | MET | B | 86 | 19.083 | 26.520 | 102.430 | 1.00 | 39.13 | | C |
| ANISOU | 4604 | CB | MET | B | 86 | 6511 | 4387 | 3971 | 414 | 600 | 433 | C |
| ATOM | 4607 | CG | MET | B | 86 | 19.947 | 26.245 | 103.653 | 1.00 | 43.95 | | C |
| ANISOU | 4607 | CG | MET | B | 86 | 7080 | 5046 | 4573 | 618 | 608 | 566 | C |
| ATOM | 4610 | SD | MET | B | 86 | 19.321 | 24.991 | 104.829 | 1.00 | 50.11 | | S |
| ANISOU | 4610 | SD | MET | B | 86 | 7995 | 5686 | 5357 | 619 | 662 | 755 | S |
| ATOM | 4611 | CE | MET | B | 86 | 19.063 | 23.557 | 103.764 | 1.00 | 49.12 | | C |
| ANISOU | 4611 | CE | MET | B | 86 | 8134 | 5204 | 5324 | 537 | 774 | 705 | C |
| ATOM | 4615 | C | MET | B | 86 | 17.308 | 27.783 | 103.716 | 1.00 | 33.62 | | C |
| ANISOU | 4615 | C | MET | B | 86 | 5611 | 3956 | 3207 | 227 | 501 | 506 | C |
| ATOM | 4616 | O | MET | B | 86 | 17.219 | 27.589 | 104.952 | 1.00 | 33.60 | | O |
| ANISOU | 4616 | O | MET | B | 86 | 5586 | 4008 | 3172 | 284 | 510 | 622 | O |
| ATOM | 4618 | N | ALA | B | 87 | 17.084 | 28.962 | 103.135 | 1.00 | 30.25 | | N |
| ANISOU | 4618 | N | ALA | B | 87 | 5064 | 3659 | 2769 | 169 | 445 | 414 | N |
| ATOM | 4619 | CA | ALA | B | 87 | 16.747 | 30.186 | 103.905 | 1.00 | 29.42 | | C |
| ANISOU | 4619 | CA | ALA | B | 87 | 4794 | 3754 | 2631 | 174 | 397 | 421 | C |
| ATOM | 4621 | CB | ALA | B | 87 | 16.707 | 31.447 | 102.939 | 1.00 | 26.57 | | C |
| ANISOU | 4621 | CB | ALA | B | 87 | 4335 | 3477 | 2284 | 130 | 351 | 317 | C |
| ATOM | 4625 | C | ALA | B | 87 | 15.458 | 30.028 | 104.713 | 1.00 | 28.92 | | C |
| ANISOU | 4625 | C | ALA | B | 87 | 4706 | 3731 | 2551 | 69 | 408 | 500 | C |
| ATOM | 4626 | O | ALA | B | 87 | 15.420 | 30.313 | 105.933 | 1.00 | 29.55 | | O |
| ANISOU | 4626 | O | ALA | B | 87 | 4722 | 3925 | 2581 | 129 | 414 | 562 | O |
| ATOM | 4628 | N | TRP | B | 88 | 14.410 | 29.493 | 104.082 | 1.00 | 29.89 | | N |
| ANISOU | 4628 | N | TRP | B | 88 | 4881 | 3771 | 2705 | -97 | 416 | 500 | N |
| ATOM | 4629 | CA | TRP | B | 88 | 13.180 | 29.156 | 104.828 | 1.00 | 31.52 | | C |
| ANISOU | 4629 | CA | TRP | B | 88 | 5061 | 4009 | 2907 | -213 | 444 | 588 | C |
| ATOM | 4631 | CB | TRP | B | 88 | 12.016 | 28.782 | 103.886 | 1.00 | 33.07 | | C |
| ANISOU | 4631 | CB | TRP | B | 88 | 5269 | 4152 | 3143 | -426 | 428 | 559 | C |
| ATOM | 4634 | CG | TRP | B | 88 | 11.305 | 29.958 | 103.345 | 1.00 | 31.23 | | C |
| ANISOU | 4634 | CG | TRP | B | 88 | 4873 | 4078 | 2915 | -480 | 364 | 507 | C |

FIG. 18 (continued)

| | | | | | | | | | | | | |
|---|---|---|---|---|---|---|---|---|---|---|---|---|
| ATOM | 4635 | CD1 | TRP | B | 88 | 11.203 | 30.317 | 102.040 | 1.00 | 31.79 | | C |
| ANISOU | 4635 | CD1 | TRP | B | 88 | 4933 | 4153 | 2992 | -546 | 301 | 424 | C |
| ATOM | 4637 | NE1 | TRP | B | 88 | 10.483 | 31.485 | 101.928 | 1.00 | 30.87 | | N |
| ANISOU | 4637 | NE1 | TRP | B | 88 | 4642 | 4202 | 2885 | -553 | 254 | 426 | N |
| ATOM | 4639 | CE2 | TRP | B | 88 | 10.122 | 31.916 | 103.174 | 1.00 | 29.62 | | C |
| ANISOU | 4639 | CE2 | TRP | B | 88 | 4383 | 4142 | 2730 | -490 | 299 | 490 | C |
| ATOM | 4640 | CD2 | TRP | B | 88 | 10.610 | 30.966 | 104.098 | 1.00 | 30.74 | | C |
| ANISOU | 4640 | CD2 | TRP | B | 88 | 4637 | 4193 | 2848 | -453 | 364 | 543 | C |
| ATOM | 4641 | CE3 | TRP | B | 88 | 10.382 | 31.175 | 105.467 | 1.00 | 31.54 | | C |
| ANISOU | 4641 | CE3 | TRP | B | 88 | 4675 | 4390 | 2919 | -390 | 421 | 613 | C |
| ATOM | 4643 | CZ3 | TRP | B | 88 | 9.651 | 32.314 | 105.868 | 1.00 | 31.24 | | C |
| ANISOU | 4643 | CZ3 | TRP | B | 88 | 4466 | 4517 | 2885 | -365 | 426 | 608 | C |
| ATOM | 4645 | CH2 | TRP | B | 88 | 9.172 | 33.241 | 104.914 | 1.00 | 30.90 | | C |
| ANISOU | 4645 | CH2 | TRP | B | 88 | 4314 | 4537 | 2892 | -389 | 368 | 557 | C |
| ATOM | 4647 | CZ2 | TRP | B | 88 | 9.385 | 33.056 | 103.569 | 1.00 | 30.84 | | C |
| ANISOU | 4647 | CZ2 | TRP | B | 88 | 4361 | 4454 | 2904 | -454 | 298 | 509 | C |
| ATOM | 4649 | C | TRP | B | 88 | 13.411 | 28.062 | 105.895 | 1.00 | 32.62 | | C |
| ANISOU | 4649 | C | TRP | B | 88 | 5309 | 4060 | 3025 | -161 | 513 | 716 | C |
| ATOM | 4650 | O | TRP | B | 88 | 12.891 | 28.124 | 107.018 | 1.00 | 35.27 | | O |
| ANISOU | 4650 | O | TRP | B | 88 | 5590 | 4495 | 3316 | -162 | 545 | 810 | O |
| ATOM | 4652 | N | THR | B | 89 | 14.217 | 27.068 | 105.566 | 1.00 | 34.28 | | N |
| ANISOU | 4652 | N | THR | B | 89 | 5677 | 4085 | 3262 | -99 | 546 | 729 | N |
| ATOM | 4653 | CA | THR | B | 89 | 14.559 | 26.035 | 106.571 | 1.00 | 34.23 | | C |
| ANISOU | 4653 | CA | THR | B | 89 | 5784 | 3981 | 3242 | -13 | 613 | 878 | C |
| ATOM | 4655 | CB | THR | B | 89 | 15.435 | 24.923 | 105.962 | 1.00 | 35.76 | | C |
| ANISOU | 4655 | CB | THR | B | 89 | 6164 | 3927 | 3495 | 68 | 663 | 877 | C |
| ATOM | 4657 | OG1 | THR | B | 89 | 14.742 | 24.340 | 104.848 | 1.00 | 34.28 | | O |
| ANISOU | 4657 | OG1 | THR | B | 89 | 6087 | 3566 | 3373 | -127 | 685 | 786 | O |
| ATOM | 4659 | CG2 | THR | B | 89 | 15.787 | 23.836 | 107.031 | 1.00 | 38.02 | | C |
| ANISOU | 4659 | CG2 | THR | B | 89 | 6575 | 4096 | 3776 | 183 | 737 | 1067 | C |
| ATOM | 4663 | C | THR | B | 89 | 15.246 | 26.634 | 107.810 | 1.00 | 31.71 | | C |
| ANISOU | 4663 | C | THR | B | 89 | 5366 | 3851 | 2831 | 167 | 590 | 952 | C |
| ATOM | 4664 | O | THR | B | 89 | 14.988 | 26.217 | 108.937 | 1.00 | 32.49 | | O |
| ANISOU | 4664 | O | THR | B | 89 | 5486 | 3987 | 2871 | 190 | 630 | 1093 | O |
| ATOM | 4666 | N | VAL | B | 90 | 16.119 | 27.604 | 107.591 | 1.00 | 32.15 | | N |
| ANISOU | 4666 | N | VAL | B | 90 | 5318 | 4034 | 2865 | 280 | 527 | 854 | N |
| ATOM | 4667 | CA | VAL | B | 90 | 16.844 | 28.269 | 108.673 | 1.00 | 31.40 | | C |
| ANISOU | 4667 | CA | VAL | B | 90 | 5118 | 4137 | 2674 | 426 | 487 | 886 | C |
| ATOM | 4669 | CB | VAL | B | 90 | 18.082 | 28.979 | 108.112 | 1.00 | 28.96 | | C |
| ANISOU | 4669 | CB | VAL | B | 90 | 4733 | 3889 | 2382 | 540 | 428 | 775 | C |
| ATOM | 4671 | CG1 | VAL | B | 90 | 18.789 | 29.790 | 109.171 | 1.00 | 27.31 | | C |
| ANISOU | 4671 | CG1 | VAL | B | 90 | 4399 | 3907 | 2072 | 649 | 371 | 775 | C |
| ATOM | 4675 | CG2 | VAL | B | 90 | 19.011 | 27.948 | 107.524 | 1.00 | 31.86 | | C |
| ANISOU | 4675 | CG2 | VAL | B | 90 | 5213 | 4082 | 2809 | 649 | 461 | 810 | C |
| ATOM | 4679 | C | VAL | B | 90 | 15.938 | 29.189 | 109.492 | 1.00 | 29.72 | | C |
| ANISOU | 4679 | C | VAL | B | 90 | 4788 | 4116 | 2389 | 352 | 480 | 875 | C |
| ATOM | 4680 | O | VAL | B | 90 | 15.960 | 29.165 | 110.725 | 1.00 | 32.97 | | O |
| ANISOU | 4680 | O | VAL | B | 90 | 5182 | 4653 | 2693 | 412 | 491 | 966 | O |
| ATOM | 4682 | N | VAL | B | 91 | 15.070 | 29.930 | 108.823 | 1.00 | 28.85 | | N |
| ANISOU | 4682 | N | VAL | B | 91 | 4605 | 4027 | 2330 | 226 | 472 | 777 | N |
| ATOM | 4683 | CA | VAL | B | 91 | 14.053 | 30.710 | 109.511 | 1.00 | 28.32 | | C |
| ANISOU | 4683 | CA | VAL | B | 91 | 4429 | 4113 | 2217 | 161 | 493 | 770 | C |
| ATOM | 4685 | CB | VAL | B | 91 | 13.181 | 31.537 | 108.515 | 1.00 | 28.61 | | C |
| ANISOU | 4685 | CB | VAL | B | 91 | 4375 | 4158 | 2339 | 49 | 475 | 669 | C |
| ATOM | 4687 | CG1 | VAL | B | 91 | 11.966 | 32.158 | 109.253 | 1.00 | 29.19 | | C |
| ANISOU | 4687 | CG1 | VAL | B | 91 | 4333 | 4373 | 2384 | -8 | 523 | 687 | C |
| ATOM | 4691 | CG2 | VAL | B | 91 | 14.019 | 32.589 | 107.815 | 1.00 | 25.34 | | C |
| ANISOU | 4691 | CG2 | VAL | B | 91 | 3904 | 3770 | 1955 | 118 | 414 | 541 | C |
| ATOM | 4695 | C | VAL | B | 91 | 13.152 | 29.842 | 110.388 | 1.00 | 29.16 | | C |
| ANISOU | 4695 | C | VAL | B | 91 | 4584 | 4215 | 2279 | 91 | 571 | 917 | C |
| ATOM | 4696 | O | VAL | B | 91 | 12.870 | 30.187 | 111.525 | 1.00 | 27.75 | | O |
| ANISOU | 4696 | O | VAL | B | 91 | 4353 | 4191 | 1998 | 122 | 604 | 960 | O |
| ATOM | 4698 | N | ASN | B | 92 | 12.689 | 28.714 | 109.853 | 1.00 | 30.01 | | N |
| ANISOU | 4698 | N | ASN | B | 92 | 4801 | 4143 | 2459 | -16 | 608 | 987 | N |
| ATOM | 4699 | CA | ASN | B | 92 | 11.834 | 27.831 | 110.613 | 1.00 | 31.12 | | C |
| ANISOU | 4699 | CA | ASN | B | 92 | 4996 | 4254 | 2576 | -108 | 694 | 1137 | C |
| ATOM | 4701 | CB | ASN | B | 92 | 11.203 | 26.738 | 109.759 | 1.00 | 33.49 | | C |
| ANISOU | 4701 | CB | ASN | B | 92 | 5404 | 4334 | 2985 | -282 | 729 | 1166 | C |
| ATOM | 4704 | CG | ASN | B | 92 | 10.053 | 27.245 | 108.942 | 1.00 | 34.91 | | C |
| ANISOU | 4704 | CG | ASN | B | 92 | 5465 | 4567 | 3235 | -461 | 706 | 1076 | C |
| ATOM | 4705 | OD1 | ASN | B | 92 | 8.991 | 27.571 | 109.484 | 1.00 | 36.63 | | O |
| ANISOU | 4705 | OD1 | ASN | B | 92 | 5560 | 4923 | 3436 | -550 | 749 | 1121 | O |
| ATOM | 4706 | ND2 | ASN | B | 92 | 10.237 | 27.294 | 107.627 | 1.00 | 33.92 | | N |
| ANISOU | 4706 | ND2 | ASN | B | 92 | 5365 | 4345 | 3179 | -513 | 642 | 958 | N |
| ATOM | 4709 | C | ASN | B | 92 | 12.582 | 27.191 | 111.765 | 1.00 | 31.50 | | C |
| ANISOU | 4709 | C | ASN | B | 92 | 5136 | 4313 | 2519 | 31 | 726 | 1284 | C |
| ATOM | 4710 | O | ASN | B | 92 | 12.002 | 26.953 | 112.788 | 1.00 | 31.76 | | O |
| ANISOU | 4710 | O | ASN | B | 92 | 5168 | 4431 | 2470 | 3 | 794 | 1406 | O |
| ATOM | 4712 | N | SER | B | 93 | 13.867 | 26.928 | 111.584 | 1.00 | 31.54 | | N |

FIG. 18 (continued)

| | | | | | | | | | | | | |
|---|---|---|---|---|---|---|---|---|---|---|---|---|
| ANISOU | 4712 | N | SER | B | 93 | 5211 | 4249 | 2522 | 187 | 678 | 1282 | N |
| ATOM | 4713 | CA | SER | B | 93 | 14.696 | 26.383 | 112.664 | 1.00 | 33.94 | | C |
| ANISOU | 4713 | CA | SER | B | 93 | 5580 | 4597 | 2718 | 352 | 685 | 1436 | C |
| ATOM | 4715 | CB | SER | B | 93 | 16.050 | 25.936 | 112.113 | 1.00 | 34.40 | | C |
| ANISOU | 4715 | CB | SER | B | 93 | 5706 | 4533 | 2829 | 514 | 639 | 1430 | C |
| ATOM | 4718 | OG | SER | B | 93 | 16.634 | 25.105 | 113.079 | 1.00 | 42.61 | | O |
| ANISOU | 4718 | OG | SER | B | 93 | 6831 | 5569 | 3788 | 661 | 660 | 1630 | O |
| ATOM | 4720 | C | SER | B | 93 | 14.894 | 27.384 | 113.811 | 1.00 | 31.81 | | C |
| ANISOU | 4720 | C | SER | B | 93 | 5185 | 4621 | 2279 | 434 | 646 | 1420 | C |
| ATOM | 4721 | O | SER | B | 93 | 14.842 | 27.026 | 115.004 | 1.00 | 31.82 | | O |
| ANISOU | 4721 | O | SER | B | 93 | 5219 | 4730 | 2143 | 486 | 682 | 1572 | O |
| ATOM | 4723 | N | ILE | B | 94 | 15.097 | 28.647 | 113.441 | 1.00 | 30.37 | | N |
| ANISOU | 4723 | N | ILE | B | 94 | 4872 | 4565 | 2103 | 438 | 581 | 1232 | N |
| ATOM | 4724 | CA | ILE | B | 94 | 15.211 | 29.724 | 114.420 | 1.00 | 30.77 | | C |
| ANISOU | 4724 | CA | ILE | B | 94 | 4812 | 4874 | 2006 | 486 | 552 | 1164 | C |
| ATOM | 4726 | CB | ILE | B | 94 | 15.569 | 31.105 | 113.758 | 1.00 | 28.69 | | C |
| ANISOU | 4726 | CB | ILE | B | 94 | 4427 | 4677 | 1796 | 483 | 484 | 942 | C |
| ATOM | 4728 | CG1 | ILE | B | 94 | 17.001 | 31.071 | 113.219 | 1.00 | 29.20 | | C |
| ANISOU | 4728 | CG1 | ILE | B | 94 | 4490 | 4705 | 1898 | 596 | 396 | 899 | C |
| ATOM | 4731 | CD1 | ILE | B | 94 | 17.262 | 32.064 | 112.118 | 1.00 | 27.32 | | C |
| ANISOU | 4731 | CD1 | ILE | B | 94 | 4175 | 4431 | 1776 | 559 | 355 | 719 | C |
| ATOM | 4735 | CG2 | ILE | B | 94 | 15.421 | 32.269 | 114.790 | 1.00 | 26.61 | | C |
| ANISOU | 4735 | CG2 | ILE | B | 94 | 4069 | 4651 | 1392 | 496 | 483 | 843 | C |
| ATOM | 4739 | C | ILE | B | 94 | 13.927 | 29.809 | 115.213 | 1.00 | 28.70 | | C |
| ANISOU | 4739 | C | ILE | B | 94 | 4528 | 4708 | 1669 | 385 | 648 | 1220 | C |
| ATOM | 4740 | O | ILE | B | 94 | 13.956 | 29.878 | 116.447 | 1.00 | 30.80 | | O |
| ANISOU | 4740 | O | ILE | B | 94 | 4792 | 5152 | 1758 | 438 | 671 | 1290 | O |
| ATOM | 4742 | N | CYS | B | 95 | 12.800 | 29.805 | 114.506 | 1.00 | 30.37 | | N |
| ANISOU | 4742 | N | CYS | B | 95 | 4713 | 4821 | 2005 | 240 | 705 | 1191 | N |
| ATOM | 4743 | CA | CYS | B | 95 | 11.494 | 29.939 | 115.154 | 1.00 | 32.29 | | C |
| ANISOU | 4743 | CA | CYS | B | 95 | 4899 | 5167 | 2203 | 137 | 810 | 1239 | C |
| ATOM | 4745 | CB | CYS | B | 95 | 10.381 | 30.179 | 114.116 | 1.00 | 33.22 | | C |
| ANISOU | 4745 | CB | CYS | B | 95 | 4935 | 5204 | 2484 | -13 | 834 | 1170 | C |
| ATOM | 4748 | SG | CYS | B | 95 | 10.551 | 31.735 | 113.210 | 1.00 | 32.78 | | S |
| ANISOU | 4748 | SG | CYS | B | 95 | 4745 | 5196 | 2513 | 24 | 754 | 943 | S |
| ATOM | 4750 | C | CYS | B | 95 | 11.175 | 28.720 | 116.017 | 1.00 | 34.28 | | C |
| ANISOU | 4750 | C | CYS | B | 95 | 5261 | 5391 | 2373 | 110 | 898 | 1463 | C |
| ATOM | 4751 | O | CYS | B | 95 | 10.606 | 28.846 | 117.109 | 1.00 | 31.93 | | O |
| ANISOU | 4751 | O | CYS | B | 95 | 4934 | 5261 | 1936 | 101 | 982 | 1534 | O |
| ATOM | 4753 | N | ASN | B | 96 | 11.569 | 27.532 | 115.551 | 1.00 | 34.95 | | N |
| ANISOU | 4753 | N | ASN | B | 96 | 5484 | 5257 | 2539 | 104 | 892 | 1579 | N |
| ATOM | 4754 | CA | ASN | B | 96 | 11.352 | 26.318 | 116.366 | 1.00 | 35.89 | | C |
| ANISOU | 4754 | CA | ASN | B | 96 | 5734 | 5310 | 2593 | 88 | 984 | 1818 | C |
| ATOM | 4756 | CB | ASN | B | 96 | 11.680 | 25.048 | 115.567 | 1.00 | 37.79 | | C |
| ANISOU | 4756 | CB | ASN | B | 96 | 6139 | 5237 | 2981 | 62 | 991 | 1907 | C |
| ATOM | 4759 | CG | ASN | B | 96 | 10.696 | 24.808 | 114.430 | 1.00 | 39.12 | | C |
| ANISOU | 4759 | CG | ASN | B | 96 | 6297 | 5235 | 3330 | -156 | 1022 | 1825 | C |
| ATOM | 4760 | OD1 | ASN | B | 96 | 9.541 | 25.234 | 114.497 | 1.00 | 41.20 | | O |
| ANISOU | 4760 | OD1 | ASN | B | 96 | 6442 | 5608 | 3605 | -307 | 1071 | 1793 | O |
| ATOM | 4761 | ND2 | ASN | B | 96 | 11.143 | 24.122 | 113.393 | 1.00 | 39.06 | | N |
| ANISOU | 4761 | ND2 | ASN | B | 96 | 6408 | 4975 | 3458 | -173 | 994 | 1787 | N |
| ATOM | 4764 | C | ASN | B | 96 | 12.131 | 26.301 | 117.678 | 1.00 | 36.50 | | C |
| ANISOU | 4764 | C | ASN | B | 96 | 5846 | 5570 | 2452 | 258 | 970 | 1937 | C |
| ATOM | 4765 | O | ASN | B | 96 | 11.581 | 25.921 | 118.716 | 1.00 | 35.64 | | O |
| ANISOU | 4765 | O | ASN | B | 96 | 5772 | 5560 | 2212 | 230 | 1066 | 2100 | O |
| ATOM | 4767 | N | THR | B | 97 | 13.400 | 26.684 | 117.636 | 1.00 | 35.03 | | N |
| ANISOU | 4767 | N | THR | B | 97 | 5646 | 5445 | 2217 | 424 | 850 | 1867 | N |
| ATOM | 4768 | CA | THR | B | 97 | 14.241 | 26.633 | 118.816 | 1.00 | 40.35 | | C |
| ANISOU | 4768 | CA | THR | B | 97 | 6341 | 6315 | 2676 | 586 | 806 | 1981 | C |
| ATOM | 4770 | CB | THR | B | 97 | 15.726 | 26.591 | 118.483 | 1.00 | 41.26 | | C |
| ANISOU | 4770 | CB | THR | B | 97 | 6456 | 6414 | 2806 | 763 | 675 | 1956 | C |
| ATOM | 4772 | OG1 | THR | B | 97 | 16.087 | 27.847 | 117.900 | 1.00 | 42.29 | | O |
| ANISOU | 4772 | OG1 | THR | B | 97 | 6450 | 6639 | 2979 | 753 | 588 | 1696 | O |
| ATOM | 4774 | CG2 | THR | B | 97 | 16.034 | 25.471 | 117.519 | 1.00 | 42.63 | | C |
| ANISOU | 4774 | CG2 | THR | B | 97 | 6755 | 6266 | 3178 | 787 | 696 | 2045 | C |
| ATOM | 4778 | C | THR | B | 97 | 14.046 | 27.829 | 119.750 | 1.00 | 40.13 | | C |
| ANISOU | 4778 | C | THR | B | 97 | 6196 | 6605 | 2448 | 590 | 796 | 1859 | C |
| ATOM | 4779 | O | THR | B | 97 | 14.254 | 27.679 | 120.931 | 1.00 | 43.20 | | O |
| ANISOU | 4779 | O | THR | B | 97 | 6614 | 7185 | 2615 | 663 | 803 | 1983 | O |
| ATOM | 4781 | N | THR | B | 98 | 13.699 | 29.006 | 119.225 | 1.00 | 38.96 | | N |
| ANISOU | 4781 | N | THR | B | 98 | 5926 | 6508 | 2371 | 522 | 779 | 1619 | N |
| ATOM | 4782 | CA | THR | B | 98 | 13.589 | 30.224 | 120.067 | 1.00 | 39.66 | | C |
| ANISOU | 4782 | CA | THR | B | 98 | 5918 | 6867 | 2283 | 535 | 779 | 1466 | C |
| ATOM | 4784 | CB | THR | B | 98 | 14.147 | 31.534 | 119.348 | 1.00 | 38.40 | | C |
| ANISOU | 4784 | CB | THR | B | 98 | 5650 | 6727 | 2213 | 548 | 682 | 1191 | C |
| ATOM | 4786 | OG1 | THR | B | 98 | 13.373 | 31.854 | 118.170 | 1.00 | 36.81 | | O |
| ANISOU | 4786 | OG1 | THR | B | 98 | 5397 | 6350 | 2239 | 447 | 721 | 1093 | O |
| ATOM | 4788 | CG2 | THR | B | 98 | 15.676 | 31.381 | 118.966 | 1.00 | 36.59 | | C |
| ANISOU | 4788 | CG2 | THR | B | 98 | 5427 | 6473 | 2003 | 665 | 532 | 1178 | C |

FIG. 18 (continued)

| | | | | | | | | | | | | |
|---|---|---|---|---|---|---|---|---|---|---|---|---|
| ATOM | 4792 | C | THR | B | 98 | 12.162 | 30.509 | 120.496 | 1.00 | 41.48 | | C |
| ANISOU | 4792 | C | THR | B | 98 | 6106 | 7170 | 2486 | 420 | 930 | 1462 | C |
| ATOM | 4793 | O | THR | B | 98 | 11.957 | 31.195 | 121.473 | 1.00 | 42.87 | | O |
| ANISOU | 4793 | O | THR | B | 98 | 6245 | 7571 | 2471 | 439 | 975 | 1395 | O |
| ATOM | 4795 | N | GLY | B | 99 | 11.182 | 30.000 | 119.741 | 1.00 | 42.32 | | N |
| ANISOU | 4795 | N | GLY | B | 99 | 6208 | 7093 | 2778 | 296 | 1011 | 1520 | N |
| ATOM | 4796 | CA | GLY | B | 99 | 9.795 | 30.405 | 119.871 | 1.00 | 41.49 | | C |
| ANISOU | 4796 | CA | GLY | B | 99 | 6009 | 7051 | 2703 | 181 | 1146 | 1488 | C |
| ATOM | 4799 | C | GLY | B | 99 | 9.461 | 31.683 | 119.097 | 1.00 | 41.45 | | C |
| ANISOU | 4799 | C | GLY | B | 99 | 5866 | 7051 | 2831 | 165 | 1122 | 1250 | C |
| ATOM | 4800 | O | GLY | B | 99 | 8.366 | 32.233 | 119.261 | 1.00 | 41.20 | | O |
| ANISOU | 4800 | O | GLY | B | 99 | 5729 | 7106 | 2821 | 108 | 1233 | 1202 | O |
| ATOM | 4802 | N | ALA | B | 100 | 10.382 | 32.162 | 118.250 | 1.00 | 39.26 | | N |
| ANISOU | 4802 | N | ALA | B | 100 | 5585 | 6682 | 2650 | 221 | 990 | 1115 | N |
| ATOM | 4803 | CA | ALA | B | 100 | 10.220 | 33.467 | 117.609 | 1.00 | 38.87 | | C |
| ANISOU | 4803 | CA | ALA | B | 100 | 5423 | 6637 | 2707 | 227 | 966 | 901 | C |
| ATOM | 4805 | CB | ALA | B | 100 | 11.526 | 33.885 | 116.851 | 1.00 | 37.41 | | C |
| ANISOU | 4805 | CB | ALA | B | 100 | 5259 | 6368 | 2587 | 296 | 820 | 780 | C |
| ATOM | 4809 | C | ALA | B | 100 | 9.039 | 33.418 | 116.638 | 1.00 | 41.43 | | C |
| ANISOU | 4809 | C | ALA | B | 100 | 5661 | 6852 | 3228 | 114 | 1017 | 916 | C |
| ATOM | 4810 | O | ALA | B | 100 | 8.802 | 32.404 | 115.968 | 1.00 | 40.10 | | O |
| ANISOU | 4810 | O | ALA | B | 100 | 5537 | 6536 | 3163 | 24 | 1004 | 1033 | O |
| ATOM | 4812 | N | GLU | B | 101 | 8.288 | 34.507 | 116.562 | 1.00 | 42.61 | | N |
| ANISOU | 4812 | N | GLU | B | 101 | 5684 | 7075 | 3429 | 119 | 1075 | 795 | N |
| ATOM | 4813 | CA | GLU | B | 101 | 7.174 | 34.558 | 115.621 | 1.00 | 44.07 | | C |
| ANISOU | 4813 | CA | GLU | B | 101 | 5754 | 7193 | 3796 | 26 | 1104 | 814 | C |
| ATOM | 4815 | CB | GLU | B | 101 | 6.358 | 35.827 | 115.824 | 1.00 | 46.02 | | C |
| ANISOU | 4815 | CB | GLU | B | 101 | 5856 | 7554 | 4076 | 80 | 1193 | 699 | C |
| ATOM | 4818 | CG | GLU | B | 101 | 5.471 | 36.168 | 114.626 | 1.00 | 47.19 | | C |
| ANISOU | 4818 | CG | GLU | B | 101 | 5863 | 7638 | 4427 | 26 | 1173 | 695 | C |
| ATOM | 4821 | CD | GLU | B | 101 | 4.348 | 37.119 | 114.972 | 1.00 | 50.01 | | C |
| ANISOU | 4821 | CD | GLU | B | 101 | 6052 | 8123 | 4825 | 80 | 1302 | 651 | C |
| ATOM | 4822 | OE1 | GLU | B | 101 | 4.357 | 37.703 | 116.097 | 1.00 | 53.18 | | O |
| ANISOU | 4822 | OE1 | GLU | B | 101 | 6464 | 8643 | 5099 | 171 | 1413 | 576 | O |
| ATOM | 4823 | OE2 | GLU | B | 101 | 3.461 | 37.270 | 114.097 | 1.00 | 52.27 | | O |
| ANISOU | 4823 | OE2 | GLU | B | 101 | 6195 | 8398 | 5267 | 35 | 1291 | 690 | O |
| ATOM | 4824 | C | GLU | B | 101 | 7.739 | 34.491 | 114.193 | 1.00 | 40.05 | | C |
| ANISOU | 4824 | C | GLU | B | 101 | 5272 | 6507 | 3440 | 2 | 968 | 770 | C |
| ATOM | 4825 | O | GLU | B | 101 | 8.711 | 35.171 | 113.888 | 1.00 | 37.15 | | O |
| ANISOU | 4825 | O | GLU | B | 101 | 4934 | 6103 | 3076 | 86 | 887 | 650 | O |
| ATOM | 4827 | N | LYS | B | 102 | 7.120 | 33.663 | 113.357 | 1.00 | 38.96 | | N |
| ANISOU | 4827 | N | LYS | B | 102 | 5122 | 6267 | 3415 | -127 | 952 | 862 | N |
| ATOM | 4828 | CA | LYS | B | 102 | 7.575 | 33.402 | 111.997 | 1.00 | 39.68 | | C |
| ANISOU | 4828 | CA | LYS | B | 102 | 5258 | 6194 | 3623 | -171 | 836 | 830 | C |
| ATOM | 4830 | CB | LYS | B | 102 | 6.956 | 32.093 | 111.516 | 1.00 | 40.34 | | C |
| ANISOU | 4830 | CB | LYS | B | 102 | 5386 | 6173 | 3769 | -339 | 844 | 952 | C |
| ATOM | 4833 | CG | LYS | B | 102 | 7.490 | 31.579 | 110.188 | 1.00 | 41.36 | | C |
| ANISOU | 4833 | CG | LYS | B | 102 | 5605 | 6122 | 3986 | -396 | 740 | 915 | C |
| ATOM | 4836 | CD | LYS | B | 102 | 6.772 | 30.316 | 109.826 | 1.00 | 43.75 | | C |
| ANISOU | 4836 | CD | LYS | B | 102 | 5960 | 6320 | 4344 | -586 | 763 | 1013 | C |
| ATOM | 4839 | CE | LYS | B | 102 | 7.200 | 29.754 | 108.478 | 1.00 | 44.40 | | C |
| ANISOU | 4839 | CE | LYS | B | 102 | 6147 | 6223 | 4501 | -663 | 673 | 955 | C |
| ATOM | 4842 | NZ | LYS | B | 102 | 6.676 | 28.337 | 108.436 | 1.00 | 47.10 | | N |
| ANISOU | 4842 | NZ | LYS | B | 102 | 6594 | 6424 | 4878 | -849 | 722 | 1052 | N |
| ATOM | 4846 | C | LYS | B | 102 | 7.212 | 34.543 | 111.044 | 1.00 | 36.73 | | C |
| ANISOU | 4846 | C | LYS | B | 102 | 4759 | 5833 | 3363 | -151 | 791 | 723 | C |
| ATOM | 4847 | O | LYS | B | 102 | 6.055 | 34.889 | 110.912 | 1.00 | 37.83 | | O |
| ANISOU | 4847 | O | LYS | B | 102 | 4753 | 6053 | 3566 | -198 | 837 | 746 | O |
| ATOM | 4849 | N | PRO | B | 103 | 8.208 | 35.146 | 110.381 | 1.00 | 36.85 | | N |
| ANISOU | 4849 | N | PRO | B | 103 | 4819 | 5776 | 3407 | -75 | 704 | 620 | N |
| ATOM | 4850 | CA | PRO | B | 103 | 7.892 | 36.200 | 109.415 | 1.00 | 34.11 | | C |
| ANISOU | 4850 | CA | PRO | B | 103 | 4371 | 5422 | 3168 | -53 | 662 | 547 | C |
| ATOM | 4852 | CB | PRO | B | 103 | 9.228 | 36.900 | 109.240 | 1.00 | 32.94 | | C |
| ANISOU | 4852 | CB | PRO | B | 103 | 4295 | 5216 | 3004 | 49 | 607 | 435 | C |
| ATOM | 4855 | CG | PRO | B | 103 | 10.192 | 35.808 | 109.340 | 1.00 | 33.92 | | C |
| ANISOU | 4855 | CG | PRO | B | 103 | 4555 | 5269 | 3063 | 35 | 567 | 473 | C |
| ATOM | 4858 | CD | PRO | B | 103 | 9.669 | 34.918 | 110.440 | 1.00 | 36.48 | | C |
| ANISOU | 4858 | CD | PRO | B | 103 | 4903 | 5656 | 3300 | -1 | 642 | 579 | C |
| ATOM | 4861 | C | PRO | B | 103 | 7.370 | 35.653 | 108.077 | 1.00 | 31.43 | | C |
| ANISOU | 4861 | C | PRO | B | 103 | 4010 | 5012 | 2920 | -178 | 588 | 595 | C |
| ATOM | 4862 | O | PRO | B | 103 | 7.572 | 34.475 | 107.735 | 1.00 | 31.19 | | O |
| ANISOU | 4862 | O | PRO | B | 103 | 4083 | 4890 | 2877 | -277 | 557 | 645 | O |
| ATOM | 4863 | N | LYS | B | 104 | 6.659 | 36.519 | 107.371 | 1.00 | 31.56 | | N |
| ANISOU | 4863 | N | LYS | B | 104 | 3893 | 5076 | 3021 | -168 | 566 | 582 | N |
| ATOM | 4864 | CA | LYS | B | 104 | 6.061 | 36.231 | 106.075 | 1.00 | 31.39 | | C |
| ANISOU | 4864 | CA | LYS | B | 104 | 3821 | 5038 | 3068 | -282 | 480 | 621 | C |
| ATOM | 4866 | CB | LYS | B | 104 | 4.820 | 37.102 | 105.865 | 1.00 | 33.93 | | C |
| ANISOU | 4866 | CB | LYS | B | 104 | 3932 | 5492 | 3469 | -258 | 495 | 663 | C |
| ATOM | 4869 | CG | LYS | B | 104 | 3.733 | 36.963 | 106.893 | 1.00 | 37.31 | | C |

FIG. 18 (continued)

| | | | | | | | | | | | | |
|---|---|---|---|---|---|---|---|---|---|---|---|---|
| ANISOU | 4869 | CG | LYS | B | 104 | 4225 | 6052 | 3898 | -277 | 606 | 729 | C |
| ATOM | 4872 | CD | LYS | B | 104 | 3.037 | 35.655 | 106.840 | 1.00 | 39.14 | | C |
| ANISOU | 4872 | CD | LYS | B | 104 | 4442 | 6308 | 4121 | -477 | 600 | 816 | C |
| ATOM | 4875 | CE | LYS | B | 104 | 1.709 | 35.751 | 107.602 | 1.00 | 42.70 | | C |
| ANISOU | 4875 | CE | LYS | B | 104 | 4688 | 6933 | 4603 | -501 | 709 | 898 | C |
| ATOM | 4878 | NZ | LYS | B | 104 | 1.585 | 34.618 | 108.507 | 1.00 | 45.38 | | N |
| ANISOU | 4878 | NZ | LYS | B | 104 | 5100 | 7265 | 4877 | -618 | 795 | 962 | N |
| ATOM | 4882 | C | LYS | B | 104 | 7.031 | 36.533 | 104.923 | 1.00 | 29.82 | | C |
| ANISOU | 4882 | C | LYS | B | 104 | 3714 | 4734 | 2881 | -254 | 385 | 556 | C |
| ATOM | 4883 | O | LYS | B | 104 | 6.681 | 36.423 | 103.766 | 1.00 | 32.79 | | O |
| ANISOU | 4883 | O | LYS | B | 104 | 4066 | 5107 | 3287 | -335 | 304 | 574 | O |
| ATOM | 4885 | N | PHE | B | 105 | 8.241 | 36.937 | 105.249 | 1.00 | 26.43 | | N |
| ANISOU | 4885 | N | PHE | B | 105 | 3382 | 4241 | 2419 | -146 | 396 | 481 | N |
| ATOM | 4886 | CA | PHE | B | 105 | 9.270 | 37.214 | 104.277 | 1.00 | 28.05 | | C |
| ANISOU | 4886 | CA | PHE | B | 105 | 3672 | 4355 | 2632 | -117 | 330 | 422 | C |
| ATOM | 4888 | CB | PHE | B | 105 | 9.344 | 38.732 | 103.986 | 1.00 | 28.42 | | C |
| ANISOU | 4888 | CB | PHE | B | 105 | 3640 | 4417 | 2739 | -12 | 333 | 381 | C |
| ATOM | 4891 | CG | PHE | B | 105 | 9.686 | 39.533 | 105.201 | 1.00 | 29.60 | | C |
| ANISOU | 4891 | CG | PHE | B | 105 | 3774 | 4591 | 2879 | 97 | 412 | 314 | C |
| ATOM | 4892 | CD1 | PHE | B | 105 | 11.016 | 39.848 | 105.497 | 1.00 | 28.34 | | C |
| ANISOU | 4892 | CD1 | PHE | B | 105 | 3701 | 4380 | 2688 | 153 | 411 | 225 | C |
| ATOM | 4894 | CE1 | PHE | B | 105 | 11.339 | 40.536 | 106.605 | 1.00 | 27.89 | | C |
| ANISOU | 4894 | CE1 | PHE | B | 105 | 3636 | 4359 | 2602 | 225 | 470 | 145 | C |
| ATOM | 4896 | CZ | PHE | B | 105 | 10.353 | 40.933 | 107.492 | 1.00 | 30.47 | | C |
| ANISOU | 4896 | CZ | PHE | B | 105 | 3885 | 4766 | 2926 | 261 | 552 | 147 | C |
| ATOM | 4898 | CE2 | PHE | B | 105 | 9.017 | 40.615 | 107.235 | 1.00 | 32.38 | | C |
| ANISOU | 4898 | CE2 | PHE | B | 105 | 4031 | 5062 | 3211 | 224 | 571 | 248 | C |
| ATOM | 4900 | CD2 | PHE | B | 105 | 8.695 | 39.906 | 106.082 | 1.00 | 30.21 | | C |
| ANISOU | 4900 | CD2 | PHE | B | 105 | 3750 | 4760 | 2970 | 133 | 490 | 334 | C |
| ATOM | 4902 | C | PHE | B | 105 | 10.557 | 36.718 | 104.893 | 1.00 | 25.42 | | C |
| ANISOU | 4902 | C | PHE | B | 105 | 3466 | 3956 | 2235 | -65 | 347 | 377 | C |
| ATOM | 4903 | O | PHE | B | 105 | 10.595 | 36.330 | 106.086 | 1.00 | 26.06 | | O |
| ANISOU | 4903 | O | PHE | B | 105 | 3564 | 4076 | 2261 | -39 | 401 | 397 | O |
| ATOM | 4905 | N | LEU | B | 106 | 11.610 | 36.761 | 104.097 | 1.00 | 24.82 | | N |
| ANISOU | 4905 | N | LEU | B | 106 | 3468 | 3801 | 2161 | -42 | 303 | 327 | N |
| ATOM | 4906 | CA | LEU | B | 106 | 12.932 | 36.319 | 104.522 | 1.00 | 23.93 | | C |
| ANISOU | 4906 | CA | LEU | B | 106 | 3450 | 3640 | 2001 | 22 | 309 | 291 | C |
| ATOM | 4908 | CB | LEU | B | 106 | 13.656 | 35.605 | 103.366 | 1.00 | 24.11 | | C |
| ANISOU | 4908 | CB | LEU | B | 106 | 3577 | 3558 | 2027 | -9 | 273 | 276 | C |
| ATOM | 4911 | CG | LEU | B | 106 | 13.090 | 34.248 | 102.935 | 1.00 | 24.95 | | C |
| ANISOU | 4911 | CG | LEU | B | 106 | 3772 | 3587 | 2122 | -118 | 270 | 326 | C |
| ATOM | 4913 | CD1 | LEU | B | 106 | 13.804 | 33.799 | 101.633 | 1.00 | 24.23 | | C |
| ANISOU | 4913 | CD1 | LEU | B | 106 | 3785 | 3393 | 2027 | -141 | 247 | 275 | C |
| ATOM | 4917 | CD2 | LEU | B | 106 | 13.209 | 33.139 | 104.023 | 1.00 | 21.33 | | C |
| ANISOU | 4917 | CD2 | LEU | B | 106 | 3388 | 3088 | 1628 | -103 | 317 | 389 | C |
| ATOM | 4921 | C | LEU | B | 106 | 13.733 | 37.534 | 104.979 | 1.00 | 24.42 | | C |
| ANISOU | 4921 | C | LEU | B | 106 | 3466 | 3744 | 2068 | 119 | 318 | 209 | C |
| ATOM | 4922 | O | LEU | B | 106 | 14.134 | 38.346 | 104.151 | 1.00 | 23.19 | | O |
| ANISOU | 4922 | O | LEU | B | 106 | 3293 | 3556 | 1961 | 131 | 298 | 164 | O |
| ATOM | 4924 | N | PRO | B | 107 | 13.990 | 37.652 | 106.301 | 1.00 | 24.07 | | N |
| ANISOU | 4924 | N | PRO | B | 107 | 3409 | 3775 | 1963 | 175 | 350 | 190 | N |
| ATOM | 4925 | CA | PRO | B | 107 | 14.884 | 38.704 | 106.754 | 1.00 | 23.53 | | C |
| ANISOU | 4925 | CA | PRO | B | 107 | 3309 | 3743 | 1886 | 239 | 351 | 88 | C |
| ATOM | 4927 | CB | PRO | B | 107 | 14.618 | 38.780 | 108.300 | 1.00 | 23.20 | | C |
| ANISOU | 4927 | CB | PRO | B | 107 | 3249 | 3818 | 1750 | 274 | 394 | 74 | C |
| ATOM | 4930 | CG | PRO | B | 107 | 13.402 | 37.888 | 108.535 | 1.00 | 24.16 | | C |
| ANISOU | 4930 | CG | PRO | B | 107 | 3372 | 3955 | 1853 | 227 | 432 | 187 | C |
| ATOM | 4933 | CD | PRO | B | 107 | 13.510 | 36.859 | 107.439 | 1.00 | 24.61 | | C |
| ANISOU | 4933 | CD | PRO | B | 107 | 3493 | 3903 | 1953 | 171 | 389 | 257 | C |
| ATOM | 4936 | C | PRO | B | 107 | 16.324 | 38.292 | 106.423 | 1.00 | 23.84 | | C |
| ANISOU | 4936 | C | PRO | B | 107 | 3396 | 3752 | 1908 | 270 | 307 | 65 | C |
| ATOM | 4937 | O | PRO | B | 107 | 16.574 | 37.228 | 105.810 | 1.00 | 22.24 | | O |
| ANISOU | 4937 | O | PRO | B | 107 | 3261 | 3484 | 1706 | 260 | 291 | 124 | O |
| ATOM | 4938 | N | ASP | B | 108 | 17.259 | 39.146 | 106.791 | 1.00 | 23.41 | | N |
| ANISOU | 4938 | N | ASP | B | 108 | 3304 | 3744 | 1848 | 303 | 296 | -29 | N |
| ATOM | 4939 | CA | ASP | B | 108 | 18.654 | 38.927 | 106.446 | 1.00 | 23.73 | | C |
| ANISOU | 4939 | CA | ASP | B | 108 | 3347 | 3783 | 1887 | 333 | 259 | -55 | C |
| ATOM | 4941 | CB | ASP | B | 108 | 19.305 | 40.261 | 106.107 | 1.00 | 23.50 | | C |
| ANISOU | 4941 | CB | ASP | B | 108 | 3260 | 3747 | 1921 | 310 | 261 | -163 | C |
| ATOM | 4944 | CG | ASP | B | 108 | 18.761 | 40.831 | 104.816 | 1.00 | 22.33 | | C |
| ANISOU | 4944 | CG | ASP | B | 108 | 3124 | 3488 | 1872 | 267 | 286 | -147 | C |
| ATOM | 4945 | OD1 | ASP | B | 108 | 18.598 | 40.044 | 103.853 | 1.00 | 22.59 | | O |
| ANISOU | 4945 | OD1 | ASP | B | 108 | 3206 | 3464 | 1914 | 256 | 278 | -76 | O |
| ATOM | 4946 | OD2 | ASP | B | 108 | 18.493 | 42.057 | 104.765 | 1.00 | 24.59 | | O |
| ANISOU | 4946 | OD2 | ASP | B | 108 | 3379 | 3742 | 2221 | 246 | 314 | -204 | O |
| ATOM | 4947 | C | ASP | B | 108 | 19.419 | 38.193 | 107.524 | 1.00 | 22.89 | | C |
| ANISOU | 4947 | C | ASP | B | 108 | 3240 | 3779 | 1677 | 398 | 229 | -29 | C |
| ATOM | 4948 | O | ASP | B | 108 | 20.264 | 37.354 | 107.193 | 1.00 | 22.23 | | O |
| ANISOU | 4948 | O | ASP | B | 108 | 3178 | 3677 | 1591 | 449 | 208 | 19 | O |

FIG. 18 (continued)

| | | | | | | | | | | | | |
|---|---|---|---|---|---|---|---|---|---|---|---|---|
| ATOM | 4950 | N | LEU | B | 109 | 19.133 | 38.533 | 108.789 | 1.00 | 24.03 | | N |
| ANISOU | 4950 | N | LEU | B | 109 | 3360 | 4038 | 1733 | 406 | 231 | -59 | N |
| ATOM | 4951 | CA | LEU | B | 109 | 19.839 | 37.976 | 109.961 | 1.00 | 25.45 | | C |
| ANISOU | 4951 | CA | LEU | B | 109 | 3531 | 4359 | 1781 | 469 | 189 | -28 | C |
| ATOM | 4953 | CB | LEU | B | 109 | 20.920 | 38.933 | 110.480 | 1.00 | 28.20 | | C |
| ANISOU | 4953 | CB | LEU | B | 109 | 3793 | 4833 | 2088 | 463 | 137 | -160 | C |
| ATOM | 4956 | CG | LEU | B | 109 | 21.951 | 39.535 | 109.513 | 1.00 | 29.76 | | C |
| ANISOU | 4956 | CG | LEU | B | 109 | 3929 | 4985 | 2394 | 436 | 114 | -237 | C |
| ATOM | 4958 | CD1 | LEU | B | 109 | 22.678 | 40.691 | 110.241 | 1.00 | 30.45 | | C |
| ANISOU | 4958 | CD1 | LEU | B | 109 | 3933 | 5199 | 2438 | 379 | 75 | -395 | C |
| ATOM | 4962 | CD2 | LEU | B | 109 | 22.933 | 38.442 | 108.956 | 1.00 | 28.59 | | C |
| ANISOU | 4962 | CD2 | LEU | B | 109 | 3770 | 4829 | 2263 | 518 | 82 | -137 | C |
| ATOM | 4966 | C | LEU | B | 109 | 18.864 | 37.720 | 111.094 | 1.00 | 26.78 | | C |
| ANISOU | 4966 | C | LEU | B | 109 | 3730 | 4605 | 1838 | 470 | 225 | 21 | C |
| ATOM | 4967 | O | LEU | B | 109 | 17.742 | 38.194 | 111.072 | 1.00 | 26.00 | | O |
| ANISOU | 4967 | O | LEU | B | 109 | 3633 | 4471 | 1773 | 422 | 287 | -2 | O |
| ATOM | 4969 | N | TYR | B | 110 | 19.282 | 36.927 | 112.060 | 1.00 | 27.25 | | N |
| ANISOU | 4969 | N | TYR | B | 110 | 3808 | 4779 | 1766 | 533 | 194 | 106 | N |
| ATOM | 4970 | CA | TYR | B | 110 | 18.623 | 36.895 | 113.351 | 1.00 | 29.97 | | C |
| ANISOU | 4970 | CA | TYR | B | 110 | 4171 | 5255 | 1961 | 535 | 227 | 132 | C |
| ATOM | 4972 | CB | TYR | B | 110 | 18.016 | 35.514 | 113.632 | 1.00 | 28.42 | | C |
| ANISOU | 4972 | CB | TYR | B | 110 | 4058 | 5017 | 1721 | 562 | 267 | 328 | C |
| ATOM | 4975 | CG | TYR | B | 110 | 17.261 | 35.469 | 114.918 | 1.00 | 28.40 | | C |
| ANISOU | 4975 | CG | TYR | B | 110 | 4075 | 5156 | 1559 | 556 | 322 | 372 | C |
| ATOM | 4976 | CD1 | TYR | B | 110 | 15.990 | 35.975 | 114.974 | 1.00 | 28.64 | | C |
| ANISOU | 4976 | CD1 | TYR | B | 110 | 4092 | 5171 | 1620 | 487 | 416 | 331 | C |
| ATOM | 4978 | CE1 | TYR | B | 110 | 15.271 | 35.965 | 116.108 | 1.00 | 29.68 | | C |
| ANISOU | 4978 | CE1 | TYR | B | 110 | 4234 | 5437 | 1606 | 481 | 488 | 364 | C |
| ATOM | 4980 | CZ | TYR | B | 110 | 15.804 | 35.474 | 117.261 | 1.00 | 31.76 | | C |
| ANISOU | 4980 | CZ | TYR | B | 110 | 4536 | 5866 | 1667 | 539 | 460 | 443 | C |
| ATOM | 4981 | OH | TYR | B | 110 | 14.989 | 35.518 | 118.346 | 1.00 | 33.82 | | O |
| ANISOU | 4981 | OH | TYR | B | 110 | 4811 | 6266 | 1771 | 524 | 552 | 472 | O |
| ATOM | 4983 | CE2 | TYR | B | 110 | 17.075 | 34.949 | 117.284 | 1.00 | 31.59 | | C |
| ANISOU | 4983 | CE2 | TYR | B | 110 | 4527 | 5876 | 1599 | 615 | 349 | 501 | C |
| ATOM | 4985 | CD2 | TYR | B | 110 | 17.819 | 34.947 | 116.084 | 1.00 | 30.78 | | C |
| ANISOU | 4985 | CD2 | TYR | B | 110 | 4400 | 5626 | 1670 | 627 | 283 | 462 | C |
| ATOM | 4987 | C | TYR | B | 110 | 19.676 | 37.260 | 114.399 | 1.00 | 30.61 | | C |
| ANISOU | 4987 | C | TYR | B | 110 | 4202 | 5545 | 1885 | 575 | 148 | 66 | C |
| ATOM | 4988 | O | TYR | B | 110 | 20.781 | 36.755 | 114.331 | 1.00 | 31.62 | | O |
| ANISOU | 4988 | O | TYR | B | 110 | 4300 | 5719 | 1995 | 640 | 69 | 118 | O |
| ATOM | 4990 | N | ASP | B | 111 | 19.305 | 38.140 | 115.336 | 1.00 | 32.96 | | N |
| ANISOU | 4990 | N | ASP | B | 111 | 4483 | 5971 | 2068 | 535 | 173 | -56 | N |
| ATOM | 4991 | CA | ASP | B | 111 | 20.162 | 38.629 | 116.418 | 1.00 | 35.65 | | C |
| ANISOU | 4991 | CA | ASP | B | 111 | 4780 | 6537 | 2228 | 538 | 96 | -156 | C |
| ATOM | 4993 | CB | ASP | B | 111 | 19.941 | 40.145 | 116.533 | 1.00 | 35.48 | | C |
| ANISOU | 4993 | CB | ASP | B | 111 | 4735 | 6514 | 2233 | 448 | 136 | -398 | C |
| ATOM | 4996 | CG | ASP | B | 111 | 20.863 | 40.811 | 117.512 | 1.00 | 37.03 | | C |
| ANISOU | 4996 | CG | ASP | B | 111 | 4886 | 6926 | 2258 | 408 | 52 | -555 | C |
| ATOM | 4997 | OD1 | ASP | B | 111 | 21.407 | 40.128 | 118.391 | 1.00 | 37.87 | | O |
| ANISOU | 4997 | OD1 | ASP | B | 111 | 4980 | 7239 | 2168 | 459 | -31 | -467 | O |
| ATOM | 4998 | OD2 | ASP | B | 111 | 21.019 | 42.027 | 117.379 | 1.00 | 36.70 | | O |
| ANISOU | 4998 | OD2 | ASP | B | 111 | 4825 | 6841 | 2280 | 322 | 69 | -764 | O |
| ATOM | 4999 | C | ASP | B | 111 | 19.793 | 37.917 | 117.717 | 1.00 | 38.07 | | C |
| ANISOU | 4999 | C | ASP | B | 111 | 5138 | 7020 | 2307 | 586 | 107 | -37 | C |
| ATOM | 5000 | O | ASP | B | 111 | 18.738 | 38.202 | 118.300 | 1.00 | 39.03 | | O |
| ANISOU | 5000 | O | ASP | B | 111 | 5302 | 7169 | 2357 | 554 | 207 | -67 | O |
| ATOM | 5002 | N | TYR | B | 112 | 20.666 | 37.026 | 118.207 | 1.00 | 41.35 | | N |
| ANISOU | 5002 | N | TYR | B | 112 | 5543 | 7568 | 2600 | 671 | 12 | 105 | N |
| ATOM | 5003 | CA | TYR | B | 112 | 20.414 | 36.329 | 119.476 | 1.00 | 43.80 | | C |
| ANISOU | 5003 | CA | TYR | B | 112 | 5909 | 8065 | 2670 | 725 | 15 | 248 | C |
| ATOM | 5005 | CB | TYR | B | 112 | 21.327 | 35.106 | 119.630 | 1.00 | 46.97 | | C |
| ANISOU | 5005 | CB | TYR | B | 112 | 6307 | 8525 | 3014 | 855 | -79 | 475 | C |
| ATOM | 5008 | CG | TYR | B | 112 | 21.067 | 34.049 | 118.594 | 1.00 | 45.85 | | C |
| ANISOU | 5008 | CG | TYR | B | 112 | 6229 | 8113 | 3078 | 906 | -20 | 645 | C |
| ATOM | 5009 | CD1 | TYR | B | 112 | 19.988 | 33.187 | 118.710 | 1.00 | 45.91 | | C |
| ANISOU | 5009 | CD1 | TYR | B | 112 | 6350 | 8000 | 3093 | 901 | 92 | 812 | C |
| ATOM | 5011 | CE1 | TYR | B | 112 | 19.753 | 32.195 | 117.757 | 1.00 | 45.21 | | C |
| ANISOU | 5011 | CE1 | TYR | B | 112 | 6336 | 7653 | 3190 | 923 | 145 | 947 | C |
| ATOM | 5013 | CZ | TYR | B | 112 | 20.602 | 32.068 | 116.678 | 1.00 | 44.02 | | C |
| ANISOU | 5013 | CZ | TYR | B | 112 | 6150 | 7370 | 3207 | 970 | 95 | 913 | C |
| ATOM | 5014 | OH | TYR | B | 112 | 20.337 | 31.094 | 115.728 | 1.00 | 43.76 | | O |
| ANISOU | 5014 | OH | TYR | B | 112 | 6209 | 7075 | 3343 | 981 | 158 | 1018 | O |
| ATOM | 5016 | CE2 | TYR | B | 112 | 21.683 | 32.922 | 116.550 | 1.00 | 43.91 | | C |
| ANISOU | 5016 | CE2 | TYR | B | 112 | 6010 | 7486 | 3186 | 989 | -8 | 763 | C |
| ATOM | 5018 | CD2 | TYR | B | 112 | 21.902 | 33.902 | 117.505 | 1.00 | 44.91 | | C |
| ANISOU | 5018 | CD2 | TYR | B | 112 | 6059 | 7864 | 3140 | 947 | -69 | 632 | C |
| ATOM | 5020 | C | TYR | B | 112 | 20.537 | 37.206 | 120.715 | 1.00 | 45.65 | | C |
| ANISOU | 5020 | C | TYR | B | 112 | 6123 | 8563 | 2659 | 678 | -15 | 86 | C |
| ATOM | 5021 | O | TYR | B | 112 | 19.981 | 36.851 | 121.757 | 1.00 | 47.71 | | O |

FIG. 18 (continued)

| | | | | | | | | | | | | |
|---|---|---|---|---|---|---|---|---|---|---|---|---|
| ANISOU | 5021 | O | TYR | B | 112 | 6446 | 8969 | 2711 | 697 | 32 | 172 | O |
| ATOM | 5023 | N | LYS | B | 113 | 21.257 | 38.328 | 120.617 | 1.00 | 45.89 | | N |
| ANISOU | 5023 | N | LYS | B | 113 | 6075 | 8655 | 2706 | 605 | -86 | -148 | N |
| ATOM | 5024 | CA | LYS | B | 113 | 21.423 | 39.237 | 121.762 | 1.00 | 48.68 | | C |
| ANISOU | 5024 | CA | LYS | B | 113 | 6422 | 9250 | 2824 | 534 | -116 | -348 | C |
| ATOM | 5026 | CB | LYS | B | 113 | 22.627 | 40.183 | 121.570 | 1.00 | 49.74 | | C |
| ANISOU | 5026 | CB | LYS | B | 113 | 6448 | 9462 | 2988 | 450 | -242 | -564 | C |
| ATOM | 5029 | CG | LYS | B | 113 | 22.909 | 41.103 | 122.759 | 1.00 | 52.97 | | C |
| ANISOU | 5029 | CG | LYS | B | 113 | 6857 | 10129 | 3142 | 350 | -291 | -797 | C |
| ATOM | 5032 | CD | LYS | B | 113 | 24.375 | 41.515 | 122.809 | 1.00 | 55.20 | | C |
| ANISOU | 5032 | CD | LYS | B | 113 | 7002 | 10590 | 3383 | 282 | -474 | -914 | C |
| ATOM | 5035 | CE | LYS | B | 113 | 24.710 | 42.296 | 124.074 | 1.00 | 58.77 | | C |
| ANISOU | 5035 | CE | LYS | B | 113 | 7455 | 11336 | 3538 | 166 | -548 | -1144 | C |
| ATOM | 5038 | NZ | LYS | B | 113 | 24.455 | 43.741 | 123.838 | 1.00 | 60.74 | | N |
| ANISOU | 5038 | NZ | LYS | B | 113 | 7747 | 11424 | 3907 | 4 | -456 | -1474 | N |
| ATOM | 5042 | C | LYS | B | 113 | 20.142 | 40.029 | 121.964 | 1.00 | 46.60 | | C |
| ANISOU | 5042 | C | LYS | B | 113 | 6235 | 8898 | 2575 | 469 | 52 | -494 | C |
| ATOM | 5043 | O | LYS | B | 113 | 19.602 | 40.057 | 123.045 | 1.00 | 47.40 | | O |
| ANISOU | 5043 | O | LYS | B | 113 | 6395 | 9166 | 2450 | 468 | 111 | -511 | O |
| ATOM | 5045 | N | GLU | B | 114 | 19.645 | 40.641 | 120.895 | 1.00 | 44.13 | | N |
| ANISOU | 5045 | N | GLU | B | 114 | 5915 | 8325 | 2526 | 430 | 137 | -583 | N |
| ATOM | 5046 | CA | GLU | B | 114 | 18.406 | 41.423 | 120.958 | 1.00 | 43.45 | | C |
| ANISOU | 5046 | CA | GLU | B | 114 | 5880 | 8133 | 2495 | 396 | 305 | -707 | C |
| ATOM | 5048 | CB | GLU | B | 114 | 18.458 | 42.558 | 119.945 | 1.00 | 42.62 | | C |
| ANISOU | 5048 | CB | GLU | B | 114 | 5746 | 7808 | 2641 | 336 | 336 | -887 | C |
| ATOM | 5051 | CG | GLU | B | 114 | 19.626 | 43.499 | 120.101 | 1.00 | 44.92 | | C |
| ANISOU | 5051 | CG | GLU | B | 114 | 6000 | 8168 | 2901 | 247 | 235 | -1111 | C |
| ATOM | 5054 | CD | GLU | B | 114 | 19.587 | 44.333 | 121.368 | 1.00 | 48.42 | | C |
| ANISOU | 5054 | CD | GLU | B | 114 | 6494 | 8788 | 3116 | 184 | 267 | -1343 | C |
| ATOM | 5055 | OE1 | GLU | B | 114 | 18.515 | 44.479 | 122.000 | 1.00 | 51.06 | | O |
| ANISOU | 5055 | OE1 | GLU | B | 114 | 6898 | 9143 | 3359 | 215 | 408 | -1373 | O |
| ATOM | 5056 | OE2 | GLU | B | 114 | 20.652 | 44.871 | 121.711 | 1.00 | 51.61 | | O |
| ANISOU | 5056 | OE2 | GLU | B | 114 | 6861 | 9315 | 3432 | 93 | 153 | -1509 | O |
| ATOM | 5057 | C | GLU | B | 114 | 17.141 | 40.597 | 120.683 | 1.00 | 41.31 | | C |
| ANISOU | 5057 | C | GLU | B | 114 | 5643 | 7751 | 2301 | 448 | 429 | -501 | C |
| ATOM | 5058 | O | GLU | B | 114 | 16.024 | 41.119 | 120.722 | 1.00 | 40.36 | | O |
| ANISOU | 5058 | O | GLU | B | 114 | 5539 | 7561 | 2235 | 439 | 575 | -565 | O |
| ATOM | 5060 | N | ASN | B | 115 | 17.318 | 39.320 | 120.385 | 1.00 | 39.83 | | N |
| ANISOU | 5060 | N | ASN | B | 115 | 5462 | 7540 | 2131 | 501 | 377 | -258 | N |
| ATOM | 5061 | CA | ASN | B | 115 | 16.193 | 38.408 | 120.148 | 1.00 | 39.45 | | C |
| ANISOU | 5061 | CA | ASN | B | 115 | 5448 | 7389 | 2150 | 521 | 483 | -55 | C |
| ATOM | 5063 | CB | ASN | B | 115 | 15.436 | 38.114 | 121.457 | 1.00 | 43.79 | | C |
| ANISOU | 5063 | CB | ASN | B | 115 | 6050 | 8130 | 2461 | 531 | 585 | 11 | C |
| ATOM | 5066 | CG | ASN | B | 115 | 16.355 | 37.626 | 122.552 | 1.00 | 46.27 | | C |
| ANISOU | 5066 | CG | ASN | B | 115 | 6397 | 8690 | 2494 | 575 | 481 | 81 | C |
| ATOM | 5067 | OD1 | ASN | B | 115 | 16.377 | 38.180 | 123.655 | 1.00 | 51.08 | | O |
| ANISOU | 5067 | OD1 | ASN | B | 115 | 7027 | 9519 | 2863 | 561 | 499 | -41 | O |
| ATOM | 5068 | ND2 | ASN | B | 115 | 17.132 | 36.591 | 122.249 | 1.00 | 47.02 | | N |
| ANISOU | 5068 | ND2 | ASN | B | 115 | 6497 | 8756 | 2612 | 635 | 372 | 275 | N |
| ATOM | 5071 | C | ASN | B | 115 | 15.255 | 38.881 | 119.037 | 1.00 | 36.84 | | C |
| ANISOU | 5071 | C | ASN | B | 115 | 5085 | 6834 | 2077 | 484 | 575 | -100 | C |
| ATOM | 5072 | O | ASN | B | 115 | 14.030 | 38.944 | 119.179 | 1.00 | 35.43 | | O |
| ANISOU | 5072 | O | ASN | B | 115 | 4902 | 6636 | 1923 | 471 | 707 | -73 | O |
| ATOM | 5074 | N | ARG | B | 116 | 15.823 | 39.220 | 117.891 | 1.00 | 34.46 | | N |
| ANISOU | 5074 | N | ARG | B | 116 | 4749 | 6375 | 1969 | 470 | 505 | -158 | N |
| ATOM | 5075 | CA | ARG | B | 116 | 14.969 | 39.711 | 116.819 | 1.00 | 31.97 | | C |
| ANISOU | 5075 | CA | ARG | B | 116 | 4399 | 5869 | 1877 | 442 | 576 | -187 | C |
| ATOM | 5077 | CB | ARG | B | 116 | 14.730 | 41.205 | 116.994 | 1.00 | 32.93 | | C |
| ANISOU | 5077 | CB | ARG | B | 116 | 4498 | 5982 | 2034 | 428 | 642 | -410 | C |
| ATOM | 5080 | CG | ARG | B | 116 | 15.954 | 42.103 | 116.855 | 1.00 | 32.17 | | C |
| ANISOU | 5080 | CG | ARG | B | 116 | 4394 | 5878 | 1953 | 399 | 554 | -590 | C |
| ATOM | 5083 | CD | ARG | B | 116 | 15.744 | 43.430 | 117.541 | 1.00 | 34.50 | | C |
| ANISOU | 5083 | CD | ARG | B | 116 | 4705 | 6202 | 2202 | 379 | 636 | -822 | C |
| ATOM | 5086 | NE | ARG | B | 116 | 16.915 | 44.293 | 117.370 | 1.00 | 34.39 | | N |
| ANISOU | 5086 | NE | ARG | B | 116 | 4684 | 6163 | 2219 | 317 | 554 | -1000 | N |
| ATOM | 5088 | CZ | ARG | B | 116 | 17.213 | 45.338 | 118.147 | 1.00 | 36.72 | | C |
| ANISOU | 5088 | CZ | ARG | B | 116 | 5011 | 6517 | 2423 | 266 | 581 | -1235 | C |
| ATOM | 5089 | NH1 | ARG | B | 116 | 16.420 | 45.702 | 119.148 | 1.00 | 37.90 | | N |
| ANISOU | 5089 | NH1 | ARG | B | 116 | 5210 | 6753 | 2439 | 287 | 699 | -1332 | N |
| ATOM | 5092 | NH2 | ARG | B | 116 | 18.317 | 46.048 | 117.900 | 1.00 | 36.51 | | N |
| ANISOU | 5092 | NH2 | ARG | B | 116 | 4967 | 6459 | 2444 | 182 | 499 | -1385 | N |
| ATOM | 5095 | C | ARG | B | 116 | 15.539 | 39.433 | 115.434 | 1.00 | 29.24 | | C |
| ANISOU | 5095 | C | ARG | B | 116 | 4039 | 5352 | 1718 | 432 | 494 | -139 | C |
| ATOM | 5096 | O | ARG | B | 116 | 16.745 | 39.347 | 115.294 | 1.00 | 29.15 | | O |
| ANISOU | 5096 | O | ARG | B | 116 | 4025 | 5363 | 1689 | 445 | 393 | -164 | O |
| ATOM | 5098 | N | PHE | B | 117 | 14.668 | 39.348 | 114.411 | 1.00 | 27.53 | | N |
| ANISOU | 5098 | N | PHE | B | 117 | 3804 | 4984 | 1673 | 406 | 540 | -79 | N |
| ATOM | 5099 | CA | PHE | B | 117 | 15.077 | 39.320 | 113.010 | 1.00 | 28.89 | | C |
| ANISOU | 5099 | CA | PHE | B | 117 | 3967 | 4997 | 2013 | 388 | 481 | -66 | C |

FIG. 18 (continued)

| | | | | | | | | | | | | |
|---|---|---|---|---|---|---|---|---|---|---|---|---|
| ATOM | 5101 | CB | PHE | B | 117 | 13.959 | 38.802 | 112.082 | 1.00 | 27.78 | | C |
| ANISOU | 5101 | CB | PHE | B | 117 | 3816 | 4742 | 1997 | 348 | 519 | 48 | C |
| ATOM | 5104 | CG | PHE | B | 117 | 13.680 | 37.319 | 112.212 | 1.00 | 27.80 | | C |
| ANISOU | 5104 | CG | PHE | B | 117 | 3874 | 4737 | 1952 | 326 | 520 | 217 | C |
| ATOM | 5105 | CD1 | PHE | B | 117 | 14.522 | 36.376 | 111.587 | 1.00 | 25.30 | | C |
| ANISOU | 5105 | CD1 | PHE | B | 117 | 3622 | 4331 | 1660 | 334 | 452 | 288 | C |
| ATOM | 5107 | CE1 | PHE | B | 117 | 14.281 | 35.014 | 111.698 | 1.00 | 28.03 | | C |
| ANISOU | 5107 | CE1 | PHE | B | 117 | 4042 | 4628 | 1979 | 315 | 467 | 439 | C |
| ATOM | 5109 | CZ | PHE | B | 117 | 13.163 | 34.563 | 112.439 | 1.00 | 29.12 | | C |
| ANISOU | 5109 | CZ | PHE | B | 117 | 4182 | 4821 | 2063 | 267 | 549 | 535 | C |
| ATOM | 5111 | CE2 | PHE | B | 117 | 12.309 | 35.498 | 113.053 | 1.00 | 28.99 | | C |
| ANISOU | 5111 | CE2 | PHE | B | 117 | 4080 | 4921 | 2014 | 258 | 619 | 470 | C |
| ATOM | 5113 | CD2 | PHE | B | 117 | 12.564 | 36.865 | 112.931 | 1.00 | 27.36 | | C |
| ANISOU | 5113 | CD2 | PHE | B | 117 | 3809 | 4748 | 1838 | 297 | 606 | 307 | C |
| ATOM | 5115 | C | PHE | B | 117 | 15.494 | 40.728 | 112.573 | 1.00 | 30.17 | | C |
| ANISOU | 5115 | C | PHE | B | 117 | 4093 | 5104 | 2268 | 379 | 475 | -237 | C |
| ATOM | 5116 | O | PHE | B | 117 | 14.955 | 41.728 | 113.081 | 1.00 | 29.70 | | O |
| ANISOU | 5116 | O | PHE | B | 117 | 4013 | 5066 | 2204 | 384 | 550 | -349 | O |
| ATOM | 5118 | N | ILE | B | 118 | 16.501 | 40.806 | 111.694 | 1.00 | 29.93 | | N |
| ANISOU | 5118 | N | ILE | B | 118 | 4058 | 4998 | 2317 | 368 | 402 | -259 | N |
| ATOM | 5119 | CA | ILE | B | 118 | 16.957 | 42.098 | 111.124 | 1.00 | 30.71 | | C |
| ANISOU | 5119 | CA | ILE | B | 118 | 4129 | 5015 | 2524 | 341 | 403 | -397 | C |
| ATOM | 5121 | CB | ILE | B | 118 | 18.425 | 42.465 | 111.482 | 1.00 | 33.30 | | C |
| ANISOU | 5121 | CB | ILE | B | 118 | 4436 | 5418 | 2796 | 319 | 330 | -509 | C |
| ATOM | 5123 | CG1 | ILE | B | 118 | 18.722 | 42.210 | 112.968 | 1.00 | 37.85 | | C |
| ANISOU | 5123 | CG1 | ILE | B | 118 | 5017 | 6193 | 3172 | 334 | 303 | -550 | C |
| ATOM | 5126 | CD1 | ILE | B | 118 | 20.183 | 42.510 | 113.374 | 1.00 | 37.19 | | C |
| ANISOU | 5126 | CD1 | ILE | B | 118 | 4884 | 6231 | 3015 | 302 | 207 | -656 | C |
| ATOM | 5130 | CG2 | ILE | B | 118 | 18.661 | 43.921 | 111.127 | 1.00 | 35.15 | | C |
| ANISOU | 5130 | CG2 | ILE | B | 118 | 4656 | 5557 | 3142 | 267 | 364 | -665 | C |
| ATOM | 5134 | C | ILE | B | 118 | 16.898 | 42.055 | 109.608 | 1.00 | 30.25 | | C |
| ANISOU | 5134 | C | ILE | B | 118 | 4068 | 4807 | 2619 | 324 | 390 | -330 | C |
| ATOM | 5135 | O | ILE | B | 118 | 17.404 | 41.118 | 108.969 | 1.00 | 26.54 | | O |
| ANISOU | 5135 | O | ILE | B | 118 | 3617 | 4313 | 2154 | 326 | 338 | -241 | O |
| ATOM | 5137 | N | GLU | B | 119 | 16.300 | 43.095 | 109.034 | 1.00 | 30.61 | | N |
| ANISOU | 5137 | N | GLU | B | 119 | 4097 | 4751 | 2784 | 316 | 442 | -372 | N |
| ATOM | 5138 | CA | GLU | B | 119 | 16.299 | 43.297 | 107.592 | 1.00 | 28.52 | | C |
| ANISOU | 5138 | CA | GLU | B | 119 | 3830 | 4361 | 2647 | 298 | 428 | -316 | C |
| ATOM | 5140 | CB | GLU | B | 119 | 14.867 | 43.611 | 107.183 | 1.00 | 31.75 | | C |
| ANISOU | 5140 | CB | GLU | B | 119 | 4211 | 4720 | 3134 | 320 | 481 | -247 | C |
| ATOM | 5143 | CG | GLU | B | 119 | 14.397 | 42.963 | 105.949 | 1.00 | 33.38 | | C |
| ANISOU | 5143 | CG | GLU | B | 119 | 4414 | 4881 | 3386 | 296 | 440 | -119 | C |
| ATOM | 5146 | CD | GLU | B | 119 | 13.039 | 43.499 | 105.558 | 1.00 | 33.31 | | C |
| ANISOU | 5146 | CD | GLU | B | 119 | 4344 | 4853 | 3460 | 323 | 479 | -53 | C |
| ATOM | 5147 | OE1 | GLU | B | 119 | 12.231 | 43.810 | 106.478 | 1.00 | 40.58 | | O |
| ANISOU | 5147 | OE1 | GLU | B | 119 | 5219 | 5825 | 4373 | 366 | 548 | -75 | O |
| ATOM | 5148 | OE2 | GLU | B | 119 | 12.786 | 43.647 | 104.347 | 1.00 | 36.34 | | O |
| ANISOU | 5148 | OE2 | GLU | B | 119 | 4717 | 5183 | 3909 | 310 | 445 | 22 | O |
| ATOM | 5149 | C | GLU | B | 119 | 17.215 | 44.471 | 107.282 | 1.00 | 27.37 | | C |
| ANISOU | 5149 | C | GLU | B | 119 | 3680 | 4143 | 2576 | 270 | 434 | -430 | C |
| ATOM | 5150 | O | GLU | B | 119 | 16.982 | 45.571 | 107.765 | 1.00 | 28.77 | | O |
| ANISOU | 5150 | O | GLU | B | 119 | 3856 | 4281 | 2794 | 273 | 494 | -533 | O |
| ATOM | 5152 | N | ILE | B | 120 | 18.281 | 44.228 | 106.516 | 1.00 | 25.83 | | N |
| ANISOU | 5152 | N | ILE | B | 120 | 3486 | 3926 | 2402 | 239 | 386 | -416 | N |
| ATOM | 5153 | CA | ILE | B | 120 | 19.241 | 45.239 | 106.186 | 1.00 | 26.63 | | C |
| ANISOU | 5153 | CA | ILE | B | 120 | 3573 | 3969 | 2577 | 188 | 396 | -510 | C |
| ATOM | 5155 | CB | ILE | B | 120 | 20.683 | 44.709 | 106.242 | 1.00 | 25.81 | | C |
| ANISOU | 5155 | CB | ILE | B | 120 | 3431 | 3955 | 2420 | 161 | 334 | -538 | C |
| ATOM | 5157 | CG1 | ILE | B | 120 | 21.080 | 44.293 | 107.671 | 1.00 | 27.39 | | C |
| ANISOU | 5157 | CG1 | ILE | B | 120 | 3605 | 4320 | 2483 | 175 | 287 | -604 | C |
| ATOM | 5160 | CD1 | ILE | B | 120 | 21.999 | 43.061 | 107.779 | 1.00 | 25.76 | | C |
| ANISOU | 5160 | CD1 | ILE | B | 120 | 3364 | 4233 | 2192 | 219 | 214 | -532 | C |
| ATOM | 5164 | CG2 | ILE | B | 120 | 21.631 | 45.804 | 105.757 | 1.00 | 30.56 | | C |
| ANISOU | 5164 | CG2 | ILE | B | 120 | 4004 | 4491 | 3118 | 81 | 356 | -625 | C |
| ATOM | 5168 | C | ILE | B | 120 | 18.954 | 45.733 | 104.762 | 1.00 | 28.15 | | C |
| ANISOU | 5168 | C | ILE | B | 120 | 3783 | 4022 | 2890 | 178 | 426 | -430 | C |
| ATOM | 5169 | O | ILE | B | 120 | 18.853 | 44.937 | 103.824 | 1.00 | 34.03 | | O |
| ANISOU | 5169 | O | ILE | B | 120 | 4543 | 4763 | 3625 | 187 | 397 | -321 | O |
| ATOM | 5171 | N | GLY | B | 121 | 18.829 | 47.041 | 104.601 | 1.00 | 26.16 | | N |
| ANISOU | 5171 | N | GLY | B | 121 | 3541 | 3654 | 2744 | 160 | 487 | -485 | N |
| ATOM | 5172 | CA | GLY | B | 121 | 18.627 | 47.625 | 103.294 | 1.00 | 24.56 | | C |
| ANISOU | 5172 | CA | GLY | B | 121 | 3360 | 3325 | 2648 | 157 | 518 | -392 | C |
| ATOM | 5175 | C | GLY | B | 121 | 19.725 | 48.585 | 102.926 | 1.00 | 23.50 | | C |
| ANISOU | 5175 | C | GLY | B | 121 | 3231 | 3101 | 2597 | 79 | 554 | -460 | C |
| ATOM | 5176 | O | GLY | B | 121 | 20.291 | 49.268 | 103.800 | 1.00 | 24.73 | | O |
| ANISOU | 5176 | O | GLY | B | 121 | 3381 | 3246 | 2771 | 24 | 579 | -609 | O |
| ATOM | 5178 | N | VAL | B | 122 | 20.033 | 48.611 | 101.626 | 1.00 | 23.48 | | N |
| ANISOU | 5178 | N | VAL | B | 122 | 3243 | 3046 | 2634 | 58 | 560 | -354 | N |
| ATOM | 5179 | CA | VAL | B | 122 | 21.055 | 49.485 | 101.064 | 1.00 | 23.51 | | C |

FIG. 18 (continued)

| | | | | | | | | | | | | |
|---|---|---|---|---|---|---|---|---|---|---|---|---|
| ANISOU | 5179 | CA | VAL | B | 122 | 3250 | 2960 | 2723 | -29 | 610 | -382 | C |
| ATOM | 5181 | CB | VAL | B | 122 | 22.313 | 48.741 | 100.523 | 1.00 | 22.63 | | C |
| ANISOU | 5181 | CB | VAL | B | 122 | 3093 | 2950 | 2554 | -83 | 580 | -374 | C |
| ATOM | 5183 | CG1 | VAL | B | 122 | 23.374 | 49.765 | 100.100 | 1.00 | 24.40 | | C |
| ANISOU | 5183 | CG1 | VAL | B | 122 | 3300 | 3091 | 2879 | -195 | 648 | -415 | C |
| ATOM | 5187 | CG2 | VAL | B | 122 | 22.930 | 47.782 | 101.580 | 1.00 | 22.86 | | C |
| ANISOU | 5187 | CG2 | VAL | B | 122 | 3058 | 3147 | 2481 | -76 | 510 | -467 | C |
| ATOM | 5191 | C | VAL | B | 122 | 20.431 | 50.309 | 99.932 | 1.00 | 24.61 | | C |
| ANISOU | 5191 | C | VAL | B | 122 | 3444 | 2948 | 2959 | -4 | 668 | -247 | C |
| ATOM | 5192 | O | VAL | B | 122 | 19.817 | 49.756 | 99.005 | 1.00 | 23.82 | | O |
| ANISOU | 5192 | O | VAL | B | 122 | 3358 | 2881 | 2810 | 48 | 635 | -103 | O |
| ATOM | 5194 | N | THR | B | 123 | 20.635 | 51.627 | 99.985 | 1.00 | 26.51 | | N |
| ANISOU | 5194 | N | THR | B | 123 | 3719 | 3023 | 3330 | -48 | 752 | -290 | N |
| ATOM | 5195 | CA | THR | B | 123 | 19.968 | 52.547 | 99.070 | 1.00 | 27.15 | | C |
| ANISOU | 5195 | CA | THR | B | 123 | 3859 | 2938 | 3518 | 1 | 818 | -146 | C |
| ATOM | 5197 | CB | THR | B | 123 | 18.691 | 53.188 | 99.704 | 1.00 | 28.31 | | C |
| ANISOU | 5197 | CB | THR | B | 123 | 4030 | 2984 | 3744 | 116 | 859 | -149 | C |
| ATOM | 5199 | OG1 | THR | B | 123 | 18.003 | 53.988 | 98.720 | 1.00 | 29.11 | | O |
| ANISOU | 5199 | OG1 | THR | B | 123 | 4175 | 2940 | 3945 | 195 | 911 | 33 | O |
| ATOM | 5201 | CG2 | THR | B | 123 | 19.026 | 54.036 | 100.978 | 1.00 | 28.44 | | C |
| ANISOU | 5201 | CG2 | THR | B | 123 | 4074 | 2895 | 3838 | 66 | 932 | -365 | C |
| ATOM | 5205 | C | THR | B | 123 | 20.896 | 53.628 | 98.528 | 1.00 | 29.22 | | C |
| ANISOU | 5205 | C | THR | B | 123 | 4164 | 3041 | 3899 | -106 | 909 | -145 | C |
| ATOM | 5206 | O | THR | B | 123 | 21.870 | 54.041 | 99.179 | 1.00 | 29.71 | | O |
| ANISOU | 5206 | O | THR | B | 123 | 4209 | 3075 | 4005 | -226 | 941 | -306 | O |
| ATOM | 5208 | N | ARG | B | 124 | 20.626 | 54.026 | 97.290 | 1.00 | 29.03 | | N |
| ANISOU | 5208 | N | ARG | B | 124 | 4186 | 2932 | 3911 | -75 | 945 | 46 | N |
| ATOM | 5209 | CA | ARG | B | 124 | 21.316 | 55.133 | 96.635 | 1.00 | 33.29 | | C |
| ANISOU | 5209 | CA | ARG | B | 124 | 4783 | 3291 | 4574 | -164 | 1053 | 100 | C |
| ATOM | 5211 | CB | ARG | B | 124 | 21.523 | 54.828 | 95.164 | 1.00 | 33.45 | | C |
| ANISOU | 5211 | CB | ARG | B | 124 | 4820 | 3372 | 4519 | -168 | 1049 | 301 | C |
| ATOM | 5214 | CG | ARG | B | 124 | 22.419 | 53.619 | 94.884 | 1.00 | 32.75 | | C |
| ANISOU | 5214 | CG | ARG | B | 124 | 4663 | 3501 | 4279 | -234 | 991 | 255 | C |
| ATOM | 5217 | CD | ARG | B | 124 | 21.925 | 52.892 | 93.670 | 1.00 | 33.78 | | C |
| ANISOU | 5217 | CD | ARG | B | 124 | 4819 | 3746 | 4270 | -167 | 941 | 431 | C |
| ATOM | 5220 | NE | ARG | B | 124 | 21.325 | 51.694 | 94.070 | 1.00 | 32.39 | | N |
| ANISOU | 5220 | NE | ARG | B | 124 | 4605 | 3726 | 3975 | -97 | 832 | 382 | N |
| ATOM | 5222 | CZ | ARG | B | 124 | 20.676 | 50.824 | 93.309 | 1.00 | 30.71 | | C |
| ANISOU | 5222 | CZ | ARG | B | 124 | 4409 | 3635 | 3625 | -42 | 759 | 483 | C |
| ATOM | 5223 | NH1 | ARG | B | 124 | 20.452 | 50.988 | 92.011 | 1.00 | 31.86 | | N |
| ANISOU | 5223 | NH1 | ARG | B | 124 | 4609 | 3794 | 3704 | -35 | 767 | 654 | N |
| ATOM | 5226 | NH2 | ARG | B | 124 | 20.195 | 49.762 | 93.927 | 1.00 | 28.26 | | N |
| ANISOU | 5226 | NH2 | ARG | B | 124 | 4063 | 3437 | 3236 | -2 | 672 | 407 | N |
| ATOM | 5229 | C | ARG | B | 124 | 20.510 | 56.423 | 96.721 | 1.00 | 34.80 | | C |
| ANISOU | 5229 | C | ARG | B | 124 | 5060 | 3229 | 4933 | -88 | 1147 | 157 | C |
| ATOM | 5230 | O | ARG | B | 124 | 20.951 | 57.461 | 96.253 | 1.00 | 36.40 | | O |
| ANISOU | 5230 | O | ARG | B | 124 | 5334 | 3233 | 5265 | -154 | 1254 | 213 | O |
| ATOM | 5232 | N | ARG | B | 125 | 19.322 | 56.340 | 97.298 | 1.00 | 35.92 | | N |
| ANISOU | 5232 | N | ARG | B | 125 | 5194 | 3377 | 5079 | 57 | 1120 | 156 | N |
| ATOM | 5233 | CA | ARG | B | 125 | 18.441 | 57.494 | 97.475 | 1.00 | 40.20 | | C |
| ANISOU | 5233 | CA | ARG | B | 125 | 5805 | 3684 | 5786 | 174 | 1218 | 207 | C |
| ATOM | 5235 | CB | ARG | B | 125 | 17.054 | 57.161 | 96.938 | 1.00 | 40.11 | | C |
| ANISOU | 5235 | CB | ARG | B | 125 | 5751 | 3755 | 5732 | 367 | 1158 | 413 | C |
| ATOM | 5238 | CG | ARG | B | 125 | 17.029 | 56.724 | 95.481 | 1.00 | 42.08 | | C |
| ANISOU | 5238 | CG | ARG | B | 125 | 5992 | 4117 | 5880 | 374 | 1089 | 652 | C |
| ATOM | 5246 | C | ARG | B | 125 | 18.365 | 57.851 | 98.961 | 1.00 | 40.83 | | C |
| ANISOU | 5246 | C | ARG | B | 125 | 5896 | 3692 | 5925 | 163 | 1268 | -46 | C |
| ATOM | 5247 | O | ARG | B | 125 | 18.981 | 57.181 | 99.784 | 1.00 | 40.54 | | O |
| ANISOU | 5247 | O | ARG | B | 125 | 5808 | 3811 | 5784 | 64 | 1208 | -234 | O |
| ATOM | 5249 | N | GLU | B | 126 | 17.600 | 58.884 | 99.306 | 1.00 | 43.17 | | N |
| ANISOU | 5249 | N | GLU | B | 126 | 6262 | 3762 | 6377 | 277 | 1379 | -48 | N |
| ATOM | 5250 | CA | GLU | B | 126 | 17.427 | 59.303 | 100.709 | 1.00 | 45.03 | | C |
| ANISOU | 5250 | CA | GLU | B | 126 | 6530 | 3918 | 6661 | 279 | 1449 | -301 | C |
| ATOM | 5252 | CB | GLU | B | 126 | 16.500 | 60.524 | 100.806 | 1.00 | 49.72 | | C |
| ANISOU | 5252 | CB | GLU | B | 126 | 7216 | 4220 | 7454 | 444 | 1601 | -255 | C |
| ATOM | 5255 | CG | GLU | B | 126 | 17.169 | 61.843 | 100.333 | 1.00 | 54.11 | | C |
| ANISOU | 5255 | CG | GLU | B | 126 | 7916 | 4432 | 8212 | 353 | 1742 | -241 | C |
| ATOM | 5258 | CD | GLU | B | 126 | 16.278 | 63.059 | 100.529 | 1.00 | 58.36 | | C |
| ANISOU | 5258 | CD | GLU | B | 126 | 8563 | 4645 | 8965 | 534 | 1912 | -212 | C |
| ATOM | 5259 | OE1 | GLU | B | 126 | 15.063 | 62.942 | 100.237 | 1.00 | 61.32 | | O |
| ANISOU | 5259 | OE1 | GLU | B | 126 | 8878 | 5065 | 9355 | 775 | 1904 | -20 | O |
| ATOM | 5260 | OE2 | GLU | B | 126 | 16.783 | 64.131 | 100.953 | 1.00 | 63.10 | | O |
| ANISOU | 5260 | OE2 | GLU | B | 126 | 9305 | 4942 | 9727 | 435 | 2058 | -376 | O |
| ATOM | 5261 | C | GLU | B | 126 | 16.881 | 58.144 | 101.542 | 1.00 | 41.97 | | C |
| ANISOU | 5261 | C | GLU | B | 126 | 6039 | 3808 | 6099 | 337 | 1346 | -383 | C |
| ATOM | 5262 | O | GLU | B | 126 | 15.891 | 57.517 | 101.147 | 1.00 | 40.15 | | O |
| ANISOU | 5262 | O | GLU | B | 126 | 5734 | 3709 | 5811 | 480 | 1284 | -214 | O |
| ATOM | 5264 | N | VAL | B | 127 | 17.514 | 57.876 | 102.693 | 1.00 | 40.78 | | N |
| ANISOU | 5264 | N | VAL | B | 127 | 5882 | 3749 | 5862 | 219 | 1327 | -635 | N |

FIG. 18 (continued)

| | | | | | | | | | | | | |
|---|---|---|---|---|---|---|---|---|---|---|---|---|
| ATOM | 5265 | CA | VAL | B | 127 | 17.296 | 56.626 | 103.450 | 1.00 | 37.97 | | C |
| ANISOU | 5265 | CA | VAL | B | 127 | 5432 | 3680 | 5313 | 235 | 1217 | -700 | C |
| ATOM | 5267 | CB | VAL | B | 127 | 18.233 | 56.487 | 104.714 | 1.00 | 38.76 | | C |
| ANISOU | 5267 | CB | VAL | B | 127 | 5537 | 3880 | 5312 | 83 | 1193 | -977 | C |
| ATOM | 5269 | CG1 | VAL | B | 127 | 19.626 | 56.006 | 104.327 | 1.00 | 38.37 | | C |
| ANISOU | 5269 | CG1 | VAL | B | 127 | 5439 | 3944 | 5197 | -90 | 1102 | -993 | C |
| ATOM | 5273 | CG2 | VAL | B | 127 | 18.280 | 57.788 | 105.540 | 1.00 | 39.52 | | C |
| ANISOU | 5273 | CG2 | VAL | B | 127 | 5743 | 3748 | 5525 | 42 | 1332 | -1197 | C |
| ATOM | 5277 | C | VAL | B | 127 | 15.859 | 56.383 | 103.923 | 1.00 | 37.80 | | C |
| ANISOU | 5277 | C | VAL | B | 127 | 5370 | 3719 | 5272 | 422 | 1241 | -650 | C |
| ATOM | 5278 | O | VAL | B | 127 | 15.461 | 55.242 | 104.121 | 1.00 | 33.26 | | O |
| ANISOU | 5278 | O | VAL | B | 127 | 4709 | 3374 | 4554 | 454 | 1147 | -601 | O |
| ATOM | 5280 | N | HIS | B | 128 | 15.106 | 57.444 | 104.204 | 1.00 | 39.84 | | N |
| ANISOU | 5280 | N | HIS | B | 128 | 5689 | 3770 | 5678 | 541 | 1380 | -677 | N |
| ATOM | 5281 | CA | HIS | B | 128 | 13.753 | 57.265 | 104.737 | 1.00 | 41.47 | | C |
| ANISOU | 5281 | CA | HIS | B | 128 | 5834 | 4047 | 5874 | 725 | 1423 | -642 | C |
| ATOM | 5283 | CB | HIS | B | 128 | 13.203 | 58.581 | 105.288 | 1.00 | 46.86 | | C |
| ANISOU | 5283 | CB | HIS | B | 128 | 6609 | 4467 | 6728 | 841 | 1612 | -750 | C |
| ATOM | 5286 | CG | HIS | B | 128 | 13.054 | 59.641 | 104.251 | 1.00 | 49.99 | | C |
| ANISOU | 5286 | CG | HIS | B | 128 | 7071 | 4584 | 7338 | 926 | 1695 | -582 | C |
| ATOM | 5287 | ND1 | HIS | B | 128 | 14.113 | 60.409 | 103.809 | 1.00 | 52.26 | | N |
| ANISOU | 5287 | ND1 | HIS | B | 128 | 7477 | 4652 | 7726 | 782 | 1734 | -627 | N |
| ATOM | 5289 | CE1 | HIS | B | 128 | 13.682 | 61.252 | 102.886 | 1.00 | 53.80 | | C |
| ANISOU | 5289 | CE1 | HIS | B | 128 | 7719 | 4619 | 8103 | 909 | 1814 | -421 | C |
| ATOM | 5291 | NE2 | HIS | B | 128 | 12.386 | 61.053 | 102.709 | 1.00 | 54.20 | | N |
| ANISOU | 5291 | NE2 | HIS | B | 128 | 7670 | 4753 | 8172 | 1137 | 1815 | -246 | N |
| ATOM | 5293 | CD2 | HIS | B | 128 | 11.970 | 60.044 | 103.544 | 1.00 | 52.12 | | C |
| ANISOU | 5293 | CD2 | HIS | B | 128 | 7296 | 4770 | 7737 | 1142 | 1743 | -347 | C |
| ATOM | 5295 | C | HIS | B | 128 | 12.792 | 56.629 | 103.705 | 1.00 | 40.15 | | C |
| ANISOU | 5295 | C | HIS | B | 128 | 5554 | 4003 | 5699 | 852 | 1341 | -354 | C |
| ATOM | 5296 | O | HIS | B | 128 | 11.885 | 55.895 | 104.087 | 1.00 | 39.23 | | O |
| ANISOU | 5296 | O | HIS | B | 128 | 5335 | 4070 | 5500 | 936 | 1309 | -311 | O |
| ATOM | 5298 | N | ILE | B | 129 | 13.049 | 56.848 | 102.410 | 1.00 | 40.15 | | N |
| ANISOU | 5298 | N | ILE | B | 129 | 5569 | 3925 | 5763 | 842 | 1301 | -163 | N |
| ATOM | 5299 | CA | ILE | B | 129 | 12.220 | 56.287 | 101.342 | 1.00 | 38.48 | | C |
| ANISOU | 5299 | CA | ILE | B | 129 | 5256 | 3844 | 5521 | 938 | 1206 | 102 | C |
| ATOM | 5301 | CB | ILE | B | 129 | 12.678 | 56.759 | 99.940 | 1.00 | 39.44 | | C |
| ANISOU | 5301 | CB | ILE | B | 129 | 5430 | 3850 | 5704 | 913 | 1185 | 293 | C |
| ATOM | 5303 | CG1 | ILE | B | 129 | 12.497 | 58.266 | 99.777 | 1.00 | 42.03 | | C |
| ANISOU | 5303 | CG1 | ILE | B | 129 | 5853 | 3867 | 6251 | 1023 | 1338 | 343 | C |
| ATOM | 5306 | CD1 | ILE | B | 129 | 13.257 | 58.825 | 98.572 | 1.00 | 43.86 | | C |
| ANISOU | 5306 | CD1 | ILE | B | 129 | 6173 | 3954 | 6539 | 953 | 1345 | 496 | C |
| ATOM | 5310 | CG2 | ILE | B | 129 | 11.893 | 56.015 | 98.849 | 1.00 | 38.32 | | C |
| ANISOU | 5310 | CG2 | ILE | B | 129 | 5183 | 3902 | 5475 | 979 | 1056 | 545 | C |
| ATOM | 5314 | C | ILE | B | 129 | 12.202 | 54.750 | 101.390 | 1.00 | 35.69 | | C |
| ANISOU | 5314 | C | ILE | B | 129 | 4809 | 3783 | 4967 | 856 | 1058 | 111 | C |
| ATOM | 5315 | O | ILE | B | 129 | 11.131 | 54.138 | 101.491 | 1.00 | 34.65 | | O |
| ANISOU | 5315 | O | ILE | B | 129 | 4568 | 3809 | 4789 | 942 | 1017 | 198 | O |
| ATOM | 5317 | N | TYR | B | 130 | 13.384 | 54.122 | 101.356 | 1.00 | 33.27 | | N |
| ANISOU | 5317 | N | TYR | B | 130 | 4543 | 3545 | 4553 | 690 | 989 | 21 | N |
| ATOM | 5318 | CA | TYR | B | 130 | 13.461 | 52.670 | 101.386 | 1.00 | 30.93 | | C |
| ANISOU | 5318 | CA | TYR | B | 130 | 4184 | 3483 | 4083 | 620 | 865 | 29 | C |
| ATOM | 5320 | CB | TYR | B | 130 | 14.856 | 52.180 | 100.919 | 1.00 | 30.28 | | C |
| ANISOU | 5320 | CB | TYR | B | 130 | 4149 | 3433 | 3923 | 469 | 803 | -13 | C |
| ATOM | 5323 | CG | TYR | B | 130 | 14.950 | 50.668 | 100.615 | 1.00 | 28.81 | | C |
| ANISOU | 5323 | CG | TYR | B | 130 | 3920 | 3451 | 3577 | 415 | 684 | 34 | C |
| ATOM | 5324 | CD1 | TYR | B | 130 | 13.886 | 49.991 | 100.032 | 1.00 | 28.65 | | C |
| ANISOU | 5324 | CD1 | TYR | B | 130 | 3840 | 3538 | 3507 | 466 | 617 | 183 | C |
| ATOM | 5326 | CE1 | TYR | B | 130 | 13.965 | 48.622 | 99.733 | 1.00 | 27.06 | | C |
| ANISOU | 5326 | CE1 | TYR | B | 130 | 3624 | 3486 | 3171 | 401 | 521 | 210 | C |
| ATOM | 5328 | CZ | TYR | B | 130 | 15.131 | 47.939 | 100.017 | 1.00 | 25.29 | | C |
| ANISOU | 5328 | CZ | TYR | B | 130 | 3441 | 3300 | 2869 | 316 | 500 | 106 | C |
| ATOM | 5329 | OH | TYR | B | 130 | 15.222 | 46.606 | 99.722 | 1.00 | 25.40 | | O |
| ANISOU | 5329 | OH | TYR | B | 130 | 3460 | 3425 | 2768 | 268 | 425 | 131 | O |
| ATOM | 5331 | CE2 | TYR | B | 130 | 16.198 | 48.589 | 100.588 | 1.00 | 25.01 | | C |
| ANISOU | 5331 | CE2 | TYR | B | 130 | 3437 | 3189 | 2876 | 279 | 554 | -24 | C |
| ATOM | 5333 | CD2 | TYR | B | 130 | 16.122 | 49.950 | 100.867 | 1.00 | 26.52 | | C |
| ANISOU | 5333 | CD2 | TYR | B | 130 | 3647 | 3234 | 3194 | 311 | 642 | -68 | C |
| ATOM | 5335 | C | TYR | B | 130 | 13.104 | 52.105 | 102.772 | 1.00 | 30.27 | | C |
| ANISOU | 5335 | C | TYR | B | 130 | 4062 | 3521 | 3918 | 630 | 878 | -115 | C |
| ATOM | 5336 | O | TYR | B | 130 | 12.593 | 50.973 | 102.896 | 1.00 | 27.74 | | O |
| ANISOU | 5336 | O | TYR | B | 130 | 3673 | 3382 | 3487 | 625 | 804 | -62 | O |
| ATOM | 5338 | N | TYR | B | 131 | 13.360 | 52.891 | 103.828 | 1.00 | 31.84 | | N |
| ANISOU | 5338 | N | TYR | B | 131 | 4314 | 3620 | 4163 | 633 | 980 | -299 | N |
| ATOM | 5339 | CA | TYR | B | 131 | 12.924 | 52.507 | 105.169 | 1.00 | 33.32 | | C |
| ANISOU | 5339 | CA | TYR | B | 131 | 4474 | 3925 | 4261 | 658 | 1014 | -429 | C |
| ATOM | 5341 | CB | TYR | B | 131 | 13.377 | 53.512 | 106.238 | 1.00 | 35.70 | | C |
| ANISOU | 5341 | CB | TYR | B | 131 | 4863 | 4101 | 4601 | 638 | 1129 | -663 | C |
| ATOM | 5344 | CG | TYR | B | 131 | 12.967 | 53.079 | 107.634 | 1.00 | 35.91 | | C |

FIG. 18 (continued)

```
ANISOU 5344  CG  TYR B 131    4870  4278  4495   658  1165  -799   C
ATOM   5345  CD1 TYR B 131   13.838  52.369 108.443  1.00 34.91         C
ANISOU 5345  CD1 TYR B 131    4761  4308  4197   540  1092  -925   C
ATOM   5347  CE1 TYR B 131   13.485  51.971 109.698  1.00 36.50         C
ANISOU 5347  CE1 TYR B 131    4953  4660  4254   557  1125 -1029   C
ATOM   5349  CZ  TYR B 131   12.222  52.258 110.182  1.00 38.41         C
ANISOU 5349  CZ  TYR B 131    5164  4902  4527   690  1247 -1021   C
ATOM   5350  OH  TYR B 131   11.855  51.845 111.454  1.00 39.45         O
ANISOU 5350  OH  TYR B 131    5292  5202  4498   704  1296 -1120   O
ATOM   5352  CE2 TYR B 131   11.329  52.969 109.401  1.00 39.11         C
ANISOU 5352  CE2 TYR B 131    5219  4837  4804   819  1326  -902   C
ATOM   5354  CD2 TYR B 131   11.712  53.373 108.130  1.00 38.22         C
ANISOU 5354  CD2 TYR B 131    5121  4573  4830   804  1276  -786   C
ATOM   5356  C   TYR B 131   11.394  52.381 105.254  1.00 34.72         C
ANISOU 5356  C   TYR B 131    4553  4168  4470   806  1055  -311   C
ATOM   5357  O   TYR B 131   10.851  51.400 105.792  1.00 33.31         O
ANISOU 5357  O   TYR B 131    4304  4176  4177   804  1020  -293   O
ATOM   5359  N   LEU B 132   10.698  53.398 104.772  1.00 36.49         N
ANISOU 5359  N   LEU B 132    4767  4241  4857   936  1140  -224   N
ATOM   5360  CA  LEU B 132    9.248  53.364 104.779  1.00 39.65         C
ANISOU 5360  CA  LEU B 132    5043  4717  5307  1091  1180   -95   C
ATOM   5362  CB  LEU B 132    8.678  54.730 104.372  1.00 42.59         C
ANISOU 5362  CB  LEU B 132    5425  4873  5884  1263  1300   -21   C
ATOM   5365  CG  LEU B 132    8.919  55.778 105.459  1.00 45.46         C
ANISOU 5365  CG  LEU B 132    5901  5046  6326  1307  1476  -251   C
ATOM   5367  CD1 LEU B 132    8.571  57.164 104.958  1.00 48.05         C
ANISOU 5367  CD1 LEU B 132    6280  5097  6879  1467  1603  -179   C
ATOM   5371  CD2 LEU B 132    8.131  55.406 106.752  1.00 46.26         C
ANISOU 5371  CD2 LEU B 132    5934  5301  6343  1372  1561  -370   C
ATOM   5375  C   LEU B 132    8.688  52.204 103.939  1.00 39.12         C
ANISOU 5375  C   LEU B 132    4855  4851  5156  1058  1035   104   C
ATOM   5376  O   LEU B 132    7.728  51.551 104.344  1.00 38.27         O
ANISOU 5376  O   LEU B 132    4629  4911  5001  1094  1031   153   O
ATOM   5378  N   GLU B 133    9.308  51.909 102.800  1.00 39.49         N
ANISOU 5378  N   GLU B 133    4937  4890  5177   972   922   204   N
ATOM   5379  CA  GLU B 133    8.903  50.776 101.963  1.00 39.16         C
ANISOU 5379  CA  GLU B 133    4812  5029  5037   909   780   357   C
ATOM   5381  CB  GLU B 133    9.764  50.780 100.711  1.00 40.59         C
ANISOU 5381  CB  GLU B 133    5071  5152  5198   829   697   433   C
ATOM   5384  CG  GLU B 133    9.376  49.803  99.641  1.00 41.89         C
ANISOU 5384  CG  GLU B 133    5178  5475  5263   765   557   583   C
ATOM   5387  CD  GLU B 133   10.324  49.905  98.446  1.00 42.10         C
ANISOU 5387  CD  GLU B 133    5301  5440  5254   692   503   639   C
ATOM   5388  OE1 GLU B 133   10.627  51.040  98.003  1.00 45.11         O
ANISOU 5388  OE1 GLU B 133    5735  5665  5739   754   565   690   O
ATOM   5389  OE2 GLU B 133   10.797  48.859  97.984  1.00 44.40         O
ANISOU 5389  OE2 GLU B 133    5626  5827  5418   574   417   627   O
ATOM   5390  C   GLU B 133    9.024  49.411 102.686  1.00 37.84         C
ANISOU 5390  C   GLU B 133    4631  5031  4716   795   725   277   C
ATOM   5391  O   GLU B 133    8.085  48.599 102.672  1.00 37.77         O
ANISOU 5391  O   GLU B 133    4513  5178  4660   786   678   366   O
ATOM   5393  N   LYS B 134   10.173  49.148 103.310  1.00 34.52         N
ANISOU 5393  N   LYS B 134    4313  4582  4220   704   730   122   N
ATOM   5394  CA  LYS B 134   10.330  47.933 104.126  1.00 34.02         C
ANISOU 5394  CA  LYS B 134    4250  4660  4017   622   693    59   C
ATOM   5396  CB  LYS B 134   11.748  47.795 104.664  1.00 32.35         C
ANISOU 5396  CB  LYS B 134    4143  4419  3732   541   683   -90   C
ATOM   5399  CG  LYS B 134   12.685  47.120 103.728  1.00 31.93         C
ANISOU 5399  CG  LYS B 134    4137  4366  3630   451   586   -47   C
ATOM   5402  CD  LYS B 134   14.052  46.891 104.362  1.00 29.57         C
ANISOU 5402  CD  LYS B 134    3902  4076  3257   384   572  -182   C
ATOM   5405  CE  LYS B 134   15.030  46.238 103.364  1.00 26.66         C
ANISOU 5405  CE  LYS B 134    3570  3706  2853   315   496  -138   C
ATOM   5408  NZ  LYS B 134   14.369  45.100 102.694  1.00 24.96         N
ANISOU 5408  NZ  LYS B 134    3341  3560  2582   297   432   -15   N
ATOM   5412  C   LYS B 134    9.357  47.841 105.309  1.00 34.77         C
ANISOU 5412  C   LYS B 134    4270  4848  4092   685   779    23   C
ATOM   5413  O   LYS B 134    8.911  46.738 105.675  1.00 34.76         O
ANISOU 5413  O   LYS B 134    4223  4988  3996   633   746    66   O
ATOM   5415  N   ALA B 135    9.065  48.983 105.927  1.00 34.43         N
ANISOU 5415  N   ALA B 135    4229  4718  4136   792   904   -60   N
ATOM   5416  CA  ALA B 135    8.217  49.035 107.096  1.00 36.31         C
ANISOU 5416  CA  ALA B 135    4408  5040  4350   864  1016  -118   C
ATOM   5418  CB  ALA B 135    8.348  50.400 107.783  1.00 37.26         C
ANISOU 5418  CB  ALA B 135    4594  5010  4554   962  1163  -277   C
ATOM   5422  C   ALA B 135    6.728  48.744 106.787  1.00 36.42         C
ANISOU 5422  C   ALA B 135    4251  5171  4417   939  1029    51   C
ATOM   5423  O   ALA B 135    5.993  48.368 107.672  1.00 32.65         O
ANISOU 5423  O   ALA B 135    3699  4819  3887   962  1103    39   O
```

FIG. 18 (continued)

| | | | | | | | | | | | | |
|---|---|---|---|---|---|---|---|---|---|---|---|---|
| ATOM | 5425 | N | ASN | B | 136 | 6.295 | 48.917 | 105.532 | 1.00 | 38.44 | | N |
| ANISOU | 5425 | N | ASN | B | 136 | 4434 | 5404 | 4767 | 970 | 955 | 213 | N |
| ATOM | 5426 | CA | ASN | B | 136 | 4.889 | 48.656 | 105.148 | 1.00 | 40.73 | | C |
| ANISOU | 5426 | CA | ASN | B | 136 | 4532 | 5836 | 5109 | 1029 | 941 | 383 | C |
| ATOM | 5428 | CB | ASN | B | 136 | 4.673 | 48.961 | 103.652 | 1.00 | 43.65 | | C |
| ANISOU | 5428 | CB | ASN | B | 136 | 4849 | 6178 | 5556 | 1055 | 831 | 556 | C |
| ATOM | 5431 | CG | ASN | B | 136 | 3.499 | 48.182 | 103.044 | 1.00 | 47.44 | | C |
| ANISOU | 5431 | CG | ASN | B | 136 | 5137 | 6868 | 6021 | 1017 | 733 | 732 | C |
| ATOM | 5432 | OD1 | ASN | B | 136 | 2.442 | 48.754 | 102.744 | 1.00 | 51.26 | | O |
| ANISOU | 5432 | OD1 | ASN | B | 136 | 5452 | 7413 | 6611 | 1153 | 757 | 863 | O |
| ATOM | 5433 | ND2 | ASN | B | 136 | 3.682 | 46.864 | 102.869 | 1.00 | 49.39 | | N |
| ANISOU | 5433 | ND2 | ASN | B | 136 | 5404 | 7225 | 6139 | 830 | 624 | 734 | N |
| ATOM | 5436 | C | ASN | B | 136 | 4.432 | 47.231 | 105.466 | 1.00 | 39.31 | | C |
| ANISOU | 5436 | C | ASN | B | 136 | 4278 | 5851 | 4806 | 896 | 883 | 427 | C |
| ATOM | 5437 | O | ASN | B | 136 | 3.274 | 47.020 | 105.785 | 1.00 | 41.19 | | O |
| ANISOU | 5437 | O | ASN | B | 136 | 4351 | 6229 | 5069 | 935 | 931 | 504 | O |
| ATOM | 5439 | N | LYS | B | 137 | 5.340 | 46.265 | 105.390 | 1.00 | 37.61 | | N |
| ANISOU | 5439 | N | LYS | B | 137 | 4181 | 5639 | 4470 | 743 | 790 | 384 | N |
| ATOM | 5440 | CA | LYS | B | 137 | 4.985 | 44.866 | 105.589 | 1.00 | 39.29 | | C |
| ANISOU | 5440 | CA | LYS | B | 137 | 4355 | 5992 | 4579 | 605 | 736 | 435 | C |
| ATOM | 5442 | CB | LYS | B | 137 | 5.777 | 43.971 | 104.656 | 1.00 | 39.07 | | C |
| ANISOU | 5442 | CB | LYS | B | 137 | 4431 | 5930 | 4482 | 464 | 594 | 460 | C |
| ATOM | 5445 | CG | LYS | B | 137 | 7.250 | 44.086 | 104.859 | 1.00 | 38.83 | | C |
| ANISOU | 5445 | CG | LYS | B | 137 | 4575 | 5779 | 4399 | 452 | 588 | 336 | C |
| ATOM | 5448 | CD | LYS | B | 137 | 7.954 | 42.787 | 104.575 | 1.00 | 37.67 | | C |
| ANISOU | 5448 | CD | LYS | B | 137 | 4526 | 5637 | 4149 | 318 | 499 | 339 | C |
| ATOM | 5451 | CE | LYS | B | 137 | 9.284 | 43.012 | 103.919 | 1.00 | 34.76 | | C |
| ANISOU | 5451 | CE | LYS | B | 137 | 4280 | 5156 | 3771 | 307 | 448 | 280 | C |
| ATOM | 5454 | NZ | LYS | B | 137 | 10.167 | 44.007 | 104.553 | 1.00 | 33.21 | | N |
| ANISOU | 5454 | NZ | LYS | B | 137 | 4141 | 4881 | 3597 | 380 | 512 | 158 | N |
| ATOM | 5458 | C | LYS | B | 137 | 5.221 | 44.399 | 107.019 | 1.00 | 41.07 | | C |
| ANISOU | 5458 | C | LYS | B | 137 | 4639 | 6267 | 4700 | 582 | 829 | 334 | C |
| ATOM | 5459 | O | LYS | B | 137 | 5.072 | 43.216 | 107.301 | 1.00 | 39.79 | | O |
| ANISOU | 5459 | O | LYS | B | 137 | 4479 | 6192 | 4449 | 467 | 800 | 378 | O |
| ATOM | 5461 | N | ILE | B | 138 | 5.601 | 45.322 | 107.910 | 1.00 | 42.52 | | N |
| ANISOU | 5461 | N | ILE | B | 138 | 4881 | 6389 | 4885 | 685 | 942 | 200 | N |
| ATOM | 5462 | CA | ILE | B | 138 | 5.822 | 44.990 | 109.306 | 1.00 | 44.47 | | C |
| ANISOU | 5462 | CA | ILE | B | 138 | 5186 | 6707 | 5004 | 672 | 1030 | 99 | C |
| ATOM | 5464 | CB | ILE | B | 138 | 6.415 | 46.168 | 110.133 | 1.00 | 46.56 | | C |
| ANISOU | 5464 | CB | ILE | B | 138 | 5542 | 6885 | 5263 | 768 | 1136 | -88 | C |
| ATOM | 5466 | CG1 | ILE | B | 138 | 7.918 | 46.327 | 109.869 | 1.00 | 45.04 | | C |
| ANISOU | 5466 | CG1 | ILE | B | 138 | 5501 | 6579 | 5036 | 706 | 1044 | -190 | C |
| ATOM | 5469 | CD1 | ILE | B | 138 | 8.626 | 47.252 | 110.939 | 1.00 | 46.42 | | C |
| ANISOU | 5469 | CD1 | ILE | B | 138 | 5778 | 6705 | 5154 | 743 | 1134 | -406 | C |
| ATOM | 5473 | CG2 | ILE | B | 138 | 6.166 | 45.927 | 111.612 | 1.00 | 48.52 | | C |
| ANISOU | 5473 | CG2 | ILE | B | 138 | 5802 | 7262 | 5369 | 779 | 1255 | -170 | C |
| ATOM | 5477 | C | ILE | B | 138 | 4.514 | 44.597 | 109.947 | 1.00 | 45.77 | | C |
| ANISOU | 5477 | C | ILE | B | 138 | 5204 | 7029 | 5155 | 688 | 1130 | 178 | C |
| ATOM | 5478 | O | ILE | B | 138 | 3.567 | 45.389 | 110.006 | 1.00 | 46.79 | | O |
| ANISOU | 5478 | O | ILE | B | 138 | 5206 | 7184 | 5389 | 810 | 1232 | 197 | O |
| ATOM | 5480 | N | LYS | B | 139 | 4.475 | 43.362 | 110.423 | 1.00 | 46.03 | | N |
| ANISOU | 5480 | N | LYS | B | 139 | 5255 | 7166 | 5069 | 570 | 1110 | 233 | N |
| ATOM | 5481 | CA | LYS | B | 139 | 3.311 | 42.819 | 111.079 | 1.00 | 49.72 | | C |
| ANISOU | 5481 | CA | LYS | B | 139 | 5590 | 7793 | 5508 | 548 | 1210 | 320 | C |
| ATOM | 5483 | CB | LYS | B | 139 | 2.897 | 41.509 | 110.396 | 1.00 | 50.73 | | C |
| ANISOU | 5483 | CB | LYS | B | 139 | 5667 | 7972 | 5637 | 381 | 1105 | 473 | C |
| ATOM | 5486 | CG | LYS | B | 139 | 1.775 | 41.612 | 109.373 | 1.00 | 51.77 | | C |
| ANISOU | 5486 | CG | LYS | B | 139 | 5599 | 8165 | 5908 | 365 | 1058 | 595 | C |
| ATOM | 5489 | CD | LYS | B | 139 | 1.844 | 42.834 | 108.496 | 1.00 | 51.60 | | C |
| ANISOU | 5489 | CD | LYS | B | 139 | 5537 | 8055 | 6011 | 500 | 1018 | 573 | C |
| ATOM | 5492 | CE | LYS | B | 139 | 1.067 | 42.604 | 107.214 | 1.00 | 52.08 | | C |
| ANISOU | 5492 | CE | LYS | B | 139 | 5446 | 8180 | 6164 | 437 | 895 | 715 | C |
| ATOM | 5495 | NZ | LYS | B | 139 | 0.727 | 43.884 | 106.554 | 1.00 | 53.34 | | N |
| ANISOU | 5495 | NZ | LYS | B | 139 | 5505 | 8304 | 6456 | 609 | 897 | 746 | N |
| ATOM | 5499 | C | LYS | B | 139 | 3.582 | 42.568 | 112.556 | 1.00 | 51.05 | | C |
| ANISOU | 5499 | C | LYS | B | 139 | 5845 | 8044 | 5508 | 552 | 1323 | 241 | C |
| ATOM | 5500 | O | LYS | B | 139 | 2.669 | 42.683 | 113.367 | 1.00 | 54.66 | | O |
| ANISOU | 5500 | O | LYS | B | 139 | 6201 | 8628 | 5940 | 599 | 1472 | 254 | O |
| ATOM | 5502 | N | SER | B | 140 | 4.835 | 42.259 | 112.898 | 1.00 | 49.73 | | N |
| ANISOU | 5502 | N | SER | B | 140 | 5854 | 7823 | 5218 | 511 | 1256 | 163 | N |
| ATOM | 5503 | CA | SER | B | 140 | 5.197 | 41.776 | 114.230 | 1.00 | 49.24 | | C |
| ANISOU | 5503 | CA | SER | B | 140 | 5885 | 7866 | 4960 | 492 | 1323 | 124 | C |
| ATOM | 5505 | CB | SER | B | 140 | 5.706 | 40.323 | 114.134 | 1.00 | 49.20 | | C |
| ANISOU | 5505 | CB | SER | B | 140 | 5964 | 7862 | 4868 | 365 | 1219 | 247 | C |
| ATOM | 5508 | OG | SER | B | 140 | 6.574 | 40.129 | 113.024 | 1.00 | 48.91 | | O |
| ANISOU | 5508 | OG | SER | B | 140 | 5995 | 7683 | 4906 | 326 | 1065 | 249 | O |
| ATOM | 5510 | C | SER | B | 140 | 6.217 | 42.669 | 114.943 | 1.00 | 46.89 | | C |
| ANISOU | 5510 | C | SER | B | 140 | 5711 | 7540 | 4566 | 565 | 1341 | -73 | C |
| ATOM | 5511 | O | SER | B | 140 | 6.758 | 43.613 | 114.367 | 1.00 | 44.75 | | O |

FIG. 18 (continued)

| | | | | | | | | | | | | |
|---|---|---|---|---|---|---|---|---|---|---|---|---|
| ANISOU | 5511 | O | SER | B | 140 | 5469 | 7140 | 4394 | 613 | 1299 | -181 | O |
| ATOM | 5513 | N | GLU | B | 141 | 6.457 | 42.354 | 116.212 | 1.00 | 45.24 | | N |
| ANISOU | 5513 | N | GLU | B | 141 | 5574 | 7463 | 4153 | 559 | 1405 | -115 | N |
| ATOM | 5514 | CA | GLU | B | 141 | 7.351 | 43.118 | 117.077 | 1.00 | 44.45 | | C |
| ANISOU | 5514 | CA | GLU | B | 141 | 5586 | 7387 | 3916 | 602 | 1423 | -314 | C |
| ATOM | 5516 | CB | GLU | B | 141 | 6.954 | 42.907 | 118.547 | 1.00 | 47.39 | | C |
| ANISOU | 5516 | CB | GLU | B | 141 | 5983 | 7958 | 4063 | 617 | 1560 | -339 | C |
| ATOM | 5519 | CG | GLU | B | 141 | 5.539 | 43.282 | 118.878 | 1.00 | 49.82 | | C |
| ANISOU | 5519 | CG | GLU | B | 141 | 6169 | 8337 | 4423 | 685 | 1756 | -322 | C |
| ATOM | 5522 | CD | GLU | B | 141 | 5.211 | 43.105 | 120.362 | 1.00 | 52.12 | | C |
| ANISOU | 5522 | CD | GLU | B | 141 | 6500 | 8840 | 4465 | 699 | 1909 | -358 | C |
| ATOM | 5523 | OE1 | GLU | B | 141 | 4.135 | 42.523 | 120.646 | 1.00 | 52.85 | | O |
| ANISOU | 5523 | OE1 | GLU | B | 141 | 6487 | 9046 | 4546 | 687 | 2030 | -212 | O |
| ATOM | 5524 | OE2 | GLU | B | 141 | 6.024 | 43.556 | 121.216 | 1.00 | 52.51 | | O |
| ANISOU | 5524 | OE2 | GLU | B | 141 | 6677 | 8951 | 4325 | 711 | 1907 | -533 | O |
| ATOM | 5525 | C | GLU | B | 141 | 8.807 | 42.699 | 116.961 | 1.00 | 42.41 | | C |
| ANISOU | 5525 | C | GLU | B | 141 | 5441 | 7098 | 3574 | 543 | 1256 | -338 | C |
| ATOM | 5526 | O | GLU | B | 141 | 9.699 | 43.443 | 117.350 | 1.00 | 45.02 | | O |
| ANISOU | 5526 | O | GLU | B | 141 | 5846 | 7423 | 3838 | 556 | 1228 | -513 | O |
| ATOM | 5528 | N | ASN | B | 142 | 9.058 | 41.501 | 116.453 | 1.00 | 38.14 | | N |
| ANISOU | 5528 | N | ASN | B | 142 | 4913 | 6541 | 3039 | 477 | 1151 | -167 | N |
| ATOM | 5529 | CA | ASN | B | 142 | 10.400 | 40.941 | 116.530 | 1.00 | 39.18 | | C |
| ANISOU | 5529 | CA | ASN | B | 142 | 5139 | 6677 | 3069 | 447 | 1014 | -163 | C |
| ATOM | 5531 | CB | ASN | B | 142 | 10.330 | 39.465 | 116.952 | 1.00 | 40.43 | | C |
| ANISOU | 5531 | CB | ASN | B | 142 | 5337 | 6914 | 3110 | 406 | 996 | 33 | C |
| ATOM | 5534 | CG | ASN | B | 142 | 9.835 | 38.550 | 115.827 | 1.00 | 38.96 | | C |
| ANISOU | 5534 | CG | ASN | B | 142 | 5120 | 6600 | 3084 | 343 | 958 | 199 | C |
| ATOM | 5535 | OD1 | ASN | B | 142 | 9.072 | 38.972 | 114.944 | 1.00 | 39.47 | | O |
| ANISOU | 5535 | OD1 | ASN | B | 142 | 5098 | 6582 | 3317 | 328 | 980 | 196 | O |
| ATOM | 5536 | ND2 | ASN | B | 142 | 10.287 | 37.296 | 115.849 | 1.00 | 39.38 | | N |
| ANISOU | 5536 | ND2 | ASN | B | 142 | 5248 | 6634 | 3080 | 307 | 898 | 343 | N |
| ATOM | 5539 | C | ASN | B | 142 | 11.194 | 41.093 | 115.237 | 1.00 | 35.75 | | C |
| ANISOU | 5539 | C | ASN | B | 142 | 4710 | 6078 | 2794 | 428 | 887 | -178 | C |
| ATOM | 5540 | O | ASN | B | 142 | 12.121 | 40.342 | 115.004 | 1.00 | 34.63 | | O |
| ANISOU | 5540 | O | ASN | B | 142 | 4620 | 5922 | 2617 | 405 | 779 | -117 | O |
| ATOM | 5542 | N | THR | B | 143 | 10.814 | 42.062 | 114.404 | 1.00 | 35.91 | | N |
| ANISOU | 5542 | N | THR | B | 143 | 4676 | 5978 | 2989 | 449 | 913 | -246 | N |
| ATOM | 5543 | CA | THR | B | 143 | 11.590 | 42.457 | 113.238 | 1.00 | 36.09 | | C |
| ANISOU | 5543 | CA | THR | B | 143 | 4710 | 5855 | 3148 | 435 | 816 | -280 | C |
| ATOM | 5545 | CB | THR | B | 143 | 10.760 | 42.347 | 111.941 | 1.00 | 36.28 | | C |
| ANISOU | 5545 | CB | THR | B | 143 | 4665 | 5773 | 3348 | 423 | 806 | -164 | C |
| ATOM | 5547 | OG1 | THR | B | 143 | 9.557 | 43.141 | 112.062 | 1.00 | 37.16 | | O |
| ANISOU | 5547 | OG1 | THR | B | 143 | 4689 | 5891 | 3539 | 482 | 921 | -178 | O |
| ATOM | 5549 | CG2 | THR | B | 143 | 10.423 | 40.878 | 111.669 | 1.00 | 34.47 | | C |
| ANISOU | 5549 | CG2 | THR | B | 143 | 4439 | 5572 | 3088 | 357 | 762 | 7 | C |
| ATOM | 5553 | C | THR | B | 143 | 12.131 | 43.876 | 113.399 | 1.00 | 35.29 | | C |
| ANISOU | 5553 | C | THR | B | 143 | 4629 | 5696 | 3085 | 463 | 843 | -478 | C |
| ATOM | 5554 | O | THR | B | 143 | 11.484 | 44.774 | 113.968 | 1.00 | 39.62 | | O |
| ANISOU | 5554 | O | THR | B | 143 | 5163 | 6250 | 3642 | 513 | 961 | -581 | O |
| ATOM | 5556 | N | HIS | B | 144 | 13.374 | 44.036 | 113.009 | 1.00 | 32.78 | | N |
| ANISOU | 5556 | N | HIS | B | 144 | 4350 | 5328 | 2778 | 426 | 746 | -540 | N |
| ATOM | 5557 | CA | HIS | B | 144 | 14.073 | 45.297 | 113.095 | 1.00 | 31.81 | | C |
| ANISOU | 5557 | CA | HIS | B | 144 | 4254 | 5135 | 2696 | 415 | 757 | -728 | C |
| ATOM | 5559 | CB | HIS | B | 144 | 15.235 | 45.119 | 114.062 | 1.00 | 34.13 | | C |
| ANISOU | 5559 | CB | HIS | B | 144 | 4587 | 5572 | 2811 | 369 | 686 | -833 | C |
| ATOM | 5562 | CG | HIS | B | 144 | 15.665 | 46.377 | 114.762 | 1.00 | 35.18 | | C |
| ANISOU | 5562 | CG | HIS | B | 144 | 4758 | 5700 | 2911 | 336 | 730 | -1071 | C |
| ATOM | 5563 | ND1 | HIS | B | 144 | 15.032 | 46.851 | 115.883 | 1.00 | 36.63 | | N |
| ANISOU | 5563 | ND1 | HIS | B | 144 | 4976 | 5963 | 2980 | 362 | 839 | -1194 | N |
| ATOM | 5565 | CE1 | HIS | B | 144 | 15.643 | 47.949 | 116.303 | 1.00 | 37.37 | | C |
| ANISOU | 5565 | CE1 | HIS | B | 144 | 5117 | 6019 | 3061 | 305 | 858 | -1424 | C |
| ATOM | 5567 | NE2 | HIS | B | 144 | 16.646 | 48.204 | 115.482 | 1.00 | 35.13 | | N |
| ANISOU | 5567 | NE2 | HIS | B | 144 | 4819 | 5639 | 2891 | 236 | 765 | -1440 | N |
| ATOM | 5569 | CD2 | HIS | B | 144 | 16.694 | 47.223 | 114.522 | 1.00 | 34.27 | | C |
| ANISOU | 5569 | CD2 | HIS | B | 144 | 4657 | 5512 | 2854 | 262 | 686 | -1220 | C |
| ATOM | 5571 | C | HIS | B | 144 | 14.560 | 45.640 | 111.681 | 1.00 | 29.97 | | C |
| ANISOU | 5571 | C | HIS | B | 144 | 4011 | 4737 | 2640 | 391 | 700 | -692 | C |
| ATOM | 5572 | O | HIS | B | 144 | 14.920 | 44.757 | 110.906 | 1.00 | 28.16 | | O |
| ANISOU | 5572 | O | HIS | B | 144 | 3774 | 4501 | 2427 | 368 | 616 | -567 | O |
| ATOM | 5574 | N | ILE | B | 145 | 14.517 | 46.912 | 111.330 | 1.00 | 29.52 | | N |
| ANISOU | 5574 | N | ILE | B | 145 | 3965 | 4538 | 2714 | 400 | 762 | -794 | N |
| ATOM | 5575 | CA | ILE | B | 145 | 14.994 | 47.375 | 110.035 | 1.00 | 28.22 | | C |
| ANISOU | 5575 | CA | ILE | B | 145 | 3800 | 4217 | 2705 | 375 | 725 | -757 | C |
| ATOM | 5577 | CB | ILE | B | 145 | 13.930 | 48.222 | 109.277 | 1.00 | 28.85 | | C |
| ANISOU | 5577 | CB | ILE | B | 145 | 3858 | 4146 | 2959 | 449 | 812 | -697 | C |
| ATOM | 5579 | CG1 | ILE | B | 145 | 12.664 | 47.420 | 108.946 | 1.00 | 29.62 | | C |
| ANISOU | 5579 | CG1 | ILE | B | 145 | 3884 | 4311 | 3061 | 506 | 814 | -520 | C |
| ATOM | 5582 | CD1 | ILE | B | 145 | 11.467 | 48.415 | 108.819 | 1.00 | 30.22 | | C |
| ANISOU | 5582 | CD1 | ILE | B | 145 | 3912 | 4297 | 3272 | 616 | 931 | -502 | C |

FIG. 18 (continued)

| | | | | | | | | | | | | |
|---|---|---|---|---|---|---|---|---|---|---|---|---|
| ATOM | 5586 | CG2 | ILE | B | 145 | 14.476 | 48.748 | 107.975 | 1.00 | 28.67 | | C |
| ANISOU | 5586 | CG2 | ILE | B | 145 | 3849 | 3971 | 3074 | 421 | 778 | -646 | C |
| ATOM | 5590 | C | ILE | B | 145 | 16.198 | 48.279 | 110.215 | 1.00 | 28.46 | | C |
| ANISOU | 5590 | C | ILE | B | 145 | 3871 | 4190 | 2754 | 299 | 714 | -929 | C |
| ATOM | 5591 | O | ILE | B | 145 | 16.204 | 49.125 | 111.096 | 1.00 | 28.82 | | O |
| ANISOU | 5591 | O | ILE | B | 145 | 3954 | 4222 | 2775 | 289 | 784 | -1101 | O |
| ATOM | 5593 | N | HIS | B | 146 | 17.202 | 48.105 | 109.366 | 1.00 | 26.00 | | N |
| ANISOU | 5593 | N | HIS | B | 146 | 3548 | 3843 | 2486 | 238 | 635 | -891 | N |
| ATOM | 5594 | CA | HIS | B | 146 | 18.395 | 48.956 | 109.376 | 1.00 | 27.37 | | C |
| ANISOU | 5594 | CA | HIS | B | 146 | 3736 | 3962 | 2700 | 140 | 622 | -1038 | C |
| ATOM | 5596 | CB | HIS | B | 146 | 19.537 | 48.249 | 110.114 | 1.00 | 27.91 | | C |
| ANISOU | 5596 | CB | HIS | B | 146 | 3768 | 4227 | 2610 | 78 | 517 | -1098 | C |
| ATOM | 5599 | CG | HIS | B | 146 | 20.691 | 49.133 | 110.477 | 1.00 | 28.45 | | C |
| ANISOU | 5599 | CG | HIS | B | 146 | 3827 | 4297 | 2685 | -45 | 498 | -1286 | C |
| ATOM | 5600 | ND1 | HIS | B | 146 | 21.494 | 48.884 | 111.567 | 1.00 | 29.91 | | N |
| ANISOU | 5600 | ND1 | HIS | B | 146 | 3977 | 4685 | 2703 | -104 | 418 | -1402 | N |
| ATOM | 5602 | CE1 | HIS | B | 146 | 22.417 | 49.818 | 111.657 | 1.00 | 31.27 | | C |
| ANISOU | 5602 | CE1 | HIS | B | 146 | 4135 | 4825 | 2922 | -237 | 410 | -1569 | C |
| ATOM | 5604 | NE2 | HIS | B | 146 | 22.263 | 50.653 | 110.646 | 1.00 | 32.75 | | N |
| ANISOU | 5604 | NE2 | HIS | B | 146 | 4358 | 4773 | 3310 | -263 | 494 | -1554 | N |
| ATOM | 5606 | CD2 | HIS | B | 146 | 21.183 | 50.258 | 109.900 | 1.00 | 30.46 | | C |
| ANISOU | 5606 | CD2 | HIS | B | 146 | 4100 | 4383 | 3092 | -134 | 546 | -1373 | C |
| ATOM | 5608 | C | HIS | B | 146 | 18.772 | 49.283 | 107.935 | 1.00 | 27.87 | | C |
| ANISOU | 5608 | C | HIS | B | 146 | 3796 | 3876 | 2918 | 114 | 619 | -944 | C |
| ATOM | 5609 | O | HIS | B | 146 | 19.142 | 48.405 | 107.153 | 1.00 | 25.87 | | O |
| ANISOU | 5609 | O | HIS | B | 146 | 3512 | 3671 | 2648 | 114 | 550 | -816 | O |
| ATOM | 5611 | N | ILE | B | 147 | 18.638 | 50.550 | 107.569 | 1.00 | 28.39 | | N |
| ANISOU | 5611 | N | ILE | B | 147 | 3905 | 3750 | 3131 | 97 | 706 | -1000 | N |
| ATOM | 5612 | CA | ILE | B | 147 | 18.956 | 50.983 | 106.212 | 1.00 | 28.67 | | C |
| ANISOU | 5612 | CA | ILE | B | 147 | 3948 | 3639 | 3305 | 72 | 719 | -897 | C |
| ATOM | 5614 | CB | ILE | B | 147 | 17.824 | 51.920 | 105.627 | 1.00 | 28.68 | | C |
| ANISOU | 5614 | CB | ILE | B | 147 | 3994 | 3442 | 3461 | 166 | 822 | -815 | C |
| ATOM | 5616 | CG1 | ILE | B | 147 | 16.434 | 51.220 | 105.664 | 1.00 | 27.43 | | C |
| ANISOU | 5616 | CG1 | ILE | B | 147 | 3797 | 3366 | 3258 | 296 | 816 | -685 | C |
| ATOM | 5619 | CD1 | ILE | B | 147 | 16.285 | 49.920 | 105.003 | 1.00 | 25.21 | | C |
| ANISOU | 5619 | CD1 | ILE | B | 147 | 3468 | 3220 | 2892 | 304 | 718 | -528 | C |
| ATOM | 5623 | CG2 | ILE | B | 147 | 18.225 | 52.447 | 104.205 | 1.00 | 27.76 | | C |
| ANISOU | 5623 | CG2 | ILE | B | 147 | 3899 | 3176 | 3472 | 134 | 837 | -690 | C |
| ATOM | 5627 | C | ILE | B | 147 | 20.293 | 51.753 | 106.205 | 1.00 | 29.55 | | C |
| ANISOU | 5627 | C | ILE | B | 147 | 4065 | 3691 | 3470 | -72 | 724 | -1031 | C |
| ATOM | 5628 | O | ILE | B | 147 | 20.546 | 52.566 | 107.101 | 1.00 | 31.50 | | O |
| ANISOU | 5628 | O | ILE | B | 147 | 4347 | 3895 | 3726 | -139 | 769 | -1222 | O |
| ATOM | 5630 | N | PHE | B | 148 | 21.121 | 51.468 | 105.206 | 1.00 | 28.40 | | N |
| ANISOU | 5630 | N | PHE | B | 148 | 3885 | 3553 | 3355 | -127 | 685 | -939 | N |
| ATOM | 5631 | CA | PHE | B | 148 | 22.310 | 52.204 | 104.889 | 1.00 | 30.25 | | C |
| ANISOU | 5631 | CA | PHE | B | 148 | 4105 | 3718 | 3670 | -268 | 706 | -1018 | C |
| ATOM | 5633 | CB | PHE | B | 148 | 23.517 | 51.266 | 104.837 | 1.00 | 29.84 | | C |
| ANISOU | 5633 | CB | PHE | B | 148 | 3950 | 3869 | 3521 | -327 | 610 | -1014 | C |
| ATOM | 5636 | CG | PHE | B | 148 | 23.837 | 50.577 | 106.156 | 1.00 | 29.46 | | C |
| ANISOU | 5636 | CG | PHE | B | 148 | 3843 | 4038 | 3312 | -327 | 519 | -1127 | C |
| ATOM | 5637 | CD1 | PHE | B | 148 | 24.755 | 51.125 | 107.027 | 1.00 | 31.40 | | C |
| ANISOU | 5637 | CD1 | PHE | B | 148 | 4041 | 4359 | 3530 | -460 | 491 | -1316 | C |
| ATOM | 5639 | CE1 | PHE | B | 148 | 25.089 | 50.477 | 108.225 | 1.00 | 31.21 | | C |
| ANISOU | 5639 | CE1 | PHE | B | 148 | 3958 | 4569 | 3333 | -456 | 392 | -1401 | C |
| ATOM | 5641 | CZ | PHE | B | 148 | 24.497 | 49.250 | 108.526 | 1.00 | 31.34 | | C |
| ANISOU | 5641 | CZ | PHE | B | 148 | 3973 | 4714 | 3219 | -312 | 339 | -1280 | C |
| ATOM | 5643 | CE2 | PHE | B | 148 | 23.587 | 48.675 | 107.639 | 1.00 | 27.71 | | C |
| ANISOU | 5643 | CE2 | PHE | B | 148 | 3565 | 4157 | 2806 | -195 | 377 | -1100 | C |
| ATOM | 5645 | CD2 | PHE | B | 148 | 23.255 | 49.345 | 106.473 | 1.00 | 28.17 | | C |
| ANISOU | 5645 | CD2 | PHE | B | 148 | 3672 | 4012 | 3021 | -205 | 459 | -1031 | C |
| ATOM | 5647 | C | PHE | B | 148 | 22.208 | 52.857 | 103.507 | 1.00 | 30.69 | | C |
| ANISOU | 5647 | C | PHE | B | 148 | 4206 | 3581 | 3872 | -270 | 780 | -874 | C |
| ATOM | 5648 | O | PHE | B | 148 | 21.756 | 52.229 | 102.547 | 1.00 | 28.53 | | O |
| ANISOU | 5648 | O | PHE | B | 148 | 3931 | 3330 | 3579 | -187 | 758 | -693 | O |
| ATOM | 5650 | N | SER | B | 149 | 22.654 | 54.106 | 103.393 | 1.00 | 33.71 | | N |
| ANISOU | 5650 | N | SER | B | 149 | 4636 | 3777 | 4394 | -376 | 868 | -954 | N |
| ATOM | 5651 | CA | SER | B | 149 | 22.897 | 54.712 | 102.076 | 1.00 | 34.74 | | C |
| ANISOU | 5651 | CA | SER | B | 149 | 4803 | 3746 | 4652 | -411 | 939 | -809 | C |
| ATOM | 5653 | CB | SER | B | 149 | 22.351 | 56.141 | 102.000 | 1.00 | 37.78 | | C |
| ANISOU | 5653 | CB | SER | B | 149 | 5305 | 3836 | 5215 | -407 | 1071 | -822 | C |
| ATOM | 5656 | OG | SER | B | 149 | 23.274 | 57.061 | 102.552 | 1.00 | 40.74 | | O |
| ANISOU | 5656 | OG | SER | B | 149 | 5701 | 4102 | 5677 | -590 | 1128 | -1016 | O |
| ATOM | 5658 | C | SER | B | 149 | 24.392 | 54.717 | 101.696 | 1.00 | 35.67 | | C |
| ANISOU | 5658 | C | SER | B | 149 | 4846 | 3929 | 4780 | -580 | 930 | -847 | C |
| ATOM | 5659 | O | SER | B | 149 | 25.258 | 54.574 | 102.532 | 1.00 | 36.35 | | O |
| ANISOU | 5659 | O | SER | B | 149 | 4853 | 4144 | 4814 | -689 | 879 | -1012 | O |
| ATOM | 5661 | N | PHE | B | 150 | 24.674 | 54.889 | 100.414 | 1.00 | 36.28 | | N |
| ANISOU | 5661 | N | PHE | B | 150 | 4935 | 3933 | 4916 | -600 | 982 | -683 | N |
| ATOM | 5662 | CA | PHE | B | 150 | 26.061 | 54.958 | 99.940 | 1.00 | 37.32 | | C |

FIG. 18 (continued)

| | | | | | | | | | | | | |
|---|---|---|---|---|---|---|---|---|---|---|---|---|
| ANISOU | 5662 | CA | PHE | B | 150 | 4985 | 4123 | 5073 | -759 | 1002 | -698 | C |
| ATOM | 5664 | CB | PHE | B | 150 | 26.131 | 54.850 | 98.400 | 1.00 | 35.70 | | C |
| ANISOU | 5664 | CB | PHE | B | 150 | 4804 | 3882 | 4877 | -731 | 1057 | -474 | C |
| ATOM | 5667 | CG | PHE | B | 150 | 25.944 | 53.462 | 97.892 | 1.00 | 33.57 | | C |
| ANISOU | 5667 | CG | PHE | B | 150 | 4491 | 3814 | 4449 | -608 | 975 | -369 | C |
| ATOM | 5668 | CD1 | PHE | B | 150 | 27.043 | 52.673 | 97.577 | 1.00 | 32.67 | | C |
| ANISOU | 5668 | CD1 | PHE | B | 150 | 4268 | 3882 | 4262 | -655 | 954 | -375 | C |
| ATOM | 5670 | CE1 | PHE | B | 150 | 26.861 | 51.359 | 97.098 | 1.00 | 31.68 | | C |
| ANISOU | 5670 | CE1 | PHE | B | 150 | 4128 | 3913 | 3997 | -536 | 895 | -292 | C |
| ATOM | 5672 | CZ | PHE | B | 150 | 25.587 | 50.860 | 96.946 | 1.00 | 30.18 | | C |
| ANISOU | 5672 | CZ | PHE | B | 150 | 4023 | 3705 | 3738 | -402 | 845 | -207 | C |
| ATOM | 5674 | CE2 | PHE | B | 150 | 24.488 | 51.648 | 97.233 | 1.00 | 29.47 | | C |
| ANISOU | 5674 | CE2 | PHE | B | 150 | 4015 | 3464 | 3719 | -360 | 856 | -187 | C |
| ATOM | 5676 | CD2 | PHE | B | 150 | 24.668 | 52.942 | 97.702 | 1.00 | 31.36 | | C |
| ANISOU | 5676 | CD2 | PHE | B | 150 | 4278 | 3538 | 4101 | -449 | 927 | -265 | C |
| ATOM | 5678 | C | PHE | B | 150 | 26.828 | 56.208 | 100.415 | 1.00 | 40.66 | | C |
| ANISOU | 5678 | C | PHE | B | 150 | 5417 | 4395 | 5637 | -961 | 1080 | -860 | C |
| ATOM | 5679 | O | PHE | B | 150 | 28.053 | 56.200 | 100.448 | 1.00 | 41.57 | | O |
| ANISOU | 5679 | O | PHE | B | 150 | 5420 | 4617 | 5760 | -1121 | 1071 | -936 | O |
| ATOM | 5681 | N | THR | B | 151 | 26.120 | 57.273 | 100.769 | 1.00 | 41.59 | | N |
| ANISOU | 5681 | N | THR | B | 151 | 5663 | 4265 | 5876 | -958 | 1162 | -916 | N |
| ATOM | 5682 | CA | THR | B | 151 | 26.764 | 58.499 | 101.207 | 1.00 | 44.08 | | C |
| ANISOU | 5682 | CA | THR | B | 151 | 6020 | 4392 | 6338 | -1163 | 1251 | -1086 | C |
| ATOM | 5684 | CB | THR | B | 151 | 26.054 | 59.729 | 100.616 | 1.00 | 46.69 | | C |
| ANISOU | 5684 | CB | THR | B | 151 | 6523 | 4358 | 6858 | -1129 | 1405 | -982 | C |
| ATOM | 5686 | OG1 | THR | B | 151 | 24.646 | 59.639 | 100.860 | 1.00 | 45.83 | | O |
| ANISOU | 5686 | OG1 | THR | B | 151 | 6499 | 4184 | 6730 | -900 | 1403 | -924 | O |
| ATOM | 5688 | CG2 | THR | B | 151 | 26.310 | 59.815 | 99.107 | 1.00 | 46.72 | | C |
| ANISOU | 5688 | CG2 | THR | B | 151 | 6538 | 4301 | 6914 | -1129 | 1470 | -718 | C |
| ATOM | 5692 | C | THR | B | 151 | 26.868 | 58.629 | 102.740 | 1.00 | 45.70 | | C |
| ANISOU | 5692 | C | THR | B | 151 | 6209 | 4666 | 6488 | -1239 | 1195 | -1371 | C |
| ATOM | 5693 | O | THR | B | 151 | 27.183 | 59.719 | 103.246 | 1.00 | 47.53 | | O |
| ANISOU | 5693 | O | THR | B | 151 | 6510 | 4709 | 6839 | -1406 | 1273 | -1552 | O |
| ATOM | 5695 | N | GLY | B | 152 | 26.626 | 57.539 | 103.477 | 1.00 | 43.25 | | N |
| ANISOU | 5695 | N | GLY | B | 152 | 5821 | 4620 | 5994 | -1130 | 1066 | -1416 | N |
| ATOM | 5696 | CA | GLY | B | 152 | 26.812 | 57.547 | 104.950 | 1.00 | 43.00 | | C |
| ANISOU | 5696 | CA | GLY | B | 152 | 5764 | 4714 | 5862 | -1206 | 997 | -1677 | C |
| ATOM | 5699 | C | GLY | B | 152 | 25.588 | 57.710 | 105.844 | 1.00 | 41.82 | | C |
| ANISOU | 5699 | C | GLY | B | 152 | 5731 | 4491 | 5669 | -1067 | 1023 | -1767 | C |
| ATOM | 5700 | O | GLY | B | 152 | 25.706 | 57.667 | 107.059 | 1.00 | 39.73 | | O |
| ANISOU | 5700 | O | GLY | B | 152 | 5454 | 4353 | 5289 | -1122 | 970 | -1978 | O |
| ATOM | 5702 | N | GLU | B | 153 | 24.402 | 57.882 | 105.272 | 1.00 | 41.58 | | N |
| ANISOU | 5702 | N | GLU | B | 153 | 5802 | 4282 | 5716 | -882 | 1106 | -1605 | N |
| ATOM | 5703 | CA | GLU | B | 153 | 23.189 | 57.972 | 106.089 | 1.00 | 42.27 | | C |
| ANISOU | 5703 | CA | GLU | B | 153 | 5973 | 4324 | 5765 | -728 | 1144 | -1672 | C |
| ATOM | 5705 | CB | GLU | B | 153 | 22.093 | 58.719 | 105.316 | 1.00 | 43.41 | | C |
| ANISOU | 5705 | CB | GLU | B | 153 | 6233 | 4177 | 6084 | -574 | 1279 | -1512 | C |
| ATOM | 5708 | CG | GLU | B | 153 | 22.377 | 60.205 | 105.125 | 1.00 | 46.42 | | C |
| ANISOU | 5708 | CG | GLU | B | 153 | 6745 | 4211 | 6683 | -690 | 1431 | -1600 | C |
| ATOM | 5711 | CD | GLU | B | 153 | 23.591 | 60.516 | 104.240 | 1.00 | 49.30 | | C |
| ANISOU | 5711 | CD | GLU | B | 153 | 7076 | 4519 | 7137 | -888 | 1437 | -1540 | C |
| ATOM | 5712 | OE1 | GLU | B | 153 | 24.538 | 61.203 | 104.734 | 1.00 | 53.07 | | O |
| ANISOU | 5712 | OE1 | GLU | B | 153 | 7571 | 4923 | 7670 | -1122 | 1467 | -1756 | O |
| ATOM | 5713 | OE2 | GLU | B | 153 | 23.604 | 60.086 | 103.054 | 1.00 | 47.86 | | O |
| ANISOU | 5713 | OE2 | GLU | B | 153 | 6848 | 4373 | 6962 | -824 | 1415 | -1285 | O |
| ATOM | 5714 | C | GLU | B | 153 | 22.700 | 56.587 | 106.545 | 1.00 | 40.04 | | C |
| ANISOU | 5714 | C | GLU | B | 153 | 5603 | 4336 | 5276 | -587 | 1022 | -1605 | C |
| ATOM | 5715 | O | GLU | B | 153 | 22.869 | 55.585 | 105.831 | 1.00 | 38.28 | | O |
| ANISOU | 5715 | O | GLU | B | 153 | 5292 | 4265 | 4987 | -533 | 938 | -1424 | O |
| ATOM | 5717 | N | GLU | B | 154 | 22.103 | 56.528 | 107.730 | 1.00 | 40.66 | | N |
| ANISOU | 5717 | N | GLU | B | 154 | 5714 | 4485 | 5250 | -532 | 1026 | -1753 | N |
| ATOM | 5718 | CA | GLU | B | 154 | 21.452 | 55.326 | 108.244 | 1.00 | 38.96 | | C |
| ANISOU | 5718 | CA | GLU | B | 154 | 5439 | 4509 | 4853 | -393 | 943 | -1680 | C |
| ATOM | 5720 | CB | GLU | B | 154 | 22.224 | 54.705 | 109.403 | 1.00 | 40.09 | | C |
| ANISOU | 5720 | CB | GLU | B | 154 | 5515 | 4929 | 4791 | -487 | 828 | -1841 | C |
| ATOM | 5723 | CG | GLU | B | 154 | 23.517 | 54.048 | 109.069 | 1.00 | 40.74 | | C |
| ANISOU | 5723 | CG | GLU | B | 154 | 5473 | 5190 | 4815 | -594 | 703 | -1799 | C |
| ATOM | 5726 | CD | GLU | B | 154 | 24.294 | 53.748 | 110.328 | 1.00 | 41.67 | | C |
| ANISOU | 5726 | CD | GLU | B | 154 | 5526 | 5563 | 4745 | -696 | 596 | -1983 | C |
| ATOM | 5727 | OE1 | GLU | B | 154 | 24.928 | 54.675 | 110.850 | 1.00 | 45.17 | | O |
| ANISOU | 5727 | OE1 | GLU | B | 154 | 5989 | 5964 | 5210 | -869 | 613 | -2203 | O |
| ATOM | 5728 | OE2 | GLU | B | 154 | 24.240 | 52.611 | 110.814 | 1.00 | 40.71 | | O |
| ANISOU | 5728 | OE2 | GLU | B | 154 | 5340 | 5679 | 4448 | -607 | 498 | -1907 | O |
| ATOM | 5729 | C | GLU | B | 154 | 20.110 | 55.678 | 108.820 | 1.00 | 39.28 | | C |
| ANISOU | 5729 | C | GLU | B | 154 | 5559 | 4459 | 4906 | -245 | 1047 | -1713 | C |
| ATOM | 5730 | O | GLU | B | 154 | 19.926 | 56.769 | 109.387 | 1.00 | 38.12 | | O |
| ANISOU | 5730 | O | GLU | B | 154 | 5514 | 4134 | 4837 | -277 | 1163 | -1897 | O |
| ATOM | 5732 | N | MET | B | 155 | 19.188 | 54.732 | 108.751 | 1.00 | 38.02 | | N |
| ANISOU | 5732 | N | MET | B | 155 | 5351 | 4428 | 4665 | -89 | 1013 | -1551 | N |

FIG. 18 (continued)

```
ATOM   5733 CA  MET B 155      17.954  54.832 109.520  1.00 38.96           C
ANISOU 5733 CA  MET B 155     5506   4546   4751     48   1101  -1589        C
ATOM   5735 CB  MET B 155      16.829  55.342 108.614  1.00 40.50           C
ANISOU 5735 CB  MET B 155     5720   4539   5129    206   1202  -1414        C
ATOM   5738 CG  MET B 155      15.546  55.679 109.322  1.00 42.84           C
ANISOU 5738 CG  MET B 155     6039   4800   5439    362   1326  -1455        C
ATOM   5741 SD  MET B 155      14.456  56.644 108.251  1.00 45.46           S
ANISOU 5741 SD  MET B 155     6391   4852   6030    544   1456  -1269        S
ATOM   5742 CE  MET B 155      13.074  56.901 109.344  1.00 45.70           C
ANISOU 5742 CE  MET B 155     6416   4902   6046    728   1608  -1355        C
ATOM   5746 C   MET B 155      17.658  53.443 110.065  1.00 36.30           C
ANISOU 5746 C   MET B 155     5089   4494   4209    102   1002  -1512        C
ATOM   5747 O   MET B 155      17.813  52.467 109.354  1.00 30.81           O
ANISOU 5747 O   MET B 155     4325   3900   3481    115    903  -1332        O
ATOM   5749 N   ALA B 156      17.243  53.352 111.328  1.00 33.98           N
ANISOU 5749 N   ALA B 156     4817   4320   3773    129   1039  -1648        N
ATOM   5750 CA  ALA B 156      16.903  52.058 111.908  1.00 33.83           C
ANISOU 5750 CA  ALA B 156     4736   4558   3561    179    965  -1558        C
ATOM   5752 CB  ALA B 156      18.102  51.453 112.670  1.00 33.38           C
ANISOU 5752 CB  ALA B 156     4653   4720   3308     59    835  -1656        C
ATOM   5756 C   ALA B 156      15.735  52.199 112.828  1.00 35.57           C
ANISOU 5756 C   ALA B 156     4980   4815   3718    287   1084  -1615        C
ATOM   5757 O   ALA B 156      15.522  53.263 113.408  1.00 38.51           O
ANISOU 5757 O   ALA B 156     5433   5070   4130    292   1208  -1806        O
ATOM   5759 N   THR B 157      15.005  51.106 112.976  1.00 35.18           N
ANISOU 5759 N   THR B 157     4868   4929   3570    365   1057  -1455        N
ATOM   5760 CA  THR B 157      13.911  51.007 113.933  1.00 36.93           C
ANISOU 5760 CA  THR B 157     5089   5247   3696    459   1170  -1483        C
ATOM   5762 CB  THR B 157      13.395  49.553 114.000  1.00 35.89           C
ANISOU 5762 CB  THR B 157     4879   5313   3444    492   1104  -1277        C
ATOM   5764 OG1 THR B 157      13.139  49.098 112.663  1.00 32.62           O
ANISOU 5764 OG1 THR B 157     4401   4816   3177    515   1041  -1066        O
ATOM   5766 CG2 THR B 157      12.111  49.469 114.868  1.00 36.53           C
ANISOU 5766 CG2 THR B 157     4936   5490   3452    592   1245  -1274        C
ATOM   5770 C   THR B 157      14.304  51.503 115.322  1.00 39.92           C
ANISOU 5770 C   THR B 157     5548   5717   3901    402   1221  -1744        C
ATOM   5771 O   THR B 157      15.314  51.065 115.890  1.00 40.20           O
ANISOU 5771 O   THR B 157     5596   5917   3762    294   1105  -1818        O
ATOM   5773 N   LYS B 158      13.511  52.449 115.830  1.00 43.66           N
ANISOU 5773 N   LYS B 158     6078   6087   4426    481   1398  -1884        N
ATOM   5774 CA  LYS B 158      13.674  53.017 117.182  1.00 47.22           C
ANISOU 5774 CA  LYS B 158     6627   6614   4702    438   1483  -2160        C
ATOM   5776 CB  LYS B 158      13.557  51.931 118.257  1.00 49.19           C
ANISOU 5776 CB  LYS B 158     6850   7183   4657    431   1439  -2125        C
ATOM   5779 CG  LYS B 158      12.183  51.303 118.394  1.00 51.07           C
ANISOU 5779 CG  LYS B 158     7015   7508   4883    574   1547  -1946        C
ATOM   5782 CD  LYS B 158      12.268  50.092 119.315  1.00 51.76           C
ANISOU 5782 CD  LYS B 158     7083   7900   4685    541   1477  -1864        C
ATOM   5785 CE  LYS B 158      10.970  49.835 120.031  1.00 54.82           C
ANISOU 5785 CE  LYS B 158     7438   8405   4984    650   1648  -1814        C
ATOM   5788 NZ  LYS B 158      11.202  49.129 121.335  1.00 57.28           N
ANISOU 5788 NZ  LYS B 158     7795   9008   4961    601   1630  -1846        N
ATOM   5792 C   LYS B 158      15.008  53.713 117.356  1.00 46.43           C
ANISOU 5792 C   LYS B 158     6607   6456   4578    265   1408  -2387        C
ATOM   5793 O   LYS B 158      15.459  53.884 118.476  1.00 46.16           O
ANISOU 5793 O   LYS B 158     6640   6566   4335    177   1404  -2606        O
ATOM   5795 N   ALA B 159      15.644  54.093 116.243  1.00 43.84           N
ANISOU 5795 N   ALA B 159     6267   5937   4454    206   1345  -2329        N
ATOM   5796 CA  ALA B 159      16.978  54.698 116.282  1.00 44.79           C
ANISOU 5796 CA  ALA B 159     6434   6009   4576     15   1265  -2519        C
ATOM   5798 CB  ALA B 159      16.926  56.077 116.967  1.00 46.00           C
ANISOU 5798 CB  ALA B 159     6733   5979   4768    -39   1422  -2836        C
ATOM   5802 C   ALA B 159      17.986  53.788 116.986  1.00 44.27           C
ANISOU 5802 C   ALA B 159     6311   6263   4248   -104   1082  -2546        C
ATOM   5803 O   ALA B 159      18.904  54.263 117.660  1.00 44.97           O
ANISOU 5803 O   ALA B 159     6437   6423   4224   -264   1029  -2779        O
ATOM   5805 N   ASP B 160      17.777  52.483 116.839  1.00 41.44           N
ANISOU 5805 N   ASP B 160     5858   6094   3792    -24    988  -2305        N
ATOM   5806 CA  ASP B 160      18.585  51.470 117.490  1.00 41.87           C
ANISOU 5806 CA  ASP B 160     5854   6453   3603    -85    823  -2269        C
ATOM   5808 CB  ASP B 160      17.688  50.460 118.225  1.00 42.20           C
ANISOU 5808 CB  ASP B 160     5886   6695   3455     34    850  -2135        C
ATOM   5811 CG  ASP B 160      18.474  49.341 118.879  1.00 42.75           C
ANISOU 5811 CG  ASP B 160     5901   7067   3275      0    685  -2051        C
ATOM   5812 OD1 ASP B 160      19.699  49.244 118.669  1.00 42.17           O
ANISOU 5812 OD1 ASP B 160     5771   7062   3189    -96    538  -2072        O
ATOM   5813 OD2 ASP B 160      17.867  48.559 119.625  1.00 44.37           O
ANISOU 5813 OD2 ASP B 160     6114   7448   3297     75    707  -1954        O
ATOM   5814 C   ASP B 160      19.366  50.808 116.359  1.00 39.68           C
```

FIG. 18 (continued)

```
ANISOU 5814  C   ASP B 160    5479   6158   3440   -107    688  -2072       C
ATOM   5815  O   ASP B 160    18.824  50.032 115.580  1.00 34.48            O
ANISOU 5815  O   ASP B 160    4777   5461   2864     -4    684  -1836       O
ATOM   5817  N   TYR B 161    20.648  51.143 116.292  1.00 40.72            N
ANISOU 5817  N   TYR B 161    5574   6327   3570   -252    584  -2185       N
ATOM   5818  CA  TYR B 161    21.514  50.750 115.210  1.00 40.58            C
ANISOU 5818  CA  TYR B 161    5464   6278   3677   -288    484  -2042       C
ATOM   5820  CB  TYR B 161    22.536  51.863 114.976  1.00 43.56            C
ANISOU 5820  CB  TYR B 161    5837   6549   4166   -467    474  -2237       C
ATOM   5823  CG  TYR B 161    21.844  53.152 114.638  1.00 44.67            C
ANISOU 5823  CG  TYR B 161    6095   6374   4502   -477    645  -2354       C
ATOM   5824  CD1 TYR B 161    21.214  53.313 113.405  1.00 44.25            C
ANISOU 5824  CD1 TYR B 161    6059   6080   4674   -381    730  -2176       C
ATOM   5826  CE1 TYR B 161    20.540  54.470 113.114  1.00 45.65            C
ANISOU 5826  CE1 TYR B 161    6341   5969   5033   -357    889  -2252       C
ATOM   5828  CZ  TYR B 161    20.476  55.470 114.077  1.00 47.49            C
ANISOU 5828  CZ  TYR B 161    6681   6129   5235   -432    982  -2530       C
ATOM   5829  OH  TYR B 161    19.856  56.656 113.855  1.00 48.53            O
ANISOU 5829  OH  TYR B 161    6932   5949   5560   -398   1156  -2619       O
ATOM   5831  CE2 TYR B 161    21.074  55.325 115.288  1.00 49.22            C
ANISOU 5831  CE2 TYR B 161    6896   6583   5223   -545    903  -2732       C
ATOM   5833  CD2 TYR B 161    21.736  54.164 115.570  1.00 48.42            C
ANISOU 5833  CD2 TYR B 161    6674   6795   4928   -563    728  -2632       C
ATOM   5835  C   TYR B 161    22.205  49.413 115.428  1.00 39.62            C
ANISOU 5835  C   TYR B 161    5240   6422   3391   -257    326  -1889       C
ATOM   5836  O   TYR B 161    23.024  49.000 114.589  1.00 38.36            O
ANISOU 5836  O   TYR B 161    4994   6263   3317   -275    246  -1777       O
ATOM   5838  N   THR B 162    21.868  48.747 116.535  1.00 39.66            N
ANISOU 5838  N   THR B 162    5260   6645   3163   -200    297  -1875       N
ATOM   5839  CA  THR B 162    22.286  47.369 116.842  1.00 38.45            C
ANISOU 5839  CA  THR B 162    5035   6727   2846   -127    171  -1686       C
ATOM   5841  CB  THR B 162    21.885  46.363 115.707  1.00 35.07            C
ANISOU 5841  CB  THR B 162    4585   6179   2561    -10    181  -1416       C
ATOM   5843  OG1 THR B 162    20.456  46.332 115.508  1.00 32.20            O
ANISOU 5843  OG1 THR B 162    4295   5675   2264     73    312  -1342       O
ATOM   5845  CG2 THR B 162    22.406  44.947 115.973  1.00 34.90            C
ANISOU 5845  CG2 THR B 162    4506   6355   2400     71     66  -1224       C
ATOM   5849  C   THR B 162    23.801  47.276 117.131  1.00 39.97            C
ANISOU 5849  C   THR B 162    5115   7129   2944   -223      6  -1748       C
ATOM   5850  O   THR B 162    24.199  46.948 118.248  1.00 37.97            O
ANISOU 5850  O   THR B 162    4836   7143   2446   -237    -88  -1790       O
ATOM   5852  N   LEU B 163    24.619  47.575 116.119  1.00 39.01            N
ANISOU 5852  N   LEU B 163    4915   6898   3007   -289    -25  -1744       N
ATOM   5853  CA  LEU B 163    26.076  47.468 116.193  1.00 40.90            C
ANISOU 5853  CA  LEU B 163    5009   7331   3202   -376   -173  -1777       C
ATOM   5855  CB  LEU B 163    26.652  47.320 114.768  1.00 38.43            C
ANISOU 5855  CB  LEU B 163    4615   6868   3117   -368   -165  -1653       C
ATOM   5858  CG  LEU B 163    26.127  46.169 113.907  1.00 35.85            C
ANISOU 5858  CG  LEU B 163    4311   6446   2865   -195   -131  -1391       C
ATOM   5860  CD1 LEU B 163    26.623  46.329 112.417  1.00 33.49            C
ANISOU 5860  CD1 LEU B 163    3963   5970   2793   -217    -90  -1323       C
ATOM   5864  CD2 LEU B 163    26.553  44.838 114.487  1.00 37.31            C
ANISOU 5864  CD2 LEU B 163    4428   6868   2878    -72   -243  -1229       C
ATOM   5868  C   LEU B 163    26.737  48.700 116.836  1.00 44.29            C
ANISOU 5868  C   LEU B 163    5420   7824   3584   -584   -204  -2071       C
ATOM   5869  O   LEU B 163    26.114  49.753 116.965  1.00 43.89            O
ANISOU 5869  O   LEU B 163    5490   7589   3598   -661    -85  -2255       O
ATOM   5871  N   ASP B 164    28.015  48.574 117.183  1.00 46.99            N
ANISOU 5871  N   ASP B 164    5605   8417   3831   -676   -360  -2116       N
ATOM   5872  CA  ASP B 164    28.804  49.709 117.647  1.00 51.52            C
ANISOU 5872  CA  ASP B 164    6136   9058   4382   -914   -408  -2398       C
ATOM   5874  CB  ASP B 164    30.030  49.262 118.478  1.00 55.80            C
ANISOU 5874  CB  ASP B 164    6489  10008   4704   -979   -622  -2421       C
ATOM   5877  CG  ASP B 164    31.084  48.488 117.669  1.00 56.57            C
ANISOU 5877  CG  ASP B 164    6375  10213   4908   -915   -719  -2213       C
ATOM   5878  OD1 ASP B 164    31.079  48.507 116.418  1.00 55.08            O
ANISOU 5878  OD1 ASP B 164    6179   9781   4967   -881   -621  -2107       O
ATOM   5879  OD2 ASP B 164    31.955  47.860 118.312  1.00 58.24            O
ANISOU 5879  OD2 ASP B 164    6419  10772   4939   -892   -894  -2154       O
ATOM   5880  C   ASP B 164    29.199  50.657 116.510  1.00 51.75            C
ANISOU 5880  C   ASP B 164    6147   8815   4701  -1052   -321  -2472       C
ATOM   5881  O   ASP B 164    29.041  50.356 115.312  1.00 47.44            O
ANISOU 5881  O   ASP B 164    5595   8077   4355   -958   -249  -2286       O
ATOM   5883  N   GLU B 165    29.714  51.813 116.906  1.00 55.79            N
ANISOU 5883  N   GLU B 165    6662   9312   5223  -1290   -326  -2749       N
ATOM   5884  CA  GLU B 165    29.998  52.901 115.982  1.00 57.45            C
ANISOU 5884  CA  GLU B 165    6894   9231   5704  -1452   -217  -2848       C
ATOM   5886  CB  GLU B 165    30.410  54.171 116.741  1.00 62.43            C
ANISOU 5886  CB  GLU B 165    7572   9848   6301  -1730   -216  -3200       C
```

FIG. 18 (continued)

| | | | | | | | | | | | | |
|---|---|---|---|---|---|---|---|---|---|---|---|---|
| ATOM | 5889 | CG | GLU | B | 165 | 29.368 | 54.694 | 117.752 | 1.00 | 64.91 | | C |
| ANISOU | 5889 | CG | GLU | B | 165 | 8101 | 10085 | 6477 | -1715 | -125 | -3403 | C |
| ATOM | 5892 | CD | GLU | B | 165 | 29.409 | 53.990 | 119.132 | 1.00 | 67.97 | | C |
| ANISOU | 5892 | CD | GLU | B | 165 | 8455 | 10871 | 6501 | -1674 | -274 | -3454 | C |
| ATOM | 5893 | OE1 | GLU | B | 165 | 28.582 | 53.075 | 119.336 | 1.00 | 66.97 | | O |
| ANISOU | 5893 | OE1 | GLU | B | 165 | 8375 | 10810 | 6261 | -1440 | -256 | -3261 | O |
| ATOM | 5894 | OE2 | GLU | B | 165 | 30.240 | 54.349 | 120.016 | 1.00 | 71.12 | | O |
| ANISOU | 5894 | OE2 | GLU | B | 165 | 8782 | 11523 | 6718 | -1882 | -406 | -3682 | O |
| ATOM | 5895 | C | GLU | B | 165 | 31.073 | 52.478 | 114.976 | 1.00 | 56.90 | | C |
| ANISOU | 5895 | C | GLU | B | 165 | 6623 | 9225 | 5772 | -1472 | -280 | -2682 | C |
| ATOM | 5896 | O | GLU | B | 165 | 30.958 | 52.776 | 113.786 | 1.00 | 53.99 | | O |
| ANISOU | 5896 | O | GLU | B | 165 | 6285 | 8592 | 5639 | -1462 | -162 | -2583 | O |
| ATOM | 5898 | N | GLU | B | 166 | 32.082 | 51.748 | 115.452 | 1.00 | 58.56 | | N |
| ANISOU | 5898 | N | GLU | B | 166 | 6625 | 9799 | 5827 | -1479 | -461 | -2636 | N |
| ATOM | 5899 | CA | GLU | B | 166 | 33.196 | 51.308 | 114.597 | 1.00 | 59.73 | | C |
| ANISOU | 5899 | CA | GLU | B | 166 | 6550 | 10052 | 6091 | -1487 | -519 | -2488 | C |
| ATOM | 5901 | CB | GLU | B | 166 | 34.394 | 50.807 | 115.440 | 1.00 | 63.46 | | C |
| ANISOU | 5901 | CB | GLU | B | 166 | 6772 | 10970 | 6370 | -1543 | -737 | -2512 | C |
| ATOM | 5904 | CG | GLU | B | 166 | 34.340 | 49.347 | 115.957 | 1.00 | 63.89 | | C |
| ANISOU | 5904 | CG | GLU | B | 166 | 6758 | 11298 | 6220 | -1276 | -858 | -2283 | C |
| ATOM | 5907 | CD | GLU | B | 166 | 35.595 | 48.964 | 116.784 | 1.00 | 68.09 | | C |
| ANISOU | 5907 | CD | GLU | B | 166 | 7019 | 12288 | 6565 | -1332 | -1084 | -2298 | C |
| ATOM | 5908 | OE1 | GLU | B | 166 | 36.520 | 48.339 | 116.202 | 1.00 | 69.71 | | O |
| ANISOU | 5908 | OE1 | GLU | B | 166 | 7001 | 12634 | 6853 | -1252 | -1140 | -2129 | O |
| ATOM | 5909 | OE2 | GLU | B | 166 | 35.663 | 49.287 | 118.008 | 1.00 | 70.78 | | O |
| ANISOU | 5909 | OE2 | GLU | B | 166 | 7363 | 12860 | 6670 | -1450 | -1205 | -2476 | O |
| ATOM | 5910 | C | GLU | B | 166 | 32.774 | 50.274 | 113.539 | 1.00 | 54.41 | | C |
| ANISOU | 5910 | C | GLU | B | 166 | 5894 | 9260 | 5520 | -1230 | -449 | -2186 | C |
| ATOM | 5911 | O | GLU | B | 166 | 33.238 | 50.332 | 112.391 | 1.00 | 51.56 | | O |
| ANISOU | 5911 | O | GLU | B | 166 | 5461 | 8780 | 5350 | -1245 | -381 | -2089 | O |
| ATOM | 5913 | N | SER | B | 167 | 31.901 | 49.338 | 113.906 | 1.00 | 51.52 | | N |
| ANISOU | 5913 | N | SER | B | 167 | 5628 | 8924 | 5023 | -1010 | -456 | -2045 | N |
| ATOM | 5914 | CA | SER | B | 167 | 31.442 | 48.326 | 112.944 | 1.00 | 47.79 | | C |
| ANISOU | 5914 | CA | SER | B | 167 | 5191 | 8329 | 4636 | -787 | -391 | -1782 | C |
| ATOM | 5916 | CB | SER | B | 167 | 30.677 | 47.198 | 113.631 | 1.00 | 46.99 | | C |
| ANISOU | 5916 | CB | SER | B | 167 | 5168 | 8333 | 4353 | -578 | -433 | -1640 | C |
| ATOM | 5919 | OG | SER | B | 167 | 31.364 | 46.757 | 114.798 | 1.00 | 52.14 | | O |
| ANISOU | 5919 | OG | SER | B | 167 | 5696 | 9332 | 4782 | -575 | -597 | -1664 | O |
| ATOM | 5921 | C | SER | B | 167 | 30.606 | 48.986 | 111.841 | 1.00 | 46.27 | | C |
| ANISOU | 5921 | C | SER | B | 167 | 5157 | 7766 | 4657 | -799 | -215 | -1767 | C |
| ATOM | 5922 | O | SER | B | 167 | 30.775 | 48.680 | 110.671 | 1.00 | 44.02 | | O |
| ANISOU | 5922 | O | SER | B | 167 | 4846 | 7367 | 4513 | -740 | -154 | -1621 | O |
| ATOM | 5924 | N | ARG | B | 168 | 29.737 | 49.921 | 112.219 | 1.00 | 47.08 | | N |
| ANISOU | 5924 | N | ARG | B | 168 | 5421 | 7690 | 4775 | -873 | -131 | -1919 | N |
| ATOM | 5925 | CA | ARG | B | 168 | 29.002 | 50.734 | 111.252 | 1.00 | 46.90 | | C |
| ANISOU | 5925 | CA | ARG | B | 168 | 5537 | 7323 | 4959 | -893 | 30 | -1912 | C |
| ATOM | 5927 | CB | ARG | B | 168 | 28.022 | 51.656 | 111.987 | 1.00 | 47.81 | | C |
| ANISOU | 5927 | CB | ARG | B | 168 | 5823 | 7288 | 5056 | -935 | 114 | -2089 | C |
| ATOM | 5930 | CG | ARG | B | 168 | 26.837 | 50.900 | 112.587 | 1.00 | 47.54 | | C |
| ANISOU | 5930 | CG | ARG | B | 168 | 5883 | 7299 | 4879 | -746 | 123 | -2003 | C |
| ATOM | 5933 | CD | ARG | B | 168 | 25.725 | 51.841 | 113.014 | 1.00 | 47.54 | | C |
| ANISOU | 5933 | CD | ARG | B | 168 | 6052 | 7098 | 4913 | -749 | 254 | -2144 | C |
| ATOM | 5936 | NE | ARG | B | 168 | 25.940 | 52.341 | 114.341 | 1.00 | 50.46 | | N |
| ANISOU | 5936 | NE | ARG | B | 168 | 6448 | 7610 | 5116 | -863 | 217 | -2391 | N |
| ATOM | 5938 | CZ | ARG | B | 168 | 25.539 | 53.527 | 114.805 | 1.00 | 50.93 | | C |
| ANISOU | 5938 | CZ | ARG | B | 168 | 6634 | 7498 | 5217 | -958 | 326 | -2622 | C |
| ATOM | 5939 | NH1 | ARG | B | 168 | 24.901 | 54.426 | 114.050 | 1.00 | 49.18 | | N |
| ANISOU | 5939 | NH1 | ARG | B | 168 | 6526 | 6936 | 5225 | -945 | 486 | -2627 | N |
| ATOM | 5942 | NH2 | ARG | B | 168 | 25.820 | 53.812 | 116.054 | 1.00 | 53.53 | | N |
| ANISOU | 5942 | NH2 | ARG | B | 168 | 6982 | 8008 | 5348 | -1067 | 273 | -2852 | N |
| ATOM | 5945 | C | ARG | B | 168 | 29.906 | 51.563 | 110.339 | 1.00 | 47.68 | | C |
| ANISOU | 5945 | C | ARG | B | 168 | 5562 | 7304 | 5249 | -1064 | 80 | -1953 | C |
| ATOM | 5946 | O | ARG | B | 168 | 29.628 | 51.699 | 109.145 | 1.00 | 46.54 | | O |
| ANISOU | 5946 | O | ARG | B | 168 | 5470 | 6947 | 5267 | -1023 | 185 | -1823 | O |
| ATOM | 5948 | N | ALA | B | 169 | 30.972 | 52.124 | 110.909 | 1.00 | 49.85 | | N |
| ANISOU | 5948 | N | ALA | B | 169 | 5716 | 7728 | 5497 | -1268 | 6 | -2132 | N |
| ATOM | 5949 | CA | ALA | B | 169 | 31.959 | 52.882 | 110.143 | 1.00 | 51.31 | | C |
| ANISOU | 5949 | CA | ALA | B | 169 | 5801 | 7837 | 5857 | -1464 | 49 | -2177 | C |
| ATOM | 5951 | CB | ALA | B | 169 | 33.058 | 53.466 | 111.099 | 1.00 | 53.21 | | C |
| ANISOU | 5951 | CB | ALA | B | 169 | 5896 | 8299 | 6023 | -1717 | -64 | -2417 | C |
| ATOM | 5955 | C | ALA | B | 169 | 32.606 | 52.045 | 109.042 | 1.00 | 49.69 | | C |
| ANISOU | 5955 | C | ALA | B | 169 | 5453 | 7707 | 5719 | -1366 | 48 | -1952 | C |
| ATOM | 5956 | O | ALA | B | 169 | 32.819 | 52.523 | 107.934 | 1.00 | 48.36 | | O |
| ANISOU | 5956 | O | ALA | B | 169 | 5292 | 7355 | 5726 | -1429 | 161 | -1886 | O |
| ATOM | 5958 | N | ARG | B | 170 | 32.933 | 50.800 | 109.355 | 1.00 | 49.74 | | N |
| ANISOU | 5958 | N | ARG | B | 170 | 5337 | 7979 | 5583 | -1207 | -68 | -1834 | N |
| ATOM | 5959 | CA | ARG | B | 170 | 33.519 | 49.901 | 108.367 | 1.00 | 50.55 | | C |
| ANISOU | 5959 | CA | ARG | B | 170 | 5317 | 8152 | 5739 | -1083 | -56 | -1631 | C |
| ATOM | 5961 | CB | ARG | B | 170 | 33.931 | 48.575 | 109.016 | 1.00 | 52.22 | | C |

FIG. 18 (continued)

| | | | | | | | | | | | | |
|---|---|---|---|---|---|---|---|---|---|---|---|---|
| ANISOU | 5961 | CB | ARG | B | 170 | 5394 | 8667 | 5780 | -906 | -196 | -1528 | C |
| ATOM | 5964 | CG | ARG | B | 170 | 35.236 | 48.685 | 109.788 | 1.00 | 57.06 | | C |
| ANISOU | 5964 | CG | ARG | B | 170 | 5754 | 9605 | 6320 | -1035 | -338 | -1631 | C |
| ATOM | 5967 | CD | ARG | B | 170 | 35.730 | 47.337 | 110.296 | 1.00 | 59.09 | | C |
| ANISOU | 5967 | CD | ARG | B | 170 | 5861 | 10160 | 6428 | -825 | -469 | -1483 | C |
| ATOM | 5970 | NE | ARG | B | 170 | 35.447 | 47.166 | 111.729 | 1.00 | 62.79 | | N |
| ANISOU | 5970 | NE | ARG | B | 170 | 6355 | 10826 | 6677 | -811 | -610 | -1560 | N |
| ATOM | 5972 | CZ | ARG | B | 170 | 34.596 | 46.281 | 112.254 | 1.00 | 61.85 | | C |
| ANISOU | 5972 | CZ | ARG | B | 170 | 6369 | 10713 | 6418 | -610 | -635 | -1447 | C |
| ATOM | 5973 | NH1 | ARG | B | 170 | 33.924 | 45.430 | 111.479 | 1.00 | 60.70 | | N |
| ANISOU | 5973 | NH1 | ARG | B | 170 | 6346 | 10382 | 6336 | -410 | -538 | -1259 | N |
| ATOM | 5976 | NH2 | ARG | B | 170 | 34.426 | 46.238 | 113.575 | 1.00 | 62.78 | | N |
| ANISOU | 5976 | NH2 | ARG | B | 170 | 6500 | 11034 | 6320 | -624 | -756 | -1525 | N |
| ATOM | 5979 | C | ARG | B | 170 | 32.578 | 49.650 | 107.181 | 1.00 | 46.18 | | C |
| ANISOU | 5979 | C | ARG | B | 170 | 4933 | 7331 | 5284 | -941 | 79 | -1463 | C |
| ATOM | 5980 | O | ARG | B | 170 | 33.031 | 49.627 | 106.021 | 1.00 | 44.24 | | O |
| ANISOU | 5980 | O | ARG | B | 170 | 4640 | 7016 | 5155 | -946 | 162 | -1360 | O |
| ATOM | 5982 | N | ILE | B | 171 | 31.288 | 49.469 | 107.476 | 1.00 | 42.62 | | N |
| ANISOU | 5982 | N | ILE | B | 171 | 4666 | 6753 | 4775 | -823 | 100 | -1438 | N |
| ATOM | 5983 | CA | ILE | B | 171 | 30.268 | 49.329 | 106.432 | 1.00 | 40.08 | | C |
| ANISOU | 5983 | CA | ILE | B | 171 | 4503 | 6193 | 4535 | -709 | 210 | -1294 | C |
| ATOM | 5985 | CB | ILE | B | 171 | 28.859 | 48.950 | 106.992 | 1.00 | 37.31 | | C |
| ANISOU | 5985 | CB | ILE | B | 171 | 4308 | 5775 | 4094 | -572 | 207 | -1265 | C |
| ATOM | 5987 | CG1 | ILE | B | 171 | 28.894 | 47.545 | 107.615 | 1.00 | 36.48 | | C |
| ANISOU | 5987 | CG1 | ILE | B | 171 | 4152 | 5884 | 3826 | -417 | 104 | -1173 | C |
| ATOM | 5990 | CD1 | ILE | B | 171 | 27.735 | 47.197 | 108.502 | 1.00 | 35.65 | | C |
| ANISOU | 5990 | CD1 | ILE | B | 171 | 4161 | 5782 | 3603 | -323 | 87 | -1173 | C |
| ATOM | 5994 | CG2 | ILE | B | 171 | 27.806 | 48.993 | 105.873 | 1.00 | 36.51 | | C |
| ANISOU | 5994 | CG2 | ILE | B | 171 | 4346 | 5438 | 4088 | -488 | 312 | -1129 | C |
| ATOM | 5998 | C | ILE | B | 171 | 30.193 | 50.622 | 105.624 | 1.00 | 40.69 | | C |
| ANISOU | 5998 | C | ILE | B | 171 | 4652 | 6020 | 4788 | -854 | 336 | -1335 | C |
| ATOM | 5999 | O | ILE | B | 171 | 30.303 | 50.589 | 104.407 | 1.00 | 38.70 | | O |
| ANISOU | 5999 | O | ILE | B | 171 | 4410 | 5666 | 4628 | -835 | 416 | -1206 | O |
| ATOM | 6001 | N | LYS | B | 172 | 30.040 | 51.760 | 106.299 | 1.00 | 42.92 | | N |
| ANISOU | 6001 | N | LYS | B | 172 | 4993 | 6202 | 5112 | -999 | 359 | -1514 | N |
| ATOM | 6002 | CA | LYS | B | 172 | 29.890 | 53.049 | 105.591 | 1.00 | 43.78 | | C |
| ANISOU | 6002 | CA | LYS | B | 172 | 5200 | 6028 | 5405 | -1128 | 494 | -1544 | C |
| ATOM | 6004 | CB | LYS | B | 172 | 29.584 | 54.179 | 106.576 | 1.00 | 45.19 | | C |
| ANISOU | 6004 | CB | LYS | B | 172 | 5474 | 6085 | 5610 | -1261 | 521 | -1770 | C |
| ATOM | 6007 | CG | LYS | B | 172 | 28.206 | 54.012 | 107.199 | 1.00 | 43.39 | | C |
| ANISOU | 6007 | CG | LYS | B | 172 | 5393 | 5790 | 5304 | -1097 | 532 | -1777 | C |
| ATOM | 6010 | CD | LYS | B | 172 | 27.836 | 55.154 | 108.140 | 1.00 | 45.75 | | C |
| ANISOU | 6010 | CD | LYS | B | 172 | 5809 | 5946 | 5630 | -1207 | 589 | -2013 | C |
| ATOM | 6013 | CE | LYS | B | 172 | 28.344 | 54.921 | 109.562 | 1.00 | 46.99 | | C |
| ANISOU | 6013 | CE | LYS | B | 172 | 5891 | 6370 | 5594 | -1292 | 465 | -2218 | C |
| ATOM | 6016 | NZ | LYS | B | 172 | 27.818 | 55.948 | 110.523 | 1.00 | 48.44 | | N |
| ANISOU | 6016 | NZ | LYS | B | 172 | 6219 | 6415 | 5772 | -1377 | 534 | -2466 | N |
| ATOM | 6020 | C | LYS | B | 172 | 31.087 | 53.390 | 104.680 | 1.00 | 45.75 | | C |
| ANISOU | 6020 | C | LYS | B | 172 | 5327 | 6284 | 5772 | -1277 | 543 | -1505 | C |
| ATOM | 6021 | O | LYS | B | 172 | 30.914 | 53.934 | 103.571 | 1.00 | 45.69 | | O |
| ANISOU | 6021 | O | LYS | B | 172 | 5398 | 6064 | 5899 | -1299 | 665 | -1396 | O |
| ATOM | 6023 | N | THR | B | 173 | 32.286 | 53.038 | 105.142 | 1.00 | 47.39 | | N |
| ANISOU | 6023 | N | THR | B | 173 | 5332 | 6753 | 5921 | -1369 | 448 | -1577 | N |
| ATOM | 6024 | CA | THR | B | 173 | 33.522 | 53.227 | 104.379 | 1.00 | 48.24 | | C |
| ANISOU | 6024 | CA | THR | B | 173 | 5273 | 6929 | 6126 | -1507 | 489 | -1540 | C |
| ATOM | 6026 | CB | THR | B | 173 | 34.791 | 52.971 | 105.259 | 1.00 | 50.47 | | C |
| ANISOU | 6026 | CB | THR | B | 173 | 5302 | 7541 | 6331 | -1626 | 353 | -1666 | C |
| ATOM | 6028 | OG1 | THR | B | 173 | 34.865 | 53.953 | 106.302 | 1.00 | 51.56 | | O |
| ANISOU | 6028 | OG1 | THR | B | 173 | 5464 | 7657 | 6467 | -1837 | 311 | -1907 | O |
| ATOM | 6030 | CG2 | THR | B | 173 | 36.090 | 53.017 | 104.426 | 1.00 | 50.74 | | C |
| ANISOU | 6030 | CG2 | THR | B | 173 | 5124 | 7689 | 6468 | -1744 | 403 | -1604 | C |
| ATOM | 6034 | C | THR | B | 173 | 33.552 | 52.341 | 103.130 | 1.00 | 45.08 | | C |
| ANISOU | 6034 | C | THR | B | 173 | 4855 | 6543 | 5730 | -1339 | 548 | -1312 | C |
| ATOM | 6035 | O | THR | B | 173 | 33.925 | 52.819 | 102.062 | 1.00 | 45.13 | | O |
| ANISOU | 6035 | O | THR | B | 173 | 4858 | 6435 | 5855 | -1422 | 667 | -1231 | O |
| ATOM | 6037 | N | ARG | B | 174 | 33.139 | 51.074 | 103.260 | 1.00 | 42.37 | | N |
| ANISOU | 6037 | N | ARG | B | 174 | 4516 | 6326 | 5255 | -1114 | 474 | -1213 | N |
| ATOM | 6038 | CA | ARG | B | 174 | 33.062 | 50.159 | 102.132 | 1.00 | 40.37 | | C |
| ANISOU | 6038 | CA | ARG | B | 174 | 4279 | 6073 | 4988 | -951 | 530 | -1024 | C |
| ATOM | 6040 | CB | ARG | B | 174 | 32.702 | 48.724 | 102.603 | 1.00 | 40.18 | | C |
| ANISOU | 6040 | CB | ARG | B | 174 | 4253 | 6199 | 4815 | -728 | 431 | -957 | C |
| ATOM | 6043 | CG | ARG | B | 174 | 32.532 | 47.667 | 101.508 | 1.00 | 38.82 | | C |
| ANISOU | 6043 | CG | ARG | B | 174 | 4127 | 6008 | 4615 | -556 | 489 | -789 | C |
| ATOM | 6046 | CD | ARG | B | 174 | 33.770 | 47.508 | 100.617 | 1.00 | 41.27 | | C |
| ANISOU | 6046 | CD | ARG | B | 174 | 4279 | 6420 | 4980 | -585 | 565 | -736 | C |
| ATOM | 6049 | NE | ARG | B | 174 | 33.483 | 46.561 | 99.552 | 1.00 | 40.16 | | N |
| ANISOU | 6049 | NE | ARG | B | 174 | 4226 | 6234 | 4799 | -427 | 636 | -602 | N |
| ATOM | 6051 | CZ | ARG | B | 174 | 34.073 | 46.509 | 98.366 | 1.00 | 42.33 | | C |
| ANISOU | 6051 | CZ | ARG | B | 174 | 4466 | 6506 | 5110 | -434 | 757 | -529 | C |

FIG. 18 (continued)

| | | | | | | | | | | | | |
|---|---|---|---|---|---|---|---|---|---|---|---|---|
| ATOM | 6052 | NH1 | ARG | B | 174 | 35.037 | 47.366 | 98.024 | 1.00 | 43.81 | | N |
| ANISOU | 6052 | NH1 | ARG | B | 174 | 4517 | 6734 | 5394 | -598 | 833 | -556 | N |
| ATOM | 6055 | NH2 | ARG | B | 174 | 33.673 | 45.584 | 97.487 | 1.00 | 41.77 | | N |
| ANISOU | 6055 | NH2 | ARG | B | 174 | 4509 | 6389 | 4974 | -287 | 813 | -433 | N |
| ATOM | 6058 | C | ARG | B | 174 | 32.076 | 50.677 | 101.073 | 1.00 | 38.23 | | C |
| ANISOU | 6058 | C | ARG | B | 174 | 4209 | 5526 | 4790 | -929 | 651 | -918 | C |
| ATOM | 6059 | O | ARG | B | 174 | 32.380 | 50.628 | 99.877 | 1.00 | 36.58 | | O |
| ANISOU | 6059 | O | ARG | B | 174 | 3999 | 5275 | 4625 | -927 | 748 | -799 | O |
| ATOM | 6061 | N | LEU | B | 175 | 30.909 | 51.149 | 101.515 | 1.00 | 35.78 | | N |
| ANISOU | 6061 | N | LEU | B | 175 | 4061 | 5052 | 4482 | -903 | 646 | -954 | N |
| ATOM | 6062 | CA | LEU | B | 175 | 29.898 | 51.731 | 100.606 | 1.00 | 36.05 | | C |
| ANISOU | 6062 | CA | LEU | B | 175 | 4273 | 4835 | 4589 | -869 | 746 | -843 | C |
| ATOM | 6064 | CB | LEU | B | 175 | 28.590 | 52.039 | 101.363 | 1.00 | 33.65 | | C |
| ANISOU | 6064 | CB | LEU | B | 175 | 4107 | 4407 | 4270 | -796 | 721 | -893 | C |
| ATOM | 6067 | CG | LEU | B | 175 | 27.780 | 50.793 | 101.813 | 1.00 | 31.65 | | C |
| ANISOU | 6067 | CG | LEU | B | 175 | 3878 | 4276 | 3873 | -612 | 629 | -844 | C |
| ATOM | 6069 | CD1 | LEU | B | 175 | 26.544 | 51.185 | 102.575 | 1.00 | 30.04 | | C |
| ANISOU | 6069 | CD1 | LEU | B | 175 | 3785 | 3966 | 3663 | -554 | 626 | -896 | C |
| ATOM | 6073 | CD2 | LEU | B | 175 | 27.406 | 49.938 | 100.620 | 1.00 | 28.03 | | C |
| ANISOU | 6073 | CD2 | LEU | B | 175 | 3462 | 3815 | 3374 | -492 | 648 | -661 | C |
| ATOM | 6077 | C | LEU | B | 175 | 30.434 | 52.983 | 99.877 | 1.00 | 38.24 | | C |
| ANISOU | 6077 | C | LEU | B | 175 | 4564 | 4944 | 5023 | -1047 | 871 | -835 | C |
| ATOM | 6078 | O | LEU | B | 175 | 30.199 | 53.178 | 98.676 | 1.00 | 36.03 | | O |
| ANISOU | 6078 | O | LEU | B | 175 | 4361 | 4545 | 4784 | -1022 | 965 | -678 | O |
| ATOM | 6080 | N | PHE | B | 176 | 31.162 | 53.816 | 100.618 | 1.00 | 40.52 | | N |
| ANISOU | 6080 | N | PHE | B | 176 | 4779 | 5230 | 5387 | -1237 | 871 | -1002 | N |
| ATOM | 6081 | CA | PHE | B | 176 | 31.776 | 55.013 | 100.073 | 1.00 | 42.97 | | C |
| ANISOU | 6081 | CA | PHE | B | 176 | 5094 | 5376 | 5859 | -1443 | 993 | -1013 | C |
| ATOM | 6083 | CB | PHE | B | 176 | 32.451 | 55.808 | 101.205 | 1.00 | 47.42 | | C |
| ANISOU | 6083 | CB | PHE | B | 176 | 5581 | 5957 | 6479 | -1663 | 957 | -1253 | C |
| ATOM | 6086 | CG | PHE | B | 176 | 33.078 | 57.096 | 100.752 | 1.00 | 50.36 | | C |
| ANISOU | 6086 | CG | PHE | B | 176 | 5968 | 6130 | 7036 | -1911 | 1090 | -1287 | C |
| ATOM | 6087 | CD1 | PHE | B | 176 | 32.408 | 58.300 | 100.909 | 1.00 | 52.94 | | C |
| ANISOU | 6087 | CD1 | PHE | B | 176 | 6488 | 6131 | 7496 | -1987 | 1185 | -1350 | C |
| ATOM | 6089 | CE1 | PHE | B | 176 | 32.973 | 59.496 | 100.488 | 1.00 | 55.42 | | C |
| ANISOU | 6089 | CE1 | PHE | B | 176 | 6837 | 6224 | 7995 | -2223 | 1321 | -1373 | C |
| ATOM | 6091 | CZ | PHE | B | 176 | 34.224 | 59.494 | 99.897 | 1.00 | 56.76 | | C |
| ANISOU | 6091 | CZ | PHE | B | 176 | 6829 | 6524 | 8212 | -2401 | 1363 | -1330 | C |
| ATOM | 6093 | CE2 | PHE | B | 176 | 34.906 | 58.295 | 99.724 | 1.00 | 55.59 | | C |
| ANISOU | 6093 | CE2 | PHE | B | 176 | 6468 | 6726 | 7928 | -2316 | 1271 | -1268 | C |
| ATOM | 6095 | CD2 | PHE | B | 176 | 34.327 | 57.104 | 100.160 | 1.00 | 52.96 | | C |
| ANISOU | 6095 | CD2 | PHE | B | 176 | 6120 | 6587 | 7417 | -2065 | 1135 | -1249 | C |
| ATOM | 6097 | C | PHE | B | 176 | 32.803 | 54.647 | 99.001 | 1.00 | 42.26 | | C |
| ANISOU | 6097 | C | PHE | B | 176 | 4872 | 5406 | 5779 | -1486 | 1056 | -889 | C |
| ATOM | 6098 | O | PHE | B | 176 | 32.866 | 55.284 | 97.949 | 1.00 | 41.47 | | O |
| ANISOU | 6098 | O | PHE | B | 176 | 4839 | 5145 | 5772 | -1551 | 1189 | -766 | O |
| ATOM | 6100 | N | THR | B | 177 | 33.615 | 53.634 | 99.287 | 1.00 | 41.44 | | N |
| ANISOU | 6100 | N | THR | B | 177 | 4579 | 5588 | 5578 | -1441 | 970 | -915 | N |
| ATOM | 6101 | CA | THR | B | 177 | 34.590 | 53.142 | 98.341 | 1.00 | 42.55 | | C |
| ANISOU | 6101 | CA | THR | B | 177 | 4577 | 5873 | 5715 | -1446 | 1038 | -807 | C |
| ATOM | 6103 | CB | THR | B | 177 | 35.450 | 52.027 | 98.938 | 1.00 | 43.95 | | C |
| ANISOU | 6103 | CB | THR | B | 177 | 4533 | 6370 | 5795 | -1367 | 927 | -857 | C |
| ATOM | 6105 | OG1 | THR | B | 177 | 36.084 | 52.512 | 100.120 | 1.00 | 46.28 | | O |
| ANISOU | 6105 | OG1 | THR | B | 177 | 4685 | 6781 | 6117 | -1533 | 832 | -1040 | O |
| ATOM | 6107 | CG2 | THR | B | 177 | 36.510 | 51.583 | 97.933 | 1.00 | 46.22 | | C |
| ANISOU | 6107 | CG2 | THR | B | 177 | 4661 | 6803 | 6098 | -1365 | 1025 | -752 | C |
| ATOM | 6111 | C | THR | B | 177 | 33.916 | 52.632 | 97.055 | 1.00 | 40.98 | | C |
| ANISOU | 6111 | C | THR | B | 177 | 4521 | 5588 | 5461 | -1280 | 1119 | -607 | C |
| ATOM | 6112 | O | THR | B | 177 | 34.399 | 52.950 | 95.958 | 1.00 | 41.72 | | O |
| ANISOU | 6112 | O | THR | B | 177 | 4605 | 5645 | 5602 | -1349 | 1251 | -497 | O |
| ATOM | 6114 | N | ILE | B | 178 | 32.817 | 51.871 | 97.182 | 1.00 | 36.70 | | N |
| ANISOU | 6114 | N | ILE | B | 178 | 4108 | 5026 | 4812 | -1082 | 1045 | -563 | N |
| ATOM | 6115 | CA | ILE | B | 178 | 32.114 | 51.352 | 96.008 | 1.00 | 36.13 | | C |
| ANISOU | 6115 | CA | ILE | B | 178 | 4171 | 4893 | 4666 | -942 | 1099 | -393 | C |
| ATOM | 6117 | CB | ILE | B | 178 | 30.931 | 50.403 | 96.369 | 1.00 | 33.67 | | C |
| ANISOU | 6117 | CB | ILE | B | 178 | 3968 | 4590 | 4235 | -749 | 992 | -375 | C |
| ATOM | 6119 | CG1 | ILE | B | 178 | 31.453 | 49.111 | 97.001 | 1.00 | 33.22 | | C |
| ANISOU | 6119 | CG1 | ILE | B | 178 | 3789 | 4752 | 4083 | -641 | 901 | -432 | C |
| ATOM | 6122 | CD1 | ILE | B | 178 | 30.428 | 48.379 | 97.749 | 1.00 | 30.56 | | C |
| ANISOU | 6122 | CD1 | ILE | B | 178 | 3534 | 4417 | 3658 | -506 | 793 | -449 | C |
| ATOM | 6126 | CG2 | ILE | B | 178 | 30.055 | 50.087 | 95.130 | 1.00 | 31.14 | | C |
| ANISOU | 6126 | CG2 | ILE | B | 178 | 3803 | 4186 | 3843 | -646 | 1038 | -211 | C |
| ATOM | 6130 | C | ILE | B | 178 | 31.616 | 52.490 | 95.107 | 1.00 | 36.64 | | C |
| ANISOU | 6130 | C | ILE | B | 178 | 4383 | 4724 | 4817 | -1021 | 1215 | -279 | C |
| ATOM | 6131 | O | ILE | B | 178 | 31.865 | 52.494 | 93.901 | 1.00 | 35.84 | | O |
| ANISOU | 6131 | O | ILE | B | 178 | 4310 | 4616 | 4693 | -1028 | 1319 | -143 | O |
| ATOM | 6133 | N | ARG | B | 179 | 30.919 | 53.440 | 95.720 | 1.00 | 37.29 | | N |
| ANISOU | 6133 | N | ARG | B | 179 | 4562 | 4617 | 4991 | -1071 | 1203 | -333 | N |
| ATOM | 6134 | CA | ARG | B | 179 | 30.386 | 54.601 | 95.042 | 1.00 | 39.65 | | C |

FIG. 18 (continued)

| | | | | | | | | | | | | |
|---|---|---|---|---|---|---|---|---|---|---|---|---|
| ANISOU | 6134 | CA | ARG | B | 179 | 5007 | 4663 | 5395 | -1126 | 1310 | -221 | C |
| ATOM | 6136 | CB | ARG | B | 179 | 29.674 | 55.501 | 96.053 | 1.00 | 40.37 | | C |
| ANISOU | 6136 | CB | ARG | B | 179 | 5186 | 4561 | 5593 | -1154 | 1288 | -335 | C |
| ATOM | 6139 | CG | ARG | B | 179 | 29.329 | 56.914 | 95.534 | 1.00 | 42.95 | | C |
| ANISOU | 6139 | CG | ARG | B | 179 | 5657 | 4582 | 6082 | -1234 | 1421 | -243 | C |
| ATOM | 6142 | CD | ARG | B | 179 | 28.359 | 57.594 | 96.467 | 1.00 | 44.08 | | C |
| ANISOU | 6142 | CD | ARG | B | 179 | 5910 | 4531 | 6307 | -1186 | 1403 | -343 | C |
| ATOM | 6145 | NE | ARG | B | 179 | 27.977 | 58.934 | 96.022 | 1.00 | 47.18 | | N |
| ANISOU | 6145 | NE | ARG | B | 179 | 6453 | 4600 | 6872 | -1232 | 1539 | -249 | N |
| ATOM | 6147 | CZ | ARG | B | 179 | 28.661 | 60.045 | 96.269 | 1.00 | 51.03 | | C |
| ANISOU | 6147 | CZ | ARG | B | 179 | 6966 | 4893 | 7529 | -1440 | 1645 | -347 | C |
| ATOM | 6148 | NH1 | ARG | B | 179 | 29.808 | 60.010 | 96.946 | 1.00 | 52.60 | | N |
| ANISOU | 6148 | NH1 | ARG | B | 179 | 7027 | 5219 | 7741 | -1644 | 1620 | -550 | N |
| ATOM | 6151 | NH2 | ARG | B | 179 | 28.206 | 61.213 | 95.814 | 1.00 | 53.12 | | N |
| ANISOU | 6151 | NH2 | ARG | B | 179 | 7393 | 4832 | 7957 | -1449 | 1780 | -233 | N |
| ATOM | 6154 | C | ARG | B | 179 | 31.480 | 55.404 | 94.334 | 1.00 | 42.41 | | C |
| ANISOU | 6154 | C | ARG | B | 179 | 5301 | 4962 | 5851 | -1320 | 1453 | -173 | C |
| ATOM | 6155 | O | ARG | B | 179 | 31.304 | 55.811 | 93.207 | 1.00 | 41.10 | | O |
| ANISOU | 6155 | O | ARG | B | 179 | 5231 | 4689 | 5696 | -1321 | 1559 | 7 | O |
| ATOM | 6157 | N | GLN | B | 180 | 32.590 | 55.616 | 95.037 | 1.00 | 45.53 | | N |
| ANISOU | 6157 | N | GLN | B | 180 | 5533 | 5451 | 6317 | -1489 | 1449 | -332 | N |
| ATOM | 6158 | CA | GLN | B | 180 | 33.767 | 56.311 | 94.521 | 1.00 | 49.32 | | C |
| ANISOU | 6158 | CA | GLN | B | 180 | 5911 | 5922 | 6906 | -1708 | 1579 | -313 | C |
| ATOM | 6160 | CB | GLN | B | 180 | 34.828 | 56.321 | 95.627 | 1.00 | 52.68 | | C |
| ANISOU | 6160 | CB | GLN | B | 180 | 6123 | 6515 | 7379 | -1872 | 1508 | -531 | C |
| ATOM | 6163 | CG | GLN | B | 180 | 36.221 | 56.687 | 95.201 | 1.00 | 57.74 | | C |
| ANISOU | 6163 | CG | GLN | B | 180 | 6574 | 7257 | 8108 | -2091 | 1614 | -531 | C |
| ATOM | 6166 | CD | GLN | B | 180 | 36.534 | 58.123 | 95.497 | 1.00 | 62.80 | | C |
| ANISOU | 6166 | CD | GLN | B | 180 | 7251 | 7671 | 8941 | -2372 | 1699 | -620 | C |
| ATOM | 6167 | OE1 | GLN | B | 180 | 37.273 | 58.422 | 96.442 | 1.00 | 66.84 | | O |
| ANISOU | 6167 | OE1 | GLN | B | 180 | 7608 | 8275 | 9513 | -2562 | 1636 | -819 | O |
| ATOM | 6168 | NE2 | GLN | B | 180 | 35.949 | 59.037 | 94.713 | 1.00 | 65.13 | | N |
| ANISOU | 6168 | NE2 | GLN | B | 180 | 7757 | 7658 | 9332 | -2402 | 1840 | -473 | N |
| ATOM | 6171 | C | GLN | B | 180 | 34.328 | 55.654 | 93.260 | 1.00 | 48.49 | | C |
| ANISOU | 6171 | C | GLN | B | 180 | 5745 | 5968 | 6709 | -1657 | 1669 | -148 | C |
| ATOM | 6172 | O | GLN | B | 180 | 34.546 | 56.315 | 92.248 | 1.00 | 48.10 | | O |
| ANISOU | 6172 | O | GLN | B | 180 | 5755 | 5807 | 6712 | -1748 | 1819 | 0 | O |
| ATOM | 6174 | N | GLU | B | 181 | 34.568 | 54.354 | 93.345 | 1.00 | 47.49 | | N |
| ANISOU | 6174 | N | GLU | B | 181 | 5509 | 6091 | 6443 | -1509 | 1588 | -175 | N |
| ATOM | 6175 | CA | GLU | B | 181 | 35.088 | 53.582 | 92.230 | 1.00 | 47.94 | | C |
| ANISOU | 6175 | CA | GLU | B | 181 | 5514 | 6306 | 6395 | -1434 | 1676 | -52 | C |
| ATOM | 6177 | CB | GLU | B | 181 | 35.462 | 52.165 | 92.678 | 1.00 | 49.26 | | C |
| ANISOU | 6177 | CB | GLU | B | 181 | 5541 | 6728 | 6446 | -1275 | 1576 | -133 | C |
| ATOM | 6180 | CG | GLU | B | 181 | 36.627 | 52.112 | 93.680 | 1.00 | 52.79 | | C |
| ANISOU | 6180 | CG | GLU | B | 181 | 5726 | 7363 | 6968 | -1379 | 1521 | -286 | C |
| ATOM | 6183 | CD | GLU | B | 181 | 37.917 | 52.691 | 93.108 | 1.00 | 57.41 | | C |
| ANISOU | 6183 | CD | GLU | B | 181 | 6129 | 8031 | 7652 | -1574 | 1671 | -259 | C |
| ATOM | 6184 | OE1 | GLU | B | 181 | 38.141 | 52.575 | 91.875 | 1.00 | 59.43 | | O |
| ANISOU | 6184 | OE1 | GLU | B | 181 | 6420 | 8296 | 7865 | -1551 | 1823 | -118 | O |
| ATOM | 6185 | OE2 | GLU | B | 181 | 38.691 | 53.281 | 93.891 | 1.00 | 60.77 | | O |
| ANISOU | 6185 | OE2 | GLU | B | 181 | 6379 | 8519 | 8191 | -1763 | 1639 | -381 | O |
| ATOM | 6186 | C | GLU | B | 181 | 34.102 | 53.518 | 91.075 | 1.00 | 45.61 | | C |
| ANISOU | 6186 | C | GLU | B | 181 | 5437 | 5894 | 5999 | -1314 | 1730 | 135 | C |
| ATOM | 6187 | O | GLU | B | 181 | 34.499 | 53.551 | 89.918 | 1.00 | 44.98 | | O |
| ANISOU | 6187 | O | GLU | B | 181 | 5373 | 5848 | 5869 | -1338 | 1866 | 269 | O |
| ATOM | 6189 | N | MET | B | 182 | 32.811 | 53.410 | 91.377 | 1.00 | 42.40 | | N |
| ANISOU | 6189 | N | MET | B | 182 | 5189 | 5374 | 5547 | -1184 | 1624 | 147 | N |
| ATOM | 6190 | CA | MET | B | 182 | 31.811 | 53.466 | 90.307 | 1.00 | 41.07 | | C |
| ANISOU | 6190 | CA | MET | B | 182 | 5213 | 5107 | 5284 | -1085 | 1655 | 333 | C |
| ATOM | 6192 | CB | MET | B | 182 | 30.393 | 53.268 | 90.844 | 1.00 | 37.93 | | C |
| ANISOU | 6192 | CB | MET | B | 182 | 4938 | 4621 | 4851 | -941 | 1517 | 324 | C |
| ATOM | 6195 | CG | MET | B | 182 | 29.954 | 51.825 | 90.950 | 1.00 | 35.72 | | C |
| ANISOU | 6195 | CG | MET | B | 182 | 4656 | 4509 | 4408 | -776 | 1403 | 281 | C |
| ATOM | 6198 | SD | MET | B | 182 | 28.243 | 51.715 | 91.547 | 1.00 | 33.98 | | S |
| ANISOU | 6198 | SD | MET | B | 182 | 4561 | 4187 | 4163 | -638 | 1260 | 289 | S |
| ATOM | 6199 | CE | MET | B | 182 | 28.071 | 49.981 | 91.894 | 1.00 | 30.91 | | C |
| ANISOU | 6199 | CE | MET | B | 182 | 4134 | 3993 | 3616 | -502 | 1145 | 201 | C |
| ATOM | 6203 | C | MET | B | 182 | 31.904 | 54.811 | 89.562 | 1.00 | 42.81 | | C |
| ANISOU | 6203 | C | MET | B | 182 | 5521 | 5133 | 5613 | -1222 | 1801 | 483 | C |
| ATOM | 6204 | O | MET | B | 182 | 31.949 | 54.842 | 88.334 | 1.00 | 43.82 | | O |
| ANISOU | 6204 | O | MET | B | 182 | 5720 | 5279 | 5649 | -1214 | 1902 | 656 | O |
| ATOM | 6206 | N | ALA | B | 183 | 31.927 | 55.901 | 90.324 | 1.00 | 43.77 | | N |
| ANISOU | 6206 | N | ALA | B | 183 | 5648 | 5061 | 5920 | -1349 | 1815 | 412 | N |
| ATOM | 6207 | CA | ALA | B | 183 | 32.023 | 57.267 | 89.763 | 1.00 | 47.57 | | C |
| ANISOU | 6207 | CA | ALA | B | 183 | 6227 | 5303 | 6543 | -1492 | 1965 | 547 | C |
| ATOM | 6209 | CB | ALA | B | 183 | 31.952 | 58.334 | 90.886 | 1.00 | 47.21 | | C |
| ANISOU | 6209 | CB | ALA | B | 183 | 6201 | 5027 | 6709 | -1619 | 1959 | 401 | C |
| ATOM | 6213 | C | ALA | B | 183 | 33.278 | 57.448 | 88.926 | 1.00 | 49.22 | | C |
| ANISOU | 6213 | C | ALA | B | 183 | 6337 | 5601 | 6763 | -1655 | 2128 | 623 | C |

FIG. 18 (continued)

| | | | | | | | | | | | | |
|---|---|---|---|---|---|---|---|---|---|---|---|---|
| ATOM | 6214 | O | ALA | B | 183 | 33.232 | 58.074 | 87.853 | 1.00 | 51.40 | | O |
| ANISOU | 6214 | O | ALA | B | 183 | 6723 | 5769 | 7036 | -1696 | 2264 | 835 | O |
| ATOM | 6216 | N | ASN | B | 184 | 34.393 | 56.892 | 89.391 | 1.00 | 49.93 | | N |
| ANISOU | 6216 | N | ASN | B | 184 | 6210 | 5904 | 6857 | -1739 | 2119 | 467 | N |
| ATOM | 6217 | CA | ASN | B | 184 | 35.648 | 56.919 | 88.626 | 1.00 | 52.77 | | C |
| ANISOU | 6217 | CA | ASN | B | 184 | 6430 | 6400 | 7219 | -1880 | 2279 | 529 | C |
| ATOM | 6219 | CB | ASN | B | 184 | 36.779 | 56.214 | 89.394 | 1.00 | 53.96 | | C |
| ANISOU | 6219 | CB | ASN | B | 184 | 6305 | 6812 | 7386 | -1934 | 2228 | 334 | C |
| ATOM | 6222 | CG | ASN | B | 184 | 37.275 | 57.019 | 90.576 | 1.00 | 56.22 | | C |
| ANISOU | 6222 | CG | ASN | B | 184 | 6476 | 7022 | 7865 | -2145 | 2182 | 151 | C |
| ATOM | 6223 | OD1 | ASN | B | 184 | 36.949 | 58.201 | 90.725 | 1.00 | 57.54 | | O |
| ANISOU | 6223 | OD1 | ASN | B | 184 | 6770 | 6914 | 8178 | -2289 | 2234 | 164 | O |
| ATOM | 6224 | ND2 | ASN | B | 184 | 38.069 | 56.381 | 91.426 | 1.00 | 56.36 | | N |
| ANISOU | 6224 | ND2 | ASN | B | 184 | 6256 | 7281 | 7879 | -2164 | 2086 | -23 | N |
| ATOM | 6227 | C | ASN | B | 184 | 35.501 | 56.284 | 87.245 | 1.00 | 52.20 | | C |
| ANISOU | 6227 | C | ASN | B | 184 | 6440 | 6448 | 6948 | -1750 | 2364 | 720 | C |
| ATOM | 6228 | O | ASN | B | 184 | 36.098 | 56.744 | 86.275 | 1.00 | 52.81 | | O |
| ANISOU | 6228 | O | ASN | B | 184 | 6517 | 6525 | 7022 | -1862 | 2543 | 868 | O |
| ATOM | 6230 | N | ARG | B | 185 | 34.699 | 55.225 | 87.162 | 1.00 | 49.05 | | N |
| ANISOU | 6230 | N | ARG | B | 185 | 6114 | 6149 | 6372 | -1527 | 2241 | 712 | N |
| ATOM | 6231 | CA | ARG | B | 185 | 34.480 | 54.535 | 85.896 | 1.00 | 49.50 | | C |
| ANISOU | 6231 | CA | ARG | B | 185 | 6267 | 6330 | 6211 | -1405 | 2302 | 857 | C |
| ATOM | 6233 | CB | ARG | B | 185 | 34.275 | 53.056 | 86.135 | 1.00 | 48.12 | | C |
| ANISOU | 6233 | CB | ARG | B | 185 | 6054 | 6348 | 5881 | -1217 | 2182 | 736 | C |
| ATOM | 6236 | CG | ARG | B | 185 | 35.443 | 52.382 | 86.773 | 1.00 | 50.45 | | C |
| ANISOU | 6236 | CG | ARG | B | 185 | 6111 | 6832 | 6225 | -1234 | 2191 | 570 | C |
| ATOM | 6239 | CD | ARG | B | 185 | 35.172 | 50.913 | 86.790 | 1.00 | 51.58 | | C |
| ANISOU | 6239 | CD | ARG | B | 185 | 6266 | 7127 | 6205 | -1029 | 2103 | 492 | C |
| ATOM | 6242 | NE | ARG | B | 185 | 36.176 | 50.148 | 87.532 | 1.00 | 53.16 | | N |
| ANISOU | 6242 | NE | ARG | B | 185 | 6238 | 7505 | 6453 | -992 | 2085 | 343 | N |
| ATOM | 6244 | CZ | ARG | B | 185 | 36.584 | 48.916 | 87.196 | 1.00 | 53.39 | | C |
| ANISOU | 6244 | CZ | ARG | B | 185 | 6220 | 7703 | 6364 | -842 | 2120 | 302 | C |
| ATOM | 6245 | NH1 | ARG | B | 185 | 36.107 | 48.283 | 86.105 | 1.00 | 51.67 | | N |
| ANISOU | 6245 | NH1 | ARG | B | 185 | 6174 | 7502 | 5957 | -736 | 2181 | 371 | N |
| ATOM | 6248 | NH2 | ARG | B | 185 | 37.484 | 48.310 | 87.971 | 1.00 | 54.22 | | N |
| ANISOU | 6248 | NH2 | ARG | B | 185 | 6104 | 7962 | 6537 | -794 | 2093 | 186 | N |
| ATOM | 6251 | C | ARG | B | 185 | 33.304 | 55.072 | 85.086 | 1.00 | 48.61 | | C |
| ANISOU | 6251 | C | ARG | B | 185 | 6393 | 6058 | 6018 | -1339 | 2299 | 1067 | C |
| ATOM | 6252 | O | ARG | B | 185 | 32.987 | 54.531 | 84.026 | 1.00 | 48.73 | | O |
| ANISOU | 6252 | O | ARG | B | 185 | 6509 | 6184 | 5824 | -1243 | 2328 | 1187 | O |
| ATOM | 6254 | N | GLY | B | 186 | 32.659 | 56.123 | 85.575 | 1.00 | 47.86 | | N |
| ANISOU | 6254 | N | GLY | B | 186 | 6388 | 5715 | 6082 | -1382 | 2266 | 1108 | N |
| ATOM | 6255 | CA | GLY | B | 186 | 31.490 | 56.679 | 84.912 | 1.00 | 47.47 | | C |
| ANISOU | 6255 | CA | GLY | B | 186 | 6545 | 5512 | 5979 | -1292 | 2249 | 1322 | C |
| ATOM | 6258 | C | GLY | B | 186 | 30.222 | 55.848 | 85.023 | 1.00 | 45.21 | | C |
| ANISOU | 6258 | C | GLY | B | 186 | 6340 | 5292 | 5545 | -1084 | 2064 | 1309 | C |
| ATOM | 6259 | O | GLY | B | 186 | 29.344 | 55.943 | 84.141 | 1.00 | 45.00 | | O |
| ANISOU | 6259 | O | GLY | B | 186 | 6456 | 5257 | 5386 | -988 | 2042 | 1505 | O |
| ATOM | 6261 | N | LEU | B | 187 | 30.115 | 55.046 | 86.095 | 1.00 | 42.13 | | N |
| ANISOU | 6261 | N | LEU | B | 187 | 5855 | 4980 | 5172 | -1021 | 1929 | 1090 | N |
| ATOM | 6262 | CA | LEU | B | 187 | 29.008 | 54.108 | 86.282 | 1.00 | 39.58 | | C |
| ANISOU | 6262 | CA | LEU | B | 187 | 5585 | 4740 | 4713 | -847 | 1760 | 1054 | C |
| ATOM | 6264 | CB | LEU | B | 187 | 29.537 | 52.715 | 86.663 | 1.00 | 38.53 | | C |
| ANISOU | 6264 | CB | LEU | B | 187 | 5341 | 4821 | 4479 | -798 | 1702 | 869 | C |
| ATOM | 6267 | CG | LEU | B | 187 | 30.501 | 52.012 | 85.695 | 1.00 | 40.12 | | C |
| ANISOU | 6267 | CG | LEU | B | 187 | 5502 | 5209 | 4532 | -818 | 1819 | 884 | C |
| ATOM | 6269 | CD1 | LEU | B | 187 | 31.185 | 50.802 | 86.351 | 1.00 | 37.59 | | C |
| ANISOU | 6269 | CD1 | LEU | B | 187 | 5044 | 5050 | 4187 | -764 | 1779 | 687 | C |
| ATOM | 6273 | CD2 | LEU | B | 187 | 29.760 | 51.582 | 84.448 | 1.00 | 41.09 | | C |
| ANISOU | 6273 | CD2 | LEU | B | 187 | 5781 | 5408 | 4424 | -737 | 1811 | 1029 | C |
| ATOM | 6277 | C | LEU | B | 187 | 27.995 | 54.543 | 87.357 | 1.00 | 37.88 | | C |
| ANISOU | 6277 | C | LEU | B | 187 | 5399 | 4363 | 4631 | -782 | 1642 | 995 | C |
| ATOM | 6278 | O | LEU | B | 187 | 26.882 | 54.064 | 87.358 | 1.00 | 34.34 | | O |
| ANISOU | 6278 | O | LEU | B | 187 | 5011 | 3948 | 4090 | -649 | 1520 | 1028 | O |
| ATOM | 6280 | N | TRP | B | 188 | 28.380 | 55.443 | 88.257 | 1.00 | 39.04 | | N |
| ANISOU | 6280 | N | TRP | B | 188 | 5500 | 4343 | 4988 | -885 | 1684 | 902 | N |
| ATOM | 6281 | CA | TRP | B | 188 | 27.535 | 55.819 | 89.396 | 1.00 | 38.51 | | C |
| ANISOU | 6281 | CA | TRP | B | 188 | 5455 | 4133 | 5044 | -827 | 1592 | 804 | C |
| ATOM | 6283 | CB | TRP | B | 188 | 28.284 | 56.783 | 90.333 | 1.00 | 40.60 | | C |
| ANISOU | 6283 | CB | TRP | B | 188 | 5665 | 4235 | 5524 | -990 | 1664 | 657 | C |
| ATOM | 6286 | CG | TRP | B | 188 | 27.397 | 57.258 | 91.432 | 1.00 | 40.19 | | C |
| ANISOU | 6286 | CG | TRP | B | 188 | 5662 | 4023 | 5586 | -927 | 1597 | 555 | C |
| ATOM | 6287 | CD1 | TRP | B | 188 | 26.814 | 58.489 | 91.544 | 1.00 | 41.98 | | C |
| ANISOU | 6287 | CD1 | TRP | B | 188 | 6007 | 3966 | 5978 | -926 | 1669 | 622 | C |
| ATOM | 6289 | NE1 | TRP | B | 188 | 26.026 | 58.533 | 92.666 | 1.00 | 40.96 | | N |
| ANISOU | 6289 | NE1 | TRP | B | 188 | 5889 | 3772 | 5901 | -839 | 1591 | 480 | N |
| ATOM | 6291 | CE2 | TRP | B | 188 | 26.088 | 57.321 | 93.305 | 1.00 | 38.68 | | C |
| ANISOU | 6291 | CE2 | TRP | B | 188 | 5491 | 3731 | 5475 | -792 | 1462 | 332 | C |
| ATOM | 6292 | CD2 | TRP | B | 188 | 26.943 | 56.489 | 92.552 | 1.00 | 38.34 | | C |

FIG. 18 (continued)

| | | | | | | | | | | | | |
|---|---|---|---|---|---|---|---|---|---|---|---|---|
| ANISOU | 6292 | CD2 | TRP | B | 188 | 5367 | 3899 | 5301 | -839 | 1461 | 376 | C |
| ATOM | 6293 | CE3 | TRP | B | 188 | 27.176 | 55.170 | 92.995 | 1.00 | 36.40 | | C |
| ANISOU | 6293 | CE3 | TRP | B | 188 | 5015 | 3902 | 4915 | -788 | 1349 | 258 | C |
| ATOM | 6295 | CZ3 | TRP | B | 188 | 26.556 | 54.738 | 94.169 | 1.00 | 35.07 | | C |
| ANISOU | 6295 | CZ3 | TRP | B | 188 | 4823 | 3772 | 4729 | -707 | 1239 | 115 | C |
| ATOM | 6297 | CH2 | TRP | B | 188 | 25.712 | 55.591 | 94.890 | 1.00 | 35.90 | | C |
| ANISOU | 6297 | CH2 | TRP | B | 188 | 5004 | 3687 | 4950 | -673 | 1245 | 72 | C |
| ATOM | 6299 | CZ2 | TRP | B | 188 | 25.476 | 56.890 | 94.484 | 1.00 | 38.23 | | C |
| ANISOU | 6299 | CZ2 | TRP | B | 188 | 5404 | 3725 | 5396 | -709 | 1358 | 170 | C |
| ATOM | 6301 | C | TRP | B | 188 | 26.158 | 56.414 | 89.036 | 1.00 | 38.39 | | C |
| ANISOU | 6301 | C | TRP | B | 188 | 5578 | 3966 | 5042 | -695 | 1562 | 985 | C |
| ATOM | 6302 | O | TRP | B | 188 | 25.137 | 55.975 | 89.580 | 1.00 | 35.46 | | O |
| ANISOU | 6302 | O | TRP | B | 188 | 5213 | 3624 | 4638 | -562 | 1439 | 943 | O |
| ATOM | 6304 | N | ASP | B | 189 | 26.121 | 57.400 | 88.135 | 1.00 | 41.18 | | N |
| ANISOU | 6304 | N | ASP | B | 189 | 6032 | 4167 | 5448 | -724 | 1675 | 1200 | N |
| ATOM | 6305 | CA | ASP | B | 189 | 24.864 | 58.082 | 87.784 | 1.00 | 43.01 | | C |
| ANISOU | 6305 | CA | ASP | B | 189 | 6382 | 4247 | 5714 | -582 | 1654 | 1402 | C |
| ATOM | 6307 | CB | ASP | B | 189 | 25.080 | 59.189 | 86.735 | 1.00 | 47.25 | | C |
| ANISOU | 6307 | CB | ASP | B | 189 | 7031 | 4612 | 6309 | -632 | 1803 | 1663 | C |
| ATOM | 6310 | CG | ASP | B | 189 | 25.783 | 60.429 | 87.295 | 1.00 | 51.30 | | C |
| ANISOU | 6310 | CG | ASP | B | 189 | 7574 | 4830 | 7087 | -788 | 1956 | 1601 | C |
| ATOM | 6311 | OD1 | ASP | B | 189 | 26.152 | 60.464 | 88.489 | 1.00 | 52.79 | | O |
| ANISOU | 6311 | OD1 | ASP | B | 189 | 7692 | 4963 | 7402 | -869 | 1942 | 1342 | O |
| ATOM | 6312 | OD2 | ASP | B | 189 | 25.986 | 61.388 | 86.510 | 1.00 | 55.23 | | O |
| ANISOU | 6312 | OD2 | ASP | B | 189 | 8175 | 5150 | 7659 | -842 | 2097 | 1818 | O |
| ATOM | 6313 | C | ASP | B | 189 | 23.786 | 57.091 | 87.298 | 1.00 | 41.52 | | C |
| ANISOU | 6313 | C | ASP | B | 189 | 6198 | 4266 | 5312 | -415 | 1501 | 1489 | C |
| ATOM | 6314 | O | ASP | B | 189 | 22.634 | 57.169 | 87.714 | 1.00 | 40.82 | | O |
| ANISOU | 6314 | O | ASP | B | 189 | 6121 | 4131 | 5256 | -276 | 1410 | 1515 | O |
| ATOM | 6316 | N | SER | B | 190 | 24.169 | 56.164 | 86.424 | 1.00 | 40.35 | | N |
| ANISOU | 6316 | N | SER | B | 190 | 6036 | 4347 | 4946 | -437 | 1480 | 1522 | N |
| ATOM | 6317 | CA | SER | B | 190 | 23.247 | 55.140 | 85.928 | 1.00 | 40.02 | | C |
| ANISOU | 6317 | CA | SER | B | 190 | 6005 | 4515 | 4688 | -320 | 1335 | 1571 | C |
| ATOM | 6319 | CB | SER | B | 190 | 23.906 | 54.317 | 84.806 | 1.00 | 40.83 | | C |
| ANISOU | 6319 | CB | SER | B | 190 | 6127 | 4831 | 4555 | -376 | 1366 | 1605 | C |
| ATOM | 6322 | OG | SER | B | 190 | 23.132 | 53.182 | 84.460 | 1.00 | 40.01 | | O |
| ANISOU | 6322 | OG | SER | B | 190 | 6033 | 4927 | 4241 | -298 | 1224 | 1586 | O |
| ATOM | 6324 | C | SER | B | 190 | 22.800 | 54.205 | 87.057 | 1.00 | 37.67 | | C |
| ANISOU | 6324 | C | SER | B | 190 | 5623 | 4296 | 4393 | -265 | 1205 | 1353 | C |
| ATOM | 6325 | O | SER | B | 190 | 21.611 | 53.885 | 87.165 | 1.00 | 36.79 | | O |
| ANISOU | 6325 | O | SER | B | 190 | 5513 | 4236 | 4231 | -152 | 1083 | 1396 | O |
| ATOM | 6327 | N | PHE | B | 191 | 23.755 | 53.799 | 87.896 | 1.00 | 35.36 | | N |
| ANISOU | 6327 | N | PHE | B | 191 | 5250 | 4023 | 4162 | -348 | 1234 | 1135 | N |
| ATOM | 6328 | CA | PHE | B | 191 | 23.470 | 52.985 | 89.079 | 1.00 | 34.53 | | C |
| ANISOU | 6328 | CA | PHE | B | 191 | 5069 | 3980 | 4070 | -304 | 1129 | 936 | C |
| ATOM | 6330 | CB | PHE | B | 191 | 24.782 | 52.581 | 89.783 | 1.00 | 32.20 | | C |
| ANISOU | 6330 | CB | PHE | B | 191 | 4677 | 3739 | 3818 | -404 | 1174 | 736 | C |
| ATOM | 6333 | CG | PHE | B | 191 | 24.595 | 51.665 | 90.965 | 1.00 | 30.28 | | C |
| ANISOU | 6333 | CG | PHE | B | 191 | 4362 | 3580 | 3563 | -355 | 1068 | 553 | C |
| ATOM | 6334 | CD1 | PHE | B | 191 | 24.059 | 50.401 | 90.803 | 1.00 | 28.44 | | C |
| ANISOU | 6334 | CD1 | PHE | B | 191 | 4138 | 3493 | 3174 | -276 | 971 | 538 | C |
| ATOM | 6336 | CE1 | PHE | B | 191 | 23.897 | 49.550 | 91.910 | 1.00 | 27.90 | | C |
| ANISOU | 6336 | CE1 | PHE | B | 191 | 4013 | 3490 | 3098 | -233 | 886 | 391 | C |
| ATOM | 6338 | CZ | PHE | B | 191 | 24.286 | 49.960 | 93.174 | 1.00 | 27.62 | | C |
| ANISOU | 6338 | CZ | PHE | B | 191 | 3907 | 3404 | 3185 | -264 | 887 | 256 | C |
| ATOM | 6340 | CE2 | PHE | B | 191 | 24.822 | 51.202 | 93.351 | 1.00 | 28.36 | | C |
| ANISOU | 6340 | CE2 | PHE | B | 191 | 3988 | 3366 | 3421 | -353 | 972 | 243 | C |
| ATOM | 6342 | CD2 | PHE | B | 191 | 24.966 | 52.068 | 92.253 | 1.00 | 30.57 | | C |
| ANISOU | 6342 | CD2 | PHE | B | 191 | 4331 | 3550 | 3736 | -401 | 1068 | 393 | C |
| ATOM | 6344 | C | PHE | B | 191 | 22.510 | 53.695 | 90.057 | 1.00 | 36.00 | | C |
| ANISOU | 6344 | C | PHE | B | 191 | 5257 | 4011 | 4411 | -230 | 1090 | 915 | C |
| ATOM | 6345 | O | PHE | B | 191 | 21.556 | 53.078 | 90.548 | 1.00 | 34.20 | | O |
| ANISOU | 6345 | O | PHE | B | 191 | 5005 | 3854 | 4136 | -136 | 979 | 877 | O |
| ATOM | 6347 | N | ARG | B | 192 | 22.743 | 54.970 | 90.331 | 1.00 | 39.21 | | N |
| ANISOU | 6347 | N | ARG | B | 192 | 5695 | 4202 | 5002 | -274 | 1192 | 937 | N |
| ATOM | 6348 | CA | ARG | B | 192 | 21.776 | 55.735 | 91.127 | 1.00 | 41.86 | | C |
| ANISOU | 6348 | CA | ARG | B | 192 | 6053 | 4366 | 5485 | -181 | 1183 | 930 | C |
| ATOM | 6350 | CB | ARG | B | 192 | 22.325 | 57.103 | 91.490 | 1.00 | 44.67 | | C |
| ANISOU | 6350 | CB | ARG | B | 192 | 6461 | 4456 | 6057 | -269 | 1323 | 902 | C |
| ATOM | 6353 | CG | ARG | B | 192 | 21.481 | 57.806 | 92.540 | 1.00 | 47.84 | | C |
| ANISOU | 6353 | CG | ARG | B | 192 | 6887 | 4675 | 6616 | -179 | 1333 | 822 | C |
| ATOM | 6356 | CD | ARG | B | 192 | 21.853 | 59.260 | 92.744 | 1.00 | 51.88 | | C |
| ANISOU | 6356 | CD | ARG | B | 192 | 7489 | 4871 | 7352 | -254 | 1487 | 815 | C |
| ATOM | 6359 | NE | ARG | B | 192 | 21.268 | 59.753 | 94.004 | 1.00 | 55.31 | | N |
| ANISOU | 6359 | NE | ARG | B | 192 | 7940 | 5156 | 7919 | -194 | 1505 | 644 | N |
| ATOM | 6361 | CZ | ARG | B | 192 | 20.075 | 60.345 | 94.139 | 1.00 | 57.75 | | C |
| ANISOU | 6361 | CZ | ARG | B | 192 | 8304 | 5314 | 8325 | -11 | 1530 | 741 | C |
| ATOM | 6362 | NH1 | ARG | B | 192 | 19.289 | 60.559 | 93.084 | 1.00 | 60.18 | | N |
| ANISOU | 6362 | NH1 | ARG | B | 192 | 8645 | 5602 | 8616 | 137 | 1524 | 1030 | N |

FIG. 18 (continued)

| | | | | | | | | | | | | |
|---|---|---|---|---|---|---|---|---|---|---|---|---|
| ATOM | 6365 | NH2 | ARG | B | 192 | 19.658 | 60.727 | 95.347 | 1.00 | 57.61 | | N |
| ANISOU | 6365 | NH2 | ARG | B | 192 | 8299 | 5178 | 8411 | 33 | 1564 | 549 | N |
| ATOM | 6368 | C | ARG | B | 192 | 20.363 | 55.813 | 90.460 | 1.00 | 41.98 | | C |
| ANISOU | 6368 | C | ARG | B | 192 | 6107 | 4398 | 5445 | -16 | 1114 | 1149 | C |
| ATOM | 6369 | O | ARG | B | 192 | 19.349 | 55.537 | 91.128 | 1.00 | 40.94 | | O |
| ANISOU | 6369 | O | ARG | B | 192 | 5933 | 4298 | 5323 | 95 | 1033 | 1108 | O |
| ATOM | 6371 | N | GLN | B | 193 | 20.311 | 56.092 | 89.152 | 1.00 | 41.26 | | N |
| ANISOU | 6371 | N | GLN | B | 193 | 6078 | 4323 | 5275 | -4 | 1139 | 1380 | N |
| ATOM | 6372 | CA | GLN | B | 193 | 19.061 | 56.222 | 88.388 | 1.00 | 43.90 | | C |
| ANISOU | 6372 | CA | GLN | B | 193 | 6435 | 4706 | 5539 | 144 | 1062 | 1618 | C |
| ATOM | 6374 | CB | GLN | B | 193 | 19.342 | 56.645 | 86.931 | 1.00 | 47.86 | | C |
| ANISOU | 6374 | CB | GLN | B | 193 | 7020 | 5224 | 5939 | 122 | 1114 | 1871 | C |
| ATOM | 6377 | CG | GLN | B | 193 | 19.669 | 58.122 | 86.697 | 1.00 | 52.49 | | C |
| ANISOU | 6377 | CG | GLN | B | 193 | 7700 | 5527 | 6717 | 115 | 1273 | 2027 | C |
| ATOM | 6380 | CD | GLN | B | 193 | 20.090 | 58.430 | 85.228 | 1.00 | 55.14 | | C |
| ANISOU | 6380 | CD | GLN | B | 193 | 8124 | 5909 | 6919 | 71 | 1336 | 2285 | C |
| ATOM | 6381 | OE1 | GLN | B | 193 | 20.728 | 57.607 | 84.553 | 1.00 | 56.51 | | O |
| ANISOU | 6381 | OE1 | GLN | B | 193 | 8293 | 6293 | 6887 | -25 | 1322 | 2255 | O |
| ATOM | 6382 | NE2 | GLN | B | 193 | 19.729 | 59.620 | 84.746 | 1.00 | 58.85 | | N |
| ANISOU | 6382 | NE2 | GLN | B | 193 | 8682 | 6175 | 7502 | 152 | 1418 | 2542 | N |
| ATOM | 6385 | C | GLN | B | 193 | 18.204 | 54.956 | 88.333 | 1.00 | 41.06 | | C |
| ANISOU | 6385 | C | GLN | B | 193 | 6005 | 4602 | 4996 | 205 | 894 | 1588 | C |
| ATOM | 6386 | O | GLN | B | 193 | 16.980 | 55.044 | 88.342 | 1.00 | 38.97 | | O |
| ANISOU | 6386 | O | GLN | B | 193 | 5701 | 4370 | 4735 | 336 | 811 | 1699 | O |
| ATOM | 6388 | N | SER | B | 194 | 18.826 | 53.780 | 88.256 | 1.00 | 38.71 | | N |
| ANISOU | 6388 | N | SER | B | 194 | 5685 | 4481 | 4543 | 110 | 850 | 1446 | N |
| ATOM | 6389 | CA | SER | B | 194 | 18.053 | 52.565 | 88.108 | 1.00 | 39.26 | | C |
| ANISOU | 6389 | CA | SER | B | 194 | 5711 | 4767 | 4439 | 141 | 704 | 1418 | C |
| ATOM | 6391 | CB | SER | B | 194 | 18.936 | 51.383 | 87.701 | 1.00 | 39.54 | | C |
| ANISOU | 6391 | CB | SER | B | 194 | 5766 | 4957 | 4300 | 35 | 697 | 1295 | C |
| ATOM | 6394 | OG | SER | B | 194 | 19.829 | 51.066 | 88.744 | 1.00 | 43.46 | | O |
| ANISOU | 6394 | OG | SER | B | 194 | 6220 | 5404 | 4888 | -20 | 748 | 1081 | O |
| ATOM | 6396 | C | SER | B | 194 | 17.217 | 52.263 | 89.376 | 1.00 | 37.06 | | C |
| ANISOU | 6396 | C | SER | B | 194 | 5348 | 4481 | 4254 | 211 | 637 | 1293 | C |
| ATOM | 6397 | O | SER | B | 194 | 16.247 | 51.512 | 89.296 | 1.00 | 39.41 | | O |
| ANISOU | 6397 | O | SER | B | 194 | 5596 | 4927 | 4450 | 252 | 516 | 1317 | O |
| ATOM | 6399 | N | GLU | B | 195 | 17.554 | 52.885 | 90.511 | 1.00 | 35.96 | | N |
| ANISOU | 6399 | N | GLU | B | 195 | 5191 | 4174 | 4298 | 214 | 717 | 1166 | N |
| ATOM | 6400 | CA | GLU | B | 195 | 16.692 | 52.831 | 91.716 | 1.00 | 36.46 | | C |
| ANISOU | 6400 | CA | GLU | B | 195 | 5183 | 4215 | 4453 | 296 | 681 | 1069 | C |
| ATOM | 6402 | CB | GLU | B | 195 | 17.508 | 53.029 | 92.998 | 1.00 | 32.41 | | C |
| ANISOU | 6402 | CB | GLU | B | 195 | 4664 | 3595 | 4055 | 236 | 757 | 844 | C |
| ATOM | 6405 | CG | GLU | B | 195 | 16.637 | 52.924 | 94.304 | 1.00 | 33.95 | | C |
| ANISOU | 6405 | CG | GLU | B | 195 | 4796 | 3788 | 4315 | 317 | 733 | 731 | C |
| ATOM | 6408 | CD | GLU | B | 195 | 17.440 | 52.879 | 95.605 | 1.00 | 31.11 | | C |
| ANISOU | 6408 | CD | GLU | B | 195 | 4427 | 3388 | 4005 | 245 | 777 | 493 | C |
| ATOM | 6409 | OE1 | GLU | B | 195 | 16.841 | 52.722 | 96.684 | 1.00 | 31.91 | | O |
| ANISOU | 6409 | OE1 | GLU | B | 195 | 4487 | 3509 | 4127 | 298 | 766 | 391 | O |
| ATOM | 6410 | OE2 | GLU | B | 195 | 18.665 | 52.989 | 95.561 | 1.00 | 28.82 | | O |
| ANISOU | 6410 | OE2 | GLU | B | 195 | 4160 | 3066 | 3722 | 132 | 821 | 410 | O |
| ATOM | 6411 | C | GLU | B | 195 | 15.541 | 53.881 | 91.644 | 1.00 | 40.17 | | C |
| ANISOU | 6411 | C | GLU | B | 195 | 5640 | 4575 | 5048 | 446 | 697 | 1242 | C |
| ATOM | 6412 | O | GLU | B | 195 | 15.766 | 55.081 | 91.425 | 1.00 | 42.13 | | O |
| ANISOU | 6412 | O | GLU | B | 195 | 5952 | 4624 | 5434 | 479 | 803 | 1335 | O |
| ATOM | 6414 | N | ARG | B | 196 | 14.321 | 53.419 | 91.873 | 1.00 | 43.23 | | N |
| ANISOU | 6414 | N | ARG | B | 196 | 5938 | 5085 | 5401 | 540 | 602 | 1283 | N |
| ATOM | 6415 | CA | ARG | B | 196 | 13.114 | 54.258 | 91.783 | 1.00 | 45.62 | | C |
| ANISOU | 6415 | CA | ARG | B | 196 | 6190 | 5332 | 5812 | 711 | 604 | 1462 | C |
| ATOM | 6417 | CB | ARG | B | 196 | 13.423 | 55.766 | 91.881 | 1.00 | 49.26 | | C |
| ANISOU | 6417 | CB | ARG | B | 196 | 6735 | 5502 | 6480 | 782 | 757 | 1524 | C |
| ATOM | 6426 | C | ARG | B | 196 | 12.449 | 53.952 | 90.459 | 1.00 | 49.58 | | C |
| ANISOU | 6426 | C | ARG | B | 196 | 6660 | 6018 | 6160 | 743 | 482 | 1694 | C |
| ATOM | 6427 | O | ARG | B | 196 | 13.125 | 53.533 | 89.514 | 1.00 | 51.44 | | O |
| ANISOU | 6427 | O | ARG | B | 196 | 6964 | 6339 | 6242 | 636 | 451 | 1731 | O |
| ATOM | 6429 | MN | MN | B | 301 | 16.649 | 40.458 | 102.484 | 0.50 | 51.43 | | MN |
| ANISOU | 6429 | MN | MN | B | 301 | 6868 | 7037 | 5638 | 187 | 285 | 15 | MN |
| ATOM | 6430 | OH2 | HOH | B | 302 | 13.347 | 41.525 | 103.018 | 1.00 | 30.86 | | O |
| ANISOU | 6430 | OH2 | HOH | B | 302 | 4113 | 4496 | 3116 | 191 | 326 | 122 | O |
| ATOM | 6433 | OH2 | HOH | B | 303 | 17.517 | 37.286 | 103.215 | 1.00 | 27.83 | | O |
| ANISOU | 6433 | OH2 | HOH | B | 303 | 4025 | 4041 | 2509 | 221 | 266 | 86 | O |
| ATOM | 6436 | OH2 | HOH | B | 304 | 16.758 | 39.411 | 99.992 | 1.00 | 33.53 | | O |
| ANISOU | 6436 | OH2 | HOH | B | 304 | 4712 | 4685 | 3342 | 106 | 247 | 85 | O |
| ATOM | 6439 | OH2 | HOH | B | 305 | 13.909 | 39.097 | 101.109 | 1.00 | 28.56 | | O |
| ANISOU | 6439 | OH2 | HOH | B | 305 | 3984 | 4147 | 2722 | 49 | 225 | 192 | O |
| ATOM | 6442 | OH2 | HOH | B | 306 | 18.617 | 34.143 | 101.068 | 1.00 | 57.23 | | O |
| ANISOU | 6442 | OH2 | HOH | B | 306 | 8039 | 7503 | 6203 | 221 | 309 | 122 | O |
| ATOM | 6445 | S | SO4 | B | 401 | 10.564 | 37.397 | 100.300 | 1.00 | 24.15 | | S |
| ANISOU | 6445 | S | SO4 | B | 401 | 3334 | 3706 | 2136 | -209 | 131 | 366 | S |
| ATOM | 6446 | O1 | SO4 | B | 401 | 11.589 | 37.577 | 101.318 | 1.00 | 24.57 | | O |

FIG. 18 (continued)

| | | | | | | | | | | | | |
|---|---|---|---|---|---|---|---|---|---|---|---|---|
| ANISOU | 6446 | O1 | SO4 | B | 401 | 3431 | 3717 | 2189 | -107 | 193 | 313 | O |
| ATOM | 6447 | O2 | SO4 | B | 401 | 9.790 | 36.265 | 100.734 | 1.00 | 26.79 | | O |
| ANISOU | 6447 | O2 | SO4 | B | 401 | 3673 | 4054 | 2450 | -317 | 135 | 402 | O |
| ATOM | 6448 | O3 | SO4 | B | 401 | 11.186 | 37.208 | 98.996 | 1.00 | 22.13 | | O |
| ANISOU | 6448 | O3 | SO4 | B | 401 | 3171 | 3399 | 1838 | -249 | 84 | 337 | O |
| ATOM | 6449 | O4 | SO4 | B | 401 | 9.774 | 38.664 | 100.295 | 1.00 | 25.26 | | O |
| ANISOU | 6449 | O4 | SO4 | B | 401 | 3330 | 3928 | 2340 | -146 | 130 | 413 | O |
| ATOM | 6450 | S | SO4 | B | 402 | 24.619 | 61.060 | 94.938 | 0.60 | 44.14 | | S |
| ANISOU | 6450 | S | SO4 | B | 402 | 6512 | 3512 | 6748 | -800 | 1721 | 214 | S |
| ATOM | 6451 | O1 | SO4 | B | 402 | 25.210 | 59.857 | 95.475 | 0.60 | 42.42 | | O |
| ANISOU | 6451 | O1 | SO4 | B | 402 | 6143 | 3610 | 6364 | -851 | 1593 | 49 | O |
| ATOM | 6452 | O2 | SO4 | B | 402 | 24.383 | 60.960 | 93.510 | 0.60 | 46.39 | | O |
| ANISOU | 6452 | O2 | SO4 | B | 402 | 6835 | 3824 | 6968 | -718 | 1742 | 517 | O |
| ATOM | 6453 | O3 | SO4 | B | 402 | 25.507 | 62.188 | 95.175 | 0.60 | 48.46 | | O |
| ANISOU | 6453 | O3 | SO4 | B | 402 | 7114 | 3815 | 7483 | -1020 | 1858 | 107 | O |
| ATOM | 6454 | O4 | SO4 | B | 402 | 23.339 | 61.299 | 95.581 | 0.60 | 46.77 | | O |
| ANISOU | 6454 | O4 | SO4 | B | 402 | 6910 | 3733 | 7128 | -608 | 1704 | 192 | O |
| ATOM | 6455 | S | SO4 | B | 403 | 18.619 | 60.631 | 89.162 | 0.40 | 66.06 | | S |
| ANISOU | 6455 | S | SO4 | B | 403 | 9481 | 6537 | 9081 | 305 | 1467 | 1882 | S |
| ATOM | 6456 | O1 | SO4 | B | 403 | 17.740 | 59.472 | 89.051 | 0.40 | 63.64 | | O |
| ANISOU | 6456 | O1 | SO4 | B | 403 | 9068 | 6534 | 8578 | 407 | 1287 | 1894 | O |
| ATOM | 6457 | O2 | SO4 | B | 403 | 20.016 | 60.204 | 89.050 | 0.40 | 64.73 | | O |
| ANISOU | 6457 | O2 | SO4 | B | 403 | 9305 | 6447 | 8841 | 80 | 1508 | 1739 | O |
| ATOM | 6458 | O3 | SO4 | B | 403 | 18.393 | 61.289 | 90.445 | 0.40 | 65.76 | | O |
| ANISOU | 6458 | O3 | SO4 | B | 403 | 9457 | 6265 | 9263 | 340 | 1542 | 1692 | O |
| ATOM | 6459 | O4 | SO4 | B | 403 | 18.287 | 61.568 | 88.091 | 0.40 | 67.77 | | O |
| ANISOU | 6459 | O4 | SO4 | B | 403 | 9796 | 6610 | 9345 | 399 | 1537 | 2214 | O |
| ATOM | 6460 | N | ALA | D | 0 | -12.871 | 35.450 | 116.896 | 1.00 | 72.26 | | N |
| ANISOU | 6460 | N | ALA | D | 0 | 9799 | 10248 | 7407 | -2399 | -2711 | -297 | N |
| ATOM | 6461 | CA | ALA | D | 0 | -11.930 | 35.094 | 115.786 | 1.00 | 71.39 | | C |
| ANISOU | 6461 | CA | ALA | D | 0 | 9399 | 10231 | 7494 | -2537 | -2656 | -21 | C |
| ATOM | 6463 | CB | ALA | D | 0 | -10.493 | 35.112 | 116.285 | 1.00 | 75.56 | | C |
| ANISOU | 6463 | CB | ALA | D | 0 | 9642 | 11171 | 7898 | -2845 | -2846 | 154 | C |
| ATOM | 6467 | C | ALA | D | 0 | -12.259 | 33.729 | 115.180 | 1.00 | 68.28 | | C |
| ANISOU | 6467 | C | ALA | D | 0 | 8751 | 9916 | 7275 | -2198 | -2362 | 178 | C |
| ATOM | 6468 | O | ALA | D | 0 | -11.366 | 33.012 | 114.719 | 1.00 | 68.80 | | O |
| ANISOU | 6468 | O | ALA | D | 0 | 8489 | 10223 | 7429 | -2204 | -2296 | 443 | O |
| ATOM | 6472 | N | MET | D | 1 | -13.542 | 33.371 | 115.194 | 1.00 | 64.88 | | N |
| ANISOU | 6472 | N | MET | D | 1 | 8475 | 9302 | 6874 | -1908 | -2185 | 34 | N |
| ATOM | 6473 | CA | MET | D | 1 | -14.058 | 32.266 | 114.366 | 1.00 | 61.29 | | C |
| ANISOU | 6473 | CA | MET | D | 1 | 7883 | 8804 | 6602 | -1650 | -1899 | 159 | C |
| ATOM | 6475 | CB | MET | D | 1 | -15.550 | 32.065 | 114.639 | 1.00 | 58.20 | | C |
| ANISOU | 6475 | CB | MET | D | 1 | 7669 | 8277 | 6169 | -1411 | -1745 | -64 | C |
| ATOM | 6478 | CG | MET | D | 1 | -16.275 | 31.067 | 113.696 | 1.00 | 55.15 | | C |
| ANISOU | 6478 | CG | MET | D | 1 | 7193 | 7806 | 5955 | -1208 | -1458 | -2 | C |
| ATOM | 6481 | SD | MET | D | 1 | -15.804 | 29.345 | 113.912 | 1.00 | 51.46 | | S |
| ANISOU | 6481 | SD | MET | D | 1 | 6497 | 7552 | 5503 | -1077 | -1239 | 314 | S |
| ATOM | 6482 | CE | MET | D | 1 | -16.771 | 28.875 | 115.336 | 1.00 | 51.45 | | C |
| ANISOU | 6482 | CE | MET | D | 1 | 6615 | 7679 | 5257 | -977 | -1151 | 194 | C |
| ATOM | 6486 | C | MET | D | 1 | -13.807 | 32.607 | 112.898 | 1.00 | 61.22 | | C |
| ANISOU | 6486 | C | MET | D | 1 | 7858 | 8602 | 6803 | -1740 | -1865 | 218 | C |
| ATOM | 6487 | O | MET | D | 1 | -13.529 | 31.732 | 112.072 | 1.00 | 59.78 | | O |
| ANISOU | 6487 | O | MET | D | 1 | 7467 | 8476 | 6770 | -1639 | -1687 | 413 | O |
| ATOM | 6489 | N | GLU | D | 2 | -13.879 | 33.899 | 112.596 | 1.00 | 63.66 | | N |
| ANISOU | 6489 | N | GLU | D | 2 | 8425 | 8666 | 7095 | -1932 | -2039 | 50 | N |
| ATOM | 6490 | CA | GLU | D | 2 | -13.621 | 34.419 | 111.255 | 1.00 | 63.22 | | C |
| ANISOU | 6490 | CA | GLU | D | 2 | 8427 | 8403 | 7191 | -2067 | -2038 | 104 | C |
| ATOM | 6492 | CB | GLU | D | 2 | -13.827 | 35.928 | 111.254 | 1.00 | 65.42 | | C |
| ANISOU | 6492 | CB | GLU | D | 2 | 9123 | 8354 | 7380 | -2265 | -2261 | -113 | C |
| ATOM | 6495 | CG | GLU | D | 2 | -14.412 | 36.460 | 109.980 | 1.00 | 64.77 | | C |
| ANISOU | 6495 | CG | GLU | D | 2 | 9275 | 7920 | 7416 | -2198 | -2216 | -172 | C |
| ATOM | 6498 | CD | GLU | D | 2 | -13.920 | 37.847 | 109.634 | 1.00 | 67.35 | | C |
| ANISOU | 6498 | CD | GLU | D | 2 | 9966 | 7950 | 7675 | -2544 | -2438 | -219 | C |
| ATOM | 6499 | OE1 | GLU | D | 2 | -13.597 | 38.628 | 110.550 | 1.00 | 69.54 | | O |
| ANISOU | 6499 | OE1 | GLU | D | 2 | 10458 | 8178 | 7784 | -2767 | -2649 | -340 | O |
| ATOM | 6500 | OE2 | GLU | D | 2 | -13.848 | 38.150 | 108.431 | 1.00 | 67.55 | | O |
| ANISOU | 6500 | OE2 | GLU | D | 2 | 10091 | 7778 | 7798 | -2614 | -2399 | -132 | O |
| ATOM | 6501 | C | GLU | D | 2 | -12.214 | 34.099 | 110.729 | 1.00 | 64.72 | | C |
| ANISOU | 6501 | C | GLU | D | 2 | 8290 | 8854 | 7447 | -2295 | -2041 | 390 | C |
| ATOM | 6502 | O | GLU | D | 2 | -12.033 | 33.874 | 109.536 | 1.00 | 63.59 | | O |
| ANISOU | 6502 | O | GLU | D | 2 | 8051 | 8657 | 7452 | -2289 | -1914 | 511 | O |
| ATOM | 6504 | N | ASP | D | 3 | -11.224 | 34.063 | 111.622 | 1.00 | 68.75 | | N |
| ANISOU | 6504 | N | ASP | D | 3 | 8604 | 9694 | 7823 | -2479 | -2184 | 489 | N |
| ATOM | 6505 | CA | ASP | D | 3 | -9.843 | 33.793 | 111.222 | 1.00 | 70.68 | | C |
| ANISOU | 6505 | CA | ASP | D | 3 | 8473 | 10294 | 8089 | -2683 | -2203 | 744 | C |
| ATOM | 6507 | CB | ASP | D | 3 | -8.874 | 34.476 | 112.185 | 1.00 | 76.54 | | C |
| ANISOU | 6507 | CB | ASP | D | 3 | 9139 | 11317 | 8627 | -3051 | -2475 | 736 | C |
| ATOM | 6510 | CG | ASP | D | 3 | -9.291 | 35.901 | 112.494 | 1.00 | 79.37 | | C |
| ANISOU | 6510 | CG | ASP | D | 3 | 9968 | 11312 | 8877 | -3351 | -2687 | 473 | C |

FIG. 18 (continued)

| | | | | | | | | | | | | | |
|---|---|---|---|---|---|---|---|---|---|---|---|---|---|
| ATOM | 6511 | OD1 | ASP | D | 3 | -8.753 | 36.834 | 111.855 | 1.00 | 81.17 | | | O |
| ANISOU | 6511 | OD1 | ASP | D | 3 | 10318 | 11418 | 9103 | -3755 | -2796 | 476 | | O |
| ATOM | 6512 | OD2 | ASP | D | 3 | -10.203 | 36.066 | 113.340 | 1.00 | 79.98 | | | O |
| ANISOU | 6512 | OD2 | ASP | D | 3 | 10321 | 11206 | 8861 | -3167 | -2728 | 260 | | O |
| ATOM | 6513 | C | ASP | D | 3 | -9.569 | 32.292 | 111.127 | 1.00 | 67.86 | | | C |
| ANISOU | 6513 | C | ASP | D | 3 | 7756 | 10225 | 7803 | -2336 | -1990 | 968 | | C |
| ATOM | 6514 | O | ASP | D | 3 | -8.827 | 31.843 | 110.248 | 1.00 | 67.73 | | | O |
| ANISOU | 6514 | O | ASP | D | 3 | 7461 | 10391 | 7883 | -2330 | -1883 | 1161 | | O |
| ATOM | 6516 | N | PHE | D | 4 | -10.168 | 31.528 | 112.035 | 1.00 | 65.16 | | | N |
| ANISOU | 6516 | N | PHE | D | 4 | 7451 | 9914 | 7392 | -2046 | -1922 | 941 | | N |
| ATOM | 6517 | CA | PHE | D | 4 | -10.170 | 30.072 | 111.947 | 1.00 | 63.44 | | | C |
| ANISOU | 6517 | CA | PHE | D | 4 | 7044 | 9827 | 7232 | -1681 | -1696 | 1129 | | C |
| ATOM | 6519 | CB | PHE | D | 4 | -10.997 | 29.479 | 113.100 | 1.00 | 63.78 | | | C |
| ANISOU | 6519 | CB | PHE | D | 4 | 7247 | 9838 | 7148 | -1460 | -1647 | 1059 | | C |
| ATOM | 6522 | CG | PHE | D | 4 | -11.434 | 28.066 | 112.859 | 1.00 | 62.34 | | | C |
| ANISOU | 6522 | CG | PHE | D | 4 | 7053 | 9595 | 7037 | -1118 | -1372 | 1190 | | C |
| ATOM | 6523 | CD1 | PHE | D | 4 | -10.546 | 27.015 | 113.024 | 1.00 | 64.02 | | | C |
| ANISOU | 6523 | CD1 | PHE | D | 4 | 7045 | 10071 | 7210 | -901 | -1314 | 1459 | | C |
| ATOM | 6525 | CE1 | PHE | D | 4 | -10.941 | 25.706 | 112.785 | 1.00 | 63.18 | | | C |
| ANISOU | 6525 | CE1 | PHE | D | 4 | 7016 | 9836 | 7153 | -593 | -1058 | 1578 | | C |
| ATOM | 6527 | CZ | PHE | D | 4 | -12.232 | 25.444 | 112.379 | 1.00 | 60.76 | | | C |
| ANISOU | 6527 | CZ | PHE | D | 4 | 6963 | 9187 | 6938 | -563 | -859 | 1420 | | C |
| ATOM | 6529 | CE2 | PHE | D | 4 | -13.130 | 26.494 | 112.210 | 1.00 | 58.86 | | | C |
| ANISOU | 6529 | CE2 | PHE | D | 4 | 6867 | 8761 | 6735 | -769 | -921 | 1147 | | C |
| ATOM | 6531 | CD2 | PHE | D | 4 | -12.729 | 27.789 | 112.449 | 1.00 | 59.54 | | | C |
| ANISOU | 6531 | CD2 | PHE | D | 4 | 6923 | 8928 | 6772 | -1012 | -1176 | 1038 | | C |
| ATOM | 6533 | C | PHE | D | 4 | -10.747 | 29.602 | 110.598 | 1.00 | 58.78 | | | C |
| ANISOU | 6533 | C | PHE | D | 4 | 6505 | 8976 | 6854 | -1523 | -1449 | 1138 | | C |
| ATOM | 6534 | O | PHE | D | 4 | -10.168 | 28.753 | 109.912 | 1.00 | 56.52 | | | O |
| ANISOU | 6534 | O | PHE | D | 4 | 5998 | 8825 | 6654 | -1364 | -1299 | 1331 | | O |
| ATOM | 6536 | N | VAL | D | 5 | -11.895 | 30.164 | 110.233 | 1.00 | 56.50 | | | N |
| ANISOU | 6536 | N | VAL | D | 5 | 6509 | 8334 | 6625 | -1542 | -1417 | 915 | | N |
| ATOM | 6537 | CA | VAL | D | 5 | -12.548 | 29.850 | 108.957 | 1.00 | 53.12 | | | C |
| ANISOU | 6537 | CA | VAL | D | 5 | 6147 | 7668 | 6368 | -1419 | -1215 | 885 | | C |
| ATOM | 6539 | CB | VAL | D | 5 | -13.901 | 30.629 | 108.810 | 1.00 | 51.27 | | | C |
| ANISOU | 6539 | CB | VAL | D | 5 | 6234 | 7107 | 6139 | -1413 | -1239 | 600 | | C |
| ATOM | 6541 | CG1 | VAL | D | 5 | -14.499 | 30.541 | 107.370 | 1.00 | 47.90 | | | C |
| ANISOU | 6541 | CG1 | VAL | D | 5 | 5869 | 6466 | 5866 | -1329 | -1085 | 560 | | C |
| ATOM | 6545 | CG2 | VAL | D | 5 | -14.911 | 30.090 | 109.813 | 1.00 | 49.08 | | | C |
| ANISOU | 6545 | CG2 | VAL | D | 5 | 6052 | 6831 | 5763 | -1228 | -1160 | 467 | | C |
| ATOM | 6549 | C | VAL | D | 5 | -11.564 | 30.095 | 107.807 | 1.00 | 54.47 | | | C |
| ANISOU | 6549 | C | VAL | D | 5 | 6139 | 7923 | 6635 | -1571 | -1211 | 1039 | | C |
| ATOM | 6550 | O | VAL | D | 5 | -11.373 | 29.236 | 106.935 | 1.00 | 51.43 | | | O |
| ANISOU | 6550 | O | VAL | D | 5 | 5610 | 7575 | 6355 | -1405 | -1012 | 1167 | | O |
| ATOM | 6552 | N | ARG | D | 6 | -10.861 | 31.223 | 107.863 | 1.00 | 58.72 | | | N |
| ANISOU | 6552 | N | ARG | D | 6 | 6683 | 8521 | 7108 | -1908 | -1426 | 1032 | | N |
| ATOM | 6553 | CA | ARG | D | 6 | -9.903 | 31.574 | 106.817 | 1.00 | 60.47 | | | C |
| ANISOU | 6553 | CA | ARG | D | 6 | 6733 | 8862 | 7381 | -2134 | -1425 | 1176 | | C |
| ATOM | 6555 | CB | ARG | D | 6 | -9.534 | 33.035 | 106.951 | 1.00 | 64.29 | | | C |
| ANISOU | 6555 | CB | ARG | D | 6 | 7398 | 9261 | 7768 | -2577 | -1672 | 1094 | | C |
| ATOM | 6558 | CG | ARG | D | 6 | -10.709 | 33.907 | 106.606 | 1.00 | 64.55 | | | C |
| ANISOU | 6558 | CG | ARG | D | 6 | 7898 | 8803 | 7825 | -2576 | -1718 | 870 | | C |
| ATOM | 6561 | CD | ARG | D | 6 | -10.603 | 35.302 | 107.167 | 1.00 | 68.18 | | | C |
| ANISOU | 6561 | CD | ARG | D | 6 | 8682 | 9078 | 8146 | -2929 | -1987 | 728 | | C |
| ATOM | 6564 | NE | ARG | D | 6 | -11.926 | 35.914 | 107.155 | 1.00 | 67.47 | | | N |
| ANISOU | 6564 | NE | ARG | D | 6 | 9041 | 8544 | 8051 | -2744 | -2026 | 480 | | N |
| ATOM | 6566 | CZ | ARG | D | 6 | -12.517 | 36.420 | 106.076 | 1.00 | 66.79 | | | C |
| ANISOU | 6566 | CZ | ARG | D | 6 | 9226 | 8124 | 8027 | -2696 | -1990 | 428 | | C |
| ATOM | 6567 | NH1 | ARG | D | 6 | -11.911 | 36.419 | 104.884 | 1.00 | 67.00 | | | N |
| ANISOU | 6567 | NH1 | ARG | D | 6 | 9152 | 8178 | 8126 | -2863 | -1905 | 611 | | N |
| ATOM | 6570 | NH2 | ARG | D | 6 | -13.729 | 36.936 | 106.195 | 1.00 | 66.16 | | | N |
| ANISOU | 6570 | NH2 | ARG | D | 6 | 9515 | 7712 | 7913 | -2456 | -2041 | 189 | | N |
| ATOM | 6573 | C | ARG | D | 6 | -8.651 | 30.700 | 106.813 | 1.00 | 62.21 | | | C |
| ANISOU | 6573 | C | ARG | D | 6 | 6504 | 9551 | 7583 | -2060 | -1355 | 1425 | | C |
| ATOM | 6574 | O | ARG | D | 6 | -8.162 | 30.303 | 105.753 | 1.00 | 62.78 | | | O |
| ANISOU | 6574 | O | ARG | D | 6 | 6383 | 9735 | 7736 | -2011 | -1203 | 1556 | | O |
| ATOM | 6576 | N | GLN | D | 7 | -8.142 | 30.400 | 108.000 | 1.00 | 63.08 | | | N |
| ANISOU | 6576 | N | GLN | D | 7 | 6447 | 9957 | 7564 | -2017 | -1470 | 1484 | | N |
| ATOM | 6577 | CA | GLN | D | 7 | -6.952 | 29.566 | 108.142 | 1.00 | 64.69 | | | C |
| ANISOU | 6577 | CA | GLN | D | 7 | 6212 | 10657 | 7711 | -1870 | -1436 | 1716 | | C |
| ATOM | 6579 | CB | GLN | D | 7 | -6.422 | 29.640 | 109.592 | 1.00 | 67.69 | | | C |
| ANISOU | 6579 | CB | GLN | D | 7 | 6462 | 11364 | 7894 | -1922 | -1656 | 1742 | | C |
| ATOM | 6582 | CG | GLN | D | 7 | -5.768 | 31.002 | 109.923 | 1.00 | 71.35 | | | C |
| ANISOU | 6582 | CG | GLN | D | 7 | 6887 | 11992 | 8229 | -2468 | -1933 | 1665 | | C |
| ATOM | 6585 | CD | GLN | D | 7 | -5.131 | 31.085 | 111.328 | 1.00 | 74.57 | | | C |
| ANISOU | 6585 | CD | GLN | D | 7 | 7122 | 12800 | 8411 | -2552 | -2172 | 1685 | | C |
| ATOM | 6586 | OE1 | GLN | D | 7 | -5.780 | 30.821 | 112.343 | 1.00 | 73.57 | | | O |
| ANISOU | 6586 | OE1 | GLN | D | 7 | 7200 | 12552 | 8203 | -2362 | -2214 | 1604 | | O |
| ATOM | 6587 | NE2 | GLN | D | 7 | -3.863 | 31.479 | 111.376 | 1.00 | 78.24 | | | N |

FIG. 18 (continued)

| | | | | | | | | | | | | |
|---|---|---|---|---|---|---|---|---|---|---|---|---|
| ANISOU | 6587 | NE2 | GLN | D | 7 | 7197 | 13779 | 8750 | -2867 | -2329 | 1786 | N |
| ATOM | 6590 | C | GLN | D | 7 | -7.170 | 28.103 | 107.727 | 1.00 | 62.88 | | C |
| ANISOU | 6590 | C | GLN | D | 7 | 5918 | 10400 | 7574 | -1377 | -1166 | 1835 | C |
| ATOM | 6591 | O | GLN | D | 7 | -6.220 | 27.448 | 107.306 | 1.00 | 65.16 | | O |
| ANISOU | 6591 | O | GLN | D | 7 | 5872 | 11031 | 7856 | -1205 | -1079 | 2020 | O |
| ATOM | 6593 | N | CYS | D | 8 | -8.408 | 27.599 | 107.805 | 1.00 | 58.66 | | N |
| ANISOU | 6593 | N | CYS | D | 8 | 5709 | 9472 | 7110 | -1160 | -1027 | 1719 | N |
| ATOM | 6594 | CA | ACYS | D | 8 | -8.652 | 26.166 | 107.652 | 0.50 | 56.58 | | C |
| ANISOU | 6594 | CA | ACYS | D | 8 | 5465 | 9142 | 6890 | -736 | -788 | 1821 | C |
| ATOM | 6595 | CA | BCYS | D | 8 | -8.664 | 26.162 | 107.654 | 0.50 | 57.50 | | C |
| ANISOU | 6595 | CA | BCYS | D | 8 | 5585 | 9255 | 7008 | -735 | -787 | 1820 | C |
| ATOM | 6598 | CB | ACYS | D | 8 | -9.117 | 25.592 | 108.992 | 0.50 | 57.64 | | C |
| ANISOU | 6598 | CB | ACYS | D | 8 | 5755 | 9246 | 6900 | -563 | -817 | 1821 | C |
| ATOM | 6599 | CB | BCYS | D | 8 | -9.230 | 25.605 | 108.950 | 0.50 | 58.69 | | C |
| ANISOU | 6599 | CB | BCYS | D | 8 | 5916 | 9342 | 7043 | -568 | -806 | 1804 | C |
| ATOM | 6604 | SG | ACYS | D | 8 | -7.832 | 25.731 | 110.300 | 0.50 | 61.79 | | S |
| ANISOU | 6604 | SG | ACYS | D | 8 | 5973 | 10305 | 7200 | -576 | -1080 | 1987 | S |
| ATOM | 6605 | SG | BCYS | D | 8 | -10.983 | 25.836 | 109.083 | 0.50 | 57.39 | | S |
| ANISOU | 6605 | SG | BCYS | D | 8 | 6165 | 8715 | 6924 | -641 | -726 | 1534 | S |
| ATOM | 6608 | C | CYS | D | 8 | -9.606 | 25.771 | 106.521 | 1.00 | 52.98 | | C |
| ANISOU | 6608 | C | CYS | D | 8 | 5227 | 8310 | 6592 | -635 | -554 | 1721 | C |
| ATOM | 6609 | O | CYS | D | 8 | -9.687 | 24.593 | 106.179 | 1.00 | 51.17 | | O |
| ANISOU | 6609 | O | CYS | D | 8 | 5029 | 8011 | 6401 | -327 | -341 | 1804 | O |
| ATOM | 6611 | N | PHE | D | 9 | -10.333 | 26.731 | 105.946 | 1.00 | 48.58 | | N |
| ANISOU | 6611 | N | PHE | D | 9 | 4848 | 7505 | 6105 | -878 | -598 | 1539 | N |
| ATOM | 6612 | CA | PHE | D | 9 | -11.104 | 26.453 | 104.740 | 1.00 | 44.56 | | C |
| ANISOU | 6612 | CA | PHE | D | 9 | 4486 | 6721 | 5723 | -803 | -404 | 1450 | C |
| ATOM | 6614 | CB | PHE | D | 9 | -12.542 | 26.994 | 104.865 | 1.00 | 41.70 | | C |
| ANISOU | 6614 | CB | PHE | D | 9 | 4431 | 6039 | 5376 | -880 | -433 | 1198 | C |
| ATOM | 6617 | CG | PHE | D | 9 | -13.400 | 26.176 | 105.773 | 1.00 | 41.20 | | C |
| ANISOU | 6617 | CG | PHE | D | 9 | 4507 | 5889 | 5258 | -713 | -340 | 1129 | C |
| ATOM | 6618 | CD1 | PHE | D | 9 | -13.910 | 24.964 | 105.341 | 1.00 | 38.60 | | C |
| ANISOU | 6618 | CD1 | PHE | D | 9 | 4255 | 5433 | 4977 | -517 | -93 | 1141 | C |
| ATOM | 6620 | CE1 | PHE | D | 9 | -14.679 | 24.188 | 106.173 | 1.00 | 39.08 | | C |
| ANISOU | 6620 | CE1 | PHE | D | 9 | 4470 | 5414 | 4963 | -427 | 9 | 1094 | C |
| ATOM | 6622 | CZ | PHE | D | 9 | -14.930 | 24.596 | 107.477 | 1.00 | 39.46 | | C |
| ANISOU | 6622 | CZ | PHE | D | 9 | 4568 | 5542 | 4882 | -496 | -131 | 1040 | C |
| ATOM | 6624 | CE2 | PHE | D | 9 | -14.438 | 25.780 | 107.933 | 1.00 | 41.44 | | C |
| ANISOU | 6624 | CE2 | PHE | D | 9 | 4739 | 5921 | 5084 | -651 | -381 | 1011 | C |
| ATOM | 6626 | CD2 | PHE | D | 9 | -13.654 | 26.583 | 107.078 | 1.00 | 42.05 | | C |
| ANISOU | 6626 | CD2 | PHE | D | 9 | 4686 | 6048 | 5241 | -778 | -491 | 1057 | C |
| ATOM | 6628 | C | PHE | D | 9 | -10.406 | 27.034 | 103.508 | 1.00 | 43.83 | | C |
| ANISOU | 6628 | C | PHE | D | 9 | 4248 | 6718 | 5687 | -967 | -401 | 1513 | C |
| ATOM | 6629 | O | PHE | D | 9 | -9.859 | 28.130 | 103.561 | 1.00 | 41.92 | | O |
| ANISOU | 6629 | O | PHE | D | 9 | 3945 | 6586 | 5398 | -1271 | -587 | 1522 | O |
| ATOM | 6631 | N | ASN | D | 10 | -10.468 | 26.299 | 102.395 | 1.00 | 44.09 | | N |
| ANISOU | 6631 | N | ASN | D | 10 | 4263 | 6688 | 5801 | -792 | -181 | 1548 | N |
| ATOM | 6632 | CA | ASN | D | 10 | -9.848 | 26.735 | 101.144 | 1.00 | 45.16 | | C |
| ANISOU | 6632 | CA | ASN | D | 10 | 4265 | 6925 | 5967 | -928 | -137 | 1614 | C |
| ATOM | 6634 | CB | ASN | D | 10 | -9.787 | 25.589 | 100.075 | 1.00 | 45.92 | | C |
| ANISOU | 6634 | CB | ASN | D | 10 | 4315 | 7010 | 6122 | -637 | 139 | 1664 | C |
| ATOM | 6637 | CG | ASN | D | 10 | -10.790 | 25.723 | 98.914 | 1.00 | 43.77 | | C |
| ANISOU | 6637 | CG | ASN | D | 10 | 4281 | 6432 | 5916 | -670 | 246 | 1510 | C |
| ATOM | 6638 | OD1 | ASN | D | 10 | -10.938 | 26.772 | 98.303 | 1.00 | 45.18 | | O |
| ANISOU | 6638 | OD1 | ASN | D | 10 | 4535 | 6540 | 6090 | -917 | 148 | 1463 | O |
| ATOM | 6639 | ND2 | ASN | D | 10 | -11.424 | 24.615 | 98.571 | 1.00 | 45.26 | | N |
| ANISOU | 6639 | ND2 | ASN | D | 10 | 4603 | 6448 | 6145 | -418 | 449 | 1442 | N |
| ATOM | 6642 | C | ASN | D | 10 | -10.471 | 28.049 | 100.647 | 1.00 | 44.01 | | C |
| ANISOU | 6642 | C | ASN | D | 10 | 4349 | 6540 | 5832 | -1232 | -272 | 1475 | C |
| ATOM | 6643 | O | ASN | D | 10 | -11.633 | 28.343 | 100.956 | 1.00 | 42.16 | | O |
| ANISOU | 6643 | O | ASN | D | 10 | 4389 | 6018 | 5611 | -1217 | -326 | 1291 | O |
| ATOM | 6645 | N | PRO | D | 11 | -9.671 | 28.861 | 99.935 | 1.00 | 45.50 | | N |
| ANISOU | 6645 | N | PRO | D | 11 | 4431 | 6869 | 5988 | -1508 | -331 | 1569 | N |
| ATOM | 6646 | CA | PRO | D | 11 | -10.049 | 30.207 | 99.500 | 1.00 | 45.84 | | C |
| ANISOU | 6646 | CA | PRO | D | 11 | 4741 | 6673 | 6003 | -1822 | -484 | 1483 | C |
| ATOM | 6648 | CB | PRO | D | 11 | -8.858 | 30.641 | 98.626 | 1.00 | 48.03 | | C |
| ANISOU | 6648 | CB | PRO | D | 11 | 4802 | 7221 | 6225 | -2103 | -458 | 1663 | C |
| ATOM | 6651 | CG | PRO | D | 11 | -7.730 | 29.867 | 99.137 | 1.00 | 49.84 | | C |
| ANISOU | 6651 | CG | PRO | D | 11 | 4598 | 7916 | 6422 | -2007 | -402 | 1818 | C |
| ATOM | 6654 | CD | PRO | D | 11 | -8.278 | 28.546 | 99.548 | 1.00 | 47.27 | | C |
| ANISOU | 6654 | CD | PRO | D | 11 | 4265 | 7527 | 6169 | -1541 | -255 | 1775 | C |
| ATOM | 6657 | C | PRO | D | 11 | -11.344 | 30.308 | 98.715 | 1.00 | 42.29 | | C |
| ANISOU | 6657 | C | PRO | D | 11 | 4609 | 5854 | 5605 | -1689 | -423 | 1317 | C |
| ATOM | 6658 | O | PRO | D | 11 | -12.100 | 31.250 | 98.930 | 1.00 | 41.78 | | O |
| ANISOU | 6658 | O | PRO | D | 11 | 4847 | 5517 | 5509 | -1784 | -587 | 1175 | O |
| ATOM | 6659 | N | MET | D | 12 | -11.564 | 29.350 | 97.815 | 1.00 | 41.26 | | N |
| ANISOU | 6659 | N | MET | D | 12 | 4408 | 5736 | 5533 | -1456 | -196 | 1328 | N |
| ATOM | 6660 | CA | MET | D | 12 | -12.766 | 29.282 | 97.002 | 1.00 | 40.67 | | C |
| ANISOU | 6660 | CA | MET | D | 12 | 4573 | 5392 | 5489 | -1318 | -125 | 1167 | C |

FIG. 18 (continued)

| | | | | | | | | | | | | |
|---|---|---|---|---|---|---|---|---|---|---|---|---|
| ATOM | 6662 | CB | MET | D | 12 | -12.709 | 28.116 | 95.999 | 1.00 | 43.61 | | C |
| ANISOU | 6662 | CB | MET | D | 12 | 4827 | 5842 | 5903 | -1106 | 138 | 1202 | C |
| ATOM | 6665 | CG | MET | D | 12 | -11.553 | 28.141 | 95.021 | 1.00 | 48.73 | | C |
| ANISOU | 6665 | CG | MET | D | 12 | 5275 | 6725 | 6514 | -1207 | 239 | 1386 | C |
| ATOM | 6668 | SD | MET | D | 12 | -11.395 | 29.694 | 94.107 | 1.00 | 55.34 | | S |
| ANISOU | 6668 | SD | MET | D | 12 | 6297 | 7470 | 7261 | -1571 | 91 | 1438 | S |
| ATOM | 6669 | CE | MET | D | 12 | -12.963 | 29.784 | 93.227 | 1.00 | 50.82 | | C |
| ANISOU | 6669 | CE | MET | D | 12 | 6070 | 6552 | 6689 | -1398 | 102 | 1227 | C |
| ATOM | 6673 | C | MET | D | 12 | -14.020 | 29.089 | 97.845 | 1.00 | 35.73 | | C |
| ANISOU | 6673 | C | MET | D | 12 | 4116 | 4579 | 4879 | -1156 | -171 | 959 | C |
| ATOM | 6674 | O | MET | D | 12 | -15.031 | 29.719 | 97.567 | 1.00 | 32.07 | | O |
| ANISOU | 6674 | O | MET | D | 12 | 3883 | 3909 | 4391 | -1138 | -257 | 794 | O |
| ATOM | 6676 | N | ILE | D | 13 | -13.940 | 28.203 | 98.839 | 1.00 | 34.49 | | N |
| ANISOU | 6676 | N | ILE | D | 13 | 3839 | 4526 | 4740 | -1024 | -107 | 975 | N |
| ATOM | 6677 | CA | ILE | D | 13 | -15.038 | 27.944 | 99.780 | 1.00 | 33.57 | | C |
| ANISOU | 6677 | CA | ILE | D | 13 | 3849 | 4298 | 4609 | -910 | -126 | 797 | C |
| ATOM | 6679 | CB | ILE | D | 13 | -14.717 | 26.697 | 100.676 | 1.00 | 34.38 | | C |
| ANISOU | 6679 | CB | ILE | D | 13 | 3825 | 4524 | 4712 | -761 | 4 | 888 | C |
| ATOM | 6681 | CG1 | ILE | D | 13 | -14.704 | 25.440 | 99.803 | 1.00 | 35.18 | | C |
| ANISOU | 6681 | CG1 | ILE | D | 13 | 3893 | 4607 | 4866 | -585 | 263 | 933 | C |
| ATOM | 6684 | CD1 | ILE | D | 13 | -14.268 | 24.157 | 100.551 | 1.00 | 36.25 | | C |
| ANISOU | 6684 | CD1 | ILE | D | 13 | 3979 | 4808 | 4985 | -396 | 402 | 1059 | C |
| ATOM | 6688 | CG2 | ILE | D | 13 | -15.714 | 26.513 | 101.846 | 1.00 | 32.57 | | C |
| ANISOU | 6688 | CG2 | ILE | D | 13 | 3716 | 4229 | 4429 | -712 | -23 | 735 | C |
| ATOM | 6692 | C | ILE | D | 13 | -15.342 | 29.219 | 100.602 | 1.00 | 34.17 | | C |
| ANISOU | 6692 | C | ILE | D | 13 | 4081 | 4287 | 4615 | -1049 | -381 | 688 | C |
| ATOM | 6693 | O | ILE | D | 13 | -16.502 | 29.616 | 100.695 | 1.00 | 33.02 | | O |
| ANISOU | 6693 | O | ILE | D | 13 | 4113 | 3994 | 4437 | -974 | -436 | 479 | O |
| ATOM | 6695 | N | VAL | D | 14 | -14.315 | 29.885 | 101.144 | 1.00 | 35.18 | | N |
| ANISOU | 6695 | N | VAL | D | 14 | 4145 | 4521 | 4700 | -1247 | -538 | 812 | N |
| ATOM | 6696 | CA | VAL | D | 14 | -14.520 | 31.094 | 101.968 | 1.00 | 36.85 | | C |
| ANISOU | 6696 | CA | VAL | D | 14 | 4558 | 4618 | 4824 | -1398 | -785 | 698 | C |
| ATOM | 6698 | CB | VAL | D | 14 | -13.188 | 31.657 | 102.554 | 1.00 | 40.82 | | C |
| ANISOU | 6698 | CB | VAL | D | 14 | 4943 | 5302 | 5266 | -1685 | -942 | 855 | C |
| ATOM | 6700 | CG1 | VAL | D | 14 | -13.407 | 33.018 | 103.239 | 1.00 | 41.60 | | C |
| ANISOU | 6700 | CG1 | VAL | D | 14 | 5339 | 5208 | 5258 | -1883 | -1205 | 712 | C |
| ATOM | 6704 | CG2 | VAL | D | 14 | -12.590 | 30.655 | 103.554 | 1.00 | 42.40 | | C |
| ANISOU | 6704 | CG2 | VAL | D | 14 | 4867 | 5796 | 5449 | -1582 | -883 | 969 | C |
| ATOM | 6708 | C | VAL | D | 14 | -15.221 | 32.160 | 101.147 | 1.00 | 38.75 | | C |
| ANISOU | 6708 | C | VAL | D | 14 | 5097 | 4583 | 5043 | -1431 | -888 | 567 | C |
| ATOM | 6709 | O | VAL | D | 14 | -16.195 | 32.778 | 101.588 | 1.00 | 40.22 | | O |
| ANISOU | 6709 | O | VAL | D | 14 | 5517 | 4595 | 5168 | -1330 | -1005 | 359 | O |
| ATOM | 6711 | N | GLU | D | 15 | -14.740 | 32.340 | 99.925 | 1.00 | 39.91 | | N |
| ANISOU | 6711 | N | GLU | D | 15 | 5238 | 4708 | 5218 | -1536 | -836 | 692 | N |
| ATOM | 6712 | CA | GLU | D | 15 | -15.279 | 33.339 | 99.024 | 1.00 | 40.91 | | C |
| ANISOU | 6712 | CA | GLU | D | 15 | 5677 | 4567 | 5298 | -1563 | -935 | 619 | C |
| ATOM | 6714 | CB | GLU | D | 15 | -14.379 | 33.386 | 97.797 | 1.00 | 42.96 | | C |
| ANISOU | 6714 | CB | GLU | D | 15 | 5860 | 4896 | 5568 | -1753 | -849 | 828 | C |
| ATOM | 6717 | CG | GLU | D | 15 | -14.630 | 34.477 | 96.821 | 1.00 | 44.81 | | C |
| ANISOU | 6717 | CG | GLU | D | 15 | 6444 | 4861 | 5722 | -1854 | -957 | 829 | C |
| ATOM | 6720 | CD | GLU | D | 15 | -13.657 | 34.369 | 95.682 | 1.00 | 46.56 | | C |
| ANISOU | 6720 | CD | GLU | D | 15 | 6531 | 5226 | 5932 | -2068 | -831 | 1053 | C |
| ATOM | 6721 | OE1 | GLU | D | 15 | -12.448 | 34.620 | 95.909 | 1.00 | 47.83 | | O |
| ANISOU | 6721 | OE1 | GLU | D | 15 | 6542 | 5568 | 6062 | -2402 | -854 | 1224 | O |
| ATOM | 6722 | OE2 | GLU | D | 15 | -14.103 | 34.005 | 94.574 | 1.00 | 47.99 | | O |
| ANISOU | 6722 | OE2 | GLU | D | 15 | 6729 | 5386 | 6118 | -1907 | -704 | 1048 | O |
| ATOM | 6723 | C | GLU | D | 15 | -16.723 | 33.038 | 98.652 | 1.00 | 38.44 | | C |
| ANISOU | 6723 | C | GLU | D | 15 | 5467 | 4146 | 4993 | -1240 | -873 | 407 | C |
| ATOM | 6724 | O | GLU | D | 15 | -17.543 | 33.950 | 98.609 | 1.00 | 40.00 | | O |
| ANISOU | 6724 | O | GLU | D | 15 | 5958 | 4127 | 5112 | -1140 | -1028 | 247 | O |
| ATOM | 6726 | N | LEU | D | 16 | -17.041 | 31.768 | 98.381 | 1.00 | 35.74 | | N |
| ANISOU | 6726 | N | LEU | D | 16 | 4893 | 3962 | 4723 | -1075 | -652 | 395 | N |
| ATOM | 6727 | CA | LEU | D | 16 | -18.424 | 31.357 | 98.148 | 1.00 | 34.36 | | C |
| ANISOU | 6727 | CA | LEU | D | 16 | 4752 | 3766 | 4537 | -825 | -582 | 175 | C |
| ATOM | 6729 | CB | LEU | D | 16 | -18.532 | 29.901 | 97.715 | 1.00 | 32.39 | | C |
| ANISOU | 6729 | CB | LEU | D | 16 | 4282 | 3665 | 4358 | -743 | -320 | 198 | C |
| ATOM | 6732 | CG | LEU | D | 16 | -17.979 | 29.560 | 96.334 | 1.00 | 34.99 | | C |
| ANISOU | 6732 | CG | LEU | D | 16 | 4560 | 4013 | 4721 | -778 | -192 | 333 | C |
| ATOM | 6734 | CD1 | LEU | D | 16 | -17.748 | 28.047 | 96.236 | 1.00 | 33.02 | | C |
| ANISOU | 6734 | CD1 | LEU | D | 16 | 4122 | 3886 | 4537 | -709 | 66 | 385 | C |
| ATOM | 6738 | CD2 | LEU | D | 16 | -18.910 | 30.084 | 95.209 | 1.00 | 34.00 | | C |
| ANISOU | 6738 | CD2 | LEU | D | 16 | 4599 | 3791 | 4529 | -679 | -244 | 198 | C |
| ATOM | 6742 | C | LEU | D | 16 | -19.321 | 31.585 | 99.357 | 1.00 | 34.08 | | C |
| ANISOU | 6742 | C | LEU | D | 16 | 4779 | 3732 | 4440 | -704 | -677 | -37 | C |
| ATOM | 6743 | O | LEU | D | 16 | -20.462 | 32.031 | 99.191 | 1.00 | 32.95 | | O |
| ANISOU | 6743 | O | LEU | D | 16 | 4759 | 3536 | 4224 | -518 | -747 | -250 | O |
| ATOM | 6745 | N | ALA | D | 17 | -18.833 | 31.251 | 100.553 | 1.00 | 33.79 | | N |
| ANISOU | 6745 | N | ALA | D | 17 | 4636 | 3794 | 4407 | -781 | -674 | 16 | N |
| ATOM | 6746 | CA | ALA | D | 17 | -19.585 | 31.508 | 101.780 | 1.00 | 35.91 | | C |

FIG. 18 (continued)

| | | | | | | | | | | | | |
|---|---|---|---|---|---|---|---|---|---|---|---|---|
| ANISOU | 6746 | CA | ALA | D | 17 | 4966 | 4090 | 4587 | -688 | -759 | -176 | C |
| ATOM | 6748 | CB | ALA | D | 17 | -18.893 | 30.878 | 102.997 | 1.00 | 35.27 | | C |
| ANISOU | 6748 | CB | ALA | D | 17 | 4739 | 4159 | 4503 | -785 | -718 | -63 | C |
| ATOM | 6752 | C | ALA | D | 17 | -19.814 | 33.002 | 102.005 | 1.00 | 38.49 | | C |
| ANISOU | 6752 | C | ALA | D | 17 | 5592 | 4217 | 4814 | -671 | -1017 | -303 | C |
| ATOM | 6753 | O | ALA | D | 17 | -20.942 | 33.407 | 102.254 | 1.00 | 37.06 | | O |
| ANISOU | 6753 | O | ALA | D | 17 | 5521 | 4018 | 4543 | -453 | -1079 | -544 | O |
| ATOM | 6755 | N | GLU | D | 18 | -18.740 | 33.801 | 101.913 | 1.00 | 44.31 | | N |
| ANISOU | 6755 | N | GLU | D | 18 | 6469 | 4819 | 5549 | -902 | -1162 | -146 | N |
| ATOM | 6756 | CA | GLU | D | 18 | -18.781 | 35.280 | 102.039 | 1.00 | 46.87 | | C |
| ANISOU | 6756 | CA | GLU | D | 18 | 7180 | 4863 | 5764 | -947 | -1416 | -236 | C |
| ATOM | 6758 | CB | GLU | D | 18 | -17.387 | 35.880 | 101.846 | 1.00 | 50.13 | | C |
| ANISOU | 6758 | CB | GLU | D | 18 | 7678 | 5188 | 6181 | -1332 | -1518 | -9 | C |
| ATOM | 6761 | CG | GLU | D | 18 | -16.429 | 35.683 | 102.995 | 1.00 | 52.03 | | C |
| ANISOU | 6761 | CG | GLU | D | 18 | 7747 | 5616 | 6406 | -1569 | -1560 | 82 | C |
| ATOM | 6764 | CD | GLU | D | 18 | -15.194 | 36.554 | 102.863 | 1.00 | 54.42 | | C |
| ANISOU | 6764 | CD | GLU | D | 18 | 8174 | 5842 | 6660 | -1993 | -1709 | 246 | C |
| ATOM | 6765 | OE1 | GLU | D | 18 | -14.510 | 36.510 | 101.806 | 1.00 | 55.08 | | O |
| ANISOU | 6765 | OE1 | GLU | D | 18 | 8176 | 5959 | 6793 | -2175 | -1635 | 441 | O |
| ATOM | 6766 | OE2 | GLU | D | 18 | -14.913 | 37.289 | 103.826 | 1.00 | 58.31 | | O |
| ANISOU | 6766 | OE2 | GLU | D | 18 | 8848 | 6260 | 7045 | -2169 | -1897 | 169 | O |
| ATOM | 6767 | C | GLU | D | 18 | -19.668 | 35.963 | 101.009 | 1.00 | 51.16 | | C |
| ANISOU | 6767 | C | GLU | D | 18 | 7989 | 5192 | 6257 | -727 | -1484 | -354 | C |
| ATOM | 6768 | O | GLU | D | 18 | -20.261 | 37.001 | 101.291 | 1.00 | 53.25 | | O |
| ANISOU | 6768 | O | GLU | D | 18 | 8594 | 5236 | 6401 | -571 | -1671 | -531 | O |
| ATOM | 6770 | N | LYS | D | 19 | -19.664 | 35.418 | 99.795 | 1.00 | 53.24 | | N |
| ANISOU | 6770 | N | LYS | D | 19 | 8124 | 5512 | 6594 | -707 | -1344 | -246 | N |
| ATOM | 6771 | CA | LYS | D | 19 | -20.532 | 35.841 | 98.690 | 1.00 | 55.48 | | C |
| ANISOU | 6771 | CA | LYS | D | 19 | 8593 | 5669 | 6819 | -469 | -1384 | -339 | C |
| ATOM | 6773 | CB | LYS | D | 19 | -20.126 | 35.080 | 97.412 | 1.00 | 54.75 | | C |
| ANISOU | 6773 | CB | LYS | D | 19 | 8309 | 5683 | 6810 | -561 | -1203 | -159 | C |
| ATOM | 6776 | CG | LYS | D | 19 | -21.051 | 35.181 | 96.183 | 1.00 | 55.78 | | C |
| ANISOU | 6776 | CG | LYS | D | 19 | 8532 | 5787 | 6876 | -310 | -1202 | -249 | C |
| ATOM | 6779 | CD | LYS | D | 19 | -20.713 | 34.035 | 95.171 | 1.00 | 54.99 | | C |
| ANISOU | 6779 | CD | LYS | D | 19 | 8148 | 5883 | 6864 | -398 | -962 | -120 | C |
| ATOM | 6782 | CE | LYS | D | 19 | -21.906 | 33.635 | 94.269 | 1.00 | 55.12 | | C |
| ANISOU | 6782 | CE | LYS | D | 19 | 8098 | 6025 | 6819 | -127 | -908 | -294 | C |
| ATOM | 6785 | NZ | LYS | D | 19 | -21.870 | 32.185 | 93.817 | 1.00 | 53.48 | | N |
| ANISOU | 6785 | NZ | LYS | D | 19 | 7565 | 6054 | 6699 | -187 | -643 | -280 | N |
| ATOM | 6789 | C | LYS | D | 19 | -21.984 | 35.553 | 99.044 | 1.00 | 54.85 | | C |
| ANISOU | 6789 | C | LYS | D | 19 | 8415 | 5747 | 6677 | -99 | -1362 | -629 | C |
| ATOM | 6790 | O | LYS | D | 19 | -22.831 | 36.438 | 98.962 | 1.00 | 57.01 | | O |
| ANISOU | 6790 | O | LYS | D | 19 | 8949 | 5889 | 6825 | 180 | -1525 | -811 | O |
| ATOM | 6792 | N | ALA | D | 20 | -22.259 | 34.309 | 99.425 | 1.00 | 53.07 | | N |
| ANISOU | 6792 | N | ALA | D | 20 | 7826 | 5817 | 6523 | -98 | -1155 | -669 | N |
| ATOM | 6793 | CA | ALA | D | 20 | -23.591 | 33.875 | 99.844 | 1.00 | 53.78 | | C |
| ANISOU | 6793 | CA | ALA | D | 20 | 7749 | 6145 | 6541 | 160 | -1090 | -938 | C |
| ATOM | 6795 | CB | ALA | D | 20 | -23.559 | 32.419 | 100.202 | 1.00 | 50.70 | | C |
| ANISOU | 6795 | CB | ALA | D | 20 | 7020 | 6010 | 6235 | 23 | -837 | -897 | C |
| ATOM | 6799 | C | ALA | D | 20 | -24.184 | 34.676 | 101.017 | 1.00 | 57.66 | | C |
| ANISOU | 6799 | C | ALA | D | 20 | 8387 | 6624 | 6900 | 344 | -1247 | -1158 | C |
| ATOM | 6800 | O | ALA | D | 20 | -25.393 | 34.824 | 101.109 | 1.00 | 61.06 | | O |
| ANISOU | 6800 | O | ALA | D | 20 | 8766 | 7220 | 7212 | 643 | -1269 | -1415 | O |
| ATOM | 6802 | N | MET | D | 21 | -23.341 | 35.185 | 101.906 | 1.00 | 59.89 | | N |
| ANISOU | 6802 | N | MET | D | 21 | 8831 | 6747 | 7178 | 171 | -1355 | -1074 | N |
| ATOM | 6803 | CA | MET | D | 21 | -23.816 | 35.940 | 103.072 | 1.00 | 62.76 | | C |
| ANISOU | 6803 | CA | MET | D | 21 | 9366 | 7084 | 7398 | 333 | -1500 | -1292 | C |
| ATOM | 6805 | CB | MET | D | 21 | -22.819 | 35.818 | 104.222 | 1.00 | 62.20 | | C |
| ANISOU | 6805 | CB | MET | D | 21 | 9279 | 7009 | 7345 | 45 | -1514 | -1172 | C |
| ATOM | 6808 | CG | MET | D | 21 | -22.683 | 34.414 | 104.795 | 1.00 | 59.62 | | C |
| ANISOU | 6808 | CG | MET | D | 21 | 8567 | 6998 | 7088 | -89 | -1281 | -1085 | C |
| ATOM | 6811 | SD | MET | D | 21 | -21.871 | 34.468 | 106.398 | 1.00 | 59.54 | | S |
| ANISOU | 6811 | SD | MET | D | 21 | 8574 | 7043 | 7006 | -290 | -1354 | -1032 | S |
| ATOM | 6812 | CE | MET | D | 21 | -23.340 | 34.449 | 107.429 | 1.00 | 60.15 | | C |
| ANISOU | 6812 | CE | MET | D | 21 | 8601 | 7357 | 6894 | 8 | -1310 | -1378 | C |
| ATOM | 6816 | C | MET | D | 21 | -24.043 | 37.421 | 102.760 | 1.00 | 67.67 | | C |
| ANISOU | 6816 | C | MET | D | 21 | 10455 | 7359 | 7896 | 542 | -1759 | -1399 | C |
| ATOM | 6817 | O | MET | D | 21 | -24.955 | 38.042 | 103.311 | 1.00 | 70.72 | | O |
| ANISOU | 6817 | O | MET | D | 21 | 10984 | 7759 | 8126 | 877 | -1866 | -1668 | O |
| ATOM | 6819 | N | LYS | D | 22 | -23.195 | 37.993 | 101.901 | 1.00 | 69.68 | | N |
| ANISOU | 6819 | N | LYS | D | 22 | 10976 | 7299 | 8199 | 347 | -1855 | -1188 | N |
| ATOM | 6820 | CA | LYS | D | 22 | -23.376 | 39.371 | 101.435 | 1.00 | 72.94 | | C |
| ANISOU | 6820 | CA | LYS | D | 22 | 11922 | 7311 | 8483 | 523 | -2094 | -1247 | C |
| ATOM | 6822 | CB | LYS | D | 22 | -22.102 | 39.903 | 100.769 | 1.00 | 73.99 | | C |
| ANISOU | 6822 | CB | LYS | D | 22 | 12334 | 7113 | 8665 | 112 | -2168 | -955 | C |
| ATOM | 6825 | CG | LYS | D | 22 | -22.085 | 41.426 | 100.596 | 1.00 | 78.41 | | C |
| ANISOU | 6825 | CG | LYS | D | 22 | 13572 | 7159 | 9063 | 180 | -2433 | -995 | C |
| ATOM | 6828 | CD | LYS | D | 22 | -20.662 | 41.991 | 100.554 | 1.00 | 80.14 | | C |
| ANISOU | 6828 | CD | LYS | D | 22 | 14059 | 7093 | 9297 | -388 | -2512 | -744 | C |

FIG. 18 (continued)

| | | | | | | | | | | | | |
|---|---|---|---|---|---|---|---|---|---|---|---|---|
| ATOM | 6831 | CE | LYS | D | 22 | -20.655 | 43.500 | 100.686 | 1.00 | 84.66 | | C |
| ANISOU | 6831 | CE | LYS | D | 22 | 15378 | 7108 | 9682 | -375 | -2780 | -821 | C |
| ATOM | 6834 | NZ | LYS | D | 22 | -20.995 | 43.937 | 102.072 | 1.00 | 86.88 | | N |
| ANISOU | 6834 | NZ | LYS | D | 22 | 15826 | 7327 | 9858 | -229 | -2904 | -1090 | N |
| ATOM | 6838 | C | LYS | D | 22 | -24.558 | 39.442 | 100.470 | 1.00 | 73.52 | | C |
| ANISOU | 6838 | C | LYS | D | 22 | 11994 | 7461 | 8481 | 964 | -2102 | -1389 | C |
| ATOM | 6839 | O | LYS | D | 22 | -25.188 | 40.493 | 100.337 | 1.00 | 78.15 | | O |
| ANISOU | 6839 | O | LYS | D | 22 | 12980 | 7808 | 8904 | 1322 | -2300 | -1544 | O |
| ATOM | 6841 | N | GLU | D | 23 | -24.855 | 38.325 | 99.814 | 1.00 | 70.77 | | N |
| ANISOU | 6841 | N | GLU | D | 23 | 11214 | 7447 | 8230 | 953 | -1898 | -1344 | N |
| ATOM | 6842 | CA | GLU | D | 23 | -26.030 | 38.204 | 98.932 | 1.00 | 72.29 | | C |
| ANISOU | 6842 | CA | GLU | D | 23 | 11294 | 7836 | 8338 | 1341 | -1890 | -1500 | C |
| ATOM | 6844 | CB | GLU | D | 23 | -26.023 | 36.848 | 98.213 | 1.00 | 70.14 | | C |
| ANISOU | 6844 | CB | GLU | D | 23 | 10569 | 7888 | 8195 | 1157 | -1642 | -1402 | C |
| ATOM | 6847 | CG | GLU | D | 23 | -26.673 | 36.814 | 96.833 | 1.00 | 71.98 | | C |
| ANISOU | 6847 | CG | GLU | D | 23 | 10779 | 8209 | 8363 | 1377 | -1655 | -1426 | C |
| ATOM | 6850 | CD | GLU | D | 23 | -26.251 | 35.580 | 96.003 | 1.00 | 70.58 | | C |
| ANISOU | 6850 | CD | GLU | D | 23 | 10283 | 8212 | 8323 | 1085 | -1419 | -1265 | C |
| ATOM | 6851 | OE1 | GLU | D | 23 | -27.135 | 34.861 | 95.489 | 1.00 | 72.46 | | O |
| ANISOU | 6851 | OE1 | GLU | D | 23 | 10229 | 8781 | 8520 | 1209 | -1316 | -1412 | O |
| ATOM | 6852 | OE2 | GLU | D | 23 | -25.030 | 35.320 | 95.855 | 1.00 | 71.61 | | O |
| ANISOU | 6852 | OE2 | GLU | D | 23 | 10450 | 8173 | 8584 | 732 | -1335 | -1002 | O |
| ATOM | 6853 | C | GLU | D | 23 | -27.343 | 38.343 | 99.699 | 1.00 | 72.16 | | C |
| ANISOU | 6853 | C | GLU | D | 23 | 11151 | 8099 | 8166 | 1774 | -1930 | -1851 | C |
| ATOM | 6854 | O | GLU | D | 23 | -28.294 | 38.935 | 99.186 | 1.00 | 74.37 | | O |
| ANISOU | 6854 | O | GLU | D | 23 | 11551 | 8418 | 8290 | 2221 | -2062 | -2026 | O |
| ATOM | 6856 | N | TYR | D | 24 | -27.379 | 37.810 | 100.924 | 1.00 | 70.25 | | N |
| ANISOU | 6856 | N | TYR | D | 24 | 10665 | 8082 | 7944 | 1657 | -1819 | -1948 | N |
| ATOM | 6857 | CA | TYR | D | 24 | -28.629 | 37.653 | 101.700 | 1.00 | 70.67 | | C |
| ANISOU | 6857 | CA | TYR | D | 24 | 10463 | 8542 | 7848 | 1992 | -1779 | -2278 | C |
| ATOM | 6859 | CB | TYR | D | 24 | -28.961 | 36.153 | 101.831 | 1.00 | 67.72 | | C |
| ANISOU | 6859 | CB | TYR | D | 24 | 9539 | 8637 | 7555 | 1759 | -1491 | -2286 | C |
| ATOM | 6862 | CG | TYR | D | 24 | -28.866 | 35.375 | 100.518 | 1.00 | 63.37 | | C |
| ANISOU | 6862 | CG | TYR | D | 24 | 8806 | 8154 | 7118 | 1603 | -1370 | -2134 | C |
| ATOM | 6869 | C | TYR | D | 24 | -28.599 | 38.351 | 103.081 | 1.00 | 72.88 | | C |
| ANISOU | 6869 | C | TYR | D | 24 | 10957 | 8722 | 8011 | 2090 | -1886 | -2434 | C |
| ATOM | 6870 | O | TYR | D | 24 | -29.258 | 37.926 | 104.048 | 1.00 | 73.90 | | O |
| ANISOU | 6870 | O | TYR | D | 24 | 10803 | 9225 | 8049 | 2176 | -1778 | -2639 | O |
| ATOM | 6872 | N | GLY | D | 25 | -27.831 | 39.436 | 103.161 | 1.00 | 74.30 | | N |
| ANISOU | 6872 | N | GLY | D | 25 | 11662 | 8397 | 8173 | 2050 | -2096 | -2342 | N |
| ATOM | 6873 | CA | GLY | D | 25 | -27.836 | 40.314 | 104.325 | 1.00 | 75.78 | | C |
| ANISOU | 6873 | CA | GLY | D | 25 | 12173 | 8409 | 8213 | 2189 | -2246 | -2522 | C |
| ATOM | 6876 | C | GLY | D | 25 | -27.374 | 39.710 | 105.638 | 1.00 | 74.02 | | C |
| ANISOU | 6876 | C | GLY | D | 25 | 11729 | 8378 | 8018 | 1875 | -2126 | -2516 | C |
| ATOM | 6877 | O | GLY | D | 25 | -27.685 | 40.248 | 106.712 | 1.00 | 77.23 | | O |
| ANISOU | 6877 | O | GLY | D | 25 | 12289 | 8796 | 8259 | 2057 | -2207 | -2741 | O |
| ATOM | 6879 | N | GLU | D | 26 | -26.623 | 38.613 | 105.576 | 1.00 | 68.91 | | N |
| ANISOU | 6879 | N | GLU | D | 26 | 10753 | 7875 | 7555 | 1435 | -1940 | -2262 | N |
| ATOM | 6880 | CA | GLU | D | 26 | -26.077 | 38.018 | 106.779 | 1.00 | 67.73 | | C |
| ANISOU | 6880 | CA | GLU | D | 26 | 10428 | 7887 | 7420 | 1142 | -1842 | -2209 | C |
| ATOM | 6882 | CB | GLU | D | 26 | -25.915 | 36.492 | 106.623 | 1.00 | 64.00 | | C |
| ANISOU | 6882 | CB | GLU | D | 26 | 9476 | 7745 | 7097 | 875 | -1568 | -2027 | C |
| ATOM | 6885 | CG | GLU | D | 26 | -27.187 | 35.691 | 106.198 | 1.00 | 62.57 | | C |
| ANISOU | 6885 | CG | GLU | D | 26 | 8923 | 7970 | 6879 | 1085 | -1378 | -2193 | C |
| ATOM | 6888 | CD | GLU | D | 26 | -28.166 | 35.348 | 107.345 | 1.00 | 63.45 | | C |
| ANISOU | 6888 | CD | GLU | D | 26 | 8799 | 8500 | 6809 | 1226 | -1262 | -2452 | C |
| ATOM | 6889 | OE1 | GLU | D | 26 | -27.922 | 35.719 | 108.516 | 1.00 | 64.85 | | O |
| ANISOU | 6889 | OE1 | GLU | D | 26 | 9108 | 8656 | 6877 | 1207 | -1326 | -2519 | O |
| ATOM | 6890 | OE2 | GLU | D | 26 | -29.191 | 34.687 | 107.065 | 1.00 | 62.59 | | O |
| ANISOU | 6890 | OE2 | GLU | D | 26 | 8360 | 8774 | 6646 | 1327 | -1099 | -2596 | O |
| ATOM | 6891 | C | GLU | D | 26 | -24.733 | 38.721 | 107.054 | 1.00 | 68.84 | | C |
| ANISOU | 6891 | C | GLU | D | 26 | 10931 | 7625 | 7600 | 806 | -2017 | -2021 | C |
| ATOM | 6892 | O | GLU | D | 26 | -23.819 | 38.681 | 106.224 | 1.00 | 68.03 | | O |
| ANISOU | 6892 | O | GLU | D | 26 | 10885 | 7322 | 7641 | 523 | -2030 | -1756 | O |
| ATOM | 6894 | N | ASP | D | 27 | -24.637 | 39.382 | 108.202 | 1.00 | 71.54 | | N |
| ANISOU | 6894 | N | ASP | D | 27 | 11511 | 7882 | 7790 | 825 | -2148 | -2177 | N |
| ATOM | 6895 | CA | ASP | D | 27 | -23.450 | 40.164 | 108.583 | 1.00 | 73.96 | | C |
| ANISOU | 6895 | CA | ASP | D | 27 | 12188 | 7831 | 8081 | 483 | -2341 | -2059 | C |
| ATOM | 6897 | CB | ASP | D | 27 | -23.872 | 41.296 | 109.546 | 1.00 | 77.74 | | C |
| ANISOU | 6897 | CB | ASP | D | 27 | 13105 | 8111 | 8320 | 720 | -2539 | -2370 | C |
| ATOM | 6900 | CG | ASP | D | 27 | -22.729 | 42.276 | 109.896 | 1.00 | 81.02 | | C |
| ANISOU | 6900 | CG | ASP | D | 27 | 14002 | 8100 | 8681 | 341 | -2771 | -2295 | C |
| ATOM | 6901 | OD1 | ASP | D | 27 | -21.546 | 41.871 | 109.974 | 1.00 | 80.92 | | O |
| ANISOU | 6901 | OD1 | ASP | D | 27 | 13826 | 8142 | 8779 | -155 | -2755 | -2031 | O |
| ATOM | 6902 | OD2 | ASP | D | 27 | -23.030 | 43.472 | 110.131 | 1.00 | 84.77 | | O |
| ANISOU | 6902 | OD2 | ASP | D | 27 | 15033 | 8198 | 8977 | 546 | -2976 | -2520 | O |
| ATOM | 6903 | C | ASP | D | 27 | -22.413 | 39.220 | 109.217 | 1.00 | 72.69 | | C |
| ANISOU | 6903 | C | ASP | D | 27 | 11689 | 7914 | 8018 | 50 | -2229 | -1822 | C |
| ATOM | 6904 | O | ASP | D | 27 | -22.495 | 38.906 | 110.405 | 1.00 | 74.12 | | O |

FIG. 18 (continued)

| | | | | | | | | | | | | |
|---|---|---|---|---|---|---|---|---|---|---|---|---|
| ANISOU | 6904 | O | ASP | D | 27 | 11742 | 8328 | 8092 | 38 | -2195 | -1918 | O |
| ATOM | 6906 | N | LEU | D | 28 | -21.428 | 38.779 | 108.431 | 1.00 | 70.88 | | N |
| ANISOU | 6906 | N | LEU | D | 28 | 11317 | 7648 | 7967 | -279 | -2177 | -1511 | N |
| ATOM | 6907 | CA | LEU | D | 28 | -20.463 | 37.766 | 108.904 | 1.00 | 68.53 | | C |
| ANISOU | 6907 | CA | LEU | D | 28 | 10654 | 7626 | 7759 | -603 | -2059 | -1269 | C |
| ATOM | 6909 | CB | LEU | D | 28 | -19.585 | 37.217 | 107.747 | 1.00 | 67.02 | | C |
| ANISOU | 6909 | CB | LEU | D | 28 | 10268 | 7434 | 7764 | -841 | -1962 | -955 | C |
| ATOM | 6912 | CG | LEU | D | 28 | -18.184 | 37.769 | 107.433 | 1.00 | 68.37 | | C |
| ANISOU | 6912 | CG | LEU | D | 28 | 10553 | 7454 | 7969 | -1263 | -2097 | -730 | C |
| ATOM | 6914 | CD1 | LEU | D | 28 | -17.180 | 37.344 | 108.455 | 1.00 | 68.90 | | C |
| ANISOU | 6914 | CD1 | LEU | D | 28 | 10394 | 7781 | 8003 | -1536 | -2121 | -602 | C |
| ATOM | 6918 | CD2 | LEU | D | 28 | -17.698 | 37.286 | 106.083 | 1.00 | 67.05 | | C |
| ANISOU | 6918 | CD2 | LEU | D | 28 | 10208 | 7303 | 7966 | -1368 | -1966 | -487 | C |
| ATOM | 6922 | C | LEU | D | 28 | -19.601 | 38.199 | 110.113 | 1.00 | 69.85 | | C |
| ANISOU | 6922 | C | LEU | D | 28 | 10939 | 7798 | 7802 | -876 | -2221 | -1267 | C |
| ATOM | 6923 | O | LEU | D | 28 | -18.856 | 37.381 | 110.659 | 1.00 | 67.89 | | O |
| ANISOU | 6923 | O | LEU | D | 28 | 10387 | 7824 | 7584 | -1081 | -2147 | -1085 | O |
| ATOM | 6925 | N | LYS | D | 29 | -19.693 | 39.465 | 110.530 | 1.00 | 72.47 | | N |
| ANISOU | 6925 | N | LYS | D | 29 | 11729 | 7831 | 7975 | -867 | -2448 | -1470 | N |
| ATOM | 6926 | CA | LYS | D | 29 | -19.145 | 39.881 | 111.832 | 1.00 | 74.70 | | C |
| ANISOU | 6926 | CA | LYS | D | 29 | 12144 | 8151 | 8087 | -1074 | -2604 | -1555 | C |
| ATOM | 6928 | CB | LYS | D | 29 | -18.802 | 41.377 | 111.828 | 1.00 | 79.26 | | C |
| ANISOU | 6928 | CB | LYS | D | 29 | 13316 | 8263 | 8537 | -1242 | -2878 | -1683 | C |
| ATOM | 6931 | CG | LYS | D | 29 | -17.496 | 41.708 | 111.095 | 1.00 | 80.41 | | C |
| ANISOU | 6931 | CG | LYS | D | 29 | 13525 | 8248 | 8777 | -1755 | -2972 | -1408 | C |
| ATOM | 6934 | CD | LYS | D | 29 | -16.283 | 41.507 | 112.005 | 1.00 | 81.76 | | C |
| ANISOU | 6934 | CD | LYS | D | 29 | 13491 | 8692 | 8883 | -2212 | -3058 | -1283 | C |
| ATOM | 6937 | CE | LYS | D | 29 | -14.989 | 41.346 | 111.217 | 1.00 | 81.84 | | C |
| ANISOU | 6937 | CE | LYS | D | 29 | 13284 | 8795 | 9018 | -2685 | -3055 | -957 | C |
| ATOM | 6940 | NZ | LYS | D | 29 | -13.799 | 41.158 | 112.128 | 1.00 | 83.80 | | N |
| ANISOU | 6940 | NZ | LYS | D | 29 | 13275 | 9394 | 9173 | -3106 | -3160 | -846 | N |
| ATOM | 6944 | C | LYS | D | 29 | -20.112 | 39.528 | 112.981 | 1.00 | 73.80 | | C |
| ANISOU | 6944 | C | LYS | D | 29 | 11929 | 8301 | 7810 | -757 | -2524 | -1802 | C |
| ATOM | 6945 | O | LYS | D | 29 | -19.675 | 39.162 | 114.076 | 1.00 | 72.96 | | O |
| ANISOU | 6945 | O | LYS | D | 29 | 11681 | 8443 | 7598 | -909 | -2534 | -1780 | O |
| ATOM | 6947 | N | ILE | D | 30 | -21.418 | 39.621 | 112.709 | 1.00 | 73.09 | | N |
| ANISOU | 6947 | N | ILE | D | 30 | 11887 | 8203 | 7680 | -318 | -2442 | -2031 | N |
| ATOM | 6948 | CA | ILE | D | 30 | -22.462 | 39.214 | 113.659 | 1.00 | 73.23 | | C |
| ANISOU | 6948 | CA | ILE | D | 30 | 11742 | 8546 | 7534 | -9 | -2319 | -2270 | C |
| ATOM | 6950 | CB | ILE | D | 30 | -23.817 | 39.915 | 113.354 | 1.00 | 74.83 | | C |
| ANISOU | 6950 | CB | ILE | D | 30 | 12152 | 8657 | 7622 | 498 | -2340 | -2604 | C |
| ATOM | 6952 | CG1 | ILE | D | 30 | -23.682 | 41.429 | 113.561 | 1.00 | 79.05 | | C |
| ANISOU | 6952 | CG1 | ILE | D | 30 | 13307 | 8730 | 7999 | 583 | -2624 | -2813 | C |
| ATOM | 6955 | CD1 | ILE | D | 30 | -24.974 | 42.200 | 113.393 | 1.00 | 81.58 | | C |
| ANISOU | 6955 | CD1 | ILE | D | 30 | 13881 | 8956 | 8159 | 1169 | -2674 | -3162 | C |
| ATOM | 6959 | CG2 | ILE | D | 30 | -24.934 | 39.355 | 114.239 | 1.00 | 74.66 | | C |
| ANISOU | 6959 | CG2 | ILE | D | 30 | 11852 | 9089 | 7427 | 790 | -2163 | -2839 | C |
| ATOM | 6963 | C | ILE | D | 30 | -22.687 | 37.706 | 113.638 | 1.00 | 68.97 | | C |
| ANISOU | 6963 | C | ILE | D | 30 | 10682 | 8424 | 7100 | -34 | -2035 | -2097 | C |
| ATOM | 6964 | O | ILE | D | 30 | -22.839 | 37.078 | 114.680 | 1.00 | 69.34 | | O |
| ANISOU | 6964 | O | ILE | D | 30 | 10541 | 8782 | 7022 | -52 | -1932 | -2124 | O |
| ATOM | 6966 | N | GLU | D | 31 | -22.699 | 37.133 | 112.442 | 1.00 | 65.47 | | N |
| ANISOU | 6966 | N | GLU | D | 31 | 10049 | 7960 | 6865 | -46 | -1910 | -1919 | N |
| ATOM | 6967 | CA | GLU | D | 31 | -23.092 | 35.744 | 112.257 | 1.00 | 61.47 | | C |
| ANISOU | 6967 | CA | GLU | D | 31 | 9128 | 7779 | 6449 | -39 | -1633 | -1798 | C |
| ATOM | 6969 | CB | GLU | D | 31 | -24.120 | 35.688 | 111.148 | 1.00 | 61.96 | | C |
| ANISOU | 6969 | CB | GLU | D | 31 | 9116 | 7845 | 6580 | 222 | -1536 | -1915 | C |
| ATOM | 6972 | CG | GLU | D | 31 | -25.437 | 36.296 | 111.552 | 1.00 | 64.52 | | C |
| ANISOU | 6972 | CG | GLU | D | 31 | 9515 | 8300 | 6700 | 607 | -1560 | -2287 | C |
| ATOM | 6975 | CD | GLU | D | 31 | -26.290 | 35.290 | 112.272 | 1.00 | 64.57 | | C |
| ANISOU | 6975 | CD | GLU | D | 31 | 9172 | 8768 | 6592 | 648 | -1316 | -2386 | C |
| ATOM | 6976 | OE1 | GLU | D | 31 | -25.944 | 34.966 | 113.412 | 1.00 | 65.51 | | O |
| ANISOU | 6976 | OE1 | GLU | D | 31 | 9262 | 9029 | 6602 | 494 | -1281 | -2347 | O |
| ATOM | 6977 | OE2 | GLU | D | 31 | -27.288 | 34.811 | 111.693 | 1.00 | 63.95 | | O |
| ANISOU | 6977 | OE2 | GLU | D | 31 | 8853 | 8928 | 6517 | 803 | -1159 | -2496 | O |
| ATOM | 6978 | C | GLU | D | 31 | -21.880 | 34.860 | 111.959 | 1.00 | 56.70 | | C |
| ANISOU | 6978 | C | GLU | D | 31 | 8325 | 7198 | 6018 | -361 | -1560 | -1429 | C |
| ATOM | 6979 | O | GLU | D | 31 | -21.760 | 34.262 | 110.894 | 1.00 | 53.62 | | O |
| ANISOU | 6979 | O | GLU | D | 31 | 7784 | 6781 | 5808 | -394 | -1437 | -1265 | O |
| ATOM | 6981 | N | THR | D | 32 | -20.990 | 34.800 | 112.944 | 1.00 | 54.62 | | N |
| ANISOU | 6981 | N | THR | D | 32 | 8064 | 7016 | 5675 | -568 | -1644 | -1317 | N |
| ATOM | 6982 | CA | THR | D | 32 | -19.691 | 34.145 | 112.821 | 1.00 | 51.36 | | C |
| ANISOU | 6982 | CA | THR | D | 32 | 7473 | 6664 | 5378 | -834 | -1631 | -981 | C |
| ATOM | 6984 | CB | THR | D | 32 | -18.775 | 34.573 | 114.003 | 1.00 | 54.32 | | C |
| ANISOU | 6984 | CB | THR | D | 32 | 7926 | 7121 | 5593 | -1040 | -1828 | -949 | C |
| ATOM | 6986 | OG1 | THR | D | 32 | -19.417 | 34.299 | 115.260 | 1.00 | 54.04 | | O |
| ANISOU | 6986 | OG1 | THR | D | 32 | 7885 | 7303 | 5345 | -919 | -1777 | -1100 | O |
| ATOM | 6988 | CG2 | THR | D | 32 | -18.493 | 36.049 | 113.926 | 1.00 | 57.25 | | C |
| ANISOU | 6988 | CG2 | THR | D | 32 | 8651 | 7201 | 5901 | -1158 | -2096 | -1106 | C |

FIG. 18 (continued)

| | | | | | | | | | | | | |
|---|---|---|---|---|---|---|---|---|---|---|---|---|
| ATOM | 6992 | C | THR | D | 32 | -19.801 | 32.613 | 112.752 | 1.00 | 46.86 | | C |
| ANISOU | 6992 | C | THR | D | 32 | 6599 | 6321 | 4884 | -799 | -1360 | -791 | C |
| ATOM | 6993 | O | THR | D | 32 | -19.109 | 31.962 | 111.968 | 1.00 | 44.49 | | O |
| ANISOU | 6993 | O | THR | D | 32 | 6146 | 6007 | 4749 | -882 | -1275 | -546 | O |
| ATOM | 6995 | N | ASN | D | 33 | -20.685 | 32.044 | 113.566 | 1.00 | 43.99 | | N |
| ANISOU | 6995 | N | ASN | D | 33 | 6178 | 6159 | 4379 | -680 | -1216 | -912 | N |
| ATOM | 6996 | CA | ASN | D | 33 | -20.896 | 30.605 | 113.562 | 1.00 | 41.34 | | C |
| ANISOU | 6996 | CA | ASN | D | 33 | 5643 | 5985 | 4078 | -678 | -951 | -748 | C |
| ATOM | 6998 | CB | ASN | D | 33 | -21.743 | 30.158 | 114.751 | 1.00 | 41.65 | | C |
| ANISOU | 6998 | CB | ASN | D | 33 | 5669 | 6269 | 3888 | -627 | -827 | -878 | C |
| ATOM | 7001 | CG | ASN | D | 33 | -20.960 | 30.118 | 116.057 | 1.00 | 43.37 | | C |
| ANISOU | 7001 | CG | ASN | D | 33 | 5931 | 6622 | 3926 | -720 | -939 | -761 | C |
| ATOM | 7002 | OD1 | ASN | D | 33 | -19.741 | 29.889 | 116.081 | 1.00 | 42.81 | | O |
| ANISOU | 7002 | OD1 | ASN | D | 33 | 5816 | 6534 | 3917 | -825 | -1034 | -502 | O |
| ATOM | 7003 | ND2 | ASN | D | 33 | -21.669 | 30.324 | 117.145 | 1.00 | 40.73 | | N |
| ANISOU | 7003 | ND2 | ASN | D | 33 | 5658 | 6471 | 3346 | -668 | -926 | -960 | N |
| ATOM | 7006 | C | ASN | D | 33 | -21.576 | 30.113 | 112.286 | 1.00 | 38.14 | | C |
| ANISOU | 7006 | C | ASN | D | 33 | 5148 | 5505 | 3837 | -603 | -770 | -770 | C |
| ATOM | 7007 | O | ASN | D | 33 | -21.226 | 29.056 | 111.779 | 1.00 | 35.03 | | O |
| ANISOU | 7007 | O | ASN | D | 33 | 4643 | 5106 | 3560 | -658 | -604 | -555 | O |
| ATOM | 7009 | N | LYS | D | 34 | -22.554 | 30.872 | 111.796 | 1.00 | 39.26 | | N |
| ANISOU | 7009 | N | LYS | D | 34 | 5354 | 5599 | 3965 | -455 | -809 | -1039 | N |
| ATOM | 7010 | CA | LYS | D | 34 | -23.234 | 30.530 | 110.536 | 1.00 | 38.31 | | C |
| ANISOU | 7010 | CA | LYS | D | 34 | 5142 | 5441 | 3974 | -378 | -674 | -1088 | C |
| ATOM | 7012 | CB | LYS | D | 34 | -24.435 | 31.466 | 110.277 | 1.00 | 39.42 | | C |
| ANISOU | 7012 | CB | LYS | D | 34 | 5342 | 5614 | 4020 | -140 | -752 | -1426 | C |
| ATOM | 7015 | CG | LYS | D | 34 | -25.443 | 30.892 | 109.264 | 1.00 | 40.18 | | C |
| ANISOU | 7015 | CG | LYS | D | 34 | 5264 | 5832 | 4170 | -58 | -576 | -1528 | C |
| ATOM | 7018 | CD | LYS | D | 34 | -26.655 | 31.815 | 108.944 | 1.00 | 41.49 | | C |
| ANISOU | 7018 | CD | LYS | D | 34 | 5446 | 6099 | 4219 | 248 | -669 | -1866 | C |
| ATOM | 7021 | CE | LYS | D | 34 | -27.666 | 31.930 | 110.107 | 1.00 | 44.47 | | C |
| ANISOU | 7021 | CE | LYS | D | 34 | 5731 | 6817 | 4350 | 383 | -616 | -2142 | C |
| ATOM | 7024 | NZ | LYS | D | 34 | -28.551 | 33.157 | 109.967 | 1.00 | 46.19 | | N |
| ANISOU | 7024 | NZ | LYS | D | 34 | 6044 | 7077 | 4428 | 776 | -789 | -2467 | N |
| ATOM | 7028 | C | LYS | D | 34 | -22.258 | 30.508 | 109.348 | 1.00 | 36.05 | | C |
| ANISOU | 7028 | C | LYS | D | 34 | 4863 | 4935 | 3901 | -465 | -715 | -859 | C |
| ATOM | 7029 | O | LYS | D | 34 | -22.354 | 29.625 | 108.494 | 1.00 | 34.29 | | O |
| ANISOU | 7029 | O | LYS | D | 34 | 4523 | 4712 | 3794 | -488 | -536 | -761 | O |
| ATOM | 7031 | N | PHE | D | 35 | -21.333 | 31.470 | 109.325 | 1.00 | 36.77 | | N |
| ANISOU | 7031 | N | PHE | D | 35 | 5099 | 4856 | 4018 | -539 | -940 | -787 | N |
| ATOM | 7032 | CA | PHE | D | 35 | -20.214 | 31.542 | 108.360 | 1.00 | 36.84 | | C |
| ANISOU | 7032 | CA | PHE | D | 35 | 5097 | 4713 | 4188 | -678 | -989 | -550 | C |
| ATOM | 7034 | CB | PHE | D | 35 | -19.302 | 32.732 | 108.723 | 1.00 | 38.26 | | C |
| ANISOU | 7034 | CB | PHE | D | 35 | 5459 | 4760 | 4317 | -835 | -1255 | -522 | C |
| ATOM | 7037 | CG | PHE | D | 35 | -18.163 | 32.998 | 107.750 | 1.00 | 39.64 | | C |
| ANISOU | 7037 | CG | PHE | D | 35 | 5620 | 4822 | 4619 | -1031 | -1317 | -298 | C |
| ATOM | 7038 | CD1 | PHE | D | 35 | -18.319 | 32.840 | 106.354 | 1.00 | 37.90 | | C |
| ANISOU | 7038 | CD1 | PHE | D | 35 | 5377 | 4496 | 4529 | -984 | -1217 | -242 | C |
| ATOM | 7040 | CE1 | PHE | D | 35 | -17.268 | 33.110 | 105.490 | 1.00 | 37.90 | | C |
| ANISOU | 7040 | CE1 | PHE | D | 35 | 5357 | 4431 | 4612 | -1183 | -1258 | -38 | C |
| ATOM | 7042 | CZ | PHE | D | 35 | -16.061 | 33.584 | 105.976 | 1.00 | 40.22 | | C |
| ANISOU | 7042 | CZ | PHE | D | 35 | 5635 | 4784 | 4864 | -1457 | -1408 | 102 | C |
| ATOM | 7044 | CE2 | PHE | D | 35 | -15.886 | 33.772 | 107.355 | 1.00 | 42.35 | | C |
| ANISOU | 7044 | CE2 | PHE | D | 35 | 5924 | 5160 | 5006 | -1516 | -1531 | 38 | C |
| ATOM | 7046 | CD2 | PHE | D | 35 | -16.941 | 33.490 | 108.230 | 1.00 | 41.91 | | C |
| ANISOU | 7046 | CD2 | PHE | D | 35 | 5916 | 5143 | 4865 | -1291 | -1486 | -161 | C |
| ATOM | 7048 | C | PHE | D | 35 | -19.416 | 30.230 | 108.345 | 1.00 | 34.29 | | C |
| ANISOU | 7048 | C | PHE | D | 35 | 4564 | 4515 | 3951 | -764 | -813 | -273 | C |
| ATOM | 7049 | O | PHE | D | 35 | -19.164 | 29.683 | 107.293 | 1.00 | 32.82 | | O |
| ANISOU | 7049 | O | PHE | D | 35 | 4292 | 4281 | 3899 | -765 | -692 | -147 | O |
| ATOM | 7051 | N | ALA | D | 36 | -19.028 | 29.744 | 109.521 | 1.00 | 34.18 | | N |
| ANISOU | 7051 | N | ALA | D | 36 | 4495 | 4657 | 3834 | -805 | -805 | -185 | N |
| ATOM | 7052 | CA | ALA | D | 36 | -18.343 | 28.461 | 109.635 | 1.00 | 34.14 | | C |
| ANISOU | 7052 | CA | ALA | D | 36 | 4343 | 4758 | 3869 | -810 | -645 | 75 | C |
| ATOM | 7054 | CB | ALA | D | 36 | -17.856 | 28.245 | 111.117 | 1.00 | 34.21 | | C |
| ANISOU | 7054 | CB | ALA | D | 36 | 4343 | 4949 | 3708 | -839 | -719 | 163 | C |
| ATOM | 7058 | C | ALA | D | 36 | -19.215 | 27.277 | 109.135 | 1.00 | 31.75 | | C |
| ANISOU | 7058 | C | ALA | D | 36 | 4013 | 4436 | 3613 | -725 | -365 | 54 | C |
| ATOM | 7059 | O | ALA | D | 36 | -18.706 | 26.342 | 108.519 | 1.00 | 32.43 | | O |
| ANISOU | 7059 | O | ALA | D | 36 | 4038 | 4484 | 3798 | -699 | -218 | 243 | O |
| ATOM | 7061 | N | ALA | D | 37 | -20.518 | 27.335 | 109.406 | 1.00 | 31.05 | | N |
| ANISOU | 7061 | N | ALA | D | 37 | 3973 | 4393 | 3433 | -689 | -292 | -190 | N |
| ATOM | 7062 | CA | ALA | D | 37 | -21.475 | 26.306 | 108.971 | 1.00 | 31.71 | | C |
| ANISOU | 7062 | CA | ALA | D | 37 | 4028 | 4496 | 3524 | -686 | -35 | -256 | C |
| ATOM | 7064 | CB | ALA | D | 37 | -22.845 | 26.480 | 109.665 | 1.00 | 31.94 | | C |
| ANISOU | 7064 | CB | ALA | D | 37 | 4052 | 4704 | 3379 | -679 | 20 | -535 | C |
| ATOM | 7068 | C | ALA | D | 37 | -21.676 | 26.266 | 107.469 | 1.00 | 29.13 | | C |
| ANISOU | 7068 | C | ALA | D | 37 | 3666 | 4050 | 3353 | -661 | 26 | -292 | C |
| ATOM | 7069 | O | ALA | D | 37 | -21.831 | 25.198 | 106.897 | 1.00 | 29.01 | | O |

FIG. 18 (continued)

| | | | | | | | | | | | | |
|---|---|---|---|---|---|---|---|---|---|---|---|---|
| ANISOU | 7069 | O | ALA | D | 37 | 3640 | 3992 | 3391 | -694 | 233 | -227 | O |
| ATOM | 7071 | N | ILE | D | 38 | -21.705 | 27.435 | 106.844 | 1.00 | 30.57 | | N |
| ANISOU | 7071 | N | ILE | D | 38 | 3872 | 4163 | 3582 | -605 | -156 | -402 | N |
| ATOM | 7072 | CA | ILE | D | 38 | -21.807 | 27.524 | 105.376 | 1.00 | 30.46 | | C |
| ANISOU | 7072 | CA | ILE | D | 38 | 3842 | 4039 | 3691 | -572 | -129 | -418 | C |
| ATOM | 7074 | CB | ILE | D | 38 | -22.001 | 28.989 | 104.897 | 1.00 | 30.19 | | C |
| ANISOU | 7074 | CB | ILE | D | 38 | 3912 | 3910 | 3648 | -488 | -361 | -559 | C |
| ATOM | 7076 | CG1 | ILE | D | 38 | -23.295 | 29.576 | 105.468 | 1.00 | 31.08 | | C |
| ANISOU | 7076 | CG1 | ILE | D | 38 | 4052 | 4146 | 3610 | -347 | -421 | -865 | C |
| ATOM | 7079 | CD1 | ILE | D | 38 | -23.238 | 31.076 | 105.595 | 1.00 | 30.88 | | C |
| ANISOU | 7079 | CD1 | ILE | D | 38 | 4229 | 3980 | 3525 | -239 | -689 | -976 | C |
| ATOM | 7083 | CG2 | ILE | D | 38 | -21.997 | 29.089 | 103.377 | 1.00 | 27.14 | | C |
| ANISOU | 7083 | CG2 | ILE | D | 38 | 3533 | 3414 | 3364 | -458 | -342 | -535 | C |
| ATOM | 7087 | C | ILE | D | 38 | -20.546 | 26.950 | 104.741 | 1.00 | 29.47 | | C |
| ANISOU | 7087 | C | ILE | D | 38 | 3681 | 3819 | 3698 | -624 | -68 | -136 | C |
| ATOM | 7088 | O | ILE | D | 38 | -20.626 | 26.188 | 103.778 | 1.00 | 28.35 | | O |
| ANISOU | 7088 | O | ILE | D | 38 | 3510 | 3630 | 3633 | -616 | 96 | -98 | O |
| ATOM | 7090 | N | CYS | D | 39 | -19.390 | 27.312 | 105.290 | 1.00 | 29.15 | | N |
| ANISOU | 7090 | N | CYS | D | 39 | 3629 | 3787 | 3661 | -674 | -202 | 44 | N |
| ATOM | 7091 | CA | CYS | D | 39 | -18.117 | 26.785 | 104.797 | 1.00 | 29.77 | | C |
| ANISOU | 7091 | CA | CYS | D | 39 | 3612 | 3867 | 3832 | -691 | -150 | 309 | C |
| ATOM | 7093 | CB | CYS | D | 39 | -16.940 | 27.440 | 105.517 | 1.00 | 30.68 | | C |
| ANISOU | 7093 | CB | CYS | D | 39 | 3670 | 4079 | 3909 | -781 | -348 | 458 | C |
| ATOM | 7096 | SG | CYS | D | 39 | -16.621 | 29.120 | 104.969 | 1.00 | 32.35 | | S |
| ANISOU | 7096 | SG | CYS | D | 39 | 3973 | 4189 | 4130 | -942 | -603 | 392 | S |
| ATOM | 7098 | C | CYS | D | 39 | -18.071 | 25.264 | 104.896 | 1.00 | 28.46 | | C |
| ANISOU | 7098 | C | CYS | D | 39 | 3425 | 3713 | 3675 | -613 | 93 | 429 | C |
| ATOM | 7099 | O | CYS | D | 39 | -17.740 | 24.575 | 103.934 | 1.00 | 27.47 | | O |
| ANISOU | 7099 | O | CYS | D | 39 | 3274 | 3527 | 3635 | -558 | 239 | 522 | O |
| ATOM | 7101 | N | THR | D | 40 | -18.513 | 24.745 | 106.032 | 1.00 | 29.92 | | N |
| ANISOU | 7101 | N | THR | D | 40 | 3667 | 3951 | 3748 | -608 | 147 | 405 | N |
| ATOM | 7102 | CA | THR | D | 40 | -18.548 | 23.307 | 106.271 | 1.00 | 30.84 | | C |
| ANISOU | 7102 | CA | THR | D | 40 | 3860 | 4022 | 3834 | -553 | 374 | 523 | C |
| ATOM | 7104 | CB | THR | D | 40 | -18.981 | 22.976 | 107.757 | 1.00 | 32.62 | | C |
| ANISOU | 7104 | CB | THR | D | 40 | 4175 | 4332 | 3886 | -588 | 390 | 516 | C |
| ATOM | 7106 | OG1 | THR | D | 40 | -18.155 | 23.679 | 108.690 | 1.00 | 31.71 | | O |
| ANISOU | 7106 | OG1 | THR | D | 40 | 3989 | 4357 | 3701 | -571 | 171 | 613 | O |
| ATOM | 7108 | CG2 | THR | D | 40 | -18.900 | 21.492 | 108.034 | 1.00 | 32.39 | | C |
| ANISOU | 7108 | CG2 | THR | D | 40 | 4305 | 4201 | 3801 | -538 | 616 | 683 | C |
| ATOM | 7112 | C | THR | D | 40 | -19.502 | 22.615 | 105.292 | 1.00 | 30.64 | | C |
| ANISOU | 7112 | C | THR | D | 40 | 3911 | 3876 | 3856 | -589 | 586 | 384 | C |
| ATOM | 7113 | O | THR | D | 40 | -19.167 | 21.601 | 104.705 | 1.00 | 29.87 | | O |
| ANISOU | 7113 | O | THR | D | 40 | 3886 | 3657 | 3807 | -530 | 759 | 498 | O |
| ATOM | 7115 | N | HIS | D | 41 | -20.708 | 23.157 | 105.129 | 1.00 | 30.89 | | N |
| ANISOU | 7115 | N | HIS | D | 41 | 3928 | 3959 | 3850 | -675 | 567 | 119 | N |
| ATOM | 7116 | CA | HIS | D | 41 | -21.684 | 22.534 | 104.228 | 1.00 | 29.28 | | C |
| ANISOU | 7116 | CA | HIS | D | 41 | 3756 | 3710 | 3659 | -747 | 749 | -42 | C |
| ATOM | 7118 | CB | HIS | D | 41 | -23.012 | 23.271 | 104.250 | 1.00 | 29.30 | | C |
| ANISOU | 7118 | CB | HIS | D | 41 | 3676 | 3878 | 3579 | -800 | 687 | -345 | C |
| ATOM | 7121 | CG | HIS | D | 41 | -24.009 | 22.699 | 103.293 | 1.00 | 28.62 | | C |
| ANISOU | 7121 | CG | HIS | D | 41 | 3568 | 3823 | 3483 | -894 | 846 | -528 | C |
| ATOM | 7122 | ND1 | HIS | D | 41 | -24.292 | 23.285 | 102.080 | 1.00 | 27.87 | | N |
| ANISOU | 7122 | ND1 | HIS | D | 41 | 3400 | 3742 | 3447 | -827 | 767 | -650 | N |
| ATOM | 7124 | CE1 | HIS | D | 41 | -25.187 | 22.551 | 101.441 | 1.00 | 30.08 | | C |
| ANISOU | 7124 | CE1 | HIS | D | 41 | 3659 | 4089 | 3681 | -954 | 931 | -810 | C |
| ATOM | 7126 | NE2 | HIS | D | 41 | -25.467 | 21.493 | 102.181 | 1.00 | 31.70 | | N |
| ANISOU | 7126 | NE2 | HIS | D | 41 | 3950 | 4290 | 3806 | -1133 | 1126 | -788 | N |
| ATOM | 7128 | CD2 | HIS | D | 41 | -24.738 | 21.561 | 103.345 | 1.00 | 28.80 | | C |
| ANISOU | 7128 | CD2 | HIS | D | 41 | 3652 | 3864 | 3427 | -1079 | 1078 | -601 | C |
| ATOM | 7130 | C | HIS | D | 41 | -21.138 | 22.496 | 102.783 | 1.00 | 29.10 | | C |
| ANISOU | 7130 | C | HIS | D | 41 | 3712 | 3573 | 3771 | -681 | 772 | 17 | C |
| ATOM | 7131 | O | HIS | D | 41 | -21.182 | 21.456 | 102.113 | 1.00 | 28.13 | | O |
| ANISOU | 7131 | O | HIS | D | 41 | 3678 | 3335 | 3674 | -700 | 970 | 43 | O |
| ATOM | 7133 | N | LEU | D | 42 | -20.619 | 23.630 | 102.335 | 1.00 | 28.99 | | N |
| ANISOU | 7133 | N | LEU | D | 42 | 3612 | 3582 | 3819 | -623 | 575 | 38 | N |
| ATOM | 7134 | CA | LEU | D | 42 | -19.946 | 23.731 | 101.036 | 1.00 | 30.04 | | C |
| ANISOU | 7134 | CA | LEU | D | 42 | 3716 | 3645 | 4055 | -574 | 583 | 127 | C |
| ATOM | 7136 | CB | LEU | D | 42 | -19.371 | 25.142 | 100.844 | 1.00 | 28.25 | | C |
| ANISOU | 7136 | CB | LEU | D | 42 | 3436 | 3443 | 3854 | -577 | 341 | 167 | C |
| ATOM | 7139 | CG | LEU | D | 42 | -20.387 | 26.258 | 100.568 | 1.00 | 28.21 | | C |
| ANISOU | 7139 | CG | LEU | D | 42 | 3479 | 3440 | 3800 | -574 | 186 | -64 | C |
| ATOM | 7141 | CD1 | LEU | D | 42 | -19.742 | 27.613 | 100.616 | 1.00 | 26.79 | | C |
| ANISOU | 7141 | CD1 | LEU | D | 42 | 3350 | 3212 | 3620 | -605 | -56 | -2 | C |
| ATOM | 7145 | CD2 | LEU | D | 42 | -21.089 | 26.051 | 99.233 | 1.00 | 28.62 | | C |
| ANISOU | 7145 | CD2 | LEU | D | 42 | 3539 | 3473 | 3863 | -543 | 274 | -190 | C |
| ATOM | 7149 | C | LEU | D | 42 | -18.849 | 22.677 | 100.886 | 1.00 | 30.91 | | C |
| ANISOU | 7149 | C | LEU | D | 42 | 3840 | 3692 | 4214 | -490 | 735 | 364 | C |
| ATOM | 7150 | O | LEU | D | 42 | -18.826 | 21.943 | 99.889 | 1.00 | 32.03 | | O |
| ANISOU | 7150 | O | LEU | D | 42 | 4032 | 3746 | 4393 | -451 | 899 | 364 | O |

FIG. 18 (continued)

| | | | | | | | | | | | | |
|---|---|---|---|---|---|---|---|---|---|---|---|---|
| ATOM | 7152 | N | GLU | D | 43 | -17.953 | 22.595 | 101.862 | 1.00 | 32.69 | | N |
| ANISOU | 7152 | N | GLU | D | 43 | 4026 | 3977 | 4417 | -433 | 674 | 553 | N |
| ATOM | 7153 | CA | GLU | D | 43 | -16.834 | 21.641 | 101.789 | 1.00 | 36.01 | | C |
| ANISOU | 7153 | CA | GLU | D | 43 | 4440 | 4385 | 4859 | -270 | 793 | 788 | C |
| ATOM | 7155 | CB | GLU | D | 43 | -15.791 | 21.852 | 102.906 | 1.00 | 38.63 | | C |
| ANISOU | 7155 | CB | GLU | D | 43 | 4658 | 4879 | 5141 | -198 | 651 | 990 | C |
| ATOM | 7158 | CG | GLU | D | 43 | -14.629 | 20.828 | 102.796 | 1.00 | 42.13 | | C |
| ANISOU | 7158 | CG | GLU | D | 43 | 5067 | 5359 | 5581 | 54 | 769 | 1231 | C |
| ATOM | 7161 | CD | GLU | D | 43 | -13.287 | 21.242 | 103.398 | 1.00 | 45.42 | | C |
| ANISOU | 7161 | CD | GLU | D | 43 | 5237 | 6061 | 5958 | 142 | 600 | 1441 | C |
| ATOM | 7162 | OE1 | GLU | D | 43 | -12.336 | 20.431 | 103.337 | 1.00 | 47.67 | | O |
| ANISOU | 7162 | OE1 | GLU | D | 43 | 5457 | 6438 | 6218 | 407 | 683 | 1631 | O |
| ATOM | 7163 | OE2 | GLU | D | 43 | -13.171 | 22.337 | 103.960 | 1.00 | 49.51 | | O |
| ANISOU | 7163 | OE2 | GLU | D | 43 | 5633 | 6728 | 6451 | -38 | 382 | 1410 | O |
| ATOM | 7164 | C | GLU | D | 43 | -17.301 | 20.180 | 101.746 | 1.00 | 34.98 | | C |
| ANISOU | 7164 | C | GLU | D | 43 | 4532 | 4066 | 4693 | -208 | 1047 | 779 | C |
| ATOM | 7165 | O | GLU | D | 43 | -16.746 | 19.378 | 101.002 | 1.00 | 33.46 | | O |
| ANISOU | 7165 | O | GLU | D | 43 | 4399 | 3780 | 4533 | -59 | 1197 | 870 | O |
| ATOM | 7167 | N | VAL | D | 44 | -18.325 | 19.838 | 102.521 | 1.00 | 35.28 | | N |
| ANISOU | 7167 | N | VAL | D | 44 | 4713 | 4046 | 4646 | -337 | 1105 | 660 | N |
| ATOM | 7168 | CA | VAL | D | 44 | -18.887 | 18.490 | 102.460 | 1.00 | 35.40 | | C |
| ANISOU | 7168 | CA | VAL | D | 44 | 4996 | 3850 | 4603 | -372 | 1353 | 632 | C |
| ATOM | 7170 | CB | VAL | D | 44 | -19.953 | 18.217 | 103.538 | 1.00 | 37.66 | | C |
| ANISOU | 7170 | CB | VAL | D | 44 | 5409 | 4142 | 4757 | -575 | 1407 | 527 | C |
| ATOM | 7172 | CG1 | VAL | D | 44 | -20.490 | 16.772 | 103.396 | 1.00 | 38.76 | | C |
| ANISOU | 7172 | CG1 | VAL | D | 44 | 5883 | 4024 | 4819 | -684 | 1681 | 511 | C |
| ATOM | 7176 | CG2 | VAL | D | 44 | -19.370 | 18.431 | 104.922 | 1.00 | 38.42 | | C |
| ANISOU | 7176 | CG2 | VAL | D | 44 | 5485 | 4342 | 4771 | -489 | 1283 | 704 | C |
| ATOM | 7180 | C | VAL | D | 44 | -19.454 | 18.179 | 101.061 | 1.00 | 35.12 | | C |
| ANISOU | 7180 | C | VAL | D | 44 | 5015 | 3709 | 4620 | -448 | 1487 | 459 | C |
| ATOM | 7181 | O | VAL | D | 44 | -19.112 | 17.147 | 100.478 | 1.00 | 37.20 | | O |
| ANISOU | 7181 | O | VAL | D | 44 | 5472 | 3775 | 4889 | -350 | 1668 | 522 | O |
| ATOM | 7183 | N | CYS | D | 45 | -20.262 | 19.075 | 100.503 | 1.00 | 33.04 | | N |
| ANISOU | 7183 | N | CYS | D | 45 | 4599 | 3577 | 4378 | -586 | 1389 | 243 | N |
| ATOM | 7184 | CA | CYS | D | 45 | -20.805 | 18.881 | 99.157 | 1.00 | 33.06 | | C |
| ANISOU | 7184 | CA | CYS | D | 45 | 4624 | 3534 | 4404 | -654 | 1483 | 72 | C |
| ATOM | 7186 | CB | CYS | D | 45 | -21.671 | 20.061 | 98.762 | 1.00 | 32.95 | | C |
| ANISOU | 7186 | CB | CYS | D | 45 | 4422 | 3715 | 4383 | -743 | 1314 | -143 | C |
| ATOM | 7189 | SG | CYS | D | 45 | -23.240 | 20.184 | 99.672 | 1.00 | 34.12 | | S |
| ANISOU | 7189 | SG | CYS | D | 45 | 4526 | 4041 | 4398 | -957 | 1309 | -400 | S |
| ATOM | 7191 | C | CYS | D | 45 | -19.731 | 18.687 | 98.075 | 1.00 | 34.06 | | C |
| ANISOU | 7191 | C | CYS | D | 45 | 4747 | 3584 | 4610 | -465 | 1530 | 206 | C |
| ATOM | 7192 | O | CYS | D | 45 | -19.876 | 17.815 | 97.199 | 1.00 | 35.15 | | O |
| ANISOU | 7192 | O | CYS | D | 45 | 5045 | 3575 | 4735 | -469 | 1711 | 139 | O |
| ATOM | 7194 | N | PHE | D | 46 | -18.673 | 19.496 | 98.135 | 1.00 | 33.49 | | N |
| ANISOU | 7194 | N | PHE | D | 46 | 4493 | 3633 | 4599 | -324 | 1376 | 380 | N |
| ATOM | 7195 | CA | PHE | D | 46 | -17.547 | 19.345 | 97.207 | 1.00 | 35.57 | | C |
| ANISOU | 7195 | CA | PHE | D | 46 | 4697 | 3907 | 4913 | -144 | 1430 | 525 | C |
| ATOM | 7197 | CB | PHE | D | 46 | -16.571 | 20.503 | 97.308 | 1.00 | 36.65 | | C |
| ANISOU | 7197 | CB | PHE | D | 46 | 4583 | 4252 | 5089 | -110 | 1229 | 678 | C |
| ATOM | 7200 | CG | PHE | D | 46 | -17.162 | 21.823 | 96.958 | 1.00 | 36.50 | | C |
| ANISOU | 7200 | CG | PHE | D | 46 | 4482 | 4309 | 5079 | -278 | 1042 | 548 | C |
| ATOM | 7201 | CD1 | PHE | D | 46 | -17.926 | 21.979 | 95.810 | 1.00 | 38.14 | | C |
| ANISOU | 7201 | CD1 | PHE | D | 46 | 4742 | 4475 | 5273 | -339 | 1078 | 376 | C |
| ATOM | 7203 | CE1 | PHE | D | 46 | -18.481 | 23.221 | 95.496 | 1.00 | 38.74 | | C |
| ANISOU | 7203 | CE1 | PHE | D | 46 | 4783 | 4605 | 5332 | -433 | 887 | 268 | C |
| ATOM | 7205 | CZ | PHE | D | 46 | -18.267 | 24.297 | 96.332 | 1.00 | 35.61 | | C |
| ANISOU | 7205 | CZ | PHE | D | 46 | 4335 | 4260 | 4935 | -485 | 672 | 319 | C |
| ATOM | 7207 | CE2 | PHE | D | 46 | -17.504 | 24.135 | 97.471 | 1.00 | 36.18 | | C |
| ANISOU | 7207 | CE2 | PHE | D | 46 | 4345 | 4379 | 5022 | -469 | 641 | 473 | C |
| ATOM | 7209 | CD2 | PHE | D | 46 | -16.953 | 22.918 | 97.775 | 1.00 | 34.93 | | C |
| ANISOU | 7209 | CD2 | PHE | D | 46 | 4185 | 4210 | 4876 | -357 | 819 | 593 | C |
| ATOM | 7211 | C | PHE | D | 46 | -16.766 | 18.059 | 97.417 | 1.00 | 36.75 | | C |
| ANISOU | 7211 | C | PHE | D | 46 | 5004 | 3920 | 5041 | 79 | 1614 | 688 | C |
| ATOM | 7212 | O | PHE | D | 46 | -16.371 | 17.424 | 96.454 | 1.00 | 37.83 | | O |
| ANISOU | 7212 | O | PHE | D | 46 | 5219 | 3976 | 5179 | 218 | 1767 | 695 | O |
| ATOM | 7214 | N | MET | D | 47 | -16.470 | 17.728 | 98.662 | 1.00 | 37.82 | | N |
| ANISOU | 7214 | N | MET | D | 47 | 5192 | 4041 | 5137 | 155 | 1588 | 827 | N |
| ATOM | 7215 | CA | MET | D | 47 | -15.923 | 16.412 | 99.004 | 1.00 | 43.26 | | C |
| ANISOU | 7215 | CA | MET | D | 47 | 6125 | 4543 | 5771 | 398 | 1760 | 976 | C |
| ATOM | 7217 | CB | MET | D | 47 | -15.784 | 16.285 | 100.513 | 1.00 | 45.26 | | C |
| ANISOU | 7217 | CB | MET | D | 47 | 6427 | 4816 | 5952 | 435 | 1679 | 1122 | C |
| ATOM | 7220 | CG | MET | D | 47 | -14.550 | 16.894 | 101.080 | 1.00 | 47.36 | | C |
| ANISOU | 7220 | CG | MET | D | 47 | 6399 | 5374 | 6223 | 629 | 1497 | 1337 | C |
| ATOM | 7223 | SD | MET | D | 47 | -14.527 | 16.553 | 102.836 | 1.00 | 50.76 | | S |
| ANISOU | 7223 | SD | MET | D | 47 | 6960 | 5802 | 6524 | 676 | 1422 | 1491 | S |
| ATOM | 7224 | CE | MET | D | 47 | -13.001 | 15.602 | 103.042 | 1.00 | 54.28 | | C |
| ANISOU | 7224 | CE | MET | D | 47 | 7422 | 6304 | 6897 | 1195 | 1468 | 1798 | C |
| ATOM | 7228 | C | MET | D | 47 | -16.788 | 15.232 | 98.532 | 1.00 | 43.39 | | C |

FIG. 18 (continued)

| | | | | | | | | | | | | |
|---|---|---|---|---|---|---|---|---|---|---|---|---|
| ANISOU | 7228 | C | MET | D | 47 | 6529 | 4223 | 5734 | 311 | 1999 | 824 | C |
| ATOM | 7229 | O | MET | D | 47 | -16.288 | 14.262 | 97.977 | 1.00 | 43.57 | | O |
| ANISOU | 7229 | O | MET | D | 47 | 6769 | 4052 | 5731 | 537 | 2171 | 877 | O |
| ATOM | 7231 | N | TYR | D | 48 | -18.082 | 15.303 | 98.806 | 1.00 | 43.24 | | N |
| ANISOU | 7231 | N | TYR | D | 48 | 6603 | 4149 | 5677 | -21 | 2010 | 628 | N |
| ATOM | 7232 | CA | TYR | D | 48 | -19.024 | 14.254 | 98.393 | 1.00 | 44.47 | | C |
| ANISOU | 7232 | CA | TYR | D | 48 | 7109 | 4028 | 5759 | -219 | 2227 | 453 | C |
| ATOM | 7234 | CB | TYR | D | 48 | -20.456 | 14.704 | 98.691 | 1.00 | 43.73 | | C |
| ANISOU | 7234 | CB | TYR | D | 48 | 6938 | 4062 | 5617 | -616 | 2184 | 215 | C |
| ATOM | 7237 | CG | TYR | D | 48 | -21.494 | 13.598 | 98.896 | 1.00 | 46.29 | | C |
| ANISOU | 7237 | CG | TYR | D | 48 | 7616 | 4161 | 5812 | -930 | 2395 | 73 | C |
| ATOM | 7238 | CD1 | TYR | D | 48 | -21.966 | 13.303 | 100.173 | 1.00 | 46.83 | | C |
| ANISOU | 7238 | CD1 | TYR | D | 48 | 7815 | 4205 | 5772 | -1106 | 2429 | 124 | C |
| ATOM | 7240 | CE1 | TYR | D | 48 | -22.938 | 12.322 | 100.378 | 1.00 | 50.04 | | C |
| ANISOU | 7240 | CE1 | TYR | D | 48 | 8550 | 4427 | 6035 | -1472 | 2633 | 0 | C |
| ATOM | 7242 | CZ | TYR | D | 48 | -23.464 | 11.636 | 99.289 | 1.00 | 51.37 | | C |
| ANISOU | 7242 | CZ | TYR | D | 48 | 8917 | 4431 | 6171 | -1677 | 2792 | -200 | C |
| ATOM | 7243 | OH | TYR | D | 48 | -24.430 | 10.679 | 99.498 | 1.00 | 53.38 | | O |
| ANISOU | 7243 | OH | TYR | D | 48 | 9504 | 4514 | 6263 | -2116 | 2994 | -333 | O |
| ATOM | 7245 | CE2 | TYR | D | 48 | -23.019 | 11.919 | 98.003 | 1.00 | 49.33 | | C |
| ANISOU | 7245 | CE2 | TYR | D | 48 | 8531 | 4195 | 6019 | -1477 | 2749 | -269 | C |
| ATOM | 7247 | CD2 | TYR | D | 48 | -22.041 | 12.898 | 97.810 | 1.00 | 46.59 | | C |
| ANISOU | 7247 | CD2 | TYR | D | 48 | 7853 | 4037 | 5811 | -1102 | 2558 | -124 | C |
| ATOM | 7249 | C | TYR | D | 48 | -18.859 | 13.968 | 96.892 | 1.00 | 44.45 | | C |
| ANISOU | 7249 | C | TYR | D | 48 | 7154 | 3948 | 5789 | -146 | 2336 | 342 | C |
| ATOM | 7250 | O | TYR | D | 48 | -18.758 | 12.816 | 96.493 | 1.00 | 45.06 | | O |
| ANISOU | 7250 | O | TYR | D | 48 | 7590 | 3723 | 5808 | -70 | 2538 | 331 | O |
| ATOM | 7252 | N | SER | D | 49 | -18.824 | 15.035 | 96.091 | 1.00 | 41.38 | | N |
| ANISOU | 7252 | N | SER | D | 49 | 6437 | 3814 | 5470 | -164 | 2198 | 265 | N |
| ATOM | 7253 | CA | SER | D | 49 | -18.667 | 14.959 | 94.625 | 1.00 | 42.89 | | C |
| ANISOU | 7253 | CA | SER | D | 49 | 6624 | 4001 | 5672 | -105 | 2275 | 162 | C |
| ATOM | 7255 | CB | SER | D | 49 | -19.314 | 16.194 | 93.987 | 1.00 | 41.38 | | C |
| ANISOU | 7255 | CB | SER | D | 49 | 6145 | 4072 | 5506 | -287 | 2102 | 5 | C |
| ATOM | 7258 | OG | SER | D | 49 | -18.789 | 17.376 | 94.549 | 1.00 | 40.56 | | O |
| ANISOU | 7258 | OG | SER | D | 49 | 5755 | 4187 | 5467 | -223 | 1886 | 150 | O |
| ATOM | 7260 | C | SER | D | 49 | -17.220 | 14.832 | 94.088 | 1.00 | 43.84 | | C |
| ANISOU | 7260 | C | SER | D | 49 | 6670 | 4163 | 5825 | 272 | 2319 | 359 | C |
| ATOM | 7261 | O | SER | D | 49 | -17.019 | 14.758 | 92.881 | 1.00 | 41.79 | | O |
| ANISOU | 7261 | O | SER | D | 49 | 6405 | 3923 | 5552 | 338 | 2398 | 282 | O |
| ATOM | 7263 | N | ASP | D | 50 | -16.228 | 14.793 | 94.972 | 1.00 | 45.40 | | N |
| ANISOU | 7263 | N | ASP | D | 50 | 6790 | 4419 | 6041 | 520 | 2270 | 603 | N |
| ATOM | 7264 | CA | ASP | D | 50 | -14.818 | 14.735 | 94.581 | 1.00 | 47.83 | | C |
| ANISOU | 7264 | CA | ASP | D | 50 | 6936 | 4879 | 6358 | 889 | 2297 | 794 | C |
| ATOM | 7266 | CB | ASP | D | 50 | -14.451 | 13.341 | 94.044 | 1.00 | 53.41 | | C |
| ANISOU | 7266 | CB | ASP | D | 50 | 8001 | 5302 | 6989 | 1188 | 2548 | 787 | C |
| ATOM | 7269 | CG | ASP | D | 50 | -12.932 | 13.107 | 93.984 | 1.00 | 57.22 | | C |
| ANISOU | 7269 | CG | ASP | D | 50 | 8313 | 5981 | 7448 | 1671 | 2583 | 1010 | C |
| ATOM | 7270 | OD1 | ASP | D | 50 | -12.219 | 13.540 | 94.916 | 1.00 | 57.52 | | O |
| ANISOU | 7270 | OD1 | ASP | D | 50 | 8093 | 6261 | 7500 | 1796 | 2435 | 1215 | O |
| ATOM | 7271 | OD2 | ASP | D | 50 | -12.446 | 12.477 | 93.007 | 1.00 | 61.41 | | O |
| ANISOU | 7271 | OD2 | ASP | D | 50 | 8952 | 6457 | 7924 | 1938 | 2758 | 968 | O |
| ATOM | 7272 | C | ASP | D | 50 | -14.496 | 15.860 | 93.576 | 1.00 | 44.90 | | C |
| ANISOU | 7272 | C | ASP | D | 50 | 6216 | 4814 | 6029 | 812 | 2196 | 770 | C |
| ATOM | 7273 | O | ASP | D | 50 | -13.902 | 15.646 | 92.506 | 1.00 | 44.16 | | O |
| ANISOU | 7273 | O | ASP | D | 50 | 6083 | 4789 | 5906 | 981 | 2312 | 769 | O |
| ATOM | 7275 | N | PHE | D | 51 | -14.921 | 17.064 | 93.944 | 1.00 | 42.09 | | N |
| ANISOU | 7275 | N | PHE | D | 51 | 5646 | 4626 | 5721 | 553 | 1982 | 748 | N |
| ATOM | 7276 | CA | PHE | D | 51 | -14.664 | 18.249 | 93.161 | 1.00 | 43.43 | | C |
| ANISOU | 7276 | CA | PHE | D | 51 | 5550 | 5038 | 5912 | 439 | 1855 | 753 | C |
| ATOM | 7278 | CB | PHE | D | 51 | -15.650 | 19.349 | 93.508 | 1.00 | 43.36 | | C |
| ANISOU | 7278 | CB | PHE | D | 51 | 5491 | 5055 | 5928 | 148 | 1648 | 635 | C |
| ATOM | 7281 | CG | PHE | D | 51 | -15.510 | 20.567 | 92.644 | 1.00 | 44.90 | | C |
| ANISOU | 7281 | CG | PHE | D | 51 | 5521 | 5418 | 6120 | 25 | 1515 | 636 | C |
| ATOM | 7282 | CD1 | PHE | D | 51 | -16.052 | 20.588 | 91.361 | 1.00 | 45.54 | | C |
| ANISOU | 7282 | CD1 | PHE | D | 51 | 5683 | 5469 | 6153 | -27 | 1580 | 490 | C |
| ATOM | 7284 | CE1 | PHE | D | 51 | -15.915 | 21.702 | 90.559 | 1.00 | 44.12 | | C |
| ANISOU | 7284 | CE1 | PHE | D | 51 | 5405 | 5419 | 5941 | -132 | 1458 | 518 | C |
| ATOM | 7286 | CZ | PHE | D | 51 | -15.221 | 22.811 | 91.033 | 1.00 | 44.41 | | C |
| ANISOU | 7286 | CZ | PHE | D | 51 | 5283 | 5591 | 6000 | -224 | 1276 | 686 | C |
| ATOM | 7288 | CE2 | PHE | D | 51 | -14.678 | 22.799 | 92.305 | 1.00 | 43.70 | | C |
| ANISOU | 7288 | CE2 | PHE | D | 51 | 5093 | 5547 | 5963 | -200 | 1207 | 809 | C |
| ATOM | 7290 | CD2 | PHE | D | 51 | -14.816 | 21.688 | 93.098 | 1.00 | 44.28 | | C |
| ANISOU | 7290 | CD2 | PHE | D | 51 | 5242 | 5520 | 6063 | -57 | 1322 | 789 | C |
| ATOM | 7292 | C | PHE | D | 51 | -13.225 | 18.733 | 93.383 | 1.00 | 43.97 | | C |
| ANISOU | 7292 | C | PHE | D | 51 | 5311 | 5406 | 5988 | 590 | 1781 | 998 | C |
| ATOM | 7293 | O | PHE | D | 51 | -12.748 | 18.803 | 94.515 | 1.00 | 45.05 | | O |
| ANISOU | 7293 | O | PHE | D | 51 | 5349 | 5631 | 6136 | 651 | 1682 | 1139 | O |
| ATOM | 7295 | N | HIS | D | 52 | -12.544 | 19.051 | 92.291 | 1.00 | 43.65 | | N |
| ANISOU | 7295 | N | HIS | D | 52 | 5106 | 5561 | 5918 | 630 | 1833 | 1042 | N |

FIG. 18 (continued)

| | | | | | | | | | | | | |
|---|---|---|---|---|---|---|---|---|---|---|---|---|
| ATOM | 7296 | CA | HIS | D | 52 | -11.188 | 19.606 | 92.334 | 1.00 | 44.65 | | C |
| ANISOU | 7296 | CA | HIS | D | 52 | 4882 | 6059 | 6025 | 697 | 1773 | 1257 | C |
| ATOM | 7298 | CB | HIS | D | 52 | -10.267 | 18.836 | 91.395 | 1.00 | 47.79 | | C |
| ANISOU | 7298 | CB | HIS | D | 52 | 5194 | 6615 | 6348 | 1003 | 1996 | 1312 | C |
| ATOM | 7301 | CG | HIS | D | 52 | -10.039 | 17.434 | 91.829 | 1.00 | 50.58 | | C |
| ANISOU | 7301 | CG | HIS | D | 52 | 5736 | 6804 | 6677 | 1400 | 2162 | 1329 | C |
| ATOM | 7302 | ND1 | HIS | D | 52 | -8.920 | 17.046 | 92.530 | 1.00 | 52.02 | | N |
| ANISOU | 7302 | ND1 | HIS | D | 52 | 5714 | 7230 | 6821 | 1721 | 2164 | 1522 | N |
| ATOM | 7304 | CE1 | HIS | D | 52 | -8.993 | 15.754 | 92.784 | 1.00 | 56.13 | | C |
| ANISOU | 7304 | CE1 | HIS | D | 52 | 6548 | 7474 | 7306 | 2075 | 2320 | 1502 | C |
| ATOM | 7306 | NE2 | HIS | D | 52 | -10.140 | 15.299 | 92.311 | 1.00 | 55.50 | | N |
| ANISOU | 7306 | NE2 | HIS | D | 52 | 6866 | 6977 | 7244 | 1928 | 2422 | 1294 | N |
| ATOM | 7308 | CD2 | HIS | D | 52 | -10.811 | 16.330 | 91.706 | 1.00 | 52.41 | | C |
| ANISOU | 7308 | CD2 | HIS | D | 52 | 6379 | 6636 | 6897 | 1521 | 2322 | 1179 | C |
| ATOM | 7310 | C | HIS | D | 52 | -11.199 | 21.081 | 91.969 | 1.00 | 40.57 | | C |
| ANISOU | 7310 | C | HIS | D | 52 | 4204 | 5703 | 5510 | 357 | 1587 | 1278 | C |
| ATOM | 7311 | O | HIS | D | 52 | -11.778 | 21.494 | 90.962 | 1.00 | 40.38 | | O |
| ANISOU | 7311 | O | HIS | D | 52 | 4283 | 5601 | 5461 | 213 | 1600 | 1166 | O |
| ATOM | 7313 | N | PHE | D | 53 | -10.551 | 21.875 | 92.801 | 1.00 | 39.85 | | N |
| ANISOU | 7313 | N | PHE | D | 53 | 3891 | 5823 | 5426 | 227 | 1406 | 1422 | N |
| ATOM | 7314 | CA | PHE | D | 53 | -10.556 | 23.324 | 92.630 | 1.00 | 39.81 | | C |
| ANISOU | 7314 | CA | PHE | D | 53 | 3815 | 5900 | 5409 | -128 | 1208 | 1449 | C |
| ATOM | 7316 | CB | PHE | D | 53 | -10.438 | 23.996 | 93.986 | 1.00 | 42.57 | | C |
| ANISOU | 7316 | CB | PHE | D | 53 | 4100 | 6293 | 5784 | -281 | 979 | 1508 | C |
| ATOM | 7319 | CG | PHE | D | 53 | -11.613 | 23.736 | 94.856 | 1.00 | 41.97 | | C |
| ANISOU | 7319 | CG | PHE | D | 53 | 4271 | 5916 | 5760 | -246 | 918 | 1355 | C |
| ATOM | 7320 | CD1 | PHE | D | 53 | -11.650 | 22.610 | 95.661 | 1.00 | 43.19 | | C |
| ANISOU | 7320 | CD1 | PHE | D | 53 | 4472 | 6011 | 5927 | 0 | 1014 | 1367 | C |
| ATOM | 7322 | CE1 | PHE | D | 53 | -12.758 | 22.354 | 96.475 | 1.00 | 43.25 | | C |
| ANISOU | 7322 | CE1 | PHE | D | 53 | 4705 | 5774 | 5955 | -17 | 980 | 1229 | C |
| ATOM | 7324 | CZ | PHE | D | 53 | -13.834 | 23.237 | 96.454 | 1.00 | 39.90 | | C |
| ANISOU | 7324 | CZ | PHE | D | 53 | 4414 | 5206 | 5542 | -232 | 846 | 1058 | C |
| ATOM | 7326 | CE2 | PHE | D | 53 | -13.816 | 24.333 | 95.639 | 1.00 | 39.56 | | C |
| ANISOU | 7326 | CE2 | PHE | D | 53 | 4346 | 5197 | 5489 | -408 | 738 | 1039 | C |
| ATOM | 7328 | CD2 | PHE | D | 53 | -12.705 | 24.585 | 94.833 | 1.00 | 40.86 | | C |
| ANISOU | 7328 | CD2 | PHE | D | 53 | 4330 | 5563 | 5630 | -439 | 777 | 1197 | C |
| ATOM | 7330 | C | PHE | D | 53 | -9.498 | 23.831 | 91.681 | 1.00 | 37.52 | | C |
| ANISOU | 7330 | C | PHE | D | 53 | 3283 | 5936 | 5038 | -237 | 1259 | 1588 | C |
| ATOM | 7331 | O | PHE | D | 53 | -9.552 | 24.965 | 91.230 | 1.00 | 38.39 | | O |
| ANISOU | 7331 | O | PHE | D | 53 | 3421 | 6057 | 5109 | -547 | 1138 | 1610 | O |
| ATOM | 7333 | N | ILE | D | 54 | -8.547 | 22.970 | 91.368 | 1.00 | 37.96 | | N |
| ANISOU | 7333 | N | ILE | D | 54 | 3120 | 6258 | 5046 | 34 | 1449 | 1682 | N |
| ATOM | 7334 | CA | ILE | D | 54 | -7.516 | 23.278 | 90.399 | 1.00 | 38.84 | | C |
| ANISOU | 7334 | CA | ILE | D | 54 | 2955 | 6752 | 5049 | -34 | 1552 | 1803 | C |
| ATOM | 7336 | CB | ILE | D | 54 | -6.072 | 23.224 | 91.030 | 1.00 | 41.99 | | C |
| ANISOU | 7336 | CB | ILE | D | 54 | 2897 | 7669 | 5386 | 41 | 1538 | 1999 | C |
| ATOM | 7338 | CG1 | ILE | D | 54 | -6.004 | 24.075 | 92.315 | 1.00 | 40.22 | | C |
| ANISOU | 7338 | CG1 | ILE | D | 54 | 2607 | 7474 | 5202 | -241 | 1260 | 2063 | C |
| ATOM | 7341 | CD1 | ILE | D | 54 | -4.610 | 24.243 | 92.923 | 1.00 | 43.12 | | C |
| ANISOU | 7341 | CD1 | ILE | D | 54 | 2489 | 8415 | 5478 | -274 | 1197 | 2246 | C |
| ATOM | 7345 | CG2 | ILE | D | 54 | -5.033 | 23.676 | 89.993 | 1.00 | 43.28 | | C |
| ANISOU | 7345 | CG2 | ILE | D | 54 | 2732 | 8301 | 5410 | -115 | 1649 | 2118 | C |
| ATOM | 7349 | C | ILE | D | 54 | -7.629 | 22.263 | 89.271 | 1.00 | 39.43 | | C |
| ANISOU | 7349 | C | ILE | D | 54 | 3132 | 6774 | 5075 | 271 | 1821 | 1709 | C |
| ATOM | 7350 | O | ILE | D | 54 | -7.771 | 21.057 | 89.515 | 1.00 | 39.56 | | O |
| ANISOU | 7350 | O | ILE | D | 54 | 3266 | 6645 | 5118 | 646 | 1958 | 1641 | O |
| ATOM | 7352 | N | ASN | D | 55 | -7.521 | 22.747 | 88.036 | 1.00 | 40.43 | | N |
| ANISOU | 7352 | N | ASN | D | 55 | 3242 | 7013 | 5105 | 105 | 1901 | 1711 | N |
| ATOM | 7353 | CA | ASN | D | 55 | -7.639 | 21.893 | 86.870 | 1.00 | 39.88 | | C |
| ANISOU | 7353 | CA | ASN | D | 55 | 3284 | 6910 | 4958 | 358 | 2150 | 1603 | C |
| ATOM | 7355 | CB | ASN | D | 55 | -8.389 | 22.630 | 85.740 | 1.00 | 38.81 | | C |
| ANISOU | 7355 | CB | ASN | D | 55 | 3369 | 6624 | 4753 | 79 | 2125 | 1521 | C |
| ATOM | 7358 | CG | ASN | D | 55 | -7.636 | 23.836 | 85.206 | 1.00 | 38.88 | | C |
| ANISOU | 7358 | CG | ASN | D | 55 | 3172 | 6957 | 4645 | -283 | 2066 | 1701 | C |
| ATOM | 7359 | OD1 | ASN | D | 55 | -6.435 | 23.952 | 85.342 | 1.00 | 40.75 | | O |
| ANISOU | 7359 | OD1 | ASN | D | 55 | 3040 | 7628 | 4816 | -312 | 2122 | 1865 | O |
| ATOM | 7360 | ND2 | ASN | D | 55 | -8.365 | 24.731 | 84.562 | 1.00 | 38.23 | | N |
| ANISOU | 7360 | ND2 | ASN | D | 55 | 3341 | 6675 | 4510 | -565 | 1955 | 1669 | N |
| ATOM | 7363 | C | ASN | D | 55 | -6.333 | 21.278 | 86.396 | 1.00 | 43.15 | | C |
| ANISOU | 7363 | C | ASN | D | 55 | 3357 | 7785 | 5251 | 645 | 2372 | 1707 | C |
| ATOM | 7364 | O | ASN | D | 55 | -5.231 | 21.529 | 86.940 | 1.00 | 44.50 | | O |
| ANISOU | 7364 | O | ASN | D | 55 | 3132 | 8390 | 5387 | 641 | 2334 | 1880 | O |
| ATOM | 7366 | N | GLU | D | 56 | -6.426 | 20.493 | 85.330 | 1.00 | 44.10 | | N |
| ANISOU | 7366 | N | GLU | D | 56 | 3608 | 7868 | 5282 | 896 | 2607 | 1588 | N |
| ATOM | 7367 | CA | GLU | D | 56 | -5.246 | 19.843 | 84.812 | 1.00 | 46.44 | | C |
| ANISOU | 7367 | CA | GLU | D | 56 | 3600 | 8606 | 5439 | 1241 | 2841 | 1653 | C |
| ATOM | 7369 | CB | GLU | D | 56 | -5.623 | 18.706 | 83.864 | 1.00 | 50.11 | | C |
| ANISOU | 7369 | CB | GLU | D | 56 | 4364 | 8848 | 5827 | 1606 | 3093 | 1454 | C |
| ATOM | 7372 | CG | GLU | D | 56 | -6.355 | 17.547 | 84.584 | 1.00 | 52.23 | | C |

FIG. 18 (continued)

| | | | | | | | | | | | | |
|---|---|---|---|---|---|---|---|---|---|---|---|---|
| ANISOU | 7372 | CG | GLU | D | 56 | 5026 | 8608 | 6210 | 1926 | 3111 | 1308 | C |
| ATOM | 7375 | CD | GLU | D | 56 | -5.482 | 16.801 | 85.622 | 1.00 | 56.03 | | C |
| ANISOU | 7375 | CD | GLU | D | 56 | 5335 | 9243 | 6713 | 2365 | 3136 | 1429 | C |
| ATOM | 7376 | OE1 | GLU | D | 56 | -4.238 | 16.730 | 85.482 | 1.00 | 60.40 | | O |
| ANISOU | 7376 | OE1 | GLU | D | 56 | 5472 | 10327 | 7150 | 2621 | 3235 | 1558 | O |
| ATOM | 7377 | OE2 | GLU | D | 56 | -6.063 | 16.271 | 86.579 | 1.00 | 57.82 | | O |
| ANISOU | 7377 | OE2 | GLU | D | 56 | 5840 | 9078 | 7050 | 2461 | 3055 | 1394 | O |
| ATOM | 7378 | C | GLU | D | 56 | -4.272 | 20.841 | 84.191 | 1.00 | 47.06 | | C |
| ANISOU | 7378 | C | GLU | D | 56 | 3268 | 9244 | 5370 | 931 | 2858 | 1823 | C |
| ATOM | 7379 | O | GLU | D | 56 | -3.090 | 20.544 | 84.116 | 1.00 | 48.25 | | O |
| ANISOU | 7379 | O | GLU | D | 56 | 3005 | 9922 | 5405 | 1153 | 2996 | 1927 | O |
| ATOM | 7381 | N | GLN | D | 57 | -4.763 | 22.024 | 83.806 | 1.00 | 43.02 | | N |
| ANISOU | 7381 | N | GLN | D | 57 | 2874 | 8626 | 4846 | 421 | 2712 | 1859 | N |
| ATOM | 7382 | CA | GLN | D | 57 | -3.923 | 23.081 | 83.212 | 1.00 | 47.68 | | C |
| ANISOU | 7382 | CA | GLN | D | 57 | 3161 | 9680 | 5275 | 15 | 2719 | 2038 | C |
| ATOM | 7384 | CB | GLN | D | 57 | -4.784 | 23.980 | 82.314 | 1.00 | 45.09 | | C |
| ANISOU | 7384 | CB | GLN | D | 57 | 3191 | 9057 | 4887 | -373 | 2642 | 2007 | C |
| ATOM | 7387 | CG | GLN | D | 57 | -5.353 | 23.270 | 81.076 | 1.00 | 44.73 | | C |
| ANISOU | 7387 | CG | GLN | D | 57 | 3402 | 8856 | 4736 | -127 | 2848 | 1834 | C |
| ATOM | 7390 | CD | GLN | D | 57 | -6.631 | 22.494 | 81.330 | 1.00 | 40.30 | | C |
| ANISOU | 7390 | CD | GLN | D | 57 | 3252 | 7740 | 4322 | 128 | 2800 | 1598 | C |
| ATOM | 7391 | OE1 | GLN | D | 57 | -7.256 | 22.581 | 82.393 | 1.00 | 39.08 | | O |
| ANISOU | 7391 | OE1 | GLN | D | 57 | 3230 | 7271 | 4347 | 93 | 2603 | 1561 | O |
| ATOM | 7392 | NE2 | GLN | D | 57 | -7.032 | 21.728 | 80.343 | 1.00 | 40.23 | | N |
| ANISOU | 7392 | NE2 | GLN | D | 57 | 3443 | 7628 | 4213 | 357 | 2987 | 1425 | N |
| ATOM | 7395 | C | GLN | D | 57 | -3.159 | 23.939 | 84.269 | 1.00 | 48.25 | | C |
| ANISOU | 7395 | C | GLN | D | 57 | 2896 | 10058 | 5380 | -315 | 2517 | 2228 | C |
| ATOM | 7396 | O | GLN | D | 57 | -2.356 | 24.842 | 83.918 | 1.00 | 50.98 | | O |
| ANISOU | 7396 | O | GLN | D | 57 | 2964 | 10826 | 5579 | -730 | 2514 | 2392 | O |
| ATOM | 7398 | N | GLY | D | 58 | -3.413 | 23.650 | 85.549 | 1.00 | 47.51 | | N |
| ANISOU | 7398 | N | GLY | D | 58 | 2840 | 9758 | 5453 | -165 | 2354 | 2203 | N |
| ATOM | 7399 | CA | GLY | D | 58 | -2.669 | 24.239 | 86.660 | 1.00 | 50.99 | | C |
| ANISOU | 7399 | CA | GLY | D | 58 | 2950 | 10508 | 5914 | -391 | 2166 | 2352 | C |
| ATOM | 7402 | C | GLY | D | 58 | -3.337 | 25.500 | 87.207 | 1.00 | 49.33 | | C |
| ANISOU | 7402 | C | GLY | D | 58 | 3012 | 9947 | 5782 | -918 | 1875 | 2372 | C |
| ATOM | 7403 | O | GLY | D | 58 | -2.608 | 26.377 | 87.731 | 1.00 | 52.46 | | O |
| ANISOU | 7403 | O | GLY | D | 58 | 3155 | 10653 | 6123 | -1318 | 1729 | 2512 | O |
| ATOM | 7405 | N | GLU | D | 59 | -4.715 | 25.625 | 87.035 | 1.00 | 46.18 | | N |
| ANISOU | 7405 | N | GLU | D | 59 | 3130 | 8929 | 5487 | -928 | 1792 | 2220 | N |
| ATOM | 7406 | CA | GLU | D | 59 | -5.345 | 26.879 | 87.405 | 1.00 | 46.15 | | C |
| ANISOU | 7406 | CA | GLU | D | 59 | 3412 | 8602 | 5522 | -1372 | 1529 | 2229 | C |
| ATOM | 7408 | CB | GLU | D | 59 | -5.592 | 27.715 | 86.141 | 1.00 | 48.14 | | C |
| ANISOU | 7408 | CB | GLU | D | 59 | 3890 | 8764 | 5639 | -1688 | 1558 | 2264 | C |
| ATOM | 7411 | CG | GLU | D | 59 | -5.988 | 29.136 | 86.429 | 1.00 | 47.61 | | C |
| ANISOU | 7411 | CG | GLU | D | 59 | 4124 | 8410 | 5557 | -2160 | 1292 | 2315 | C |
| ATOM | 7414 | CD | GLU | D | 59 | -5.956 | 30.033 | 85.216 | 1.00 | 49.48 | | C |
| ANISOU | 7414 | CD | GLU | D | 59 | 4569 | 8621 | 5609 | -2509 | 1321 | 2416 | C |
| ATOM | 7415 | OE1 | GLU | D | 59 | -5.981 | 29.567 | 84.049 | 1.00 | 49.81 | | O |
| ANISOU | 7415 | OE1 | GLU | D | 59 | 4610 | 8769 | 5545 | -2357 | 1531 | 2403 | O |
| ATOM | 7416 | OE2 | GLU | D | 59 | -5.892 | 31.252 | 85.439 | 1.00 | 51.47 | | O |
| ANISOU | 7416 | OE2 | GLU | D | 59 | 5027 | 8729 | 5800 | -2956 | 1126 | 2515 | O |
| ATOM | 7417 | C | GLU | D | 59 | -6.611 | 26.632 | 88.220 | 1.00 | 44.16 | | C |
| ANISOU | 7417 | C | GLU | D | 59 | 3514 | 7826 | 5438 | -1192 | 1381 | 2057 | C |
| ATOM | 7418 | O | GLU | D | 59 | -7.273 | 25.615 | 88.056 | 1.00 | 38.88 | | O |
| ANISOU | 7418 | O | GLU | D | 59 | 2991 | 6948 | 4835 | -824 | 1505 | 1912 | O |
| ATOM | 7420 | N | SER | D | 60 | -6.892 | 27.543 | 89.153 | 1.00 | 46.30 | | N |
| ANISOU | 7420 | N | SER | D | 60 | 3911 | 7917 | 5762 | -1469 | 1123 | 2067 | N |
| ATOM | 7421 | CA | SER | D | 60 | -8.095 | 27.497 | 90.006 | 1.00 | 44.65 | | C |
| ANISOU | 7421 | CA | SER | D | 60 | 4016 | 7265 | 5684 | -1351 | 966 | 1902 | C |
| ATOM | 7423 | CB | SER | D | 60 | -8.079 | 28.657 | 91.024 | 1.00 | 44.73 | | C |
| ANISOU | 7423 | CB | SER | D | 60 | 4110 | 7183 | 5704 | -1696 | 685 | 1938 | C |
| ATOM | 7426 | OG | SER | D | 60 | -8.175 | 29.928 | 90.357 | 1.00 | 44.24 | | O |
| ANISOU | 7426 | OG | SER | D | 60 | 4285 | 6981 | 5543 | -2081 | 570 | 1989 | O |
| ATOM | 7428 | C | SER | D | 60 | -9.374 | 27.632 | 89.174 | 1.00 | 45.78 | | C |
| ANISOU | 7428 | C | SER | D | 60 | 4545 | 7019 | 5829 | -1300 | 968 | 1743 | C |
| ATOM | 7429 | O | SER | D | 60 | -9.406 | 28.401 | 88.232 | 1.00 | 46.68 | | O |
| ANISOU | 7429 | O | SER | D | 60 | 4797 | 7102 | 5839 | -1518 | 951 | 1790 | O |
| ATOM | 7431 | N | ILE | D | 61 | -10.430 | 26.903 | 89.527 | 1.00 | 46.58 | | N |
| ANISOU | 7431 | N | ILE | D | 61 | 4822 | 6851 | 6026 | -1032 | 983 | 1558 | N |
| ATOM | 7432 | CA | ILE | D | 61 | -11.701 | 27.090 | 88.837 | 1.00 | 48.21 | | C |
| ANISOU | 7432 | CA | ILE | D | 61 | 5347 | 6756 | 6215 | -999 | 949 | 1387 | C |
| ATOM | 7434 | CB | ILE | D | 61 | -12.035 | 25.914 | 87.875 | 1.00 | 48.02 | | C |
| ANISOU | 7434 | CB | ILE | D | 61 | 5346 | 6732 | 6167 | -736 | 1193 | 1271 | C |
| ATOM | 7436 | CG1 | ILE | D | 61 | -11.968 | 24.560 | 88.587 | 1.00 | 47.37 | | C |
| ANISOU | 7436 | CG1 | ILE | D | 61 | 5175 | 6649 | 6175 | -452 | 1340 | 1211 | C |
| ATOM | 7439 | CD1 | ILE | D | 61 | -13.003 | 23.585 | 88.051 | 1.00 | 45.44 | | C |
| ANISOU | 7439 | CD1 | ILE | D | 61 | 5141 | 6195 | 5929 | -271 | 1477 | 992 | C |
| ATOM | 7443 | CG2 | ILE | D | 61 | -11.126 | 25.921 | 86.640 | 1.00 | 49.39 | | C |
| ANISOU | 7443 | CG2 | ILE | D | 61 | 5387 | 7170 | 6210 | -781 | 1362 | 1399 | C |

FIG. 18 (continued)

| | | | | | | | | | | | | |
|---|---|---|---|---|---|---|---|---|---|---|---|---|
| ATOM | 7447 | C | ILE | D | 61 | -12.847 | 27.262 | 89.818 | 1.00 | 49.48 | | C |
| ANISOU | 7447 | C | ILE | D | 61 | 5703 | 6639 | 6460 | -951 | 776 | 1219 | C |
| ATOM | 7448 | O | ILE | D | 61 | -12.762 | 26.849 | 90.990 | 1.00 | 47.77 | | O |
| ANISOU | 7448 | O | ILE | D | 61 | 5394 | 6431 | 6325 | -876 | 747 | 1211 | O |
| ATOM | 7450 | N | VAL | D | 62 | -13.922 | 27.868 | 89.317 | 1.00 | 52.95 | | N |
| ANISOU | 7450 | N | VAL | D | 62 | 6403 | 6864 | 6852 | -974 | 663 | 1086 | N |
| ATOM | 7451 | CA | VAL | D | 62 | -15.209 | 27.916 | 90.029 | 1.00 | 53.39 | | C |
| ANISOU | 7451 | CA | VAL | D | 62 | 6619 | 6714 | 6953 | -871 | 536 | 876 | C |
| ATOM | 7453 | CB | VAL | D | 62 | -16.138 | 29.047 | 89.510 | 1.00 | 54.20 | | C |
| ANISOU | 7453 | CB | VAL | D | 62 | 6994 | 6637 | 6961 | -907 | 337 | 783 | C |
| ATOM | 7455 | CG1 | VAL | D | 62 | -17.139 | 29.461 | 90.593 | 1.00 | 53.87 | | C |
| ANISOU | 7455 | CG1 | VAL | D | 62 | 7064 | 6451 | 6951 | -831 | 153 | 610 | C |
| ATOM | 7459 | CG2 | VAL | D | 62 | -15.349 | 30.255 | 89.050 | 1.00 | 55.30 | | C |
| ANISOU | 7459 | CG2 | VAL | D | 62 | 7254 | 6750 | 7009 | -1147 | 220 | 982 | C |
| ATOM | 7463 | C | VAL | D | 62 | -15.923 | 26.565 | 89.840 | 1.00 | 53.38 | | C |
| ANISOU | 7463 | C | VAL | D | 62 | 6594 | 6703 | 6987 | -661 | 727 | 703 | C |
| ATOM | 7464 | O | VAL | D | 62 | -17.086 | 26.383 | 90.244 | 1.00 | 54.52 | | O |
| ANISOU | 7464 | O | VAL | D | 62 | 6831 | 6742 | 7144 | -589 | 676 | 502 | O |
| ATOM | 7466 | N | HIS | D | 74 | -18.331 | 12.796 | 84.863 | 1.00 | 70.02 | | N |
| ANISOU | 7466 | N | HIS | D | 74 | 10702 | 7335 | 8568 | 189 | 3091 | -832 | N |
| ATOM | 7467 | CA | HIS | D | 74 | -18.374 | 12.574 | 86.308 | 1.00 | 69.55 | | C |
| ANISOU | 7467 | CA | HIS | D | 74 | 10695 | 7115 | 8616 | 173 | 3056 | -702 | C |
| ATOM | 7469 | CB | HIS | D | 74 | -17.855 | 13.804 | 87.060 | 1.00 | 68.97 | | C |
| ANISOU | 7469 | CB | HIS | D | 74 | 10205 | 7328 | 8672 | 242 | 2843 | -452 | C |
| ATOM | 7472 | CG | HIS | D | 74 | -18.087 | 15.098 | 86.342 | 1.00 | 68.68 | | C |
| ANISOU | 7472 | CG | HIS | D | 74 | 9851 | 7619 | 8627 | 116 | 2660 | -470 | C |
| ATOM | 7473 | ND1 | HIS | D | 74 | -17.256 | 15.550 | 85.336 | 1.00 | 70.40 | | N |
| ANISOU | 7473 | ND1 | HIS | D | 74 | 9915 | 8038 | 8794 | 280 | 2684 | -383 | N |
| ATOM | 7475 | CE1 | HIS | D | 74 | -17.700 | 16.716 | 84.891 | 1.00 | 69.09 | | C |
| ANISOU | 7475 | CE1 | HIS | D | 74 | 9547 | 8096 | 8609 | 112 | 2494 | -400 | C |
| ATOM | 7477 | NE2 | HIS | D | 74 | -18.784 | 17.039 | 85.579 | 1.00 | 67.91 | | N |
| ANISOU | 7477 | NE2 | HIS | D | 74 | 9389 | 7917 | 8497 | -109 | 2344 | -510 | N |
| ATOM | 7479 | CD2 | HIS | D | 74 | -19.048 | 16.044 | 86.491 | 1.00 | 67.57 | | C |
| ANISOU | 7479 | CD2 | HIS | D | 74 | 9543 | 7634 | 8496 | -136 | 2452 | -558 | C |
| ATOM | 7481 | C | HIS | D | 74 | -19.779 | 12.195 | 86.787 | 1.00 | 66.64 | | C |
| ANISOU | 7481 | C | HIS | D | 74 | 10514 | 6596 | 8210 | -241 | 3038 | -921 | C |
| ATOM | 7482 | O | HIS | D | 74 | -20.781 | 12.545 | 86.159 | 1.00 | 67.03 | | O |
| ANISOU | 7482 | O | HIS | D | 74 | 10480 | 6804 | 8183 | -531 | 2960 | -1145 | O |
| ATOM | 7484 | N | ARG | D | 75 | -19.825 | 11.484 | 87.910 | 1.00 | 63.49 | | N |
| ANISOU | 7484 | N | ARG | D | 75 | 10354 | 5927 | 7841 | -262 | 3109 | -846 | N |
| ATOM | 7485 | CA | ARG | D | 75 | -21.053 | 10.896 | 88.434 | 1.00 | 60.24 | | C |
| ANISOU | 7485 | CA | ARG | D | 75 | 10180 | 5345 | 7363 | -680 | 3152 | -1038 | C |
| ATOM | 7487 | CB | ARG | D | 75 | -20.722 | 9.954 | 89.590 | 1.00 | 61.46 | | C |
| ANISOU | 7487 | CB | ARG | D | 75 | 10700 | 5126 | 7525 | -597 | 3278 | -880 | C |
| ATOM | 7490 | CG | ARG | D | 75 | -21.940 | 9.452 | 90.362 | 1.00 | 61.47 | | C |
| ANISOU | 7490 | CG | ARG | D | 75 | 10917 | 4991 | 7449 | -1078 | 3321 | -1024 | C |
| ATOM | 7493 | CD | ARG | D | 75 | -21.547 | 8.411 | 91.368 | 1.00 | 63.23 | | C |
| ANISOU | 7493 | CD | ARG | D | 75 | 11609 | 4777 | 7640 | -980 | 3471 | -851 | C |
| ATOM | 7496 | NE | ARG | D | 75 | -22.690 | 7.953 | 92.156 | 1.00 | 63.98 | | N |
| ANISOU | 7496 | NE | ARG | D | 75 | 11911 | 4763 | 7637 | -1492 | 3529 | -965 | N |
| ATOM | 7498 | CZ | ARG | D | 75 | -22.663 | 6.921 | 92.998 | 1.00 | 65.92 | | C |
| ANISOU | 7498 | CZ | ARG | D | 75 | 12674 | 4576 | 7796 | -1560 | 3684 | -858 | C |
| ATOM | 7499 | NH1 | ARG | D | 75 | -21.541 | 6.231 | 93.196 | 1.00 | 67.40 | | N |
| ANISOU | 7499 | NH1 | ARG | D | 75 | 13233 | 4388 | 7987 | -1082 | 3782 | -630 | N |
| ATOM | 7502 | NH2 | ARG | D | 75 | -23.760 | 6.590 | 93.667 | 1.00 | 66.92 | | N |
| ANISOU | 7502 | NH2 | ARG | D | 75 | 12943 | 4671 | 7811 | -2098 | 3743 | -970 | N |
| ATOM | 7505 | C | ARG | D | 75 | -22.059 | 11.933 | 88.915 | 1.00 | 55.55 | | C |
| ANISOU | 7505 | C | ARG | D | 75 | 9212 | 5095 | 6800 | -985 | 2939 | -1113 | C |
| ATOM | 7506 | O | ARG | D | 75 | -23.264 | 11.751 | 88.753 | 1.00 | 54.39 | | O |
| ANISOU | 7506 | O | ARG | D | 75 | 9096 | 5016 | 6552 | -1374 | 2941 | -1369 | O |
| ATOM | 7508 | N | PHE | D | 76 | -21.558 | 13.006 | 89.525 | 1.00 | 51.85 | | N |
| ANISOU | 7508 | N | PHE | D | 76 | 8393 | 4857 | 6452 | -803 | 2755 | -903 | N |
| ATOM | 7509 | CA | PHE | D | 76 | -22.410 | 13.991 | 90.187 | 1.00 | 47.93 | | C |
| ANISOU | 7509 | CA | PHE | D | 76 | 7587 | 4645 | 5981 | -1009 | 2553 | -953 | C |
| ATOM | 7511 | CB | PHE | D | 76 | -21.929 | 14.232 | 91.612 | 1.00 | 45.64 | | C |
| ANISOU | 7511 | CB | PHE | D | 76 | 7234 | 4325 | 5783 | -897 | 2487 | -717 | C |
| ATOM | 7514 | CG | PHE | D | 76 | -21.980 | 13.008 | 92.486 | 1.00 | 47.25 | | C |
| ANISOU | 7514 | CG | PHE | D | 76 | 7815 | 4199 | 5940 | -979 | 2671 | -671 | C |
| ATOM | 7515 | CD1 | PHE | D | 76 | -23.202 | 12.512 | 92.933 | 1.00 | 48.61 | | C |
| ANISOU | 7515 | CD1 | PHE | D | 76 | 8123 | 4337 | 6007 | -1386 | 2741 | -865 | C |
| ATOM | 7517 | CE1 | PHE | D | 76 | -23.261 | 11.403 | 93.747 | 1.00 | 50.38 | | C |
| ANISOU | 7517 | CE1 | PHE | D | 76 | 8751 | 4228 | 6162 | -1505 | 2917 | -802 | C |
| ATOM | 7519 | CZ | PHE | D | 76 | -22.085 | 10.746 | 94.109 | 1.00 | 52.53 | | C |
| ANISOU | 7519 | CZ | PHE | D | 76 | 9313 | 4178 | 6469 | -1145 | 3011 | -543 | C |
| ATOM | 7521 | CE2 | PHE | D | 76 | -20.856 | 11.226 | 93.664 | 1.00 | 50.84 | | C |
| ANISOU | 7521 | CE2 | PHE | D | 76 | 8908 | 4049 | 6360 | -694 | 2935 | -365 | C |
| ATOM | 7523 | CD2 | PHE | D | 76 | -20.811 | 12.355 | 92.863 | 1.00 | 47.96 | | C |
| ANISOU | 7523 | CD2 | PHE | D | 76 | 8125 | 4033 | 6063 | -650 | 2773 | -429 | C |
| ATOM | 7525 | C | PHE | D | 76 | -22.450 | 15.319 | 89.443 | 1.00 | 46.78 | | C |

FIG. 18 (continued)

| | | | | | | | | | | | | |
|---|---|---|---|---|---|---|---|---|---|---|---|---|
| ANISOU | 7525 | C | PHE | D | 76 | 7086 | 4832 | 5855 | -932 | 2342 | -972 | C |
| ATOM | 7526 | O | PHE | D | 76 | -21.429 | 15.799 | 88.975 | 1.00 | 47.95 | | O |
| ANISOU | 7526 | O | PHE | D | 76 | 7134 | 5026 | 6059 | -675 | 2305 | -797 | O |
| ATOM | 7528 | N | GLU | D | 77 | -23.642 | 15.898 | 89.342 | 1.00 | 46.18 | | N |
| ANISOU | 7528 | N | GLU | D | 77 | 6831 | 5005 | 5712 | -1156 | 2209 | -1182 | N |
| ATOM | 7529 | CA | GLU | D | 77 | -23.795 | 17.289 | 88.977 | 1.00 | 44.41 | | C |
| ANISOU | 7529 | CA | GLU | D | 77 | 6308 | 5070 | 5497 | -1058 | 1968 | -1173 | C |
| ATOM | 7531 | CB | GLU | D | 77 | -25.095 | 17.507 | 88.204 | 1.00 | 47.00 | | C |
| ANISOU | 7531 | CB | GLU | D | 77 | 6526 | 5657 | 5676 | -1247 | 1886 | -1473 | C |
| ATOM | 7534 | CG | GLU | D | 77 | -25.121 | 18.821 | 87.440 | 1.00 | 48.05 | | C |
| ANISOU | 7534 | CG | GLU | D | 77 | 6456 | 6022 | 5777 | -1073 | 1656 | -1451 | C |
| ATOM | 7537 | CD | GLU | D | 77 | -24.299 | 18.761 | 86.181 | 1.00 | 50.42 | | C |
| ANISOU | 7537 | CD | GLU | D | 77 | 6857 | 6255 | 6045 | -938 | 1720 | -1366 | C |
| ATOM | 7538 | OE1 | GLU | D | 77 | -24.733 | 18.070 | 85.233 | 1.00 | 52.56 | | O |
| ANISOU | 7538 | OE1 | GLU | D | 77 | 7232 | 6551 | 6186 | -1053 | 1824 | -1563 | O |
| ATOM | 7539 | OE2 | GLU | D | 77 | -23.221 | 19.391 | 86.148 | 1.00 | 52.34 | | O |
| ANISOU | 7539 | OE2 | GLU | D | 77 | 7070 | 6444 | 6374 | -743 | 1673 | -1113 | O |
| ATOM | 7540 | C | GLU | D | 77 | -23.816 | 18.072 | 90.279 | 1.00 | 42.67 | | C |
| ANISOU | 7540 | C | GLU | D | 77 | 5924 | 4929 | 5360 | -1019 | 1814 | -1053 | C |
| ATOM | 7541 | O | GLU | D | 77 | -24.551 | 17.705 | 91.207 | 1.00 | 39.54 | | O |
| ANISOU | 7541 | O | GLU | D | 77 | 5540 | 4549 | 4935 | -1200 | 1848 | -1149 | O |
| ATOM | 7543 | N | ILE | D | 78 | -22.994 | 19.121 | 90.376 | 1.00 | 39.55 | | N |
| ANISOU | 7543 | N | ILE | D | 78 | 5395 | 4582 | 5049 | -815 | 1656 | -847 | N |
| ATOM | 7544 | CA | ILE | D | 78 | -22.959 | 19.940 | 91.580 | 1.00 | 40.65 | | C |
| ANISOU | 7544 | CA | ILE | D | 78 | 5407 | 4786 | 5252 | -778 | 1493 | -748 | C |
| ATOM | 7546 | CB | ILE | D | 78 | -21.553 | 20.531 | 91.872 | 1.00 | 41.07 | | C |
| ANISOU | 7546 | CB | ILE | D | 78 | 5413 | 4780 | 5411 | -597 | 1421 | -451 | C |
| ATOM | 7548 | CG1 | ILE | D | 78 | -20.511 | 19.422 | 91.884 | 1.00 | 44.03 | | C |
| ANISOU | 7548 | CG1 | ILE | D | 78 | 5918 | 4982 | 5830 | -496 | 1632 | -289 | C |
| ATOM | 7551 | CD1 | ILE | D | 78 | -19.117 | 19.898 | 92.209 | 1.00 | 45.16 | | C |
| ANISOU | 7551 | CD1 | ILE | D | 78 | 5948 | 5161 | 6051 | -329 | 1571 | -10 | C |
| ATOM | 7555 | CG2 | ILE | D | 78 | -21.548 | 21.274 | 93.239 | 1.00 | 40.75 | | C |
| ANISOU | 7555 | CG2 | ILE | D | 78 | 5280 | 4788 | 5415 | -595 | 1257 | -375 | C |
| ATOM | 7559 | C | ILE | D | 78 | -23.966 | 21.067 | 91.405 | 1.00 | 38.28 | | C |
| ANISOU | 7559 | C | ILE | D | 78 | 4945 | 4722 | 4880 | -789 | 1273 | -918 | C |
| ATOM | 7560 | O | ILE | D | 78 | -23.883 | 21.810 | 90.443 | 1.00 | 38.69 | | O |
| ANISOU | 7560 | O | ILE | D | 78 | 4961 | 4843 | 4895 | -693 | 1157 | -914 | O |
| ATOM | 7562 | N | ILE | D | 79 | -24.907 | 21.190 | 92.335 | 1.00 | 35.79 | | N |
| ANISOU | 7562 | N | ILE | D | 79 | 4542 | 4537 | 4519 | -881 | 1218 | -1062 | N |
| ATOM | 7563 | CA | ILE | D | 79 | -25.910 | 22.249 | 92.298 | 1.00 | 36.79 | | C |
| ANISOU | 7563 | CA | ILE | D | 79 | 4504 | 4919 | 4556 | -818 | 1005 | -1242 | C |
| ATOM | 7565 | CB | ILE | D | 79 | -27.364 | 21.658 | 92.559 | 1.00 | 37.74 | | C |
| ANISOU | 7565 | CB | ILE | D | 79 | 4501 | 5301 | 4538 | -1021 | 1078 | -1548 | C |
| ATOM | 7567 | CG1 | ILE | D | 79 | -27.686 | 20.558 | 91.541 | 1.00 | 39.45 | | C |
| ANISOU | 7567 | CG1 | ILE | D | 79 | 4794 | 5514 | 4680 | -1222 | 1260 | -1685 | C |
| ATOM | 7570 | CD1 | ILE | D | 79 | -29.061 | 19.841 | 91.818 | 1.00 | 41.28 | | C |
| ANISOU | 7570 | CD1 | ILE | D | 79 | 4904 | 6024 | 4756 | -1531 | 1361 | -1986 | C |
| ATOM | 7574 | CG2 | ILE | D | 79 | -28.417 | 22.743 | 92.502 | 1.00 | 37.68 | | C |
| ANISOU | 7574 | CG2 | ILE | D | 79 | 4282 | 5625 | 4409 | -877 | 853 | -1750 | C |
| ATOM | 7578 | C | ILE | D | 79 | -25.572 | 23.357 | 93.317 | 1.00 | 36.77 | | C |
| ANISOU | 7578 | C | ILE | D | 79 | 4462 | 4900 | 4607 | -673 | 814 | -1123 | C |
| ATOM | 7579 | O | ILE | D | 79 | -25.632 | 24.558 | 93.002 | 1.00 | 35.70 | | O |
| ANISOU | 7579 | O | ILE | D | 79 | 4311 | 4810 | 4444 | -505 | 598 | -1121 | O |
| ATOM | 7581 | N | GLU | D | 80 | -25.219 | 22.937 | 94.529 | 1.00 | 37.98 | | N |
| ANISOU | 7581 | N | GLU | D | 80 | 4643 | 4970 | 4818 | -742 | 891 | -1025 | N |
| ATOM | 7582 | CA | GLU | D | 80 | -24.729 | 23.823 | 95.571 | 1.00 | 39.85 | | C |
| ANISOU | 7582 | CA | GLU | D | 80 | 4871 | 5168 | 5101 | -641 | 733 | -899 | C |
| ATOM | 7584 | CB | GLU | D | 80 | -24.489 | 23.014 | 96.845 | 1.00 | 41.83 | | C |
| ANISOU | 7584 | CB | GLU | D | 80 | 5159 | 5363 | 5373 | -749 | 867 | -816 | C |
| ATOM | 7587 | CG | GLU | D | 80 | -24.126 | 23.827 | 98.097 | 1.00 | 42.35 | | C |
| ANISOU | 7587 | CG | GLU | D | 80 | 5207 | 5437 | 5448 | -678 | 710 | -728 | C |
| ATOM | 7590 | CD | GLU | D | 80 | -25.056 | 24.978 | 98.359 | 1.00 | 43.56 | | C |
| ANISOU | 7590 | CD | GLU | D | 80 | 5277 | 5765 | 5508 | -575 | 511 | -935 | C |
| ATOM | 7591 | OE1 | GLU | D | 80 | -25.926 | 24.835 | 99.225 | 1.00 | 46.11 | | O |
| ANISOU | 7591 | OE1 | GLU | D | 80 | 5521 | 6267 | 5731 | -623 | 543 | -1098 | O |
| ATOM | 7592 | OE2 | GLU | D | 80 | -24.905 | 26.054 | 97.736 | 1.00 | 44.05 | | O |
| ANISOU | 7592 | OE2 | GLU | D | 80 | 5374 | 5786 | 5577 | -433 | 322 | -932 | O |
| ATOM | 7593 | C | GLU | D | 80 | -23.425 | 24.522 | 95.161 | 1.00 | 40.81 | | C |
| ANISOU | 7593 | C | GLU | D | 80 | 5064 | 5127 | 5316 | -539 | 628 | -650 | C |
| ATOM | 7594 | O | GLU | D | 80 | -22.625 | 23.972 | 94.408 | 1.00 | 40.47 | | O |
| ANISOU | 7594 | O | GLU | D | 80 | 5065 | 4984 | 5326 | -550 | 749 | -511 | O |
| ATOM | 7596 | N | GLY | D | 81 | -23.202 | 25.729 | 95.666 | 1.00 | 41.02 | | N |
| ANISOU | 7596 | N | GLY | D | 81 | 5106 | 5138 | 5343 | -457 | 412 | -602 | N |
| ATOM | 7597 | CA | GLY | D | 81 | -22.007 | 26.492 | 95.275 | 1.00 | 41.57 | | C |
| ANISOU | 7597 | CA | GLY | D | 81 | 5244 | 5078 | 5471 | -439 | 304 | -374 | C |
| ATOM | 7600 | C | GLY | D | 81 | -22.207 | 27.427 | 94.089 | 1.00 | 42.52 | | C |
| ANISOU | 7600 | C | GLY | D | 81 | 5453 | 5173 | 5532 | -364 | 166 | -403 | C |
| ATOM | 7601 | O | GLY | D | 81 | -21.321 | 28.198 | 93.772 | 1.00 | 43.69 | | O |
| ANISOU | 7601 | O | GLY | D | 81 | 5688 | 5215 | 5696 | -396 | 65 | -224 | O |

FIG. 18 (continued)

| | | | | | | | | | | | | |
|---|---|---|---|---|---|---|---|---|---|---|---|---|
| ATOM | 7603 | N | ARG | D | 82 | -23.355 | 27.339 | 93.418 | 1.00 | 43.47 | | N |
| ANISOU | 7603 | N | ARG | D | 82 | 5550 | 5408 | 5558 | -284 | 163 | -620 | N |
| ATOM | 7604 | CA | ARG | D | 82 | -23.736 | 28.295 | 92.376 | 1.00 | 44.79 | | C |
| ANISOU | 7604 | CA | ARG | D | 82 | 5825 | 5569 | 5626 | -155 | -3 | -666 | C |
| ATOM | 7606 | CB | ARG | D | 82 | -24.396 | 27.584 | 91.201 | 1.00 | 44.63 | | C |
| ANISOU | 7606 | CB | ARG | D | 82 | 5736 | 5693 | 5527 | -145 | 110 | -802 | C |
| ATOM | 7609 | CG | ARG | D | 82 | -23.701 | 26.324 | 90.717 | 1.00 | 43.96 | | C |
| ANISOU | 7609 | CG | ARG | D | 82 | 5611 | 5576 | 5516 | -296 | 369 | -706 | C |
| ATOM | 7612 | CD | ARG | D | 82 | -24.552 | 25.704 | 89.630 | 1.00 | 44.11 | | C |
| ANISOU | 7612 | CD | ARG | D | 82 | 5588 | 5750 | 5423 | -302 | 450 | -903 | C |
| ATOM | 7615 | NE | ARG | D | 82 | -24.022 | 24.436 | 89.143 | 1.00 | 44.12 | | N |
| ANISOU | 7615 | NE | ARG | D | 82 | 5603 | 5693 | 5466 | -428 | 706 | -862 | N |
| ATOM | 7617 | CZ | ARG | D | 82 | -23.302 | 24.289 | 88.033 | 1.00 | 44.64 | | C |
| ANISOU | 7617 | CZ | ARG | D | 82 | 5742 | 5707 | 5512 | -418 | 786 | -747 | C |
| ATOM | 7618 | NH1 | ARG | D | 82 | -22.996 | 25.335 | 87.258 | 1.00 | 44.93 | | N |
| ANISOU | 7618 | NH1 | ARG | D | 82 | 5847 | 5741 | 5481 | -331 | 635 | -635 | N |
| ATOM | 7621 | NH2 | ARG | D | 82 | -22.879 | 23.076 | 87.693 | 1.00 | 44.50 | | N |
| ANISOU | 7621 | NH2 | ARG | D | 82 | 5762 | 5627 | 5519 | -490 | 1027 | -743 | N |
| ATOM | 7624 | C | ARG | D | 82 | -24.751 | 29.268 | 92.960 | 1.00 | 46.30 | | C |
| ANISOU | 7624 | C | ARG | D | 82 | 6055 | 5824 | 5715 | 34 | -219 | -858 | C |
| ATOM | 7625 | O | ARG | D | 82 | -25.277 | 29.017 | 94.024 | 1.00 | 47.29 | | O |
| ANISOU | 7625 | O | ARG | D | 82 | 6071 | 6059 | 5838 | 38 | -196 | -989 | O |
| ATOM | 7627 | N | ASP | D | 83 | -25.029 | 30.370 | 92.277 | 1.00 | 49.55 | | N |
| ANISOU | 7627 | N | ASP | D | 83 | 6640 | 6167 | 6018 | 213 | -423 | -873 | N |
| ATOM | 7628 | CA | ASP | D | 83 | -26.149 | 31.213 | 92.693 | 1.00 | 52.80 | | C |
| ANISOU | 7628 | CA | ASP | D | 83 | 7089 | 6675 | 6297 | 488 | -624 | -1097 | C |
| ATOM | 7630 | CB | ASP | D | 83 | -25.971 | 32.677 | 92.258 | 1.00 | 57.35 | | C |
| ANISOU | 7630 | CB | ASP | D | 83 | 8016 | 6998 | 6777 | 680 | -884 | -1010 | C |
| ATOM | 7633 | CG | ASP | D | 83 | -26.332 | 32.919 | 90.805 | 1.00 | 60.26 | | C |
| ANISOU | 7633 | CG | ASP | D | 83 | 8479 | 7402 | 7015 | 825 | -950 | -1006 | C |
| ATOM | 7634 | OD1 | ASP | D | 83 | -25.566 | 32.463 | 89.929 | 1.00 | 60.58 | | O |
| ANISOU | 7634 | OD1 | ASP | D | 83 | 8531 | 7385 | 7104 | 623 | -822 | -823 | O |
| ATOM | 7635 | OD2 | ASP | D | 83 | -27.371 | 33.593 | 90.549 | 1.00 | 63.76 | | O |
| ANISOU | 7635 | OD2 | ASP | D | 83 | 8989 | 7950 | 7285 | 1170 | -1137 | -1187 | O |
| ATOM | 7636 | C | ASP | D | 83 | -27.448 | 30.595 | 92.165 | 1.00 | 52.15 | | C |
| ANISOU | 7636 | C | ASP | D | 83 | 6766 | 6951 | 6096 | 602 | -569 | -1365 | C |
| ATOM | 7637 | O | ASP | D | 83 | -27.451 | 29.936 | 91.110 | 1.00 | 50.65 | | O |
| ANISOU | 7637 | O | ASP | D | 83 | 6510 | 6845 | 5890 | 512 | -458 | -1353 | O |
| ATOM | 7639 | N | ARG | D | 84 | -28.539 | 30.814 | 92.908 | 1.00 | 51.43 | | N |
| ANISOU | 7639 | N | ARG | D | 84 | 6532 | 7107 | 5902 | 788 | -645 | -1618 | N |
| ATOM | 7640 | CA | ARG | D | 84 | -29.801 | 30.087 | 92.703 | 1.00 | 49.80 | | C |
| ANISOU | 7640 | CA | ARG | D | 84 | 6003 | 7345 | 5573 | 812 | -561 | -1902 | C |
| ATOM | 7642 | CB | ARG | D | 84 | -30.905 | 30.648 | 93.598 | 1.00 | 51.05 | | C |
| ANISOU | 7642 | CB | ARG | D | 84 | 6012 | 7795 | 5589 | 1081 | -684 | -2168 | C |
| ATOM | 7645 | CG | ARG | D | 84 | -30.703 | 30.361 | 95.063 | 1.00 | 48.64 | | C |
| ANISOU | 7645 | CG | ARG | D | 84 | 5648 | 7472 | 5361 | 926 | -576 | -2170 | C |
| ATOM | 7648 | CD | ARG | D | 84 | -31.836 | 30.904 | 95.886 | 1.00 | 49.78 | | C |
| ANISOU | 7648 | CD | ARG | D | 84 | 5622 | 7962 | 5332 | 1210 | -678 | -2456 | C |
| ATOM | 7651 | NE | ARG | D | 84 | -33.079 | 30.141 | 95.751 | 1.00 | 50.51 | | N |
| ANISOU | 7651 | NE | ARG | D | 84 | 5302 | 8613 | 5275 | 1153 | -561 | -2737 | N |
| ATOM | 7653 | CZ | ARG | D | 84 | -33.415 | 29.083 | 96.496 | 1.00 | 49.70 | | C |
| ANISOU | 7653 | CZ | ARG | D | 84 | 4950 | 8762 | 5172 | 816 | -323 | -2827 | C |
| ATOM | 7654 | NH1 | ARG | D | 84 | -32.608 | 28.626 | 97.452 | 1.00 | 48.65 | | N |
| ANISOU | 7654 | NH1 | ARG | D | 84 | 4942 | 8366 | 5178 | 555 | -183 | -2649 | N |
| ATOM | 7657 | NH2 | ARG | D | 84 | -34.566 | 28.472 | 96.286 | 1.00 | 51.18 | | N |
| ANISOU | 7657 | NH2 | ARG | D | 84 | 4767 | 9482 | 5195 | 721 | -229 | -3092 | N |
| ATOM | 7660 | C | ARG | D | 84 | -30.285 | 30.070 | 91.276 | 1.00 | 51.03 | | C |
| ANISOU | 7660 | C | ARG | D | 84 | 6128 | 7660 | 5603 | 920 | -617 | -1970 | C |
| ATOM | 7661 | O | ARG | D | 84 | -30.816 | 29.065 | 90.815 | 1.00 | 51.86 | | O |
| ANISOU | 7661 | O | ARG | D | 84 | 5999 | 8042 | 5664 | 742 | -465 | -2110 | O |
| ATOM | 7663 | N | THR | D | 85 | -30.111 | 31.180 | 90.574 | 1.00 | 52.97 | | N |
| ANISOU | 7663 | N | THR | D | 85 | 6639 | 7721 | 5767 | 1194 | -840 | -1871 | N |
| ATOM | 7664 | CA | THR | D | 85 | -30.645 | 31.324 | 89.224 | 1.00 | 55.08 | | C |
| ANISOU | 7664 | CA | THR | D | 85 | 6903 | 8160 | 5864 | 1366 | -938 | -1935 | C |
| ATOM | 7666 | CB | THR | D | 85 | -30.584 | 32.812 | 88.797 | 1.00 | 58.65 | | C |
| ANISOU | 7666 | CB | THR | D | 85 | 7730 | 8366 | 6188 | 1756 | -1232 | -1831 | C |
| ATOM | 7668 | OG1 | THR | D | 85 | -30.557 | 33.639 | 89.976 | 1.00 | 61.41 | | O |
| ANISOU | 7668 | OG1 | THR | D | 85 | 8230 | 8538 | 6566 | 1925 | -1354 | -1849 | O |
| ATOM | 7670 | CG2 | THR | D | 85 | -31.805 | 33.202 | 87.994 | 1.00 | 61.58 | | C |
| ANISOU | 7670 | CG2 | THR | D | 85 | 7999 | 9106 | 6295 | 2155 | -1424 | -2047 | C |
| ATOM | 7674 | C | THR | D | 85 | -29.931 | 30.372 | 88.233 | 1.00 | 54.65 | | C |
| ANISOU | 7674 | C | THR | D | 85 | 6852 | 8026 | 5886 | 1043 | -737 | -1789 | C |
| ATOM | 7675 | O | THR | D | 85 | -30.566 | 29.754 | 87.359 | 1.00 | 52.89 | | O |
| ANISOU | 7675 | O | THR | D | 85 | 6452 | 8101 | 5542 | 1007 | -688 | -1942 | O |
| ATOM | 7677 | N | MET | D | 86 | -28.618 | 30.217 | 88.397 | 1.00 | 53.31 | | N |
| ANISOU | 7677 | N | MET | D | 86 | 6864 | 7493 | 5899 | 807 | -616 | -1514 | N |
| ATOM | 7678 | CA | MET | D | 86 | -27.869 | 29.266 | 87.573 | 1.00 | 52.88 | | C |
| ANISOU | 7678 | CA | MET | D | 86 | 6805 | 7374 | 5915 | 538 | -400 | -1386 | C |
| ATOM | 7680 | CB | MET | D | 86 | -26.365 | 29.578 | 87.614 | 1.00 | 54.44 | | C |

FIG. 18 (continued)

| | | | | | | | | | | | | | |
|---|---|---|---|---|---|---|---|---|---|---|---|---|---|
| ANISOU | 7680 | CB | MET | D | 86 | 7229 | 7201 | 6254 | 398 | -351 | -1052 | | C |
| ATOM | 7683 | CG | MET | D | 86 | -25.491 | 28.587 | 86.842 | 1.00 | 54.78 | | | C |
| ANISOU | 7683 | CG | MET | D | 86 | 7252 | 7200 | 6363 | 170 | -109 | -919 | | C |
| ATOM | 7686 | SD | MET | D | 86 | -26.080 | 28.172 | 85.184 | 1.00 | 61.01 | | | S |
| ANISOU | 7686 | SD | MET | D | 86 | 8025 | 8203 | 6952 | 213 | -79 | -1045 | | S |
| ATOM | 7687 | CE | MET | D | 86 | -24.670 | 27.269 | 84.515 | 1.00 | 58.20 | | | C |
| ANISOU | 7687 | CE | MET | D | 86 | 7721 | 7701 | 6692 | -15 | 204 | -826 | | C |
| ATOM | 7691 | C | MET | D | 86 | -28.149 | 27.821 | 88.024 | 1.00 | 48.24 | | | C |
| ANISOU | 7691 | C | MET | D | 86 | 5967 | 6958 | 5403 | 274 | -144 | -1537 | | C |
| ATOM | 7692 | O | MET | D | 86 | -28.166 | 26.902 | 87.214 | 1.00 | 48.14 | | | O |
| ANISOU | 7692 | O | MET | D | 86 | 5902 | 7030 | 5360 | 116 | 14 | -1589 | | O |
| ATOM | 7694 | N | ALA | D | 87 | -28.371 | 27.654 | 89.318 | 1.00 | 44.13 | | | N |
| ANISOU | 7694 | N | ALA | D | 87 | 5338 | 6469 | 4961 | 222 | -106 | -1606 | | N |
| ATOM | 7695 | CA | ALA | D | 87 | -28.652 | 26.355 | 89.923 | 1.00 | 40.96 | | | C |
| ANISOU | 7695 | CA | ALA | D | 87 | 4764 | 6187 | 4613 | -48 | 131 | -1726 | | C |
| ATOM | 7697 | CB | ALA | D | 87 | -28.523 | 26.449 | 91.439 | 1.00 | 34.15 | | | C |
| ANISOU | 7697 | CB | ALA | D | 87 | 3872 | 5259 | 3843 | -79 | 145 | -1694 | | C |
| ATOM | 7701 | C | ALA | D | 87 | -30.033 | 25.822 | 89.509 | 1.00 | 42.25 | | | C |
| ANISOU | 7701 | C | ALA | D | 87 | 4683 | 6774 | 4598 | -101 | 153 | -2052 | | C |
| ATOM | 7702 | O | ALA | D | 87 | -30.160 | 24.650 | 89.131 | 1.00 | 41.89 | | | O |
| ANISOU | 7702 | O | ALA | D | 87 | 4589 | 6785 | 4540 | -376 | 358 | -2138 | | O |
| ATOM | 7704 | N | TRP | D | 88 | -31.063 | 26.673 | 89.535 | 1.00 | 41.62 | | | N |
| ANISOU | 7704 | N | TRP | D | 88 | 4455 | 7003 | 4355 | 164 | -61 | -2245 | | N |
| ATOM | 7705 | CA | TRP | D | 88 | -32.356 | 26.262 | 88.991 | 1.00 | 42.59 | | | C |
| ANISOU | 7705 | CA | TRP | D | 88 | 4293 | 7619 | 4272 | 131 | -71 | -2560 | | C |
| ATOM | 7707 | CB | TRP | D | 88 | -33.445 | 27.303 | 89.265 | 1.00 | 43.43 | | | C |
| ANISOU | 7707 | CB | TRP | D | 88 | 4204 | 8104 | 4194 | 515 | -322 | -2766 | | C |
| ATOM | 7710 | CG | TRP | D | 88 | -33.980 | 27.219 | 90.637 | 1.00 | 42.51 | | | C |
| ANISOU | 7710 | CG | TRP | D | 88 | 3886 | 8189 | 4079 | 469 | -264 | -2905 | | C |
| ATOM | 7711 | CD1 | TRP | D | 88 | -33.877 | 28.166 | 91.607 | 1.00 | 42.60 | | | C |
| ANISOU | 7711 | CD1 | TRP | D | 88 | 3979 | 8089 | 4119 | 747 | -397 | -2861 | | C |
| ATOM | 7713 | NE1 | TRP | D | 88 | -34.509 | 27.746 | 92.743 | 1.00 | 42.60 | | | N |
| ANISOU | 7713 | NE1 | TRP | D | 88 | 3725 | 8383 | 4078 | 605 | -278 | -3035 | | N |
| ATOM | 7715 | CE2 | TRP | D | 88 | -35.021 | 26.494 | 92.548 | 1.00 | 42.90 | | | C |
| ANISOU | 7715 | CE2 | TRP | D | 88 | 3530 | 8706 | 4064 | 186 | -57 | -3182 | | C |
| ATOM | 7716 | CD2 | TRP | D | 88 | -34.711 | 26.122 | 91.224 | 1.00 | 43.35 | | | C |
| ANISOU | 7716 | CD2 | TRP | D | 88 | 3696 | 8645 | 4129 | 93 | -47 | -3117 | | C |
| ATOM | 7717 | CE3 | TRP | D | 88 | -35.124 | 24.872 | 90.763 | 1.00 | 44.29 | | | C |
| ANISOU | 7717 | CE3 | TRP | D | 88 | 3669 | 8972 | 4187 | -339 | 158 | -3261 | | C |
| ATOM | 7719 | CZ3 | TRP | D | 88 | -35.837 | 24.037 | 91.628 | 1.00 | 46.66 | | | C |
| ANISOU | 7719 | CZ3 | TRP | D | 88 | 3730 | 9583 | 4417 | -700 | 351 | -3447 | | C |
| ATOM | 7721 | CH2 | TRP | D | 88 | -36.132 | 24.434 | 92.943 | 1.00 | 46.20 | | | C |
| ANISOU | 7721 | CH2 | TRP | D | 88 | 3546 | 9663 | 4345 | -606 | 347 | -3488 | | C |
| ATOM | 7723 | CZ2 | TRP | D | 88 | -35.729 | 25.658 | 93.423 | 1.00 | 45.50 | | | C |
| ANISOU | 7723 | CZ2 | TRP | D | 88 | 3588 | 9381 | 4318 | -147 | 142 | -3366 | | C |
| ATOM | 7725 | C | TRP | D | 88 | -32.309 | 25.928 | 87.500 | 1.00 | 43.15 | | | C |
| ANISOU | 7725 | C | TRP | D | 88 | 4419 | 7729 | 4248 | 83 | -65 | -2571 | | C |
| ATOM | 7726 | O | TRP | D | 88 | -33.005 | 25.019 | 87.062 | 1.00 | 43.48 | | | O |
| ANISOU | 7726 | O | TRP | D | 88 | 4275 | 8071 | 4176 | -163 | 48 | -2791 | | O |
| ATOM | 7728 | N | THR | D | 89 | -31.509 | 26.669 | 86.732 | 1.00 | 43.19 | | | N |
| ANISOU | 7728 | N | THR | D | 89 | 4686 | 7447 | 4275 | 287 | -184 | -2342 | | N |
| ATOM | 7729 | CA | THR | D | 89 | -31.292 | 26.368 | 85.325 | 1.00 | 45.62 | | | C |
| ANISOU | 7729 | CA | THR | D | 89 | 5089 | 7755 | 4489 | 240 | -160 | -2313 | | C |
| ATOM | 7731 | CB | THR | D | 89 | -30.334 | 27.378 | 84.632 | 1.00 | 45.50 | | | C |
| ANISOU | 7731 | CB | THR | D | 89 | 5393 | 7408 | 4486 | 464 | -296 | -2015 | | C |
| ATOM | 7733 | OG1 | THR | D | 89 | -30.865 | 28.707 | 84.734 | 1.00 | 47.50 | | | O |
| ANISOU | 7733 | OG1 | THR | D | 89 | 5703 | 7730 | 4615 | 858 | -592 | -2027 | | O |
| ATOM | 7735 | CG2 | THR | D | 89 | -30.138 | 27.018 | 83.144 | 1.00 | 46.90 | | | C |
| ANISOU | 7735 | CG2 | THR | D | 89 | 5660 | 7631 | 4531 | 407 | -252 | -1994 | | C |
| ATOM | 7739 | C | THR | D | 89 | -30.714 | 24.969 | 85.181 | 1.00 | 44.72 | | | C |
| ANISOU | 7739 | C | THR | D | 89 | 5022 | 7485 | 4487 | -154 | 148 | -2291 | | C |
| ATOM | 7740 | O | THR | D | 89 | -31.091 | 24.233 | 84.277 | 1.00 | 47.56 | | | O |
| ANISOU | 7740 | O | THR | D | 89 | 5332 | 8020 | 4720 | -315 | 229 | -2449 | | O |
| ATOM | 7742 | N | VAL | D | 90 | -29.803 | 24.610 | 86.081 | 1.00 | 43.34 | | | N |
| ANISOU | 7742 | N | VAL | D | 90 | 4962 | 6977 | 4529 | -289 | 307 | -2104 | | N |
| ATOM | 7743 | CA | VAL | D | 90 | -29.212 | 23.275 | 86.073 | 1.00 | 43.48 | | | C |
| ANISOU | 7743 | CA | VAL | D | 90 | 5074 | 6798 | 4647 | -594 | 598 | -2069 | | C |
| ATOM | 7745 | CB | VAL | D | 90 | -27.959 | 23.239 | 86.949 | 1.00 | 42.28 | | | C |
| ANISOU | 7745 | CB | VAL | D | 90 | 5076 | 6268 | 4719 | -597 | 700 | -1780 | | C |
| ATOM | 7747 | CG1 | VAL | D | 90 | -27.461 | 21.792 | 87.132 | 1.00 | 42.64 | | | C |
| ANISOU | 7747 | CG1 | VAL | D | 90 | 5237 | 6113 | 4850 | -851 | 997 | -1762 | | C |
| ATOM | 7751 | CG2 | VAL | D | 90 | -26.880 | 24.114 | 86.290 | 1.00 | 41.74 | | | C |
| ANISOU | 7751 | CG2 | VAL | D | 90 | 5168 | 6001 | 4691 | -407 | 603 | -1508 | | C |
| ATOM | 7755 | C | VAL | D | 90 | -30.203 | 22.163 | 86.461 | 1.00 | 44.20 | | | C |
| ANISOU | 7755 | C | VAL | D | 90 | 5012 | 7118 | 4664 | -908 | 751 | -2353 | | C |
| ATOM | 7756 | O | VAL | D | 90 | -30.291 | 21.145 | 85.782 | 1.00 | 43.65 | | | O |
| ANISOU | 7756 | O | VAL | D | 90 | 5013 | 7042 | 4529 | -1146 | 919 | -2470 | | O |
| ATOM | 7758 | N | VAL | D | 91 | -30.931 | 22.378 | 87.555 | 1.00 | 45.31 | | | N |
| ANISOU | 7758 | N | VAL | D | 91 | 4963 | 7458 | 4796 | -926 | 700 | -2467 | | N |

FIG. 18 (continued)

| | | | | | | | | | | | | |
|---|---|---|---|---|---|---|---|---|---|---|---|---|
| ATOM | 7759 | CA | VAL | D | 91 | -32.007 | 21.479 | 87.991 | 1.00 | 46.87 | | C |
| ANISOU | 7759 | CA | VAL | D | 91 | 4970 | 7958 | 4879 | -1261 | 829 | -2747 | C |
| ATOM | 7761 | CB | VAL | D | 91 | -32.648 | 22.009 | 89.334 | 1.00 | 46.44 | | C |
| ANISOU | 7761 | CB | VAL | D | 91 | 4695 | 8135 | 4817 | -1194 | 752 | -2820 | C |
| ATOM | 7763 | CG1 | VAL | D | 91 | -33.911 | 21.238 | 89.719 | 1.00 | 48.30 | | C |
| ANISOU | 7763 | CG1 | VAL | D | 91 | 4659 | 8815 | 4879 | -1553 | 867 | -3135 | C |
| ATOM | 7767 | CG2 | VAL | D | 91 | -31.641 | 21.917 | 90.449 | 1.00 | 43.18 | | C |
| ANISOU | 7767 | CG2 | VAL | D | 91 | 4485 | 7310 | 4612 | -1199 | 854 | -2553 | C |
| ATOM | 7771 | C | VAL | D | 91 | -33.067 | 21.270 | 86.892 | 1.00 | 50.17 | | C |
| ANISOU | 7771 | C | VAL | D | 91 | 5191 | 8815 | 5056 | -1361 | 765 | -3048 | C |
| ATOM | 7772 | O | VAL | D | 91 | -33.450 | 20.130 | 86.592 | 1.00 | 51.38 | | O |
| ANISOU | 7772 | O | VAL | D | 91 | 5362 | 9036 | 5124 | -1756 | 951 | -3226 | O |
| ATOM | 7774 | N | ASN | D | 92 | -33.540 | 22.356 | 86.283 | 1.00 | 51.32 | | N |
| ANISOU | 7774 | N | ASN | D | 92 | 5178 | 9251 | 5068 | -1010 | 497 | -3109 | N |
| ATOM | 7775 | CA | ASN | D | 92 | -34.564 | 22.235 | 85.234 | 1.00 | 54.31 | | C |
| ANISOU | 7775 | CA | ASN | D | 92 | 5333 | 10116 | 5184 | -1057 | 397 | -3395 | C |
| ATOM | 7777 | CB | ASN | D | 92 | -35.175 | 23.594 | 84.897 | 1.00 | 55.72 | | C |
| ANISOU | 7777 | CB | ASN | D | 92 | 5325 | 10642 | 5205 | -562 | 65 | -3445 | C |
| ATOM | 7780 | CG | ASN | D | 92 | -36.050 | 24.103 | 86.000 | 1.00 | 56.70 | | C |
| ANISOU | 7780 | CG | ASN | D | 92 | 5138 | 11131 | 5273 | -422 | -32 | -3598 | C |
| ATOM | 7781 | OD1 | ASN | D | 92 | -36.973 | 23.423 | 86.408 | 1.00 | 60.67 | | O |
| ANISOU | 7781 | OD1 | ASN | D | 92 | 5331 | 12062 | 5658 | -728 | 70 | -3866 | O |
| ATOM | 7782 | ND2 | ASN | D | 92 | -35.750 | 25.282 | 86.515 | 1.00 | 55.10 | | N |
| ANISOU | 7782 | ND2 | ASN | D | 92 | 5033 | 10763 | 5141 | 15 | -216 | -3437 | N |
| ATOM | 7785 | C | ASN | D | 92 | -34.035 | 21.573 | 83.985 | 1.00 | 54.47 | | C |
| ANISOU | 7785 | C | ASN | D | 92 | 5585 | 9942 | 5169 | -1209 | 500 | -3366 | C |
| ATOM | 7786 | O | ASN | D | 92 | -34.768 | 20.848 | 83.302 | 1.00 | 57.70 | | O |
| ANISOU | 7786 | O | ASN | D | 92 | 5873 | 10664 | 5387 | -1489 | 548 | -3634 | O |
| ATOM | 7788 | N | SER | D | 93 | -32.758 | 21.810 | 83.689 | 1.00 | 51.95 | | N |
| ANISOU | 7788 | N | SER | D | 93 | 5588 | 9137 | 5015 | -1044 | 539 | -3057 | N |
| ATOM | 7789 | CA | SER | D | 93 | -32.102 | 21.123 | 82.584 | 1.00 | 51.70 | | C |
| ANISOU | 7789 | CA | SER | D | 93 | 5799 | 8887 | 4958 | -1171 | 680 | -3012 | C |
| ATOM | 7791 | CB | SER | D | 93 | -30.678 | 21.654 | 82.373 | 1.00 | 49.98 | | C |
| ANISOU | 7791 | CB | SER | D | 93 | 5858 | 8225 | 4907 | -925 | 694 | -2645 | C |
| ATOM | 7794 | OG | SER | D | 93 | -30.116 | 21.038 | 81.221 | 1.00 | 54.87 | | O |
| ANISOU | 7794 | OG | SER | D | 93 | 6677 | 8713 | 5457 | -1007 | 828 | -2630 | O |
| ATOM | 7796 | C | SER | D | 93 | -32.096 | 19.603 | 82.825 | 1.00 | 50.94 | | C |
| ANISOU | 7796 | C | SER | D | 93 | 5827 | 8632 | 4895 | -1630 | 981 | -3146 | C |
| ATOM | 7797 | O | SER | D | 93 | -32.497 | 18.848 | 81.964 | 1.00 | 53.25 | | O |
| ANISOU | 7797 | O | SER | D | 93 | 6156 | 9055 | 5023 | -1873 | 1058 | -3362 | O |
| ATOM | 7799 | N | ILE | D | 94 | -31.660 | 19.174 | 84.005 | 1.00 | 49.01 | | N |
| ANISOU | 7799 | N | ILE | D | 94 | 5681 | 8097 | 4843 | -1749 | 1141 | -3022 | N |
| ATOM | 7800 | CA | ILE | D | 94 | -31.666 | 17.757 | 84.401 | 1.00 | 50.26 | | C |
| ANISOU | 7800 | CA | ILE | D | 94 | 6031 | 8039 | 5026 | -2169 | 1425 | -3119 | C |
| ATOM | 7802 | CB | ILE | D | 94 | -31.079 | 17.596 | 85.828 | 1.00 | 49.08 | | C |
| ANISOU | 7802 | CB | ILE | D | 94 | 5990 | 7571 | 5089 | -2171 | 1541 | -2902 | C |
| ATOM | 7804 | CG1 | ILE | D | 94 | -29.553 | 17.715 | 85.773 | 1.00 | 46.49 | | C |
| ANISOU | 7804 | CG1 | ILE | D | 94 | 5928 | 6779 | 4958 | -1889 | 1604 | -2559 | C |
| ATOM | 7807 | CD1 | ILE | D | 94 | -28.917 | 17.752 | 87.130 | 1.00 | 45.81 | | C |
| ANISOU | 7807 | CD1 | ILE | D | 94 | 5904 | 6441 | 5060 | -1820 | 1660 | -2327 | C |
| ATOM | 7811 | CG2 | ILE | D | 94 | -31.542 | 16.279 | 86.480 | 1.00 | 51.45 | | C |
| ANISOU | 7811 | CG2 | ILE | D | 94 | 6433 | 7768 | 5347 | -2645 | 1787 | -3051 | C |
| ATOM | 7815 | C | ILE | D | 94 | -33.077 | 17.137 | 84.349 | 1.00 | 52.66 | | C |
| ANISOU | 7815 | C | ILE | D | 94 | 6122 | 8782 | 5105 | -2591 | 1448 | -3499 | C |
| ATOM | 7816 | O | ILE | D | 94 | -33.280 | 16.060 | 83.767 | 1.00 | 54.60 | | O |
| ANISOU | 7816 | O | ILE | D | 94 | 6549 | 8961 | 5235 | -2955 | 1615 | -3684 | O |
| ATOM | 7818 | N | CYS | D | 95 | -34.045 | 17.816 | 84.956 | 1.00 | 52.45 | | N |
| ANISOU | 7818 | N | CYS | D | 95 | 5710 | 9222 | 4997 | -2550 | 1284 | -3629 | N |
| ATOM | 7819 | CA | CYS | D | 95 | -35.457 | 17.395 | 84.903 | 1.00 | 55.87 | | C |
| ANISOU | 7819 | CA | CYS | D | 95 | 5822 | 10225 | 5180 | -2932 | 1275 | -4004 | C |
| ATOM | 7821 | CB | CYS | D | 95 | -36.302 | 18.361 | 85.729 | 1.00 | 55.84 | | C |
| ANISOU | 7821 | CB | CYS | D | 95 | 5376 | 10722 | 5118 | -2724 | 1084 | -4083 | C |
| ATOM | 7824 | SG | CYS | D | 95 | -35.969 | 18.213 | 87.494 | 1.00 | 52.67 | | S |
| ANISOU | 7824 | SG | CYS | D | 95 | 5053 | 10045 | 4915 | -2815 | 1245 | -3899 | S |
| ATOM | 7826 | C | CYS | D | 95 | -36.031 | 17.310 | 83.487 | 1.00 | 59.35 | | C |
| ANISOU | 7826 | C | CYS | D | 95 | 6152 | 11024 | 5376 | -2997 | 1165 | -4251 | C |
| ATOM | 7827 | O | CYS | D | 95 | -36.822 | 16.386 | 83.166 | 1.00 | 61.86 | | O |
| ANISOU | 7827 | O | CYS | D | 95 | 6407 | 11602 | 5496 | -3499 | 1272 | -4554 | O |
| ATOM | 7829 | N | ASN | D | 96 | -35.663 | 18.270 | 82.637 | 1.00 | 57.99 | | N |
| ANISOU | 7829 | N | ASN | D | 96 | 5967 | 10880 | 5186 | -2526 | 948 | -4128 | N |
| ATOM | 7830 | CA | ASN | D | 96 | -36.150 | 18.266 | 81.238 | 1.00 | 62.05 | | C |
| ANISOU | 7830 | CA | ASN | D | 96 | 6394 | 11742 | 5442 | -2533 | 820 | -4336 | C |
| ATOM | 7832 | CB | ASN | D | 96 | -35.910 | 19.623 | 80.540 | 1.00 | 63.27 | | C |
| ANISOU | 7832 | CB | ASN | D | 96 | 6487 | 12002 | 5550 | -1935 | 527 | -4168 | C |
| ATOM | 7835 | CG | ASN | D | 96 | -36.929 | 20.700 | 80.948 | 1.00 | 66.35 | | C |
| ANISOU | 7835 | CG | ASN | D | 96 | 6440 | 12963 | 5807 | -1610 | 241 | -4280 | C |
| ATOM | 7836 | OD1 | ASN | D | 96 | -38.140 | 20.513 | 80.820 | 1.00 | 72.75 | | O |
| ANISOU | 7836 | OD1 | ASN | D | 96 | 6863 | 14409 | 6371 | -1781 | 156 | -4611 | O |
| ATOM | 7837 | ND2 | ASN | D | 96 | -36.433 | 21.838 | 81.410 | 1.00 | 64.66 | | N |

FIG. 18 (continued)

| | | | | | | | | | | | | |
|---|---|---|---|---|---|---|---|---|---|---|---|---|
| ANISOU | 7837 | ND2 | ASN | D | 96 | 6294 | 12540 | 5734 | -1131 | 90 | -4016 | N |
| ATOM | 7840 | C | ASN | D | 96 | -35.519 | 17.155 | 80.415 | 1.00 | 61.65 | | C |
| ANISOU | 7840 | C | ASN | D | 96 | 6746 | 11298 | 5380 | -2833 | 1045 | -4361 | C |
| ATOM | 7841 | O | ASN | D | 96 | -36.153 | 16.624 | 79.501 | 1.00 | 65.44 | | O |
| ANISOU | 7841 | O | ASN | D | 96 | 7171 | 12082 | 5611 | -3107 | 1034 | -4646 | O |
| ATOM | 7843 | N | THR | D | 97 | -34.269 | 16.810 | 80.719 | 1.00 | 57.92 | | N |
| ANISOU | 7843 | N | THR | D | 97 | 6675 | 10178 | 5154 | -2760 | 1242 | -4078 | N |
| ATOM | 7844 | CA | THR | D | 97 | -33.548 | 15.802 | 79.940 | 1.00 | 58.57 | | C |
| ANISOU | 7844 | CA | THR | D | 97 | 7177 | 9850 | 5225 | -2937 | 1462 | -4085 | C |
| ATOM | 7846 | CB | THR | D | 97 | -32.030 | 15.998 | 80.000 | 1.00 | 55.52 | | C |
| ANISOU | 7846 | CB | THR | D | 97 | 7110 | 8904 | 5081 | -2580 | 1565 | -3706 | C |
| ATOM | 7848 | OG1 | THR | D | 97 | -31.617 | 16.133 | 81.356 | 1.00 | 52.95 | | O |
| ANISOU | 7848 | OG1 | THR | D | 97 | 6792 | 8329 | 4998 | -2511 | 1626 | -3488 | O |
| ATOM | 7850 | CG2 | THR | D | 97 | -31.616 | 17.233 | 79.225 | 1.00 | 55.16 | | C |
| ANISOU | 7850 | CG2 | THR | D | 97 | 6960 | 8995 | 5005 | -2120 | 1340 | -3522 | C |
| ATOM | 7854 | C | THR | D | 97 | -33.875 | 14.390 | 80.408 | 1.00 | 60.33 | | C |
| ANISOU | 7854 | C | THR | D | 97 | 7624 | 9877 | 5421 | -3503 | 1730 | -4285 | C |
| ATOM | 7855 | O | THR | D | 97 | -34.199 | 13.533 | 79.596 | 1.00 | 61.61 | | O |
| ANISOU | 7855 | O | THR | D | 97 | 7955 | 10062 | 5391 | -3844 | 1827 | -4540 | O |
| ATOM | 7857 | N | THR | D | 98 | -33.801 | 14.166 | 81.720 | 1.00 | 59.00 | | N |
| ANISOU | 7857 | N | THR | D | 98 | 7487 | 9507 | 5423 | -3617 | 1845 | -4168 | N |
| ATOM | 7858 | CA | THR | D | 98 | -34.068 | 12.844 | 82.302 | 1.00 | 60.57 | | C |
| ANISOU | 7858 | CA | THR | D | 98 | 7971 | 9450 | 5593 | -4164 | 2111 | -4307 | C |
| ATOM | 7860 | CB | THR | D | 98 | -33.309 | 12.656 | 83.634 | 1.00 | 57.57 | | C |
| ANISOU | 7860 | CB | THR | D | 98 | 7812 | 8596 | 5468 | -4069 | 2262 | -4006 | C |
| ATOM | 7862 | OG1 | THR | D | 98 | -33.773 | 13.609 | 84.594 | 1.00 | 55.01 | | O |
| ANISOU | 7862 | OG1 | THR | D | 98 | 7065 | 8630 | 5205 | -3919 | 2098 | -3933 | O |
| ATOM | 7864 | CG2 | THR | D | 98 | -31.806 | 12.830 | 83.435 | 1.00 | 52.30 | | C |
| ANISOU | 7864 | CG2 | THR | D | 98 | 7446 | 7413 | 5013 | -3582 | 2313 | -3665 | C |
| ATOM | 7868 | C | THR | D | 98 | -35.551 | 12.577 | 82.547 | 1.00 | 65.54 | | C |
| ANISOU | 7868 | C | THR | D | 98 | 8259 | 10655 | 5988 | -4690 | 2075 | -4662 | C |
| ATOM | 7869 | O | THR | D | 98 | -35.988 | 11.411 | 82.556 | 1.00 | 67.79 | | O |
| ANISOU | 7869 | O | THR | D | 98 | 8791 | 10828 | 6138 | -5276 | 2276 | -4881 | O |
| ATOM | 7871 | N | GLY | D | 99 | -36.329 | 13.642 | 82.757 | 1.00 | 66.23 | | N |
| ANISOU | 7871 | N | GLY | D | 99 | 7791 | 11367 | 6007 | -4493 | 1825 | -4727 | N |
| ATOM | 7872 | CA | GLY | D | 99 | -37.756 | 13.469 | 83.025 | 1.00 | 70.82 | | C |
| ANISOU | 7872 | CA | GLY | D | 99 | 7945 | 12619 | 6343 | -4952 | 1783 | -5071 | C |
| ATOM | 7875 | C | GLY | D | 99 | -38.016 | 13.182 | 84.490 | 1.00 | 71.81 | | C |
| ANISOU | 7875 | C | GLY | D | 99 | 8031 | 12703 | 6552 | -5223 | 1935 | -5013 | C |
| ATOM | 7876 | O | GLY | D | 99 | -39.127 | 12.803 | 84.862 | 1.00 | 76.81 | | O |
| ANISOU | 7876 | O | GLY | D | 99 | 8372 | 13835 | 6978 | -5727 | 1981 | -5288 | O |
| ATOM | 7878 | N | ALA | D | 100 | -36.984 | 13.349 | 85.318 | 1.00 | 69.02 | | N |
| ANISOU | 7878 | N | ALA | D | 100 | 7960 | 11788 | 6475 | -4910 | 2018 | -4657 | N |
| ATOM | 7879 | CA | ALA | D | 100 | -37.116 | 13.259 | 86.761 | 1.00 | 69.24 | | C |
| ANISOU | 7879 | CA | ALA | D | 100 | 7948 | 11771 | 6587 | -5055 | 2132 | -4549 | C |
| ATOM | 7881 | CB | ALA | D | 100 | -35.729 | 13.352 | 87.428 | 1.00 | 66.28 | | C |
| ANISOU | 7881 | CB | ALA | D | 100 | 7975 | 10693 | 6515 | -4665 | 2213 | -4135 | C |
| ATOM | 7885 | C | ALA | D | 100 | -38.006 | 14.413 | 87.209 | 1.00 | 70.18 | | C |
| ANISOU | 7885 | C | ALA | D | 100 | 7431 | 12616 | 6619 | -4809 | 1896 | -4656 | C |
| ATOM | 7886 | O | ALA | D | 100 | -37.931 | 15.505 | 86.639 | 1.00 | 67.02 | | O |
| ANISOU | 7886 | O | ALA | D | 100 | 6790 | 12441 | 6234 | -4276 | 1635 | -4619 | O |
| ATOM | 7888 | N | GLU | D | 101 | -38.867 | 14.170 | 88.200 | 1.00 | 74.36 | | N |
| ANISOU | 7888 | N | GLU | D | 101 | 7706 | 13518 | 7030 | -5189 | 1990 | -4796 | N |
| ATOM | 7889 | CA | GLU | D | 101 | -39.698 | 15.245 | 88.749 | 1.00 | 76.22 | | C |
| ANISOU | 7889 | CA | GLU | D | 101 | 7338 | 14452 | 7170 | -4907 | 1788 | -4906 | C |
| ATOM | 7891 | CB | GLU | D | 101 | -40.742 | 14.700 | 89.743 | 1.00 | 80.85 | | C |
| ANISOU | 7891 | CB | GLU | D | 101 | 7643 | 15516 | 7560 | -5485 | 1960 | -5116 | C |
| ATOM | 7894 | CG | GLU | D | 101 | -40.142 | 14.040 | 90.989 | 1.00 | 80.88 | | C |
| ANISOU | 7894 | CG | GLU | D | 101 | 8065 | 14954 | 7711 | -5736 | 2224 | -4866 | C |
| ATOM | 7897 | CD | GLU | D | 101 | -41.067 | 14.082 | 92.184 | 1.00 | 83.53 | | C |
| ANISOU | 7897 | CD | GLU | D | 101 | 8016 | 15844 | 7879 | -6028 | 2314 | -4994 | C |
| ATOM | 7898 | OE1 | GLU | D | 101 | -42.234 | 13.650 | 92.055 | 1.00 | 89.92 | | O |
| ANISOU | 7898 | OE1 | GLU | D | 101 | 8456 | 17309 | 8398 | -6572 | 2380 | -5328 | O |
| ATOM | 7899 | OE2 | GLU | D | 101 | -40.617 | 14.543 | 93.258 | 1.00 | 83.16 | | O |
| ANISOU | 7899 | OE2 | GLU | D | 101 | 8023 | 15603 | 7971 | -5732 | 2322 | -4766 | O |
| ATOM | 7900 | C | GLU | D | 101 | -38.864 | 16.399 | 89.391 | 1.00 | 70.90 | | C |
| ANISOU | 7900 | C | GLU | D | 101 | 6699 | 13498 | 6743 | -4207 | 1634 | -4585 | C |
| ATOM | 7901 | O | GLU | D | 101 | -37.850 | 16.177 | 90.077 | 1.00 | 66.39 | | O |
| ANISOU | 7901 | O | GLU | D | 101 | 6530 | 12298 | 6398 | -4134 | 1763 | -4282 | O |
| ATOM | 7903 | N | LYS | D | 102 | -39.327 | 17.620 | 89.125 | 1.00 | 70.93 | | N |
| ANISOU | 7903 | N | LYS | D | 102 | 6288 | 13990 | 6671 | -3702 | 1346 | -4668 | N |
| ATOM | 7904 | CA | LYS | D | 102 | -38.757 | 18.875 | 89.627 | 1.00 | 67.82 | | C |
| ANISOU | 7904 | CA | LYS | D | 102 | 5887 | 13435 | 6446 | -3046 | 1150 | -4435 | C |
| ATOM | 7906 | CB | LYS | D | 102 | -39.548 | 20.037 | 89.001 | 1.00 | 70.79 | | C |
| ANISOU | 7906 | CB | LYS | D | 102 | 5829 | 14429 | 6639 | -2560 | 828 | -4621 | C |
| ATOM | 7909 | CG | LYS | D | 102 | -39.383 | 21.411 | 89.636 | 1.00 | 71.26 | | C |
| ANISOU | 7909 | CG | LYS | D | 102 | 5802 | 14498 | 6775 | -1914 | 605 | -4489 | C |
| ATOM | 7912 | CD | LYS | D | 102 | -38.294 | 22.262 | 88.975 | 1.00 | 69.44 | | C |
| ANISOU | 7912 | CD | LYS | D | 102 | 5935 | 13727 | 6723 | -1410 | 424 | -4195 | C |

FIG. 18 (continued)

| | | | | | | | | | | | | |
|---|---|---|---|---|---|---|---|---|---|---|---|---|
| ATOM | 7915 | CE | LYS | D | 102 | -38.772 | 23.712 | 88.817 | 1.00 | 70.85 | | C |
| ANISOU | 7915 | CE | LYS | D | 102 | 5902 | 14238 | 6780 | -753 | 90 | -4252 | C |
| ATOM | 7918 | NZ | LYS | D | 102 | -39.856 | 23.794 | 87.760 | 1.00 | 75.08 | | N |
| ANISOU | 7918 | NZ | LYS | D | 102 | 6068 | 15442 | 7016 | -676 | -76 | -4551 | N |
| ATOM | 7922 | C | LYS | D | 102 | -38.802 | 18.961 | 91.158 | 1.00 | 65.69 | | C |
| ANISOU | 7922 | C | LYS | D | 102 | 5561 | 13160 | 6237 | -3091 | 1256 | -4354 | C |
| ATOM | 7923 | O | LYS | D | 102 | -39.868 | 18.886 | 91.753 | 1.00 | 65.60 | | O |
| ANISOU | 7923 | O | LYS | D | 102 | 5152 | 13748 | 6024 | -3312 | 1297 | -4598 | O |
| ATOM | 7925 | N | PRO | D | 103 | -37.637 | 19.145 | 91.804 | 1.00 | 62.09 | | N |
| ANISOU | 7925 | N | PRO | D | 103 | 5481 | 12073 | 6036 | -2877 | 1297 | -4016 | N |
| ATOM | 7926 | CA | PRO | D | 103 | -37.677 | 19.282 | 93.254 | 1.00 | 60.56 | | C |
| ANISOU | 7926 | CA | PRO | D | 103 | 5238 | 11898 | 5874 | -2895 | 1377 | -3942 | C |
| ATOM | 7928 | CB | PRO | D | 103 | -36.202 | 19.300 | 93.655 | 1.00 | 56.78 | | C |
| ANISOU | 7928 | CB | PRO | D | 103 | 5235 | 10661 | 5678 | -2702 | 1419 | -3552 | C |
| ATOM | 7931 | CG | PRO | D | 103 | -35.467 | 19.741 | 92.422 | 1.00 | 55.57 | | C |
| ANISOU | 7931 | CG | PRO | D | 103 | 5256 | 10222 | 5637 | -2375 | 1265 | -3431 | C |
| ATOM | 7934 | CD | PRO | D | 103 | -36.267 | 19.249 | 91.264 | 1.00 | 57.91 | | C |
| ANISOU | 7934 | CD | PRO | D | 103 | 5392 | 10865 | 5747 | -2619 | 1272 | -3702 | C |
| ATOM | 7937 | C | PRO | D | 103 | -38.387 | 20.575 | 93.648 | 1.00 | 61.20 | | C |
| ANISOU | 7937 | C | PRO | D | 103 | 4898 | 12513 | 5841 | -2423 | 1135 | -4086 | C |
| ATOM | 7938 | O | PRO | D | 103 | -38.380 | 21.538 | 92.873 | 1.00 | 59.22 | | O |
| ANISOU | 7938 | O | PRO | D | 103 | 4567 | 12350 | 5583 | -1943 | 876 | -4103 | O |
| ATOM | 7939 | N | LYS | D | 104 | -39.018 | 20.578 | 94.820 | 1.00 | 62.67 | | N |
| ANISOU | 7939 | N | LYS | D | 104 | 4844 | 13054 | 5913 | -2550 | 1223 | -4195 | N |
| ATOM | 7940 | CA | LYS | D | 104 | -39.721 | 21.767 | 95.322 | 1.00 | 65.18 | | C |
| ANISOU | 7940 | CA | LYS | D | 104 | 4775 | 13894 | 6099 | -2070 | 1016 | -4358 | C |
| ATOM | 7942 | CB | LYS | D | 104 | -40.776 | 21.393 | 96.386 | 1.00 | 68.73 | | C |
| ANISOU | 7942 | CB | LYS | D | 104 | 4832 | 14967 | 6315 | -2408 | 1189 | -4593 | C |
| ATOM | 7945 | CG | LYS | D | 104 | -41.714 | 20.222 | 96.000 | 1.00 | 73.78 | | C |
| ANISOU | 7945 | CG | LYS | D | 104 | 5213 | 16087 | 6733 | -3105 | 1399 | -4850 | C |
| ATOM | 7948 | CD | LYS | D | 104 | -42.972 | 20.661 | 95.270 | 1.00 | 77.72 | | C |
| ANISOU | 7948 | CD | LYS | D | 104 | 5108 | 17473 | 6948 | -2961 | 1229 | -5228 | C |
| ATOM | 7951 | CE | LYS | D | 104 | -43.707 | 19.464 | 94.647 | 1.00 | 81.82 | | C |
| ANISOU | 7951 | CE | LYS | D | 104 | 5448 | 18370 | 7270 | -3709 | 1413 | -5461 | C |
| ATOM | 7954 | NZ | LYS | D | 104 | -45.101 | 19.802 | 94.196 | 1.00 | 86.76 | | N |
| ANISOU | 7954 | NZ | LYS | D | 104 | 5355 | 20060 | 7551 | -3659 | 1278 | -5873 | N |
| ATOM | 7958 | C | LYS | D | 104 | -38.693 | 22.750 | 95.901 | 1.00 | 62.59 | | C |
| ANISOU | 7958 | C | LYS | D | 104 | 4758 | 13039 | 5985 | -1561 | 867 | -4077 | C |
| ATOM | 7959 | O | LYS | D | 104 | -38.922 | 23.959 | 95.935 | 1.00 | 63.14 | | O |
| ANISOU | 7959 | O | LYS | D | 104 | 4695 | 13292 | 6003 | -1007 | 619 | -4144 | O |
| ATOM | 7961 | N | PHE | D | 105 | -37.554 | 22.199 | 96.326 | 1.00 | 61.13 | | N |
| ANISOU | 7961 | N | PHE | D | 105 | 5007 | 12200 | 6022 | -1758 | 1015 | -3770 | N |
| ATOM | 7962 | CA | PHE | D | 105 | -36.449 | 22.929 | 96.946 | 1.00 | 57.62 | | C |
| ANISOU | 7962 | CA | PHE | D | 105 | 4873 | 11239 | 5779 | -1410 | 909 | -3484 | C |
| ATOM | 7964 | CB | PHE | D | 105 | -36.215 | 22.409 | 98.383 | 1.00 | 61.02 | | C |
| ANISOU | 7964 | CB | PHE | D | 105 | 5406 | 11553 | 6226 | -1673 | 1107 | -3374 | C |
| ATOM | 7967 | CG | PHE | D | 105 | -35.821 | 20.950 | 98.446 | 1.00 | 62.64 | | C |
| ANISOU | 7967 | CG | PHE | D | 105 | 5870 | 11446 | 6485 | -2222 | 1397 | -3237 | C |
| ATOM | 7968 | CD1 | PHE | D | 105 | -34.476 | 20.569 | 98.495 | 1.00 | 60.74 | | C |
| ANISOU | 7968 | CD1 | PHE | D | 105 | 6064 | 10545 | 6468 | -2217 | 1453 | -2899 | C |
| ATOM | 7970 | CE1 | PHE | D | 105 | -34.118 | 19.224 | 98.524 | 1.00 | 61.45 | | C |
| ANISOU | 7970 | CE1 | PHE | D | 105 | 6447 | 10314 | 6588 | -2647 | 1711 | -2777 | C |
| ATOM | 7972 | CZ | PHE | D | 105 | -35.097 | 18.239 | 98.500 | 1.00 | 64.14 | | C |
| ANISOU | 7972 | CZ | PHE | D | 105 | 6690 | 10945 | 6737 | -3162 | 1923 | -2987 | C |
| ATOM | 7974 | CE2 | PHE | D | 105 | -36.446 | 18.596 | 98.455 | 1.00 | 67.92 | | C |
| ANISOU | 7974 | CE2 | PHE | D | 105 | 6693 | 12126 | 6987 | -3251 | 1878 | -3329 | C |
| ATOM | 7976 | CD2 | PHE | D | 105 | -36.801 | 19.946 | 98.421 | 1.00 | 67.45 | | C |
| ANISOU | 7976 | CD2 | PHE | D | 105 | 6301 | 12430 | 6899 | -2745 | 1612 | -3454 | C |
| ATOM | 7978 | C | PHE | D | 105 | -35.203 | 22.688 | 96.121 | 1.00 | 52.72 | | C |
| ANISOU | 7978 | C | PHE | D | 105 | 4651 | 9992 | 5386 | -1396 | 906 | -3198 | C |
| ATOM | 7979 | O | PHE | D | 105 | -35.114 | 21.666 | 95.467 | 1.00 | 50.81 | | O |
| ANISOU | 7979 | O | PHE | D | 105 | 4515 | 9634 | 5158 | -1745 | 1070 | -3193 | O |
| ATOM | 7981 | N | LEU | D | 106 | -34.244 | 23.617 | 96.183 | 1.00 | 49.55 | | N |
| ANISOU | 7981 | N | LEU | D | 106 | 4476 | 9206 | 5144 | -1015 | 729 | -2973 | N |
| ATOM | 7982 | CA | LEU | D | 106 | -32.907 | 23.428 | 95.623 | 1.00 | 45.17 | | C |
| ANISOU | 7982 | CA | LEU | D | 106 | 4277 | 8082 | 4803 | -1006 | 745 | -2669 | C |
| ATOM | 7984 | CB | LEU | D | 106 | -32.066 | 24.702 | 95.672 | 1.00 | 41.90 | | C |
| ANISOU | 7984 | CB | LEU | D | 106 | 4035 | 7381 | 4504 | -595 | 508 | -2478 | C |
| ATOM | 7987 | CG | LEU | D | 106 | -31.884 | 25.574 | 94.458 | 1.00 | 40.07 | | C |
| ANISOU | 7987 | CG | LEU | D | 106 | 3878 | 7076 | 4272 | -293 | 296 | -2448 | C |
| ATOM | 7989 | CD1 | LEU | D | 106 | -30.743 | 26.518 | 94.771 | 1.00 | 36.41 | | C |
| ANISOU | 7989 | CD1 | LEU | D | 106 | 3684 | 6200 | 3950 | -75 | 147 | -2183 | C |
| ATOM | 7993 | CD2 | LEU | D | 106 | -31.613 | 24.757 | 93.196 | 1.00 | 37.64 | | C |
| ANISOU | 7993 | CD2 | LEU | D | 106 | 3642 | 6668 | 3990 | -486 | 412 | -2407 | C |
| ATOM | 7997 | C | LEU | D | 106 | -32.136 | 22.363 | 96.380 | 1.00 | 43.31 | | C |
| ANISOU | 7997 | C | LEU | D | 106 | 4271 | 7501 | 4683 | -1324 | 986 | -2463 | C |
| ATOM | 7998 | O | LEU | D | 106 | -31.887 | 22.502 | 97.561 | 1.00 | 45.61 | | O |
| ANISOU | 7998 | O | LEU | D | 106 | 4604 | 7729 | 4998 | -1311 | 1004 | -2371 | O |
| ATOM | 8000 | N | PRO | D | 107 | -31.776 | 21.274 | 95.698 | 1.00 | 42.32 | | N |

FIG. 18 (continued)

| | | | | | | | | | | | | |
|---|---|---|---|---|---|---|---|---|---|---|---|---|
| ANISOU | 8000 | N | PRO | D | 107 | 4321 | 7153 | 4606 | -1591 | 1168 | -2397 | N |
| ATOM | 8001 | CA | PRO | D | 107 | -30.930 | 20.265 | 96.314 | 1.00 | 40.43 | | C |
| ANISOU | 8001 | CA | PRO | D | 107 | 4371 | 6521 | 4471 | -1805 | 1380 | -2172 | C |
| ATOM | 8003 | CB | PRO | D | 107 | -31.381 | 18.969 | 95.619 | 1.00 | 42.47 | | C |
| ANISOU | 8003 | CB | PRO | D | 107 | 4725 | 6767 | 4644 | -2198 | 1604 | -2303 | C |
| ATOM | 8006 | CG | PRO | D | 107 | -32.005 | 19.407 | 94.348 | 1.00 | 44.07 | | C |
| ANISOU | 8006 | CG | PRO | D | 107 | 4727 | 7253 | 4764 | -2114 | 1472 | -2516 | C |
| ATOM | 8009 | CD | PRO | D | 107 | -32.173 | 20.891 | 94.336 | 1.00 | 42.61 | | C |
| ANISOU | 8009 | CD | PRO | D | 107 | 4318 | 7297 | 4575 | -1690 | 1186 | -2545 | C |
| ATOM | 8012 | C | PRO | D | 107 | -29.442 | 20.587 | 96.087 | 1.00 | 37.45 | | C |
| ANISOU | 8012 | C | PRO | D | 107 | 4229 | 5705 | 4294 | -1545 | 1310 | -1855 | C |
| ATOM | 8013 | O | PRO | D | 107 | -29.103 | 21.639 | 95.554 | 1.00 | 33.89 | | O |
| ANISOU | 8013 | O | PRO | D | 107 | 3730 | 5251 | 3897 | -1255 | 1103 | -1808 | O |
| ATOM | 8014 | N | ASP | D | 108 | -28.583 | 19.691 | 96.534 | 1.00 | 38.05 | | N |
| ANISOU | 8014 | N | ASP | D | 108 | 4562 | 5441 | 4455 | -1651 | 1481 | -1639 | N |
| ATOM | 8015 | CA | ASP | D | 108 | -27.157 | 19.902 | 96.503 | 1.00 | 37.41 | | C |
| ANISOU | 8015 | CA | ASP | D | 108 | 4645 | 5031 | 4537 | -1421 | 1433 | -1340 | C |
| ATOM | 8017 | CB | ASP | D | 108 | -26.545 | 19.373 | 97.791 | 1.00 | 37.53 | | C |
| ANISOU | 8017 | CB | ASP | D | 108 | 4814 | 4862 | 4583 | -1461 | 1530 | -1137 | C |
| ATOM | 8020 | CG | ASP | D | 108 | -26.952 | 20.193 | 98.997 | 1.00 | 38.20 | | C |
| ANISOU | 8020 | CG | ASP | D | 108 | 4742 | 5161 | 4610 | -1415 | 1396 | -1179 | C |
| ATOM | 8021 | OD1 | ASP | D | 108 | -26.967 | 21.454 | 98.914 | 1.00 | 38.15 | | O |
| ANISOU | 8021 | OD1 | ASP | D | 108 | 4583 | 5287 | 4625 | -1200 | 1168 | -1222 | O |
| ATOM | 8022 | OD2 | ASP | D | 108 | -27.265 | 19.557 | 100.023 | 1.00 | 37.93 | | O |
| ANISOU | 8022 | OD2 | ASP | D | 108 | 4776 | 5148 | 4490 | -1597 | 1527 | -1171 | O |
| ATOM | 8023 | C | ASP | D | 108 | -26.432 | 19.291 | 95.312 | 1.00 | 37.19 | | C |
| ANISOU | 8023 | C | ASP | D | 108 | 4789 | 4765 | 4578 | -1391 | 1534 | -1250 | C |
| ATOM | 8024 | O | ASP | D | 108 | -25.500 | 19.937 | 94.777 | 1.00 | 34.36 | | O |
| ANISOU | 8024 | O | ASP | D | 108 | 4430 | 4308 | 4319 | -1159 | 1422 | -1087 | O |
| ATOM | 8026 | N | LEU | D | 109 | -26.830 | 18.058 | 94.951 | 1.00 | 37.80 | | N |
| ANISOU | 8026 | N | LEU | D | 109 | 5032 | 4747 | 4584 | -1642 | 1754 | -1356 | N |
| ATOM | 8027 | CA | LEU | D | 109 | -26.279 | 17.297 | 93.819 | 1.00 | 38.03 | | C |
| ANISOU | 8027 | CA | LEU | D | 109 | 5269 | 4542 | 4638 | -1632 | 1887 | -1325 | C |
| ATOM | 8029 | CB | LEU | D | 109 | -25.259 | 16.245 | 94.300 | 1.00 | 39.50 | | C |
| ANISOU | 8029 | CB | LEU | D | 109 | 5784 | 4339 | 4888 | -1583 | 2077 | -1091 | C |
| ATOM | 8032 | CG | LEU | D | 109 | -24.155 | 16.598 | 95.303 | 1.00 | 38.65 | | C |
| ANISOU | 8032 | CG | LEU | D | 109 | 5676 | 4122 | 4888 | -1331 | 2005 | -792 | C |
| ATOM | 8034 | CD1 | LEU | D | 109 | -23.362 | 15.371 | 95.683 | 1.00 | 40.84 | | C |
| ANISOU | 8034 | CD1 | LEU | D | 109 | 6300 | 4045 | 5173 | -1269 | 2206 | -606 | C |
| ATOM | 8038 | CD2 | LEU | D | 109 | -23.228 | 17.638 | 94.764 | 1.00 | 37.19 | | C |
| ANISOU | 8038 | CD2 | LEU | D | 109 | 5312 | 4010 | 4810 | -1047 | 1831 | -649 | C |
| ATOM | 8042 | C | LEU | D | 109 | -27.343 | 16.523 | 93.034 | 1.00 | 40.12 | | C |
| ANISOU | 8042 | C | LEU | D | 109 | 5579 | 4907 | 4756 | -1949 | 2014 | -1614 | C |
| ATOM | 8043 | O | LEU | D | 109 | -28.428 | 16.262 | 93.527 | 1.00 | 38.89 | | O |
| ANISOU | 8043 | O | LEU | D | 109 | 5337 | 4963 | 4478 | -2244 | 2059 | -1810 | O |
| ATOM | 8045 | N | TYR | D | 110 | -27.003 | 16.118 | 91.808 | 1.00 | 40.82 | | N |
| ANISOU | 8045 | N | TYR | D | 110 | 5806 | 4867 | 4838 | -1913 | 2081 | -1649 | N |
| ATOM | 8046 | CA | TYR | D | 110 | -27.742 | 15.071 | 91.119 | 1.00 | 42.93 | | C |
| ANISOU | 8046 | CA | TYR | D | 110 | 6242 | 5108 | 4964 | -2249 | 2251 | -1893 | C |
| ATOM | 8048 | CB | TYR | D | 110 | -28.388 | 15.554 | 89.814 | 1.00 | 42.92 | | C |
| ANISOU | 8048 | CB | TYR | D | 110 | 6035 | 5417 | 4856 | -2264 | 2130 | -2125 | C |
| ATOM | 8051 | CG | TYR | D | 110 | -29.291 | 14.509 | 89.125 | 1.00 | 45.84 | | C |
| ANISOU | 8051 | CG | TYR | D | 110 | 6539 | 5835 | 5042 | -2683 | 2283 | -2427 | C |
| ATOM | 8052 | CD1 | TYR | D | 110 | -30.556 | 14.224 | 89.624 | 1.00 | 47.60 | | C |
| ANISOU | 8052 | CD1 | TYR | D | 110 | 6612 | 6360 | 5115 | -3091 | 2313 | -2671 | C |
| ATOM | 8054 | CE1 | TYR | D | 110 | -31.389 | 13.292 | 89.030 | 1.00 | 50.95 | | C |
| ANISOU | 8054 | CE1 | TYR | D | 110 | 7145 | 6862 | 5351 | -3545 | 2446 | -2958 | C |
| ATOM | 8056 | CZ | TYR | D | 110 | -30.968 | 12.632 | 87.876 | 1.00 | 53.15 | | C |
| ANISOU | 8056 | CZ | TYR | D | 110 | 7725 | 6881 | 5590 | -3562 | 2544 | -3019 | C |
| ATOM | 8057 | OH | TYR | D | 110 | -31.804 | 11.707 | 87.276 | 1.00 | 56.48 | | O |
| ANISOU | 8057 | OH | TYR | D | 110 | 8285 | 7371 | 5804 | -4054 | 2668 | -3328 | O |
| ATOM | 8059 | CE2 | TYR | D | 110 | -29.709 | 12.910 | 87.337 | 1.00 | 50.85 | | C |
| ANISOU | 8059 | CE2 | TYR | D | 110 | 7586 | 6290 | 5444 | -3106 | 2523 | -2781 | C |
| ATOM | 8061 | CD2 | TYR | D | 110 | -28.883 | 13.853 | 87.960 | 1.00 | 46.70 | | C |
| ANISOU | 8061 | CD2 | TYR | D | 110 | 6909 | 5731 | 5106 | -2685 | 2393 | -2484 | C |
| ATOM | 8063 | C | TYR | D | 110 | -26.752 | 13.954 | 90.841 | 1.00 | 45.09 | | C |
| ANISOU | 8063 | C | TYR | D | 110 | 6946 | 4905 | 5281 | -2186 | 2467 | -1749 | C |
| ATOM | 8064 | O | TYR | D | 110 | -25.594 | 14.200 | 90.460 | 1.00 | 45.32 | | O |
| ANISOU | 8064 | O | TYR | D | 110 | 7021 | 4778 | 5420 | -1833 | 2445 | -1540 | O |
| ATOM | 8066 | N | ASP | D | 111 | -27.227 | 12.736 | 91.057 | 1.00 | 48.02 | | N |
| ANISOU | 8066 | N | ASP | D | 111 | 7639 | 5061 | 5545 | -2533 | 2679 | -1867 | N |
| ATOM | 8067 | CA | ASP | D | 111 | -26.451 | 11.526 | 90.952 | 1.00 | 50.55 | | C |
| ANISOU | 8067 | CA | ASP | D | 111 | 8465 | 4874 | 5869 | -2486 | 2904 | -1758 | C |
| ATOM | 8069 | CB | ASP | D | 111 | -26.753 | 10.654 | 92.172 | 1.00 | 53.77 | | C |
| ANISOU | 8069 | CB | ASP | D | 111 | 9178 | 5036 | 6215 | -2763 | 3061 | -1700 | C |
| ATOM | 8072 | CG | ASP | D | 111 | -25.918 | 9.392 | 92.243 | 1.00 | 59.00 | | C |
| ANISOU | 8072 | CG | ASP | D | 111 | 10442 | 5109 | 6865 | -2650 | 3285 | -1550 | C |
| ATOM | 8073 | OD1 | ASP | D | 111 | -25.451 | 8.870 | 91.201 | 1.00 | 60.53 | | O |
| ANISOU | 8073 | OD1 | ASP | D | 111 | 10888 | 5072 | 7040 | -2511 | 3379 | -1611 | O |

FIG. 18 (continued)

| | | | | | | | | | | | | |
|---|---|---|---|---|---|---|---|---|---|---|---|---|
| ATOM | 8074 | OD2 | ASP | D | 111 | -25.759 | 8.890 | 93.372 | 1.00 | 61.90 | | O |
| ANISOU | 8074 | OD2 | ASP | D | 111 | 11065 | 5238 | 7218 | -2688 | 3372 | -1376 | O |
| ATOM | 8075 | C | ASP | D | 111 | -26.923 | 10.889 | 89.668 | 1.00 | 52.17 | | C |
| ANISOU | 8075 | C | ASP | D | 111 | 8846 | 5039 | 5937 | -2711 | 3004 | -2032 | C |
| ATOM | 8076 | O | ASP | D | 111 | -27.996 | 10.295 | 89.626 | 1.00 | 53.19 | | O |
| ANISOU | 8076 | O | ASP | D | 111 | 9067 | 5235 | 5908 | -3193 | 3090 | -2287 | O |
| ATOM | 8078 | N | TYR | D | 112 | -26.143 | 11.026 | 88.601 | 1.00 | 52.79 | | N |
| ANISOU | 8078 | N | TYR | D | 112 | 8955 | 5049 | 6052 | -2395 | 2993 | -1994 | N |
| ATOM | 8079 | CA | TYR | D | 112 | -26.490 | 10.338 | 87.329 | 1.00 | 56.82 | | C |
| ANISOU | 8079 | CA | TYR | D | 112 | 9691 | 5487 | 6410 | -2584 | 3101 | -2259 | C |
| ATOM | 8081 | CB | TYR | D | 112 | -25.584 | 10.798 | 86.202 | 1.00 | 58.28 | | C |
| ANISOU | 8081 | CB | TYR | D | 112 | 9796 | 5713 | 6635 | -2175 | 3053 | -2184 | C |
| ATOM | 8084 | CG | TYR | D | 112 | -25.797 | 12.222 | 85.816 | 1.00 | 55.98 | | C |
| ANISOU | 8084 | CG | TYR | D | 112 | 8993 | 5900 | 6377 | -2040 | 2794 | -2169 | C |
| ATOM | 8085 | CD1 | TYR | D | 112 | -26.991 | 12.642 | 85.234 | 1.00 | 57.17 | | C |
| ANISOU | 8085 | CD1 | TYR | D | 112 | 8893 | 6446 | 6384 | -2312 | 2660 | -2445 | C |
| ATOM | 8087 | CE1 | TYR | D | 112 | -27.170 | 13.989 | 84.860 | 1.00 | 55.51 | | C |
| ANISOU | 8087 | CE1 | TYR | D | 112 | 8271 | 6638 | 6183 | -2120 | 2406 | -2413 | C |
| ATOM | 8089 | CZ | TYR | D | 112 | -26.138 | 14.889 | 85.062 | 1.00 | 52.58 | | C |
| ANISOU | 8089 | CZ | TYR | D | 112 | 7772 | 6237 | 5967 | -1730 | 2304 | -2110 | C |
| ATOM | 8090 | OH | TYR | D | 112 | -26.246 | 16.224 | 84.721 | 1.00 | 52.17 | | O |
| ANISOU | 8090 | OH | TYR | D | 112 | 7411 | 6498 | 5915 | -1547 | 2059 | -2053 | O |
| ATOM | 8092 | CE2 | TYR | D | 112 | -24.952 | 14.476 | 85.628 | 1.00 | 52.66 | | C |
| ANISOU | 8092 | CE2 | TYR | D | 112 | 7980 | 5909 | 6120 | -1517 | 2440 | -1851 | C |
| ATOM | 8094 | CD2 | TYR | D | 112 | -24.790 | 13.157 | 86.003 | 1.00 | 54.22 | | C |
| ANISOU | 8094 | CD2 | TYR | D | 112 | 8555 | 5740 | 6305 | -1635 | 2676 | -1879 | C |
| ATOM | 8096 | C | TYR | D | 112 | -26.455 | 8.815 | 87.377 | 1.00 | 60.26 | | C |
| ANISOU | 8096 | C | TYR | D | 112 | 10750 | 5403 | 6742 | -2810 | 3372 | -2340 | C |
| ATOM | 8097 | O | TYR | D | 112 | -26.968 | 8.159 | 86.469 | 1.00 | 62.67 | | O |
| ANISOU | 8097 | O | TYR | D | 112 | 11284 | 5642 | 6886 | -3094 | 3467 | -2614 | O |
| ATOM | 8099 | N | LYS | D | 113 | -25.845 | 8.249 | 88.414 | 1.00 | 60.05 | | N |
| ANISOU | 8099 | N | LYS | D | 113 | 11037 | 4992 | 6786 | -2679 | 3488 | -2104 | N |
| ATOM | 8100 | CA | LYS | D | 113 | -25.760 | 6.805 | 88.562 | 1.00 | 63.90 | | C |
| ANISOU | 8100 | CA | LYS | D | 113 | 12210 | 4905 | 7163 | -2848 | 3742 | -2141 | C |
| ATOM | 8102 | CB | LYS | D | 113 | -24.560 | 6.450 | 89.450 | 1.00 | 65.12 | | C |
| ANISOU | 8102 | CB | LYS | D | 113 | 12647 | 4667 | 7429 | -2376 | 3816 | -1783 | C |
| ATOM | 8105 | CG | LYS | D | 113 | -23.931 | 5.101 | 89.154 | 1.00 | 70.79 | | C |
| ANISOU | 8105 | CG | LYS | D | 113 | 14099 | 4745 | 8052 | -2208 | 4057 | -1771 | C |
| ATOM | 8108 | CD | LYS | D | 113 | -23.374 | 4.449 | 90.424 | 1.00 | 72.99 | | C |
| ANISOU | 8108 | CD | LYS | D | 113 | 14789 | 4598 | 8345 | -2016 | 4152 | -1478 | C |
| ATOM | 8111 | CE | LYS | D | 113 | -22.686 | 3.117 | 90.122 | 1.00 | 77.95 | | C |
| ANISOU | 8111 | CE | LYS | D | 113 | 16205 | 4549 | 8863 | -1742 | 4381 | -1454 | C |
| ATOM | 8114 | NZ | LYS | D | 113 | -22.381 | 2.377 | 91.388 | 1.00 | 81.02 | | N |
| ANISOU | 8114 | NZ | LYS | D | 113 | 17091 | 4484 | 9209 | -1643 | 4476 | -1190 | N |
| ATOM | 8118 | C | LYS | D | 113 | -27.078 | 6.234 | 89.142 | 1.00 | 66.58 | | C |
| ANISOU | 8118 | C | LYS | D | 113 | 12703 | 5251 | 7344 | -3547 | 3824 | -2349 | C |
| ATOM | 8119 | O | LYS | D | 113 | -27.599 | 5.199 | 88.662 | 1.00 | 69.14 | | O |
| ANISOU | 8119 | O | LYS | D | 113 | 13495 | 5287 | 7490 | -3962 | 3996 | -2586 | O |
| ATOM | 8121 | N | GLU | D | 114 | -27.612 | 6.906 | 90.164 | 1.00 | 62.87 | | N |
| ANISOU | 8121 | N | GLU | D | 114 | 11848 | 5124 | 6918 | -3699 | 3708 | -2273 | N |
| ATOM | 8122 | CA | GLU | D | 114 | -28.892 | 6.540 | 90.760 | 1.00 | 66.67 | | C |
| ANISOU | 8122 | CA | GLU | D | 114 | 12337 | 5761 | 7234 | -4366 | 3775 | -2466 | C |
| ATOM | 8124 | CB | GLU | D | 114 | -28.821 | 6.646 | 92.280 | 1.00 | 66.50 | | C |
| ANISOU | 8124 | CB | GLU | D | 114 | 12305 | 5702 | 7258 | -4362 | 3784 | -2214 | C |
| ATOM | 8127 | CG | GLU | D | 114 | -27.749 | 5.750 | 92.900 | 1.00 | 69.36 | | C |
| ANISOU | 8127 | CG | GLU | D | 114 | 13302 | 5393 | 7658 | -4063 | 3944 | -1908 | C |
| ATOM | 8130 | CD | GLU | D | 114 | -28.288 | 4.471 | 93.528 | 1.00 | 75.92 | | C |
| ANISOU | 8130 | CD | GLU | D | 114 | 14781 | 5776 | 8288 | -4600 | 4188 | -1937 | C |
| ATOM | 8131 | OE1 | GLU | D | 114 | -29.222 | 3.831 | 92.984 | 1.00 | 79.30 | | O |
| ANISOU | 8131 | OE1 | GLU | D | 114 | 15417 | 6183 | 8533 | -5204 | 4310 | -2241 | O |
| ATOM | 8132 | OE2 | GLU | D | 114 | -27.759 | 4.104 | 94.598 | 1.00 | 79.10 | | O |
| ANISOU | 8132 | OE2 | GLU | D | 114 | 15508 | 5848 | 8700 | -4433 | 4256 | -1645 | O |
| ATOM | 8133 | C | GLU | D | 114 | -30.075 | 7.354 | 90.223 | 1.00 | 65.49 | | C |
| ANISOU | 8133 | C | GLU | D | 114 | 11578 | 6307 | 6997 | -4684 | 3608 | -2774 | C |
| ATOM | 8134 | O | GLU | D | 114 | -31.233 | 6.991 | 90.449 | 1.00 | 69.74 | | O |
| ANISOU | 8134 | O | GLU | D | 114 | 12071 | 7074 | 7353 | -5293 | 3674 | -3010 | O |
| ATOM | 8136 | N | ASN | D | 115 | -29.784 | 8.423 | 89.492 | 1.00 | 61.81 | | N |
| ANISOU | 8136 | N | ASN | D | 115 | 10662 | 6187 | 6636 | -4276 | 3397 | -2771 | N |
| ATOM | 8137 | CA | ASN | D | 115 | -30.808 | 9.280 | 88.879 | 1.00 | 60.27 | | C |
| ANISOU | 8137 | CA | ASN | D | 115 | 9900 | 6651 | 6348 | -4440 | 3204 | -3040 | C |
| ATOM | 8139 | CB | ASN | D | 115 | -31.514 | 8.575 | 87.708 | 1.00 | 64.82 | | C |
| ANISOU | 8139 | CB | ASN | D | 115 | 10629 | 7289 | 6711 | -4864 | 3280 | -3395 | C |
| ATOM | 8142 | CG | ASN | D | 115 | -30.789 | 8.780 | 86.385 | 1.00 | 63.31 | | C |
| ANISOU | 8142 | CG | ASN | D | 115 | 10496 | 7005 | 6553 | -4473 | 3221 | -3402 | C |
| ATOM | 8143 | OD1 | ASN | D | 115 | -30.465 | 7.815 | 85.689 | 1.00 | 67.18 | | O |
| ANISOU | 8143 | OD1 | ASN | D | 115 | 11474 | 7090 | 6960 | -4569 | 3391 | -3497 | O |
| ATOM | 8144 | ND2 | ASN | D | 115 | -30.536 | 10.040 | 86.028 | 1.00 | 57.85 | | N |
| ANISOU | 8144 | ND2 | ASN | D | 115 | 9341 | 6679 | 5961 | -4037 | 2986 | -3305 | N |
| ATOM | 8147 | C | ASN | D | 115 | -31.776 | 9.812 | 89.918 | 1.00 | 59.31 | | C |

FIG. 18 (continued)

| | | | | | | | | | | | | |
|---|---|---|---|---|---|---|---|---|---|---|---|---|
| ANISOU | 8147 | C | ASN | D | 115 | 9364 | 6996 | 6175 | -4695 | 3123 | -3097 | C |
| ATOM | 8148 | O | ASN | D | 115 | -33.008 | 9.625 | 89.866 | 1.00 | 59.72 | | O |
| ANISOU | 8148 | O | ASN | D | 115 | 9209 | 7456 | 6028 | -5209 | 3137 | -3394 | O |
| ATOM | 8150 | N | ARG | D | 116 | -31.156 | 10.473 | 90.886 | 1.00 | 55.21 | | N |
| ANISOU | 8150 | N | ARG | D | 116 | 8719 | 6434 | 5824 | -4321 | 3041 | -2811 | N |
| ATOM | 8151 | CA | ARG | D | 116 | -31.861 | 11.178 | 91.909 | 1.00 | 54.92 | | C |
| ANISOU | 8151 | CA | ARG | D | 116 | 8272 | 6832 | 5762 | -4406 | 2939 | -2825 | C |
| ATOM | 8153 | CB | ARG | D | 116 | -32.158 | 10.247 | 93.089 | 1.00 | 57.46 | | C |
| ANISOU | 8153 | CB | ARG | D | 116 | 8906 | 6937 | 5991 | -4832 | 3160 | -2768 | C |
| ATOM | 8156 | CG | ARG | D | 116 | -30.933 | 9.769 | 93.872 | 1.00 | 56.88 | | C |
| ANISOU | 8156 | CG | ARG | D | 116 | 9304 | 6251 | 6057 | -4542 | 3269 | -2398 | C |
| ATOM | 8159 | CD | ARG | D | 116 | -31.259 | 8.495 | 94.619 | 1.00 | 61.09 | | C |
| ANISOU | 8159 | CD | ARG | D | 116 | 10347 | 6431 | 6434 | -5048 | 3534 | -2380 | C |
| ATOM | 8162 | NE | ARG | D | 116 | -30.146 | 7.972 | 95.408 | 1.00 | 61.14 | | N |
| ANISOU | 8162 | NE | ARG | D | 116 | 10837 | 5861 | 6533 | -4747 | 3632 | -2022 | N |
| ATOM | 8164 | CZ | ARG | D | 116 | -30.107 | 6.742 | 95.933 | 1.00 | 66.38 | | C |
| ANISOU | 8164 | CZ | ARG | D | 116 | 12131 | 6021 | 7071 | -5055 | 3870 | -1931 | C |
| ATOM | 8165 | NH1 | ARG | D | 116 | -31.106 | 5.871 | 95.736 | 1.00 | 70.70 | | N |
| ANISOU | 8165 | NH1 | ARG | D | 116 | 12933 | 6534 | 7395 | -5745 | 4054 | -2179 | N |
| ATOM | 8168 | NH2 | ARG | D | 116 | -29.053 | 6.362 | 96.645 | 1.00 | 66.98 | | N |
| ANISOU | 8168 | NH2 | ARG | D | 116 | 12611 | 5617 | 7221 | -4679 | 3922 | -1589 | N |
| ATOM | 8171 | C | ARG | D | 116 | -31.038 | 12.393 | 92.346 | 1.00 | 50.03 | | C |
| ANISOU | 8171 | C | ARG | D | 116 | 7397 | 6266 | 5347 | -3812 | 2731 | -2561 | C |
| ATOM | 8172 | O | ARG | D | 116 | -29.788 | 12.420 | 92.276 | 1.00 | 45.53 | | O |
| ANISOU | 8172 | O | ARG | D | 116 | 7054 | 5304 | 4944 | -3416 | 2731 | -2291 | O |
| ATOM | 8174 | N | PHE | D | 117 | -31.767 | 13.412 | 92.772 | 1.00 | 50.90 | | N |
| ANISOU | 8174 | N | PHE | D | 117 | 7023 | 6895 | 5421 | -3760 | 2551 | -2660 | N |
| ATOM | 8175 | CA | PHE | D | 117 | -31.178 | 14.538 | 93.462 | 1.00 | 48.16 | | C |
| ANISOU | 8175 | CA | PHE | D | 117 | 6469 | 6604 | 5225 | -3307 | 2366 | -2442 | C |
| ATOM | 8177 | CB | PHE | D | 117 | -32.169 | 15.701 | 93.498 | 1.00 | 48.26 | | C |
| ANISOU | 8177 | CB | PHE | D | 117 | 5958 | 7230 | 5150 | -3216 | 2144 | -2648 | C |
| ATOM | 8180 | CG | PHE | D | 117 | -32.494 | 16.241 | 92.140 | 1.00 | 48.56 | | C |
| ANISOU | 8180 | CG | PHE | D | 117 | 5792 | 7524 | 5135 | -3070 | 1983 | -2823 | C |
| ATOM | 8181 | CD1 | PHE | D | 117 | -31.664 | 17.166 | 91.539 | 1.00 | 46.45 | | C |
| ANISOU | 8181 | CD1 | PHE | D | 117 | 5514 | 7133 | 5003 | -2605 | 1797 | -2655 | C |
| ATOM | 8183 | CE1 | PHE | D | 117 | -31.954 | 17.652 | 90.264 | 1.00 | 47.46 | | C |
| ANISOU | 8183 | CE1 | PHE | D | 117 | 5497 | 7483 | 5053 | -2468 | 1650 | -2794 | C |
| ATOM | 8185 | CZ | PHE | D | 117 | -33.094 | 17.233 | 89.608 | 1.00 | 48.88 | | C |
| ANISOU | 8185 | CZ | PHE | D | 117 | 5499 | 8052 | 5019 | -2774 | 1668 | -3120 | C |
| ATOM | 8187 | CE2 | PHE | D | 117 | -33.919 | 16.324 | 90.194 | 1.00 | 52.04 | | C |
| ANISOU | 8187 | CE2 | PHE | D | 117 | 5874 | 8610 | 5290 | -3262 | 1847 | -3306 | C |
| ATOM | 8189 | CD2 | PHE | D | 117 | -33.627 | 15.829 | 91.463 | 1.00 | 51.81 | | C |
| ANISOU | 8189 | CD2 | PHE | D | 117 | 6026 | 8322 | 5337 | -3422 | 2013 | -3152 | C |
| ATOM | 8191 | C | PHE | D | 117 | -30.787 | 14.099 | 94.875 | 1.00 | 48.89 | | C |
| ANISOU | 8191 | C | PHE | D | 117 | 6781 | 6442 | 5354 | -3374 | 2492 | -2225 | C |
| ATOM | 8192 | O | PHE | D | 117 | -31.400 | 13.201 | 95.434 | 1.00 | 49.97 | | O |
| ANISOU | 8192 | O | PHE | D | 117 | 7081 | 6555 | 5351 | -3815 | 2685 | -2307 | O |
| ATOM | 8194 | N | ILE | D | 118 | -29.740 | 14.720 | 95.420 | 1.00 | 47.32 | | N |
| ANISOU | 8194 | N | ILE | D | 118 | 6603 | 6054 | 5323 | -2959 | 2383 | -1942 | N |
| ATOM | 8195 | CA | ILE | D | 118 | -29.320 | 14.505 | 96.797 | 1.00 | 47.01 | | C |
| ANISOU | 8195 | CA | ILE | D | 118 | 6718 | 5840 | 5306 | -2946 | 2448 | -1722 | C |
| ATOM | 8197 | CB | ILE | D | 118 | -27.891 | 13.939 | 96.918 | 1.00 | 47.31 | | C |
| ANISOU | 8197 | CB | ILE | D | 118 | 7144 | 5353 | 5478 | -2679 | 2525 | -1397 | C |
| ATOM | 8199 | CG1 | ILE | D | 118 | -27.701 | 12.691 | 96.062 | 1.00 | 49.81 | | C |
| ANISOU | 8199 | CG1 | ILE | D | 118 | 7877 | 5292 | 5755 | -2835 | 2737 | -1432 | C |
| ATOM | 8202 | CD1 | ILE | D | 118 | -26.232 | 12.244 | 95.913 | 1.00 | 49.39 | | C |
| ANISOU | 8202 | CD1 | ILE | D | 118 | 8150 | 4788 | 5829 | -2442 | 2789 | -1142 | C |
| ATOM | 8206 | CG2 | ILE | D | 118 | -27.608 | 13.585 | 98.364 | 1.00 | 48.45 | | C |
| ANISOU | 8206 | CG2 | ILE | D | 118 | 7471 | 5348 | 5590 | -2709 | 2599 | -1189 | C |
| ATOM | 8210 | C | ILE | D | 118 | -29.368 | 15.860 | 97.532 | 1.00 | 45.04 | | C |
| ANISOU | 8210 | C | ILE | D | 118 | 6099 | 5913 | 5100 | -2672 | 2216 | -1689 | C |
| ATOM | 8211 | O | ILE | D | 118 | -28.919 | 16.885 | 97.006 | 1.00 | 41.39 | | O |
| ANISOU | 8211 | O | ILE | D | 118 | 5455 | 5521 | 4748 | -2326 | 2008 | -1649 | O |
| ATOM | 8213 | N | GLU | D | 119 | -29.987 | 15.830 | 98.707 | 1.00 | 46.06 | | N |
| ANISOU | 8213 | N | GLU | D | 119 | 6148 | 6239 | 5113 | -2865 | 2264 | -1727 | N |
| ATOM | 8214 | CA | GLU | D | 119 | -30.020 | 16.926 | 99.676 | 1.00 | 44.99 | | C |
| ANISOU | 8214 | CA | GLU | D | 119 | 5755 | 6355 | 4983 | -2636 | 2087 | -1692 | C |
| ATOM | 8216 | CB | GLU | D | 119 | -31.459 | 17.139 | 100.187 | 1.00 | 46.74 | | C |
| ANISOU | 8216 | CB | GLU | D | 119 | 5655 | 7110 | 4994 | -2899 | 2111 | -1985 | C |
| ATOM | 8219 | CG | GLU | D | 119 | -31.664 | 18.288 | 101.215 | 1.00 | 47.51 | | C |
| ANISOU | 8219 | CG | GLU | D | 119 | 5485 | 7514 | 5052 | -2649 | 1938 | -2011 | C |
| ATOM | 8222 | CD | GLU | D | 119 | -31.211 | 19.650 | 100.693 | 1.00 | 46.09 | | C |
| ANISOU | 8222 | CD | GLU | D | 119 | 5150 | 7355 | 5007 | -2170 | 1645 | -1999 | C |
| ATOM | 8223 | OE1 | GLU | D | 119 | -31.295 | 19.881 | 99.476 | 1.00 | 49.40 | | O |
| ANISOU | 8223 | OE1 | GLU | D | 119 | 5500 | 7794 | 5474 | -2073 | 1563 | -2090 | O |
| ATOM | 8224 | OE2 | GLU | D | 119 | -30.751 | 20.493 | 101.483 | 1.00 | 42.99 | | O |
| ANISOU | 8224 | OE2 | GLU | D | 119 | 4739 | 6940 | 4656 | -1909 | 1496 | -1895 | O |
| ATOM | 8225 | C | GLU | D | 119 | -29.097 | 16.502 | 100.811 | 1.00 | 43.12 | | C |
| ANISOU | 8225 | C | GLU | D | 119 | 5805 | 5792 | 4788 | -2574 | 2159 | -1388 | C |

FIG. 18 (continued)

| | | | | | | | | | | | | |
|---|---|---|---|---|---|---|---|---|---|---|---|---|
| ATOM | 8226 | O | GLU | D | 119 | -29.379 | 15.517 | 101.488 | 1.00 | 47.17 | | O |
| ANISOU | 8226 | O | GLU | D | 119 | 6547 | 6199 | 5176 | -2887 | 2366 | -1349 | O |
| ATOM | 8228 | N | ILE | D | 120 | -27.994 | 17.237 | 100.974 | 1.00 | 39.74 | | N |
| ANISOU | 8228 | N | ILE | D | 120 | 5372 | 5214 | 4512 | -2187 | 1983 | -1171 | N |
| ATOM | 8229 | CA | ILE | D | 120 | -26.963 | 16.959 | 101.960 | 1.00 | 40.48 | | C |
| ANISOU | 8229 | CA | ILE | D | 120 | 5688 | 5045 | 4646 | -2051 | 1999 | -869 | C |
| ATOM | 8231 | CB | ILE | D | 120 | -25.551 | 17.135 | 101.358 | 1.00 | 39.47 | | C |
| ANISOU | 8231 | CB | ILE | D | 120 | 5650 | 4644 | 4704 | -1708 | 1904 | -632 | C |
| ATOM | 8233 | CG1 | ILE | D | 120 | -25.238 | 16.006 | 100.375 | 1.00 | 41.46 | | C |
| ANISOU | 8233 | CG1 | ILE | D | 120 | 6181 | 4585 | 4987 | -1761 | 2093 | -596 | C |
| ATOM | 8236 | CD1 | ILE | D | 120 | -24.019 | 16.294 | 99.514 | 1.00 | 39.46 | | C |
| ANISOU | 8236 | CD1 | ILE | D | 120 | 5919 | 4184 | 4892 | -1427 | 2007 | -433 | C |
| ATOM | 8240 | CG2 | ILE | D | 120 | -24.495 | 17.197 | 102.472 | 1.00 | 39.17 | | C |
| ANISOU | 8240 | CG2 | ILE | D | 120 | 5708 | 4484 | 4689 | -1507 | 1839 | -343 | C |
| ATOM | 8244 | C | ILE | D | 120 | -27.122 | 17.910 | 103.162 | 1.00 | 40.12 | | C |
| ANISOU | 8244 | C | ILE | D | 120 | 5443 | 5261 | 4540 | -1954 | 1845 | -872 | C |
| ATOM | 8245 | O | ILE | D | 120 | -27.431 | 19.085 | 102.974 | 1.00 | 40.55 | | O |
| ANISOU | 8245 | O | ILE | D | 120 | 5223 | 5566 | 4619 | -1794 | 1646 | -1020 | O |
| ATOM | 8247 | N | GLY | D | 121 | -26.976 | 17.384 | 104.382 | 1.00 | 41.10 | | N |
| ANISOU | 8247 | N | GLY | D | 121 | 5739 | 5318 | 4557 | -2051 | 1940 | -724 | N |
| ATOM | 8248 | CA | GLY | D | 121 | -26.952 | 18.209 | 105.577 | 1.00 | 39.08 | | C |
| ANISOU | 8248 | CA | GLY | D | 121 | 5345 | 5273 | 4229 | -1940 | 1798 | -700 | C |
| ATOM | 8251 | C | GLY | D | 121 | -25.801 | 17.889 | 106.502 | 1.00 | 37.78 | | C |
| ANISOU | 8251 | C | GLY | D | 121 | 5407 | 4876 | 4071 | -1790 | 1778 | -376 | C |
| ATOM | 8252 | O | GLY | D | 121 | -25.329 | 16.757 | 106.544 | 1.00 | 39.35 | | O |
| ANISOU | 8252 | O | GLY | D | 121 | 5921 | 4775 | 4254 | -1843 | 1942 | -179 | O |
| ATOM | 8254 | N | VAL | D | 122 | -25.368 | 18.894 | 107.262 | 1.00 | 36.46 | | N |
| ANISOU | 8254 | N | VAL | D | 122 | 5098 | 4851 | 3904 | -1591 | 1566 | -331 | N |
| ATOM | 8255 | CA | VAL | D | 122 | -24.340 | 18.724 | 108.269 | 1.00 | 36.50 | | C |
| ANISOU | 8255 | CA | VAL | D | 122 | 5255 | 4740 | 3874 | -1450 | 1508 | -49 | C |
| ATOM | 8257 | CB | VAL | D | 122 | -22.981 | 19.424 | 107.880 | 1.00 | 34.26 | | C |
| ANISOU | 8257 | CB | VAL | D | 122 | 4887 | 4361 | 3770 | -1144 | 1283 | 125 | C |
| ATOM | 8259 | CG1 | VAL | D | 122 | -21.909 | 19.099 | 108.889 | 1.00 | 32.92 | | C |
| ANISOU | 8259 | CG1 | VAL | D | 122 | 4846 | 4125 | 3537 | -1000 | 1228 | 418 | C |
| ATOM | 8263 | CG2 | VAL | D | 122 | -22.493 | 19.057 | 106.416 | 1.00 | 32.44 | | C |
| ANISOU | 8263 | CG2 | VAL | D | 122 | 4683 | 3921 | 3722 | -1056 | 1338 | 170 | C |
| ATOM | 8267 | C | VAL | D | 122 | -24.884 | 19.324 | 109.576 | 1.00 | 37.96 | | C |
| ANISOU | 8267 | C | VAL | D | 122 | 5341 | 5211 | 3870 | -1511 | 1439 | -145 | C |
| ATOM | 8268 | O | VAL | D | 122 | -25.423 | 20.435 | 109.575 | 1.00 | 36.80 | | O |
| ANISOU | 8268 | O | VAL | D | 122 | 4957 | 5311 | 3716 | -1456 | 1291 | -377 | O |
| ATOM | 8270 | N | THR | D | 123 | -24.723 | 18.596 | 110.679 | 1.00 | 40.96 | | N |
| ANISOU | 8270 | N | THR | D | 123 | 5935 | 5550 | 4080 | -1594 | 1544 | 35 | N |
| ATOM | 8271 | CA | THR | D | 123 | -25.297 | 18.980 | 111.974 | 1.00 | 42.18 | | C |
| ANISOU | 8271 | CA | THR | D | 123 | 6032 | 5990 | 4005 | -1688 | 1528 | -51 | C |
| ATOM | 8273 | CB | THR | D | 123 | -26.639 | 18.195 | 112.279 | 1.00 | 45.16 | | C |
| ANISOU | 8273 | CB | THR | D | 123 | 6466 | 6527 | 4165 | -2073 | 1811 | -204 | C |
| ATOM | 8275 | OG1 | THR | D | 123 | -27.230 | 18.695 | 113.484 | 1.00 | 44.01 | | O |
| ANISOU | 8275 | OG1 | THR | D | 123 | 6209 | 6731 | 3783 | -2140 | 1796 | -321 | O |
| ATOM | 8277 | CG2 | THR | D | 123 | -26.427 | 16.668 | 112.426 | 1.00 | 47.48 | | C |
| ANISOU | 8277 | CG2 | THR | D | 123 | 7177 | 6491 | 4371 | -2275 | 2061 | 52 | C |
| ATOM | 8281 | C | THR | D | 123 | -24.298 | 18.780 | 113.115 | 1.00 | 43.69 | | C |
| ANISOU | 8281 | C | THR | D | 123 | 6403 | 6107 | 4089 | -1552 | 1446 | 243 | C |
| ATOM | 8282 | O | THR | D | 123 | -23.466 | 17.885 | 113.058 | 1.00 | 44.42 | | O |
| ANISOU | 8282 | O | THR | D | 123 | 6742 | 5923 | 4212 | -1466 | 1507 | 526 | O |
| ATOM | 8284 | N | ARG | D | 124 | -24.386 | 19.634 | 114.135 | 1.00 | 43.73 | | N |
| ANISOU | 8284 | N | ARG | D | 124 | 6288 | 6376 | 3952 | -1501 | 1297 | 162 | N |
| ATOM | 8285 | CA | ARG | D | 124 | -23.655 | 19.460 | 115.397 | 1.00 | 47.85 | | C |
| ANISOU | 8285 | CA | ARG | D | 124 | 6965 | 6921 | 4295 | -1419 | 1223 | 400 | C |
| ATOM | 8287 | CB | ARG | D | 124 | -23.190 | 20.797 | 115.950 | 1.00 | 46.96 | | C |
| ANISOU | 8287 | CB | ARG | D | 124 | 6661 | 7011 | 4171 | -1244 | 925 | 307 | C |
| ATOM | 8290 | CG | ARG | D | 124 | -22.295 | 21.561 | 115.039 | 1.00 | 45.42 | | C |
| ANISOU | 8290 | CG | ARG | D | 124 | 6321 | 6700 | 4236 | -1053 | 702 | 322 | C |
| ATOM | 8293 | CD | ARG | D | 124 | -22.711 | 23.015 | 115.063 | 1.00 | 45.07 | | C |
| ANISOU | 8293 | CD | ARG | D | 124 | 6091 | 6835 | 4201 | -1011 | 501 | 21 | C |
| ATOM | 8296 | NE | ARG | D | 124 | -23.282 | 23.388 | 113.807 | 1.00 | 42.93 | | N |
| ANISOU | 8296 | NE | ARG | D | 124 | 5700 | 6498 | 4114 | -1006 | 523 | -177 | N |
| ATOM | 8298 | CZ | ARG | D | 124 | -23.889 | 24.541 | 113.569 | 1.00 | 42.45 | | C |
| ANISOU | 8298 | CZ | ARG | D | 124 | 5518 | 6549 | 4064 | -938 | 390 | -464 | C |
| ATOM | 8299 | NH1 | ARG | D | 124 | -24.047 | 25.461 | 114.516 | 1.00 | 41.94 | | N |
| ANISOU | 8299 | NH1 | ARG | D | 124 | 5448 | 6652 | 3837 | -876 | 234 | -619 | N |
| ATOM | 8302 | NH2 | ARG | D | 124 | -24.357 | 24.758 | 112.356 | 1.00 | 41.22 | | N |
| ANISOU | 8302 | NH2 | ARG | D | 124 | 5271 | 6326 | 4063 | -909 | 412 | -604 | N |
| ATOM | 8305 | C | ARG | D | 124 | -24.516 | 18.810 | 116.486 | 1.00 | 50.53 | | C |
| ANISOU | 8305 | C | ARG | D | 124 | 7465 | 7413 | 4321 | -1672 | 1436 | 396 | C |
| ATOM | 8306 | O | ARG | D | 124 | -24.027 | 18.622 | 117.598 | 1.00 | 51.97 | | O |
| ANISOU | 8306 | O | ARG | D | 124 | 7802 | 7638 | 4306 | -1620 | 1390 | 592 | O |
| ATOM | 8308 | N | ARG | D | 125 | -25.777 | 18.495 | 116.172 | 1.00 | 52.62 | | N |
| ANISOU | 8308 | N | ARG | D | 125 | 7678 | 7800 | 4517 | -1958 | 1662 | 174 | N |
| ATOM | 8309 | CA | ARG | D | 125 | -26.701 | 17.844 | 117.113 | 1.00 | 58.19 | | C |

FIG. 18 (continued)

| | | | | | | | | | | | | |
|---|---|---|---|---|---|---|---|---|---|---|---|---|
| ANISOU | 8309 | CA | ARG | D | 125 | 8512 | 8694 | 4902 | -2284 | 1906 | 152 | C |
| ATOM | 8311 | CB | ARG | D | 125 | -28.020 | 18.617 | 117.170 | 1.00 | 58.97 | | C |
| ANISOU | 8311 | CB | ARG | D | 125 | 8260 | 9258 | 4890 | -2426 | 1951 | -253 | C |
| ATOM | 8314 | CG | ARG | D | 125 | -27.839 | 20.088 | 117.451 | 1.00 | 59.01 | | C |
| ANISOU | 8314 | CG | ARG | D | 125 | 7999 | 9492 | 4932 | -2112 | 1663 | -451 | C |
| ATOM | 8317 | CD | ARG | D | 125 | -29.128 | 20.808 | 117.750 | 1.00 | 62.38 | | C |
| ANISOU | 8317 | CD | ARG | D | 125 | 8120 | 10407 | 5175 | -2175 | 1714 | -840 | C |
| ATOM | 8320 | NE | ARG | D | 125 | -29.306 | 20.988 | 119.197 | 1.00 | 68.16 | | N |
| ANISOU | 8320 | NE | ARG | D | 125 | 8893 | 11425 | 5581 | -2209 | 1737 | -849 | N |
| ATOM | 8322 | CZ | ARG | D | 125 | -30.239 | 20.409 | 119.963 | 1.00 | 72.14 | | C |
| ANISOU | 8322 | CZ | ARG | D | 125 | 9391 | 12255 | 5765 | -2524 | 2003 | -911 | C |
| ATOM | 8323 | NH1 | ARG | D | 125 | -31.151 | 19.570 | 119.462 | 1.00 | 73.89 | | N |
| ANISOU | 8323 | NH1 | ARG | D | 125 | 9561 | 12581 | 5933 | -2889 | 2284 | -982 | N |
| ATOM | 8326 | NH2 | ARG | D | 125 | -30.260 | 20.686 | 121.269 | 1.00 | 74.96 | | N |
| ANISOU | 8326 | NH2 | ARG | D | 125 | 9794 | 12865 | 5824 | -2504 | 1991 | -911 | N |
| ATOM | 8329 | C | ARG | D | 125 | -26.944 | 16.392 | 116.675 | 1.00 | 60.39 | | C |
| ANISOU | 8329 | C | ARG | D | 125 | 9127 | 8666 | 5152 | -2575 | 2197 | 314 | C |
| ATOM | 8330 | O | ARG | D | 125 | -26.346 | 15.931 | 115.705 | 1.00 | 59.45 | | O |
| ANISOU | 8330 | O | ARG | D | 125 | 9140 | 8192 | 5257 | -2464 | 2192 | 435 | O |
| ATOM | 8332 | N | GLU | D | 126 | -27.808 | 15.683 | 117.398 | 1.00 | 63.77 | | N |
| ANISOU | 8332 | N | GLU | D | 126 | 9718 | 9228 | 5284 | -2959 | 2455 | 310 | N |
| ATOM | 8333 | CA | GLU | D | 126 | -28.166 | 14.294 | 117.070 | 1.00 | 67.01 | | C |
| ANISOU | 8333 | CA | GLU | D | 126 | 10515 | 9331 | 5613 | -3330 | 2754 | 442 | C |
| ATOM | 8335 | CB | GLU | D | 126 | -29.205 | 13.790 | 118.077 | 1.00 | 73.10 | | C |
| ANISOU | 8335 | CB | GLU | D | 126 | 11394 | 10381 | 5999 | -3806 | 3020 | 402 | C |
| ATOM | 8338 | CG | GLU | D | 126 | -28.770 | 13.855 | 119.527 | 1.00 | 75.82 | | C |
| ANISOU | 8338 | CG | GLU | D | 126 | 11916 | 10819 | 6072 | -3699 | 2967 | 627 | C |
| ATOM | 8341 | CD | GLU | D | 126 | -28.207 | 12.547 | 120.028 | 1.00 | 80.87 | | C |
| ANISOU | 8341 | CD | GLU | D | 126 | 13203 | 10986 | 6537 | -3798 | 3118 | 1048 | C |
| ATOM | 8342 | OE1 | GLU | D | 126 | -27.401 | 11.942 | 119.282 | 1.00 | 80.61 | | O |
| ANISOU | 8342 | OE1 | GLU | D | 126 | 13462 | 10452 | 6713 | -3593 | 3082 | 1251 | O |
| ATOM | 8343 | OE2 | GLU | D | 126 | -28.571 | 12.134 | 121.165 | 1.00 | 84.10 | | O |
| ANISOU | 8343 | OE2 | GLU | D | 126 | 13846 | 11529 | 6581 | -4057 | 3273 | 1176 | O |
| ATOM | 8344 | C | GLU | D | 126 | -28.759 | 14.233 | 115.675 | 1.00 | 64.87 | | C |
| ANISOU | 8344 | C | GLU | D | 126 | 10063 | 9031 | 5553 | -3482 | 2827 | 193 | C |
| ATOM | 8345 | O | GLU | D | 126 | -29.687 | 14.991 | 115.397 | 1.00 | 63.19 | | O |
| ANISOU | 8345 | O | GLU | D | 126 | 9415 | 9255 | 5338 | -3579 | 2810 | -154 | O |
| ATOM | 8347 | N | VAL | D | 127 | -28.237 | 13.347 | 114.810 | 1.00 | 64.37 | | N |
| ANISOU | 8347 | N | VAL | D | 127 | 10334 | 8479 | 5646 | -3472 | 2902 | 357 | N |
| ATOM | 8348 | CA | VAL | D | 127 | -28.546 | 13.371 | 113.350 | 1.00 | 61.22 | | C |
| ANISOU | 8348 | CA | VAL | D | 127 | 9767 | 8011 | 5482 | -3521 | 2915 | 139 | C |
| ATOM | 8350 | CB | VAL | D | 127 | -27.917 | 12.188 | 112.525 | 1.00 | 61.96 | | C |
| ANISOU | 8350 | CB | VAL | D | 127 | 10349 | 7504 | 5690 | -3519 | 3039 | 348 | C |
| ATOM | 8352 | CG1 | VAL | D | 127 | -26.514 | 12.526 | 112.045 | 1.00 | 59.50 | | C |
| ANISOU | 8352 | CG1 | VAL | D | 127 | 10041 | 6924 | 5640 | -2951 | 2805 | 544 | C |
| ATOM | 8356 | CG2 | VAL | D | 127 | -27.971 | 10.865 | 113.276 | 1.00 | 65.94 | | C |
| ANISOU | 8356 | CG2 | VAL | D | 127 | 11460 | 7663 | 5930 | -3824 | 3292 | 605 | C |
| ATOM | 8360 | C | VAL | D | 127 | -30.023 | 13.348 | 112.984 | 1.00 | 62.62 | | C |
| ANISOU | 8360 | C | VAL | D | 127 | 9679 | 8578 | 5536 | -3998 | 3096 | -216 | C |
| ATOM | 8361 | O | VAL | D | 127 | -30.410 | 13.962 | 111.980 | 1.00 | 57.35 | | O |
| ANISOU | 8361 | O | VAL | D | 127 | 8647 | 8106 | 5037 | -3929 | 3001 | -484 | O |
| ATOM | 8363 | N | HIS | D | 128 | -30.835 | 12.626 | 113.772 | 1.00 | 66.21 | | N |
| ANISOU | 8363 | N | HIS | D | 128 | 10312 | 9167 | 5679 | -4490 | 3355 | -213 | N |
| ATOM | 8364 | CA | HIS | D | 128 | -32.239 | 12.434 | 113.432 | 1.00 | 69.81 | | C |
| ANISOU | 8364 | CA | HIS | D | 128 | 10516 | 10033 | 5977 | -5023 | 3560 | -540 | C |
| ATOM | 8366 | CB | HIS | D | 128 | -32.916 | 11.422 | 114.382 | 1.00 | 76.38 | | C |
| ANISOU | 8366 | CB | HIS | D | 128 | 11680 | 10906 | 6434 | -5628 | 3881 | -443 | C |
| ATOM | 8369 | CG | HIS | D | 128 | -32.972 | 11.867 | 115.817 | 1.00 | 78.46 | | C |
| ANISOU | 8369 | CG | HIS | D | 128 | 11862 | 11499 | 6450 | -5567 | 3868 | -360 | C |
| ATOM | 8370 | ND1 | HIS | D | 128 | -31.957 | 11.612 | 116.717 | 1.00 | 79.36 | | N |
| ANISOU | 8370 | ND1 | HIS | D | 128 | 12401 | 11245 | 6507 | -5303 | 3803 | 19 | N |
| ATOM | 8372 | CE1 | HIS | D | 128 | -32.276 | 12.121 | 117.895 | 1.00 | 79.89 | | C |
| ANISOU | 8372 | CE1 | HIS | D | 128 | 12287 | 11748 | 6321 | -5317 | 3803 | -9 | C |
| ATOM | 8374 | NE2 | HIS | D | 128 | -33.454 | 12.709 | 117.789 | 1.00 | 79.60 | | N |
| ANISOU | 8374 | NE2 | HIS | D | 128 | 11712 | 12351 | 6180 | -5549 | 3871 | -397 | N |
| ATOM | 8376 | CD2 | HIS | D | 128 | -33.919 | 12.552 | 116.506 | 1.00 | 79.55 | | C |
| ANISOU | 8376 | CD2 | HIS | D | 128 | 11535 | 12331 | 6360 | -5711 | 3908 | -618 | C |
| ATOM | 8378 | C | HIS | D | 128 | -32.999 | 13.757 | 113.414 | 1.00 | 67.86 | | C |
| ANISOU | 8378 | C | HIS | D | 128 | 9585 | 10468 | 5730 | -4862 | 3405 | -905 | C |
| ATOM | 8379 | O | HIS | D | 128 | -33.941 | 13.938 | 112.643 | 1.00 | 68.24 | | O |
| ANISOU | 8379 | O | HIS | D | 128 | 9273 | 10878 | 5776 | -5065 | 3449 | -1227 | O |
| ATOM | 8381 | N | ILE | D | 129 | -32.575 | 14.689 | 114.254 | 1.00 | 66.39 | | N |
| ANISOU | 8381 | N | ILE | D | 129 | 9238 | 10455 | 5530 | -4469 | 3210 | -863 | N |
| ATOM | 8382 | CA | ILE | D | 129 | -33.272 | 15.963 | 114.394 | 1.00 | 64.79 | | C |
| ANISOU | 8382 | CA | ILE | D | 129 | 8471 | 10860 | 5286 | -4260 | 3062 | -1202 | C |
| ATOM | 8384 | CB | ILE | D | 129 | -32.654 | 16.850 | 115.527 | 1.00 | 63.63 | | C |
| ANISOU | 8384 | CB | ILE | D | 129 | 8299 | 10796 | 5080 | -3863 | 2863 | -1106 | C |
| ATOM | 8386 | CG1 | ILE | D | 129 | -32.864 | 16.198 | 116.900 | 1.00 | 67.65 | | C |
| ANISOU | 8386 | CG1 | ILE | D | 129 | 9048 | 11418 | 5238 | -4182 | 3076 | -943 | C |

FIG. 18 (continued)

| | | | | | | | | | | | | |
|---|---|---|---|---|---|---|---|---|---|---|---|---|
| ATOM | 8389 | CD1 | ILE | D | 129 | -31.874 | 16.671 | 117.989 | 1.00 | 66.81 | | C |
| ANISOU | 8389 | CD1 | ILE | D | 129 | 9119 | 11183 | 5084 | -3823 | 2887 | -712 | C |
| ATOM | 8393 | CG2 | ILE | D | 129 | -33.257 | 18.242 | 115.508 | 1.00 | 61.97 | | C |
| ANISOU | 8393 | CG2 | ILE | D | 129 | 7581 | 11101 | 4864 | -3550 | 2675 | -1468 | C |
| ATOM | 8397 | C | ILE | D | 129 | -33.271 | 16.715 | 113.071 | 1.00 | 60.60 | | C |
| ANISOU | 8397 | C | ILE | D | 129 | 7636 | 10348 | 5039 | -3955 | 2856 | -1414 | C |
| ATOM | 8398 | O | ILE | D | 129 | -34.322 | 17.117 | 112.579 | 1.00 | 60.51 | | O |
| ANISOU | 8398 | O | ILE | D | 129 | 7211 | 10816 | 4965 | -4045 | 2875 | -1754 | O |
| ATOM | 8400 | N | TYR | D | 130 | -32.083 | 16.911 | 112.501 | 1.00 | 56.79 | | N |
| ANISOU | 8400 | N | TYR | D | 130 | 7350 | 9381 | 4847 | -3583 | 2658 | -1208 | N |
| ATOM | 8401 | CA | TYR | D | 130 | -31.967 | 17.649 | 111.258 | 1.00 | 53.65 | | C |
| ANISOU | 8401 | CA | TYR | D | 130 | 6717 | 8962 | 4706 | -3287 | 2457 | -1365 | C |
| ATOM | 8403 | CB | TYR | D | 130 | -30.525 | 18.155 | 111.054 | 1.00 | 50.34 | | C |
| ANISOU | 8403 | CB | TYR | D | 130 | 6469 | 8111 | 4547 | -2835 | 2207 | -1115 | C |
| ATOM | 8406 | CG | TYR | D | 130 | -30.397 | 19.168 | 109.961 | 1.00 | 47.56 | | C |
| ANISOU | 8406 | CG | TYR | D | 130 | 5872 | 7784 | 4416 | -2508 | 1974 | -1273 | C |
| ATOM | 8407 | CD1 | TYR | D | 130 | -31.306 | 20.212 | 109.863 | 1.00 | 48.14 | | C |
| ANISOU | 8407 | CD1 | TYR | D | 130 | 5568 | 8304 | 4417 | -2370 | 1857 | -1602 | C |
| ATOM | 8409 | CE1 | TYR | D | 130 | -31.204 | 21.150 | 108.889 | 1.00 | 45.80 | | C |
| ANISOU | 8409 | CE1 | TYR | D | 130 | 5111 | 7999 | 4292 | -2058 | 1638 | -1725 | C |
| ATOM | 8411 | CZ | TYR | D | 130 | -30.164 | 21.084 | 107.994 | 1.00 | 43.18 | | C |
| ANISOU | 8411 | CZ | TYR | D | 130 | 4960 | 7237 | 4208 | -1914 | 1541 | -1522 | C |
| ATOM | 8412 | OH | TYR | D | 130 | -30.109 | 22.044 | 107.037 | 1.00 | 42.25 | | O |
| ANISOU | 8412 | OH | TYR | D | 130 | 4705 | 7122 | 4227 | -1634 | 1331 | -1638 | O |
| ATOM | 8414 | CE2 | TYR | D | 130 | -29.217 | 20.080 | 108.071 | 1.00 | 42.50 | | C |
| ANISOU | 8414 | CE2 | TYR | D | 130 | 5196 | 6748 | 4204 | -2029 | 1656 | -1210 | C |
| ATOM | 8416 | CD2 | TYR | D | 130 | -29.337 | 19.126 | 109.060 | 1.00 | 45.24 | | C |
| ANISOU | 8416 | CD2 | TYR | D | 130 | 5735 | 7075 | 4378 | -2301 | 1864 | -1085 | C |
| ATOM | 8418 | C | TYR | D | 130 | -32.458 | 16.825 | 110.062 | 1.00 | 53.65 | | C |
| ANISOU | 8418 | C | TYR | D | 130 | 6748 | 8872 | 4762 | -3600 | 2615 | -1465 | C |
| ATOM | 8419 | O | TYR | D | 130 | -32.981 | 17.381 | 109.113 | 1.00 | 51.75 | | O |
| ANISOU | 8419 | O | TYR | D | 130 | 6192 | 8867 | 4603 | -3504 | 2517 | -1717 | O |
| ATOM | 8421 | N | TYR | D | 131 | -32.309 | 15.507 | 110.123 | 1.00 | 56.24 | | N |
| ANISOU | 8421 | N | TYR | D | 131 | 7486 | 8858 | 5024 | -3971 | 2853 | -1273 | N |
| ATOM | 8422 | CA | TYR | D | 131 | -32.912 | 14.620 | 109.120 | 1.00 | 59.83 | | C |
| ANISOU | 8422 | CA | TYR | D | 131 | 8018 | 9247 | 5467 | -4376 | 3039 | -1401 | C |
| ATOM | 8424 | CB | TYR | D | 131 | -32.595 | 13.152 | 109.412 | 1.00 | 63.40 | | C |
| ANISOU | 8424 | CB | TYR | D | 131 | 9070 | 9202 | 5818 | -4756 | 3300 | -1139 | C |
| ATOM | 8427 | CG | TYR | D | 131 | -33.205 | 12.214 | 108.404 | 1.00 | 66.13 | | C |
| ANISOU | 8427 | CG | TYR | D | 131 | 9560 | 9437 | 6130 | -5220 | 3494 | -1288 | C |
| ATOM | 8428 | CD1 | TYR | D | 131 | -32.579 | 11.959 | 107.194 | 1.00 | 65.06 | | C |
| ANISOU | 8428 | CD1 | TYR | D | 131 | 9605 | 8890 | 6224 | -5032 | 3431 | -1252 | C |
| ATOM | 8430 | CE1 | TYR | D | 131 | -33.145 | 11.097 | 106.263 | 1.00 | 67.20 | | C |
| ANISOU | 8430 | CE1 | TYR | D | 131 | 10035 | 9055 | 6443 | -5473 | 3603 | -1414 | C |
| ATOM | 8432 | CZ | TYR | D | 131 | -34.349 | 10.486 | 106.538 | 1.00 | 71.35 | | C |
| ANISOU | 8432 | CZ | TYR | D | 131 | 10522 | 9902 | 6686 | -6151 | 3838 | -1610 | C |
| ATOM | 8433 | OH | TYR | D | 131 | -34.912 | 9.633 | 105.617 | 1.00 | 74.43 | | O |
| ANISOU | 8433 | OH | TYR | D | 131 | 11081 | 10196 | 7005 | -6643 | 4001 | -1789 | O |
| ATOM | 8435 | CE2 | TYR | D | 131 | -34.993 | 10.728 | 107.721 | 1.00 | 73.18 | | C |
| ANISOU | 8435 | CE2 | TYR | D | 131 | 10541 | 10580 | 6685 | -6365 | 3916 | -1641 | C |
| ATOM | 8437 | CD2 | TYR | D | 131 | -34.421 | 11.586 | 108.653 | 1.00 | 70.61 | | C |
| ANISOU | 8437 | CD2 | TYR | D | 131 | 10074 | 10342 | 6411 | -5880 | 3746 | -1481 | C |
| ATOM | 8439 | C | TYR | D | 131 | -34.428 | 14.788 | 109.005 | 1.00 | 63.10 | | C |
| ANISOU | 8439 | C | TYR | D | 131 | 7978 | 10332 | 5664 | -4747 | 3147 | -1787 | C |
| ATOM | 8440 | O | TYR | D | 131 | -34.931 | 14.967 | 107.887 | 1.00 | 62.00 | | O |
| ANISOU | 8440 | O | TYR | D | 131 | 7581 | 10378 | 5596 | -4772 | 3096 | -2026 | O |
| ATOM | 8442 | N | LEU | D | 132 | -35.144 | 14.703 | 110.133 | 1.00 | 66.43 | | N |
| ANISOU | 8442 | N | LEU | D | 132 | 8289 | 11152 | 5799 | -5035 | 3297 | -1847 | N |
| ATOM | 8443 | CA | LEU | D | 132 | -36.606 | 14.843 | 110.131 | 1.00 | 71.49 | | C |
| ANISOU | 8443 | CA | LEU | D | 132 | 8438 | 12539 | 6187 | -5399 | 3419 | -2222 | C |
| ATOM | 8445 | CB | LEU | D | 132 | -37.205 | 14.471 | 111.493 | 1.00 | 75.74 | | C |
| ANISOU | 8445 | CB | LEU | D | 132 | 8985 | 13416 | 6377 | -5798 | 3652 | -2201 | C |
| ATOM | 8448 | CG | LEU | D | 132 | -37.033 | 13.000 | 111.897 | 1.00 | 78.80 | | C |
| ANISOU | 8448 | CG | LEU | D | 132 | 9979 | 13346 | 6615 | -6394 | 3954 | -1929 | C |
| ATOM | 8450 | CD1 | LEU | D | 132 | -37.310 | 12.829 | 113.383 | 1.00 | 82.30 | | C |
| ANISOU | 8450 | CD1 | LEU | D | 132 | 10503 | 14033 | 6734 | -6637 | 4128 | -1819 | C |
| ATOM | 8454 | CD2 | LEU | D | 132 | -37.927 | 12.062 | 111.016 | 1.00 | 82.90 | | C |
| ANISOU | 8454 | CD2 | LEU | D | 132 | 10500 | 13977 | 7022 | -7067 | 4180 | -2129 | C |
| ATOM | 8458 | C | LEU | D | 132 | -37.068 | 16.239 | 109.680 | 1.00 | 70.65 | | C |
| ANISOU | 8458 | C | LEU | D | 132 | 7737 | 12958 | 6150 | -4913 | 3156 | -2535 | C |
| ATOM | 8459 | O | LEU | D | 132 | -38.091 | 16.361 | 109.000 | 1.00 | 71.56 | | O |
| ANISOU | 8459 | O | LEU | D | 132 | 7433 | 13589 | 6166 | -5077 | 3178 | -2860 | O |
| ATOM | 8461 | N | GLU | D | 133 | -36.305 | 17.281 | 110.017 | 1.00 | 68.71 | | N |
| ANISOU | 8461 | N | GLU | D | 133 | 7480 | 12569 | 6059 | -4316 | 2898 | -2440 | N |
| ATOM | 8462 | CA | GLU | D | 133 | -36.576 | 18.623 | 109.489 | 1.00 | 68.04 | | C |
| ANISOU | 8462 | CA | GLU | D | 133 | 6973 | 12816 | 6063 | -3795 | 2621 | -2695 | C |
| ATOM | 8464 | CB | GLU | D | 133 | -35.521 | 19.607 | 109.986 | 1.00 | 65.89 | | C |
| ANISOU | 8464 | CB | GLU | D | 133 | 6856 | 12223 | 5955 | -3239 | 2362 | -2519 | C |
| ATOM | 8467 | CG | GLU | D | 133 | -35.885 | 21.068 | 109.756 | 1.00 | 66.64 | | C |

FIG. 18 (continued)

| | | | | | | | | | | | | |
|---|---|---|---|---|---|---|---|---|---|---|---|---|
| ANISOU | 8467 | CG | GLU | D | 133 | 6593 | 12661 | 6068 | -2709 | 2091 | -2786 | C |
| ATOM | 8470 | CD | GLU | D | 133 | -35.023 | 22.042 | 110.573 | 1.00 | 65.17 | | C |
| ANISOU | 8470 | CD | GLU | D | 133 | 6569 | 12244 | 5947 | -2271 | 1871 | -2659 | C |
| ATOM | 8471 | OE1 | GLU | D | 133 | -34.954 | 21.887 | 111.819 | 1.00 | 66.34 | | O |
| ANISOU | 8471 | OE1 | GLU | D | 133 | 6810 | 12476 | 5922 | -2378 | 1967 | -2579 | O |
| ATOM | 8472 | OE2 | GLU | D | 133 | -34.425 | 22.962 | 109.959 | 1.00 | 63.90 | | O |
| ANISOU | 8472 | OE2 | GLU | D | 133 | 6459 | 11828 | 5991 | -1851 | 1603 | -2641 | O |
| ATOM | 8473 | C | GLU | D | 133 | -36.619 | 18.600 | 107.951 | 1.00 | 66.32 | | C |
| ANISOU | 8473 | C | GLU | D | 133 | 6679 | 12487 | 6033 | -3738 | 2525 | -2796 | C |
| ATOM | 8474 | O | GLU | D | 133 | -37.523 | 19.176 | 107.325 | 1.00 | 67.01 | | O |
| ANISOU | 8474 | O | GLU | D | 133 | 6328 | 13086 | 6045 | -3623 | 2436 | -3115 | O |
| ATOM | 8476 | N | LYS | D | 134 | -35.670 | 17.876 | 107.366 | 1.00 | 64.48 | | N |
| ANISOU | 8476 | N | LYS | D | 134 | 6875 | 11616 | 6009 | -3817 | 2556 | -2529 | N |
| ATOM | 8477 | CA | LYS | D | 134 | -35.569 | 17.741 | 105.923 | 1.00 | 64.59 | | C |
| ANISOU | 8477 | CA | LYS | D | 134 | 6893 | 11457 | 6192 | -3781 | 2486 | -2588 | C |
| ATOM | 8479 | CB | LYS | D | 134 | -34.152 | 17.310 | 105.523 | 1.00 | 61.79 | | C |
| ANISOU | 8479 | CB | LYS | D | 134 | 7026 | 10352 | 6100 | -3628 | 2450 | -2239 | C |
| ATOM | 8482 | CG | LYS | D | 134 | -33.103 | 18.426 | 105.626 | 1.00 | 58.32 | | C |
| ANISOU | 8482 | CG | LYS | D | 134 | 6614 | 9677 | 5868 | -3045 | 2169 | -2075 | C |
| ATOM | 8485 | CD | LYS | D | 134 | -31.801 | 18.028 | 104.917 | 1.00 | 56.18 | | C |
| ANISOU | 8485 | CD | LYS | D | 134 | 6707 | 8795 | 5844 | -2892 | 2131 | -1788 | C |
| ATOM | 8488 | CE | LYS | D | 134 | -30.840 | 19.209 | 104.668 | 1.00 | 52.41 | | C |
| ANISOU | 8488 | CE | LYS | D | 134 | 6190 | 8154 | 5570 | -2380 | 1841 | -1674 | C |
| ATOM | 8491 | NZ | LYS | D | 134 | -31.500 | 20.449 | 104.149 | 1.00 | 51.19 | | N |
| ANISOU | 8491 | NZ | LYS | D | 134 | 5683 | 8363 | 5405 | -2115 | 1626 | -1938 | N |
| ATOM | 8495 | C | LYS | D | 134 | -36.627 | 16.754 | 105.384 | 1.00 | 68.56 | | C |
| ANISOU | 8495 | C | LYS | D | 134 | 7283 | 12257 | 6509 | -4379 | 2720 | -2806 | C |
| ATOM | 8496 | O | LYS | D | 134 | -37.406 | 17.107 | 104.503 | 1.00 | 68.01 | | O |
| ANISOU | 8496 | O | LYS | D | 134 | 6838 | 12609 | 6394 | -4358 | 2638 | -3092 | O |
| ATOM | 8498 | N | ALA | D | 135 | -36.659 | 15.543 | 105.949 | 1.00 | 72.07 | | N |
| ANISOU | 8498 | N | ALA | D | 135 | 8069 | 12493 | 6823 | -4917 | 3001 | -2670 | N |
| ATOM | 8499 | CA | ALA | D | 135 | -37.582 | 14.463 | 105.536 | 1.00 | 77.24 | | C |
| ANISOU | 8499 | CA | ALA | D | 135 | 8727 | 13344 | 7277 | -5608 | 3256 | -2847 | C |
| ATOM | 8501 | CB | ALA | D | 135 | -37.301 | 13.192 | 106.333 | 1.00 | 79.63 | | C |
| ANISOU | 8501 | CB | ALA | D | 135 | 9591 | 13207 | 7458 | -6116 | 3547 | -2592 | C |
| ATOM | 8505 | C | ALA | D | 135 | -39.085 | 14.805 | 105.599 | 1.00 | 83.22 | | C |
| ANISOU | 8505 | C | ALA | D | 135 | 8843 | 15028 | 7750 | -5877 | 3303 | -3252 | C |
| ATOM | 8506 | O | ALA | D | 135 | -39.870 | 14.323 | 104.776 | 1.00 | 83.68 | | O |
| ANISOU | 8506 | O | ALA | D | 135 | 8718 | 15382 | 7694 | -6287 | 3387 | -3493 | O |
| ATOM | 8508 | N | ASN | D | 136 | -39.485 | 15.649 | 106.545 | 1.00 | 86.51 | | N |
| ANISOU | 8508 | N | ASN | D | 136 | 8898 | 15937 | 8033 | -5629 | 3241 | -3346 | N |
| ATOM | 8509 | CA | ASN | D | 136 | -40.858 | 16.158 | 106.561 | 1.00 | 93.52 | | C |
| ANISOU | 8509 | CA | ASN | D | 136 | 9101 | 17779 | 8654 | -5718 | 3244 | -3751 | C |
| ATOM | 8511 | CB | ASN | D | 136 | -41.110 | 16.956 | 107.838 | 1.00 | 94.43 | | C |
| ANISOU | 8511 | CB | ASN | D | 136 | 8958 | 18313 | 8608 | -5433 | 3220 | -3796 | C |
| ATOM | 8514 | CG | ASN | D | 136 | -41.122 | 16.079 | 109.075 | 1.00 | 97.17 | | C |
| ANISOU | 8514 | CG | ASN | D | 136 | 9595 | 18582 | 8744 | -5971 | 3523 | -3612 | C |
| ATOM | 8515 | OD1 | ASN | D | 136 | -41.337 | 14.865 | 108.992 | 1.00 | 98.97 | | O |
| ANISOU | 8515 | OD1 | ASN | D | 136 | 10091 | 18657 | 8856 | -6668 | 3788 | -3544 | O |
| ATOM | 8516 | ND2 | ASN | D | 136 | -40.880 | 16.688 | 110.230 | 1.00 | 96.68 | | N |
| ANISOU | 8516 | ND2 | ASN | D | 136 | 9526 | 18599 | 8611 | -5659 | 3484 | -3527 | N |
| ATOM | 8519 | C | ASN | D | 136 | -41.208 | 17.009 | 105.335 | 1.00 | 95.72 | | C |
| ANISOU | 8519 | C | ASN | D | 136 | 8965 | 18375 | 9029 | -5281 | 2975 | -4009 | C |
| ATOM | 8520 | O | ASN | D | 136 | -42.308 | 17.565 | 105.261 | 1.00 | 97.76 | | O |
| ANISOU | 8520 | O | ASN | D | 136 | 8616 | 19457 | 9069 | -5210 | 2925 | -4355 | O |
| ATOM | 8522 | N | LYS | D | 137 | -40.275 | 17.092 | 104.384 | 1.00 | 96.51 | | N |
| ANISOU | 8522 | N | LYS | D | 137 | 9392 | 17850 | 9428 | -4980 | 2809 | -3837 | N |
| ATOM | 8523 | CA | LYS | D | 137 | -40.450 | 17.843 | 103.141 | 1.00 | 99.29 | | C |
| ANISOU | 8523 | CA | LYS | D | 137 | 9465 | 18382 | 9879 | -4565 | 2549 | -4021 | C |
| ATOM | 8525 | CB | LYS | D | 137 | -39.456 | 19.027 | 103.100 | 1.00 | 95.62 | | C |
| ANISOU | 8525 | CB | LYS | D | 137 | 9153 | 17505 | 9673 | -3794 | 2251 | -3837 | C |
| ATOM | 8528 | CG | LYS | D | 137 | -38.278 | 18.896 | 102.098 | 1.00 | 92.84 | | C |
| ANISOU | 8528 | CG | LYS | D | 137 | 9235 | 16412 | 9627 | -3607 | 2141 | -3584 | C |
| ATOM | 8531 | CD | LYS | D | 137 | -37.217 | 19.988 | 102.277 | 1.00 | 88.99 | | C |
| ANISOU | 8531 | CD | LYS | D | 137 | 8934 | 15511 | 9367 | -2972 | 1888 | -3367 | C |
| ATOM | 8534 | CE | LYS | D | 137 | -35.839 | 19.415 | 102.624 | 1.00 | 87.10 | | C |
| ANISOU | 8534 | CE | LYS | D | 137 | 9234 | 14519 | 9342 | -3022 | 1965 | -2974 | C |
| ATOM | 8537 | NZ | LYS | D | 137 | -35.386 | 18.361 | 101.666 | 1.00 | 86.63 | | N |
| ANISOU | 8537 | NZ | LYS | D | 137 | 9482 | 14042 | 9390 | -3311 | 2095 | -2862 | N |
| ATOM | 8541 | C | LYS | D | 137 | -40.316 | 16.985 | 101.869 | 1.00100.57 | | | C |
| ANISOU | 8541 | C | LYS | D | 137 | 9842 | 18247 | 10123 | -4902 | 2604 | -4024 | C |
| ATOM | 8542 | O | LYS | D | 137 | -40.365 | 17.528 | 100.762 | 1.00100.78 | | | O |
| ANISOU | 8542 | O | LYS | D | 137 | 9700 | 18363 | 10230 | -4574 | 2392 | -4142 | O |
| ATOM | 8544 | N | ILE | D | 138 | -40.160 | 15.663 | 102.010 | 1.00103.74 | | | N |
| ANISOU | 8544 | N | ILE | D | 138 | 10646 | 18286 | 10483 | -5541 | 2882 | -3901 | N |
| ATOM | 8545 | CA | ILE | D | 138 | -40.045 | 14.773 | 100.838 | 1.00104.42 | | | C |
| ANISOU | 8545 | CA | ILE | D | 138 | 10999 | 18057 | 10619 | -5892 | 2955 | -3929 | C |
| ATOM | 8547 | CB | ILE | D | 138 | -39.441 | 13.369 | 101.157 | 1.00105.66 | | | C |
| ANISOU | 8547 | CB | ILE | D | 138 | 11844 | 17506 | 10796 | -6428 | 3243 | -3676 | C |

FIG. 18 (continued)

| | | | | | | | | | | | | | |
|---|---|---|---|---|---|---|---|---|---|---|---|---|---|
| ATOM | 8549 | CG1 | ILE | D | 138 | -38.190 | 13.452 | 102.029 | 1.00101.78 | | | | C |
| ANISOU | 8549 | CG1 | ILE | D | 138 | 11813 | 16352 | 10506 | -6056 | 3233 | -3271 | | C |
| ATOM | 8552 | CD1 | ILE | D | 138 | -37.895 | 12.159 | 102.778 | 1.00104.09 | | | | C |
| ANISOU | 8552 | CD1 | ILE | D | 138 | 12700 | 16144 | 10705 | -6581 | 3533 | -3044 | | C |
| ATOM | 8556 | CG2 | ILE | D | 138 | -39.088 | 12.632 | 99.849 | 1.00105.25 | | | | C |
| ANISOU | 8556 | CG2 | ILE | D | 138 | 12138 | 17009 | 10843 | -6600 | 3266 | -3689 | | C |
| ATOM | 8560 | C | ILE | D | 138 | -41.426 | 14.537 | 100.221 | 1.00110.58 | | | | C |
| ANISOU | 8560 | C | ILE | D | 138 | 11270 | 19628 | 11117 | -6351 | 3004 | -4340 | | C |
| ATOM | 8561 | O | ILE | D | 138 | -42.424 | 14.386 | 100.942 | 1.00115.13 | | | | O |
| ANISOU | 8561 | O | ILE | D | 138 | 11481 | 20848 | 11413 | -6751 | 3151 | -4535 | | O |
| ATOM | 8563 | N | LYS | D | 139 | -41.474 | 14.495 | 98.889 | 1.00111.30 | | | | N |
| ANISOU | 8563 | N | LYS | D | 139 | 11321 | 19709 | 11259 | -6308 | 2883 | -4474 | | N |
| ATOM | 8564 | CA | LYS | D | 139 | -42.725 | 14.280 | 98.161 | 1.00116.81 | | | | C |
| ANISOU | 8564 | CA | LYS | D | 139 | 11523 | 21175 | 11683 | -6724 | 2891 | -4873 | | C |
| ATOM | 8566 | CB | LYS | D | 139 | -43.319 | 15.621 | 97.709 | 1.00116.87 | | | | C |
| ANISOU | 8566 | CB | LYS | D | 139 | 10872 | 21899 | 11636 | -6079 | 2573 | -5107 | | C |
| ATOM | 8569 | CG | LYS | D | 139 | -43.552 | 16.627 | 98.833 | 1.00116.56 | | | | C |
| ANISOU | 8569 | CG | LYS | D | 139 | 10490 | 22250 | 11549 | -5614 | 2489 | -5108 | | C |
| ATOM | 8572 | CD | LYS | D | 139 | -44.397 | 17.814 | 98.368 | 1.00117.96 | | | | C |
| ANISOU | 8572 | CD | LYS | D | 139 | 9997 | 23243 | 11581 | -5045 | 2202 | -5409 | | C |
| ATOM | 8575 | CE | LYS | D | 139 | -44.421 | 18.940 | 99.409 | 1.00117.01 | | | | C |
| ANISOU | 8575 | CE | LYS | D | 139 | 9664 | 23342 | 11453 | -4430 | 2081 | -5386 | | C |
| ATOM | 8578 | NZ | LYS | D | 139 | -45.422 | 20.009 | 99.089 | 1.00119.34 | | | | N |
| ANISOU | 8578 | NZ | LYS | D | 139 | 9291 | 24520 | 11534 | -3890 | 1835 | -5721 | | N |
| ATOM | 8582 | C | LYS | D | 139 | -42.492 | 13.381 | 96.949 | 1.00117.47 | | | | C |
| ANISOU | 8582 | C | LYS | D | 139 | 11969 | 20859 | 11804 | -7091 | 2947 | -4910 | | C |
| ATOM | 8583 | O | LYS | D | 139 | -43.222 | 12.413 | 96.729 | 1.00121.82 | | | | O |
| ANISOU | 8583 | O | LYS | D | 139 | 12515 | 21646 | 12125 | -7853 | 3144 | -5118 | | O |
| ATOM | 8585 | N | THR | D | 143 | -35.983 | 13.286 | 95.625 | 1.00 | 67.95 | | | N |
| ANISOU | 8585 | N | THR | D | 143 | 8148 | 10773 | 6896 | -5147 | 2739 | -3365 | | N |
| ATOM | 8586 | CA | THR | D | 143 | -34.757 | 13.710 | 96.290 | 1.00 | 64.59 | | | C |
| ANISOU | 8586 | CA | THR | D | 143 | 7958 | 9883 | 6700 | -4661 | 2676 | -3004 | | C |
| ATOM | 8588 | CB | THR | D | 143 | -34.794 | 15.201 | 96.741 | 1.00 | 63.39 | | | C |
| ANISOU | 8588 | CB | THR | D | 143 | 7364 | 10106 | 6614 | -4145 | 2412 | -2987 | | C |
| ATOM | 8590 | OG1 | THR | D | 143 | -35.230 | 16.041 | 95.663 | 1.00 | 63.43 | | | O |
| ANISOU | 8590 | OG1 | THR | D | 143 | 7014 | 10487 | 6598 | -3887 | 2191 | -3190 | | O |
| ATOM | 8592 | CG2 | THR | D | 143 | -33.397 | 15.667 | 97.183 | 1.00 | 59.77 | | | C |
| ANISOU | 8592 | CG2 | THR | D | 143 | 7161 | 9151 | 6397 | -3662 | 2319 | -2625 | | C |
| ATOM | 8596 | C | THR | D | 143 | -34.451 | 12.830 | 97.500 | 1.00 | 63.92 | | | C |
| ANISOU | 8596 | C | THR | D | 143 | 8271 | 9431 | 6583 | -4943 | 2907 | -2796 | | C |
| ATOM | 8597 | O | THR | D | 143 | -35.338 | 12.499 | 98.278 | 1.00 | 66.11 | | | O |
| ANISOU | 8597 | O | THR | D | 143 | 8431 | 10026 | 6660 | -5380 | 3042 | -2918 | | O |
| ATOM | 8599 | N | HIS | D | 144 | -33.165 | 12.514 | 97.644 | 1.00 | 58.83 | | | N |
| ANISOU | 8599 | N | HIS | D | 144 | 8076 | 8155 | 6120 | -4654 | 2940 | -2471 | | N |
| ATOM | 8600 | CA | HIS | D | 144 | -32.615 | 11.588 | 98.628 | 1.00 | 58.54 | | | C |
| ANISOU | 8600 | CA | HIS | D | 144 | 8539 | 7637 | 6066 | -4808 | 3142 | -2213 | | C |
| ATOM | 8602 | CB | HIS | D | 144 | -31.630 | 10.642 | 97.903 | 1.00 | 58.76 | | | C |
| ANISOU | 8602 | CB | HIS | D | 144 | 9140 | 6993 | 6195 | -4713 | 3257 | -2051 | | C |
| ATOM | 8605 | CG | HIS | D | 144 | -31.249 | 9.416 | 98.679 | 1.00 | 61.32 | | | C |
| ANISOU | 8605 | CG | HIS | D | 144 | 10091 | 6772 | 6438 | -4944 | 3499 | -1837 | | C |
| ATOM | 8606 | ND1 | HIS | D | 144 | -31.852 | 8.195 | 98.483 | 1.00 | 66.43 | | | N |
| ANISOU | 8606 | ND1 | HIS | D | 144 | 11162 | 7184 | 6893 | -5534 | 3745 | -1968 | | N |
| ATOM | 8608 | CE1 | HIS | D | 144 | -31.307 | 7.298 | 99.284 | 1.00 | 68.06 | | | C |
| ANISOU | 8608 | CE1 | HIS | D | 144 | 11960 | 6853 | 7049 | -5582 | 3916 | -1703 | | C |
| ATOM | 8610 | NE2 | HIS | D | 144 | -30.373 | 7.894 | 100.001 | 1.00 | 63.87 | | | N |
| ANISOU | 8610 | NE2 | HIS | D | 144 | 11351 | 6251 | 6666 | -5033 | 3780 | -1411 | | N |
| ATOM | 8612 | CD2 | HIS | D | 144 | -30.308 | 9.217 | 99.633 | 1.00 | 61.02 | | | C |
| ANISOU | 8612 | CD2 | HIS | D | 144 | 10364 | 6359 | 6462 | -4655 | 3523 | -1495 | | C |
| ATOM | 8614 | C | HIS | D | 144 | -31.917 | 12.495 | 99.651 | 1.00 | 54.65 | | | C |
| ANISOU | 8614 | C | HIS | D | 144 | 7902 | 7165 | 5696 | -4341 | 2984 | -1966 | | C |
| ATOM | 8615 | O | HIS | D | 144 | -31.317 | 13.503 | 99.275 | 1.00 | 50.95 | | | O |
| ANISOU | 8615 | O | HIS | D | 144 | 7206 | 6753 | 5399 | -3852 | 2758 | -1903 | | O |
| ATOM | 8617 | N | ILE | D | 145 | -32.035 | 12.162 | 100.938 | 1.00 | 55.82 | | | N |
| ANISOU | 8617 | N | ILE | D | 145 | 8189 | 7289 | 5730 | -4530 | 3102 | -1839 | | N |
| ATOM | 8618 | CA | ILE | D | 145 | -31.449 | 12.954 | 102.009 | 1.00 | 52.16 | | | C |
| ANISOU | 8618 | CA | ILE | D | 145 | 7608 | 6875 | 5337 | -4151 | 2962 | -1629 | | C |
| ATOM | 8620 | CB | ILE | D | 145 | -32.472 | 13.236 | 103.114 | 1.00 | 53.91 | | | C |
| ANISOU | 8620 | CB | ILE | D | 145 | 7546 | 7594 | 5343 | -4432 | 3010 | -1765 | | C |
| ATOM | 8622 | CG1 | ILE | D | 145 | -33.714 | 13.943 | 102.531 | 1.00 | 54.22 | | | C |
| ANISOU | 8622 | CG1 | ILE | D | 145 | 7019 | 8299 | 5283 | -4553 | 2922 | -2154 | | C |
| ATOM | 8625 | CD1 | ILE | D | 145 | -34.905 | 14.022 | 103.488 | 1.00 | 57.42 | | | C |
| ANISOU | 8625 | CD1 | ILE | D | 145 | 7110 | 9287 | 5419 | -4915 | 3027 | -2350 | | C |
| ATOM | 8629 | CG2 | ILE | D | 145 | -31.810 | 14.062 | 104.206 | 1.00 | 50.65 | | | C |
| ANISOU | 8629 | CG2 | ILE | D | 145 | 7051 | 7203 | 4992 | -4028 | 2855 | -1559 | | C |
| ATOM | 8633 | C | ILE | D | 145 | -30.267 | 12.213 | 102.628 | 1.00 | 52.42 | | | C |
| ANISOU | 8633 | C | ILE | D | 145 | 8170 | 6316 | 5431 | -3988 | 3051 | -1258 | | C |
| ATOM | 8634 | O | ILE | D | 145 | -30.382 | 11.007 | 102.902 | 1.00 | 54.52 | | | O |
| ANISOU | 8634 | O | ILE | D | 145 | 8899 | 6255 | 5563 | -4346 | 3289 | -1181 | | O |
| ATOM | 8636 | N | HIS | D | 146 | -29.158 | 12.937 | 102.858 | 1.00 | 47.52 | | | N |

FIG. 18 (continued)

| | | | | | | | | | | | | |
|---|---|---|---|---|---|---|---|---|---|---|---|---|
| ANISOU | 8636 | N | HIS | D | 146 | 7490 | 5577 | 4987 | -3460 | 2857 | -1032 | N |
| ATOM | 8637 | CA | HIS | D | 146 | -27.985 | 12.399 | 103.542 | 1.00 | 48.39 | | C |
| ANISOU | 8637 | CA | HIS | D | 146 | 8004 | 5244 | 5140 | -3215 | 2892 | -675 | C |
| ATOM | 8639 | CB | HIS | D | 146 | -26.903 | 12.055 | 102.514 | 1.00 | 49.14 | | C |
| ANISOU | 8639 | CB | HIS | D | 146 | 8321 | 4940 | 5411 | -2882 | 2876 | -541 | C |
| ATOM | 8642 | CG | HIS | D | 146 | -25.851 | 11.122 | 103.030 | 1.00 | 51.20 | | C |
| ANISOU | 8642 | CG | HIS | D | 146 | 9081 | 4711 | 5659 | -2672 | 2976 | -211 | C |
| ATOM | 8643 | ND1 | HIS | D | 146 | -25.124 | 10.292 | 102.202 | 1.00 | 52.13 | | N |
| ANISOU | 8643 | ND1 | HIS | D | 146 | 9570 | 4397 | 5840 | -2489 | 3077 | -119 | N |
| ATOM | 8645 | CE1 | HIS | D | 146 | -24.272 | 9.590 | 102.930 | 1.00 | 54.89 | | C |
| ANISOU | 8645 | CE1 | HIS | D | 146 | 10322 | 4392 | 6140 | -2252 | 3138 | 183 | C |
| ATOM | 8647 | NE2 | HIS | D | 146 | -24.437 | 9.916 | 104.200 | 1.00 | 54.87 | | N |
| ANISOU | 8647 | NE2 | HIS | D | 146 | 10231 | 4578 | 6041 | -2315 | 3081 | 294 | N |
| ATOM | 8649 | CD2 | HIS | D | 146 | -25.413 | 10.878 | 104.288 | 1.00 | 52.23 | | C |
| ANISOU | 8649 | CD2 | HIS | D | 146 | 9414 | 4733 | 5698 | -2578 | 2986 | 44 | C |
| ATOM | 8651 | C | HIS | D | 146 | -27.453 | 13.409 | 104.586 | 1.00 | 47.34 | | C |
| ANISOU | 8651 | C | HIS | D | 146 | 7627 | 5315 | 5046 | -2884 | 2686 | -522 | C |
| ATOM | 8652 | O | HIS | D | 146 | -26.921 | 14.471 | 104.225 | 1.00 | 43.74 | | O |
| ANISOU | 8652 | O | HIS | D | 146 | 6871 | 4997 | 4753 | -2529 | 2457 | -521 | O |
| ATOM | 8654 | N | ILE | D | 147 | -27.589 | 13.070 | 105.872 | 1.00 | 48.63 | | N |
| ANISOU | 8654 | N | ILE | D | 147 | 7953 | 5484 | 5039 | -3030 | 2770 | -392 | N |
| ATOM | 8655 | CA | ILE | D | 147 | -27.094 | 13.927 | 106.960 | 1.00 | 47.70 | | C |
| ANISOU | 8655 | CA | ILE | D | 147 | 7655 | 5552 | 4916 | -2754 | 2586 | -253 | C |
| ATOM | 8657 | CB | ILE | D | 147 | -28.152 | 14.076 | 108.126 | 1.00 | 49.54 | | C |
| ANISOU | 8657 | CB | ILE | D | 147 | 7760 | 6162 | 4900 | -3080 | 2665 | -378 | C |
| ATOM | 8659 | CG1 | ILE | D | 147 | -29.539 | 14.449 | 107.591 | 1.00 | 49.33 | | C |
| ANISOU | 8659 | CG1 | ILE | D | 147 | 7362 | 6581 | 4798 | -3390 | 2710 | -764 | C |
| ATOM | 8662 | CD1 | ILE | D | 147 | -29.551 | 15.720 | 106.692 | 1.00 | 46.13 | | C |
| ANISOU | 8662 | CD1 | ILE | D | 147 | 6524 | 6424 | 4578 | -3062 | 2457 | -963 | C |
| ATOM | 8666 | CG2 | ILE | D | 147 | -27.714 | 15.153 | 109.087 | 1.00 | 46.62 | | C |
| ANISOU | 8666 | CG2 | ILE | D | 147 | 7158 | 6027 | 4528 | -2774 | 2442 | -308 | C |
| ATOM | 8670 | C | ILE | D | 147 | -25.783 | 13.387 | 107.545 | 1.00 | 47.97 | | C |
| ANISOU | 8670 | C | ILE | D | 147 | 8048 | 5205 | 4972 | -2451 | 2570 | 125 | C |
| ATOM | 8671 | O | ILE | D | 147 | -25.666 | 12.194 | 107.810 | 1.00 | 52.11 | | O |
| ANISOU | 8671 | O | ILE | D | 147 | 9042 | 5378 | 5381 | -2586 | 2768 | 291 | O |
| ATOM | 8673 | N | PHE | D | 148 | -24.817 | 14.284 | 107.754 | 1.00 | 45.97 | | N |
| ANISOU | 8673 | N | PHE | D | 148 | 7581 | 5038 | 4847 | -2046 | 2327 | 254 | N |
| ATOM | 8674 | CA | PHE | D | 148 | -23.586 | 14.002 | 108.511 | 1.00 | 47.49 | | C |
| ANISOU | 8674 | CA | PHE | D | 148 | 7985 | 5036 | 5025 | -1725 | 2255 | 597 | C |
| ATOM | 8676 | CB | PHE | D | 148 | -22.343 | 14.392 | 107.701 | 1.00 | 45.84 | | C |
| ANISOU | 8676 | CB | PHE | D | 148 | 7644 | 4738 | 5035 | -1311 | 2091 | 719 | C |
| ATOM | 8679 | CG | PHE | D | 148 | -22.117 | 13.576 | 106.463 | 1.00 | 45.84 | | C |
| ANISOU | 8679 | CG | PHE | D | 148 | 7857 | 4422 | 5137 | -1261 | 2238 | 716 | C |
| ATOM | 8680 | CD1 | PHE | D | 148 | -21.353 | 12.411 | 106.507 | 1.00 | 48.95 | | C |
| ANISOU | 8680 | CD1 | PHE | D | 148 | 8682 | 4433 | 5485 | -1060 | 2369 | 963 | C |
| ATOM | 8682 | CE1 | PHE | D | 148 | -21.109 | 11.662 | 105.340 | 1.00 | 50.53 | | C |
| ANISOU | 8682 | CE1 | PHE | D | 148 | 9109 | 4326 | 5765 | -974 | 2508 | 939 | C |
| ATOM | 8684 | CZ | PHE | D | 148 | -21.614 | 12.092 | 104.126 | 1.00 | 48.08 | | C |
| ANISOU | 8684 | CZ | PHE | D | 148 | 8570 | 4121 | 5579 | -1115 | 2509 | 676 | C |
| ATOM | 8686 | CE2 | PHE | D | 148 | -22.381 | 13.256 | 104.066 | 1.00 | 45.04 | | C |
| ANISOU | 8686 | CE2 | PHE | D | 148 | 7747 | 4129 | 5238 | -1312 | 2367 | 447 | C |
| ATOM | 8688 | CD2 | PHE | D | 148 | -22.622 | 14.000 | 105.242 | 1.00 | 44.41 | | C |
| ANISOU | 8688 | CD2 | PHE | D | 148 | 7462 | 4330 | 5082 | -1366 | 2233 | 465 | C |
| ATOM | 8690 | C | PHE | D | 148 | -23.546 | 14.820 | 109.806 | 1.00 | 47.07 | | C |
| ANISOU | 8690 | C | PHE | D | 148 | 7739 | 5290 | 4857 | -1672 | 2092 | 638 | C |
| ATOM | 8691 | O | PHE | D | 148 | -23.874 | 16.004 | 109.789 | 1.00 | 43.72 | | O |
| ANISOU | 8691 | O | PHE | D | 148 | 6938 | 5187 | 4486 | -1654 | 1921 | 440 | O |
| ATOM | 8693 | N | SER | D | 149 | -23.147 | 14.191 | 110.920 | 1.00 | 51.07 | | N |
| ANISOU | 8693 | N | SER | D | 149 | 8538 | 5682 | 5183 | -1631 | 2139 | 892 | N |
| ATOM | 8694 | CA | SER | D | 149 | -22.830 | 14.921 | 112.166 | 1.00 | 51.75 | | C |
| ANISOU | 8694 | CA | SER | D | 149 | 8475 | 6038 | 5148 | -1512 | 1957 | 976 | C |
| ATOM | 8696 | CB | SER | D | 149 | -23.522 | 14.284 | 113.361 | 1.00 | 55.73 | | C |
| ANISOU | 8696 | CB | SER | D | 149 | 9247 | 6576 | 5351 | -1792 | 2127 | 1039 | C |
| ATOM | 8699 | OG | SER | D | 149 | -22.706 | 13.299 | 113.967 | 1.00 | 60.66 | | O |
| ANISOU | 8699 | OG | SER | D | 149 | 10302 | 6899 | 5847 | -1620 | 2181 | 1396 | O |
| ATOM | 8701 | C | SER | D | 149 | -21.313 | 15.017 | 112.397 | 1.00 | 51.91 | | C |
| ANISOU | 8701 | C | SER | D | 149 | 8505 | 5983 | 5236 | -1078 | 1759 | 1270 | C |
| ATOM | 8702 | O | SER | D | 149 | -20.558 | 14.216 | 111.859 | 1.00 | 53.49 | | O |
| ANISOU | 8702 | O | SER | D | 149 | 8929 | 5888 | 5508 | -862 | 1822 | 1463 | O |
| ATOM | 8704 | N | PHE | D | 150 | -20.878 | 16.013 | 113.178 | 1.00 | 51.86 | | N |
| ANISOU | 8704 | N | PHE | D | 150 | 8243 | 6271 | 5192 | -948 | 1518 | 1282 | N |
| ATOM | 8705 | CA | PHE | D | 150 | -19.451 | 16.229 | 113.478 | 1.00 | 52.19 | | C |
| ANISOU | 8705 | CA | PHE | D | 150 | 8208 | 6357 | 5266 | -583 | 1301 | 1534 | C |
| ATOM | 8707 | CB | PHE | D | 150 | -19.224 | 17.586 | 114.182 | 1.00 | 49.51 | | C |
| ANISOU | 8707 | CB | PHE | D | 150 | 7538 | 6379 | 4894 | -565 | 1022 | 1433 | C |
| ATOM | 8710 | CG | PHE | D | 150 | -19.318 | 18.768 | 113.257 | 1.00 | 46.96 | | C |
| ANISOU | 8710 | CG | PHE | D | 150 | 6883 | 6169 | 4791 | -598 | 878 | 1189 | C |
| ATOM | 8711 | CD1 | PHE | D | 150 | -18.171 | 19.338 | 112.702 | 1.00 | 46.31 | | C |
| ANISOU | 8711 | CD1 | PHE | D | 150 | 6589 | 6139 | 4869 | -399 | 683 | 1280 | C |

FIG. 18 (continued)

| | | | | | | | | | | | | |
|---|---|---|---|---|---|---|---|---|---|---|---|---|
| ATOM | 8713 | CE1 | PHE | D | 150 | -18.271 | 20.436 | 111.802 | 1.00 | 43.32 | | C |
| ANISOU | 8713 | CE1 | PHE | D | 150 | 5968 | 5819 | 4672 | -458 | 559 | 1073 | C |
| ATOM | 8715 | CZ | PHE | D | 150 | -19.503 | 20.944 | 111.474 | 1.00 | 41.05 | | C |
| ANISOU | 8715 | CZ | PHE | D | 150 | 5647 | 5546 | 4404 | -643 | 613 | 778 | C |
| ATOM | 8717 | CE2 | PHE | D | 150 | -20.643 | 20.378 | 112.005 | 1.00 | 42.92 | | C |
| ANISOU | 8717 | CE2 | PHE | D | 150 | 6030 | 5792 | 4487 | -812 | 802 | 667 | C |
| ATOM | 8719 | CD2 | PHE | D | 150 | -20.551 | 19.290 | 112.891 | 1.00 | 45.31 | | C |
| ANISOU | 8719 | CD2 | PHE | D | 150 | 6578 | 6027 | 4608 | -824 | 945 | 874 | C |
| ATOM | 8721 | C | PHE | D | 150 | -18.839 | 15.073 | 114.304 | 1.00 | 56.58 | | C |
| ANISOU | 8721 | C | PHE | D | 150 | 9149 | 6731 | 5619 | -399 | 1377 | 1877 | C |
| ATOM | 8722 | O | PHE | D | 150 | -17.614 | 14.889 | 114.303 | 1.00 | 57.88 | | O |
| ANISOU | 8722 | O | PHE | D | 150 | 9295 | 6887 | 5811 | -35 | 1249 | 2115 | O |
| ATOM | 8724 | N | THR | D | 151 | -19.697 | 14.310 | 114.986 | 1.00 | 59.44 | | N |
| ANISOU | 8724 | N | THR | D | 151 | 9855 | 6969 | 5759 | -648 | 1585 | 1902 | N |
| ATOM | 8725 | CA | THR | D | 151 | -19.278 | 13.146 | 115.785 | 1.00 | 63.80 | | C |
| ANISOU | 8725 | CA | THR | D | 151 | 10881 | 7282 | 6076 | -506 | 1684 | 2236 | C |
| ATOM | 8727 | CB | THR | D | 151 | -20.057 | 13.052 | 117.122 | 1.00 | 66.29 | | C |
| ANISOU | 8727 | CB | THR | D | 151 | 11375 | 7741 | 6073 | -792 | 1760 | 2251 | C |
| ATOM | 8729 | OG1 | THR | D | 151 | -21.413 | 12.618 | 116.894 | 1.00 | 67.41 | | O |
| ANISOU | 8729 | OG1 | THR | D | 151 | 11684 | 7781 | 6150 | -1269 | 2043 | 2052 | O |
| ATOM | 8731 | CG2 | THR | D | 151 | -20.038 | 14.390 | 117.833 | 1.00 | 64.70 | | C |
| ANISOU | 8731 | CG2 | THR | D | 151 | 10737 | 8010 | 5835 | -799 | 1512 | 2096 | C |
| ATOM | 8735 | C | THR | D | 151 | -19.377 | 11.792 | 115.056 | 1.00 | 66.07 | | C |
| ANISOU | 8735 | C | THR | D | 151 | 11655 | 7069 | 6379 | -503 | 1948 | 2349 | C |
| ATOM | 8736 | O | THR | D | 151 | -19.053 | 10.761 | 115.645 | 1.00 | 69.54 | | O |
| ANISOU | 8736 | O | THR | D | 151 | 12582 | 7229 | 6613 | -364 | 2043 | 2635 | O |
| ATOM | 8738 | N | GLY | D | 152 | -19.801 | 11.788 | 113.788 | 1.00 | 63.53 | | N |
| ANISOU | 8738 | N | GLY | D | 152 | 11246 | 6615 | 6277 | -641 | 2057 | 2130 | N |
| ATOM | 8739 | CA | GLY | D | 152 | -19.724 | 10.584 | 112.960 | 1.00 | 64.70 | | C |
| ANISOU | 8739 | CA | GLY | D | 152 | 11845 | 6276 | 6461 | -587 | 2275 | 2213 | C |
| ATOM | 8742 | C | GLY | D | 152 | -21.021 | 9.906 | 112.537 | 1.00 | 65.83 | | C |
| ANISOU | 8742 | C | GLY | D | 152 | 12289 | 6181 | 6543 | -1111 | 2567 | 2016 | C |
| ATOM | 8743 | O | GLY | D | 152 | -21.001 | 9.068 | 111.636 | 1.00 | 64.94 | | O |
| ANISOU | 8743 | O | GLY | D | 152 | 12503 | 5676 | 6495 | -1104 | 2731 | 2010 | O |
| ATOM | 8745 | N | GLU | D | 153 | -22.150 | 10.237 | 113.161 | 1.00 | 66.86 | | N |
| ANISOU | 8745 | N | GLU | D | 153 | 12311 | 6564 | 6528 | -1575 | 2641 | 1842 | N |
| ATOM | 8746 | CA | GLU | D | 153 | -23.411 | 9.576 | 112.794 | 1.00 | 69.33 | | C |
| ANISOU | 8746 | CA | GLU | D | 153 | 12864 | 6732 | 6748 | -2134 | 2924 | 1645 | C |
| ATOM | 8748 | CB | GLU | D | 153 | -24.564 | 9.830 | 113.794 | 1.00 | 72.04 | | C |
| ANISOU | 8748 | CB | GLU | D | 153 | 13106 | 7425 | 6843 | -2619 | 3022 | 1514 | C |
| ATOM | 8751 | CG | GLU | D | 153 | -24.221 | 10.350 | 115.206 | 1.00 | 73.82 | | C |
| ANISOU | 8751 | CG | GLU | D | 153 | 13234 | 7935 | 6881 | -2457 | 2871 | 1684 | C |
| ATOM | 8754 | CD | GLU | D | 153 | -23.378 | 9.397 | 116.027 | 1.00 | 78.26 | | C |
| ANISOU | 8754 | CD | GLU | D | 153 | 14368 | 8127 | 7239 | -2210 | 2898 | 2104 | C |
| ATOM | 8755 | OE1 | GLU | D | 153 | -22.281 | 9.011 | 115.576 | 1.00 | 80.55 | | O |
| ANISOU | 8755 | OE1 | GLU | D | 153 | 14843 | 8105 | 7657 | -1746 | 2807 | 2314 | O |
| ATOM | 8756 | OE2 | GLU | D | 153 | -23.800 | 9.059 | 117.143 | 1.00 | 80.32 | | O |
| ANISOU | 8756 | OE2 | GLU | D | 153 | 14884 | 8442 | 7191 | -2452 | 3004 | 2227 | O |
| ATOM | 8757 | C | GLU | D | 153 | -23.840 | 10.022 | 111.388 | 1.00 | 65.21 | | C |
| ANISOU | 8757 | C | GLU | D | 153 | 11999 | 6300 | 6478 | -2240 | 2923 | 1321 | C |
| ATOM | 8758 | O | GLU | D | 153 | -23.475 | 11.106 | 110.936 | 1.00 | 62.13 | | O |
| ANISOU | 8758 | O | GLU | D | 153 | 11112 | 6199 | 6295 | -1989 | 2701 | 1203 | O |
| ATOM | 8760 | N | GLU | D | 154 | -24.595 | 9.168 | 110.698 | 1.00 | 66.44 | | N |
| ANISOU | 8760 | N | GLU | D | 154 | 12458 | 6194 | 6593 | -2627 | 3166 | 1187 | N |
| ATOM | 8761 | CA | GLU | D | 154 | -25.217 | 9.515 | 109.423 | 1.00 | 62.90 | | C |
| ANISOU | 8761 | CA | GLU | D | 154 | 11702 | 5878 | 6319 | -2815 | 3185 | 854 | C |
| ATOM | 8763 | CB | GLU | D | 154 | -24.517 | 8.807 | 108.270 | 1.00 | 63.93 | | C |
| ANISOU | 8763 | CB | GLU | D | 154 | 12141 | 5550 | 6600 | -2571 | 3241 | 913 | C |
| ATOM | 8766 | CG | GLU | D | 154 | -23.062 | 9.140 | 108.069 | 1.00 | 61.60 | | C |
| ANISOU | 8766 | CG | GLU | D | 154 | 11748 | 5177 | 6482 | -1912 | 3039 | 1135 | C |
| ATOM | 8769 | CD | GLU | D | 154 | -22.489 | 8.374 | 106.889 | 1.00 | 62.25 | | C |
| ANISOU | 8769 | CD | GLU | D | 154 | 12139 | 4839 | 6675 | -1689 | 3135 | 1154 | C |
| ATOM | 8770 | OE1 | GLU | D | 154 | -21.866 | 7.322 | 107.125 | 1.00 | 66.11 | | O |
| ANISOU | 8770 | OE1 | GLU | D | 154 | 13190 | 4868 | 7058 | -1463 | 3244 | 1400 | O |
| ATOM | 8771 | OE2 | GLU | D | 154 | -22.699 | 8.803 | 105.736 | 1.00 | 59.39 | | O |
| ANISOU | 8771 | OE2 | GLU | D | 154 | 11488 | 4601 | 6478 | -1729 | 3107 | 917 | O |
| ATOM | 8772 | C | GLU | D | 154 | -26.675 | 9.082 | 109.392 | 1.00 | 65.53 | | C |
| ANISOU | 8772 | C | GLU | D | 154 | 12097 | 6332 | 6470 | -3494 | 3420 | 601 | C |
| ATOM | 8773 | O | GLU | D | 154 | -27.028 | 8.069 | 109.974 | 1.00 | 64.81 | | O |
| ANISOU | 8773 | O | GLU | D | 154 | 12511 | 5969 | 6143 | -3838 | 3642 | 722 | O |
| ATOM | 8775 | N | MET | D | 155 | -27.515 | 9.843 | 108.693 | 1.00 | 64.78 | | N |
| ANISOU | 8775 | N | MET | D | 155 | 11493 | 6657 | 6462 | -3691 | 3369 | 253 | N |
| ATOM | 8776 | CA | MET | D | 155 | -28.885 | 9.402 | 108.422 | 1.00 | 68.62 | | C |
| ANISOU | 8776 | CA | MET | D | 155 | 11967 | 7322 | 6783 | -4337 | 3586 | -28 | C |
| ATOM | 8778 | CB | MET | D | 155 | -29.881 | 10.021 | 109.426 | 1.00 | 70.17 | | C |
| ANISOU | 8778 | CB | MET | D | 155 | 11779 | 8108 | 6775 | -4639 | 3600 | -180 | C |
| ATOM | 8781 | CG | MET | D | 155 | -31.150 | 9.189 | 109.647 | 1.00 | 74.98 | | C |
| ANISOU | 8781 | CG | MET | D | 155 | 12547 | 8847 | 7094 | -5392 | 3898 | -340 | C |
| ATOM | 8784 | SD | MET | D | 155 | -32.032 | 9.591 | 111.165 | 1.00 | 78.83 | | S |

FIG. 18 (continued)

| | | | | | | | | | | | | |
|---|---|---|---|---|---|---|---|---|---|---|---|---|
| ANISOU | 8784 | SD | MET | D | 155 | 12767 | 9925 | 7261 | -5709 | 3979 | -386 | S |
| ATOM | 8785 | CE | MET | D | 155 | -33.279 | 8.315 | 111.208 | 1.00 | 84.87 | | C |
| ANISOU | 8785 | CE | MET | D | 155 | 13864 | 10696 | 7688 | -6656 | 4373 | -510 | C |
| ATOM | 8789 | C | MET | D | 155 | -29.249 | 9.721 | 106.963 | 1.00 | 65.49 | | C |
| ANISOU | 8789 | C | MET | D | 155 | 11268 | 7052 | 6563 | -4365 | 3535 | -329 | C |
| ATOM | 8790 | O | MET | D | 155 | -29.103 | 10.855 | 106.505 | 1.00 | 64.15 | | O |
| ANISOU | 8790 | O | MET | D | 155 | 10596 | 7205 | 6574 | -4035 | 3306 | -456 | O |
| ATOM | 8792 | N | ALA | D | 156 | -29.674 | 8.696 | 106.230 | 1.00 | 66.37 | | N |
| ANISOU | 8792 | N | ALA | D | 156 | 11743 | 6871 | 6605 | -4758 | 3744 | -429 | N |
| ATOM | 8793 | CA | ALA | D | 156 | -30.014 | 8.828 | 104.818 | 1.00 | 64.96 | | C |
| ANISOU | 8793 | CA | ALA | D | 156 | 11354 | 6776 | 6551 | -4820 | 3714 | -708 | C |
| ATOM | 8795 | CB | ALA | D | 156 | -28.935 | 8.165 | 103.957 | 1.00 | 63.75 | | C |
| ANISOU | 8795 | CB | ALA | D | 156 | 11656 | 6013 | 6553 | -4478 | 3730 | -546 | C |
| ATOM | 8799 | C | ALA | D | 156 | -31.373 | 8.218 | 104.499 | 1.00 | 67.94 | | C |
| ANISOU | 8799 | C | ALA | D | 156 | 11742 | 7360 | 6714 | -5558 | 3927 | -1009 | C |
| ATOM | 8800 | O | ALA | D | 156 | -31.834 | 7.324 | 105.203 | 1.00 | 68.88 | | O |
| ANISOU | 8800 | O | ALA | D | 156 | 12256 | 7319 | 6595 | -6051 | 4157 | -944 | O |
| ATOM | 8802 | N | THR | D | 157 | -31.995 | 8.699 | 103.423 | 1.00 | 67.73 | | N |
| ANISOU | 8802 | N | THR | D | 157 | 11286 | 7699 | 6750 | -5645 | 3846 | -1333 | N |
| ATOM | 8803 | CA | THR | D | 157 | -33.206 | 8.080 | 102.886 | 1.00 | 73.82 | | C |
| ANISOU | 8803 | CA | THR | D | 157 | 12042 | 8686 | 7322 | -6340 | 4026 | -1649 | C |
| ATOM | 8805 | CB | THR | D | 157 | -33.583 | 8.666 | 101.496 | 1.00 | 71.04 | | C |
| ANISOU | 8805 | CB | THR | D | 157 | 11242 | 8671 | 7081 | -6248 | 3874 | -1963 | C |
| ATOM | 8807 | OG1 | THR | D | 157 | -33.904 | 10.059 | 101.626 | 1.00 | 67.32 | | O |
| ANISOU | 8807 | OG1 | THR | D | 157 | 10062 | 8838 | 6677 | -5909 | 3633 | -2091 | O |
| ATOM | 8809 | CG2 | THR | D | 157 | -34.786 | 7.911 | 100.880 | 1.00 | 75.31 | | C |
| ANISOU | 8809 | CG2 | THR | D | 157 | 11793 | 9433 | 7391 | -7006 | 4058 | -2299 | C |
| ATOM | 8813 | C | THR | D | 157 | -33.045 | 6.546 | 102.779 | 1.00 | 79.01 | | C |
| ANISOU | 8813 | C | THR | D | 157 | 13521 | 8653 | 7848 | -6761 | 4300 | -1536 | C |
| ATOM | 8814 | O | THR | D | 157 | -32.121 | 6.058 | 102.132 | 1.00 | 78.53 | | O |
| ANISOU | 8814 | O | THR | D | 157 | 13906 | 8007 | 7926 | -6439 | 4299 | -1397 | O |
| ATOM | 8816 | N | LYS | D | 158 | -33.930 | 5.816 | 103.454 | 1.00 | 86.04 | | N |
| ANISOU | 8816 | N | LYS | D | 158 | 14625 | 9616 | 8449 | -7468 | 4537 | -1591 | N |
| ATOM | 8817 | CA | LYS | D | 158 | -33.984 | 4.338 | 103.430 | 1.00 | 91.90 | | C |
| ANISOU | 8817 | CA | LYS | D | 158 | 16208 | 9709 | 9002 | -8007 | 4822 | -1513 | C |
| ATOM | 8819 | CB | LYS | D | 158 | -34.446 | 3.872 | 102.036 | 1.00 | 94.53 | | C |
| ANISOU | 8819 | CB | LYS | D | 158 | 16608 | 9984 | 9325 | -8357 | 4874 | -1836 | C |
| ATOM | 8822 | CG | LYS | D | 158 | -35.869 | 4.316 | 101.655 | 1.00 | 95.93 | | C |
| ANISOU | 8822 | CG | LYS | D | 158 | 16082 | 11023 | 9344 | -8939 | 4868 | -2266 | C |
| ATOM | 8825 | CD | LYS | D | 158 | -36.237 | 3.838 | 100.240 | 1.00 | 97.97 | | C |
| ANISOU | 8825 | CD | LYS | D | 158 | 16432 | 11213 | 9581 | -9257 | 4895 | -2580 | C |
| ATOM | 8828 | CE | LYS | D | 158 | -37.644 | 3.224 | 100.180 | 1.00104.59 | | | C |
| ANISOU | 8828 | CE | LYS | D | 158 | 17184 | 12478 | 10079 | -10286 | 5100 | -2913 | C |
| ATOM | 8831 | NZ | LYS | D | 158 | -37.942 | 2.664 | 98.828 | 1.00107.44 | | | N |
| ANISOU | 8831 | NZ | LYS | D | 158 | 17718 | 12714 | 10392 | -10630 | 5127 | -3215 | N |
| ATOM | 8835 | C | LYS | D | 158 | -32.673 | 3.606 | 103.845 | 1.00 | 92.52 | | C |
| ANISOU | 8835 | C | LYS | D | 158 | 17091 | 8911 | 9151 | -7553 | 4869 | -1087 | C |
| ATOM | 8836 | O | LYS | D | 158 | -32.459 | 2.390 | 103.469 | 1.00 | 97.92 | | O |
| ANISOU | 8836 | O | LYS | D | 158 | 18576 | 8892 | 9739 | -7794 | 5062 | -1026 | O |
| ATOM | 8838 | N | ALA | D | 159 | -31.826 | 4.328 | 104.638 | 1.00 | 88.88 | | N |
| ANISOU | 8838 | N | ALA | D | 159 | 16437 | 8506 | 8829 | -6903 | 4692 | -807 | N |
| ATOM | 8839 | CA | ALA | D | 159 | -30.526 | 3.810 | 105.110 | 1.00 | 88.45 | | C |
| ANISOU | 8839 | CA | ALA | D | 159 | 17001 | 7769 | 8836 | -6356 | 4685 | -395 | C |
| ATOM | 8841 | CB | ALA | D | 159 | -30.702 | 2.505 | 105.863 | 1.00 | 94.02 | | C |
| ANISOU | 8841 | CB | ALA | D | 159 | 18564 | 7913 | 9248 | -6829 | 4962 | -194 | C |
| ATOM | 8845 | C | ALA | D | 159 | -29.498 | 3.646 | 103.987 | 1.00 | 86.01 | | C |
| ANISOU | 8845 | C | ALA | D | 159 | 16901 | 7018 | 8762 | -5786 | 4594 | -356 | C |
| ATOM | 8846 | O | ALA | D | 159 | -28.532 | 2.873 | 104.113 | 1.00 | 87.93 | | O |
| ANISOU | 8846 | O | ALA | D | 159 | 17798 | 6608 | 9005 | -5418 | 4650 | -73 | O |
| ATOM | 8848 | N | ASP | D | 160 | -29.682 | 4.425 | 102.917 | 1.00 | 81.59 | | N |
| ANISOU | 8848 | N | ASP | D | 160 | 15763 | 6853 | 8384 | -5663 | 4443 | -632 | N |
| ATOM | 8849 | CA | ASP | D | 160 | -28.925 | 4.251 | 101.695 | 1.00 | 78.97 | | C |
| ANISOU | 8849 | CA | ASP | D | 160 | 15585 | 6189 | 8229 | -5256 | 4393 | -669 | C |
| ATOM | 8851 | CB | ASP | D | 160 | -29.923 | 4.128 | 100.547 | 1.00 | 81.42 | | C |
| ANISOU | 8851 | CB | ASP | D | 160 | 15731 | 6718 | 8485 | -5777 | 4457 | -1077 | C |
| ATOM | 8854 | CG | ASP | D | 160 | -29.300 | 4.262 | 99.184 | 1.00 | 81.13 | | C |
| ANISOU | 8854 | CG | ASP | D | 160 | 15649 | 6546 | 8632 | -5365 | 4364 | -1182 | C |
| ATOM | 8855 | OD1 | ASP | D | 160 | -28.046 | 4.278 | 99.024 | 1.00 | 81.16 | | O |
| ANISOU | 8855 | OD1 | ASP | D | 160 | 15828 | 6215 | 8796 | -4693 | 4291 | -943 | O |
| ATOM | 8856 | OD2 | ASP | D | 160 | -30.111 | 4.364 | 98.239 | 1.00 | 83.16 | | O |
| ANISOU | 8856 | OD2 | ASP | D | 160 | 15655 | 7094 | 8846 | -5733 | 4365 | -1524 | O |
| ATOM | 8857 | C | ASP | D | 160 | -27.982 | 5.455 | 101.566 | 1.00 | 72.67 | | C |
| ANISOU | 8857 | C | ASP | D | 160 | 14222 | 5690 | 7701 | -4512 | 4110 | -549 | C |
| ATOM | 8858 | O | ASP | D | 160 | -28.416 | 6.588 | 101.276 | 1.00 | 65.26 | | O |
| ANISOU | 8858 | O | ASP | D | 160 | 12585 | 5347 | 6864 | -4486 | 3932 | -742 | O |
| ATOM | 8860 | N | TYR | D | 161 | -26.691 | 5.187 | 101.787 | 1.00 | 71.00 | | N |
| ANISOU | 8860 | N | TYR | D | 161 | 14337 | 5060 | 7579 | -3912 | 4071 | -231 | N |
| ATOM | 8861 | CA | TYR | D | 161 | -25.710 | 6.227 | 102.031 | 1.00 | 67.33 | | C |
| ANISOU | 8861 | CA | TYR | D | 161 | 13408 | 4862 | 7314 | -3273 | 3822 | -46 | C |

FIG. 18 (continued)

| | | | | | | | | | | | | |
|---|---|---|---|---|---|---|---|---|---|---|---|---|
| ATOM | 8863 | CB | TYR | D | 161 | -24.815 | 5.836 | 103.223 | 1.00 | 69.99 | | C |
| ANISOU | 8863 | CB | TYR | D | 161 | 14103 | 4906 | 7583 | -2915 | 3819 | 344 | C |
| ATOM | 8866 | CG | TYR | D | 161 | -25.584 | 5.625 | 104.545 | 1.00 | 72.44 | | C |
| ANISOU | 8866 | CG | TYR | D | 161 | 14555 | 5301 | 7669 | -3363 | 3912 | 418 | C |
| ATOM | 8867 | CD1 | TYR | D | 161 | -26.061 | 6.712 | 105.289 | 1.00 | 69.27 | | C |
| ANISOU | 8867 | CD1 | TYR | D | 161 | 13558 | 5492 | 7270 | -3465 | 3764 | 357 | C |
| ATOM | 8869 | CE1 | TYR | D | 161 | -26.761 | 6.524 | 106.498 | 1.00 | 72.48 | | C |
| ANISOU | 8869 | CE1 | TYR | D | 161 | 14075 | 6023 | 7443 | -3868 | 3865 | 416 | C |
| ATOM | 8871 | CZ | TYR | D | 161 | -26.992 | 5.237 | 106.981 | 1.00 | 77.47 | | C |
| ANISOU | 8871 | CZ | TYR | D | 161 | 15442 | 6161 | 7832 | -4217 | 4117 | 560 | C |
| ATOM | 8872 | OH | TYR | D | 161 | -27.683 | 5.062 | 108.167 | 1.00 | 79.06 | | O |
| ANISOU | 8872 | OH | TYR | D | 161 | 15751 | 6512 | 7776 | -4648 | 4231 | 629 | O |
| ATOM | 8874 | CE2 | TYR | D | 161 | -26.523 | 4.137 | 106.263 | 1.00 | 80.49 | | C |
| ANISOU | 8874 | CE2 | TYR | D | 161 | 16482 | 5891 | 8210 | -4127 | 4259 | 632 | C |
| ATOM | 8876 | CD2 | TYR | D | 161 | -25.819 | 4.343 | 105.045 | 1.00 | 78.08 | | C |
| ANISOU | 8876 | CD2 | TYR | D | 161 | 16032 | 5490 | 8145 | -3678 | 4154 | 548 | C |
| ATOM | 8878 | C | TYR | D | 161 | -24.918 | 6.579 | 100.764 | 1.00 | 64.86 | | C |
| ANISOU | 8878 | C | TYR | D | 161 | 12903 | 4535 | 7207 | -2814 | 3715 | -101 | C |
| ATOM | 8879 | O | TYR | D | 161 | -23.947 | 7.334 | 100.833 | 1.00 | 61.92 | | O |
| ANISOU | 8879 | O | TYR | D | 161 | 12205 | 4329 | 6992 | -2284 | 3528 | 68 | O |
| ATOM | 8881 | N | THR | D | 162 | -25.363 | 6.044 | 99.619 | 1.00 | 65.77 | | N |
| ANISOU | 8881 | N | THR | D | 162 | 13211 | 4484 | 7295 | -3063 | 3839 | -349 | N |
| ATOM | 8882 | CA | THR | D | 162 | -24.913 | 6.447 | 98.273 | 1.00 | 62.63 | | C |
| ANISOU | 8882 | CA | THR | D | 162 | 12571 | 4175 | 7052 | -2762 | 3754 | -482 | C |
| ATOM | 8884 | CB | THR | D | 162 | -25.187 | 7.964 | 97.986 | 1.00 | 58.34 | | C |
| ANISOU | 8884 | CB | THR | D | 162 | 11229 | 4285 | 6651 | -2694 | 3505 | -613 | C |
| ATOM | 8886 | OG1 | THR | D | 162 | -26.593 | 8.211 | 98.032 | 1.00 | 58.70 | | O |
| ANISOU | 8886 | OG1 | THR | D | 162 | 11026 | 4693 | 6584 | -3265 | 3518 | -896 | O |
| ATOM | 8888 | CG2 | THR | D | 162 | -24.676 | 8.369 | 96.594 | 1.00 | 55.92 | | C |
| ANISOU | 8888 | CG2 | THR | D | 162 | 10720 | 4054 | 6475 | -2393 | 3427 | -715 | C |
| ATOM | 8892 | C | THR | D | 162 | -23.444 | 6.116 | 97.973 | 1.00 | 63.21 | | C |
| ANISOU | 8892 | C | THR | D | 162 | 12893 | 3902 | 7222 | -2089 | 3750 | -235 | C |
| ATOM | 8893 | O | THR | D | 162 | -23.141 | 5.390 | 97.020 | 1.00 | 62.84 | | O |
| ANISOU | 8893 | O | THR | D | 162 | 13211 | 3512 | 7154 | -1976 | 3876 | -318 | O |
| ATOM | 8895 | N | LEU | D | 163 | -22.537 | 6.696 | 98.752 | 1.00 | 61.36 | | N |
| ANISOU | 8895 | N | LEU | D | 163 | 12418 | 3816 | 7079 | -1636 | 3596 | 45 | N |
| ATOM | 8896 | CA | LEU | D | 163 | -21.103 | 6.557 | 98.516 | 1.00 | 62.04 | | C |
| ANISOU | 8896 | CA | LEU | D | 163 | 12579 | 3741 | 7250 | -966 | 3559 | 278 | C |
| ATOM | 8898 | CB | LEU | D | 163 | -20.370 | 7.815 | 99.007 | 1.00 | 58.11 | | C |
| ANISOU | 8898 | CB | LEU | D | 163 | 11457 | 3724 | 6897 | -625 | 3303 | 452 | C |
| ATOM | 8901 | CG | LEU | D | 163 | -20.760 | 9.163 | 98.387 | 1.00 | 53.09 | | C |
| ANISOU | 8901 | CG | LEU | D | 163 | 10171 | 3602 | 6398 | -767 | 3120 | 260 | C |
| ATOM | 8903 | CD1 | LEU | D | 163 | -19.987 | 10.248 | 99.113 | 1.00 | 50.80 | | C |
| ANISOU | 8903 | CD1 | LEU | D | 163 | 9420 | 3672 | 6208 | -472 | 2885 | 466 | C |
| ATOM | 8907 | CD2 | LEU | D | 163 | -20.513 | 9.244 | 96.869 | 1.00 | 50.90 | | C |
| ANISOU | 8907 | CD2 | LEU | D | 163 | 9801 | 3345 | 6193 | -642 | 3149 | 100 | C |
| ATOM | 8911 | C | LEU | D | 163 | -20.542 | 5.324 | 99.209 | 1.00 | 67.69 | | C |
| ANISOU | 8911 | C | LEU | D | 163 | 13991 | 3906 | 7824 | -724 | 3711 | 524 | C |
| ATOM | 8912 | O | LEU | D | 163 | -21.199 | 4.715 | 100.079 | 1.00 | 70.00 | | O |
| ANISOU | 8912 | O | LEU | D | 163 | 14683 | 3957 | 7957 | -1086 | 3819 | 570 | O |
| ATOM | 8914 | N | ASP | D | 164 | -19.333 | 4.933 | 98.818 | 1.00 | 70.45 | | N |
| ANISOU | 8914 | N | ASP | D | 164 | 14505 | 4059 | 8204 | -103 | 3726 | 684 | N |
| ATOM | 8915 | CA | ASP | D | 164 | -18.635 | 3.829 | 99.485 | 1.00 | 76.65 | | C |
| ANISOU | 8915 | CA | ASP | D | 164 | 15938 | 4341 | 8845 | 289 | 3835 | 952 | C |
| ATOM | 8917 | CB | ASP | D | 164 | -17.419 | 3.426 | 98.670 | 1.00 | 80.89 | | C |
| ANISOU | 8917 | CB | ASP | D | 164 | 16590 | 4732 | 9413 | 984 | 3871 | 1025 | C |
| ATOM | 8920 | CG | ASP | D | 164 | -16.449 | 4.577 | 98.491 | 1.00 | 79.25 | | C |
| ANISOU | 8920 | CG | ASP | D | 164 | 15596 | 5138 | 9376 | 1409 | 3653 | 1126 | C |
| ATOM | 8921 | OD1 | ASP | D | 164 | -16.866 | 5.623 | 97.925 | 1.00 | 74.64 | | O |
| ANISOU | 8921 | OD1 | ASP | D | 164 | 14436 | 4991 | 8932 | 1109 | 3544 | 941 | O |
| ATOM | 8922 | OD2 | ASP | D | 164 | -15.282 | 4.433 | 98.928 | 1.00 | 83.47 | | O |
| ANISOU | 8922 | OD2 | ASP | D | 164 | 16103 | 5728 | 9886 | 2030 | 3587 | 1392 | O |
| ATOM | 8923 | C | ASP | D | 164 | -18.158 | 4.193 | 100.887 | 1.00 | 76.63 | | C |
| ANISOU | 8923 | C | ASP | D | 164 | 15768 | 4536 | 8812 | 511 | 3680 | 1265 | C |
| ATOM | 8924 | O | ASP | D | 164 | -18.123 | 5.358 | 101.267 | 1.00 | 71.33 | | O |
| ANISOU | 8924 | O | ASP | D | 164 | 14440 | 4406 | 8255 | 464 | 3476 | 1284 | O |
| ATOM | 8926 | N | GLU | D | 165 | -17.781 | 3.166 | 101.641 | 1.00 | 83.59 | | N |
| ANISOU | 8926 | N | GLU | D | 165 | 17299 | 4948 | 9515 | 766 | 3777 | 1509 | N |
| ATOM | 8927 | CA | GLU | D | 165 | -17.205 | 3.309 | 102.979 | 1.00 | 85.79 | | C |
| ANISOU | 8927 | CA | GLU | D | 165 | 17530 | 5355 | 9712 | 1064 | 3639 | 1839 | C |
| ATOM | 8929 | CB | GLU | D | 165 | -16.673 | 1.946 | 103.453 | 1.00 | 92.44 | | C |
| ANISOU | 8929 | CB | GLU | D | 165 | 19239 | 5552 | 10331 | 1478 | 3778 | 2097 | C |
| ATOM | 8932 | CG | GLU | D | 165 | -15.622 | 1.971 | 104.577 | 1.00 | 95.01 | | C |
| ANISOU | 8932 | CG | GLU | D | 165 | 19519 | 6022 | 10560 | 2093 | 3610 | 2479 | C |
| ATOM | 8935 | CD | GLU | D | 165 | -16.162 | 2.446 | 105.920 | 1.00 | 94.02 | | C |
| ANISOU | 8935 | CD | GLU | D | 165 | 19245 | 6137 | 10339 | 1710 | 3504 | 2610 | C |
| ATOM | 8936 | OE1 | GLU | D | 165 | -16.259 | 1.609 | 106.850 | 1.00 | 98.97 | | O |
| ANISOU | 8936 | OE1 | GLU | D | 165 | 20524 | 6355 | 10725 | 1726 | 3585 | 2842 | O |
| ATOM | 8937 | OE2 | GLU | D | 165 | -16.475 | 3.651 | 106.048 | 1.00 | 89.75 | | O |

FIG. 18 (continued)

```
ANISOU 8937  OE2 GLU D 165    17973   6181   9946   1412   3343   2484      O
ATOM   8938  C   GLU D 165    -16.088    4.347 103.029  1.00 83.74          C
ANISOU 8938  C   GLU D 165    16528   5687   9605   1582   3387   1970      C
ATOM   8939  O   GLU D 165    -16.106    5.243 103.878  1.00 82.30          O
ANISOU 8939  O   GLU D 165    15877   5940   9452   1473   3198   2055      O
ATOM   8941  N   GLU D 166    -15.132    4.230 102.110  1.00 84.21          N
ANISOU 8941  N   GLU D 166    16481   5775   9739   2114   3392   1971      N
ATOM   8942  CA  GLU D 166    -13.881    4.978 102.217  1.00 82.93          C
ANISOU 8942  CA  GLU D 166    15705   6141   9662   2665   3181   2145      C
ATOM   8944  CB  GLU D 166    -12.855    4.506 101.172  1.00 85.71          C
ANISOU 8944  CB  GLU D 166    16097   6438  10029   3285   3262   2145      C
ATOM   8947  CG  GLU D 166    -12.682    2.974 101.113  1.00 91.73          C
ANISOU 8947  CG  GLU D 166    17759   6495  10597   3666   3480   2227      C
ATOM   8950  CD  GLU D 166    -11.359    2.527 100.496  1.00 95.20          C
ANISOU 8950  CD  GLU D 166    18185   6991  10996   4513   3509   2323      C
ATOM   8951  OE1 GLU D 166    -10.875    3.170  99.534  1.00 93.82          O
ANISOU 8951  OE1 GLU D 166    17441   7251  10956   4638   3477   2192      O
ATOM   8952  OE2 GLU D 166    -10.809    1.519 100.977  1.00 99.72          O
ANISOU 8952  OE2 GLU D 166    19333   7177  11378   5069   3569   2532      O
ATOM   8953  C   GLU D 166    -14.127    6.481 102.105  1.00 77.17          C
ANISOU 8953  C   GLU D 166    14171   6031   9118   2309   2982   2012      C
ATOM   8954  O   GLU D 166    -13.611    7.246 102.919  1.00 75.72          O
ANISOU 8954  O   GLU D 166    13552   6270   8949   2427   2769   2174      O
ATOM   8956  N   SER D 167    -14.928    6.871 101.104  1.00 74.13          N
ANISOU 8956  N   SER D 167    13640   5676   8850   1879   3048   1715      N
ATOM   8957  CA  SER D 167    -15.329    8.263 100.844  1.00 68.57          C
ANISOU 8957  CA  SER D 167    12277   5470   8305   1522   2877   1554      C
ATOM   8959  CB  SER D 167    -16.250    8.320  99.617  1.00 67.23          C
ANISOU 8959  CB  SER D 167    12132   5209   8205   1129   2996   1230      C
ATOM   8962  OG  SER D 167    -15.647    7.747  98.477  1.00 69.41          O
ANISOU 8962  OG  SER D 167    12566   5319   8488   1460   3129   1180      O
ATOM   8964  C   SER D 167    -16.067    8.929 102.015  1.00 65.41          C
ANISOU 8964  C   SER D 167    11708   5266   7880   1125   2743   1567      C
ATOM   8965  O   SER D 167    -15.771   10.062 102.391  1.00 60.91          O
ANISOU 8965  O   SER D 167    10614   5141   7390   1120   2525   1606      O
ATOM   8967  N   ARG D 168    -17.052    8.222 102.559  1.00 66.25          N
ANISOU 8967  N   ARG D 168    12278   5038   7854    765   2885   1518      N
ATOM   8968  CA  ARG D 168    -17.744    8.672 103.763  1.00 65.79          C
ANISOU 8968  CA  ARG D 168    12127   5151   7719    422   2799   1544      C
ATOM   8970  CB  ARG D 168    -18.865    7.707 104.140  1.00 68.35          C
ANISOU 8970  CB  ARG D 168    13020   5080   7871    -30   3020   1469      C
ATOM   8973  CG  ARG D 168    -19.998    7.628 103.110  1.00 67.96          C
ANISOU 8973  CG  ARG D 168    12994   4965   7860   -525   3161   1124      C
ATOM   8976  CD  ARG D 168    -21.190    6.843 103.645  1.00 71.36          C
ANISOU 8976  CD  ARG D 168    13882   5137   8095  -1094   3361   1037      C
ATOM   8979  NE  ARG D 168    -20.791    5.545 104.173  1.00 75.84          N
ANISOU 8979  NE  ARG D 168    15191   5143   8481   -935   3525   1279      N
ATOM   8981  CZ  ARG D 168    -21.487    4.817 105.042  1.00 79.64          C
ANISOU 8981  CZ  ARG D 168    16157   5362   8741  -1328   3679   1348      C
ATOM   8982  NH1 ARG D 168    -22.652    5.226 105.521  1.00 78.90          N
ANISOU 8982  NH1 ARG D 168    15840   5569   8569  -1927   3706   1179      N
ATOM   8985  NH2 ARG D 168    -21.006    3.652 105.437  1.00 84.26          N
ANISOU 8985  NH2 ARG D 168    17477   5381   9156  -1106   3813   1593      N
ATOM   8988  C   ARG D 168    -16.762    8.862 104.931  1.00 66.83          C
ANISOU 8988  C   ARG D 168    12151   5460   7779    814   2628   1856      C
ATOM   8989  O   ARG D 168    -16.888    9.814 105.709  1.00 64.97          O
ANISOU 8989  O   ARG D 168    11535   5600   7552    675   2445   1866      O
ATOM   8991  N   ALA D 169    -15.766    7.986 105.027  1.00 70.22          N
ANISOU 8991  N   ALA D 169    12908   5648   8124   1334   2675   2097      N
ATOM   8992  CA  ALA D 169    -14.708    8.122 106.035  1.00 71.95          C
ANISOU 8992  CA  ALA D 169    12989   6095   8255   1783   2494   2399      C
ATOM   8994  CB  ALA D 169    -13.790    6.894 106.014  1.00 76.44          C
ANISOU 8994  CB  ALA D 169    14054   6301   8689   2390   2596   2638      C
ATOM   8998  C   ALA D 169    -13.890    9.417 105.863  1.00 68.63          C
ANISOU 8998  C   ALA D 169    11814   6276   7986   1944   2239   2397      C
ATOM   8999  O   ALA D 169    -13.565   10.075 106.851  1.00 67.33          O
ANISOU 8999  O   ALA D 169    11361   6453   7770   1966   2035   2520      O
ATOM   9001  N   ARG D 170    -13.560    9.775 104.627  1.00 67.36          N
ANISOU 9001  N   ARG D 170    11364   6241   7987   2023   2254   2258      N
ATOM   9002  CA  ARG D 170    -12.853   11.040 104.361  1.00 66.53          C
ANISOU 9002  CA  ARG D 170    10580   6683   8015   2074   2033   2244      C
ATOM   9004  CB  ARG D 170    -12.526   11.194 102.874  1.00 67.18          C
ANISOU 9004  CB  ARG D 170    10465   6823   8235   2165   2112   2105      C
ATOM   9007  CG  ARG D 170    -11.076   10.891 102.537  1.00 72.27          C
ANISOU 9007  CG  ARG D 170    10927   7681   8850   2758   2095   2292      C
ATOM   9010  CD  ARG D 170    -10.793   11.095 101.056  1.00 72.41          C
ANISOU 9010  CD  ARG D 170    10734   7797   8981   2809   2189   2144      C
ATOM   9013  NE  ARG D 170    -11.224    9.923 100.289  1.00 76.58          N
ANISOU 9013  NE  ARG D 170    11812   7816   9470   2917   2454   2033      N
```

FIG. 18 (continued)

```
ATOM   9015  CZ  ARG D 170     -12.195   9.891  99.373  1.00 75.70           C
ANISOU 9015  CZ  ARG D 170    11873   7462   9426   2546   2587   1776        C
ATOM   9016  NH1 ARG D 170     -12.883  10.988  99.044  1.00 72.65           N
ANISOU 9016  NH1 ARG D 170    11148   7299   9157   2077   2481   1602        N
ATOM   9019  NH2 ARG D 170     -12.470   8.734  98.765  1.00 78.25           N
ANISOU 9019  NH2 ARG D 170    12740   7311   9679   2665   2822   1686        N
ATOM   9022  C   ARG D 170     -13.648  12.264 104.812  1.00 61.04           C
ANISOU 9022  C   ARG D 170     9560   6249   7384   1578   1872   2090        C
ATOM   9023  O   ARG D 170     -13.075  13.219 105.348  1.00 58.84           O
ANISOU 9023  O   ARG D 170     8864   6374   7121   1601   1643   2164        O
ATOM   9025  N   ILE D 171     -14.959  12.235 104.563  1.00 57.65           N
ANISOU 9025  N   ILE D 171     9323   5605   6978   1139   1991   1860        N
ATOM   9026  CA  ILE D 171     -15.865  13.293 105.006  1.00 54.14           C
ANISOU 9026  CA  ILE D 171     8627   5381   6562    714   1864   1686        C
ATOM   9028  CB  ILE D 171     -17.270  13.147 104.358  1.00 52.89           C
ANISOU 9028  CB  ILE D 171     8630   5037   6429    290   2025   1397        C
ATOM   9030  CG1 ILE D 171     -17.173  13.347 102.836  1.00 50.79           C
ANISOU 9030  CG1 ILE D 171     8220   4769   6309    320   2071   1244        C
ATOM   9033  CD1 ILE D 171     -18.505  13.309 102.092  1.00 48.82           C
ANISOU 9033  CD1 ILE D 171     8052   4424   6074    -79   2191    944        C
ATOM   9037  CG2 ILE D 171     -18.250  14.156 104.959  1.00 51.34           C
ANISOU 9037  CG2 ILE D 171     8193   5094   6218    -75   1902   1219        C
ATOM   9041  C   ILE D 171     -15.940  13.331 106.540  1.00 55.00           C
ANISOU 9041  C   ILE D 171     8809   5577   6512    675   1766   1828        C
ATOM   9042  O   ILE D 171     -15.728  14.382 107.144  1.00 52.60           O
ANISOU 9042  O   ILE D 171     8157   5613   6216    621   1547   1829        O
ATOM   9044  N   LYS D 172     -16.184  12.177 107.162  1.00 58.79           N
ANISOU 9044  N   LYS D 172     9777   5734   6825    709   1928   1956        N
ATOM   9045  CA  LYS D 172     -16.257  12.074 108.620  1.00 60.20           C
ANISOU 9045  CA  LYS D 172    10093   5971   6810    683   1862   2117        C
ATOM   9047  CB  LYS D 172     -16.616  10.632 109.032  1.00 63.99           C
ANISOU 9047  CB  LYS D 172    11235   5980   7097    681   2098   2256        C
ATOM   9050  CG  LYS D 172     -18.059  10.212 108.695  1.00 63.56           C
ANISOU 9050  CG  LYS D 172    11464   5674   7013    147   2332   2015        C
ATOM   9053  CD  LYS D 172     -18.383   8.762 109.093  1.00 67.99           C
ANISOU 9053  CD  LYS D 172    12753   5720   7360     77   2577   2163        C
ATOM   9056  CE  LYS D 172     -18.048   7.767 107.969  1.00 70.43           C
ANISOU 9056  CE  LYS D 172    13458   5577   7726    290   2755   2163        C
ATOM   9059  NZ  LYS D 172     -18.144   6.314 108.372  1.00 74.78           N
ANISOU 9059  NZ  LYS D 172    14824   5540   8049    315   2975   2350        N
ATOM   9063  C   LYS D 172     -14.959  12.531 109.314  1.00 61.74           C
ANISOU 9063  C   LYS D 172     9999   6497   6962   1075   1616   2355        C
ATOM   9064  O   LYS D 172     -14.999  13.193 110.348  1.00 61.61           O
ANISOU 9064  O   LYS D 172     9807   6751   6851    970   1447   2385        O
ATOM   9066  N   THR D 173     -13.814  12.176 108.737  1.00 63.87           N
ANISOU 9066  N   THR D 173    10203   6784   7282   1525   1597   2508        N
ATOM   9067  CA  THR D 173     -12.505  12.591 109.262  1.00 64.89           C
ANISOU 9067  CA  THR D 173     9980   7313   7361   1902   1361   2720        C
ATOM   9069  CB  THR D 173     -11.355  11.868 108.503  1.00 68.34           C
ANISOU 9069  CB  THR D 173    10425   7725   7817   2451   1420   2878        C
ATOM   9071  OG1 THR D 173     -11.353  10.489 108.882  1.00 71.83           O
ANISOU 9071  OG1 THR D 173    11470   7740   8083   2758   1585   3064        O
ATOM   9073  CG2 THR D 173      -9.969  12.489 108.800  1.00 69.16           C
ANISOU 9073  CG2 THR D 173     9994   8392   7891   2787   1165   3044        C
ATOM   9077  C   THR D 173     -12.330  14.104 109.186  1.00 60.30           C
ANISOU 9077  C   THR D 173     8819   7189   6905   1663   1126   2578        C
ATOM   9078  O   THR D 173     -11.885  14.733 110.141  1.00 60.39           O
ANISOU 9078  O   THR D 173     8594   7532   6819   1667    905   2664        O
ATOM   9080  N   ARG D 174     -12.696  14.691 108.056  1.00 56.82           N
ANISOU 9080  N   ARG D 174     8188   6744   6658   1443   1168   2357        N
ATOM   9081  CA  ARG D 174     -12.628  16.138 107.910  1.00 53.43           C
ANISOU 9081  CA  ARG D 174     7309   6658   6336   1188    958   2215        C
ATOM   9083  CB  ARG D 174     -13.066  16.547 106.510  1.00 52.30           C
ANISOU 9083  CB  ARG D 174     7067   6424   6380   1007   1048   2002        C
ATOM   9086  CG  ARG D 174     -13.101  18.049 106.274  1.00 50.94           C
ANISOU 9086  CG  ARG D 174     6532   6519   6306    732    843   1853        C
ATOM   9089  CD  ARG D 174     -11.835  18.732 106.765  1.00 53.21           C
ANISOU 9089  CD  ARG D 174     6459   7208   6549    838    607   2015        C
ATOM   9092  NE  ARG D 174     -11.842  20.143 106.410  1.00 51.79           N
ANISOU 9092  NE  ARG D 174     6016   7207   6456    540    429   1874        N
ATOM   9094  CZ  ARG D 174     -11.051  21.064 106.953  1.00 53.37           C
ANISOU 9094  CZ  ARG D 174     5936   7738   6605    444    188   1934        C
ATOM   9095  NH1 ARG D 174     -10.171  20.744 107.912  1.00 56.01           N
ANISOU 9095  NH1 ARG D 174     6151   8333   6798    637     79   2130        N
ATOM   9098  NH2 ARG D 174     -11.164  22.322 106.552  1.00 51.70           N
ANISOU 9098  NH2 ARG D 174     5590   7591   6463    144     47   1794        N
ATOM   9101  C   ARG D 174     -13.490  16.842 108.962  1.00 50.83           C
ANISOU 9101  C   ARG D 174     6993   6397   5923    854    843   2096        C
ATOM   9102  O   ARG D 174     -13.054  17.812 109.575  1.00 49.56           O
```

FIG. 18 (continued)

| | | | | | | | | | | | | |
|---|---|---|---|---|---|---|---|---|---|---|---|---|
| ANISOU | 9102 | O | ARG | D | 174 | 6551 | 6552 | 5727 | 781 | 607 | 2103 | O |
| ATOM | 9104 | N | LEU | D | 175 | -14.712 | 16.363 | 109.165 | 1.00 | 49.00 | | N |
| ANISOU | 9104 | N | LEU | D | 175 | 7086 | 5893 | 5641 | 635 | 1013 | 1972 | N |
| ATOM | 9105 | CA | LEU | D | 175 | -15.590 | 16.974 | 110.166 | 1.00 | 48.70 | | C |
| ANISOU | 9105 | CA | LEU | D | 175 | 7052 | 5958 | 5494 | 344 | 935 | 1841 | C |
| ATOM | 9107 | CB | LEU | D | 175 | -17.003 | 16.387 | 110.123 | 1.00 | 48.30 | | C |
| ANISOU | 9107 | CB | LEU | D | 175 | 7305 | 5655 | 5393 | 64 | 1169 | 1671 | C |
| ATOM | 9110 | CG | LEU | D | 175 | -17.835 | 16.547 | 108.843 | 1.00 | 46.61 | | C |
| ANISOU | 9110 | CG | LEU | D | 175 | 7046 | 5324 | 5340 | -136 | 1291 | 1413 | C |
| ATOM | 9112 | CD1 | LEU | D | 175 | -19.173 | 15.779 | 109.011 | 1.00 | 46.49 | | C |
| ANISOU | 9112 | CD1 | LEU | D | 175 | 7332 | 5120 | 5211 | -440 | 1531 | 1275 | C |
| ATOM | 9116 | CD2 | LEU | D | 175 | -18.046 | 18.041 | 108.476 | 1.00 | 43.98 | | C |
| ANISOU | 9116 | CD2 | LEU | D | 175 | 6343 | 5244 | 5125 | -262 | 1088 | 1198 | C |
| ATOM | 9120 | C | LEU | D | 175 | -15.007 | 16.837 | 111.574 | 1.00 | 51.52 | | C |
| ANISOU | 9120 | C | LEU | D | 175 | 7453 | 6483 | 5639 | 490 | 802 | 2056 | C |
| ATOM | 9121 | O | LEU | D | 175 | -15.145 | 17.753 | 112.386 | 1.00 | 49.81 | | O |
| ANISOU | 9121 | O | LEU | D | 175 | 7070 | 6511 | 5345 | 338 | 619 | 1975 | O |
| ATOM | 9123 | N | PHE | D | 176 | -14.370 | 15.696 | 111.864 | 1.00 | 55.13 | | N |
| ANISOU | 9123 | N | PHE | D | 176 | 8163 | 6802 | 5982 | 806 | 887 | 2323 | N |
| ATOM | 9124 | CA | PHE | D | 176 | -13.717 | 15.490 | 113.167 | 1.00 | 58.10 | | C |
| ANISOU | 9124 | CA | PHE | D | 176 | 8589 | 7358 | 6128 | 1010 | 745 | 2562 | C |
| ATOM | 9126 | CB | PHE | D | 176 | -13.159 | 14.069 | 113.301 | 1.00 | 63.99 | | C |
| ANISOU | 9126 | CB | PHE | D | 176 | 9722 | 7851 | 6742 | 1413 | 880 | 2855 | C |
| ATOM | 9129 | CG | PHE | D | 176 | -12.431 | 13.813 | 114.610 | 1.00 | 67.50 | | C |
| ANISOU | 9129 | CG | PHE | D | 176 | 10227 | 8501 | 6920 | 1688 | 716 | 3129 | C |
| ATOM | 9130 | CD1 | PHE | D | 176 | -13.127 | 13.350 | 115.733 | 1.00 | 69.71 | | C |
| ANISOU | 9130 | CD1 | PHE | D | 176 | 10893 | 8641 | 6953 | 1545 | 787 | 3207 | C |
| ATOM | 9132 | CE1 | PHE | D | 176 | -12.456 | 13.103 | 116.943 | 1.00 | 73.64 | | C |
| ANISOU | 9132 | CE1 | PHE | D | 176 | 11469 | 9338 | 7174 | 1816 | 626 | 3473 | C |
| ATOM | 9134 | CZ | PHE | D | 176 | -11.076 | 13.327 | 117.041 | 1.00 | 74.93 | | C |
| ANISOU | 9134 | CZ | PHE | D | 176 | 11279 | 9883 | 7308 | 2238 | 379 | 3647 | C |
| ATOM | 9136 | CE2 | PHE | D | 176 | -10.369 | 13.784 | 115.929 | 1.00 | 73.80 | | C |
| ANISOU | 9136 | CE2 | PHE | D | 176 | 10713 | 9916 | 7411 | 2360 | 317 | 3561 | C |
| ATOM | 9138 | CD2 | PHE | D | 176 | -11.049 | 14.026 | 114.718 | 1.00 | 69.96 | | C |
| ANISOU | 9138 | CD2 | PHE | D | 176 | 10192 | 9189 | 7199 | 2082 | 492 | 3309 | C |
| ATOM | 9140 | C | PHE | D | 176 | -12.595 | 16.493 | 113.354 | 1.00 | 56.69 | | C |
| ANISOU | 9140 | C | PHE | D | 176 | 7935 | 7632 | 5972 | 1128 | 444 | 2610 | C |
| ATOM | 9141 | O | PHE | D | 176 | -12.482 | 17.127 | 114.398 | 1.00 | 55.90 | | O |
| ANISOU | 9141 | O | PHE | D | 176 | 7712 | 7802 | 5726 | 1034 | 247 | 2615 | O |
| ATOM | 9143 | N | THR | D | 177 | -11.783 | 16.637 | 112.314 | 1.00 | 56.18 | | N |
| ANISOU | 9143 | N | THR | D | 177 | 7608 | 7663 | 6076 | 1299 | 419 | 2630 | N |
| ATOM | 9144 | CA | THR | D | 177 | -10.682 | 17.584 | 112.285 | 1.00 | 56.75 | | C |
| ANISOU | 9144 | CA | THR | D | 177 | 7198 | 8185 | 6178 | 1343 | 160 | 2664 | C |
| ATOM | 9146 | CB | THR | D | 177 | -9.954 | 17.515 | 110.897 | 1.00 | 57.80 | | C |
| ANISOU | 9146 | CB | THR | D | 177 | 7099 | 8366 | 6496 | 1513 | 229 | 2678 | C |
| ATOM | 9148 | OG1 | THR | D | 177 | -9.615 | 16.150 | 110.593 | 1.00 | 60.46 | | O |
| ANISOU | 9148 | OG1 | THR | D | 177 | 7698 | 8488 | 6787 | 1947 | 422 | 2862 | O |
| ATOM | 9150 | CG2 | THR | D | 177 | -8.700 | 18.380 | 110.868 | 1.00 | 58.04 | | C |
| ANISOU | 9150 | CG2 | THR | D | 177 | 6611 | 8920 | 6522 | 1538 | -18 | 2745 | C |
| ATOM | 9154 | C | THR | D | 177 | -11.163 | 19.020 | 112.549 | 1.00 | 54.43 | | C |
| ANISOU | 9154 | C | THR | D | 177 | 6699 | 8055 | 5928 | 913 | -23 | 2425 | C |
| ATOM | 9155 | O | THR | D | 177 | -10.522 | 19.745 | 113.319 | 1.00 | 55.47 | | O |
| ANISOU | 9155 | O | THR | D | 177 | 6591 | 8540 | 5947 | 859 | -274 | 2461 | O |
| ATOM | 9157 | N | ILE | D | 178 | -12.280 | 19.430 | 111.918 | 1.00 | 49.86 | | N |
| ANISOU | 9157 | N | ILE | D | 178 | 6226 | 7228 | 5490 | 625 | 92 | 2172 | N |
| ATOM | 9158 | CA | ILE | D | 178 | -12.821 | 20.783 | 112.127 | 1.00 | 47.68 | | C |
| ANISOU | 9158 | CA | ILE | D | 178 | 5824 | 7051 | 5241 | 282 | -74 | 1929 | C |
| ATOM | 9160 | CB | ILE | D | 178 | -14.007 | 21.131 | 111.160 | 1.00 | 44.25 | | C |
| ANISOU | 9160 | CB | ILE | D | 178 | 5486 | 6356 | 4972 | 65 | 67 | 1661 | C |
| ATOM | 9162 | CG1 | ILE | D | 178 | -13.489 | 21.418 | 109.747 | 1.00 | 43.51 | | C |
| ANISOU | 9162 | CG1 | ILE | D | 178 | 5208 | 6246 | 5079 | 85 | 85 | 1651 | C |
| ATOM | 9165 | CD1 | ILE | D | 178 | -14.525 | 21.270 | 108.618 | 1.00 | 41.06 | | C |
| ANISOU | 9165 | CD1 | ILE | D | 178 | 5031 | 5661 | 4910 | -13 | 278 | 1459 | C |
| ATOM | 9169 | CG2 | ILE | D | 178 | -14.790 | 22.365 | 111.660 | 1.00 | 41.79 | | C |
| ANISOU | 9169 | CG2 | ILE | D | 178 | 5154 | 6105 | 4619 | -204 | -85 | 1404 | C |
| ATOM | 9173 | C | ILE | D | 178 | -13.231 | 20.955 | 113.593 | 1.00 | 48.79 | | C |
| ANISOU | 9173 | C | ILE | D | 178 | 6087 | 7295 | 5156 | 194 | -175 | 1907 | C |
| ATOM | 9174 | O | ILE | D | 178 | -12.825 | 21.913 | 114.238 | 1.00 | 48.70 | | O |
| ANISOU | 9174 | O | ILE | D | 178 | 5905 | 7539 | 5061 | 74 | -418 | 1858 | O |
| ATOM | 9176 | N | ARG | D | 179 | -14.028 | 20.030 | 114.112 | 1.00 | 49.37 | | N |
| ANISOU | 9176 | N | ARG | D | 179 | 6475 | 7173 | 5110 | 225 | 17 | 1940 | N |
| ATOM | 9177 | CA | ARG | D | 179 | -14.477 | 20.094 | 115.497 | 1.00 | 52.49 | | C |
| ANISOU | 9177 | CA | ARG | D | 179 | 7010 | 7675 | 5258 | 137 | -40 | 1929 | C |
| ATOM | 9179 | CB | ARG | D | 179 | -15.331 | 18.872 | 115.819 | 1.00 | 54.09 | | C |
| ANISOU | 9179 | CB | ARG | D | 179 | 7596 | 7617 | 5338 | 143 | 236 | 2002 | C |
| ATOM | 9182 | CG | ARG | D | 179 | -15.661 | 18.714 | 117.297 | 1.00 | 57.20 | | C |
| ANISOU | 9182 | CG | ARG | D | 179 | 8171 | 8137 | 5426 | 87 | 208 | 2062 | C |
| ATOM | 9185 | CD | ARG | D | 179 | -16.846 | 17.806 | 117.511 | 1.00 | 58.77 | | C |
| ANISOU | 9185 | CD | ARG | D | 179 | 8731 | 8091 | 5510 | -80 | 506 | 2035 | C |

FIG. 18 (continued)

| | | | | | | | | | | | | |
|---|---|---|---|---|---|---|---|---|---|---|---|---|
| ATOM | 9188 | NE | ARG | D | 179 | -16.927 | 17.413 | 118.915 | 1.00 | 63.05 | | N |
| ANISOU | 9188 | NE | ARG | D | 179 | 9494 | 8740 | 5721 | -80 | 500 | 2188 | N |
| ATOM | 9190 | CZ | ARG | D | 179 | -16.379 | 16.311 | 119.405 | 1.00 | 66.59 | | C |
| ANISOU | 9190 | CZ | ARG | D | 179 | 10247 | 9059 | 5994 | 150 | 560 | 2518 | C |
| ATOM | 9191 | NH1 | ARG | D | 179 | -15.712 | 15.476 | 118.605 | 1.00 | 67.98 | | N |
| ANISOU | 9191 | NH1 | ARG | D | 179 | 10543 | 8987 | 6298 | 426 | 636 | 2714 | N |
| ATOM | 9194 | NH2 | ARG | D | 179 | -16.492 | 16.043 | 120.704 | 1.00 | 69.79 | | N |
| ANISOU | 9194 | NH2 | ARG | D | 179 | 10863 | 9582 | 6072 | 133 | 543 | 2655 | N |
| ATOM | 9197 | C | ARG | D | 179 | -13.313 | 20.155 | 116.486 | 1.00 | 55.93 | | C |
| ANISOU | 9197 | C | ARG | D | 179 | 7319 | 8428 | 5503 | 316 | -274 | 2150 | C |
| ATOM | 9198 | O | ARG | D | 179 | -13.349 | 20.910 | 117.458 | 1.00 | 55.24 | | O |
| ANISOU | 9198 | O | ARG | D | 179 | 7171 | 8566 | 5253 | 181 | -461 | 2064 | O |
| ATOM | 9200 | N | GLN | D | 180 | -12.303 | 19.319 | 116.250 | 1.00 | 60.01 | | N |
| ANISOU | 9200 | N | GLN | D | 180 | 7806 | 8981 | 6015 | 646 | -261 | 2425 | N |
| ATOM | 9201 | CA | GLN | D | 180 | -11.116 | 19.245 | 117.123 | 1.00 | 64.24 | | C |
| ANISOU | 9201 | CA | GLN | D | 180 | 8180 | 9881 | 6348 | 885 | -489 | 2660 | C |
| ATOM | 9203 | CB | GLN | D | 180 | -10.182 | 18.117 | 116.669 | 1.00 | 67.83 | | C |
| ANISOU | 9203 | CB | GLN | D | 180 | 8652 | 10316 | 6806 | 1341 | -408 | 2952 | C |
| ATOM | 9206 | CG | GLN | D | 180 | -8.983 | 17.861 | 117.574 | 1.00 | 73.08 | | C |
| ANISOU | 9206 | CG | GLN | D | 180 | 9154 | 11389 | 7223 | 1678 | -633 | 3220 | C |
| ATOM | 9209 | CD | GLN | D | 180 | -9.361 | 17.175 | 118.874 | 1.00 | 77.15 | | C |
| ANISOU | 9209 | CD | GLN | D | 180 | 10052 | 11830 | 7431 | 1787 | -617 | 3380 | C |
| ATOM | 9210 | OE1 | GLN | D | 180 | -9.107 | 15.981 | 119.051 | 1.00 | 81.23 | | O |
| ANISOU | 9210 | OE1 | GLN | D | 180 | 10871 | 12177 | 7814 | 2180 | -505 | 3644 | O |
| ATOM | 9211 | NE2 | GLN | D | 180 | -9.965 | 17.926 | 119.795 | 1.00 | 76.92 | | N |
| ANISOU | 9211 | NE2 | GLN | D | 180 | 10046 | 11914 | 7265 | 1452 | -725 | 3222 | N |
| ATOM | 9214 | C | GLN | D | 180 | -10.362 | 20.578 | 117.161 | 1.00 | 63.48 | | C |
| ANISOU | 9214 | C | GLN | D | 180 | 7660 | 10177 | 6283 | 700 | -790 | 2547 | C |
| ATOM | 9215 | O | GLN | D | 180 | -10.011 | 21.067 | 118.232 | 1.00 | 63.96 | | O |
| ANISOU | 9215 | O | GLN | D | 180 | 7631 | 10541 | 6131 | 636 | -1016 | 2560 | O |
| ATOM | 9217 | N | GLU | D | 181 | -10.133 | 21.162 | 115.986 | 1.00 | 62.22 | | N |
| ANISOU | 9217 | N | GLU | D | 181 | 7273 | 9999 | 6368 | 583 | -789 | 2433 | N |
| ATOM | 9218 | CA | GLU | D | 181 | -9.487 | 22.482 | 115.880 | 1.00 | 62.57 | | C |
| ANISOU | 9218 | CA | GLU | D | 181 | 6975 | 10349 | 6451 | 318 | -1051 | 2310 | C |
| ATOM | 9220 | CB | GLU | D | 181 | -9.170 | 22.823 | 114.412 | 1.00 | 62.48 | | C |
| ANISOU | 9220 | CB | GLU | D | 181 | 6763 | 10278 | 6698 | 246 | -984 | 2258 | C |
| ATOM | 9223 | CG | GLU | D | 181 | -7.863 | 22.255 | 113.938 | 1.00 | 66.23 | | C |
| ANISOU | 9223 | CG | GLU | D | 181 | 6925 | 11061 | 7176 | 537 | -998 | 2500 | C |
| ATOM | 9226 | CD | GLU | D | 181 | -6.689 | 22.822 | 114.728 | 1.00 | 70.74 | | C |
| ANISOU | 9226 | CD | GLU | D | 181 | 7132 | 12190 | 7557 | 480 | -1303 | 2594 | C |
| ATOM | 9227 | OE1 | GLU | D | 181 | -6.198 | 22.128 | 115.650 | 1.00 | 74.27 | | O |
| ANISOU | 9227 | OE1 | GLU | D | 181 | 7559 | 12874 | 7788 | 782 | -1378 | 2789 | O |
| ATOM | 9228 | OE2 | GLU | D | 181 | -6.292 | 23.978 | 114.452 | 1.00 | 71.14 | | O |
| ANISOU | 9228 | OE2 | GLU | D | 181 | 6942 | 12436 | 7653 | 111 | -1475 | 2467 | O |
| ATOM | 9229 | C | GLU | D | 181 | -10.321 | 23.606 | 116.498 | 1.00 | 59.66 | | C |
| ANISOU | 9229 | C | GLU | D | 181 | 6725 | 9919 | 6023 | -43 | -1174 | 2031 | C |
| ATOM | 9230 | O | GLU | D | 181 | -9.782 | 24.489 | 117.164 | 1.00 | 59.47 | | O |
| ANISOU | 9230 | O | GLU | D | 181 | 6546 | 10182 | 5867 | -227 | -1438 | 1974 | O |
| ATOM | 9232 | N | MET | D | 182 | -11.633 | 23.574 | 116.287 | 1.00 | 55.41 | | N |
| ANISOU | 9232 | N | MET | D | 182 | 6461 | 9031 | 5561 | -138 | -987 | 1842 | N |
| ATOM | 9233 | CA | MET | D | 182 | -12.498 | 24.540 | 116.957 | 1.00 | 54.03 | | C |
| ANISOU | 9233 | CA | MET | D | 182 | 6419 | 8818 | 5291 | -390 | -1083 | 1568 | C |
| ATOM | 9235 | CB | MET | D | 182 | -13.955 | 24.358 | 116.559 | 1.00 | 51.03 | | C |
| ANISOU | 9235 | CB | MET | D | 182 | 6275 | 8116 | 4999 | -441 | -842 | 1368 | C |
| ATOM | 9238 | CG | MET | D | 182 | -14.297 | 24.861 | 115.149 | 1.00 | 48.55 | | C |
| ANISOU | 9238 | CG | MET | D | 182 | 5909 | 7587 | 4952 | -531 | -775 | 1214 | C |
| ATOM | 9241 | SD | MET | D | 182 | -16.091 | 24.878 | 115.017 | 1.00 | 45.62 | | S |
| ANISOU | 9241 | SD | MET | D | 182 | 5758 | 6983 | 4591 | -609 | -565 | 920 | S |
| ATOM | 9242 | CE | MET | D | 182 | -16.296 | 25.238 | 113.278 | 1.00 | 43.59 | | C |
| ANISOU | 9242 | CE | MET | D | 182 | 5429 | 6507 | 4626 | -641 | -495 | 814 | C |
| ATOM | 9246 | C | MET | D | 182 | -12.378 | 24.425 | 118.476 | 1.00 | 56.07 | | C |
| ANISOU | 9246 | C | MET | D | 182 | 6753 | 9311 | 5240 | -359 | -1210 | 1630 | C |
| ATOM | 9247 | O | MET | D | 182 | -12.249 | 25.436 | 119.149 | 1.00 | 57.21 | | O |
| ANISOU | 9247 | O | MET | D | 182 | 6858 | 9624 | 5256 | -550 | -1438 | 1475 | O |
| ATOM | 9249 | N | ALA | D | 183 | -12.448 | 23.202 | 119.004 | 1.00 | 57.79 | | N |
| ANISOU | 9249 | N | ALA | D | 183 | 7126 | 9513 | 5318 | -128 | -1060 | 1851 | N |
| ATOM | 9250 | CA | ALA | D | 183 | -12.355 | 22.968 | 120.459 | 1.00 | 61.69 | | C |
| ANISOU | 9250 | CA | ALA | D | 183 | 7730 | 10228 | 5480 | -72 | -1163 | 1948 | C |
| ATOM | 9252 | CB | ALA | D | 183 | -12.554 | 21.482 | 120.783 | 1.00 | 62.94 | | C |
| ANISOU | 9252 | CB | ALA | D | 183 | 8156 | 10246 | 5513 | 190 | -936 | 2218 | C |
| ATOM | 9256 | C | ALA | D | 183 | -11.039 | 23.481 | 121.062 | 1.00 | 64.77 | | C |
| ANISOU | 9256 | C | ALA | D | 183 | 7844 | 11048 | 5717 | -53 | -1494 | 2057 | C |
| ATOM | 9257 | O | ALA | D | 183 | -11.029 | 23.981 | 122.182 | 1.00 | 66.59 | | O |
| ANISOU | 9257 | O | ALA | D | 183 | 8106 | 11501 | 5693 | -162 | -1675 | 1981 | O |
| ATOM | 9259 | N | ASN | D | 184 | -9.941 | 23.381 | 120.314 | 1.00 | 67.62 | | N |
| ANISOU | 9259 | N | ASN | D | 184 | 7914 | 11566 | 6214 | 66 | -1573 | 2214 | N |
| ATOM | 9260 | CA | ASN | D | 184 | -8.637 | 23.869 | 120.789 | 1.00 | 72.10 | | C |
| ANISOU | 9260 | CA | ASN | D | 184 | 8139 | 12625 | 6631 | 48 | -1889 | 2310 | C |
| ATOM | 9262 | CB | ASN | D | 184 | -7.520 | 23.446 | 119.832 | 1.00 | 74.43 | | C |

FIG. 18 (continued)

| | | | | | | | | | | | | |
|---|---|---|---|---|---|---|---|---|---|---|---|---|
| ANISOU | 9262 | CB | ASN | D | 184 | 8099 | 13107 | 7075 | 261 | -1887 | 2517 | C |
| ATOM | 9265 | CG | ASN | D | 184 | -7.360 | 21.938 | 119.750 | 1.00 | 76.59 | | C |
| ANISOU | 9265 | CG | ASN | D | 184 | 8505 | 13286 | 7310 | 757 | -1689 | 2818 | C |
| ATOM | 9266 | OD1 | ASN | D | 184 | -7.900 | 21.192 | 120.574 | 1.00 | 76.96 | | O |
| ANISOU | 9266 | OD1 | ASN | D | 184 | 8886 | 13187 | 7170 | 926 | -1598 | 2922 | O |
| ATOM | 9267 | ND2 | ASN | D | 184 | -6.626 | 21.482 | 118.738 | 1.00 | 78.10 | | N |
| ANISOU | 9267 | ND2 | ASN | D | 184 | 8471 | 13542 | 7662 | 992 | -1612 | 2957 | N |
| ATOM | 9270 | C | ASN | D | 184 | -8.606 | 25.387 | 120.956 | 1.00 | 71.97 | | C |
| ANISOU | 9270 | C | ASN | D | 184 | 8018 | 12721 | 6606 | -387 | -2130 | 2019 | C |
| ATOM | 9271 | O | ASN | D | 184 | -8.077 | 25.904 | 121.953 | 1.00 | 75.38 | | O |
| ANISOU | 9271 | O | ASN | D | 184 | 8353 | 13503 | 6785 | -511 | -2395 | 1993 | O |
| ATOM | 9273 | N | ARG | D | 185 | -9.175 | 26.086 | 119.976 | 1.00 | 67.97 | | N |
| ANISOU | 9273 | N | ARG | D | 185 | 7568 | 11901 | 6355 | -610 | -2043 | 1801 | N |
| ATOM | 9274 | CA | ARG | D | 185 | -9.299 | 27.546 | 120.001 | 1.00 | 67.78 | | C |
| ANISOU | 9274 | CA | ARG | D | 185 | 7569 | 11847 | 6339 | -1009 | -2241 | 1508 | C |
| ATOM | 9276 | CB | ARG | D | 185 | -9.431 | 28.079 | 118.568 | 1.00 | 66.16 | | C |
| ANISOU | 9276 | CB | ARG | D | 185 | 7329 | 11368 | 6441 | -1161 | -2152 | 1406 | C |
| ATOM | 9279 | CG | ARG | D | 185 | -8.253 | 27.737 | 117.669 | 1.00 | 68.14 | | C |
| ANISOU | 9279 | CG | ARG | D | 185 | 7216 | 11855 | 6820 | -1105 | -2154 | 1635 | C |
| ATOM | 9282 | CD | ARG | D | 185 | -8.714 | 27.375 | 116.277 | 1.00 | 67.09 | | C |
| ANISOU | 9282 | CD | ARG | D | 185 | 7130 | 11386 | 6975 | -1003 | -1894 | 1644 | C |
| ATOM | 9285 | NE | ARG | D | 185 | -7.615 | 27.210 | 115.320 | 1.00 | 69.19 | | N |
| ANISOU | 9285 | NE | ARG | D | 185 | 7047 | 11887 | 7357 | -982 | -1887 | 1822 | N |
| ATOM | 9287 | CZ | ARG | D | 185 | -7.136 | 28.172 | 114.521 | 1.00 | 70.33 | | C |
| ANISOU | 9287 | CZ | ARG | D | 185 | 7049 | 12072 | 7602 | -1314 | -1981 | 1747 | C |
| ATOM | 9288 | NH1 | ARG | D | 185 | -7.631 | 29.411 | 114.561 | 1.00 | 69.77 | | N |
| ANISOU | 9288 | NH1 | ARG | D | 185 | 7204 | 11771 | 7535 | -1682 | -2112 | 1501 | N |
| ATOM | 9291 | NH2 | ARG | D | 185 | -6.138 | 27.896 | 113.673 | 1.00 | 71.26 | | N |
| ANISOU | 9291 | NH2 | ARG | D | 185 | 6816 | 12465 | 7797 | -1271 | -1939 | 1923 | N |
| ATOM | 9294 | C | ARG | D | 185 | -10.489 | 28.032 | 120.850 | 1.00 | 66.88 | | C |
| ANISOU | 9294 | C | ARG | D | 185 | 7798 | 11534 | 6079 | -1105 | -2230 | 1238 | C |
| ATOM | 9295 | O | ARG | D | 185 | -10.783 | 29.227 | 120.879 | 1.00 | 66.10 | | O |
| ANISOU | 9295 | O | ARG | D | 185 | 7818 | 11321 | 5976 | -1377 | -2369 | 961 | O |
| ATOM | 9297 | N | GLY | D | 186 | -11.171 | 27.113 | 121.536 | 1.00 | 66.95 | | N |
| ANISOU | 9297 | N | GLY | D | 186 | 7988 | 11502 | 5947 | -879 | -2059 | 1317 | N |
| ATOM | 9298 | CA | GLY | D | 186 | -12.294 | 27.467 | 122.399 | 1.00 | 66.92 | | C |
| ANISOU | 9298 | CA | GLY | D | 186 | 8266 | 11397 | 5765 | -946 | -2019 | 1073 | C |
| ATOM | 9301 | C | GLY | D | 186 | -13.519 | 27.974 | 121.657 | 1.00 | 64.03 | | C |
| ANISOU | 9301 | C | GLY | D | 186 | 8074 | 10666 | 5590 | -1019 | -1850 | 788 | C |
| ATOM | 9302 | O | GLY | D | 186 | -14.313 | 28.731 | 122.211 | 1.00 | 63.67 | | O |
| ANISOU | 9302 | O | GLY | D | 186 | 8209 | 10570 | 5415 | -1113 | -1891 | 501 | O |
| ATOM | 9304 | N | LEU | D | 187 | -13.672 | 27.557 | 120.402 | 1.00 | 62.78 | | N |
| ANISOU | 9304 | N | LEU | D | 187 | 7855 | 10279 | 5718 | -947 | -1667 | 859 | N |
| ATOM | 9305 | CA | LEU | D | 187 | -14.801 | 27.978 | 119.563 | 1.00 | 60.57 | | C |
| ANISOU | 9305 | CA | LEU | D | 187 | 7702 | 9690 | 5623 | -984 | -1515 | 609 | C |
| ATOM | 9307 | CB | LEU | D | 187 | -14.322 | 28.204 | 118.132 | 1.00 | 58.92 | | C |
| ANISOU | 9307 | CB | LEU | D | 187 | 7357 | 9319 | 5710 | -1026 | -1511 | 662 | C |
| ATOM | 9310 | CG | LEU | D | 187 | -13.158 | 29.182 | 117.947 | 1.00 | 60.44 | | C |
| ANISOU | 9310 | CG | LEU | D | 187 | 7408 | 9631 | 5925 | -1238 | -1793 | 676 | C |
| ATOM | 9312 | CD1 | LEU | D | 187 | -12.541 | 28.980 | 116.573 | 1.00 | 58.50 | | C |
| ANISOU | 9312 | CD1 | LEU | D | 187 | 6978 | 9312 | 5938 | -1239 | -1722 | 832 | C |
| ATOM | 9316 | CD2 | LEU | D | 187 | -13.612 | 30.614 | 118.145 | 1.00 | 60.26 | | C |
| ANISOU | 9316 | CD2 | LEU | D | 187 | 7593 | 9460 | 5843 | -1445 | -1975 | 350 | C |
| ATOM | 9320 | C | LEU | D | 187 | -15.943 | 26.962 | 119.533 | 1.00 | 59.00 | | C |
| ANISOU | 9320 | C | LEU | D | 187 | 7629 | 9370 | 5420 | -848 | -1197 | 612 | C |
| ATOM | 9321 | O | LEU | D | 187 | -17.090 | 27.329 | 119.284 | 1.00 | 59.62 | | O |
| ANISOU | 9321 | O | LEU | D | 187 | 7809 | 9314 | 5531 | -872 | -1085 | 353 | O |
| ATOM | 9323 | N | TRP | D | 188 | -15.632 | 25.694 | 119.783 | 1.00 | 58.70 | | N |
| ANISOU | 9323 | N | TRP | D | 188 | 7594 | 9388 | 5320 | -707 | -1054 | 902 | N |
| ATOM | 9324 | CA | TRP | D | 188 | -16.584 | 24.611 | 119.560 | 1.00 | 57.17 | | C |
| ANISOU | 9324 | CA | TRP | D | 188 | 7546 | 9031 | 5143 | -640 | -734 | 945 | C |
| ATOM | 9326 | CB | TRP | D | 188 | -15.935 | 23.256 | 119.860 | 1.00 | 58.38 | | C |
| ANISOU | 9326 | CB | TRP | D | 188 | 7771 | 9202 | 5208 | -462 | -630 | 1314 | C |
| ATOM | 9329 | CG | TRP | D | 188 | -16.934 | 22.154 | 119.808 | 1.00 | 58.08 | | C |
| ANISOU | 9329 | CG | TRP | D | 188 | 7965 | 8973 | 5129 | -467 | -304 | 1354 | C |
| ATOM | 9330 | CD1 | TRP | D | 188 | -17.454 | 21.472 | 120.859 | 1.00 | 59.73 | | C |
| ANISOU | 9330 | CD1 | TRP | D | 188 | 8399 | 9239 | 5057 | -495 | -173 | 1436 | C |
| ATOM | 9332 | NE1 | TRP | D | 188 | -18.365 | 20.549 | 120.420 | 1.00 | 59.58 | | N |
| ANISOU | 9332 | NE1 | TRP | D | 188 | 8569 | 8995 | 5072 | -577 | 140 | 1440 | N |
| ATOM | 9334 | CE2 | TRP | D | 188 | -18.457 | 20.628 | 119.055 | 1.00 | 57.06 | | C |
| ANISOU | 9334 | CE2 | TRP | D | 188 | 8138 | 8480 | 5063 | -579 | 206 | 1347 | C |
| ATOM | 9335 | CD2 | TRP | D | 188 | -17.574 | 21.641 | 118.635 | 1.00 | 56.19 | | C |
| ANISOU | 9335 | CD2 | TRP | D | 188 | 7770 | 8466 | 5112 | -500 | -65 | 1298 | C |
| ATOM | 9336 | CE3 | TRP | D | 188 | -17.481 | 21.935 | 117.268 | 1.00 | 53.33 | | C |
| ANISOU | 9336 | CE3 | TRP | D | 188 | 7266 | 7947 | 5047 | -493 | -53 | 1213 | C |
| ATOM | 9338 | CZ3 | TRP | D | 188 | -18.264 | 21.220 | 116.380 | 1.00 | 51.87 | | C |
| ANISOU | 9338 | CZ3 | TRP | D | 188 | 7186 | 7531 | 4990 | -545 | 210 | 1162 | C |
| ATOM | 9340 | CH2 | TRP | D | 188 | -19.137 | 20.224 | 116.828 | 1.00 | 53.48 | | C |
| ANISOU | 9340 | CH2 | TRP | D | 188 | 7637 | 7651 | 5034 | -646 | 467 | 1193 | C |

FIG. 18 (continued)

| | | | | | | | | | | | | |
|---|---|---|---|---|---|---|---|---|---|---|---|---|
| ATOM | 9342 | CZ2 | TRP | D | 188 | -19.250 | 19.916 | 118.162 | 1.00 | 56.23 | | C |
| ANISOU | 9342 | CZ2 | TRP | D | 188 | 8142 | 8136 | 5088 | -676 | 477 | 1292 | C |
| ATOM | 9344 | C | TRP | D | 188 | -17.906 | 24.727 | 120.348 | 1.00 | 57.09 | | C |
| ANISOU | 9344 | C | TRP | D | 188 | 7692 | 9073 | 4927 | -731 | -604 | 709 | C |
| ATOM | 9345 | O | TRP | D | 188 | -18.979 | 24.587 | 119.772 | 1.00 | 54.81 | | O |
| ANISOU | 9345 | O | TRP | D | 188 | 7437 | 8660 | 4726 | -781 | -399 | 540 | O |
| ATOM | 9347 | N | ASP | D | 189 | -17.831 | 24.970 | 121.651 | 1.00 | 59.75 | | N |
| ANISOU | 9347 | N | ASP | D | 189 | 8097 | 9638 | 4968 | -754 | -721 | 691 | N |
| ATOM | 9348 | CA | ASP | D | 189 | -19.033 | 25.030 | 122.490 | 1.00 | 60.37 | | C |
| ANISOU | 9348 | CA | ASP | D | 189 | 8302 | 9833 | 4801 | -830 | -581 | 477 | C |
| ATOM | 9350 | CB | ASP | D | 189 | -18.686 | 25.327 | 123.950 | 1.00 | 65.04 | | C |
| ANISOU | 9350 | CB | ASP | D | 189 | 8968 | 10702 | 5044 | -840 | -752 | 490 | C |
| ATOM | 9353 | CG | ASP | D | 189 | -17.840 | 24.235 | 124.598 | 1.00 | 68.17 | | C |
| ANISOU | 9353 | CG | ASP | D | 189 | 9446 | 11185 | 5271 | -744 | -750 | 890 | C |
| ATOM | 9354 | OD1 | ASP | D | 189 | -18.196 | 23.043 | 124.496 | 1.00 | 68.73 | | O |
| ANISOU | 9354 | OD1 | ASP | D | 189 | 9662 | 11133 | 5319 | -714 | -489 | 1096 | O |
| ATOM | 9355 | OD2 | ASP | D | 189 | -16.824 | 24.578 | 125.243 | 1.00 | 72.02 | | O |
| ANISOU | 9355 | OD2 | ASP | D | 189 | 9873 | 11870 | 5620 | -698 | -1019 | 996 | O |
| ATOM | 9356 | C | ASP | D | 189 | -20.025 | 26.075 | 121.974 | 1.00 | 58.18 | | C |
| ANISOU | 9356 | C | ASP | D | 189 | 7974 | 9508 | 4625 | -878 | -579 | 78 | C |
| ATOM | 9357 | O | ASP | D | 189 | -21.236 | 25.811 | 121.926 | 1.00 | 58.93 | | O |
| ANISOU | 9357 | O | ASP | D | 189 | 8090 | 9638 | 4662 | -916 | -346 | -91 | O |
| ATOM | 9359 | N | SER | D | 190 | -19.524 | 27.245 | 121.574 | 1.00 | 55.69 | | N |
| ANISOU | 9359 | N | SER | D | 190 | 7598 | 9124 | 4438 | -875 | -835 | -70 | N |
| ATOM | 9360 | CA | SER | D | 190 | -20.370 | 28.267 | 120.954 | 1.00 | 52.58 | | C |
| ANISOU | 9360 | CA | SER | D | 190 | 7205 | 8623 | 4148 | -855 | -859 | -423 | C |
| ATOM | 9362 | CB | SER | D | 190 | -19.585 | 29.557 | 120.742 | 1.00 | 53.25 | | C |
| ANISOU | 9362 | CB | SER | D | 190 | 7323 | 8599 | 4311 | -893 | -1179 | -531 | C |
| ATOM | 9365 | OG | SER | D | 190 | -20.421 | 30.565 | 120.182 | 1.00 | 53.74 | | O |
| ANISOU | 9365 | OG | SER | D | 190 | 7463 | 8515 | 4442 | -823 | -1214 | -864 | O |
| ATOM | 9367 | C | SER | D | 190 | -20.969 | 27.776 | 119.617 | 1.00 | 49.24 | | C |
| ANISOU | 9367 | C | SER | D | 190 | 6700 | 8017 | 3991 | -826 | -649 | -423 | C |
| ATOM | 9368 | O | SER | D | 190 | -22.197 | 27.808 | 119.425 | 1.00 | 46.45 | | O |
| ANISOU | 9368 | O | SER | D | 190 | 6328 | 7716 | 3604 | -795 | -483 | -659 | O |
| ATOM | 9370 | N | PHE | D | 191 | -20.099 | 27.325 | 118.704 | 1.00 | 47.46 | | N |
| ANISOU | 9370 | N | PHE | D | 191 | 6404 | 7623 | 4004 | -832 | -658 | -172 | N |
| ATOM | 9371 | CA | PHE | D | 191 | -20.526 | 26.713 | 117.432 | 1.00 | 45.38 | | C |
| ANISOU | 9371 | CA | PHE | D | 191 | 6079 | 7187 | 3975 | -814 | -456 | -137 | C |
| ATOM | 9373 | CB | PHE | D | 191 | -19.308 | 26.209 | 116.652 | 1.00 | 42.47 | | C |
| ANISOU | 9373 | CB | PHE | D | 191 | 5641 | 6683 | 3814 | -793 | -491 | 168 | C |
| ATOM | 9376 | CG | PHE | D | 191 | -19.637 | 25.626 | 115.305 | 1.00 | 39.13 | | C |
| ANISOU | 9376 | CG | PHE | D | 191 | 5176 | 6071 | 3620 | -771 | -302 | 196 | C |
| ATOM | 9377 | CD1 | PHE | D | 191 | -20.080 | 26.438 | 114.262 | 1.00 | 36.44 | | C |
| ANISOU | 9377 | CD1 | PHE | D | 191 | 4790 | 5613 | 3443 | -768 | -350 | -10 | C |
| ATOM | 9379 | CE1 | PHE | D | 191 | -20.381 | 25.897 | 112.997 | 1.00 | 35.83 | | C |
| ANISOU | 9379 | CE1 | PHE | D | 191 | 4672 | 5387 | 3554 | -753 | -183 | 8 | C |
| ATOM | 9381 | CZ | PHE | D | 191 | -20.242 | 24.537 | 112.762 | 1.00 | 35.49 | | C |
| ANISOU | 9381 | CZ | PHE | D | 191 | 4661 | 5278 | 3547 | -752 | 40 | 216 | C |
| ATOM | 9383 | CE2 | PHE | D | 191 | -19.779 | 23.706 | 113.784 | 1.00 | 38.49 | | C |
| ANISOU | 9383 | CE2 | PHE | D | 191 | 5129 | 5725 | 3772 | -737 | 93 | 434 | C |
| ATOM | 9385 | CD2 | PHE | D | 191 | -19.484 | 24.261 | 115.072 | 1.00 | 39.49 | | C |
| ANISOU | 9385 | CD2 | PHE | D | 191 | 5269 | 6038 | 3699 | -743 | -83 | 430 | C |
| ATOM | 9387 | C | PHE | D | 191 | -21.548 | 25.583 | 117.653 | 1.00 | 47.55 | | C |
| ANISOU | 9387 | C | PHE | D | 191 | 6392 | 7534 | 4142 | -860 | -142 | -133 | C |
| ATOM | 9388 | O | PHE | D | 191 | -22.581 | 25.556 | 117.013 | 1.00 | 44.33 | | O |
| ANISOU | 9388 | O | PHE | D | 191 | 5933 | 7117 | 3793 | -880 | 8 | -329 | O |
| ATOM | 9390 | N | ARG | D | 192 | -21.277 | 24.690 | 118.603 | 1.00 | 53.53 | | N |
| ANISOU | 9390 | N | ARG | D | 192 | 7250 | 8383 | 4708 | -894 | -53 | 86 | N |
| ATOM | 9391 | CA | ARG | D | 192 | -22.194 | 23.591 | 118.906 | 1.00 | 56.82 | | C |
| ANISOU | 9391 | CA | ARG | D | 192 | 7763 | 8847 | 4978 | -1008 | 253 | 118 | C |
| ATOM | 9393 | CB | ARG | D | 192 | -21.586 | 22.641 | 119.929 | 1.00 | 61.18 | | C |
| ANISOU | 9393 | CB | ARG | D | 192 | 8498 | 9433 | 5317 | -1012 | 301 | 437 | C |
| ATOM | 9396 | CG | ARG | D | 192 | -22.538 | 21.532 | 120.278 | 1.00 | 64.40 | | C |
| ANISOU | 9396 | CG | ARG | D | 192 | 9070 | 9856 | 5542 | -1191 | 625 | 481 | C |
| ATOM | 9399 | CD | ARG | D | 192 | -21.879 | 20.417 | 121.026 | 1.00 | 68.80 | | C |
| ANISOU | 9399 | CD | ARG | D | 192 | 9893 | 10329 | 5917 | -1165 | 695 | 857 | C |
| ATOM | 9402 | NE | ARG | D | 192 | -22.799 | 19.686 | 121.898 | 1.00 | 72.92 | | N |
| ANISOU | 9402 | NE | ARG | D | 192 | 10615 | 10965 | 6128 | -1387 | 950 | 873 | N |
| ATOM | 9404 | CZ | ARG | D | 192 | -24.043 | 19.286 | 121.594 | 1.00 | 74.19 | | C |
| ANISOU | 9404 | CZ | ARG | D | 192 | 10780 | 11163 | 6245 | -1652 | 1230 | 697 | C |
| ATOM | 9405 | NH1 | ARG | D | 192 | -24.602 | 19.510 | 120.404 | 1.00 | 72.50 | | N |
| ANISOU | 9405 | NH1 | ARG | D | 192 | 10382 | 10881 | 6283 | -1707 | 1293 | 476 | N |
| ATOM | 9408 | NH2 | ARG | D | 192 | -24.743 | 18.629 | 122.511 | 1.00 | 76.84 | | N |
| ANISOU | 9408 | NH2 | ARG | D | 192 | 11304 | 11638 | 6251 | -1890 | 1455 | 747 | N |
| ATOM | 9411 | C | ARG | D | 192 | -23.553 | 24.058 | 119.429 | 1.00 | 58.47 | | C |
| ANISOU | 9411 | C | ARG | D | 192 | 7918 | 9311 | 4988 | -1091 | 354 | -220 | C |
| ATOM | 9412 | O | ARG | D | 192 | -24.598 | 23.571 | 118.978 | 1.00 | 58.01 | | O |
| ANISOU | 9412 | O | ARG | D | 192 | 7811 | 9299 | 4930 | -1211 | 592 | -346 | O |
| ATOM | 9414 | N | GLN | D | 193 | -23.539 | 24.983 | 120.386 | 1.00 | 60.65 | | N |

FIG. 18 (continued)

| | | | | | | | | | | | | |
|---|---|---|---|---|---|---|---|---|---|---|---|---|
| ANISOU | 9414 | N | GLN | D | 193 | 8191 | 9783 | 5070 | -1031 | 177 | -379 | N |
| ATOM | 9415 | CA | GLN | D | 193 | -24.774 | 25.441 | 121.024 | 1.00 | 63.65 | | C |
| ANISOU | 9415 | CA | GLN | D | 193 | 8513 | 10463 | 5210 | -1055 | 272 | -709 | C |
| ATOM | 9417 | CB | GLN | D | 193 | -24.490 | 26.038 | 122.416 | 1.00 | 68.08 | | C |
| ANISOU | 9417 | CB | GLN | D | 193 | 9163 | 11233 | 5472 | -1010 | 113 | -766 | C |
| ATOM | 9420 | CG | GLN | D | 193 | -24.681 | 25.035 | 123.583 | 1.00 | 72.65 | | C |
| ANISOU | 9420 | CG | GLN | D | 193 | 9865 | 12017 | 5723 | -1160 | 311 | -581 | C |
| ATOM | 9423 | CD | GLN | D | 193 | -23.882 | 23.731 | 123.426 | 1.00 | 73.72 | | C |
| ANISOU | 9423 | CD | GLN | D | 193 | 10150 | 11928 | 5930 | -1237 | 408 | -139 | C |
| ATOM | 9424 | OE1 | GLN | D | 193 | -24.464 | 22.650 | 123.255 | 1.00 | 74.97 | | O |
| ANISOU | 9424 | OE1 | GLN | D | 193 | 10387 | 12049 | 6048 | -1404 | 697 | -24 | O |
| ATOM | 9425 | NE2 | GLN | D | 193 | -22.550 | 23.831 | 123.491 | 1.00 | 73.30 | | N |
| ANISOU | 9425 | NE2 | GLN | D | 193 | 10148 | 11739 | 5964 | -1114 | 165 | 100 | N |
| ATOM | 9428 | C | GLN | D | 193 | -25.588 | 26.415 | 120.156 | 1.00 | 62.06 | | C |
| ANISOU | 9428 | C | GLN | D | 193 | 8156 | 10280 | 5144 | -930 | 221 | -1069 | C |
| ATOM | 9429 | O | GLN | D | 193 | -26.803 | 26.515 | 120.326 | 1.00 | 63.28 | | O |
| ANISOU | 9429 | O | GLN | D | 193 | 8193 | 10711 | 5140 | -935 | 377 | -1340 | O |
| ATOM | 9431 | N | SER | D | 194 | -24.942 | 27.094 | 119.208 | 1.00 | 59.22 | | N |
| ANISOU | 9431 | N | SER | D | 194 | 7790 | 9656 | 5054 | -815 | 14 | -1064 | N |
| ATOM | 9432 | CA | SER | D | 194 | -25.656 | 28.021 | 118.322 | 1.00 | 57.98 | | C |
| ANISOU | 9432 | CA | SER | D | 194 | 7543 | 9472 | 5017 | -659 | -55 | -1370 | C |
| ATOM | 9434 | CB | SER | D | 194 | -24.679 | 28.896 | 117.520 | 1.00 | 57.70 | | C |
| ANISOU | 9434 | CB | SER | D | 194 | 7588 | 9112 | 5223 | -569 | -329 | -1313 | C |
| ATOM | 9437 | OG | SER | D | 194 | -24.123 | 28.200 | 116.413 | 1.00 | 56.80 | | O |
| ANISOU | 9437 | OG | SER | D | 194 | 7426 | 8782 | 5373 | -644 | -261 | -1067 | O |
| ATOM | 9439 | C | SER | D | 194 | -26.649 | 27.342 | 117.365 | 1.00 | 55.97 | | C |
| ANISOU | 9439 | C | SER | D | 194 | 7121 | 9288 | 4856 | -714 | 190 | -1448 | C |
| ATOM | 9440 | O | SER | D | 194 | -27.536 | 28.008 | 116.848 | 1.00 | 54.99 | | O |
| ANISOU | 9440 | O | SER | D | 194 | 6882 | 9277 | 4736 | -561 | 171 | -1743 | O |
| ATOM | 9442 | N | GLU | D | 195 | -26.531 | 26.030 | 117.162 | 1.00 | 54.46 | | N |
| ANISOU | 9442 | N | GLU | D | 195 | 6938 | 9043 | 4714 | -923 | 412 | -1199 | N |
| ATOM | 9443 | CA | GLU | D | 195 | -27.458 | 25.305 | 116.289 | 1.00 | 54.81 | | C |
| ANISOU | 9443 | CA | GLU | D | 195 | 6847 | 9159 | 4821 | -1048 | 650 | -1279 | C |
| ATOM | 9445 | CB | GLU | D | 195 | -26.941 | 23.894 | 115.961 | 1.00 | 52.14 | | C |
| ANISOU | 9445 | CB | GLU | D | 195 | 6639 | 8593 | 4578 | -1263 | 842 | -946 | C |
| ATOM | 9448 | CG | GLU | D | 195 | -27.878 | 23.128 | 114.996 | 1.00 | 50.61 | | C |
| ANISOU | 9448 | CG | GLU | D | 195 | 6341 | 8446 | 4442 | -1448 | 1083 | -1046 | C |
| ATOM | 9451 | CD | GLU | D | 195 | -27.246 | 21.927 | 114.316 | 1.00 | 48.32 | | C |
| ANISOU | 9451 | CD | GLU | D | 195 | 6235 | 7813 | 4311 | -1589 | 1221 | -752 | C |
| ATOM | 9452 | OE1 | GLU | D | 195 | -28.002 | 21.088 | 113.787 | 1.00 | 43.12 | | O |
| ANISOU | 9452 | OE1 | GLU | D | 195 | 5566 | 7185 | 3633 | -1826 | 1454 | -810 | O |
| ATOM | 9453 | OE2 | GLU | D | 195 | -25.995 | 21.834 | 114.282 | 1.00 | 45.31 | | O |
| ANISOU | 9453 | OE2 | GLU | D | 195 | 6004 | 7149 | 4061 | -1458 | 1095 | -479 | O |
| ATOM | 9454 | C | GLU | D | 195 | -28.886 | 25.203 | 116.849 | 1.00 | 60.40 | | C |
| ANISOU | 9454 | C | GLU | D | 195 | 7381 | 10314 | 5255 | -1137 | 851 | -1564 | C |
| ATOM | 9455 | O | GLU | D | 195 | -29.834 | 25.204 | 116.069 | 1.00 | 63.74 | | O |
| ANISOU | 9455 | O | GLU | D | 195 | 7602 | 10909 | 5707 | -1146 | 949 | -1780 | O |
| ATOM | 9457 | N | ARG | D | 196 | -29.037 | 25.097 | 118.169 | 1.00 | 62.97 | | N |
| ANISOU | 9457 | N | ARG | D | 196 | 7760 | 10870 | 5296 | -1210 | 916 | -1565 | N |
| ATOM | 9458 | CA | ARG | D | 196 | -30.345 | 24.826 | 118.796 | 1.00 | 67.06 | | C |
| ANISOU | 9458 | CA | ARG | D | 196 | 8099 | 11873 | 5510 | -1359 | 1158 | -1798 | C |
| ATOM | 9460 | CB | ARG | D | 196 | -30.172 | 24.391 | 120.256 | 1.00 | 69.57 | | C |
| ANISOU | 9460 | CB | ARG | D | 196 | 8571 | 12343 | 5520 | -1512 | 1256 | -1657 | C |
| ATOM | 9469 | C | ARG | D | 196 | -31.302 | 26.021 | 118.737 | 1.00 | 70.38 | | C |
| ANISOU | 9469 | C | ARG | D | 196 | 8271 | 12643 | 5826 | -1068 | 1059 | -2234 | C |
| ATOM | 9470 | O | ARG | D | 196 | -31.830 | 26.343 | 117.666 | 1.00 | 71.31 | | O |
| ANISOU | 9470 | O | ARG | D | 196 | 8210 | 12793 | 6091 | -943 | 1028 | -2414 | O |
| ATOM | 9472 | MN | MN | D | 301 | -28.199 | 23.378 | 98.969 | 0.50 | 60.19 | | MN |
| ANISOU | 9472 | MN | MN | D | 301 | 7070 | 8507 | 7291 | -933 | 837 | -1536 | MN |
| ATOM | 9473 | MN | MN | D | 302 | -27.840 | 20.860 | 101.908 | 0.40 | 49.24 | | MN |
| ANISOU | 9473 | MN | MN | D | 302 | 5975 | 6942 | 5790 | -1487 | 1329 | -1259 | MN |
| ATOM | 9474 | OH2 | HOH | D | 303 | -28.106 | 23.725 | 96.898 | 1.00 | 34.38 | | O |
| ANISOU | 9474 | OH2 | HOH | D | 303 | 3810 | 5182 | 4071 | -798 | 743 | -1570 | O |
| ATOM | 9477 | OH2 | HOH | D | 304 | -27.648 | 26.518 | 96.463 | 1.00 | 43.38 | | O |
| ANISOU | 9477 | OH2 | HOH | D | 304 | 5042 | 6217 | 5222 | -248 | 225 | -1507 | O |
| ATOM | 9480 | S | SO4 | D | 401 | -34.249 | 25.520 | 99.273 | 0.70 | 46.89 | | S |
| ANISOU | 9480 | S | SO4 | D | 401 | 4094 | 8983 | 4739 | -474 | 518 | -2968 | S |
| ATOM | 9481 | O1 | SO4 | D | 401 | -33.136 | 24.663 | 98.851 | 0.70 | 42.00 | | O |
| ANISOU | 9481 | O1 | SO4 | D | 401 | 3765 | 7875 | 4320 | -743 | 652 | -2683 | O |
| ATOM | 9482 | O2 | SO4 | D | 401 | -35.106 | 25.721 | 98.090 | 0.70 | 45.27 | | O |
| ANISOU | 9482 | O2 | SO4 | D | 401 | 3661 | 9124 | 4414 | -341 | 419 | -3188 | O |
| ATOM | 9483 | O3 | SO4 | D | 401 | -33.753 | 26.784 | 99.817 | 0.70 | 41.48 | | O |
| ANISOU | 9483 | O3 | SO4 | D | 401 | 3575 | 8090 | 4096 | -68 | 291 | -2892 | O |
| ATOM | 9484 | O4 | SO4 | D | 401 | -35.017 | 24.909 | 100.363 | 0.70 | 49.38 | | O |
| ANISOU | 9484 | O4 | SO4 | D | 401 | 4190 | 9679 | 4894 | -745 | 712 | -3121 | O |
| ATOM | 9485 | S | SO4 | D | 402 | -20.006 | 17.139 | 121.294 | 0.60 | 67.62 | | S |
| ANISOU | 9485 | S | SO4 | D | 402 | 10536 | 9543 | 5615 | -850 | 926 | 1874 | S |
| ATOM | 9486 | O1 | SO4 | D | 402 | -19.236 | 17.503 | 120.118 | 0.60 | 64.90 | | O |
| ANISOU | 9486 | O1 | SO4 | D | 402 | 9959 | 9087 | 5611 | -649 | 787 | 1857 | O |

FIG. 18 (continued)

| | | | | | | | | | | | | |
|---|---|---|---|---|---|---|---|---|---|---|---|---|
| ATOM | 9487 | O2 | SO4 | D | 402 | -19.775 | 18.109 | 122.362 | 0.60 | 68.47 | | O |
| ANISOU | 9487 | O2 | SO4 | D | 402 | 10468 | 10015 | 5531 | -816 | 687 | 1791 | O |
| ATOM | 9488 | O3 | SO4 | D | 402 | -19.581 | 15.818 | 121.749 | 0.60 | 71.79 | | O |
| ANISOU | 9488 | O3 | SO4 | D | 402 | 11494 | 9831 | 5951 | -734 | 1053 | 2254 | O |
| ATOM | 9489 | O4 | SO4 | D | 402 | -21.427 | 17.084 | 120.968 | 0.60 | 66.61 | | O |
| ANISOU | 9489 | O4 | SO4 | D | 402 | 10410 | 9414 | 5485 | -1201 | 1184 | 1601 | O |
| ATOM | 9490 | S | SO4 | D | 403 | -27.976 | 17.391 | 121.040 | 0.60 | 75.73 | | S |
| ANISOU | 9490 | S | SO4 | D | 403 | 11010 | 11694 | 6071 | -2784 | 2218 | 237 | S |
| ATOM | 9491 | O1 | SO4 | D | 403 | -26.715 | 16.929 | 120.465 | 0.60 | 74.53 | | O |
| ANISOU | 9491 | O1 | SO4 | D | 403 | 11100 | 11055 | 6164 | -2538 | 2088 | 552 | O |
| ATOM | 9492 | O2 | SO4 | D | 403 | -27.870 | 18.821 | 121.305 | 0.60 | 73.88 | | O |
| ANISOU | 9492 | O2 | SO4 | D | 403 | 10446 | 11751 | 5875 | -2486 | 1945 | -11 | O |
| ATOM | 9493 | O3 | SO4 | D | 403 | -28.246 | 16.692 | 122.294 | 0.60 | 80.02 | | O |
| ANISOU | 9493 | O3 | SO4 | D | 403 | 11831 | 12355 | 6218 | -3035 | 2409 | 414 | O |
| ATOM | 9494 | O4 | SO4 | D | 403 | -29.069 | 17.148 | 120.103 | 0.60 | 74.90 | | O |
| ANISOU | 9494 | O4 | SO4 | D | 403 | 10724 | 11691 | 6043 | -3073 | 2426 | -17 | O |
| ATOM | 9495 | OH2 | HOH | S | 1 | 0.062 | 24.684 | 82.901 | 1.00 | 25.69 | | O |
| ATOM | 9498 | OH2 | HOH | S | 2 | 5.041 | 26.744 | 99.774 | 1.00 | 29.91 | | O |
| ATOM | 9501 | OH2 | HOH | S | 3 | 19.523 | 48.003 | 90.624 | 1.00 | 22.84 | | O |
| ATOM | 9504 | OH2 | HOH | S | 5 | 7.249 | 35.813 | 101.210 | 1.00 | 28.70 | | O |
| ATOM | 9507 | OH2 | HOH | S | 8 | 5.868 | 38.932 | 108.633 | 1.00 | 28.84 | | O |
| ATOM | 9510 | OH2 | HOH | S | 9 | -4.974 | 17.727 | 71.021 | 1.00 | 47.03 | | O |
| ATOM | 9513 | OH2 | HOH | S | 10 | 10.927 | 40.922 | 101.134 | 1.00 | 25.85 | | O |
| ATOM | 9516 | OH2 | HOH | S | 11 | 1.098 | 34.251 | 97.084 | 1.00 | 31.46 | | O |
| ATOM | 9519 | OH2 | HOH | S | 12 | -3.767 | 42.767 | 76.878 | 1.00 | 33.68 | | O |
| ATOM | 9522 | OH2 | HOH | S | 14 | 12.299 | 37.857 | 88.546 | 1.00 | 28.93 | | O |
| ATOM | 9525 | OH2 | HOH | S | 15 | 3.680 | 36.673 | 99.056 | 1.00 | 29.58 | | O |
| ATOM | 9528 | OH2 | HOH | S | 19 | 27.950 | 36.385 | 114.949 | 1.00 | 37.32 | | O |
| ATOM | 9531 | OH2 | HOH | S | 20 | -23.713 | 22.455 | 110.675 | 1.00 | 29.10 | | O |
| ATOM | 9534 | OH2 | HOH | S | 21 | -1.009 | 22.921 | 80.906 | 1.00 | 29.12 | | O |
| ATOM | 9537 | OH2 | HOH | S | 22 | -4.475 | 35.464 | 92.443 | 1.00 | 24.81 | | O |
| ATOM | 9540 | OH2 | HOH | S | 23 | 8.782 | 23.580 | 111.171 | 1.00 | 36.80 | | O |
| ATOM | 9543 | OH2 | HOH | S | 24 | 3.067 | 40.236 | 104.679 | 1.00 | 30.93 | | O |
| ATOM | 9546 | OH2 | HOH | S | 26 | 25.608 | 54.437 | 105.241 | 1.00 | 26.93 | | O |
| ATOM | 9549 | OH2 | HOH | S | 27 | 16.461 | 27.165 | 96.651 | 1.00 | 35.66 | | O |
| ATOM | 9552 | OH2 | HOH | S | 28 | 29.704 | 33.968 | 85.233 | 1.00 | 43.78 | | O |
| ATOM | 9555 | OH2 | HOH | S | 29 | 12.541 | 45.953 | 116.919 | 1.00 | 47.52 | | O |
| ATOM | 9558 | OH2 | HOH | S | 30 | 9.690 | 41.870 | 68.637 | 1.00 | 33.34 | | O |
| ATOM | 9561 | OH2 | HOH | S | 31 | 19.724 | 46.723 | 86.346 | 1.00 | 30.74 | | O |
| ATOM | 9564 | OH2 | HOH | S | 32 | 13.930 | 31.423 | 93.968 | 1.00 | 30.78 | | O |
| ATOM | 9567 | OH2 | HOH | S | 33 | -2.096 | 18.086 | 85.105 | 1.00 | 32.48 | | O |
| ATOM | 9570 | OH2 | HOH | S | 34 | 11.121 | 28.090 | 99.161 | 1.00 | 30.81 | | O |
| ATOM | 9573 | OH2 | HOH | S | 35 | 3.273 | 34.095 | 98.573 | 1.00 | 32.91 | | O |
| ATOM | 9576 | OH2 | HOH | S | 37 | 19.321 | 46.250 | 99.994 | 1.00 | 22.33 | | O |
| ATOM | 9579 | OH2 | HOH | S | 38 | -7.678 | 20.563 | 76.781 | 1.00 | 40.12 | | O |
| ATOM | 9582 | OH2 | HOH | S | 40 | 13.780 | 23.868 | 109.878 | 1.00 | 36.26 | | O |
| ATOM | 9585 | OH2 | HOH | S | 41 | -9.073 | 20.418 | 94.927 | 1.00 | 44.90 | | O |
| ATOM | 9588 | OH2 | HOH | S | 42 | -4.991 | 29.737 | 89.751 | 1.00 | 35.50 | | O |
| ATOM | 9591 | OH2 | HOH | S | 43 | 12.715 | 38.965 | 85.275 | 1.00 | 57.53 | | O |
| ATOM | 9594 | OH2 | HOH | S | 44 | 19.802 | 53.492 | 84.952 | 1.00 | 42.01 | | O |
| ATOM | 9597 | OH2 | HOH | S | 45 | 14.553 | 54.161 | 97.433 | 1.00 | 34.06 | | O |
| ATOM | 9600 | OH2 | HOH | S | 48 | 4.616 | 51.945 | 105.181 | 1.00 | 58.84 | | O |
| ATOM | 9603 | OH2 | HOH | S | 51 | 11.476 | 28.483 | 86.843 | 1.00 | 35.13 | | O |
| ATOM | 9606 | OH2 | HOH | S | 52 | 21.205 | 49.503 | 96.599 | 1.00 | 27.24 | | O |
| ATOM | 9609 | OH2 | HOH | S | 53 | 6.598 | 35.101 | 68.723 | 1.00 | 38.82 | | O |
| ATOM | 9612 | OH2 | HOH | S | 54 | 12.418 | 45.152 | 100.982 | 1.00 | 32.90 | | O |
| ATOM | 9615 | OH2 | HOH | S | 55 | 2.765 | 47.906 | 90.848 | 1.00 | 42.28 | | O |
| ATOM | 9618 | OH2 | HOH | S | 56 | 34.091 | 49.452 | 82.599 | 1.00 | 46.87 | | O |
| ATOM | 9621 | OH2 | HOH | S | 57 | 18.039 | 33.685 | 85.188 | 1.00 | 39.86 | | O |
| ATOM | 9624 | OH2 | HOH | S | 58 | 34.743 | 40.618 | 83.700 | 1.00 | 48.99 | | O |
| ATOM | 9627 | OH2 | HOH | S | 59 | 5.836 | 42.154 | 79.337 | 1.00 | 36.16 | | O |
| ATOM | 9630 | OH2 | HOH | S | 60 | 19.672 | 48.371 | 113.647 | 1.00 | 32.80 | | O |
| ATOM | 9633 | OH2 | HOH | S | 61 | -11.286 | 35.969 | 97.938 | 1.00 | 32.16 | | O |
| ATOM | 9636 | OH2 | HOH | S | 63 | 21.313 | 35.851 | 85.625 | 1.00 | 32.91 | | O |
| ATOM | 9639 | OH2 | HOH | S | 64 | 10.917 | 25.957 | 96.584 | 1.00 | 28.98 | | O |
| ATOM | 9642 | OH2 | HOH | S | 65 | 19.332 | 32.806 | 96.412 | 1.00 | 42.40 | | O |
| ATOM | 9645 | OH2 | HOH | S | 66 | 4.367 | 33.324 | 109.829 | 1.00 | 53.36 | | O |
| ATOM | 9648 | OH2 | HOH | S | 67 | -1.545 | 29.274 | 91.562 | 1.00 | 44.97 | | O |
| ATOM | 9651 | OH2 | HOH | S | 69 | 33.158 | 31.375 | 91.673 | 1.00 | 45.84 | | O |
| ATOM | 9654 | OH2 | HOH | S | 71 | 13.049 | 24.535 | 92.838 | 1.00 | 29.36 | | O |
| ATOM | 9657 | OH2 | HOH | S | 72 | 5.198 | 45.062 | 83.047 | 1.00 | 37.65 | | O |
| ATOM | 9660 | OH2 | HOH | S | 74 | 33.408 | 46.948 | 94.390 | 1.00 | 31.17 | | O |
| ATOM | 9663 | OH2 | HOH | S | 75 | 27.533 | 49.208 | 82.074 | 1.00 | 39.57 | | O |
| ATOM | 9666 | OH2 | HOH | S | 82 | 16.239 | 24.966 | 92.440 | 1.00 | 48.38 | | O |
| ATOM | 9669 | OH2 | HOH | S | 85 | 17.867 | 13.953 | 86.983 | 1.00 | 47.68 | | O |
| ATOM | 9672 | OH2 | HOH | S | 88 | 20.835 | 37.732 | 97.703 | 1.00 | 37.50 | | O |
| ATOM | 9675 | OH2 | HOH | S | 89 | 3.564 | 39.911 | 68.945 | 1.00 | 42.81 | | O |
| ATOM | 9678 | OH2 | HOH | S | 91 | 36.527 | 48.533 | 94.837 | 1.00 | 60.18 | | O |
| ATOM | 9681 | OH2 | HOH | S | 92 | 24.908 | 30.650 | 89.450 | 1.00 | 38.14 | | O |

FIG. 18 (continued)

| | | | | | | | | | | | | |
|---|---|---|---|---|---|---|---|---|---|---|---|---|
| ATOM | 9684 | OH2 | HOH | S | 94 | 11.632 | 49.466 | 93.909 | 1.00 | 33.32 | | O |
| ATOM | 9687 | OH2 | HOH | S | 96 | 26.591 | 56.493 | 84.785 | 1.00 | 36.27 | | O |
| ATOM | 9690 | OH2 | HOH | S | 97 | -5.487 | 31.790 | 97.868 | 1.00 | 36.30 | | O |
| ATOM | 9693 | OH2 | HOH | S | 100 | 34.188 | 41.639 | 98.410 | 1.00 | 40.19 | | O |
| ATOM | 9696 | OH2 | HOH | S | 101 | -0.804 | 41.114 | 68.120 | 1.00 | 44.55 | | O |
| ATOM | 9699 | OH2 | HOH | S | 103 | -37.794 | 26.572 | 97.040 | 1.00 | 46.79 | | O |
| ATOM | 9702 | OH2 | HOH | S | 104 | 13.549 | 40.945 | 72.882 | 1.00 | 65.75 | | O |
| ATOM | 9705 | OH2 | HOH | S | 105 | -29.764 | 17.249 | 113.916 | 1.00 | 38.77 | | O |
| ATOM | 9708 | OH2 | HOH | S | 106 | -8.974 | 30.410 | 103.171 | 1.00 | 59.38 | | O |
| ATOM | 9711 | OH2 | HOH | S | 107 | 5.989 | 44.845 | 80.533 | 1.00 | 39.34 | | O |
| ATOM | 9714 | OH2 | HOH | S | 108 | 24.144 | 31.363 | 110.307 | 1.00 | 34.68 | | O |
| ATOM | 9717 | OH2 | HOH | S | 109 | 37.679 | 51.033 | 89.708 | 1.00 | 43.85 | | O |
| ATOM | 9720 | OH2 | HOH | S | 111 | 5.975 | 32.614 | 106.422 | 1.00 | 43.47 | | O |
| ATOM | 9723 | OH2 | HOH | S | 113 | 22.157 | 47.075 | 97.344 | 1.00 | 26.37 | | O |
| ATOM | 9726 | OH2 | HOH | S | 114 | -3.099 | 38.607 | 73.976 | 1.00 | 28.74 | | O |
| ATOM | 9729 | OH2 | HOH | S | 116 | 44.282 | 22.944 | 108.107 | 1.00 | 31.20 | | O |
| ATOM | 9732 | OH2 | HOH | S | 117 | 33.011 | 34.445 | 91.356 | 1.00 | 31.59 | | O |
| ATOM | 9735 | OH2 | HOH | S | 118 | 29.897 | 35.602 | 117.409 | 1.00 | 53.61 | | O |
| ATOM | 9738 | OH2 | HOH | S | 119 | 41.255 | 21.524 | 106.323 | 1.00 | 30.67 | | O |
| ATOM | 9741 | OH2 | HOH | S | 120 | 42.707 | 28.196 | 113.002 | 1.00 | 37.53 | | O |
| ATOM | 9744 | OH2 | HOH | S | 121 | 15.791 | 55.030 | 99.670 | 1.00 | 35.09 | | O |
| ATOM | 9747 | OH2 | HOH | S | 124 | 21.900 | 52.545 | 118.132 | 1.00 | 54.35 | | O |
| ATOM | 9750 | OH2 | HOH | S | 125 | -6.232 | 22.730 | 74.247 | 1.00 | 36.81 | | O |
| ATOM | 9753 | OH2 | HOH | S | 127 | 12.798 | 57.322 | 94.863 | 1.00 | 44.97 | | O |
| ATOM | 9756 | OH2 | HOH | S | 128 | 24.930 | 35.392 | 78.917 | 1.00 | 57.13 | | O |
| ATOM | 9759 | OH2 | HOH | S | 129 | 23.777 | 57.180 | 99.188 | 1.00 | 48.48 | | O |
| ATOM | 9762 | OH2 | HOH | S | 130 | 21.212 | 47.901 | 84.571 | 1.00 | 51.00 | | O |
| ATOM | 9765 | OH2 | HOH | S | 131 | 4.954 | 29.418 | 100.967 | 1.00 | 35.15 | | O |
| ATOM | 9768 | OH2 | HOH | S | 132 | 29.868 | 26.486 | 110.735 | 1.00 | 55.71 | | O |
| ATOM | 9771 | OH2 | HOH | S | 133 | 3.126 | 28.599 | 72.699 | 1.00 | 34.84 | | O |
| ATOM | 9774 | OH2 | HOH | S | 135 | 5.645 | 47.068 | 78.246 | 1.00 | 51.58 | | O |
| ATOM | 9777 | OH2 | HOH | S | 136 | -5.273 | 33.831 | 67.850 | 1.00 | 43.08 | | O |
| ATOM | 9780 | OH2 | HOH | S | 137 | -14.918 | 24.947 | 122.809 | 1.00 | 44.97 | | O |
| ATOM | 9783 | OH2 | HOH | S | 138 | 9.119 | 24.625 | 98.165 | 1.00 | 34.50 | | O |
| ATOM | 9786 | OH2 | HOH | S | 139 | 5.104 | 40.611 | 106.505 | 1.00 | 34.38 | | O |
| ATOM | 9789 | OH2 | HOH | S | 140 | -2.923 | 42.899 | 67.198 | 1.00 | 48.20 | | O |
| ATOM | 9792 | OH2 | HOH | S | 141 | 22.957 | 34.693 | 87.184 | 1.00 | 35.39 | | O |
| ATOM | 9795 | OH2 | HOH | S | 142 | 28.947 | 31.208 | 89.292 | 1.00 | 39.24 | | O |
| ATOM | 9798 | OH2 | HOH | S | 143 | 18.605 | 56.537 | 112.175 | 1.00 | 40.47 | | O |
| ATOM | 9801 | OH2 | HOH | S | 144 | 30.729 | 63.473 | 95.899 | 1.00 | 54.64 | | O |
| ATOM | 9804 | OH2 | HOH | S | 146 | 26.971 | 31.036 | 91.036 | 1.00 | 35.24 | | O |
| ATOM | 9807 | OH2 | HOH | S | 147 | 15.740 | 16.650 | 82.748 | 1.00 | 54.25 | | O |
| ATOM | 9810 | OH2 | HOH | S | 149 | 13.573 | 33.187 | 73.056 | 1.00 | 43.92 | | O |
| ATOM | 9813 | OH2 | HOH | S | 151 | 11.241 | 22.617 | 84.242 | 1.00 | 40.27 | | O |
| ATOM | 9816 | OH2 | HOH | S | 152 | -10.240 | 28.122 | 82.876 | 1.00 | 50.11 | | O |
| ATOM | 9819 | OH2 | HOH | S | 153 | 25.069 | 27.725 | 108.791 | 1.00 | 49.49 | | O |
| ATOM | 9822 | OH2 | HOH | S | 158 | 9.398 | 38.471 | 80.725 | 1.00 | 45.92 | | O |
| ATOM | 9825 | OH2 | HOH | S | 160 | -3.411 | 31.863 | 94.902 | 1.00 | 42.07 | | O |
| ATOM | 9828 | OH2 | HOH | S | 161 | 1.898 | 45.841 | 107.676 | 1.00 | 38.52 | | O |
| ATOM | 9831 | OH2 | HOH | S | 162 | 33.085 | 52.958 | 118.057 | 1.00 | 59.62 | | O |
| ATOM | 9834 | OH2 | HOH | S | 166 | -2.729 | 34.774 | 64.059 | 1.00 | 45.98 | | O |
| ATOM | 9837 | OH2 | HOH | S | 167 | 28.992 | 55.856 | 103.150 | 1.00 | 40.37 | | O |
| ATOM | 9840 | OH2 | HOH | S | 168 | 14.598 | 32.835 | 75.586 | 1.00 | 47.84 | | O |
| ATOM | 9843 | OH2 | HOH | S | 169 | 6.714 | 48.607 | 82.148 | 1.00 | 50.86 | | O |
| ATOM | 9846 | OH2 | HOH | S | 170 | 14.765 | 27.208 | 80.401 | 1.00 | 42.36 | | O |
| ATOM | 9849 | OH2 | HOH | S | 172 | 16.318 | 34.406 | 120.533 | 1.00 | 39.23 | | O |
| ATOM | 9852 | OH2 | HOH | S | 174 | -1.284 | 30.830 | 93.093 | 1.00 | 41.69 | | O |
| ATOM | 9855 | OH2 | HOH | S | 176 | 14.363 | 18.570 | 86.552 | 1.00 | 57.69 | | O |
| ATOM | 9858 | OH2 | HOH | S | 177 | 3.188 | 25.041 | 101.342 | 1.00 | 44.26 | | O |
| ATOM | 9861 | OH2 | HOH | S | 183 | 3.664 | 30.745 | 112.620 | 1.00 | 52.41 | | O |
| ATOM | 9864 | OH2 | HOH | S | 185 | 5.232 | 33.369 | 104.030 | 1.00 | 43.55 | | O |
| ATOM | 9867 | OH2 | HOH | S | 187 | 12.519 | 24.561 | 95.399 | 1.00 | 33.52 | | O |
| ATOM | 9870 | OH2 | HOH | S | 188 | -1.326 | 43.943 | 70.814 | 1.00 | 43.18 | | O |
| ATOM | 9873 | OH2 | HOH | S | 189 | 3.963 | 36.432 | 101.856 | 1.00 | 36.70 | | O |
| ATOM | 9876 | OH2 | HOH | S | 190 | 13.096 | 48.395 | 92.768 | 1.00 | 32.67 | | O |
| ATOM | 9879 | OH2 | HOH | S | 195 | 16.586 | 41.620 | 75.485 | 1.00 | 51.42 | | O |
| ATOM | 9882 | OH2 | HOH | S | 197 | 31.672 | 57.668 | 97.534 | 1.00 | 45.87 | | O |
| ATOM | 9885 | OH2 | HOH | S | 198 | 29.997 | 58.567 | 99.589 | 1.00 | 52.75 | | O |
| ATOM | 9888 | OH2 | HOH | S | 200 | -11.243 | 24.518 | 83.712 | 1.00 | 45.06 | | O |
| ATOM | 9891 | OH2 | HOH | S | 201 | -2.349 | 14.997 | 88.345 | 1.00 | 35.80 | | O |
| ATOM | 9894 | OH2 | HOH | S | 202 | 0.205 | 29.849 | 95.949 | 1.00 | 34.75 | | O |
| ATOM | 9897 | OH2 | HOH | S | 203 | 1.605 | 21.146 | 98.630 | 1.00 | 42.38 | | O |
| ATOM | 9900 | OH2 | HOH | S | 204 | -11.191 | 45.278 | 98.416 | 1.00 | 52.72 | | O |
| ATOM | 9903 | OH2 | HOH | S | 205 | 2.547 | 47.080 | 87.805 | 1.00 | 44.74 | | O |
| ATOM | 9906 | OH2 | HOH | S | 206 | 27.768 | 45.382 | 82.105 | 1.00 | 37.85 | | O |
| ATOM | 9909 | OH2 | HOH | S | 207 | 12.706 | 44.426 | 118.819 | 1.00 | 52.70 | | O |
| ATOM | 9912 | OH2 | HOH | S | 208 | 13.041 | 41.258 | 120.479 | 1.00 | 44.83 | | O |
| ATOM | 9915 | OH2 | HOH | S | 209 | 9.458 | 40.556 | 120.132 | 1.00 | 48.26 | | O |

FIG. 18 (continued)

SEQUENCE LISTING

<160> NUMBER OF SEQ ID NOS: 23

<210> SEQ ID NO 1
<211> LENGTH: 2148
<212> TYPE: DNA
<213> ORGANISM: Influenza A virus -continued

```
<220> FEATURE:
<221> NAME/KEY: CDS
<222> LOCATION: (1)..(2148)
<223> OTHER INFORMATION: PA-subunit of the Influenza A virus
      (A/Victoria/3/1975 (H3N2)) RNA-dependent RNA polymerase

<400> SEQUENCE: 1

atg gaa gat ttt gtg cga caa tgc ttc aat ccg atg att gtc gag ctt       48
Met Glu Asp Phe Val Arg Gln Cys Phe Asn Pro Met Ile Val Glu Leu
1               5                   10                  15

gca gaa aag gca atg aaa gag tat gga gag gat ctg aaa atc gaa aca       96
Ala Glu Lys Ala Met Lys Glu Tyr Gly Glu Asp Leu Lys Ile Glu Thr
            20                  25                  30

aac aaa ttt gca gca ata tgc act cac ttg gag gta tgt ttc atg tat      144
Asn Lys Phe Ala Ala Ile Cys Thr His Leu Glu Val Cys Phe Met Tyr
        35                  40                  45

tca gat ttt cac ttc atc aat gaa caa ggc gag tca ata gtg gta gag      192
Ser Asp Phe His Phe Ile Asn Glu Gln Gly Glu Ser Ile Val Val Glu
    50                  55                  60

ctt gat gat cca aat gca ctg tta aag cac aga ttt gaa ata ata gag      240
Leu Asp Asp Pro Asn Ala Leu Leu Lys His Arg Phe Glu Ile Ile Glu
65                  70                  75                  80

gga aga gac cga aca atg gcc tgg aca gta gta aac agt att tgc aac      288
Gly Arg Asp Arg Thr Met Ala Trp Thr Val Val Asn Ser Ile Cys Asn
                85                  90                  95

act act gga gct gag aaa ccg aag ttt ctg cca gat ttg tat gat tac      336
Thr Thr Gly Ala Glu Lys Pro Lys Phe Leu Pro Asp Leu Tyr Asp Tyr
            100                 105                 110

aag gag aat aga ttc ata gag att gga gta aca agg aga gaa gtc cac      384
Lys Glu Asn Arg Phe Ile Glu Ile Gly Val Thr Arg Arg Glu Val His
        115                 120                 125

ata tac tac ctt gaa aag gcc aat aaa att aaa tct gag aat aca cac      432
Ile Tyr Tyr Leu Glu Lys Ala Asn Lys Ile Lys Ser Glu Asn Thr His
    130                 135                 140

atc cac att ttc tca ttc act ggg gag gaa atg gcc aca aag gcc gac      480
Ile His Ile Phe Ser Phe Thr Gly Glu Glu Met Ala Thr Lys Ala Asp
145                 150                 155                 160

tac act ctt gat gag gaa agc agg gct agg atc aaa acc agg cta ttt      528
Tyr Thr Leu Asp Glu Glu Ser Arg Ala Arg Ile Lys Thr Arg Leu Phe
                165                 170                 175

acc ata aga caa gaa atg gcc aac aga ggc ctc tgg gat tcc ttt cgt      576
Thr Ile Arg Gln Glu Met Ala Asn Arg Gly Leu Trp Asp Ser Phe Arg
            180                 185                 190

cag tcc gaa aga ggc gaa gaa aca att gaa gaa aga ttt gaa atc aca      624
Gln Ser Glu Arg Gly Glu Glu Thr Ile Glu Glu Arg Phe Glu Ile Thr
        195                 200                 205

gga act atg cgc agg ctt gcc gac caa agt ctc ccg ccg aac ttc tcc      672
Gly Thr Met Arg Arg Leu Ala Asp Gln Ser Leu Pro Pro Asn Phe Ser
    210                 215                 220

tgc ctt gag aat ttt aga gcc tat gtg gat gga ttc gaa ccg aac ggc      720
Cys Leu Glu Asn Phe Arg Ala Tyr Val Asp Gly Phe Glu Pro Asn Gly
225                 230                 235                 240

tgc att gag ggc aag ctt tct caa atg tcc aaa gaa gtg aat gca aaa      768
Cys Ile Glu Gly Lys Leu Ser Gln Met Ser Lys Glu Val Asn Ala Lys
                245                 250                 255

att gaa cct ttt ctg aag aca aca cca aga cca atc aaa ctt ccg gat      816
Ile Glu Pro Phe Leu Lys Thr Thr Pro Arg Pro Ile Lys Leu Pro Asp
            260                 265                 270

ggc cct cct tgt ttt cag cgg tcc aaa ttc ctt ctg atg gat gct tta      864
Gly Pro Pro Cys Phe Gln Arg Ser Lys Phe Leu Leu Met Asp Ala Leu
        275                 280                 285
```

-continued

```
aaa tta agc att gaa gac cca agt cac gaa gga gag gga ata cca cta      912
Lys Leu Ser Ile Glu Asp Pro Ser His Glu Gly Glu Gly Ile Pro Leu
    290                 295                 300

tat gat gcg atc aag tgc atg aga aca ttc ttt gga tgg aaa gaa ccc      960
Tyr Asp Ala Ile Lys Cys Met Arg Thr Phe Phe Gly Trp Lys Glu Pro
305                 310                 315                 320

tat atc gtc aaa cca cac gaa agg gga ata aat tca aat tat ctg ctg     1008
Tyr Ile Val Lys Pro His Glu Arg Gly Ile Asn Ser Asn Tyr Leu Leu
                325                 330                 335

tca tgg aag caa gta ctg gca gaa cta cag gac att gaa aat gag gag     1056
Ser Trp Lys Gln Val Leu Ala Glu Leu Gln Asp Ile Glu Asn Glu Glu
            340                 345                 350

aag att cca aga act aaa aac atg aag aaa acg agt cag cta aag tgg     1104
Lys Ile Pro Arg Thr Lys Asn Met Lys Lys Thr Ser Gln Leu Lys Trp
        355                 360                 365

gca ctt ggt gag aac atg gca cca gag aaa gta gac ttt gac aac tgt     1152
Ala Leu Gly Glu Asn Met Ala Pro Glu Lys Val Asp Phe Asp Asn Cys
    370                 375                 380

aga gac ata agc gat ttg aag cag tat gat agt gac gaa cct gaa tta     1200
Arg Asp Ile Ser Asp Leu Lys Gln Tyr Asp Ser Asp Glu Pro Glu Leu
385                 390                 395                 400

agg tca ctt tca agc tgg atc cag aat gag ttc aac aag gca tgc gag     1248
Arg Ser Leu Ser Ser Trp Ile Gln Asn Glu Phe Asn Lys Ala Cys Glu
                405                 410                 415

ctg act gat tca atc tgg ata gag ctc gat gag att gga gaa gac gtg     1296
Leu Thr Asp Ser Ile Trp Ile Glu Leu Asp Glu Ile Gly Glu Asp Val
            420                 425                 430

gct cca att gaa tac att gca agc atg agg agg aat tat ttc aca gca     1344
Ala Pro Ile Glu Tyr Ile Ala Ser Met Arg Arg Asn Tyr Phe Thr Ala
        435                 440                 445

gag gtg tcc cat tgc aga gcc aca gaa tac ata atg aag ggg gta tac     1392
Glu Val Ser His Cys Arg Ala Thr Glu Tyr Ile Met Lys Gly Val Tyr
    450                 455                 460

att aat act gcc ttg ctt aat gca tcc tgt gca gca atg gat gat ttc     1440
Ile Asn Thr Ala Leu Leu Asn Ala Ser Cys Ala Ala Met Asp Asp Phe
465                 470                 475                 480

caa cta att ccc atg ata agc aag tgc aga act aaa gag gga agg cga     1488
Gln Leu Ile Pro Met Ile Ser Lys Cys Arg Thr Lys Glu Gly Arg Arg
                485                 490                 495

aaa acc aat tta tat gga ttc atc ata aag gga aga tct cac tta agg     1536
Lys Thr Asn Leu Tyr Gly Phe Ile Ile Lys Gly Arg Ser His Leu Arg
            500                 505                 510

aat gac acc gac gtg gta aac ttt gtg agc atg gag ttt tct ctc act     1584
Asn Asp Thr Asp Val Val Asn Phe Val Ser Met Glu Phe Ser Leu Thr
        515                 520                 525

gac ccg aga ctt gag cca cat aaa tgg gag aaa tac tgt gtc ctt gag     1632
Asp Pro Arg Leu Glu Pro His Lys Trp Glu Lys Tyr Cys Val Leu Glu
    530                 535                 540

ata gga gat atg cta cta aga agt gcc ata ggc cag atg tca agg cct     1680
Ile Gly Asp Met Leu Leu Arg Ser Ala Ile Gly Gln Met Ser Arg Pro
545                 550                 555                 560

atg ttc ttg tat gtg agg aca aat gga aca tca aag att aaa atg aaa     1728
Met Phe Leu Tyr Val Arg Thr Asn Gly Thr Ser Lys Ile Lys Met Lys
                565                 570                 575

tgg gga atg gag atg aga cgt tgc ctc ctt cag tca ctc caa caa atc     1776
Trp Gly Met Glu Met Arg Arg Cys Leu Leu Gln Ser Leu Gln Gln Ile
            580                 585                 590

gag agc atg att gaa gcc gag tcc tct gtt aaa gag aaa gac atg acc     1824
Glu Ser Met Ile Glu Ala Glu Ser Ser Val Lys Glu Lys Asp Met Thr
```

-continued

```
        595                 600                 605

aaa gag ttt ttt gag aat aaa tca gaa aca tgg ccc att ggg gag tct      1872
Lys Glu Phe Phe Glu Asn Lys Ser Glu Thr Trp Pro Ile Gly Glu Ser
    610                 615                 620

ccc aag gga gtg gaa gaa ggt tcc att ggg aag gtc tgt agg act tta      1920
Pro Lys Gly Val Glu Glu Gly Ser Ile Gly Lys Val Cys Arg Thr Leu
625                 630                 635                 640

ttg gcc aag tcg gta ttc aat agc ctg tat gca tcc cca caa ttg gaa      1968
Leu Ala Lys Ser Val Phe Asn Ser Leu Tyr Ala Ser Pro Gln Leu Glu
                645                 650                 655

gga ttt tca gcg gag tca aga aaa ctg ctt ctt gtc gtt cag gct ctt      2016
Gly Phe Ser Ala Glu Ser Arg Lys Leu Leu Leu Val Val Gln Ala Leu
            660                 665                 670

agg gac aac ctt gaa cct gga acc ttt gat ctt ggg ggg cta tat gaa      2064
Arg Asp Asn Leu Glu Pro Gly Thr Phe Asp Leu Gly Gly Leu Tyr Glu
        675                 680                 685

gca att gag gag tgc ctg att aat gat ccc tgg gtt ttg ctt aat gcg      2112
Ala Ile Glu Glu Cys Leu Ile Asn Asp Pro Trp Val Leu Leu Asn Ala
    690                 695                 700

tct tgg ttc aac tcc ttc cta aca cat gca tta aga                      2148
Ser Trp Phe Asn Ser Phe Leu Thr His Ala Leu Arg
705                 710                 715


<210> SEQ ID NO 2
<211> LENGTH: 716
<212> TYPE: PRT
<213> ORGANISM: Influenza A virus

<400> SEQUENCE: 2

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Val Val Glu
    50                  55                  60

Leu Asp Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Asn Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Asn Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asp Gln Ser Leu Pro Pro Asn Phe Ser
    210                 215                 220
```

-continued

```
Cys Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Lys Thr Thr Pro Arg Pro Ile Lys Leu Pro Asp
            260                 265                 270

Gly Pro Pro Cys Phe Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Tyr Ile Val Lys Pro His Glu Arg Gly Ile Asn Ser Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Arg Thr Lys Asn Met Lys Lys Thr Ser Gln Leu Lys Trp
        355                 360                 365

Ala Leu Gly Glu Asn Met Ala Pro Glu Lys Val Asp Phe Asp Asn Cys
    370                 375                 380

Arg Asp Ile Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu
                405                 410                 415

Leu Thr Asp Ser Ile Trp Ile Glu Leu Asp Glu Ile Gly Glu Asp Val
            420                 425                 430

Ala Pro Ile Glu Tyr Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Met Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Gly Ser Ile Gly Lys Val Cys Arg Thr Leu
625                 630                 635                 640
```

-continued

```
Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Val Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Arg
705                 710                 715


<210> SEQ ID NO 3
<211> LENGTH: 2181
<212> TYPE: DNA
<213> ORGANISM: Influenza B virus
<220> FEATURE:
<221> NAME/KEY: CDS
<222> LOCATION: (1)..(2181)
<223> OTHER INFORMATION: PA-subunit of the Influenza B virus
      (B/Ann Arbor/1/1966 [wild-type]) RNA-dependent RNA polymerase

<400> SEQUENCE: 3

atg gat act ttt att aca aga aat ttc cag act aca ata ata caa aag       48
Met Asp Thr Phe Ile Thr Arg Asn Phe Gln Thr Thr Ile Ile Gln Lys
1               5                   10                  15

gcc aaa aac aca atg gca gaa ttt agt gaa gat cct gaa tta caa cca       96
Ala Lys Asn Thr Met Ala Glu Phe Ser Glu Asp Pro Glu Leu Gln Pro
            20                  25                  30

gca atg cta ttc aac atc tgc gtc cat ctg gag gtc tgc tat gta ata      144
Ala Met Leu Phe Asn Ile Cys Val His Leu Glu Val Cys Tyr Val Ile
        35                  40                  45

agt gat atg aat ttt ctt gat gaa gaa gga aaa aca tat aca gca tta      192
Ser Asp Met Asn Phe Leu Asp Glu Glu Gly Lys Thr Tyr Thr Ala Leu
    50                  55                  60

gaa gga caa gga aaa gaa caa aac ttg aga cca caa tat gaa gtg att      240
Glu Gly Gln Gly Lys Glu Gln Asn Leu Arg Pro Gln Tyr Glu Val Ile
65                  70                  75                  80

gag gga atg cca aga aac ata gca tgg atg gtt caa aga tcc tta gcc      288
Glu Gly Met Pro Arg Asn Ile Ala Trp Met Val Gln Arg Ser Leu Ala
                85                  90                  95

caa gag cat gga ata gag act cca agg tat ctg gct gat ttg ttc gat      336
Gln Glu His Gly Ile Glu Thr Pro Arg Tyr Leu Ala Asp Leu Phe Asp
            100                 105                 110

tat aaa acc aag agg ttt ata gaa gtt gga ata aca aag gga ttg gct      384
Tyr Lys Thr Lys Arg Phe Ile Glu Val Gly Ile Thr Lys Gly Leu Ala
        115                 120                 125

gac gat tac ttt tgg aaa aag aaa gaa aag ctg ggg aat agc atg gaa      432
Asp Asp Tyr Phe Trp Lys Lys Lys Glu Lys Leu Gly Asn Ser Met Glu
    130                 135                 140

ctg atg ata ttc agc tac aat caa gac tat tcg tta agt aat gaa cac      480
Leu Met Ile Phe Ser Tyr Asn Gln Asp Tyr Ser Leu Ser Asn Glu His
145                 150                 155                 160

tca ttg gat gag gaa gga aaa ggg aga gtg cta agc aga ctc aca gaa      528
Ser Leu Asp Glu Glu Gly Lys Gly Arg Val Leu Ser Arg Leu Thr Glu
                165                 170                 175

ctt cag gct gag tta agt ctg aaa aat cta tgg caa gtt ctc ata gga      576
Leu Gln Ala Glu Leu Ser Leu Lys Asn Leu Trp Gln Val Leu Ile Gly
            180                 185                 190

gaa gaa gat att gaa aaa gga att gac ttc aaa ctt gga caa aca ata      624
Glu Glu Asp Ile Glu Lys Gly Ile Asp Phe Lys Leu Gly Gln Thr Ile
        195                 200                 205
```

-continued tct aaa cta agg gac ata tct gtt cca gct ggt ttc tcc aat ttt gaa 672
Ser Lys Leu Arg Asp Ile Ser Val Pro Ala Gly Phe Ser Asn Phe Glu
210 215 220 gga atg agg agc tac ata gac aat ata gat cct aaa gga gca ata gag 720
Gly Met Arg Ser Tyr Ile Asp Asn Ile Asp Pro Lys Gly Ala Ile Glu
225 230 235 240 aga aat cta gca agg atg tct ccc tta gta tca gtt aca ccc aaa aag 768
Arg Asn Leu Ala Arg Met Ser Pro Leu Val Ser Val Thr Pro Lys Lys
245 250 255 tta aaa tgg gag gac cta aga cca ata ggg cct cac att tac agc cat 816
Leu Lys Trp Glu Asp Leu Arg Pro Ile Gly Pro His Ile Tyr Ser His
260 265 270 gag cta cca gaa gtt cca tat aat gcc ttt ctt cta atg tct gat gag 864
Glu Leu Pro Glu Val Pro Tyr Asn Ala Phe Leu Leu Met Ser Asp Glu
275 280 285 ttg ggg ctg gct aat atg act gaa ggg aag tcc aag aaa cca aag acc 912
Leu Gly Leu Ala Asn Met Thr Glu Gly Lys Ser Lys Lys Pro Lys Thr
290 295 300 tta gcc aaa gaa tgt cta gaa aag tac tca aca cta cgg gat caa act 960
Leu Ala Lys Glu Cys Leu Glu Lys Tyr Ser Thr Leu Arg Asp Gln Thr
305 310 315 320 gac cca ata tta ata atg aaa agc gaa aaa gct aac gaa aac ttc tta 1008
Asp Pro Ile Leu Ile Met Lys Ser Glu Lys Ala Asn Glu Asn Phe Leu
325 330 335 tgg aag ttg tgg agg gac tgt gta aat aca ata agt aat gag gaa aca 1056
Trp Lys Leu Trp Arg Asp Cys Val Asn Thr Ile Ser Asn Glu Glu Thr
340 345 350 agt aac gaa tta cag aaa acc aat tat gcc aag tgg gcc aca gga gat 1104
Ser Asn Glu Leu Gln Lys Thr Asn Tyr Ala Lys Trp Ala Thr Gly Asp
355 360 365 gga tta aca tac cag aaa ata atg aaa gaa gta gca ata gat gac gaa 1152
Gly Leu Thr Tyr Gln Lys Ile Met Lys Glu Val Ala Ile Asp Asp Glu
370 375 380 aca atg tac caa gaa gag ccc aaa ata cct aat aaa tgt aga gtg gct 1200
Thr Met Tyr Gln Glu Glu Pro Lys Ile Pro Asn Lys Cys Arg Val Ala
385 390 395 400 gct tgg gtt caa aca gag atg aat cta ttg agc act ctg aca agt aaa 1248
Ala Trp Val Gln Thr Glu Met Asn Leu Leu Ser Thr Leu Thr Ser Lys
405 410 415 agg gcc ctg gat cta cca gaa ata ggg cca gac gta gca ccc gtg gag 1296
Arg Ala Leu Asp Leu Pro Glu Ile Gly Pro Asp Val Ala Pro Val Glu
420 425 430 cat gta ggg agt gaa aga agg aaa tac ttt gtt aat gaa atc aac tac 1344
His Val Gly Ser Glu Arg Arg Lys Tyr Phe Val Asn Glu Ile Asn Tyr
435 440 445 tgt aag gcc tct acc gtt atg atg aag tat gta ctt ttt cac act tca 1392
Cys Lys Ala Ser Thr Val Met Met Lys Tyr Val Leu Phe His Thr Ser
450 455 460 tta tta aat gaa agc aat gcc agc atg gga aaa tat aaa gta ata cca 1440
Leu Leu Asn Glu Ser Asn Ala Ser Met Gly Lys Tyr Lys Val Ile Pro
465 470 475 480 ata acc aac aga gta gta aat gaa aaa gga gaa agt ttt gac ata ctt 1488
Ile Thr Asn Arg Val Val Asn Glu Lys Gly Glu Ser Phe Asp Ile Leu
485 490 495 tat ggt ctg gcg gtt aaa ggg caa tct cat ctg agg gga gat act gat 1536
Tyr Gly Leu Ala Val Lys Gly Gln Ser His Leu Arg Gly Asp Thr Asp
500 505 510 gtt gta aca gtt gtg act ttc gaa ttt agt agt aca gat ccc aga gtg 1584
Val Val Thr Val Val Thr Phe Glu Phe Ser Ser Thr Asp Pro Arg Val

```
        515                 520                 525

gac tca gga aag tgg cca aaa tat act gta ttt aga att ggt tcc tta      1632
Asp Ser Gly Lys Trp Pro Lys Tyr Thr Val Phe Arg Ile Gly Ser Leu
    530                 535                 540

ttt gtg agt gga agg gaa aaa tct gtg tac cta tat tgc cga gtg aat      1680
Phe Val Ser Gly Arg Glu Lys Ser Val Tyr Leu Tyr Cys Arg Val Asn
545                 550                 555                 560

ggt aca aac aag atc caa atg aaa tgg gga atg gaa gct aga aga tgt      1728
Gly Thr Asn Lys Ile Gln Met Lys Trp Gly Met Glu Ala Arg Arg Cys
            565                 570                 575

ctg ctt caa tca atg caa caa atg gaa gca att gtt gat caa gaa tca      1776
Leu Leu Gln Ser Met Gln Gln Met Glu Ala Ile Val Asp Gln Glu Ser
            580                 585                 590

tcg ata caa gga tat gac atg acc aaa gct tgt ttc aag gga gac aga      1824
Ser Ile Gln Gly Tyr Asp Met Thr Lys Ala Cys Phe Lys Gly Asp Arg
        595                 600                 605

gtg aat agt ccc aaa act ttc agt att ggg act caa gaa gga aaa cta      1872
Val Asn Ser Pro Lys Thr Phe Ser Ile Gly Thr Gln Glu Gly Lys Leu
    610                 615                 620

gta aaa gga tcc ttt ggg aaa gca cta aga gta ata ttc acc aaa tgt      1920
Val Lys Gly Ser Phe Gly Lys Ala Leu Arg Val Ile Phe Thr Lys Cys
625                 630                 635                 640

ttg atg cac tat gta ttt gga aat gcc caa ttg gag ggg ttt agt gcc      1968
Leu Met His Tyr Val Phe Gly Asn Ala Gln Leu Glu Gly Phe Ser Ala
            645                 650                 655

gaa tct agg aga ctt cta ctg tta att cag gca tta aag gac aga aag      2016
Glu Ser Arg Arg Leu Leu Leu Leu Ile Gln Ala Leu Lys Asp Arg Lys
            660                 665                 670

ggc cct tgg gta ttc gac tta gag gga atg tat tct gga ata gaa gaa      2064
Gly Pro Trp Val Phe Asp Leu Glu Gly Met Tyr Ser Gly Ile Glu Glu
        675                 680                 685

tgt att agt aac aac cct tgg gta ata cag agt gca tac tgg ttt aat      2112
Cys Ile Ser Asn Asn Pro Trp Val Ile Gln Ser Ala Tyr Trp Phe Asn
    690                 695                 700

gaa tgg ttg ggc ttt gaa aaa gag ggg agt aaa gta tta gaa tca ata      2160
Glu Trp Leu Gly Phe Glu Lys Glu Gly Ser Lys Val Leu Glu Ser Ile
705                 710                 715                 720

gat gaa ata atg gat gaa tga                                          2181
Asp Glu Ile Met Asp Glu
            725


<210> SEQ ID NO 4
<211> LENGTH: 726
<212> TYPE: PRT
<213> ORGANISM: Influenza B virus

<400> SEQUENCE: 4

Met Asp Thr Phe Ile Thr Arg Asn Phe Gln Thr Thr Ile Ile Gln Lys
1               5                   10                  15

Ala Lys Asn Thr Met Ala Glu Phe Ser Glu Asp Pro Glu Leu Gln Pro
            20                  25                  30

Ala Met Leu Phe Asn Ile Cys Val His Leu Glu Val Cys Tyr Val Ile
        35                  40                  45

Ser Asp Met Asn Phe Leu Asp Glu Glu Gly Lys Thr Tyr Thr Ala Leu
    50                  55                  60

Glu Gly Gln Gly Lys Glu Gln Asn Leu Arg Pro Gln Tyr Glu Val Ile
65                  70                  75                  80

Glu Gly Met Pro Arg Asn Ile Ala Trp Met Val Gln Arg Ser Leu Ala
                85                  90                  95
```

-continued

```
Gln Glu His Gly Ile Glu Thr Pro Arg Tyr Leu Ala Asp Leu Phe Asp
            100                 105                 110

Tyr Lys Thr Lys Arg Phe Ile Glu Val Gly Ile Thr Lys Gly Leu Ala
        115                 120                 125

Asp Asp Tyr Phe Trp Lys Lys Lys Glu Lys Leu Gly Asn Ser Met Glu
    130                 135                 140

Leu Met Ile Phe Ser Tyr Asn Gln Asp Tyr Ser Leu Ser Asn Glu His
145                 150                 155                 160

Ser Leu Asp Glu Glu Gly Lys Gly Arg Val Leu Ser Arg Leu Thr Glu
                165                 170                 175

Leu Gln Ala Glu Leu Ser Leu Lys Asn Leu Trp Gln Val Leu Ile Gly
            180                 185                 190

Glu Glu Asp Ile Glu Lys Gly Ile Asp Phe Lys Leu Gly Gln Thr Ile
        195                 200                 205

Ser Lys Leu Arg Asp Ile Ser Val Pro Ala Gly Phe Ser Asn Phe Glu
    210                 215                 220

Gly Met Arg Ser Tyr Ile Asp Asn Ile Asp Pro Lys Gly Ala Ile Glu
225                 230                 235                 240

Arg Asn Leu Ala Arg Met Ser Pro Leu Val Ser Val Thr Pro Lys Lys
                245                 250                 255

Leu Lys Trp Glu Asp Leu Arg Pro Ile Gly Pro His Ile Tyr Ser His
            260                 265                 270

Glu Leu Pro Glu Val Pro Tyr Asn Ala Phe Leu Leu Met Ser Asp Glu
        275                 280                 285

Leu Gly Leu Ala Asn Met Thr Glu Gly Lys Ser Lys Lys Pro Lys Thr
    290                 295                 300

Leu Ala Lys Glu Cys Leu Glu Lys Tyr Ser Thr Leu Arg Asp Gln Thr
305                 310                 315                 320

Asp Pro Ile Leu Ile Met Lys Ser Glu Lys Ala Asn Glu Asn Phe Leu
                325                 330                 335

Trp Lys Leu Trp Arg Asp Cys Val Asn Thr Ile Ser Asn Glu Glu Thr
            340                 345                 350

Ser Asn Glu Leu Gln Lys Thr Asn Tyr Ala Lys Trp Ala Thr Gly Asp
        355                 360                 365

Gly Leu Thr Tyr Gln Lys Ile Met Lys Glu Val Ala Ile Asp Asp Glu
    370                 375                 380

Thr Met Tyr Gln Glu Glu Pro Lys Ile Pro Asn Lys Cys Arg Val Ala
385                 390                 395                 400

Ala Trp Val Gln Thr Glu Met Asn Leu Leu Ser Thr Leu Thr Ser Lys
                405                 410                 415

Arg Ala Leu Asp Leu Pro Glu Ile Gly Pro Asp Val Ala Pro Val Glu
            420                 425                 430

His Val Gly Ser Glu Arg Arg Lys Tyr Phe Val Asn Glu Ile Asn Tyr
        435                 440                 445

Cys Lys Ala Ser Thr Val Met Met Lys Tyr Val Leu Phe His Thr Ser
    450                 455                 460

Leu Leu Asn Glu Ser Asn Ala Ser Met Gly Lys Tyr Lys Val Ile Pro
465                 470                 475                 480

Ile Thr Asn Arg Val Val Asn Glu Lys Gly Glu Ser Phe Asp Ile Leu
                485                 490                 495

Tyr Gly Leu Ala Val Lys Gly Gln Ser His Leu Arg Gly Asp Thr Asp
            500                 505                 510
```

```
Val Val Thr Val Val Thr Phe Glu Phe Ser Ser Thr Asp Pro Arg Val
        515                 520                 525

Asp Ser Gly Lys Trp Pro Lys Tyr Thr Val Phe Arg Ile Gly Ser Leu
    530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Arg Cys
                565                 570                 575

Leu Leu Gln Ser Met Gln Gln Met Glu Ala Ile Val Asp Gln Glu Ser
            580                 585                 590

Ser Ile Gln Gly Tyr Asp Met Thr Lys Ala Cys Phe Lys Gly Asp Arg
        595                 600                 605

Val Asn Ser Pro Lys Thr Phe Ser Ile Gly Thr Gln Glu Gly Lys Leu
    610                 615                 620

Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
                645                 650                 655

Glu Ser Arg Arg Leu Leu Leu Leu Ile Gln Ala Leu Lys Asp Arg Lys
            660                 665                 670

Gly Pro Trp Val Phe Asp Leu Glu Gly Met Tyr Ser Gly Ile Glu Glu
        675                 680                 685

Cys Ile Ser Asn Asn Pro Trp Val Ile Gln Ser Ala Tyr Trp Phe Asn
    690                 695                 700

Glu Trp Leu Gly Phe Glu Lys Glu Gly Ser Lys Val Leu Glu Ser Ile
705                 710                 715                 720

Asp Glu Ile Met Asp Glu
                725


<210> SEQ ID NO 5
<211> LENGTH: 2127
<212> TYPE: DNA
<213> ORGANISM: Influenza C virus
<220> FEATURE:
<221> NAME/KEY: CDS
<222> LOCATION: (1)..(2127)
<223> OTHER INFORMATION: PA-subunit of the Influenza C virus
      (C/Johannesburg/1/66) RNA-dependent RNA polymerase

<400> SEQUENCE: 5

atg tcg aaa act ttt gcc gaa ata gca gag act ttt cta gag cca gaa       48
Met Ser Lys Thr Phe Ala Glu Ile Ala Glu Thr Phe Leu Glu Pro Glu
1               5                   10                  15

gct gta aga ata gcc aaa gaa gca gtg gaa gaa tat ggg gat cac gaa       96
Ala Val Arg Ile Ala Lys Glu Ala Val Glu Glu Tyr Gly Asp His Glu
            20                  25                  30

aga aaa ata ata caa att gga ata cac ttt caa gtt tgc tgc atg ttc      144
Arg Lys Ile Ile Gln Ile Gly Ile His Phe Gln Val Cys Cys Met Phe
        35                  40                  45

tgt gat gag tat ttg agt aca aat ggg agt gat aga ttt gtg ctc att      192
Cys Asp Glu Tyr Leu Ser Thr Asn Gly Ser Asp Arg Phe Val Leu Ile
    50                  55                  60

gaa gga aga aaa aga gga act gca gtg tct tta caa aat gag cta tgt      240
Glu Gly Arg Lys Arg Gly Thr Ala Val Ser Leu Gln Asn Glu Leu Cys
65                  70                  75                  80

aaa agt tat gat ctt gaa cca cta cct ttt ctt tgt gac att ttc gac      288
Lys Ser Tyr Asp Leu Glu Pro Leu Pro Phe Leu Cys Asp Ile Phe Asp
                85                  90                  95
```

-continued aga gaa gag aaa caa ttc gtt gaa att gga ata aca aga aaa gca gat 336
Arg Glu Glu Lys Gln Phe Val Glu Ile Gly Ile Thr Arg Lys Ala Asp
100 105 110 gat agc tat ttt caa tcc aag ttt ggt aaa ctt gga aat agc tgc aag 384
Asp Ser Tyr Phe Gln Ser Lys Phe Gly Lys Leu Gly Asn Ser Cys Lys
115 120 125 ata ttt gta ttc tcc tat gat gga aga ttg gac aaa aat tgt gaa ggc 432
Ile Phe Val Phe Ser Tyr Asp Gly Arg Leu Asp Lys Asn Cys Glu Gly
130 135 140 cct atg gag gaa caa aaa ttg aga atc ttc agt ttt ctt gca act gct 480
Pro Met Glu Glu Gln Lys Leu Arg Ile Phe Ser Phe Leu Ala Thr Ala
145 150 155 160 gct gat ttt ctt agg aaa gaa aac atg ttt aac gaa atc ttc tta cca 528
Ala Asp Phe Leu Arg Lys Glu Asn Met Phe Asn Glu Ile Phe Leu Pro
165 170 175 gac aat gaa gaa acc atc att gaa atg aag aaa gga aaa aca ttt cta 576
Asp Asn Glu Glu Thr Ile Ile Glu Met Lys Lys Gly Lys Thr Phe Leu
180 185 190 gaa ttg agg gat gaa agt gtt cct tta cct ttc caa act tat gaa cag 624
Glu Leu Arg Asp Glu Ser Val Pro Leu Pro Phe Gln Thr Tyr Glu Gln
195 200 205 atg aaa gat tac tgt gaa aaa ttt aaa gga aat cca aga gaa tta gct 672
Met Lys Asp Tyr Cys Glu Lys Phe Lys Gly Asn Pro Arg Glu Leu Ala
210 215 220 tct aaa gta agc caa atg caa agc aac att aaa ttg cca ata aaa cat 720
Ser Lys Val Ser Gln Met Gln Ser Asn Ile Lys Leu Pro Ile Lys His
225 230 235 240 tat gag cag aat aaa ttt cga caa ata cgt cta cca aag gga cca atg 768
Tyr Glu Gln Asn Lys Phe Arg Gln Ile Arg Leu Pro Lys Gly Pro Met
245 250 255 gca ccc tat acc cac aag ttc tta atg gaa gaa gca tgg atg ttt aca 816
Ala Pro Tyr Thr His Lys Phe Leu Met Glu Glu Ala Trp Met Phe Thr
260 265 270 aaa att agt gat cct gaa aga tca aga gct ggt gaa att ctc att gat 864
Lys Ile Ser Asp Pro Glu Arg Ser Arg Ala Gly Glu Ile Leu Ile Asp
275 280 285 ttc ttc aag aaa ggg aat ctt tct gca atc aga ccc aaa gac aaa ccg 912
Phe Phe Lys Lys Gly Asn Leu Ser Ala Ile Arg Pro Lys Asp Lys Pro
290 295 300 tta caa ggg aaa tat ccc ata cat tac aaa aat ctt tgg aat cag att 960
Leu Gln Gly Lys Tyr Pro Ile His Tyr Lys Asn Leu Trp Asn Gln Ile
305 310 315 320 aaa gca gca ata gcc gat aga acc atg gta ata aat gaa aat gat cat 1008
Lys Ala Ala Ile Ala Asp Arg Thr Met Val Ile Asn Glu Asn Asp His
325 330 335 tca gaa ttt ctt gga gga att gga aga gcc tct aaa aag atc cca gag 1056
Ser Glu Phe Leu Gly Gly Ile Gly Arg Ala Ser Lys Lys Ile Pro Glu
340 345 350 att tct cta aca caa gat gta ata aca aca gaa gga tta aaa caa tca 1104
Ile Ser Leu Thr Gln Asp Val Ile Thr Thr Glu Gly Leu Lys Gln Ser
355 360 365 gag aat aag ttg cca gaa cca aga tct ttc cct aga tgg ttc aat gct 1152
Glu Asn Lys Leu Pro Glu Pro Arg Ser Phe Pro Arg Trp Phe Asn Ala
370 375 380 gag tgg atg tgg gca ata aag gat tct gac ctt act gga tgg gtg ccc 1200
Glu Trp Met Trp Ala Ile Lys Asp Ser Asp Leu Thr Gly Trp Val Pro
385 390 395 400 atg gca gaa tac cct cct gct gat aat gaa ttg gaa gat tac gct gaa 1248
Met Ala Glu Tyr Pro Pro Ala Asp Asn Glu Leu Glu Asp Tyr Ala Glu
405 410 415

```
cat cta aat aaa acc atg gaa ggg gtc ttg caa gga aca aat tgc gca     1296
His Leu Asn Lys Thr Met Glu Gly Val Leu Gln Gly Thr Asn Cys Ala
            420                 425                 430

aga gaa atg ggg aaa tgc att ctt act gtt ggg gca cta atg act gaa     1344
Arg Glu Met Gly Lys Cys Ile Leu Thr Val Gly Ala Leu Met Thr Glu
        435                 440                 445

tgt aga cta ttt cct ggg aaa ata aaa gtg gtg ccc ata tat gct aga     1392
Cys Arg Leu Phe Pro Gly Lys Ile Lys Val Val Pro Ile Tyr Ala Arg
    450                 455                 460

agt aaa gaa agg aaa tca atg caa gaa ggg ctt ccg gtg ccc tca gaa     1440
Ser Lys Glu Arg Lys Ser Met Gln Glu Gly Leu Pro Val Pro Ser Glu
465                 470                 475                 480

atg gac tgt tta ttt ggt ata tgc gtc aag tca aaa tca cat tta aac     1488
Met Asp Cys Leu Phe Gly Ile Cys Val Lys Ser Lys Ser His Leu Asn
                485                 490                 495

aag gat gat gga atg tac aca ata ata aca ttt gaa ttc tca ata aga     1536
Lys Asp Asp Gly Met Tyr Thr Ile Ile Thr Phe Glu Phe Ser Ile Arg
            500                 505                 510

gag cct aat tta gaa aaa cat caa aaa tat act gta ttt gaa gct gga     1584
Glu Pro Asn Leu Glu Lys His Gln Lys Tyr Thr Val Phe Glu Ala Gly
        515                 520                 525

cac aca aca gtt aga atg aag aaa gga gag tca gtt att gga aga gaa     1632
His Thr Thr Val Arg Met Lys Lys Gly Glu Ser Val Ile Gly Arg Glu
    530                 535                 540

gtc cct ctt tat tta tac tgt agg aca act gcc ctt tcc aaa att aag     1680
Val Pro Leu Tyr Leu Tyr Cys Arg Thr Thr Ala Leu Ser Lys Ile Lys
545                 550                 555                 560

aat gac tgg cta tca aaa gct aga aga tgt ttc atc aca act atg gac     1728
Asn Asp Trp Leu Ser Lys Ala Arg Arg Cys Phe Ile Thr Thr Met Asp
                565                 570                 575

aca gtg gaa act ata tgt cta aga gag tca gca aag gct gaa gaa aat     1776
Thr Val Glu Thr Ile Cys Leu Arg Glu Ser Ala Lys Ala Glu Glu Asn
            580                 585                 590

cta gtt gaa aaa aca tta aac gaa aaa caa atg tgg att ggg aaa aaa     1824
Leu Val Glu Lys Thr Leu Asn Glu Lys Gln Met Trp Ile Gly Lys Lys
        595                 600                 605

aat gga gag tta att gct caa cct tta aga gaa gct tta agg gta cag     1872
Asn Gly Glu Leu Ile Ala Gln Pro Leu Arg Glu Ala Leu Arg Val Gln
    610                 615                 620

ctg gta caa caa ttt tat ttc tgc atc tat aat gac agt caa ttg gaa     1920
Leu Val Gln Gln Phe Tyr Phe Cys Ile Tyr Asn Asp Ser Gln Leu Glu
625                 630                 635                 640

ggc ttt tgt aat gag cag aag aaa atc cta atg gct ctt gaa ggt gac     1968
Gly Phe Cys Asn Glu Gln Lys Lys Ile Leu Met Ala Leu Glu Gly Asp
                645                 650                 655

aag aaa aat aaa tca tct ttt gga ttt aat cca gaa gga tta tta gaa     2016
Lys Lys Asn Lys Ser Ser Phe Gly Phe Asn Pro Glu Gly Leu Leu Glu
            660                 665                 670

aag att gaa gag tgt ctt ata aat aat ccg atg tgc ctt ttt atg gct     2064
Lys Ile Glu Glu Cys Leu Ile Asn Asn Pro Met Cys Leu Phe Met Ala
        675                 680                 685

caa agg ttg aat gaa ctt gtg att gag gcc tca aaa aga ggc gct aag     2112
Gln Arg Leu Asn Glu Leu Val Ile Glu Ala Ser Lys Arg Gly Ala Lys
    690                 695                 700

ttt ttc aaa act gat                                                 2127
Phe Phe Lys Thr Asp
705

<210> SEQ ID NO 6
```

-continued

<211> LENGTH: 709
<212> TYPE: PRT
<213> ORGANISM: Influenza C virus

<400> SEQUENCE: 6

```
Met Ser Lys Thr Phe Ala Glu Ile Ala Glu Thr Phe Leu Glu Pro Glu
1               5                   10                  15

Ala Val Arg Ile Ala Lys Glu Ala Val Glu Glu Tyr Gly Asp His Glu
            20                  25                  30

Arg Lys Ile Ile Gln Ile Gly Ile His Phe Gln Val Cys Cys Met Phe
        35                  40                  45

Cys Asp Glu Tyr Leu Ser Thr Asn Gly Ser Asp Arg Phe Val Leu Ile
    50                  55                  60

Glu Gly Arg Lys Arg Gly Thr Ala Val Ser Leu Gln Asn Glu Leu Cys
65                  70                  75                  80

Lys Ser Tyr Asp Leu Glu Pro Leu Pro Phe Leu Cys Asp Ile Phe Asp
                85                  90                  95

Arg Glu Glu Lys Gln Phe Val Glu Ile Gly Ile Thr Arg Lys Ala Asp
            100                 105                 110

Asp Ser Tyr Phe Gln Ser Lys Phe Gly Lys Leu Gly Asn Ser Cys Lys
        115                 120                 125

Ile Phe Val Phe Ser Tyr Asp Gly Arg Leu Asp Lys Asn Cys Glu Gly
    130                 135                 140

Pro Met Glu Glu Gln Lys Leu Arg Ile Phe Ser Phe Leu Ala Thr Ala
145                 150                 155                 160

Ala Asp Phe Leu Arg Lys Glu Asn Met Phe Asn Glu Ile Phe Leu Pro
                165                 170                 175

Asp Asn Glu Glu Thr Ile Ile Glu Met Lys Lys Gly Lys Thr Phe Leu
            180                 185                 190

Glu Leu Arg Asp Glu Ser Val Pro Leu Pro Phe Gln Thr Tyr Glu Gln
        195                 200                 205

Met Lys Asp Tyr Cys Glu Lys Phe Lys Gly Asn Pro Arg Glu Leu Ala
    210                 215                 220

Ser Lys Val Ser Gln Met Gln Ser Asn Ile Lys Leu Pro Ile Lys His
225                 230                 235                 240

Tyr Glu Gln Asn Lys Phe Arg Gln Ile Arg Leu Pro Lys Gly Pro Met
                245                 250                 255

Ala Pro Tyr Thr His Lys Phe Leu Met Glu Glu Ala Trp Met Phe Thr
            260                 265                 270

Lys Ile Ser Asp Pro Glu Arg Ser Arg Ala Gly Glu Ile Leu Ile Asp
        275                 280                 285

Phe Phe Lys Lys Gly Asn Leu Ser Ala Ile Arg Pro Lys Asp Lys Pro
    290                 295                 300

Leu Gln Gly Lys Tyr Pro Ile His Tyr Lys Asn Leu Trp Asn Gln Ile
305                 310                 315                 320

Lys Ala Ala Ile Ala Asp Arg Thr Met Val Ile Asn Glu Asn Asp His
                325                 330                 335

Ser Glu Phe Leu Gly Gly Ile Gly Arg Ala Ser Lys Lys Ile Pro Glu
            340                 345                 350

Ile Ser Leu Thr Gln Asp Val Ile Thr Thr Glu Gly Leu Lys Gln Ser
        355                 360                 365

Glu Asn Lys Leu Pro Glu Pro Arg Ser Phe Pro Arg Trp Phe Asn Ala
    370                 375                 380

Glu Trp Met Trp Ala Ile Lys Asp Ser Asp Leu Thr Gly Trp Val Pro
```

-continued

```
385                 390                 395                 400

Met Ala Glu Tyr Pro Pro Ala Asp Asn Glu Leu Glu Asp Tyr Ala Glu
                405                 410                 415

His Leu Asn Lys Thr Met Glu Gly Val Leu Gln Gly Thr Asn Cys Ala
            420                 425                 430

Arg Glu Met Gly Lys Cys Ile Leu Thr Val Gly Ala Leu Met Thr Glu
        435                 440                 445

Cys Arg Leu Phe Pro Gly Lys Ile Lys Val Val Pro Ile Tyr Ala Arg
    450                 455                 460

Ser Lys Glu Arg Lys Ser Met Gln Glu Gly Leu Pro Val Pro Ser Glu
465                 470                 475                 480

Met Asp Cys Leu Phe Gly Ile Cys Val Lys Ser Lys Ser His Leu Asn
                485                 490                 495

Lys Asp Asp Gly Met Tyr Thr Ile Ile Thr Phe Glu Phe Ser Ile Arg
            500                 505                 510

Glu Pro Asn Leu Glu Lys His Gln Lys Tyr Thr Val Phe Glu Ala Gly
        515                 520                 525

His Thr Thr Val Arg Met Lys Lys Gly Glu Ser Val Ile Gly Arg Glu
    530                 535                 540

Val Pro Leu Tyr Leu Tyr Cys Arg Thr Thr Ala Leu Ser Lys Ile Lys
545                 550                 555                 560

Asn Asp Trp Leu Ser Lys Ala Arg Arg Cys Phe Ile Thr Thr Met Asp
                565                 570                 575

Thr Val Glu Thr Ile Cys Leu Arg Glu Ser Ala Lys Ala Glu Glu Asn
            580                 585                 590

Leu Val Glu Lys Thr Leu Asn Glu Lys Gln Met Trp Ile Gly Lys Lys
        595                 600                 605

Asn Gly Glu Leu Ile Ala Gln Pro Leu Arg Glu Ala Leu Arg Val Gln
    610                 615                 620

Leu Val Gln Gln Phe Tyr Phe Cys Ile Tyr Asn Asp Ser Gln Leu Glu
625                 630                 635                 640

Gly Phe Cys Asn Glu Gln Lys Lys Ile Leu Met Ala Leu Glu Gly Asp
                645                 650                 655

Lys Lys Asn Lys Ser Ser Phe Gly Phe Asn Pro Glu Gly Leu Leu Glu
            660                 665                 670

Lys Ile Glu Glu Cys Leu Ile Asn Asn Pro Met Cys Leu Phe Met Ala
        675                 680                 685

Gln Arg Leu Asn Glu Leu Val Ile Glu Ala Ser Lys Arg Gly Ala Lys
    690                 695                 700

Phe Phe Lys Thr Asp
705


<210> SEQ ID NO 7
<211> LENGTH: 2148
<212> TYPE: DNA
<213> ORGANISM: Influenza A virus
<220> FEATURE:
<221> NAME/KEY: CDS
<222> LOCATION: (1)..(2148)
<223> OTHER INFORMATION: PA-subunit of the Influenza A virus
      (A/duck/Vietnam/1/2007(H5N1)) RNA-dependent RNA-Polymerase

<400> SEQUENCE: 7

atg gaa gac ttt gtg cga caa tgc ttc aat cca atg att gtc gag ctt        48
Met Glu Asp Phe Val Arg Gln Cys Phe Asn Pro Met Ile Val Glu Leu
1               5                   10                  15
```

```
gca gaa aag gca atg aaa gaa tat ggg gaa gat ccg aaa atc gaa acg       96
Ala Glu Lys Ala Met Lys Glu Tyr Gly Glu Asp Pro Lys Ile Glu Thr
            20                  25                  30

aac aag ttt gct gca ata tgc aca cat ttg gag gtc tgt ttc atg tat      144
Asn Lys Phe Ala Ala Ile Cys Thr His Leu Glu Val Cys Phe Met Tyr
        35                  40                  45

tcg gat ttt cac ttt att gat gaa cgg agt gaa tca ata att gta gaa      192
Ser Asp Phe His Phe Ile Asp Glu Arg Ser Glu Ser Ile Ile Val Glu
    50                  55                  60

tct gga gat ccg aat gca tta ttg aaa cac cga ttt gaa ata att gaa      240
Ser Gly Asp Pro Asn Ala Leu Leu Lys His Arg Phe Glu Ile Ile Glu
65                  70                  75                  80

gga aga gac cga acg atg gcc tgg act gtg gtg aat agt att tgc aac      288
Gly Arg Asp Arg Thr Met Ala Trp Thr Val Val Asn Ser Ile Cys Asn
                85                  90                  95

acc aca gga gtt gag aaa cct aaa ttt ctc cca gat ttg tat gac tac      336
Thr Thr Gly Val Glu Lys Pro Lys Phe Leu Pro Asp Leu Tyr Asp Tyr
            100                 105                 110

aaa gag aat cga ttc att gaa att gga gtg aca cgg agg gaa gtt cat      384
Lys Glu Asn Arg Phe Ile Glu Ile Gly Val Thr Arg Arg Glu Val His
        115                 120                 125

aca tac tat ctg gag aaa gcc aac aag ata aag tcc gag aag aca cat      432
Thr Tyr Tyr Leu Glu Lys Ala Asn Lys Ile Lys Ser Glu Lys Thr His
    130                 135                 140

att cac ata ttc tca ttc aca ggg gag gaa atg gcc acc aaa gcg gac      480
Ile His Ile Phe Ser Phe Thr Gly Glu Glu Met Ala Thr Lys Ala Asp
145                 150                 155                 160

tac acc ctt gat gaa gag agc agg gca aga att aaa acc agg ctg ttc      528
Tyr Thr Leu Asp Glu Glu Ser Arg Ala Arg Ile Lys Thr Arg Leu Phe
                165                 170                 175

acc ata agg cag gaa atg gcc agt agg ggt cta tgg gat tcc ttt cgt      576
Thr Ile Arg Gln Glu Met Ala Ser Arg Gly Leu Trp Asp Ser Phe Arg
            180                 185                 190

caa tcc gag aga ggc gaa gag aca att gaa gaa aaa ttt gaa atc act      624
Gln Ser Glu Arg Gly Glu Glu Thr Ile Glu Glu Lys Phe Glu Ile Thr
        195                 200                 205

gga acc atg cgc aga ctt gca gac caa agt ctc ccg ccg aac ttc tcc      672
Gly Thr Met Arg Arg Leu Ala Asp Gln Ser Leu Pro Pro Asn Phe Ser
    210                 215                 220

agc ctt gaa aac ttt aga gcc tat gtg gat gga ttc gaa ccg aac ggc      720
Ser Leu Glu Asn Phe Arg Ala Tyr Val Asp Gly Phe Glu Pro Asn Gly
225                 230                 235                 240

tgc att gag ggc aag ctt tct caa atg tca aaa gaa gtg aat gcc aga      768
Cys Ile Glu Gly Lys Leu Ser Gln Met Ser Lys Glu Val Asn Ala Arg
                245                 250                 255

att gag cca ttt tta aag aca acg cca cgc tct ctc aga cta cct gat      816
Ile Glu Pro Phe Leu Lys Thr Thr Pro Arg Ser Leu Arg Leu Pro Asp
            260                 265                 270

ggg cct cct tgc tct cag cga tcg aag ttc ctg ctg atg gat gcc ctt      864
Gly Pro Pro Cys Ser Gln Arg Ser Lys Phe Leu Leu Met Asp Ala Leu
        275                 280                 285

aaa tta agt atc gaa gac ccg agt cat gag ggg gag ggg ata cca cta      912
Lys Leu Ser Ile Glu Asp Pro Ser His Glu Gly Glu Gly Ile Pro Leu
    290                 295                 300

tac gat gca atc aaa tgc atg aag aca ttt ttc ggc tgg aaa gaa ccc      960
Tyr Asp Ala Ile Lys Cys Met Lys Thr Phe Phe Gly Trp Lys Glu Pro
305                 310                 315                 320

aac atc gtg aaa cca cat gaa aaa ggt ata aac ccc aat tac ctc ctg     1008
Asn Ile Val Lys Pro His Glu Lys Gly Ile Asn Pro Asn Tyr Leu Leu
                325                 330                 335
```

```
gct tgg aag caa gtg ctg gca gaa ctc caa gat att gaa aat gag gag      1056
Ala Trp Lys Gln Val Leu Ala Glu Leu Gln Asp Ile Glu Asn Glu Glu
            340                 345                 350

aaa atc ccg aaa aca aag aac atg aaa aaa aca agc cag ttg aag tgg      1104
Lys Ile Pro Lys Thr Lys Asn Met Lys Lys Thr Ser Gln Leu Lys Trp
        355                 360                 365

gca ctc ggt gaa aac atg gca cca gag aaa gta gac ttt gag gac tgc      1152
Ala Leu Gly Glu Asn Met Ala Pro Glu Lys Val Asp Phe Glu Asp Cys
    370                 375                 380

aaa gat att agc gat cta aga cag tat gac agt gat gaa cca gag tct      1200
Lys Asp Ile Ser Asp Leu Arg Gln Tyr Asp Ser Asp Glu Pro Glu Ser
385                 390                 395                 400

aga tca cta gca agc tgg att cag agt gaa ttc aac aag gca tgt gaa      1248
Arg Ser Leu Ala Ser Trp Ile Gln Ser Glu Phe Asn Lys Ala Cys Glu
                405                 410                 415

ttg aca gat tcg agt tgg att gaa ctt gat gag ata gga gaa gac gta      1296
Leu Thr Asp Ser Ser Trp Ile Glu Leu Asp Glu Ile Gly Glu Asp Val
            420                 425                 430

gct cca att gag cac att gca agt atg aga agg aac tat ttt aca gcg      1344
Ala Pro Ile Glu His Ile Ala Ser Met Arg Arg Asn Tyr Phe Thr Ala
        435                 440                 445

gaa gta tcc cat tgc agg gcc act gaa tac ata atg aag gga gtg tac      1392
Glu Val Ser His Cys Arg Ala Thr Glu Tyr Ile Met Lys Gly Val Tyr
    450                 455                 460

ata aac aca gcc ctg ttg aat gca tcc tgt gca gcc atg gat gac ttt      1440
Ile Asn Thr Ala Leu Leu Asn Ala Ser Cys Ala Ala Met Asp Asp Phe
465                 470                 475                 480

caa ctg att cca atg ata agc aaa tgc aga acc aaa gaa gga aga cgg      1488
Gln Leu Ile Pro Met Ile Ser Lys Cys Arg Thr Lys Glu Gly Arg Arg
                485                 490                 495

aaa act aat ctg tat gga ttc att ata aaa ggg aga tcc cac ttg agg      1536
Lys Thr Asn Leu Tyr Gly Phe Ile Ile Lys Gly Arg Ser His Leu Arg
            500                 505                 510

aat gat act gat gtg gta aat ttt gtg agt atg gaa ttc tct ctt act      1584
Asn Asp Thr Asp Val Val Asn Phe Val Ser Met Glu Phe Ser Leu Thr
        515                 520                 525

gat ccg agg ctg gag cca cac aag tgg gaa aag tac tgt gtc ctc gag      1632
Asp Pro Arg Leu Glu Pro His Lys Trp Glu Lys Tyr Cys Val Leu Glu
    530                 535                 540

ata gga gac atg ctc ctc cgg act gca gta ggc caa gtt tca agg ccc      1680
Ile Gly Asp Met Leu Leu Arg Thr Ala Val Gly Gln Val Ser Arg Pro
545                 550                 555                 560

atg ttc ctg tat gta aga acc aat gga acc tcc aag atc aaa atg aaa      1728
Met Phe Leu Tyr Val Arg Thr Asn Gly Thr Ser Lys Ile Lys Met Lys
                565                 570                 575

tgg ggc atg gaa atg agg cgg tgc ctt ctt caa tcc ctt caa caa att      1776
Trp Gly Met Glu Met Arg Arg Cys Leu Leu Gln Ser Leu Gln Gln Ile
            580                 585                 590

gaa agc atg att gaa gcc gag tct tct gtc aaa gag aag gac atg acc      1824
Glu Ser Met Ile Glu Ala Glu Ser Ser Val Lys Glu Lys Asp Met Thr
        595                 600                 605

aaa gaa ttc ttt gaa aac aaa tca gaa aca tgg cca att gga gag tcc      1872
Lys Glu Phe Phe Glu Asn Lys Ser Glu Thr Trp Pro Ile Gly Glu Ser
    610                 615                 620

ccc aag gga gtg gag gaa ggc tcc atc gga aag gtg tgc aga acc ttg      1920
Pro Lys Gly Val Glu Glu Gly Ser Ile Gly Lys Val Cys Arg Thr Leu
625                 630                 635                 640

ctg gcg aag tct gtg ttc aac agt tta tat gca tct cca caa ctc gag      1968
Leu Ala Lys Ser Val Phe Asn Ser Leu Tyr Ala Ser Pro Gln Leu Glu
```

```
                645                 650                 655

ggg ttt tca gct gaa tca aga aaa ttg ctt ctc att tct cag gca ctt     2016
Gly Phe Ser Ala Glu Ser Arg Lys Leu Leu Leu Ile Ser Gln Ala Leu
            660                 665                 670

agg gac aac ctg gaa cct ggg acc ttc gat ctt gga ggg cta tat gaa     2064
Arg Asp Asn Leu Glu Pro Gly Thr Phe Asp Leu Gly Gly Leu Tyr Glu
        675                 680                 685

gca att gag gag tgc ctg att aac gat ccc tgg gtt ttg ctt aat gcg     2112
Ala Ile Glu Glu Cys Leu Ile Asn Asp Pro Trp Val Leu Leu Asn Ala
    690                 695                 700

tct tgg ttc aac tcc ttc ctc gca cat gca ctg aaa                     2148
Ser Trp Phe Asn Ser Phe Leu Ala His Ala Leu Lys
705                 710                 715


<210> SEQ ID NO 8
<211> LENGTH: 716
<212> TYPE: PRT
<213> ORGANISM: Influenza A virus

<400> SEQUENCE: 8

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Ser Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Thr Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Arg Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Arg
                245                 250                 255

Ile Glu Pro Phe Leu Lys Thr Thr Pro Arg Ser Leu Arg Leu Pro Asp
            260                 265                 270

Gly Pro Pro Cys Ser Gln Arg Ser Lys Phe Leu Leu Met Asp Ala Leu
        275                 280                 285
```

-continued

```
Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Leu
                325                 330                 335

Ala Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Glu Asp Cys
    370                 375                 380

Lys Asp Ile Ser Asp Leu Arg Gln Tyr Asp Ser Asp Glu Pro Glu Ser
385                 390                 395                 400

Arg Ser Leu Ala Ser Trp Ile Gln Ser Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Thr Ala Val Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Ser Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700
```

-continued

Ser Trp Phe Asn Ser Phe Leu Ala His Ala Leu Lys
705 710 715

<210> SEQ ID NO 9
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: residues 20 to 30 of the PA-subunit of the Influenza A virus (A/Victoria/3/1975(H3N2)) RNA-dependent RNA polymerase

<400> SEQUENCE: 9

Ala Met Lys Glu Tyr Gly Glu Asp Leu Lys Ile
1 5 10

<210> SEQ ID NO 10
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: residues 35 to 45 of the PA-subunit of the Influenza A virus (A/Victoria/3/1975(H3N2)) RNA-dependent RNA polymerase

<400> SEQUENCE: 10

Phe Ala Ala Ile Cys Thr His Leu Glu Val Cys
1 5 10

<210> SEQ ID NO 11
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: residues 75 to 85 of the PA-subunit of the Influenza A virus (A/Victoria/3/1975(H3N2)) RNA-dependent RNA polymerase

<400> SEQUENCE: 11

Arg Phe Glu Ile Ile Glu Gly Arg Asp Arg Thr
1 5 10

<210> SEQ ID NO 12
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: residues 80 to 90 of the PA-subunit of the Influenza A virus (A/Victoria/3/1975(H3N2)) RNA-dependent RNA polymerase

<400> SEQUENCE: 12

Glu Gly Arg Asp Arg Thr Met Ala Trp Thr Val
1 5 10

<210> SEQ ID NO 13
<211> LENGTH: 11
<212> TYPE: PRT
<213> ORGANISM: Influenza A virus
<220> FEATURE:
<221> NAME/KEY: CHAIN
<222> LOCATION: (1)..(11)

```
<223> OTHER INFORMATION: residues 100 to 110 of the PA-subunit of the
      Influenza A virus (A/Victoria/3/1975(H3N2)) RNA-dependent RNA
      polymerase

<400> SEQUENCE: 13

Ala Glu Lys Pro Lys Phe Leu Pro Asp Leu Tyr
1               5                   10


<210> SEQ ID NO 14
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: residues 115 to 125 of the PA-subunit of the
      Influenza A virus (A/Victoria/3/1975(H3N2)) RNA-dependent RNA
      polymerase

<400> SEQUENCE: 14

Asn Arg Phe Ile Glu Ile Gly Val Thr Arg Arg
1               5                   10


<210> SEQ ID NO 15
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: residues 125 to 135 of the PA-subunit of the
      Influenza A virus (A/Victoria/3/1975(H3N2)) RNA-dependent RNA
      polymerase

<400> SEQUENCE: 15

Arg Glu Val His Ile Tyr Tyr Leu Glu Lys Ala
1               5                   10


<210> SEQ ID NO 16
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: residues 130 to 140 of the PA-subunit of the
      Influenza A virus (A/Victoria/3/1975(H3N2)) RNA-dependent RNA
      polymerase

<400> SEQUENCE: 16

Tyr Tyr Leu Glu Lys Ala Asn Lys Ile Lys Ser
1               5                   10


<210> SEQ ID NO 17
<211> LENGTH: 11
<212> TYPE: PRT
<213> ORGANISM: Influenza A virus
<220> FEATURE:
<221> NAME/KEY: CHAIN
<222> LOCATION: (1)..(11)
<223> OTHER INFORMATION: residues 135 to 145 of the PA-subunit of the
      Influenza A virus (A/Victoria/3/1975(H3N2)) RNA-dependent RNA
      polymerase

<400> SEQUENCE: 17

Ala Asn Lys Ile Lys Ser Glu Asn Thr His Ile
1               5                   10


<210> SEQ ID NO 18
```

-continued

<211> LENGTH: 51
<212> TYPE: RNA
<213> ORGANISM: Artificial Sequence
<220> FEATURE:
<223> OTHER INFORMATION: U-rich RNA

<400> SEQUENCE: 18
ggccauccug uuuuuuuccc uuuuuuuuuu ucuuuuuuuu uuuuuuuuuu u 51

<210> SEQ ID NO 19
<211> LENGTH: 7
<212> TYPE: PRT
<213> ORGANISM: Artificial Sequence
<220> FEATURE:
<223> OTHER INFORMATION: peptide linker

<400> SEQUENCE: 19

Gly Met Gly Ser Gly Met Ala
1 5

<210> SEQ ID NO 20
<211> LENGTH: 7
<212> TYPE: PRT
<213> ORGANISM: Influenza A virus
<220> FEATURE:
<221> NAME/KEY: CHAIN
<222> LOCATION: (1)..(7)
<223> OTHER INFORMATION: residues 107 to 112 of the PA-subunit of the Influenza A virus (A/Victoria/3/1975(H3N2)) RNA-dependent RNA polymerase

<400> SEQUENCE: 20

Pro Asp Leu Tyr Asp Tyr Lys
1 5

<210> SEQ ID NO 21
<211> LENGTH: 7
<212> TYPE: PRT
<213> ORGANISM: Artificial Sequence
<220> FEATURE:
<223> OTHER INFORMATION: TEV cleavage site

<400> SEQUENCE: 21

Glu Asn Leu Tyr Phe Gln Gly
1 5

<210> SEQ ID NO 22
<211> LENGTH: 216
<212> TYPE: PRT
<213> ORGANISM: Artificial Sequence
<220> FEATURE:
<223> OTHER INFORMATION: PA-Nter

<400> SEQUENCE: 22

Gly Met Gly Ser Gly Met Ala Met Glu Asp Phe Val Arg Gln Cys Phe
1 5 10 15

Asn Pro Met Ile Val Glu Leu Ala Glu Lys Ala Met Lys Glu Tyr Gly
20 25 30

Glu Asp Leu Lys Ile Glu Thr Asn Lys Phe Ala Ala Ile Cys Thr His
35 40 45

Leu Glu Val Cys Phe Met Tyr Ser Asp Phe His Phe Ile Asn Glu Gln
50 55 60

Gly Glu Ser Ile Val Val Glu Leu Asp Asp Pro Asn Ala Leu Leu Lys
65 70 75 80

His Arg Phe Glu Ile Ile Glu Gly Arg Asp Arg Thr Met Ala Trp Thr

-continued

```
                85                  90                  95

Val Val Asn Ser Ile Cys Asn Thr Thr Gly Ala Glu Lys Pro Lys Phe
            100                 105                 110

Leu Pro Asp Leu Tyr Asp Tyr Lys Glu Asn Arg Phe Ile Glu Ile Gly
        115                 120                 125

Val Thr Arg Arg Glu Val His Ile Tyr Tyr Leu Glu Lys Ala Asn Lys
    130                 135                 140

Ile Lys Ser Glu Asn Thr His Ile His Ile Phe Ser Phe Thr Gly Glu
145                 150                 155                 160

Glu Met Ala Thr Lys Ala Asp Tyr Thr Leu Asp Glu Glu Ser Arg Ala
                165                 170                 175

Arg Ile Lys Thr Arg Leu Phe Thr Ile Arg Gln Glu Met Ala Asn Arg
            180                 185                 190

Gly Leu Trp Asp Ser Phe Arg Gln Ser Glu Arg Gly Glu Glu Thr Ile
        195                 200                 205

Glu Glu Arg Phe Glu Ile Thr Gly
    210                 215


<210> SEQ ID NO 23
<211> LENGTH: 7
<212> TYPE: PRT
<213> ORGANISM: Influenza A virus
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa at position 7 is Ser or Gly

<400> SEQUENCE: 23

Glu Xaa Xaa Tyr Xaa Gln Xaa
1               5
```

POLYPEPTIDE FRAGMENTS COMPRISING ENDONUCLEASE ACTIVITY AND THEIR USE

CROSS REFERENCES

This application is a continuation application to U.S. patent application Ser. No. 13/140,626, filed on Jun. 16, 2011, which is a National Stage filing of International Application Serial No. PCT/EP2009/009161, filed Dec. 18, 2009, which claims the benefit of U.S. Provisional Application Ser. No. 61/203,259 filed Dec. 19, 2008, the disclosures of which are expressly incorporated herein by reference.

TECHNICAL FIELD OF INVENTION

The present invention relates to polypeptide fragments comprising an amino-terminal fragment of the PA subunit of a viral RNA-dependent RNA polymerase or variants thereof possessing endonuclease activity, wherein said PA subunit is from a virus belonging to the Orthomyxoviridae family. This invention also relates to (i) crystals of the polypeptide fragments which are suitable for structure determination of said polypeptide fragments using X-ray crystallography and (ii) computational methods using the structural coordinates of said polypeptide to screen for and design compounds that modulate, preferably inhibit the endonucleolytically active site within the polypeptide fragment. In addition, this invention relates to methods identifying compounds that bind to the PA polypeptide fragments possessing endonuclease activity and preferably inhibit said endonucleolytic activity, preferably in a high throughput setting. This invention also relates to compounds and pharmaceutical compositions comprising the identified compounds for the treatment of disease conditions due to viral infections caused by viruses of the Orthomyxoviridae family.

STATEMENT REGARDING SEQUENCE LISTING

The Sequence Listing associated with this application is provided in text format submitted electronically via EFS-Web, and is hereby incorporated by reference into the specification.

BACKGROUND OF THE INVENTION

Influenza is responsible for much morbidity and mortality in the world and is considered by many as belonging to the most significant viral threats to humans. Annual Influenza epidemics swipe the globe and occasional new virulent strains cause pandemics of great destructive power. At present the primary means of controlling Influenza virus epidemics is vaccination. However, mutant Influenza viruses are rapidly generated which escape the effects of vaccination. In the light of the fact that it takes approximately 6 months to generate a new Influenza vaccine, alternative therapeutic means, i.e., antiviral medication, are required especially as the first line of defense against a rapidly spreading pandemic.

An excellent starting point for the development of antiviral medication is structural data of essential viral proteins. Thus, the crystal structure determination of the Influenza virus surface antigen neuraminidase (von Itzstein et al., 1993, Nature 363:418-423) led directly to the development of neuraminidase inhibitors with anti-viral activity preventing the release of virus from the cells, however, not the virus production. These and their derivatives have subsequently developed into the anti-Influenza drugs, zanamivir (Glaxo) and oseltamivir (Roche), which are currently being stockpiled by many countries as a first line of defense against an eventual pandemic. However, these medicaments provide only a reduction in the duration of the clinical disease. Alternatively, other anti-Influenza compounds such as amantadine and rimantadine target an ion channel protein, i.e., the M2 protein, in the viral membrane interfering with the uncoating of the virus inside the cell. However, they have not been extensively used due to their side effects and the rapid development of resistant virus mutants (Magden et al., 2005, Appl. Microbiol. Biotechnol. 66:612-621). In addition, more unspecific viral drugs, such as ribavirin, have been shown to work for treatment of Influenza infections (Eriksson et al., 1977, Antimicrob. Agents Chemother. 11:946-951). However, ribavirin is only approved in a few countries, probably due to severe side effects (Furuta et al., 2005, Antimicrob. Agents Chemother. 49:981-986). Clearly, new antiviral compounds are needed, preferably directed against different targets.

Influenza virus A, B, C and Isavirus as well as Thogotovirus belong to the family of Orthomyxoviridae which, as well as the family of the Bunyaviridae, including the Hantavirus, Nairovirus, Orthobunyavirus, Phlebovirus, and Tospovirus, are negative stranded RNA viruses. Their genome is segmented and comes in ribonucleoprotein particles that include the RNA dependent RNA polymerase which carries out (i) the initial copying of the single-stranded virion RNA (vRNA) into viral mRNAs and (ii) the vRNA replication. For the generation of viral mRNA the polymerase makes use of the so called "cap-snatching" mechanism (Plotch et al., 1981, Cell 23:847-858; Kukkonen et al., 2005, Arch. Virol. 150:533-556; Leahy et al., 1997, J. Virol. 71:8347-8351; Noah and Krug, 2005, Adv. Virus Res. 65:121-145). The polymerase is composed of three subunits: PB1 (polymerase basic protein), PB2, and PA. For the cap-snatching mechanism, the viral polymerase binds via its PB2 subunit to the 5' RNA cap of cellular mRNA molecules which are cleaved at nucleotide 10 to 13 by the endonucleolytic activity of the polymerase. The capped RNA fragments serve as primers for the synthesis of viral mRNAs by the nucleotidyl-transferase center in the PB1 subunit (Li et al., 2001, EMBO J. 20:2078-2086). Finally, the viral mRNAs are 3 '-end poly-adenylated by stuttering of the polymerase at an oligo-U motif at the 5'-end of the template. Recent studies have precisely defined the structural domain of PB2 responsible for cap-binding (Fechter et al., 2003, J. Biol. Chem. 278:20381-20388; Guilligay et al., 2008 Nat. Struct. Mol. Biol. 15:500-506). The endonucleolytic activity of the polymerase has hitherto been thought to reside in the PB1 subunit (Li et al, supra).

The polymerase complex seems to be an appropriate antiviral drug target since it is essential for synthesis of viral mRNA and viral replication and contains several functional active sites likely to be significantly different from those found in host cell proteins (Magden et al., supra). Thus, for example, there have been attempts to interfere with the assembly of polymerase subunits by a 25-amino-acid peptide resembling the PA-binding domain within PB1 (Ghanem et al., 2007, J. Virol. 81:7801-7804). Moreover, there have been attempts to interfere with viral transcription by nucleoside analogs, such as 2'-deoxy-2'-fluoroguanosine (Tisdale et al., 1995, Antimicrob. Agents Chemother. 39:2454-2458) and it has been shown that T-705, a substituted pyrazine compound may function as a specific inhibitor of Influenza virus RNA polymerase (Furuta et al., supra). Furthermore, the endonuclease activity of the polymerase has been targeted and a series of 4-substituted 2,4-dioxobutanoic acid compounds has been identified as selective inhibitors of this activity in Influenza viruses (Tomassini et al., 1994, Antimicrob. Agents Chemother. 38:2827-2837). In addition, flutimide, a substituted 2,6-diketopiperazine, identified in extracts of *Delitschia confertaspora*, a fungal species, has been shown to inhibit the endonuclease of Influenza virus (Tomassini et al., 1996, Antimicrob. Agents Chemother. 40:1189-1193). However, the inhibitory action of compounds on the endonucleolytic activity of the viral polymerase was hitherto only studied in the context of the entire trimeric complex of the polymerase.

The PA subunit of the polymerase is functionally the least well-characterised, although it has been implicated in both cap-binding and endonuclease activity, vRNA replication, and a controversial protease activity. PA (716 residues in influenza A) is separable by trypsination at residue 213. The recently determined crystal structure of the C-terminal two-thirds of PA bound to a PB1 N-terminal peptide provided the first structural insight into both a large part of the PA subunit, whose function, however, still remains unclear, and the exact nature of one of the critical inter-subunit interactions (He et al., 2008, Nature 454:1123-1126; Obayashi et al., 2008, Nature 454:1127-1131). Systematic mutation of conserved residues in the PA amino-terminal domain have identified residues important for protein stability, promoter binding, cap-binding and endonuclease activity of the polymerase complex (Hara et al., 2006, J. Virol. 80:7789-7798). The enzymology of the endonuclease within the context of intact viral ribonucleoprotein particles (RNPs) has been extensively studied.

However, hitherto it was not possible to study the endonuclease activity of the PA subunit in the context of a polypeptide fragment possessing the endonucleolytic activity, since it was not known which domain is responsible for said activity. The present inventors surprisingly found that, contrary to the general opinion in the field, the endonucleolytic activity resides exclusively within the amino-terminal region of the PA subunit. The inventors have achieved to structurally characterize said domain by X-ray crystallography and identified the endonucleolytic active center within the amino-terminal PA polypeptide fragment.

Thus, the present invention provides the unique opportunity to study the endonucleolytic activity of the viral polymerase in the context of a polypeptide fragment which will considerably simplify the development of new anti-viral compounds targeting the endonuclease activity of the viral polymerase as well as the optimization of previously identified compounds. The surprising achievement of the present inventors to recombinantly produce PA polypeptide fragments possessing the endonucleolytic activity of the viral polymerase allows for performing in vitro high-throughput screening for inhibitors of a functional site on the viral polymerase using easily obtainable material from a straightforward expression system. Furthermore, the structural data of the endonucleolytic PA polypeptide fragment as well as of the enzymatically active center therein allows for directed design of inhibitors and in silico screening for potentially therapeutic compounds.

It is an object of the present invention to provide (i) high resolution structural data of the endonucleolytic amino-terminal domain of the viral polymerase PA subunit by X-ray crystallography, (ii) computational as well as in vitro methods, preferably in a high-throughput setting, for identifying compounds that can modulate, preferably inhibit, the endonuclease activity of the viral polymerase, preferably by blocking the endonucleolytic active site within the PA subunit, and (iii) pharmacological compositions comprising such compounds for the treatment of infectious diseases caused by viruses using the cap snatching mechanism for synthesis of viral mRNA.

SUMMARY OF THE INVENTION

In a first aspect, the present invention relates to a polypeptide fragment comprising an amino-terminal fragment of the PA subunit of a viral RNA-dependent RNA polymerase possessing endonuclease activity, wherein said PA subunit is from a virus belonging to the Orthomyxoviridae family.

In a further aspect, the present invention relates to an isolated polynucleotide encoding an isolated polypeptide fragment according to the present invention.

In a further aspect, the present invention relates to recombinant vector comprising the isolated polynucleotide according to the present invention.

In a further aspect, the present invention relates to a recombinant host cell comprising the isolated polynucleotide according to the invention or the recombinant vector according to the present invention.

In a further aspect, the present invention relates to a method for identifying compounds which modulate the endonuclease activity of the PA subunit of a viral RNA-dependent RNA polymerise from the Orthomyxoviridae family, comprising the steps of (a) constructing a computer model of the active site defined by the structure coordinates of the polypeptide fragment according to the present invention as shown in FIG. 18; (b) selecting a potential modulating compound by a method selected from the group consisting of:

(i) assembling molecular fragments into said compound, (ii) selecting a compound from a small molecule database, and (iii) de novo ligand design of said compound;

(c) employing computational means to perform a fitting program operation between computer models of the said compound and the said active site in order to provide an energy-minimized configuration of the said compound in the active site; and (d) evaluating the results of said fitting operation to quantify the association between the said compound and the active site model, whereby evaluating the ability of said compound to associate with the said active site.

In a further aspect, the present invention relates to a compound identifiable by the method according to the present invention, wherein said compound is able to modulate, preferably inhibit the endonuclease activity of the PA subunit or variant thereof.

In a further aspect, the present invention relates to a method for identifying compounds which modulate the endonuclease activity of the PA subunit or polypeptide variants thereof, comprising the steps of (i) contacting the polypeptide fragment according to the invention or the recombinant host cell according to the invention with a test compound and (ii) analyzing the ability of said test compound to modulate the endonuclease activity of said PA subunit polypeptide fragment.

In a further aspect, the present invention relates to a pharmaceutical composition producible according to the in vitro method of the present invention.

In a further aspect, the present invention relates to a compound identifiable by the in vitro method according to the invention, wherein said compound is able to modulate, preferably inhibit the endonuclease activity of the PA subunit or variant thereof In a further aspect, the present invention relates to an antibody directed against the active site of the PA subunit or variant thereof In a father aspect, the present invention relates to the use of a compound according to the present invention, a pharmaceutical composition according to the present invention, or an antibody according to the present invention for the manufacture of a medicament for treating, ameliorating, or preventing disease conditions caused by viral infections with viruses of the Orthomyxoviridae family.

BRIEF DESCRIPTION OF THE DRAWINGS

FIG. 2: Effects of different metal ions on thermal stability of PA-Nter (SEQ ID NO: 22). Summary of the different melting points (Tm) extracted from the thermal shift assay at pH 8.0 with different metal ions. The effect of $CoCl_2$ on protein stability at pH 7.0 was investigated but not interpretable due to quenching by the metal.

FIG. 18: Refined atomic structure coordinates for PA polypeptide fragment amino acids 1 to 209 according to amino acids 1 to 209 of the amino acid sequence set forth in SEQ ID NO: 2. There are three molecules in the asymmetric unit denoted A, B, and D. The file header gives information about the structure refinement. "Atom" refers to the element whose coordinates are measured. The first letter in the column defines the element. The 3-letter code of the respective amino acid is given and the amino acid sequence position. The first 3 values in the line "Atom" define the atomic position of the element as measured. The fourth value corresponds to the occupancy and the fifth (last) value is the temperature factor (B factor). The occupancy factor refers to the fraction of the molecules in which each atom occupies the position specified by the coordinates. A value of "1" indicates that each atom has the same conformation, i.e., the same position, in all molecules of the crystal. B is a thermal factor that measures movement of the atom around its atomic center. The anisotropic temperature factors are given in the lines marked "ANISOU". This nomenclature corresponds to the PDB file format.

DETAILED DESCRIPTION OF THE INVENTION

Figure 1:
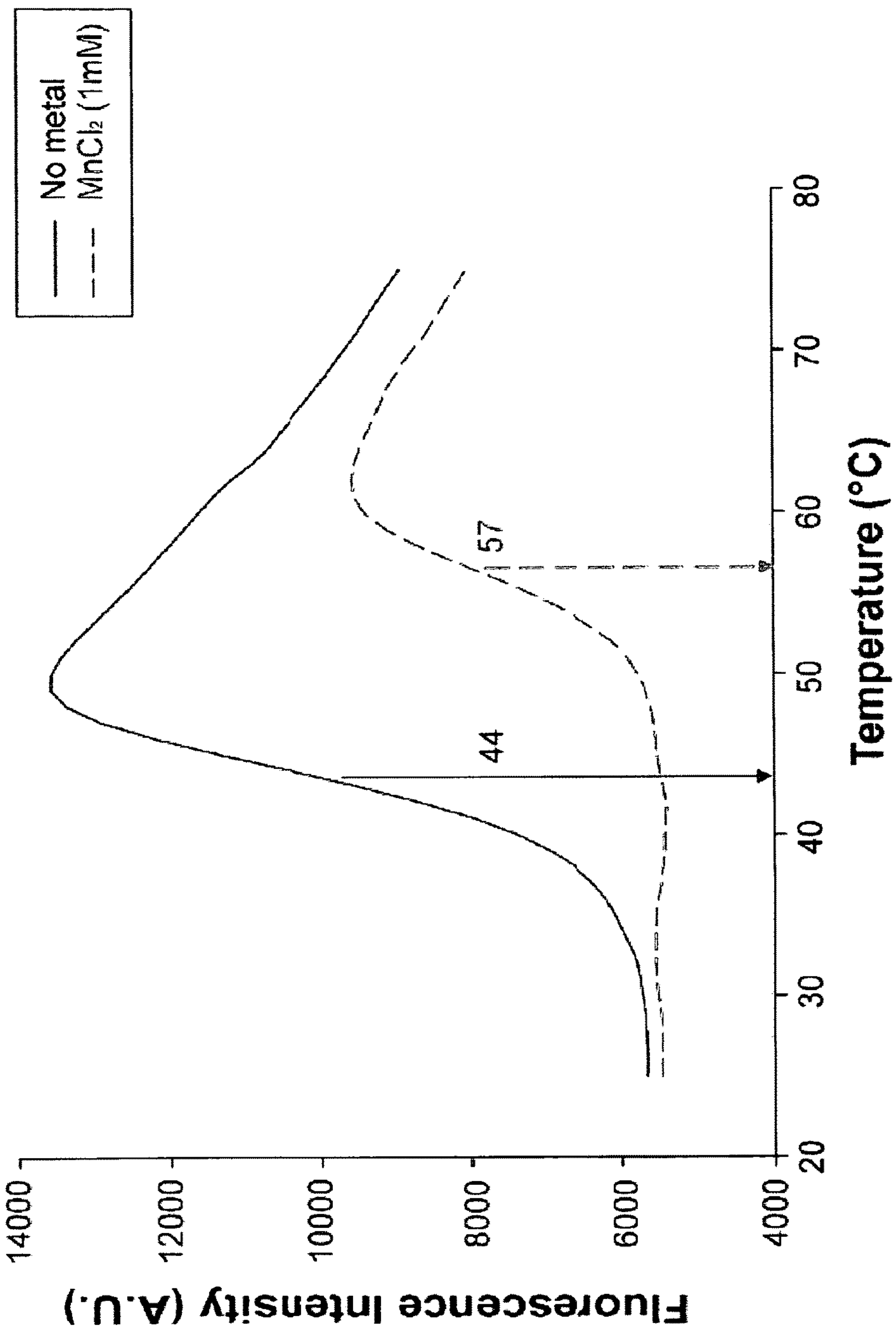
FIG. 1: Assay of thermal stability of the PA-Nter (SEQ ID NO: 22) structure using Thermofluor. The thermal shift assay was performed with different metal ions. For clarity, only the results obtained in absence of metal ion (full black line) or in presence of 1 mM $MnCl_2$ (dashed line) are shown. Arrows indicate the apparent melting temperature Tm.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment the polypeptide fragment of the present invention corresponds to amino acids 1 to 209 of the amino acid sequence set forth in SEQ ID NO: 2 and in another preferred embodiment the PA polypeptide fragment according to the present invention may be tagged with a peptide-tag that is preferably cleavable from the PA polypeptide fragment, preferably using a TEV protease, it is a preferred embodiment of the invention that the polypeptide fragment corresponding to amino acids 1 to 209 of the amino acid sequence set forth in SEQ ID NO: 2 is tagged with a peptide-tag that is cleavable from the PA polypeptide using a TEV protease.

Preferably, the terms used herein are defined as described in "A multilingual glossary of biotechnological terms: (TUPAC Recommendations)", H. G. W. Leuenberger, B. Nagel, and H. Kolbl, Eds., Helvetica Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., *Molecular Cloning: A Laboratory Manual,* 2nd Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

DEFINITIONS

The term "polypeptide fragment" refers to a part of a protein which is composed of a single amino acid chain. The term "protein" comprises polypeptide fragments that resume a secondary and tertiary structure and additionally refers to proteins that are made up of several amino acid chains, i.e., several subunits, forming quartenary structures. The term "peptide" refers to short amino acid chains of up to 50 amino acids that do not necessarily assume secondary or tertiary structures. A "peptoid" is a peptidomimetic that results from the oligomeric assembly of N-substituted glycines.

Figure 11:
FIG. 11: Sequence alignment of polypeptide fragments derived from the PA-subunit of representative influenza strains: A/Victoria/3/1975 (human H3N2; amino acid residues 1 to 209 of SEQ ID NO: 2), A/Duck/Vietman/1/2007 (avian H5N1; amino acid residues 1 to 209 of SEQ ID NO: 8), B/Ann Arbor/1/1966 (amino acid residues 1 to 206 of SEQ ID NO: 4) and C/Johannesburg/1/1966 (amino acid residues 1 to 189 of SEQ ID NO: 6). The secondary structure of A/Victoria/3/1975 is shown over the sequence alignment. The boxed sequences indicate sequence similarity between the four sequences. Residues in a solid black background are identical between the four sequences. The triangles indicate the key active site residues.

Residues in two or more polypeptides are said to "correspond" to each other if the residues occupy an analogous position in the polypeptide structures. As is well known in the art, analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (ebi.ac.uk/clustalw) or Align (ebi.ac.uk/emboss/align/index.html) using standard settings, preferably for Align EMBOSS::needle, Matrix: Blosum62, Gap Open 10.0, Gap Extend 0.5. Those skilled in the art understand that it may be necessary to introduce gaps in either sequence to produce a satisfactory alignment. For example, residues 1 to 196 in the Influenza A virus PA subunit correspond to residues 1 to 195 and 1 to 178 in the Influenza B and C virus PA subunits, respectively. Residues in two or more PA subunits are said to "correspond" if the residues are aligned in the best sequence alignment. The "best sequence alignment" between two polypeptides is defined as the alignment that produces the largest number of aligned identical residues. The "region of best sequence alignment" ends and, thus, determines the metes and bounds of the length of the comparison sequence for the purpose of the determination of the similarity score, if the sequence similarity, preferably identity, between two aligned sequences drops to less than 30%, preferably less than 20%, more preferably less than 10% over a length of 10, 20 or 30 amino acids. A part of the best sequence alignment for the amino acid sequences of Influenza A (aa 1 to 209), B (aa 1 to 206), and C (aa 1 to 189) PA subunits is shown in FIG. 11.

For example, amino acids Tyr24, His41, Glu80, Arg84, Leu106, Asp108, Glu119, Ile120, Tyr130, Glu133, Lys134, and Lys137 of the amino acid sequence set forth in SEQ ID NO: 2 (Influenza A virus PA subunit) correspond to amino acids Phe24, His41, Glu81, Arg85, Leu107, Asp109, Glu120, Val121, Tyr131, Lys134, Lys135, and Lys138 of the amino acid sequence set forth in SEQ ID NO: 4 (Influenza B virus PA subunit) and amino acids Ala24, His41, Glu65, Arg69, Leu91, Asp93, Glu104, Ile105, Tyr115, Ser118, Lys119, and Lys122 of the amino acid sequence set forth in SEQ ID NO: 6 (Influenza C virus PA subunit), respectively.

The present invention includes Influenza virus RNA-dependent RNA polymerase PA subunit fragments possessing endonuclease activity. The term "RNA-dependent RNA polymerase subunit PA" preferably refers to the PA subunit of Influenza A, Influenza B, or Influenza C virus, preferably having an amino acid sequence as set out in SEQ ID NO: 2, 4, or 6. "RNA-dependent RNA polymerase subunit PA variants" have at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with the amino acid sequence set forth in SEQ ID NO: 2, 4, or 6. It is preferred that when a naturally occurring PA variant is aligned with a PA subunit according to SEQ ID NO: 2, 4, or 6 that the alignment will be over the entire length of the two proteins and, thus, that the alignment score will be determined on this basis. It is, however, possible that the natural variant may comprise C-terminal/N-terminal or internal deletions or additions, e.g., through N- or C-terminal fusions. In this case, only the best aligned region is used for the assessment of similarity and identity, respectively. Preferably and as set out in more detail below, fragments derived from these variants show the indicated similarity and identity, respectively, preferably within the region required for endonuclease activity. Accordingly, any alignment between SEQ ID NO: 2, 4, or 6 and a PA variant should preferably comprise the endonuclease active site. Thus, the above sequence similarity and identity, respectively, to SEQ ID NO: 2, 4, or 6 occurs at least over a length of 100, 110, 120, 130, 140, 150, 160, 165, 170, 180, 190, 200, 210, 220, 230, 240, 250, 300 or more amino acids, preferably comprising the endonuclease active site. A large number of natural PA variants of sequences according to SEQ ID NO: 2, 4, or 6 are known and have been described in the literature. All these PA variants are comprised and can be the basis for the polypeptide fragments of the present invention. Preferred examples of the Influenza A PA subunit, if SEQ ID NO: 2 is used as reference sequence, comprise mutations at one or more of positions Phe4, Ala20, Leu28, Glu31, Val44, Tyr48, Asn55, Gln57, Gly58, Val62, Leu65, Asp66, Thr85, Gly99, Ala100, Glu101, Ile118, Ile129, Asn142, Ile145, Glu154, Lys158, Asp164, Ile171, Lys172, Ile178, Asn184, and/or Arg204. In a preferred embodiment, said variant comprises one or more of the following mutations: Phe4Leu, Ala20Thr, Leu28Pro, Glu31Lys, Val44Ala, Tyr48His, Asn55Asp, Gln57Arg, Gly58Ser, Val62Ile, Leu65Ser, Asp66Gly, Thr85Ala, Gly99Lys, Ala100Val, Glu101Asp, Ile118Thr, Ile129Thr, Asn142Lys, Ile145Leu, Glu154Gly, Lys158Gln, Asp164Val, Ile171Val, Lys172Arg, Ile178Val, Asn184Ser, Asn184Arg, and/or Arg204Lys. Preferred variants of the Influenza B virus PA subunit, if SEQ ID NO: 4 is used as reference sequence, include mutations at one or more of the following amino acid positions: Thr60, Asn86, Arg105, Asn158, His160, and/or Ile196. In a preferred embodiment the Influenza B virus PA subunit variant comprises one or more of the following mutations: Thr60Ala, Asn86Thr, Arg105Lys, Asn158Asp, His160Ser, and/or Ile196Val. Preferred variants of the Influenza C virus PA subunit, if SEQ ID NO: 6 is used as reference sequence, include mutations at one or more of the following amino acid positions: Thr11, Leu53, Ser58, Gly70, and/or Ala111. In a preferred embodiment, said mutations are as follows: Thr11Ala, Leu53Met, Ser58Asn, Gly70Arg, and/or Ala111Thr.

The polypeptide fragments of the present invention are, thus, based on RNA-dependent RNA polymerase subunit PA or variants thereof as defined above. Accordingly, in the following specification the terms "polypeptide fragment(s)" and "PA polypeptide fragments" always comprise such fragments derived both from the PA proteins as set out in SEQ ID NO: 2, 4, or 6 and fragments derived from PA protein variants thereof, as set out above, possessing endonuclease activity. However, the specification also uses the term "PA polypeptide fragment variants" or "PA fragment variants" to specifically refer to PA fragments possessing endonuclease activity that are derived from RNA-dependent RNA polymerase subunit PA variants. The PA polypeptide fragments of the present invention thus preferably comprise, essentially consist or consist of sequences of naturally occurring viral PA subunits, preferably Influenza virus PA subunit. It is, however, also envisioned that the PA fragment variants further contain amino acid substitutions at 1, 2, 3, 4, 5, 6, 7, 8, 9, 10, 11, 12, 13, 14, 15 or more amino acid positions, and have at least 60%, 65%, 70%, 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with the amino acid sequence set forth in SEQ ID NO: 2, 4, or 6. It is understood that PA fragments of the present invention may comprise additional amino acids not derived from PA, like, e.g., tags, enzymes etc., such additional amino acids will not be considered in such an alignment, i.e., are excluded from the calculation of the alignment score. In a preferred embodiment, the above indicated alignment score is obtained when aligning the sequence of the fragment with SEQ ID NO: 2, 4, or 6 at least over a length of 70, 80, 90, 100, 110, 120, 130, 140, 150, 160, 165, 170, 180, or 190 amino acids, wherein the respective sequence of SEQ ID NO: 2, 4, or 6, preferably comprises the endonuclease active site.

In a preferred embodiment, the PA polypeptide fragment variants comprise at least the amino acid residues corresponding to amino acid residues 1 to 196 of Influenza A virus PA or consist of amino acid residues 1 to 196 (derived from SEQ ID NO: 2) and have at least 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with amino acid residues 1 to 196 of the sequence set forth in SEQ ID NO: 2, more preferably the PA polypeptide fragment variants comprise at least the amino acid residues corresponding to amino acid residues 1 to 209 of Influenza A virus PA or consist of amino acid residues 1 to 209 (derived from SEQ ID NO: 2) and have at least 70%, more preferably 75%, more preferably 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with the amino acid residues 1 to 209 of the amino acid sequence set forth in SEQ ID NO: 2, more preferably the PA polypeptide fragment variants comprise at least the amino acid residues corresponding to amino acid residues 1 to 213 of Influenza A virus PA or consist of amino acid residues 1 to 213 (derived from SEQ ID NO: 2) and have at least 60%, more preferably 65%, more preferably 70%, more preferably 75%, more preferably 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with amino acid residues 1 to 213 of the amino acid sequence set forth in SEQ ID NO: 2. In preferred embodiments, the Influenza A virus PA polypeptide fragment variants of the present invention comprise mutations, preferably naturally occurring mutations such as mutations in one or more of the following amino acid residues when compared to SEQ ID NO: 2: Phe4, Ala20, Leu28, Glu31, Val44, Tyr48, Asn55, Gln57, Gly58, Val62, Leu65, Asp66, Thr85, Gly99, Ala100, Glu101, Ile118, Ile129, Asn142, Ile145, Glu154, Lys158, Asp164, Ile171, Lys172, Ile178, Asn184, and/or Arg204. In a preferred embodiment, said variant comprises one or more of the following mutations: Phe4Leu, Ala20Thr, Leu28Pro, Glu31Lys, Val44Ala, Tyr48His, Asn55Asp, Gln57Arg, Gly58Ser, Val62Ile, Leu65Ser, Asp66Gly, Thr85Ala, Gly99Lys, Ala100Val, Glu101Asp, Ile118Thr, Ile129Thr, Asn142Lys, Ile145Leu, Glu154Gly, Lys158Gln, Asp164Val, Ile171Val, Lys172Arg, Ile178Val, Asn184Ser, Asn184Arg, and/or Arg204Lys.

In a preferred embodiment, the PA polypeptide fragment variants comprise at least the amino acid residues corresponding to amino acid residues 1 to 195 of Influenza B virus PA or consist of amino acid residues 1 to 195 (derived from SEQ ID NO: 4) and have at least 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with amino acid residues 1 to 195 of the amino acid sequence set forth in SEQ ID NO: 4, more preferably the PA polypeptide fragment variants comprise at least the amino acid residues corresponding to amino acid residues 1 to 206 of Influenza B virus PA or consist of amino acid residues 1 to 206 (derived from SEQ ID NO: 4) and have at least 70%, more preferably 75%, more preferably 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with the amino acid residues 1 to 206 of the sequence set forth in SEQ ID NO: 4, more preferably the PA polypeptide fragment variants comprise at least the amino acid residues corresponding to amino acid residues 1 to 210 of Influenza B virus PA or consist of amino acid residues 1 to 210 (derived from SEQ ID NO: 4) and have at least 60%, more preferably 65%, more preferably 70%, more preferably 75%, more preferably 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with amino acid residues 1 to 210 of the amino acid sequence set forth in SEQ ID NO: 4. In preferred embodiments, the Influenza B virus PA polypeptide fragment variants of the present invention comprise mutations, preferably naturally occurring mutations, at one ore more of the following amino acid positions compared to SEQ ID NO: 4: Thr60, Asn86, Arg105, Asn158, His160, and/or Ile196. In a preferred embodiment the Influenza B virus PA subunit variant comprises one or more of the following mutations: Thr60Ala, Asn86Thr, Arg105Lys, Asn158Asp, His160Ser, and/or Ile196Val.

In a preferred embodiment, the PA polypeptide fragment variants comprise at least the amino acid residues corresponding to amino acid residues 1 to 178 of Influenza C virus PA or consist of amino acid residues 1 to 178 (derived from SEQ ID NO: 6) and have at least 80%, more preferably 85%, more preferably 90%, most preferably 95% sequence similarity over the entire length of the fragment with amino acid residues 1 to 178 of the amino acid sequence set forth in SEQ ID NO: 6, more preferably the PA polypeptide fragment variants comprise at least the amino acid residues corresponding to amino acid residues 1 to 189 of Influenza C virus PA or consist of amino acid residues 1 to 189 (derived from SEQ ID NO: 6) and have at least 70%, more preferably 75%, more preferably 80%, more preferably 85%, most preferably 90% sequence similarity over the entire length of the fragment with amino acid residues 1 to 189 of the amino acid sequence set forth in SEQ ID NO: 6, more preferably the PA polypeptide fragment variants comprise at least the amino acid residues corresponding to amino acid residues 1 to 193 of Influenza C virus PA or consist of amino acid residues 1 to 193 (derived from SEQ ID NO: 6) and have at least 60%, more preferably 65%, more preferably 70%, more preferably 75%, more preferably 80%, more preferably 85%, most preferably 90% sequence similarity over the entire length of the fragment with amino acid residues 1 to 193 of the amino acid sequence set forth in SEQ ID NO: 6. In preferred embodiments, the Influenza C virus PA polypeptide fragment variants of the present invention comprise mutations, preferably naturally occurring mutations such as mutations in one or more of the following amino acid residues when compared to SEQ ID NO: 6: Thr11, Leu53, Ser58, Gly70, and/or Ala111. In a preferred embodiment, said mutations are as follows: Thr1 1 Ala, Leu53Met, Ser58Asn, Gly70Arg, and/or Ala111 Thr.

In the context of the present invention, the term "PA-Nter" (SEQ ID NO: 22) refers to a polypeptide fragment which consists of amino acid residues 1 to 209 of the amino acid sequence as set forth in SEQ ID NO: 2 with an additional amino-terminal linker, i.e., GMGSGMA (SEQ ID NO: 19).

If a PA polypeptide fragment of the present invention comprises one of the above outlined amino acid residues, it is preferred that the other amino acid residues are not derived from the respective Influenza A, B, or C virus PA protein.

The term "sequence similarity" means that amino acids at the same position of the best sequence alignment are identical or similar, preferably identical. "Similar amino acids" possess similar characteristics, such as polarity, solubility, hydrophilicity, hydrophobicity, charge, or size. Similar amino acids are preferably leucine, isoleucine, and valine; phenylalanine, tryptophan, and tyrosine; lysine, arginine, and histidine; glutamic acid and aspartic acid; glycine, alanine, and serine; threonine, asparagine, glutamine, and methionine. The skilled person is well aware of sequence similarity searching tools, e.g., available on the World Wide Web (e.g., ebi.ac.uk/Tools/similarity.html).

The term "soluble", as used herein, refers to a polypeptide fragment which remains in the supernatant after centrifugation for 30 min at 100,000×g in an aqueous buffer under physiologically isotonic conditions, for example, 0.14 M sodium chloride or sucrose, at a protein concentration of at least 200 μg/ml, preferably of at least 500 μg/ml, preferably of at least 1 mg/ml, more preferably of at least 2 mg/ml, even more preferably of at least 3 mg/ml, even more preferably of at least 4 mg/ml, most preferably of at least 5 mg/ml in the absence of denaturants such as guanidine or urea in effective concentrations. A protein fragment that is tested for its solubility is preferably expressed in one of the cellular expression systems indicated below.

The term "purified" in reference to a polypeptide, does not require absolute purity such as a homogenous preparation, rather it represents an indication that the polypeptide is relatively purer than in the natural environment. Generally, a purified polypeptide is substantially free of other proteins, lipids, carbohydrates, or other materials with which it is naturally associated, preferably at a functionally significant level, for example, at least 85% pure, more preferably at least 95% pure, most preferably at least 99% pure. The expression "purified to an extent to be suitable for crystallization" refers to a protein that is 85% to 100%, preferably 90% to 100%, more preferably 95% to 100% pure and can be concentrated to higher than 3 mg/ml, preferably higher than 10 mg/ml, more preferably higher than 18 mg/ml without precipitation. A skilled artisan can purify a polypeptide using standard techniques for protein purification. A substantially pure polypeptide will yield a single major band on a non-reducing polyacrylamide gel.

The term "associate" as used in the context of identifying compounds with the methods of the present invention refers to a condition of proximity between a moiety (i.e., chemical entity or compound or portions or fragments thereof), and an endonuclease active site of the PA subunit. The association may be non-covalent, i.e., where the juxtaposition is energetically favored by, for example, hydrogen-bonding, van der Waals, electrostatic, or hydrophobic interactions, or it may be covalent.

The term "endonuclease activity" or "endonucleolytic activity" refers to an enzymatic activity which results in the cleavage of the phosphodiester bond within a polynucleotide chain. In the context of the present invention, the polypeptide fragments possess an endonucleolytic activity, which is preferably not selective for the polynucleotide type, i.e., the polypeptide fragments according to the present invention preferably exhibit endonucleolytic activity for DNA and RNA, preferably for single stranded DNA (ssDNA) or single stranded RNA (ssRNA). In this context, "Single stranded" means that a stretch of preferably at least 3 nucleotides, preferably at least 5 nucleotides, more preferably at least 10 nucleotides within the polynucleotide chain are single stranded, i.e., not base paired to another nucleotide. Preferably, the endonucleolytic activity of the polypeptide fragments according to the present invention is not dependent on recognition sites, i.e., specific nucleotide sequences, but results in unspecific cleavage of polynucleotide chains. For example, the skilled person may test for endonucleolytic activity of polypeptide fragments according to the present invention by incubating RNA or DNA substrates such as panhandle RNA or a linear or circular single stranded DNA, e.g., the circular M13mp18 DNA (MBI Fermentas), with or without the respective polypeptide fragment, for example, at 37° C. for a certain period of time such as for 5, 10, 20, 40, 60, or 80 minutes, and test for the integrity of the polynucleotides, for example, by gel electrophoresis.

The term "nucleotide" as used herein refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms, e.g., as described in Komberg and Baker, DNA Replication, 2nd Ed. (Freeman, San Francisco, 1992) and further include, but are not limited to, synthetic nucleosides having modified base moieties and/or modified sugar moieties, e.g., described generally by Scheit, Nucleotide Analogs (John Wiley, N.Y., 1980).

The term "isolated polynucleotide" refers to polynucleotides that were (i) isolated from their natural environment, (ii) amplified by polymerase chain reaction, or (iii) wholly or partially synthesized, and means a single or double-stranded polymer of deoxyribonucleotide or ribonucleotide bases and includes DNA and RNA molecules, both sense and anti-sense strands. The term comprises cDNA, genomic DNA, and recombinant DNA. A polynucleotide may consist of an entire gene, or a portion thereof.

The term "recombinant vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

"Recombinant host cell", as used herein, refers to a host cell that comprises a polynucleotide that codes for a polypeptide fragment of interest, i.e., the PA polypeptide fragment or variants thereof according to the invention. This polynucleotide may be found inside the host cell (i) freely dispersed as such, (ii) incorporated in a recombinant vector, or (iii) integrated into the host cell genome or mitochondrial DNA. The recombinant cell can be used for expression of a polynucleotide of interest or for amplification of the polynucleotide or the recombinant vector of the invention. The term "recombinant host cell" includes the progeny of the original cell which has been transformed, transfected, or infected with the polynucleotide or the recombinant vector of the invention. A recombinant host cell may be a bacterial cell such as an *E. coli* cell, a yeast cell such as *Saccharomyces cerevisiae* or *Pichia pastoris*, a plant cell, an insect cell such as SF9 or Hi5 cells, or a mammalian cell. Preferred examples of mammalian cells are Chinese hamster ovary (CHO) cells, green African monkey kidney (COS) cells, human embryonic kidney (HEK293) cells, HELA cells, and the like.

As used herein, the term "crystal" or "crystalline" means a structure (such as a three-dimensional solid aggregate) in which the plane faces intersect at definite angles and in which there is a regular structure (such as internal structure) of the constituent chemical species. The term "crystal" can include any one of: a solid physical crystal form such as an experimentally prepared crystal, a crystal structure derivable from the crystal (including secondary and/or tertiary and/or quaternary structural elements), a 2D and/or 3D model based on the crystal structure, a representation thereof such as a schematic representation thereof or a diagrammatic representation thereof, or a data set thereof for a computer. In one aspect, the crystal is usable in X-ray crystallography techniques. Here, the crystals used can withstand exposure to X-ray beams and are used to produce diffraction pattern data necessary to solve the X-ray crystallographic structure. A crystal may be characterized as being capable of diffracting X-rays in a pattern defined by one of the crystal forms depicted in T. L. Blundell and L. N. Johnson, "Protein Crystallography", Academic Press, New York (1976).

The term "unit cell" refers to a basic parallelepiped shaped block. The entire volume of a crystal may be constructed by regular assembly of such blocks. Each unit cell comprises a complete representation of the unit of pattern, the repetition of which builds up the crystal.

The term "space group" refers to the arrangement of symmetry elements of a crystal. In a space group designation the capital letter indicates the lattice type and the other symbols represent symmetry operations that can be carried out on the contents of the asymmetric unit without changing its appearance.

The term "structure coordinates" refers to a set of values that define the position of one or more amino acid residues with reference to a system of axes. The term refers to a data set that defines the three-dimensional structure of a molecule or molecules (e.g., Cartesian coordinates, temperature factors, and occupancies). Structural coordinates can be slightly modified and still render nearly identical three-dimensional structures. A measure of a unique set of structural coordinates is the root mean square deviation of the resulting structure. Structural coordinates that render three-dimensional structures (in particular, a three-dimensional structure of an enzymatically active center) that deviate from one another by a root mean square deviation of less than 3 Å, 2 Å, 1.5 Å, 1.0 Å, or 0.5 Å may be viewed by a person of ordinary skill in the art as very similar.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a variant of the PA polypeptide fragment or the enzymatically active center therein from the backbone of the PA polypeptide fragment or the enzymatically active center therein as defined by the structure coordinates of the PA polypeptide fragment PA-Nter (SEQ ID NO: 22) according to FIG. 18.

As used herein, the term "constructing a computer model" includes the quantitative and qualitative analysis of molecular structure and/or function based on atomic structural information and interaction models. The term "modeling" includes conventional numeric-based molecular dynamic and energy minimization models, interactive computer graphic models, modified molecular mechanics models, distance geometry, and other structure-based constraint models.

The term "fitting program operation" refers to an operation that utilizes the structure coordinates of a chemical entity, an enzymatically active center, a binding pocket, molecule or molecular complex, or portion thereof, to associate the chemical entity with the enzymatically active center, the binding pocket, molecule or molecular complex, or portion thereof. This may be achieved by positioning, rotating or translating the chemical entity in the enzymatically active center to match the shape and electrostatic complementarity of the enzymatically active center. Covalent interactions, non-covalent interactions such as hydrogen bond, electrostatic, hydrophobic, van der Waals interactions, and non-complementary electrostatic interactions such as repulsive charge-charge, dipole-dipole and charge-dipole interactions may be optimized. Alternatively, one may minimize the deformation energy of binding of the chemical entity to the enzymatically active center.

As used herein, the term "test compound" refers to an agent comprising a compound, molecule, or complex that is being tested for its ability to inhibit the endonucleolytic activity of the polypeptide fragment of interest, i.e., the PA polypeptide fragment of the invention or variants thereof possessing endonucleolytic activity. Test compounds can be any agents including, but not restricted to, peptides, peptoids, polypeptides, proteins (including antibodies), lipids, metals, nucleotides, nucleotide analogs, nucleosides, nucleic acids, small organic or inorganic molecules, chemical compounds, elements, saccharides, isotopes, carbohydrates, imaging agents, lipoproteins, glycoproteins, enzymes, analytical probes, polyamines, and combinations and derivatives thereof. The term "small molecules" refers to molecules that have a molecular weight between 50 and about 2,500 Daltons, preferably in the range of 200-800 Daltons. In addition, a test compound according to the present invention may optionally comprise a detectable label. Such labels include, but are not limited to, enzymatic labels, radioisotope or radioactive compounds or elements, fluorescent compounds or metals, chemiluminescent compounds and bioluminescent compounds. Well known methods may be used for attaching such a detectable label to a test compound. The test compound of the invention may also comprise complex mixtures of substances, such as extracts containing natural products, or the products of mixed combinatorial syntheses. These can also be tested and the component that inhibits the endonucleolytic activity of the target polypeptide fragment can be purified from the mixture in a subsequent step. Test compounds can be derived or selected from libraries of synthetic or natural compounds. For instance, synthetic compound libraries are commercially available from Maybridge Chemical Co. (Trevillet, Cornwall, UK), ChemBridge Corporation (San Diego, Calif.), or Aldrich (Milwaukee, Wis.). A natural compound library is, for example, available from TimTec LLC (Newark, Del.). Alternatively, libraries of natural compounds in the form of bacterial, fungal, plant and animal cell and tissue extracts can be used. Additionally, test compounds can be synthetically produced using combinatorial chemistry either as individual compounds or as mixtures. A collection of compounds made using combinatorial chemistry is referred to herein as a combinatorial library.

In the context of the present invention, "a compound which modulates the endonucleolytic activity" may increase or decrease, preferably inhibit the endonucleolytic activity of the PA subunit or the viral RNA-dependent RNA polymerase or a variant thereof. Preferably, such a compound is specific for the endonucleolytic activity of the viral PA subunit or variant thereof and does not modulate, preferably decrease the endonucleolytic activity of other endonucleases, in particular mammalian endonucleases.

The term "a compound which decreases the endonucleolytic activity" means a compound which decreases the endonucleolytic activity of the PA subunit of the viral RNA-dependent RNA polymerase from the Orthomyxoviridae family or a variant thereof by 50%, more preferably by 60%, even more preferably by 70%, even more preferably by 80%, even more preferably by 90%, and most preferably by 100% compared to the endonucleolytic activity of the PA subunit or a variant thereof without said compound but with otherwise the same reaction conditions, i.e., buffer conditions, reaction time and temperature. It is most preferred that the compound which decreases the endonucleolytic activity of the PA subunit or a variant thereof inhibits said activity, i.e., decreases said activity by at least 95%, preferably by 100% compared to the activity without the compound. It is particularly preferred that the compound that decreases or inhibits the endonucleolytic activity of the PA subunit or a variant thereof specifically decreases or inhibits the endonucleolytic activity of the PA subunit or a variant thereof but does not inhibit the endonucleolytic activity of other endonucleases such as RNase H or restriction endonucleases to the same extent, preferably not at all. For example, the skilled person may set up the following samples with the same buffer and reaction conditions as well as substrate and endonuclease concentrations: (1) substrate such as panhandle RNA, endonucleolytically active PA polypeptide fragment or variant thereof, (2) substrate such as panhandle RNA, endonucleolytically active PA polypeptide fragment or variant thereof, test compound, (3) substrate such as panhandle RNA, reference endonuclease such as RNAse H, (4) substrate such as panhandle RNA, reference nucleotide such as RNAse H, test compound. After incubation of the samples, the skilled person may analyze the substrate, for example, by gel electrophoresis. Test compounds which result in cleaved substrate in sample (2) and intact substrate in sample (4) are preferred.

The term "in a high-throughput setting" refers to high-throughput screening assays and techniques of various types which are used to screen libraries of test compounds for their ability to inhibit the endonuclease activity of the polypeptide fragment of interest. Typically, the high-throughput assays are performed in a multi-well format and include cell-free as well as cell-based assays.

The term "antibody" refers to both monoclonal and polyclonal antibodies, i.e., any immunoglobulin protein or portion thereof which is capable of recognizing an antigen or hapten, i.e., the PA polypeptide fragment possessing endonucleolytic activity or a peptide thereof. In a preferred embodiment, the antibody is capable of binding to the enzymatically (endonucleolytically) active center within the PA polypeptide fragment or variant thereof Antigen-binding portions of the antibody may be produced by recombinant DNA techniques or by enzymatic or chemical cleavage of intact antibodies. In some embodiments, antigen-binding portions include Fab, Fab', $F(ab')_2$, Fd, Fv, dAb, and complementarity determining region (CDR) fragments, single-chain antibodies (scFv), chimeric antibodies such as humanized antibodies, diabodies, and polypeptides that contain at least a portion of an antibody that is sufficient to confer specific antigen binding to the polypeptide.

The term "pharmaceutically acceptable salt" refers to a salt of a compound identifiable by the methods of the present invention or a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci. 66:1-19 (1977)).

The term "excipient" when used herein is intended to indicate all substances in a pharmaceutical formulation which are not active ingredients such as, e.g., carriers, binders, lubricants, thickeners, surface active agents, preservatives, emulsifiers, buffers, flavoring agents, or colorants.

The term "pharmaceutically acceptable carrier" includes, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

DETAILED DESCRIPTION

The present invention establishes for the first time a unique role for the PA subunit of influenza virus polymerase and contradicts the widely held view that the endonuclease active site is located within the PB1 subunit. The present inventors surprisingly found that a small independently folded domain derived from the N-terminus of the PA subunit exhibits the functional properties of the endonuclease reported for the trimeric complex, although this activity was thought to be detectable only in the trimeric complex. Moreover, the inventors found that this PA polypeptide fragment can easily be produced by recombinant means and thus is suitable for in vitro studies on the endonucleolytic activity and its modulation as well as for crystallization to obtain structural information in particular on the active site.

It is one aspect of the present invention to provide a polypeptide fragment comprising an amino-terminal fragment of the PA subunit of a viral RNA-dependent RNA polymerase possessing endonuclease activity, wherein said PA subunit is from a virus belonging to the Orthomyxoviridae family. Preferably, the polypeptide fragment is soluble in an aqueous solution. The minimal length of the polypeptide fragment of the present invention is determined by its ability to cleave polynucleotide chains such as panhandle RNA or single stranded DNA, i.e., the minimal length of the polypeptide is determined by its endonucleolytic activity. Preferably, the endonuclease activity is not dependent on the polynucleotide type, and thus, may be exerted on DNA and RNA, preferably on single stranded DNA and RNA. Preferably, the endonuclease activity is not dependent on specific recognition sites within the substrate polynucleotide.

In a preferred embodiment, the polypeptide fragment is suitable for crystallization, i.e., preferably the polypeptide fragment is crystallizable. Preferably, the crystals obtainable from the polypeptide fragment according to the invention are suitable for structure determination of the polypeptide fragment using X-ray crystallography. Preferably, said crystals are greater than 25 micron cubes and preferably are radiation stable enough to permit more than 85% diffraction data completeness at resolution of preferably 3.5 Å or better to be collected upon exposure to monochromatic X-rays.

In one embodiment, the polypeptide fragment is crystallizable using (i) an aqueous protein solution, i.e., the crystallization solution, with a protein concentration of 5 to 10 mg/ml, e.g., 5, 5.5, 6, 6.5, 7, 7.5, 8, 8.5, 9, 9.5, or 10 mg/ml, preferably of 8 to 10 mg/ml in a buffer system such as Tris-HC 1 at concentrations ranging from 10 mM to 3 M, preferably 10 mM to 2 M, more preferably 20 mM to 1 M, at pH 3 to pH 9, preferably pH 4 to pH 9, more preferably pH 7 to pH 9 and (ii) a precipitant/reservoir solution comprising one or more compounds such as sodium formate, ammonium sulphate, lithium sulphate, magnesium acetate, manganese acetate, or ethylene glycol. Optionally, the protein solution may contain one or more salts such as monovalent salts, e.g., NaCl, KCl, or LiCl, preferably NaCl, at concentrations ranging from 10 mM to 1 M, preferably 20 mM to 500 mM, more preferably 50 mM to 200 mM, and/or divalent salts, e.g., $MnCl_2$, $CaCl_2$, $MgCl_2$, $ZnCl_2$, or $CoCl_2$, preferably $MnCl_2$, at concentrations ranging from 0.1 to 50 mM, preferably 0.5 to 25 mM, more preferably 1 to 10 mM. Preferably, the precipitant/reservoir solution comprises $Li_2SO_4$ at concentrations ranging from 0.5 to 2 M, preferably 1 to 1.5 M, a buffer system such as MES at concentrations ranging from 20 mM to 1 M, preferably 50 mM to 500 mM, more preferably 75 to 150 mM, at preferably pH 4 to 8, more preferably pH 5 to 7, magnesium acetate and/or manganese acetate at concentrations ranging from 1 to 100 mM, preferably from 5 to 20 mM, and/or ethylene glycol at concentrations ranging from 1% to 20%, preferably 2% to 8%, more preferably 2 to 4%. The PA polypeptide fragment or variant thereof is preferably 85% to 100% pure, more preferably 90% to 100% pure, even more preferably 95% to 100% pure in the crystallization solution. To produce crystals, the protein solution suitable for crystallization may be mixed with an equal volume of the precipitant solution. In a preferred embodiment, the crystallization medium comprises 0.05 to 2 preferably 0.8 to 1.2 of protein solution suitable for crystallization mixed with a similar, preferably equal volume of precipitant solution comprising 1.0 to 1.4 M $Li_2SO_4$, 80 to 120 mM MES pH 5.5 to pH 6.5, 5 to 15 mM magnesium acetate and/or manganese acetate, and 2 to 4% ethylene glycol. In another embodiment, the precipitant solution comprises, preferably essentially consists of or consists of 1.2 M $Li_2SO_4$, 100 mM MES pH 6.0, 10 mM magnesium acetate and/or 10 mM manganese acetate, preferably 10 mM magnesium acetate, and 3% ethylene glycol, and the crystallization/protein solution comprises, preferably essentially consists or consists of 5 to 10 mg/ml protein, 20 mM Tris pH 8.0, 100 mM NaCl, and 2.5 mM $MnCl_2$.

Crystals can be grown by any method known to the person skilled in the art including, but not limited to, hanging and sitting drop techniques, sandwich-drop, dialysis, and microbatch or microtube batch devices. It would be readily apparent to one of skill in the art to vary the crystallization conditions disclosed above to identify other crystallization conditions that would produce crystals of PA polypeptide fragments of the inventions or variants thereof alone or in complex with a compound. Such variations include, but are not limited to, adjusting pH, protein concentration and/or crystallization temperature, changing the identity or concentration of salt and/or precipitant used, using a different method for crystallization, or introducing additives such as detergents (e.g., TWEEN 20 (monolaurate), LDOA, Brij 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

Microseeding may be used to increase the size and quality of crystals. In brief, micro-crystals are crushed to yield a stock seed solution. The stock seed solution is diluted in series. Using a needle, glass rod or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

Figure 12:
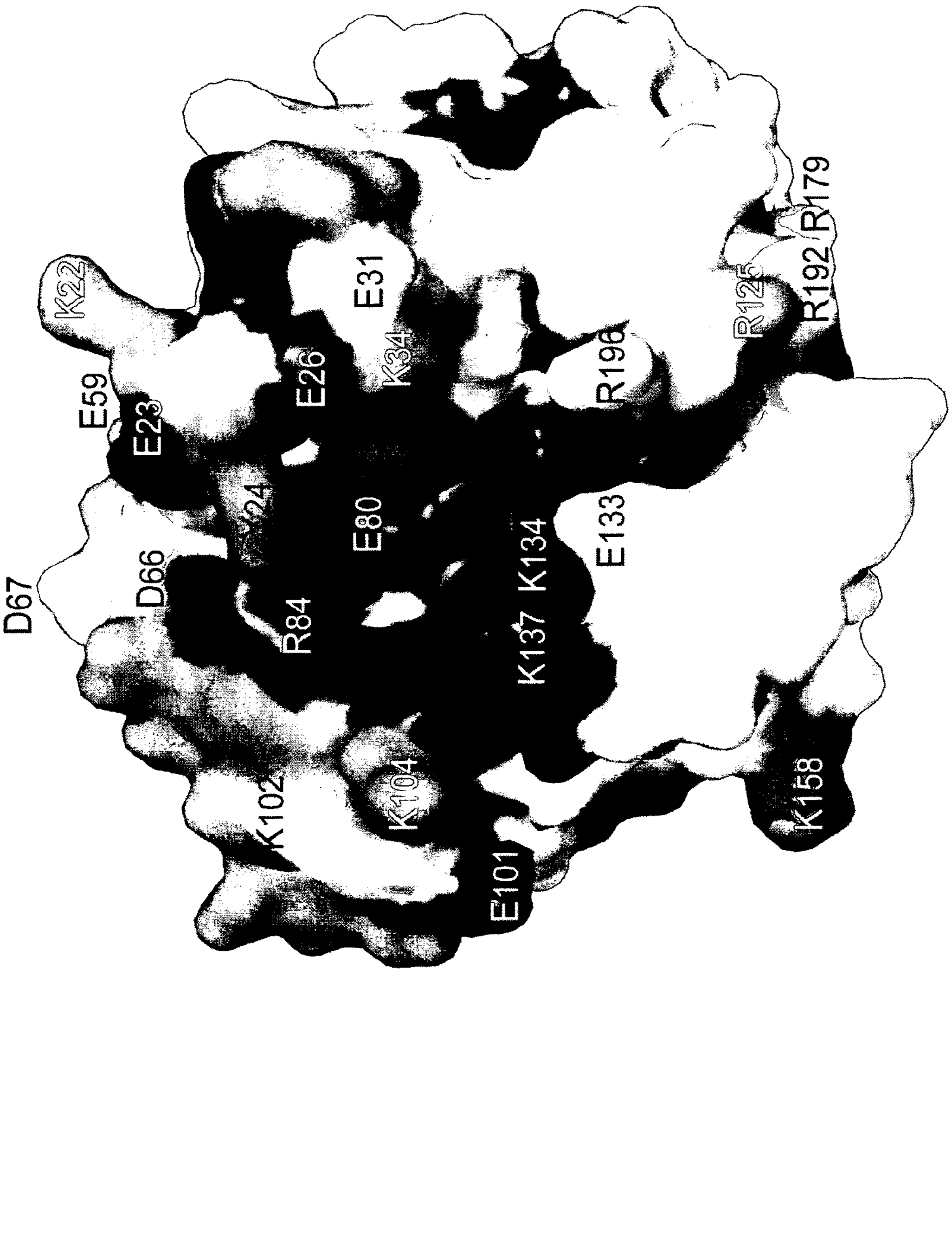
FIG. 12: Representation of PA-Nter (SEQ ID NO: 22) shaded according to residue conservation as based on the sequence alignment shown in FIG. 11, with grey (not conserved), grey (equivalent residues) and black (100% conserved).
Figure 13:
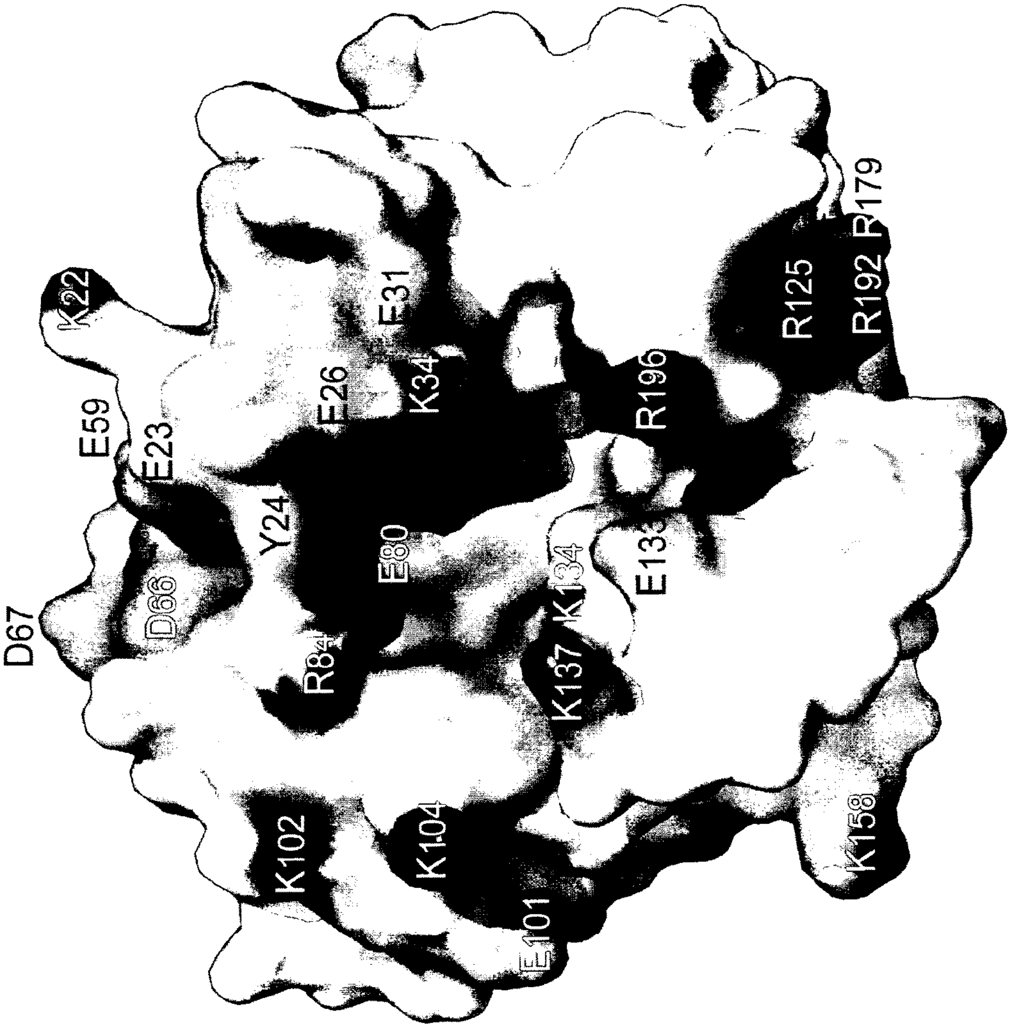
FIG. 13: Electrostatic surface potential of PA-Nter (SEQ ID NO: 22). The orientation is as in FIG. 12. Electrostatic surface potential of PA-Nter (SEQ ID NO: 22) in the absence of metal ions. The potential scale ranges from −10.0 kT/e (medium grey, acidic residues Asp(D) and Glu(E)) to 3.0 kT/e (dark grey, basic residues Lys(K) and Arg(R)).

The manner of obtaining the structure coordinates as shown in FIG. 18, interpretation of the coordinates and their utility in understanding the protein structure, as described herein, are commonly understood by the skilled person and by reference to standard texts such as J. Drenth, "Principles of protein X-ray crystallography", $2^{nd}$ Ed., Springer Advanced Texts in Chemistry, New York (1999); and G. E. Schulz and R. H. Schirmer, "Principles of Protein Structure", Springer Verlag, New York (1985). For example, X-ray diffraction data is first acquired, often using cryoprotected (e.g., with 20% to 30% glycerol) crystals frozen to 100 K, e.g., using a beamline at a synchrotron facility or a rotating anode as an X-ray source. Then, the phase problem is solved by a generally known method, e.g., multiwavelength anomalous diffraction (MAD), multiple isomorphous replacement (MIR), single wavelength anomalous diffraction (SAD), or molecular replacement (MR). The substructure may be solved using SHELXD (Schneider and Sheldrick, 2002, Acta Crystallogr. D. Biol. Crystallogr. (Pt 10 Pt 2), 1772-1779), phases calculated with SHARP (Vonrhein et al., 2006, Methods Mol. Biol. 364:215-30), and improved with solvent flattening and non-crystallographic symmetry averaging, e.g., with RESOLVE (Terwilliger, 2000, Acta Cryst. D. Biol. Crystallogr. 56:965-972). Model autobuilding can be done, e.g., with ARP/wARP (Perrakis et al., 1999, Nat. Struct. Biol. 6:458-63) and refinement with, e.g., REFMAC (Murshudov, 1997, Acta Crystallogr. D. Biol. Crystallogr. 53: 240-255). The skilled person can use the structure coordinates (FIG. 18) as input for secondary analysis, including the determination of electrostatic surface potential (see FIG. 13), which aids in the determination of side groups in test compounds, which are likely to interact with a surface area of the PA of a given electrostatic potential, preferably in the active site. In order to use the structure coordinates generated for the PA polypeptide fragment it is necessary to convert the structure coordinates into a three-dimensional shape. This is achieved through the use of commercially available software that is capable of generating three-dimensional graphical representations of molecules or portions thereof from a set of structure coordinates. An example for such a computer program is MODELER (Sali and Blundell, 1993, J. Mol. Biol. 234:779-815 as implemented in the Insight II Homology software package (Insight II (97.0), Molecular Simulations Incorporated, San Diego, Calif.)). Such a three-dimensional graphical representations can be use with suitable programs including (i) Gaussian 92, revision C (Frisch, Gaussian, Incorporated, Pittsburgh, Pa.), (ii) AMBER, version 4.0 (Kollman, University of California, San Francisco, Calif.), (iii) QUANTA/CHARMM (Molecular Simulations Incorporated, San Diego, Calif.), (iv) OPLS-AA (Jorgensen, 1998, Encyclopedia of Computational Chemistry, Schleyer, Ed., Wiley, New York, Vol. 3, pp. 1986-1989), and (v) Insight II/Discover (Biosysm Technologies Incorporated, San Diego, Calif.) to generate graphic representations of, e.g. electrostatic potential. Similarly, the structural information can be combined with information on the conservation of residues as depicted in FIG. 11 at the various amino acid positions (see FIG. 12) to highlight those residues at the surface of the PA and/or in the active site, which are particularly conserved between different virus isolates and, consequently, are likely to be also present in mutants of those[[s]] viruses or other isolates. This suitable in the skilled person is able to derive information on the relevance of the residues Furthermore, the structure coordinates (FIG. 18) of the Influenza A virus PA fragment PA-Nter (SEQ ID NO: 22) provided by the present invention are useful for the structure determination of PA polypeptides of other viruses from the Orthomyxoviridae family, or PA polypeptide variants that have amino acid substitutions, deletions, and/or insertions using the method of molecular replacement.

In a preferred embodiment of the polypeptide fragment according to the invention, the PA subunit is from Influenza A, B, or C virus or is a variant thereof, preferably from Influenza A virus or a variant thereof. Preferably, the amino terminal PA fragment comprised within the polypeptide fragment according to the present invention corresponds to, preferably essentially consists or consists of at least amino acids 1 to 196, preferably amino acids 1 to 209, preferably amino acids 1 to 213 of the PA subunit of the RNA-dependent RNA polymerase of Influenza A virus or variants thereof, i.e., amino acid residues 1 to 196, 1 to 209, or 1 to 213 of the amino acid sequence as set forth in SEQ ID NO: 2.

In a preferred embodiment, the polypeptide fragment according to the present invention is purified to an extent to be suitable for crystallization, preferably it is 85% to 100%, more preferably 90% to 100%, most preferably 95% to 100% pure.

In another embodiment, the polypeptide fragment according to the invention is capable of binding to divalent cations. Preferably, the polypeptide fragment according to the present invention is bound to one or more divalent cation(s), preferably it is bound to two divalent cations. In this context, the divalent cation is preferably selected form the group consisting of manganese, cobalt, calcium, magnesium, and zinc, and is more preferably manganese or cobalt, most preferably manganese. Thus, in a preferred embodiment, the polypeptide of the present invention is present in complex with two manganese cations. In a preferred embodiment, the divalent cations are coordinated by amino acids corresponding to amino acids Glu80 and Asp108 (first cation) and amino acids corresponding to amino acids His41, Asp108, and Glu119 (second cation) as set forth in SEQ ID NO: 2.

In a preferred embodiment of the polypeptide fragment according to the present invention, (i) the N-terminus is identical to or corresponds to amino acid position 15 or lower, e.g., at position 15, 14, 13, 12, 11, 10, 9, 8, 7, 6, 5, 4, 3, 2, or 1, and the C-terminus is identical to or corresponds to an amino acid at a position selected from positions 186 to 220, e.g., 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, or 220 of the amino acid sequence of the PA subunit according to SEQ ID NO: 2; preferably the N-terminus is identical to or corresponds to amino acid position 15 or lower, e.g., at position 15, 14, 13, 12, 11, 10, 9, 8, 7, 6, 5, 4, 3, 2, or 1 and the C-terminus is identical to or corresponds to an amino acid at a position selected from 196 to 220 of the amino acid sequence of the PA subunit according to SEQ ID NO: 2; more preferably the N-terminus is identical to or corresponds to amino acid position 15 or lower, e.g., at position 15, 14, 13, 12, 11, 10, 9, 8, 7, 6, 5, 4, 3, 2, or 1, and the C-terminus is identical to or corresponds to an amino acid at a position selected from 196 to 209 of the amino acid sequence of the PA subunit according to SEQ ID NO: 2, (ii) the N-terminus is identical to or corresponds to amino acid position 15 or lower, e.g., amino acid position 15, 14, 13, 12, 11, 10, 9, 8, 7, 6, 5, 4, 3, 2, or 1, and the C-terminus is identical to or corresponds to an amino acid at a position selected from positions 185 to 217, e.g., 135, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, or 217 of the amino acid sequence of the PA subunit according to SEQ ID NO: 4; preferably the N-terminus is identical to or corresponds to amino acid position 15 or lower, e.g., amino acid position 15, 14, 13, 12, 11, 10, 9, 8, 7, 6, 5, 4, 3, 2, or 1, and the C-terminus is identical to or corresponds to an amino acid at a position selected from positions 195 to 217 of the amino acid sequence of the PA subunit according to SEQ ID NO: 4; more preferably the N-terminus is identical to or corresponds to amino acid position 15 or lower, e.g., amino acid position 15, 14, 13, 12, 11, 10, 9, 8, 7, 6, 5, 4, 3, 2, or 1, and the C-terminus is identical to or corresponds to an amino acid at a position 195 to 206 of the amino acid sequence according to SEQ ID NO: 4, or (iii) the N-terminus is identical to or corresponds to amino acid position 15 or lower, e.g., amino acid position 15, 14, 13, 12, 11, 10, 9, 8, 7, 6, 5, 4, 3, 2, or 1, and the C-terminus is identical to or corresponds to an amino acid at a position selected from positions 168 to 200, e.g., amino acid position 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 of the amino acid sequence of the PA subunit according to SEQ ID NO: 6; preferably the N-terminus is identical to or corresponds to amino acid position 15 or lower, e.g., amino acid position 15, 14, 13, 12, 11, 10, 9, 8, 7, 6, 5, 4, 3, 2, or 1, and the C-terminus is identical to or corresponds to an amino acid at a position selected from positions 178 to 200 of the amino acid sequence according to SEQ ID NO: 6, and variants thereof, which retain the endonuclease activity; more preferably the N-terminus is identical to or corresponds to amino acid position 15 or lower, e.g., amino acid position 15, 14, 13, 12, 11, 10, 9, 8, 7, 6, 5, 4, 3, 2, or 1, and the C-terminus is identical to or corresponds to an amino acid at a position selected from positions 178 to 189 of the amino acid sequence according to SEQ ID NO: 6; and in each case variants of the amino acid sequence according to SEQ ID NO: 2, 4 or 6, which retain endonuclease activity.

In another embodiment said polypeptide fragment has or corresponds to an amino acid sequence selected from the group of amino acid sequences consisting of amino acids 5 to 196, 10 to 196, 15 to 196, 20 to 196, 5 to 209, 10 to 209, 15 to 209, 20 to 209 of the amino acid sequence set forth in SEQ ID NO: 2 and variants thereof, which retain the endonucleolytic activity. In another embodiment said PA polypeptide fragment has or corresponds to amino acids selected from the group of amino acid sequences consisting of amino acids 5 to 195, 10 to 195, 15 to 195, 20 to 195, 5 to 206, 10 to 206, 15 to 206, 20 to 206 of the amino acid sequence set forth in SEQ ID NO: 4 and variants thereof, which retain the endonucleolytic activity. In another embodiment said PA polypeptide fragment has or corresponds to amino acids selected from the group of amino acid sequences consisting of amino acids 5 to 178, 10 to 178, 15 to 178, 20 to 178, 5 to 189, 10 to 189, 15 to 189, 20 to 189 of the amino acid sequence set forth in SEQ ID NO: 6 and variants thereof, which retain the endonucleolytic activity. In preferred embodiments, said polypeptide fragments comprise amino acid substitutions, insertions, or deletions, preferably naturally occurring mutations as set forth above.

In another preferred embodiment, the polypeptide fragment according to the present invention consists of amino acids 1 to 209 of the amino acid sequence set forth in SEQ ID NO: 2 and has the structure defined by the structure coordinates as shown in FIG. 18.

In another embodiment, the polypeptide fragment according to the present invention has a crystalline form, preferably with space group $P4_32_12$, with unit cell dimensions of preferably a=b=6.71±0.2 nm, c=30.29 nm±0.4 nm. In another embodiment, the crystals according to the invention are hexagonal plates with preferred unit cell dimensions of a=b=6.79 nm, c=49.4 nm, $\alpha$=$\beta$90°, and $\gamma$=120° having preferably a trigonal or hexagonal space group. Preferably, the crystal of the polypeptide fragment diffracts X-rays to a resolution of 2.8 Å or higher, preferably 2.6 Å or higher, more preferably 2.5 Å or higher, even more preferably 2.4 Å or higher, most preferably 2.1 Å or higher.

It is another aspect of the present invention to provide an isolated polynucleotide coding for the above-mentioned PA polypeptide fragments and variants thereof. The molecular biology methods applied for obtaining such isolated nucleotide fragments are generally known to the person skilled in the art (for standard molecular biology methods see Sambrook et al., Eds., "Molecular Cloning: A Laboratory Manual", Cold Spring Harbor Laboratory Press, Cold Spring Harbor, N.Y. (1989), which is incorporated herein by reference). For example, RNA can be isolated from Influenza virus infected cells and cDNA generated applying reverse transcription polymerase chain reaction (RT-PCR) using either random primers (e.g., random hexamers of decamers) or primers specific for the generation of the fragments of interest. The fragments of interest can then be amplified by standard PCR using fragment specific primers.

In a preferred embodiment the isolated polynucleotide coding for the preferred embodiments of the PA polypeptide fragments are derived from SEQ ID NO: 1 (Influenza A), 3 (Influenza B), or 6 (Influenza C). In this context, "derived" refers to the fact that SEQ ID NO: 1, 2, and 3 encode the full-length PA polypeptides and, thus, polynucleotides coding for preferred PA polypeptide fragments may comprise deletions at the 3'- and/or 5'-ends of the polynucleotide as required by the respectively encoded PA polypeptide fragment.

In one embodiment, the present invention relates to a recombinant vector comprising said isolated polynucleotide. The person skilled in the art is well aware of techniques used for the incorporation of polynucleotide sequences of interest into vectors (also see Sambrook et al., 1989, supra). Such vectors include any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors may be expression vectors suitable for prokaryotic or eukaryotic expression. Said plasmids may include an origin of replication (ori), a multiple cloning site, and regulatory sequences such as promoter (constitutive or inducible), transcription initiation site, ribosomal binding site, transcription termination site, polyadenylation signal, and selection marker such as antibiotic resistance or auxotrophic marker based on complementation of a mutation or deletion. In one embodiment the polynucleotide sequence of interest is operably linked to the regulatory sequences.

In another embodiment, said vector includes nucleotide sequences coding for epitope-, peptide-, or protein-tags that facilitate purification of polypeptide fragments of interest. Such epitope-, peptide-, or protein-tags include, but are not limited to, hemagglutinin- (HA-), FLAG-, myc-tag, poly-His-tag, glutathione-S-transferase- (GST-), maltose-binding-protein-(MBP-), NusA-, and thioredoxin-tag, or fluorescent protein-tags such as (enhanced) green fluorescent protein ((E)GFP), (enhanced) yellow fluorescent protein ((E)YFP), red fluorescent protein (RFP) derived from Discosoma species (DsRed) or monomeric (mRFP), cyan fluorescence protein (CFP), and the like. In a preferred embodiment, the epitope-, peptide-, or protein-tags can be cleaved off the polypeptide fragment of interest, for example, using a protease such as thrombin, Factor Xa, PreScission, TEV protease, and the like. Preferably, the tag can be cleaved off with a TEV protease. The recognition sites for such proteases are well known to the person skilled in the art. For example, the seven amino acid consensus sequence of the TEV protease recognition site is Glu-X-X-Tyr-X-Gln-Gly/Ser (SEQ ID NO: 23), wherein X may be any amino acid and is in the context of the present invention preferably Glu-Asn-Leu-Tyr-Phe-Gln-Gly (SEQ ID NO: 21). In another embodiment, the vector includes functional sequences that lead to secretion of the polypeptide fragment of interest into the culture medium of the recombinant host cells or into the periplasmic space of bacteria. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

In another aspect, the present invention provides a recombinant host cell comprising said isolated polynucleotide or said recombinant vector. The recombinant host cells may be prokaryotic cells such as arches and bacterial cells or eukaryotic cells such as yeast, plant, insect, or mammalian cells. In a preferred embodiment the host cell is a bacterial cell such as an *E. coli* cell. The person skilled in the art is well aware of methods for introducing said isolated polynucleotide or said recombinant vector into said host cell. For example, bacterial cells can be readily transformed using, for example, chemical transformation, e.g., the calcium chloride method, or electroporation. Yeast cells may be transformed, for example, using the lithium acetate transformation method or electroporation. Other eukaryotic cells can be transfected, for example, using commercially available liposome-based transfection kits such as Lipofectamine™ (Invitrogen), commercially available lipid-based transfection kits such as Fugene (Roche Diagnostics), polyethylene glycol-based transfection, calcium phosphate precipitation, gene gun (biolistic), electroporation, or viral infection. In a preferred embodiment of the invention, the recombinant host cell expresses the polynucleotide fragment of interest. In an even more preferred embodiment, said expression leads to soluble polypeptide fragments of the invention. These polypeptide fragments may be purified using protein purification methods well known to the person skilled in the art, optionally taking advantage of the above-mentioned epitope-, peptide-, or protein-tags.

In another aspect, the present invention relates to a method for identifying compounds which modulate the endonuclease activity of the PA subunit of a viral RNA-dependent RNA polymerase from the Orthomyxoviridae family or a variant thereof, comprising the steps of (a) constructing a computer model of the active site defined by the structure coordinates of the polypeptide fragment according to the present invention shown in FIG. 18;

(b) selecting a potential activity modulating compound by a method selected from the group consisting of:

(i) assembling molecular fragments into said compound, (ii) selecting a compound from a small molecule database, and (iii) de novo ligand design of said compound;

(c) employing computational means to perform a fitting program operation between computer models of the said compound and the said active site in order to provide an energy-minimized configuration of the said compound in the active site; and (d) evaluating the results of said fitting operation to quantify the association between the said compound and the active site model, whereby evaluating the ability of said compound to associate with the said active site.

Preferably, the modulating compound binds to the endonucleolytically active site within the PA subunit or variant thereof. The modulating compound may increase or decrease, preferably decrease said endonucleolytic activity.

In a preferred embodiment of this aspect of the present invention, the compound that modulates the endonuclease activity of the PA subunit or a variant thereof decreases said activity, more preferably said compound inhibits said activity. Preferably, the compound decreases the endonucleolytic activity of the PA subunit or a variant thereof by 50%, more preferably by 60%, even more preferably by 70%, even more preferably by 80%, even more preferably by 90%, and most preferably by 100% compared to the endonucleolytic activity of the PA subunit or a variant thereof without said compound but with otherwise the same reaction conditions, i.e., buffer conditions, reaction time and temperature. It is particularly preferred that the compound specifically decreases or inhibits the endonucleolytic activity of the PA subunit or a variant thereof but does not decrease or inhibit the endonucleolytic activity of other endonucleases, in particular of mammalian endonucleases, to the same extent, preferably not at all.

For the first time, the present invention permits the use of molecular design techniques to identify, select, or design of compounds potentially modulating the endonucleolytic activity of the PA subunit or variants thereof, based on the structure coordinates of the endonucleolytically active site according to FIG. 18. Such a predictive model is valuable in light of the higher costs associated with the preparation and testing of the many diverse compounds that may possibly modulate the endonucleolytic activity. In order to use the structure coordinates generated for the PA polypeptide fragment it is necessary to convert the structure coordinates into a three-dimensional shape. This is achieved through the use of commercially available software that is capable of generating three-dimensional graphical representations of molecules or portions thereof from a set of structure coordinates.

An example for such a computer program is MODELER (Sali and Blundell, 1993, J. Mol. Biol. 234:779-815 as implemented in the Insight II Homology software package (Insight II (97.0), Molecular Simulations Incorporated, San Diego, Calif.)).

One skilled in the art may use several methods to screen chemical entities or fragments for their ability to modulate the endonucleolytic activity of the PA subunit or PA polypeptide variants. This process may begin by a visual inspection of, for example, a three-dimensional computer model of the endonucleolytically active site of PA based on the structural coordinates according to FIG. 18. Selected fragments or chemical compounds may then be positioned in a variety of orientations or docked within the active site. Docking may be accomplished using software such as Cerius, Quanta, and Sybyl (Tripos Associates, St. Louis, Mo.), followed by energy minimization and molecular dynamics with standard molecular dynamics force fields such as OPLS-AA, CHARMM, and AMBER. Additional specialized computer programs that may assist the person skilled in the art in the process of selecting suitable compounds or fragments include, for example, (i) AUTODOCK (Goodsell et al., 1990, Proteins: Struct., Funct., Genet. 8: 195-202; AUTODOCK is available from The Scripps Research Institute, La Jolla, Calif.) and (ii) DOCK (Kuntz et al., 1982, J. Mol. Biol. 161:269-288; DOCK is available from the University of California, San Francisco, Calif.).

Once suitable compounds or fragments have been selected, they can be designed or assembled into a single compound or complex. This manual model building is performed using software such as Quanta or Sybyl. Useful programs aiding the skilled person in connecting individual compounds or fragments include, for example, (i) CAVEAT (Bartlett et al., 1989, in Molecular Recognition in Chemical and Biological Problems, Special Publication, Royal Chem. Soc. 78:182-196; Lauri and Bartlett, 1994, J. Comp. Aid. Mol. Des. 8:51-66; CAVEAT is available from the University of California, Berkley, Calif.), (ii) 3D Database systems such as ISIS (MDL Information Systems, San Leandro, Calif.; reviewed in Martin, 1992, J. Med. Chem. 35:2145-2154), and (iii) HOOK (Eisen et al., 1994, Proteins: Struct., Funct., Genet. 19:199-221; HOOK is available from Molecular Simulations Incorporated, San Diego, Calif.).

Another approach enabled by this invention, is the computational screening of small molecule databases for compounds that can bind in whole or part to the endonucleolytically active site of the PA subunit or active sites of PA polypeptide variants. In this screening, the quality of fit of such compounds to the active site may be judged either by shape complementarity or by estimated interaction energy (Meng et al., 1992, J. Comp. Chem. 13:505-524).

Alternatively, a potential modulator for the endonucleolytic activity of the PA subunit or polypeptide variant thereof, preferably an inhibitor of the endonucleolytic activity, may be designed de novo on the basis of the 3D structure of the PA polypeptide fragment according to FIG. 18. There are various de novo ligand design methods available to the person skilled in the art. Such methods include (i) LUDI (Bohm, 1992, J. Comp. Aid. Mol. Des. 6:61-78; LUDI is available from Molecular Simulations Incorporated, San Diego, Calif.), (ii) LEGEND (Nishibata and Itai, Tetrahedron 47:8985-8990; LEGEND is available from Molecular Simulations Incorporated, San Diego, Calif.), (iii) LeapFrog (available from Tripos Associates, St. Louis, Mo.), (iv) SPROUT (Gillet et al., 1993, J. Comp. Aid. Mol. Des. 7:127-153; SPROUT is available from the University of Leeds, UK), (v) GROUPBUILD (Rotstein and Murcko, 1993, J. Med. Chem. 36:1700-1710), and (vi) GROW (Moon and Howe, 1991, Proteins 11:314-328).

In addition, several molecular modeling techniques (hereby incorporated by reference) that may support the person skilled in the art in de novo design and modeling of potential modulators and/or inhibitors of the endonucleolytically active site, preferably binding partners of the endonucleolytically active site, have been described and include, for example, Cohen et al., 1990, J. Med. Chem. 33:883-894; Navia and Murcko, 1992, Curr. Opin. Struct. Biol. 2:202-210; Balbes et al., 1994, Reviews in Computational Chemistry, Vol. 5, Lipkowitz and Boyd, Eds., VCH, New York, pp. 37-380; Guida, 1994, Curr. Opin. Struct. Biol. 4:777-781.

A molecule designed or selected as binding to the endonucleolytically active site of the PA subunit or variants thereof may be further computationally optimized so that in its bound state it preferably lacks repulsive electrostatic interaction with the target region. Such non-complementary (e.g., electrostatic) interactions include repulsive charge-charge, dipole-dipole and charge-dipole interactions. Specifically, the sum of all electrostatic interactions between the binding compound and the binding pocket in a bound state, preferably make a neutral or favorable contribution to the enthalpy of binding. Specific computer programs that can evaluate a compound deformation energy and electrostatic interaction are available in the art. Examples of suitable programs include (i) Gaussian 92, revision C (Frisch, Gaussian, Incorporated, Pittsburgh, Pa.), (ii) AMBER, version 4.0 (Kollman, University of California, San Francisco, Calif.), (iii) QUANTA/CHARMM (Molecular Simulations Incorporated, San Diego, Calif.), (iv) OPLS-AA (Jorgensen, 1998, Encyclopedia of Computational Chemistry, Schleyer, Ed., Wiley, New York, Vol. 3, pp. 1986-1989), and (v) Insight II/Discover (Biosysm Technologies Incorporated, San Diego, Calif.). These programs may be implemented, for instance, using a Silicon Graphics workstation, IRIS 4D/35 or IBM RISC/6000 workstation model 550. Other hardware systems and software packages are known to those skilled in the art.

Once a molecule of interest has been selected or designed, as described above, substitutions may then be made in some of its atoms or side groups in order to improve or modify its binding properties. Generally, initial substitutions are conservative, i.e., the replacement group will approximate the same size, shape, hydrophobicity and charge as the original group. It should, of course, be understood that components known in the art to alter conformation should be avoided. Such substituted chemical compounds may then be analyzed for efficiency of fit to the endonucleolytically active site of the PA subunit or variant thereof by the same computer methods described in detail above.

In one embodiment of the above-described method of the invention, the endonucleolytically active site of the PA subunit or variant thereof comprises amino acids corresponding to amino acids Asp108, Ile120, and Lys134 of the PA subunit according to SEQ ID NO: 2. In another embodiment, said active site comprises amino acids corresponding to amino acids Asp108, Ile120, Lys134, and His41 according to SEQ ID NO: 2. In another embodiment, said active site comprises amino acids corresponding to amino acids Asp108, Ile120, Lys134, and Glu80 according to SEQ ID NO: 2. In another embodiment, said active site comprises amino acids corresponding to amino acids Asp108, Ile120, Lys134, and Glu119 according to SEQ ID NO: 2. In another embodiment, said active site comprises amino acids corresponding to amino acids Asp108, Ile120, Lys134, His41, Glu80, and Glu119 according to SEQ ID NO: 2. In yet another embodiment, said active site comprises amino acids corresponding to amino acids Asp108, Ile120, Lys134, His41, Glu80, Glu119, and Tyr24 according to SEQ ID NO: 2. In yet another embodiment, said active site comprises amino acids corresponding to amino acids Asp108, Ile120, Lys134, His41, Glu80, Glu119, and Arg84 according to SEQ ID NO: 2. In yet another embodiment, said active site comprises amino acids corresponding to amino acids Asp108, Ile120, Lys134, His41, Glu80, Glu119, and Leu106 according to SEQ ID NO: 2. In yet another embodiment, said active site comprises amino acids corresponding to amino acids Asp108, Ile120, Lys134, His41, Glu80, Glu119, and Tyr130 according to SEQ ID NO: 2. In yet another embodiment, said active site comprises amino acids corresponding to amino acids Asp108, Ile120, Lys134, His41, Glu80, Glu119, and Glu133 according to SEQ ID NO: 2. In yet another embodiment, said active site comprises amino acids corresponding to amino acids Asp108, Ile120, Lys134, His41, Glu80, Glu119, and Lys137 according to SEQ ID NO: 2. In another embodiment, said active site comprises amino acids corresponding to amino acids Asp108, Ile 120, Lys134, His41, Glu80, Glu119, Tyr24, Arg84, and Leu106 according to SEQ ID NO: 2. In another embodiment, said active site comprises amino acids corresponding to amino acids Asp108, Ile 120, Lys134, His41, Glu80, Glu119, Tyr130, Glu133, and Lys137 according to SEQ ID NO: 2. In another embodiment, said active site comprises amino acids corresponding to amino acids Asp108, Ile 120, Lys134, His41, Glu80, Glu119, Tyr24, Arg84, Leu106, Tyr130, Glu133, and Lys137 according to SEQ ID NO: 2.

In a further aspect of the above-described method of the invention, the endonucleolytically active site of the PA subunit or a variant thereof is defined by the structure coordinates of the PA SEQ ID NO: 2 amino acids Asp108, Ile120, and Lys134 according to FIG. 18. In another embodiment, said active site is defined by the structure coordinates of PA SEQ ID NO: 2 amino acids Asp108, Ile120, Lys134, and His41 according to FIG. 18. In another embodiment, said active site is defined by the structure coordinates of PA SEQ ID NO: 2 amino acids Asp108, Ile120, Lys134, and Glu80 according to FIG. 18. In another embodiment, said active site is defined by the structure coordinates of PA SEQ ID NO: 2 amino acids Asp108, Ile120, Lys134, and Glu119 according to FIG. 18. In another embodiment, said active site is defined by the structure coordinates of PA SEQ ID NO: 2 amino acids Asp108, Ile120, Lys134, His41, Glu80, and Glu119 according to FIG. 18. In another embodiment, said active site is defined by the structure coordinates of PA SEQ ID NO: 2 amino acids Asp108, Ile120, Lys134, His41, Glu80, Glu119, and Tyr24 according to FIG. 18. In yet another embodiment, said active site is defined by the structure coordinates of PA SEQ ID NO: 2 amino acids Asp108, Ile120, Lys134, His41, Glu80, Glu119, and Arg84 according to FIG. 18. In another embodiment, said active site is defined by the structure coordinates of PA SEQ ID NO: 2 amino acids Asp108, Ile120, Lys134, His41, Glu80, Glu119, and Leu106 according to FIG. 18. In another embodiment, said active site is defined by the structure coordinates of PA SEQ ID NO: 2 amino acids Asp108, Ile120, Lys134, His41, Glu80, Glu119, and Tyr130 according to FIG. 18. In another embodiment, said active site is defined by the structure coordinates of PA SEQ ID NO: 2 amino acids Asp108, Ile120, Lys134, His41, Glu80, Glu119, and Glu133 according to FIG. 18. In another embodiment, said active site is defined by the structure coordinates of PA SEQ ID NO: 2 amino acids Asp108, Ile120, Lys134, His41, Glu80, Glu119, and Lys137 according to FIG. 18. In another embodiment, said active site is defined by the structure coordinates of PA SEQ ID NO: 2 amino acids Asp108, Ile120, Lys134, His41, Glu80, Glu119, Tyr24, Arg84, and Leu106 according to FIG. 18. In another embodiment, said active site is defined by the structure coordinates of PA SEQ ID NO: 2 amino acids Asp108, Ile120, Lys134, His41, Glu80, Glu119, Tyr130, Glu133, and Lys137 according to FIG. 18. In another embodiment, said active site is defined by the structure coordinates of PA SEQ ID NO: 2 amino acids Asp108, Ile120, Lys134, His41, Glu80, Glu119, Tyr24, Arg84, Leu106, Tyr130, Glu133, and Lys137 according to FIG. 18.

In one aspect, the present invention provides a method for computational screening according to the above-described method for compounds able to modulate and/or associate with an endonucleolytically active site that is a variant to the endonucleolytically active site of the PA subunit according to FIG. 18. In one embodiment, said variant of said active site has a root mean square deviation from the backbone atoms of amino acids Asp108, Ile120, and Lys134, of amino acids Asp108, Ile120, Lys134, and His41, of amino acids Asp108, Ile120, Lys134, and Glu80, of amino acids Asp108, Ile120, Lys134, and Glu119, of amino acids Asp108, Ile120, Lys134, His41, Glu80, and Glu119, of amino acids Asp108, Ile120, Lys134, His41, Glu80, Glu119, and Tyr24, of amino acids Asp108, Ile120, Lys134, His41, Glu80, Glu119, and Arg84, of amino acids Asp108, Ile120, Lys134, His41, Glu80, Glu119, and Leu106, of amino acids Asp108, Ile120, Lys134, His41, Glu80, Glu119, and Tyr130, of amino acids Asp108, Ile120, Lys134, His41, Glu80, Glu119, and Glu133, of amino acids Asp108, Ile120, Lys134, His41, Glu80, Glu119, and Lys137, of amino acids Asp108, Ile120, Lys134, His41, Glu80, Glu119, Tyr24, Arg84, and Leu106, of amino acids Asp108, Ile120, Lys134, His41, Glu80, Glu119, Tyr130, Glu133, and Lys137, of amino acids Asp108, Ile120, Lys134, His41, Glu80, Glu119, Tyr24, Arg84, Leu106, Tyr130, Glu133, and Lys137 according to FIG. 18 of not more than 3 Å. In another embodiment, the said root mean square deviation is not more than 2.5 Å. In another embodiment, the said root mean square deviation is not more than 2 Å. In another embodiment, the said root mean square deviation is not more than 1.5 Å. In another embodiment, the said root mean square deviation is not more than 1 Å. In another embodiment, the said root mean square deviation is not more than 0.5 Å.

If computer modeling according to the methods described hereinabove indicates binding of a compound to the active site of the PA subunit or a variant thereof, said compound may be synthesized and optionally said compound or a pharmaceutically acceptable salt thereof may be formulated with one or more pharmaceutically acceptable excipient(s) and/or carrier(s). Thus, the above-described method may comprise the further step of (e) synthesizing said compound and optionally formulating said compound or a pharmaceutically acceptable salt thereof with one or more pharmaceutically acceptable excipient(s) and/or carrier(s). Optionally, the ability of said compound or of a pharmaceutically acceptable salt thereof or of a formulation thereof to modulate, preferably decrease, preferably inhibit the endonucleolytic activity of the PA subunit or variant thereof may be tested in vitro or in vivo comprising the further step of (1) contacting said compound with the PA polypeptide fragment or variant thereof or the recombinant host cell of the invention and to determine the ability of said compound to (i) bind to the active site and/or (ii) to modulate, decrease, or inhibit the endonucleolytic activity of the PA subunit polypeptide fragment or variant thereof. The quality of fit of such compounds to the active site may be judged either by shape complementarity or by estimated interaction energy (Meng et al., 1992, J. Comp. Chem. 13:505-524). Methods for synthesizing said compounds are well known to the person skilled in the art or such compounds may be commercially available.

It is another aspect of the invention to provide a compound identifiable by the above-described method, wherein said compound is able to modulate the endonuclease activity of the PA subunit or variant thereof. In another aspect, the present invention refers to a compound identifiable by the above-described method, wherein said compound is able to decrease, preferably inhibit the endonuclease activity of the PA subunit or variant thereof, e.g., the PA subunit polypeptide or variant thereof according to the present invention. Compounds of the present invention can be any agents including, but not restricted to, peptides, peptoids, polypeptides, proteins (including antibodies), lipids, metals, nucleotides, nucleosides, nucleic acids, small organic or inorganic molecules, chemical compounds, elements, saccharides, isotopes, carbohydrates, imaging agents, lipoproteins, glycoproteins, enzymes, analytical probes, polyamines, and combinations and derivatives thereof. The term "small molecules" refers to molecules that have a molecular weight between 50 and about 2,500 Daltons, preferably in the range of 200-800 Daltons. In addition, a test compound according to the present invention may optionally comprise a detectable label. Such labels include, but are not limited to, enzymatic labels, radioisotope or radioactive compounds or elements, fluorescent compounds or metals, chemiluminescent compounds and bioluminescent compounds. In a preferred embodiment of the compound according to the present invention, the compound is not a 4-substituted 2-dioxobutanoic acid, a 4-substituted 4-dioxobutanoic acid, a 4-substituted 2,4-dioxobutanoic acid, a pyrazine-2,6-dione or a substituted pyrazine-2,6-dione such as flutimide, an N-hydroxamic acid, or an N-hydroxymide. In particular, the compound according to the present invention is not a compound according to Formula I:

Formula I

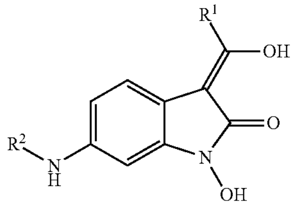

$R^1$ = Me, Et, Ph $R^2$ = acyl, carbamoyl, sulfonyl.

In a further aspect, the present invention provides a method for identifying compounds which bind to the endonucleolytically active site, preferably modulate, more preferably decrease, most preferably inhibit the endonuclease activity of the PA subunit or polypeptide variants thereof, comprising the steps of (i) contacting the PA polypeptide fragment according to the present invention or a recombinant host cell according to the present invention with a test compound and (ii) analyzing the ability of said test compound to bind to the endonucleolytically active site, to modulate, to decrease, or to inhibit the endonuclease activity of said PA subunit polypeptide fragment.

In one embodiment, the interaction between the PA polypeptide fragment or variant thereof and a test compound may be analyzed in form of a pull down assay. For example, the PA polypeptide fragment may be purified and may be immobilized on beads. In one embodiment, the PA polypeptide fragment immobilized on beads may be contacted, for example, with (i) another purified protein, polypeptide fragment, or peptide, (ii) a mixture of proteins, polypeptide fragments, or peptides, or (iii) a cell or tissue extract, and binding of proteins, polypeptide fragments, or peptides may be verified by polyacrylamide gel electrophoresis in combination with coomassie staining or Western blotting. Unknown binding partners may be identified by mass spectrometric analysis.

In another embodiment, the interaction between the PA polypeptide fragment or variant thereof and a test compound may be analyzed in form of an enzyme-linked immunosorbent assay (ELISA)-based experiment. In one embodiment, the PA polypeptide fragment or variant thereof according to the invention may be immobilized on the surface of an ELISA plate and contacted with the test compound. Binding of the test compound may be verified, for example, for proteins, polypeptides, peptides, and epitope-tagged compounds by antibodies specific for the test compound or the epitope-tag. These antibodies might be directly coupled to an enzyme or detected with a secondary antibody coupled to said enzyme that—in combination with the appropriate substrates—carries out chemiluminescent reactions (e.g., horseradish peroxidase) or colorimetric reactions (e.g., alkaline phosphatase). In another embodiment, binding of compounds that cannot be detected by antibodies might be verified by labels directly coupled to the test compounds. Such labels may include enzymatic labels, radioisotope or radioactive compounds or elements, fluorescent compounds or metals, chemiluminescent compounds and bioluminescent compounds. In another embodiment, the test compounds might be immobilized on the ELISA plate and contacted with the PA polypeptide fragment or variants thereof according to the invention. Binding of said polypeptide may be verified by a PA polypeptide fragment specific antibody and chemiluminescence or colorimetric reactions as described above.

In a further embodiment, purified PA polypeptide fragments may be incubated with a peptide array and binding of the PA polypeptide fragments to specific peptide spots corresponding to a specific peptide sequence may be analyzed, for example, by PA polypeptide specific antibodies, antibodies that are directed against an epitope-tag fused to the PA polypeptide fragment, or by a fluorescence signal emitted by a fluorescent tag coupled to the PA polypeptide fragment.

In another embodiment, the recombinant host cell according to the present invention is contacted with a test compound. This may be achieved by co-expression of test proteins or polypeptides and verification of interaction, for example, by fluorescence resonance energy transfer (FRET) or co-immunoprecipitation. In another embodiment, directly labeled test compounds may be added to the medium of the recombinant host cells. The potential of the test compound to penetrate membranes and bind to the PA polypeptide fragment may be, for example, verified by immunoprecipitation of said polypeptide and verification of the presence of the label.

In another embodiment, the ability of the test compound to modulate, preferably decrease, more preferably inhibit the endonucleolytic activity of the PA subunit polypeptide fragment or variant thereof is assessed. For example, the purified PA subunit polypeptide fragment and a substrate thereof such as panhandle RNA or single stranded DNA are contacted in presence or absence of varying amounts of the test compound and incubated for a certain period of time, for example, for 5, 10, 15, 20, 30, 40, 60, or 90 minutes. The reaction conditions are chosen such that the PA subunit polypeptide is endonucleolytically active without the test compound. The substrate is then analyzed for degradation/endonucleolytic cleavage, for example, by gel electrophoresis. Alternatively, such a test may comprise a labeled substrate molecule which provides a signal when the substrate molecule is endonucleolytically cleaved but does not provide a signal if it is intact. For example, the substrate polynucleotide chain may be labeled with fluorescent reporter molecule and a fluorescence quencher such that the fluorescent reporter is quenched as long as the substrate polynucleotide chain is intact. In case the substrate polynucleotide chain is cleaved, the fluorescent reporter and the quencher are separated, thus, the fluorescent reporter emits a signal which may be detected, for example, by an ELISA reader. This experimental setting may be applied in a multi-well plate format and is suitable for high throughput screening of compounds regarding their ability to modulate, decrease, or inhibit the endonuclease activity of the PA subunit polypeptide fragment or variants thereof.

In a preferred embodiment, the above-described method for identifying compounds which associate with the endonucleolytically active site, modulate, decrease, or inhibit the endonucleolytic activity of the PA subunit polypeptide fragment or variant thereof is performed in a high-throughput setting. In a preferred embodiment, said method is carried out in a multi-well microtiter plate as described above using PA polypeptide fragments or variants thereof according to the present invention and labeled test compounds.

In a preferred embodiment, the test compounds are derived from libraries of synthetic or natural compounds. For instance, synthetic compound libraries are commercially available from Maybridge Chemical Co. (Trevillet, Cornwall, UK), ChemBridge Corporation (San Diego, Calif.), or Aldrich (Milwaukee, Wis.). A natural compound library is, for example, available from TimTec LLC (Newark, Del.). Alternatively, libraries of natural compounds in the form of bacterial, fungal, plant, and animal extracts can be used. Additionally, test compounds can be synthetically produced using combinatorial chemistry either as individual compounds or as mixtures.

In another embodiment, the inhibitory effect of the identified compound on the Influenza virus life cycle may be tested in an in vivo setting. A cell line that is susceptible for Influenza virus infection such as 293T human embryonic kidney cells, Madin-Darby canine kidney cells, or chicken embryo fibroblasts may be infected with Influenza virus in presence or absence of the identified compound. In a preferred embodiment, the identified compound may be added to the culture medium of the cells in various concentrations. Viral plaque formation may be used as read out for the infectious capacity of the Influenza virus and may be compared between cells that have been treated with the identified compound and cells that have not been treated.

In a further embodiment of the invention, the test compound applied in any of the above described methods is a small molecule. In a preferred embodiment, said small molecule is derived from a library, e.g., a small molecule inhibitor library. In another embodiment, said test compound is a peptide or protein. In a preferred embodiment, said peptide or protein is derived from a peptide or protein library.

In another embodiment of the above-described methods for computational as well as in vitro identification of compounds that associate with the endonucleolytically active site, modulate, decrease, or inhibit the endonucleolytic activity of the PA subunit polypeptide fragment or variant thereof according to the present invention, said methods further comprise the step of formulating the identifiable compound or a pharmaceutically acceptable salt thereof with one or more pharmaceutically acceptable excipient(s) and/or carrier(s). In another aspect the present invention provides a pharmaceutical composition producible according to the afore-mentioned method. A compound according to the present invention can be administered alone but, in human therapy, will generally be administered in admixture with a suitable pharmaceutical excipient, diluent, or carrier selected with regard to the intended route of administration and standard pharmaceutical practice (see hereinafter).

In the aspect of computational modeling or screening of a binding partner for the endonucleolytically active site, a modulator, and/or inhibitor of the endonucleolytic activity of the PA subunit polypeptide fragment or variant thereof according to the present invention, it may be possible to introduce into the molecule of interest, chemical moieties that may be beneficial for a molecule that is to be administered as a pharmaceutical. For example, it may be possible to introduce into or omit from the molecule of interest, chemical moieties that may not directly affect binding of the molecule to the target area but which contribute, for example, to the overall solubility of the molecule in a pharmaceutically acceptable carrier, the bioavailability of the molecule and/or the toxicity of the molecule. Considerations and methods for optimizing the pharmacology of the molecules of interest can be found, for example, in "Goodman and Gilman's The Pharmacological Basis of Therapeutics", $8^{th}$ Edition, Goodman, Gilman, Rall, Nies, & Taylor, Eds., Pergamon Press (1985); Jorgensen & Duffy, 2000, Bioorg. Med. Chem. Lett. 10:1155-1158. Furthermore, the computer program "Qik Prop" can be used to provide rapid predictions for physically significant descriptions and pharmaceutically-relevant properties of an organic molecule of interest. A 'Rule of Five' probability scheme can be used to estimate oral absorption of the newly synthesized compounds (Lipinski et al., 1997, Adv. Drug Deliv. Rev. 23:3-25). Programs suitable for pharmacophore selection and design include (i) DISCO (Abbot Laboratories, Abbot Park, Ill.), (ii) Catalyst (Bio-CAD Corp., Mountain View, Calif.), and (iii) Chem DBS-3D (Chemical Design Ltd., Oxford, UK).

The pharmaceutical composition contemplated by the present invention may be formulated in various ways well known to one of skill in the art. For example, the pharmaceutical composition of the present invention may be in solid form such as in the form of tablets, pills, capsules (including soft gel capsules), cachets, lozenges, ovules, powder, granules, or suppositories, or in liquid form such as in the form of elixirs, solutions, emulsions, or suspensions.

Solid administration forms may contain excipients such as microcrystalline cellulose, lactose, sodium citrate, calcium carbonate, dibasic calcium phosphate, glycine, and starch (preferably corn, potato, or tapioca starch), disintegrants such as sodium starch glycolate, croscarmellose sodium, and certain complex silicates, and granulation binders such as polyvinylpyrrolidone, hydroxypropylmethyl cellulose (HPMC), hydroxypropylcellulose HPC), sucrose, gelatin, and acacia. Additionally, lubricating agents such as magnesium stearate, stearic acid, glyceryl behenate, and talc may be included. Solid compositions of a similar type may also be employed as fillers in gelatin capsules. Preferred excipients in this regard include lactose, starch, a cellulose, milk sugar, or high molecular weight polyethylene glycols.

For aqueous suspensions, solutions, elixirs, and emulsions suitable for oral administration the compound may be combined with various sweetening or flavoring agents, coloring matter or dyes, with emulsifying and/or suspending agents and with diluents such as water, ethanol, propylene glycol, and glycerin, and combinations thereof.

The pharmaceutical composition of the present invention may contain release rate modifiers including, for example, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer, and mixtures thereof.

The pharmaceutical composition of the present invention may be in the form of fast dispersing or dissolving dosage formulations (FDDFs) and may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavoring, polyethylene glycol, fumed silica, silicon dioxide, sodium starch glycolate, sodium stearyl fumarate, sorbitol, xylitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

The pharmaceutical composition of the present invention suitable for parenteral administration is best used in the form of a sterile aqueous solution which may contain other substances, for example, enough salts or glucose to make the solution isotonic with blood. The aqueous solutions should be suitably buffered (preferably to a pH of from 3 to 9), if necessary.

The pharmaceutical composition suitable for intranasal administration and administration by inhalation is best delivered in the form of a dry powder inhaler or an aerosol spray from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-25 heptafluoropropane (HFA 227EA™), carbon dioxide, or another suitable gas. The pressurized container, pump, spray or nebulizer may contain a solution or suspension of the active compound, e.g., using a mixture of ethanol and the propellant as the solvent, which may additionally contain a lubricant, e.g., sorbitan trioleate.

It is another aspect of the invention to provide a compound identifiable by the above-described method, wherein the compound is able to modulate the endonuclease activity of the PA subunit or variant thereof. In another aspect, the present invention refers to a compound identifiable by the above-described method, wherein the compound is able to decrease, preferably inhibit the endonuclease activity of the PA subunit or variant thereof, e.g., the PA subunit polypeptide or variant thereof according to the present invention. Compounds of the present invention can be any agents as described above for the in silico screening methods. In a preferred embodiment of the compound according to the present invention, the compound is not a 4-substituted 2-dioxobutanoic acid, a 4-substituted 4-dioxobutanoic acid, a 4-substituted 2,4-dioxobutanoic acid, a pyrazine-2,6-dione or a substituted pyrazine-2,6-dione such as flutimide, an N-hydroxamic acid, or an N-hydroxymide. In particular, the compound according to the present invention is not a compound according to Formula I:

Formula I

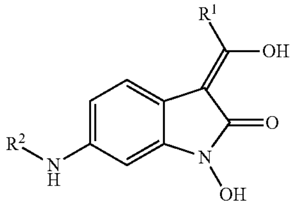

$R^1$ = Me, Et, Ph $R^2$ = acyl, carbamoyl, sulfonyl.

In another aspect, the present invention provides an antibody directed against the endonuclease domain of the PA subunit. In a preferred embodiment, said antibody recognizes the endonuclease domain by recognition of a polypeptide fragment selected from the group of polypeptides defined by SEQ ID NO: 9 to 17, i.e., amino acids 20 to 30 (SEQ ID NO: 9), 35 to 45 (SEQ ID NO: 10), 75 to 85 (SEQ ID NO: 11), 80 to 90 (SEQ ID NO: 12), 100 to 110 (SEQ ID NO: 13), 107 to 112 (SEQ ID NO: 20), 115 to 125 (SEQ ID NO: 14), 125 to 135 (SEQ ID NO: 15), 130 to 140 (SEQ ID NO: 16), and 135 to 145 (SEQ ID NO: 17) of the amino acid sequence as set forth in SEQ ID NO: 2. Preferably said antibody recognizes the amino sequence PDLYDYK (SEQ ID NO: 20). In particular, said antibody specifically binds to an epitope comprising one or more of above indicated amino acids, which define the active site. In this context, the term epitope has its art recognized meaning and preferably refers to stretches of 4 to 20 amino acids, preferably 5 to 18, 5 to 15, or 7 to 14 amino acids. Accordingly, preferred epitopes have a length of 4 to 20, 5 to 18, preferably 5 to 15, or 7 to 14 amino acids and comprise one or more of Asp108, Ile120, Lys134, His41, Glu80, Glu119, Tyr24, Arg84, Leu106, Tyr130, Glu133, and/or Lys137 of SEQ ID NO: 2 or one or more corresponding amino acid(s).

The antibody of the present invention may be a monoclonal or polyclonal antibody or portions thereof. Antigen-binding portions may be produced by recombinant DNA techniques or by enzymatic or chemical cleavage of intact antibodies. In some embodiments, antigen-binding portions include Fab, Fab', $F(ab')_2$, Fd, Fv, dAb, and complementarity determining region (CDR) fragments, single-chain antibodies (scFv), chimeric antibodies such as humanized antibodies, diabodies, and polypeptides that contain at least a portion of an antibody that is sufficient to confer specific antigen binding to the polypeptide. The antibody of the present invention is generated according to standard protocols. For example, a polyclonal antibody may be generated by immunizing an animal such as mouse, rat, rabbit, goat, sheep, pig, cattle, or horse with the antigen of interest optionally in combination with an adjuvant such as Freund's complete or incomplete adjuvant, RIBI (muramyl dipeptides), or ISCOM (immunostimulating complexes) according to standard methods well known to the person skilled in the art. The polyclonal antiserum directed against the endonuclease domain of PA or fragments thereof is obtained from the animal by bleeding or sacrificing the immunized animal. The serum (i) may be used as it is obtained from the animal, (ii) an immunoglobulin fraction may be obtained from the serum, or (iii) the antibodies specific for the endonuclease domain of PA or fragments thereof may be purified from the serum. Monoclonal antibodies may be generated by methods well known to the person skilled in the art. In brief, the animal is sacrificed after immunization and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. Immortalized cells are screened using the PA endonuclease domain or a fragment thereof. Cells that produce antibodies directed against the PA endonuclease domain or a fragment thereof, e.g., hybridomas, are selected, cloned, and further screened for desirable characteristics including robust growth, high antibody production, and desirable antibody characteristics. Hybridomas can be expanded (i) in vivo in syngeneic animals, (ii) in animals that lack an immune system, e.g., nude mice, or (iii) in cell culture in vitro. Methods of selecting, cloning, and expanding hybridomas are well known to those of ordinary skill in the art. The skilled person may refer to standard texts such as "Antibodies: A Laboratory Manual", Harlow and Lane, Eds., Cold Spring Harbor Laboratory Press, Cold Spring Harbor, N.Y. (1990), which is incorporated herein by reference, for support regarding generation of antibodies.

In another aspect, the present invention relates to the use of a compound identifiable by the above-described methods that is able to bind to the endonucleolytically active site of the PA subunit polypeptide fragment or variant thereof, and/or is able to modulate, preferably decrease, more preferably inhibit the endonucleolytic activity of the PA subunit polypeptide fragment or variant thereof, the pharmaceutical composition described above, or the antibody of the present invention for the manufacture of a medicament for treating, ameliorating, or preventing disease conditions caused by viral infections with negative-sense single stranded RNA viruses of the family of Orthomyxoviridae. In a preferred embodiment, said disease conditions are caused by viral infections with Influenza A virus, Influenza B virus, Influenza C virus, Isavirus, or Thogotovirus. In an even more preferred embodiment, said disease condition is caused by an infection with a virus species selected from the group consisting of Influenza A virus, Influenza B virus, Influenza C virus, most preferably Influenza A virus.

For treating, ameliorating, or preventing said disease conditions the medicament of the present invention can be administered to an animal patient, preferably a mammalian patient, preferably a human patient, orally, buccally, sublingually, intranasally, via pulmonary routes such as by inhalation, via rectal routes, or parenterally, for example, intracavemosally, intravenously, intra-arterially, intraperitoneally, intrathecally, intraventricularly, intra-urethrally intrasternally, intracranially, intramuscularly, or subcutaneously, they may be administered by infusion or needleless injection techniques.

The pharmaceutical compositions of the present invention may be formulated in various ways well known to one of skill in the art and as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation administered in the use of the present invention may be varied or adjusted from about 1 mg to about 1000 mg per $m^2$, preferably about 5 mg to about 150 mg/$m^2$ according to the particular application and the potency of the active component.

The compounds employed in the medical use of the invention are administered at an initial dosage of about 0.05 mg/kg to about 20 mg/kg daily. A daily dose range of about 0.05 mg/kg to about 2 mg/kg is preferred, with a daily dose range of about 0.05 mg/kg to about 1 mg/kg being most preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

EXAMPLES

The Examples are designed in order to further illustrate the present invention and serve a better understanding. They are not to be construed as limiting the scope of the invention in any way.

Summary of the Examples

PA-Nter (SEQ ID NO: 22), residues 1-209 of the amino acid sequence set forth in SEQ ID NO: 2 (A/Victoria/3/1975 (H3N2)) was expressed in *E. coli* and purified by affinity and gel filtration chromatography. The influence of metal ions on thermal stability was tested by thermofluor assays (Ericsson et al., 2006, Anal. Biochem. 357:289-298). The endonuclease activity was tested by incubation at 37° C. of 13 μM PA-Nter (SEQ ID NO: 22) with 10 μM of various RNA substrates: Alu-RNA; 110 nucleotides of the Alu-domain of *P. horikoshii*, SRP RNA, *C. albicans* tRNA Asn, U-rich RNA (5'-GGCCAUCCUGU$_7$CCCU$_{11}$CU$_{19}$-3'; SEQ ID NO: 18, Saito et al., 2008, Nature 454:523-527), panhandle RNA (ph-RNA) of 81 nucleotides (Baudin et al., 1994, EMBO J. 13:3158-3165), short ph-RNA of 36 nucleotides comprising just the conserved 3'- and 5'-ends with a short linker, and circular single stranded DNA (M13mp18) (Fermentas). Crystals diffracting to 2 Å resolution were obtained at 20° C. by the hanging drop method using a protein solution of 5-10 mg/ml in 20 mM Tris pH 8.0, 100 mM NaCl, and 2.5 mM $MnCl_2$ and a reservoir composition of 1.2 M $Li_2SO_4$, 100 mM MES pH 6.0, 10 mM magnesium acetate and 3% ethylene glycol. Diffraction data were collected on beamlines ID14-4 and ID23-1 at the European Synchrotron Radiation Facility (ESRF). The structure was solved by the single-wavelength anomalous dispersion (SAD) method using a gadolinium chloride soaked crystal. Nine sites were found by SHELXD (Schneider and Sheldrick, 2002, Acta Crystallogr. D. Biol. Crystallogr. 58:1772-1779) and refined with SHARP (de La Fortelle et al., 1997, Methods in Enzymology 276:472-494). After three-fold NCS averaging with RESOLVE (Terwilliger, 2002, Acta Crystallogr. D.

Biol. Crystallogr. 58:2213-2215) an interpretable map was obtained and much of the model could be built with ARP/wARP (Perrakis et al., 1999, Nat. Struct. Biol. 6:458-463). Additionally, data were measured on a native crystal at the manganese K edge (X-ray wavelength 1.89 Å) to reveal the location and identity of bound manganese ions through anomalous difference Fourier synthesis. There are three molecules in the asymmetric unit denoted A, B, and D. The metal ion structure is best defined in molecule A. The crystallographic statistics are summarized in Table 1 and more details available in the experimental Examples below.

TABLE 1

Data collection and refinement statistics of PA-Nter (SEQ ID NO: 22)

| | PA-Nter (SEQ ID NO: 22) native | PA-Nter (SEQ ID NO: 22) Mn K-edge | PA-Nter (SEQ ID NO: 22) Gd derivative |
|---|---|---|---|
| Data collection | | | |
| Beamline (ESRF) | ID14-4 | ID23-1 | ID14-4 |
| Wavelength (A) | 0.976 | 1.892 | 1.008 |
| Space group | $P4_32_12$ | $P4_32_12$ | $P4_32_12$ |
| Cell dimensions | | | |
| a, b, c (A) | 67.1, 67.1, 302.9 | 67.9, 67.9, 300.8 | 67.8, 67.8, 300.4 |
| α, β, γ (°) | 90.0, 90.0, 90.0 | 90.0, 90.0, 90.0 | 90.0, 106.24, 90.0 |
| Resolution (A) | 50-2.05 (2.05-2.10)* | 30-2.60 (2.6-2.7)* | 30-2.5 (2.5-2.6)* |
| $R_{merge}$ | 0.056 (0.690) | 0.055 (0.484) | 0.058 (0.539) |
| //σ/ | 17.6 (2.2) | 17.8 (2.5) | 14.5 (2.1) |
| Completeness (%) | 93.2 (99.4) | 99.7 (99.8) | 97.9 (98.0) |
| Redundancy | 4.84 (5.64) | 3.66 (3.44) | 3.63 (3.15) |
| Refinement | | | |
| Resolution (A) | 30-2.05 (2.05-2.10)* | | |
| Total No. reflections/free | 39715/2118 | | |
| $R_{work}$ | 0.217 (0.278) | | |
| $R_{free}$ | 0.268 (0.320) | | |
| No. atoms | | | |
| Protein | 4742 | | |
| Water/sulphate/Mn ions | 152/8/5 | | |
| Average B-factors ($A^2$) | | | |
| All atoms | 45.8 | | |
| Chains A, B, D | 41.5, 40.0, 57.0 | | |
| R.m.s. deviations | | | |
| Bondlengths (A) | 0.014 | | |
| Bondangles (°) | 1.363 | | |
| Ramachandran Plot** | | | |
| Favoured (%) | 98.1 | | |
| Allowed (%) | 99.8 | | |

Example 1

Cloning, Expression and Purification

The DNA coding for PA residues 1-209 of the amino acid sequence set forth in SEQ ID NO: 2 (A/Victoria/3/1975 (H3N2)) was cloned into a pET-M11 expression vector (EMBL) between the NcoI and XhoI sites. A polypeptide linker having the amino acid sequence GMGSGMA (SEQ ID NO: 19) was engineered after the tobacco etch virus (TEV) cleavage site to obtain a 100% cleavage by TEV protease. This vector was used to transform the BL21(DE3)-RIL-CodonPlus *E. coli* strain (Stratagene). The protein was expressed in LB medium overnight at 15° C. after induction with 0.1 mM isopropyl-β-thiogalactopyranoside (ITPG). The protein was purified by an immobilised metal affinity column (IMAC). A second IMAC step was performed after cleavage using a His-tagged TEV protease, followed by gel filtration on a Superdex 200 column (GE Healthcare). Finally, the protein was concentrated to 5 to 10 mg/ml.

Example 2

Endonuclease Assay

All ribonucleic acid substrates for endonuclease assays were obtained by in vitro T7 transcription as described previously (Price et al., 1995, J. Mol. Biol. 249:398-408). Two structured RNAs were used: Alu-RNA; 110 nucleotides comprising the Alu-domain of *Pyrococcus horikoshii* signal recognition particle (SRP) RNA (unpublished construct) and *Candida albicans* $tRNA^{Asn}$ composed of 76 nucleotides (unpublished construct). We also used a uridine-rich unstructured RNA of 51 nucleotides (U-rich RNA; 5'-GGCCAUCCUGU$_7$CCCU$_{11}$CU$_{19}$-3'; SEQ ID NO: 18) (Saito et al., 2008, Nature 454:523-527) and two partially folded RNAs derived from influenza A virus genomic RNA segment 5: a panhandle RNA (ph-RNA) of 81 nucleotides (Baudin et al., 1994, EMBO J. 13:3158-3165) and a shorter panhandle RNA (short ph-RNA) of 36 nucleotides comprising just the conserved 3'- and 5'-ends with a short linker (unpublished construct). The endonuclease activity was also tested using a circular single stranded DNA (M13mp18) (Fermentas).

RNA cleavage was performed by incubating 13 μM PA-Nter (SEQ ID NO: 22) with various RNA substrates (all at 10 μM) at 37° C. in a final volume of 50 μL. The reaction buffer was 20 mM Tris-HCl pH 8, 100 mM NaCl, 10 mM β-mercaptoethanol, and 1 mM metal salts. Incubations were stopped by addition of EGTA at a final concentration of 20 mM. The reaction products were loaded on 8 M urea polyacrylamide gels (8% or 15%) and stained with methylene blue. The effect of divalent cations on the RNAse activity of PA-Nter (SEQ ID NO: 22) was tested at pH 8 (with β-mercaptoethanol) and pH 7 (without β-mercaptoethanol) by incubating ph-RNA with PA-Nter (SEQ ID NO: 22) in the presence of different metal salts: $MnCl_2$, $CaCl_2$, $MgCl_2$, $ZnCl_2$ (or $NiCl_2$ at pH 7) and $CoCl_2$. For DNA cleavage, circular single stranded M13mp18 DNA was used. In the 10 μL reaction volume (same buffer as for RNA), 100 ng/μL, of purified plasmid M13mp18 was incubated for 60 minutes in the presence of PA-Nter (SEQ ID NO: 22) and 1 mM $MnCl_2$. The reaction products were loaded on a 0.8% agarose gel and stained with ethidium bromide. For endonuclease inhibition by 2,4-Dioxo-4-phenylbutanoic acid (DPBA), PA-Nter (SEQ ID NO: 22) and ph-RNA or single stranded M13mp18 DNA were incubated in the presence of 1 mM $MnCl_2$ and increasing concentrations of DPBA. Because DPBA is poorly soluble in water, a stock solution of 65 mM DPBA was prepared in 50% ethanol that was further diluted so that only 1 P μL of DPBA solution had to be added to each reaction mix to obtain the required final concentration. Addition of the inhibitor in ethanol did not change the pH of the reaction mixture and the addition of the same concentration of ethanol alone had no effect on nuclease activity (not shown).

Figure 5:
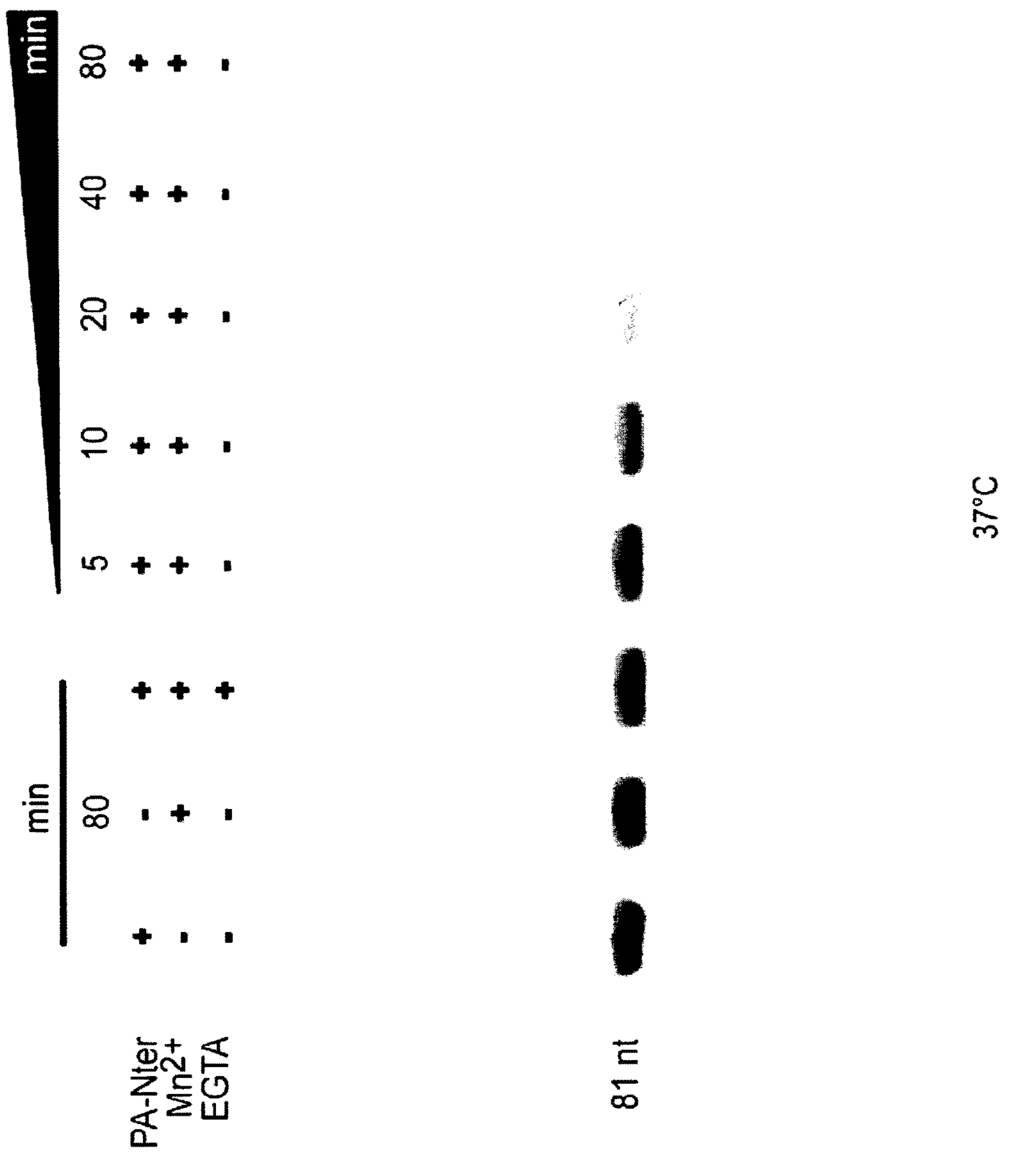
FIG. 5: Time series of the endonuclease activity of PA-Nter (SEQ ID NO: 22). 10 μM purified panhandle RNA (ph-RNA) was incubated with 13 μM PA-Nter plus 1 mM $MnCl_2$. The incubation at 37° C. was stopped by adding 20 mM EGTA after 5, 10, 20, 40, and 80 minutes (lanes 4 to 8, respectively). As controls, ph-RNA was incubated for 80 minutes at 37° C. with only PA-Nter (SEQ ID NO: 22) (lane 1) only $MnCl_2$ (lane 2) or PA-Nter (SEQ ID NO: 22) and $MnCl_2$ plus 20 mM EGTA. The reaction products were loaded on an 8% acrylamide/8 M urea gel and stained with methylene blue.
Figure 6:
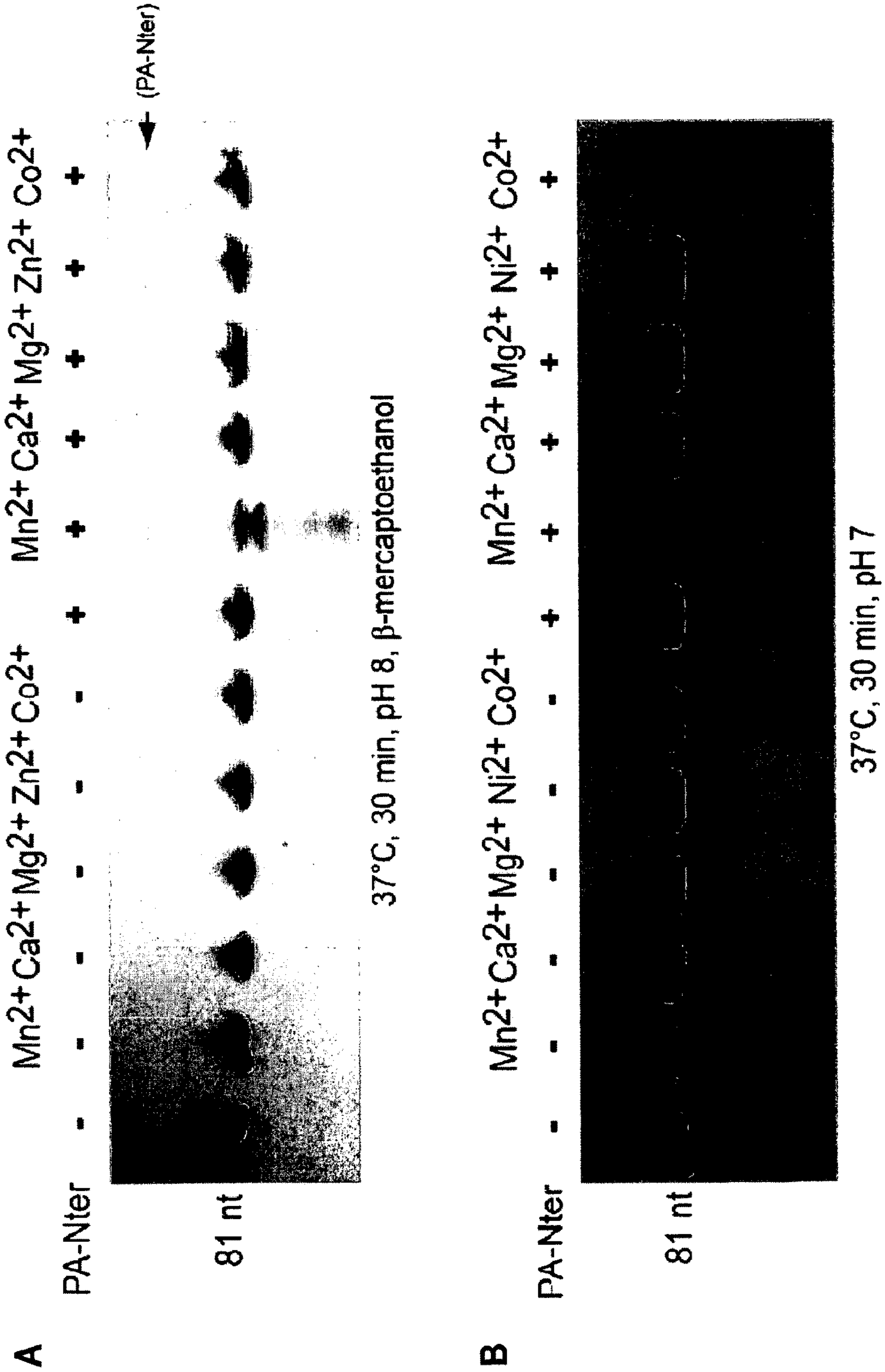
FIG. 6: Effect of divalent cations on PA-Nter (SEQ ID NO: 22) endonuclease (RNase) activity. In the top panel (A), purified ph-RNA plus PA-Nter (SEQ ID NO: 22) were incubated at pH 8 in the presence of β-mercaptoethanol and 1.5 mM $MnCl_2$, $CaCl_2$, $MgCl_2$, $ZnCl_2$, or $CoCl_2$. In the bottom panel (B), ph-RNA and PA-Nter (SEQ ID NO: 22) were incubated at pH 7 with 1.5 mM $MnCl_2$, $CaCl_2$, $MgCl_2$, $NiCl_2$, or $CoCl_2$. After 30 minutes the reactions were stopped by adding 20 mM EGTA. Controls were performed using either salts or PA-Nter (SEQ ID NO: 22) alone as indicated. The reaction products were loaded on 8% or 15% (for bottom panel) acrylamide/8 M urea and stained with methylene blue. Note that at pH 7, $CoCl_2$ stimulated the endonuclease stronger than $MnCl_2$. At pH 8, $CoCl_2$ precipitates and, thus, does not activate the endonuclease activity.
Figure 7:
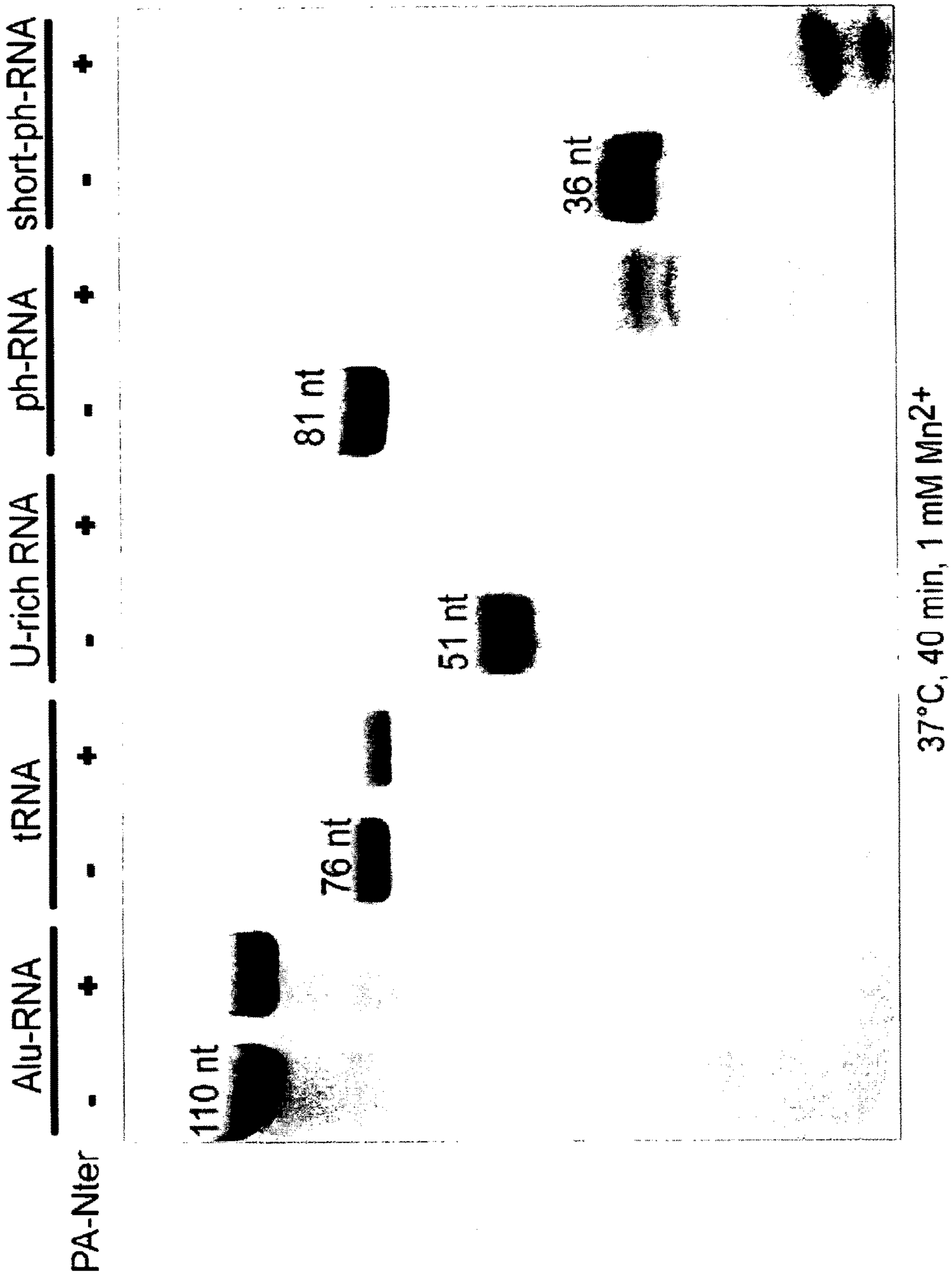
FIG. 7: PA-Nter (SEQ ID NO: 22) endonuclease (RNase) activity on different RNA substrates. SRP Alu-RNA, tRNA, U-rich RNA, ph-RNA or short ph-RNA were incubated with PA-Nter (SEQ ID NO: 22) plus 1 mM $MnCl_2$ (lanes 2, 4, 6, 8, and 10) or in the absence of PA-Nter (SEQ ID NO: 22; lanes 1, 3, 5, 7, and 9). The digestion was performed at 37° C. After 40 minutes the reaction was stopped by adding 20 mM EGTA. The reaction products were loaded on a 15% acrylamide/8 M urea gel and stained with methylene blue.
Figure 8:
FIG. 8: Endonuclease activity of PA-Nter (SEQ ID NO: 22) on single stranded DNA. Single stranded DNA plasmid M13mp18 (100 ng/μl) (Fermentas) was incubated for 60 minutes at 37° C. in the presence of PA-Nter (SEQ ID NO: 22) plus $MnCl_2$ (lane 4). The reaction was stopped by adding 20 mM EGTA. As controls, M13mp18 was incubated with 1 mM $MnCl_2$ only (lane 2) or PA-Nter (SEQ ID NO: 22) plus $MnCl_2$ and 20 mM EGTA (lane 3). The reaction products were loaded on a 0.8% agarose gel and stained with ethidium bromide.
Figure 9:
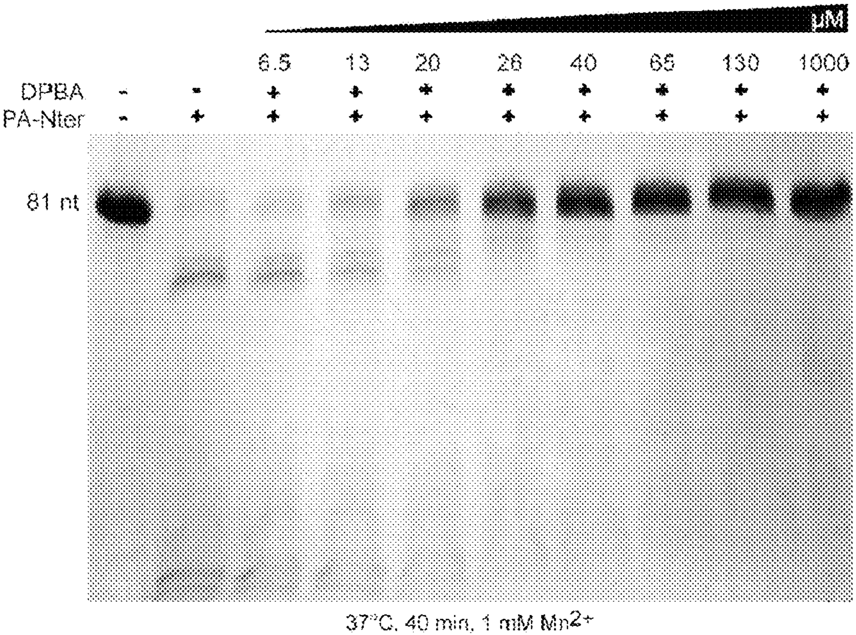
FIG. 9: Inhibition of PA-Nter (SEQ ID NO: 22) endonuclease activity by 2,4-Dioxo-4-phenylbutanoic acid (DPBA). Cleavage of ph-RNA (A) or M13mp18 ssDNA (B) by PA-Nter (SEQ ID NO: 22) was tested at 37° C. during 40 minutes in the presence of 1 mM $MnCl_2$ and increasing concentrations of DPBA (0, 6.5, 13, 20, 26, 40, 65, 130, and 1000 μM). As a control, ph-RNA or ssDNA was incubated with 1 mM $MnCl_2$ alone (lanes 1). The reaction products were loaded on 8% acrylamide/8 M urea and stained with methylene blue (A) or on a 0.8% agarose gel and stained with ethidium bromide (B).
Figure 9:
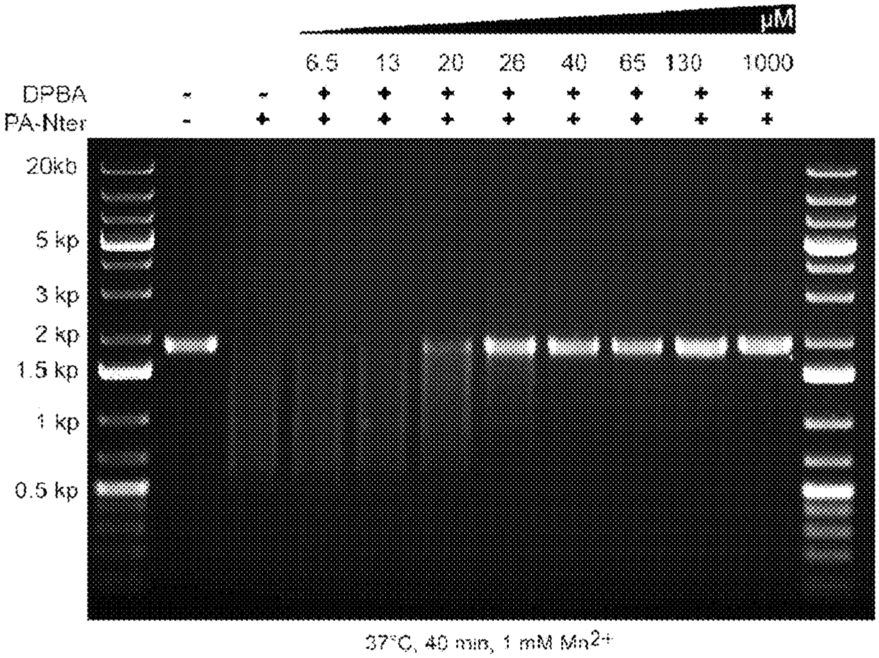

Using a partially structured 81nt ph-RNA it could be demonstrated that PA-Nter (SEQ ID NO: 22) has intrinsic RNase activity that is divalent cation dependent (FIG. 5). Consistent with the results on RNPs (Doan et al., 1999, Biochemistry 38:5612-5619, strong activity was observed at pH 8 with manganese and weaker activity with magnesium ions. At pH 7, the PA-Nter (SEQ ID NO: 22) endonuclease activity was also observed with cobalt (FIG. 6). After 40 minutes incubation highly structured RNAs such as tRNA and SRP Alu-RNA were relatively resistant to degradation, partially structured ph- and short-ph-RNAs were partially degraded and unstructured U-rich RNA was completely degraded, suggesting that the enzyme is single-strand specific (FIG. 7). The enzyme also completely degraded circular ssDNA showing that it is a nonspecific endonuclease (FIG. 8). The endonuclease activity on both RNA and DNA was inhibited in a dose dependent manner by the compound 2,4-dioxo-4-phenylbutanoic acid, a known inhibitor of influenza endonuclease (FIG. 9). The $K_i$ for this compound is estimated at 26 μM, in excellent agreement with the $IC_{50}$ reported for the same compound inhibiting cleavage of capped RNA by the intact influenza virus polymerase (Tomassini et al., 1994, Antimicrob. Agents Chemother 38:2827-2837).

Example 3

Thermal Shift Assay

Thermal shift assays were performed with 10 μM of PA-Nter (SEQ ID NO: 22) in 20 mM Tris-HCl pH 7.0 or 8.0, 100 mM NaCl and a 5× dilution of SYPRO Orange dye (Invitrogen) as described (Ericsson et al., 2006, Anal. Biochem. 357:289-298). The dye was excited at 490 nm and the emission light was recorded at 575 nm while the temperature was increased by increments of 1° C. per minute from 25 to 75° C. Control assays were carried out in the absence of protein or dye to check that no fluorescence signal was recorded.

Figure 4:
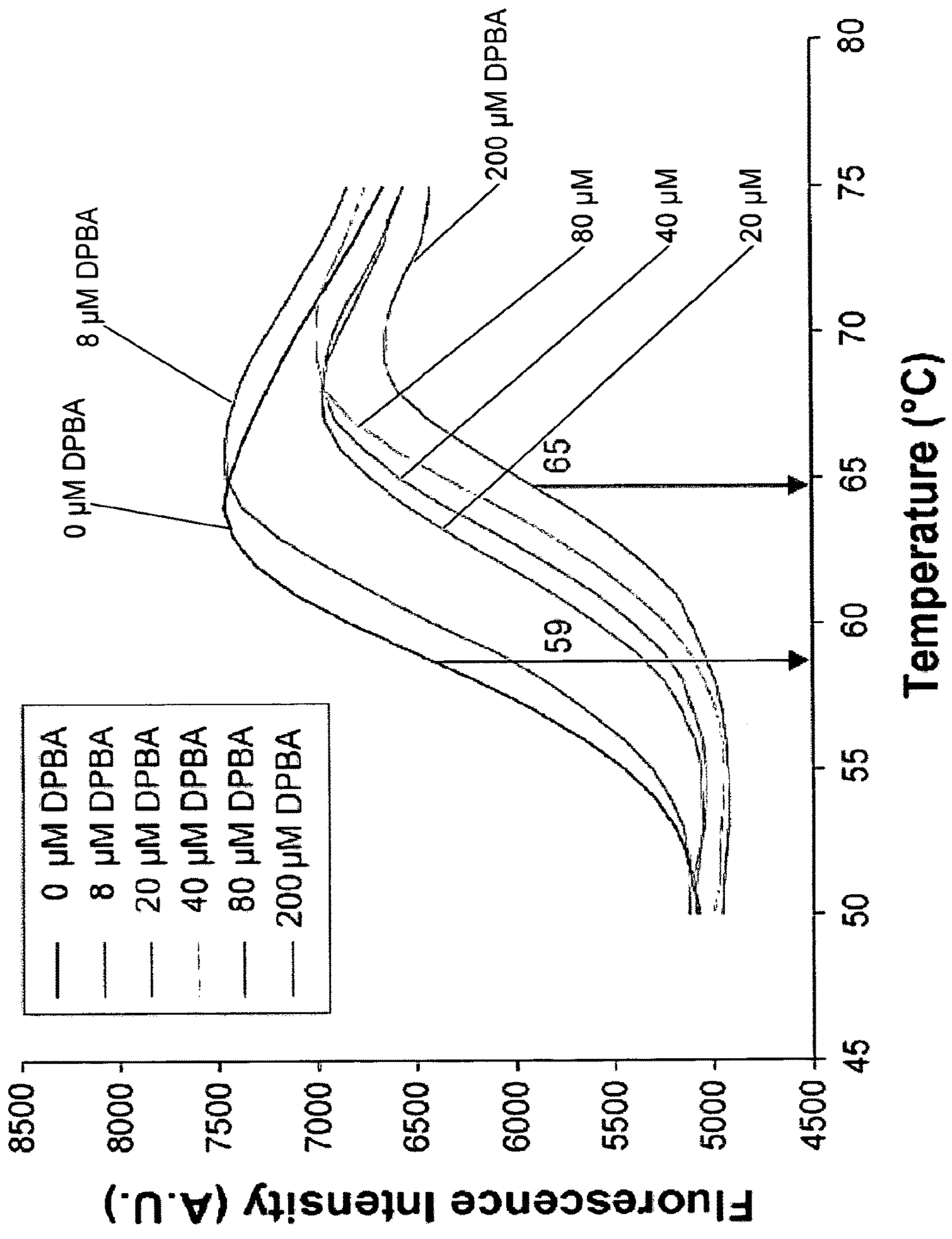
FIG. 4: Assay of thermal stability with 2,4-Dioxo-4-phenylbutanoic acid (DPBA). Thermal shift assay with different concentrations of DPBA. DPBA further stabilizes PA-Nter (SEQ ID NO: 22) in the presence of $MnCl_2$.

The thermal shift assay was performed to investigate the thermal stability of PA-Nter (SEQ ID NO: 22) in presence and absence of divalent cations. The experiments revealed a significant increase in thermal stability (apparent melting temperature shifts from 44° C. to 57° C.) upon addition of manganese ions and to a lesser extent upon addition of calcium and magnesium ions (FIGS. 1 and 2). Titrating the compound 2,4-dioxo-4-phenylbutanoic acid, a known inhibitor of influenza endonuclease, to manganese bound PA-Nter (SEQ ID NO: 22) increases the thermal stability even further (apparent melting temperature shifts from 59° C. to 65° C.) (FIG. 4), whereas the inhibitor has no effect on metal-free enzyme (data not shown).

Example 4

Far UV Circular Dichroism (CD) Spectroscopy

Far-UV CD spectra were recorded with 1 mM path length at 20° C. on a JASCO model J-810 CD spectro-polarimeter equipped with a Peltier thermostat. The PA-Nter (SEQ ID NO: 22) concentration was 10 uM in 10 mM Tris-HCl, pH 8.0, 10 mM NaCl in the presence or absence of 1 mM $MnCl_2$. Mean residue ellipticity was calculated using the number of residues (PA-Nter (SEQ ID NO: 22) is 209 residues long plus 7 additional residues before the starting methionine). Wavelength scans were recorded from 200 to 260 run and averaged over eight consecutive scans (0.5 nm increment, 1 s response, 1 nm bandwidth and 50 nm/min scanning speed).

Figure 3:
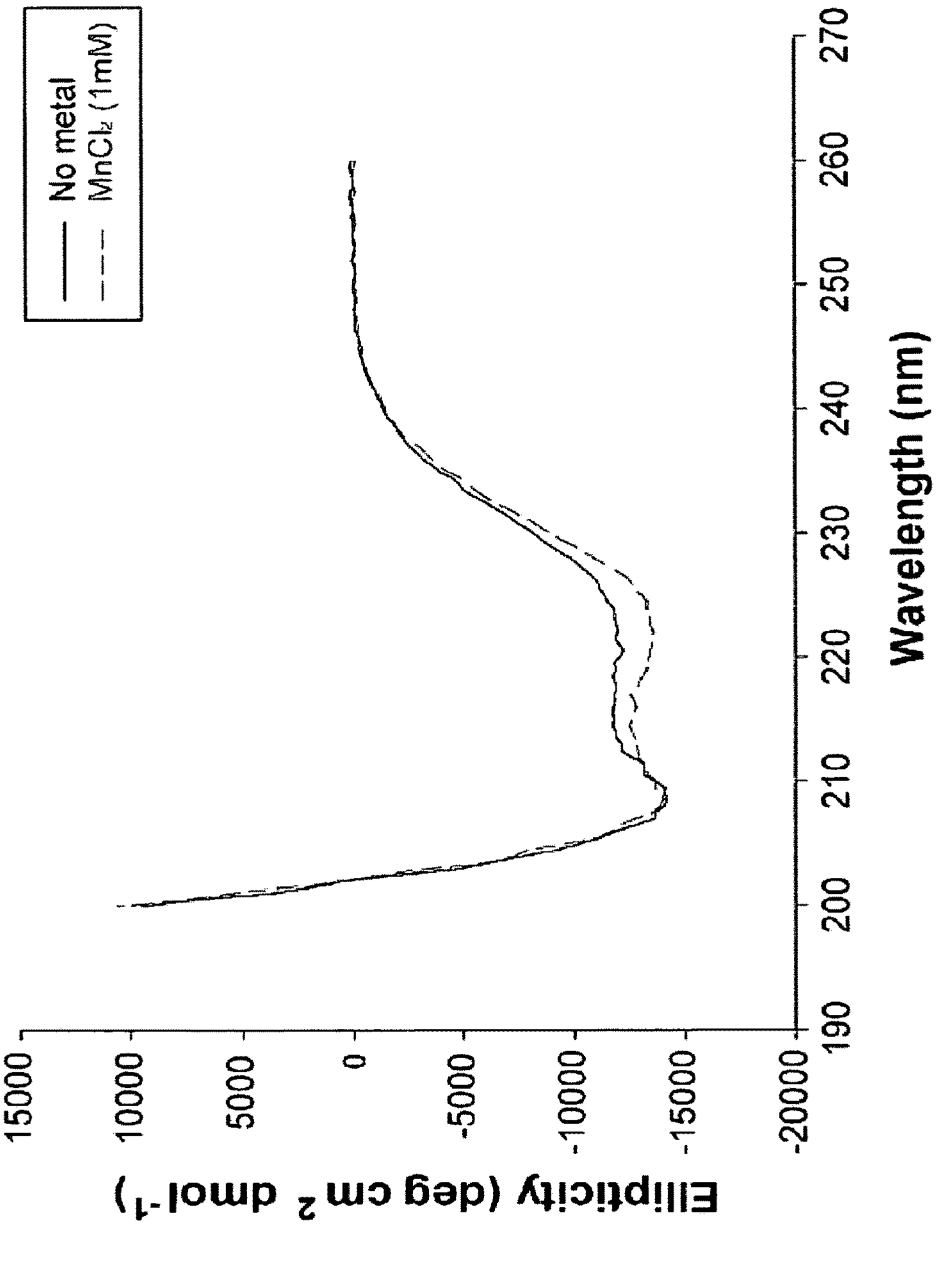
FIG. 3: Effect of manganese on the structure of PA-Nter (SEQ ID NO: 22) observed by far UV CD spectra. The secondary structure content of PA-Nter (SEQ ID NO: 22) was monitored in absence (full line) or presence of 1 mM $MnCl_2$ (dashed line).

The structural effect of manganese binding to PA-Nter (SEQ ID NO: 22), investigated by CD spectroscopy, revealed a significant increase in helical content (estimated 8 to 9 residues) upon addition of 1 mM $Mn^{2+}$ (FIG. 3).

Example 5

Crystallization and Crystallography

Initial sitting drop screening was carried out at 20° C. mixing 100 nL of protein solution (6 mg/ml) with 100 nL of well solution using a Cartesian robot. Subsequently, larger crystals were obtained at 20° C. by the hanging drop method following a ratio of 1:1 well:protein solutions. The protein solution was at 5-10 mg/ml in 20 mM Tris-HCl pH 8.0, 100 mM NaCl, 2.5 mM $MnCl_2$. The reservoir composition was 100 mM MES pH 6.0, 1.2 M $Li_2SO_4$, 10 mM magnesium acetate, 3% ethylene glycol after refinement of the crystallisation condition. Crystals appeared after 1-2 weeks and were typically of a volume of 50×50×15 $\mu m^3$.

Crystals were frozen in liquid nitrogen in the presence of 22% ethylene glycol for cryoprotection. Diffraction data were collected at 100 K on beamlines ID14-4 and ID23-1 at the European Synchrotron Radiation Facility (ESRF) and all data were integrated and scaled in the space group $P4_32_12$ using the XDS suite (Kabsch, 1993, J. Appl. Cryst. 26:795-800). The best native data were collected to 2.05 Å resolution at a wavelength of 0.976 Å, after soaking with additional 10 mM $MnCl_2$ for 2 minutes. Additionally, data was measured on native crystals at a wavelength of 1.89 Å (close to the manganese K edge) to reveal the location and identity of any bound manganese ions. The structure was solved with a highly redundant data set to 2.5 Å resolution collected at a wavelength of 1.008 Å from a crystal soaked for 6 h in mother liquor containing 5 mM $GdCl_3$. Three initial Gd sites were located on the basis of their anomalous differences using SHELXD (Schneider and Sheldrick, 2002, Acta Crystallogr. D. Biol. Crystallogr. 58:1772-1779) as implemented in HKL2MAP (Pape and Schneider, 2004, J. Appl. Cryst. 37:843-844). These initial sites were refined and experimental phases to 3.5 Å were calculated using the single anomalous dispersion (SAD) procedure in SHARP (de La Fortelle et al., 1997, Methods in Enzymology 276:472-494). After several iterative cycles a further 6 sites were identified in the residual maps and the phases were refined to 2.5 Å. These initial phases were improved with the density modification package SOLOMON in SHARP. Finally, a clearly interpretable map was obtained by using 3-fold NCS operators identified from the 9 Gd sites by RESOLVE (Terwilliger, 2002, Acta Crystallogr. D. Biol. Crystallogr. 58:2213-2215) for averaging with DM (Cowtan, 1994, Joint CCP4 and ESF-EACBM Newsletter on Protein Crystallography 31:34-38) as implemented in CCP4 (Collaborative Computational Project, 1994, Acta Crystallogr. D. Biol. Crystallogr. 50:760-763). This averaged map was of sufficient quality for RESOLVE (Terwilliger, 2003, Acta Crystallogr. D. Biol. Crystallogr. 59:45-49) to build 396 out of 648 possible amino acids, of which 85 could be sequence assigned. A manually modified model and a subsequent high resolution data set to 2.05 Å were then put into ARP/wARP (Perrakis et al., 1999, Nat. Struct. Biol. 6:458-463) resulting in a more complete model. This model was refined with Refmac (Murshudov, 1997, Acta Crystallogr. D. Biol. Crystallogr. 53:240-255) iterated with manual rebuilding cycles in 0 (Jones et al., 1991, Acta Crystallogr. A 47:110-119). Using TLS refinement and tight NCS restraints on parts of the structure, the final R-factor (R-free) is 0.233 (0.291). According to MOLPROBITY (Lovell et al., 2003, Proteins 50:437-450), 97.5%, 99.8% are respectively in the favoured and allowed region of the Ramachandran plot. The crystallographic details are summarized in Table 1. There are three molecules in the asymmetric unit denoted A, B, and D. The metal ion structure is best defined in molecule A. Different molecules have regions 69-74 and 134-143 more or less well ordered. 6 residues of the N-terminal tag and residues 204-209 are not visible. Molecule D is the least well ordered overall (Table 1). In the described structure the crystal contact between two of the molecules (B and D) exhibits multiple conformations perhaps accounting for the relatively high R-factor of the native data for the resolution. Structure figures were drawn with PyMOL (DeLano, 2002, available on the World Wide Web at pymol.sourceforge.net). The sequence alignment in FIG. 11 was drawn with ESPript (espript.ibcp.fr/ESPript/cgi-bin/ESPript.cgi) (Gouet et al., 1999, Bioinformatics 15:305-308). The electrostatic surface (FIG. 13) was calculated using DelPhi (Rocchia et al., 2002, J. Comput. Chem. 23:128-137). Structural similarity searches were performed with MSDFOLD (available on the World Wide Web at ebi.ac.uk/msdsrv/ssm/cgi-bin/ssm-server) and Dalilite (available on the World Wide Web at ebi.ac.uk/Tools/dalilite/index.html).

Figure 10:
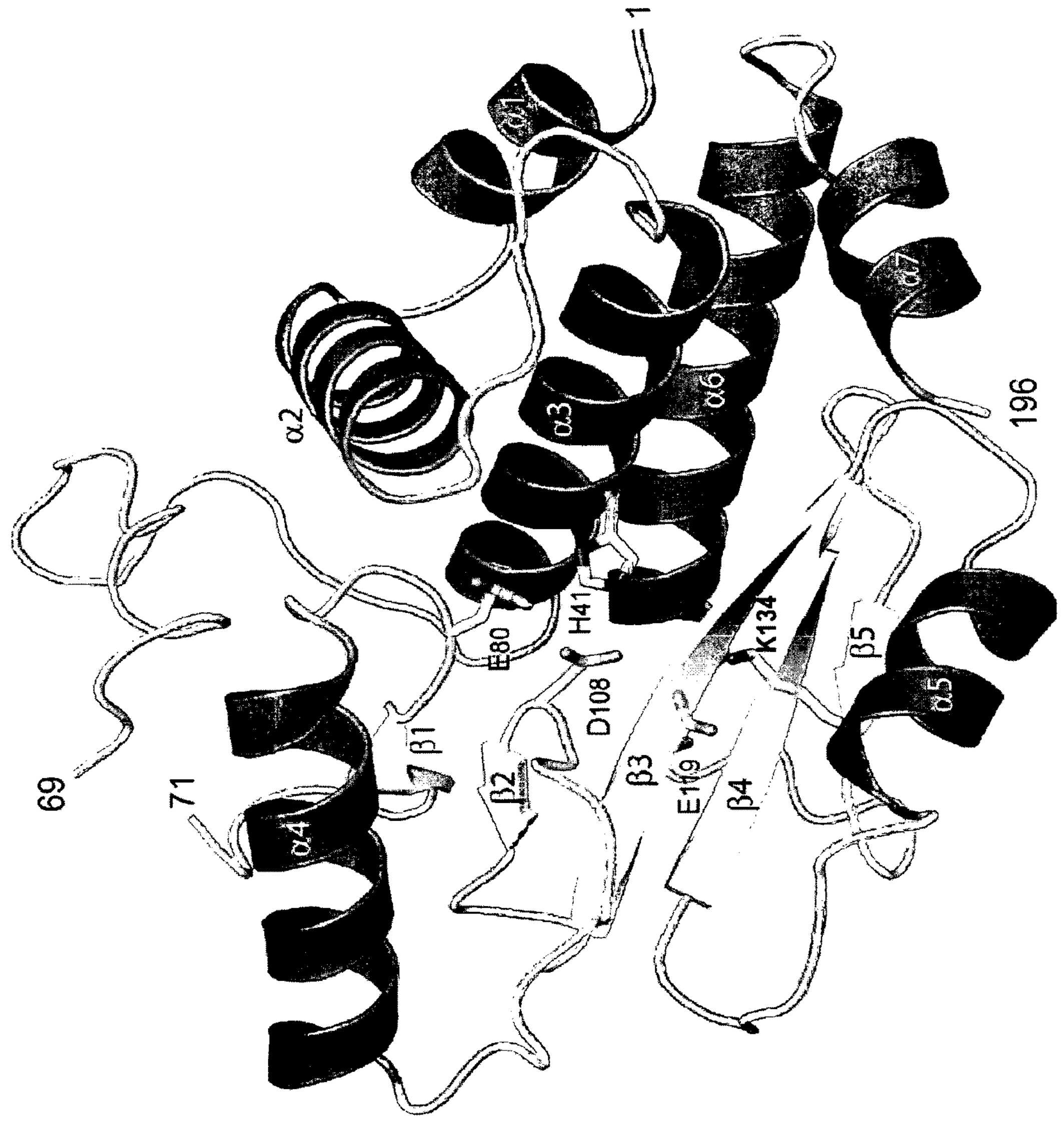
FIG. 10: Three-dimensional structure of PA-Nter (SEQ ID NO: 22). Ribbon diagram of the structure of influenza PA-Nter (SEQ ID NO: 22) with α-helices (medium grey) and β-strands (light grey). The key active site residues are indicated in stick representation.
Figure 14:
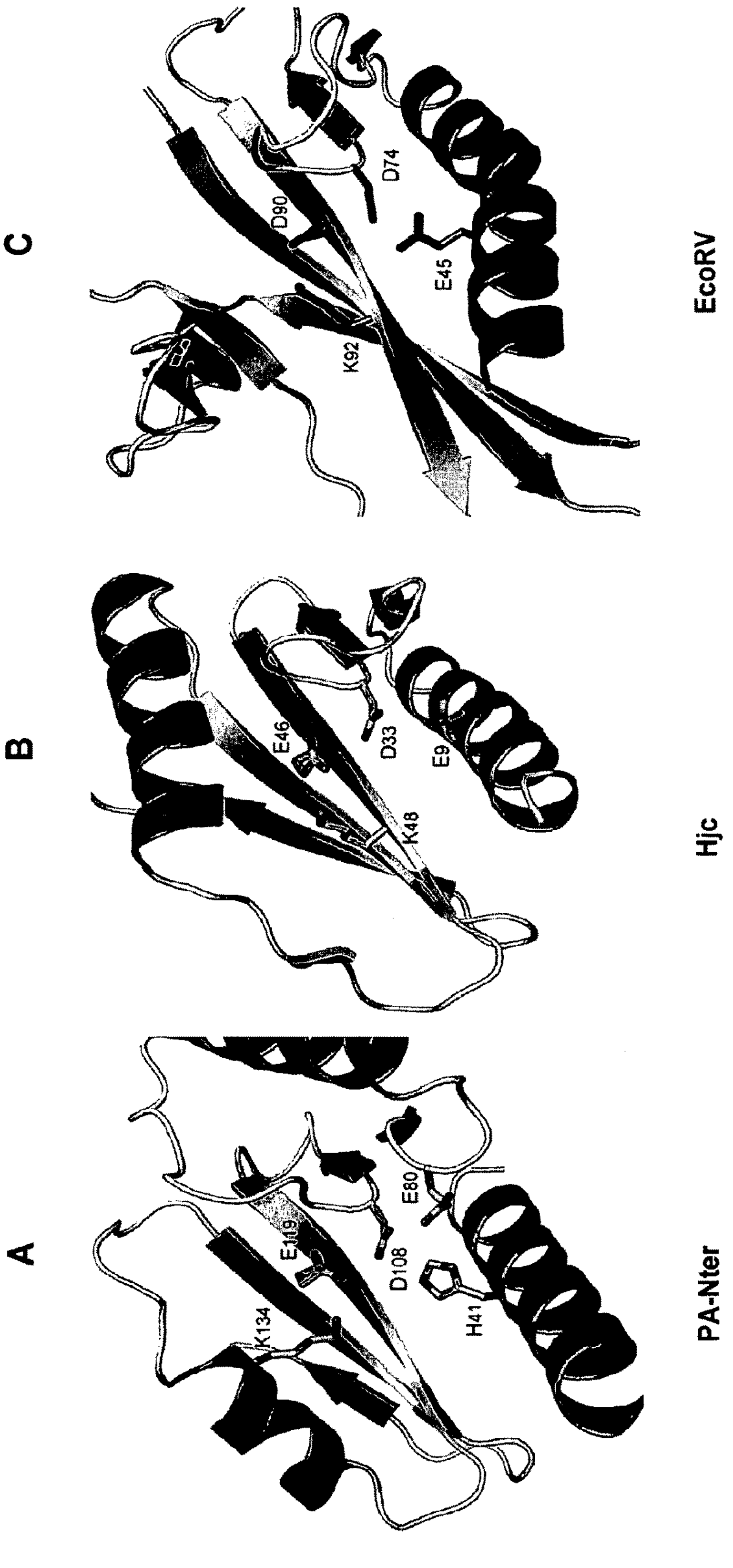
FIG. 14: Comparison of PA-Nter (SEQ ID NO: 22) with other nucleases of the PD-(D/E)XK superfamily. Comparison of PA-Nter (SEQ ID NO: 22; left, A), *P. furiosus* Holliday junction resolvase Hjc (PDB entry 1GEF) (middle, B) and *E. coli* EcoRV restriction enzyme (PDB entry 1 STX, product complex with DNA and manganese) (right, C) after superposition of the conserved core active site structural motif. The rootmean-square-deviations are 2.9 Å for 77 aligned Cα atoms of Hjc and 2.46 (3.1) A for 55 (72) aligned Cα atoms of EcoRV. Secondary-structure elements are as in FIG. 10 with key active sites residues in stick representation.
Figure 16:
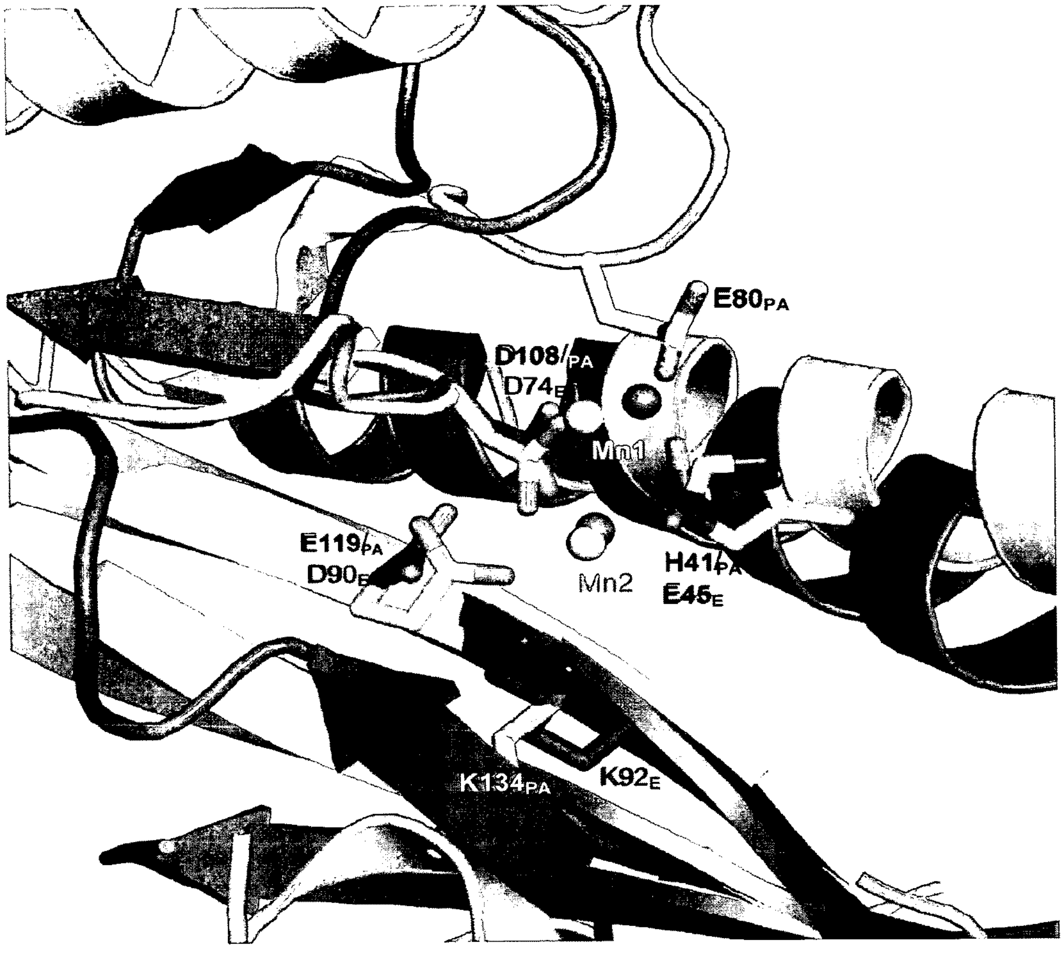
FIG. 16: Superposition of the active sites of influenza PA-Nter (SEQ ID NO: 22) and *E. coli* EcoRV restriction enzyme. PA-Nter (SEQ ID NO: 22) secondary structure elements and active sites residues (indicated with PA) are shown in light grey with the manganese ions in medium grey. Superposed are the equivalent elements of EcoRV (PDB entry 1 STX) (Horton and Perona, 2004, Biochemistry 43:6841-6857) in dark grey (indicated with E) for the protein and dark grey for the manganese ions. Key active site metal binding and catalytic functional groups of the two proteins align.

We grew small square-plate crystals of PA-Nter (SEQ ID NO: 22) in the presence of both manganese and magnesium that diffracted to about 2 Å resolution, with three independent molecules in the asymmetric unit. The crystal structure reveals a single, folded domain with residues 1-196 visible, comprising seven a-helices and a mixed, five-stranded β-sheet (FIG. 10). The structure based sequence alignment amongst influenza A, B and C viruses (FIG. 11) projected onto a surface representation reveals a very highly conserved depression that is strongly negatively charged due to a concentration of acidic residues (FIGS. 12 and 13), suggestive of an active site. A structure similarity search gave no high scoring hits indicating that the global fold is novel. The most similar protein found is the archaeal Holliday junction resolvase Hjc from *Pyrococcus furiosus* (Nishino et al., 2001, Structure 9:197-204). The structural alignment of PA-Nter (SEQ ID NO: 22) with Hjc superposes helix α3 and strands β1-5 (FIG. 14, left and middle panel) encompassing a structural motif characteristic of many nucleases including resolvases and type II restriction enzymes. The motif includes catalytically important divalent metal ion binding acidic residues Asp33 and Glu46 of Hjc upon which Asp108 and Glu119 of PA-Nter (SEQ ID NO: 22) exactly superpose. Structural alignment of PA-Nter (SEQ ID NO: 22) with type II restriction endonucleases such as BamHI or EcoRV reveals a similar superposition of active site elements (FIG. 14, right panel). Catalytically important Glu45, Asp74, Asp90 and Lys92 of EcoRV align with His41, Asp108, Glu119 and Lys134 of PA-Nter (SEQ ID NO: 22), respectively, although the lysines are positioned differently in the primary sequence (FIG. 16). The conserved lysine is implicated in stabilizing the attacking hydroxide nucleophile during catalysis. Thus PA-Nter (SEQ ID NO: 22) is a new member of the PD-(D/E)XK nuclease superfamily which encompasses a diversity of enzymes involved in various aspects of DNA metabolism. In PA-Nter (SEQ ID NO: 22), the characteristic motif occurs at 107-PDLYDYK (SEQ ID NO: 20), although the separation between the two acidic residues is unusually short and the putative catalytically important lysine (Lys134) has 'migrated' to an alternative position, as in some other members of the superfamily. Within this family, PA-Nter (SEQ ID NO: 22) is unusual in that it is biologically functional as an RNase and has a histidine in the active site.

Figure 15:
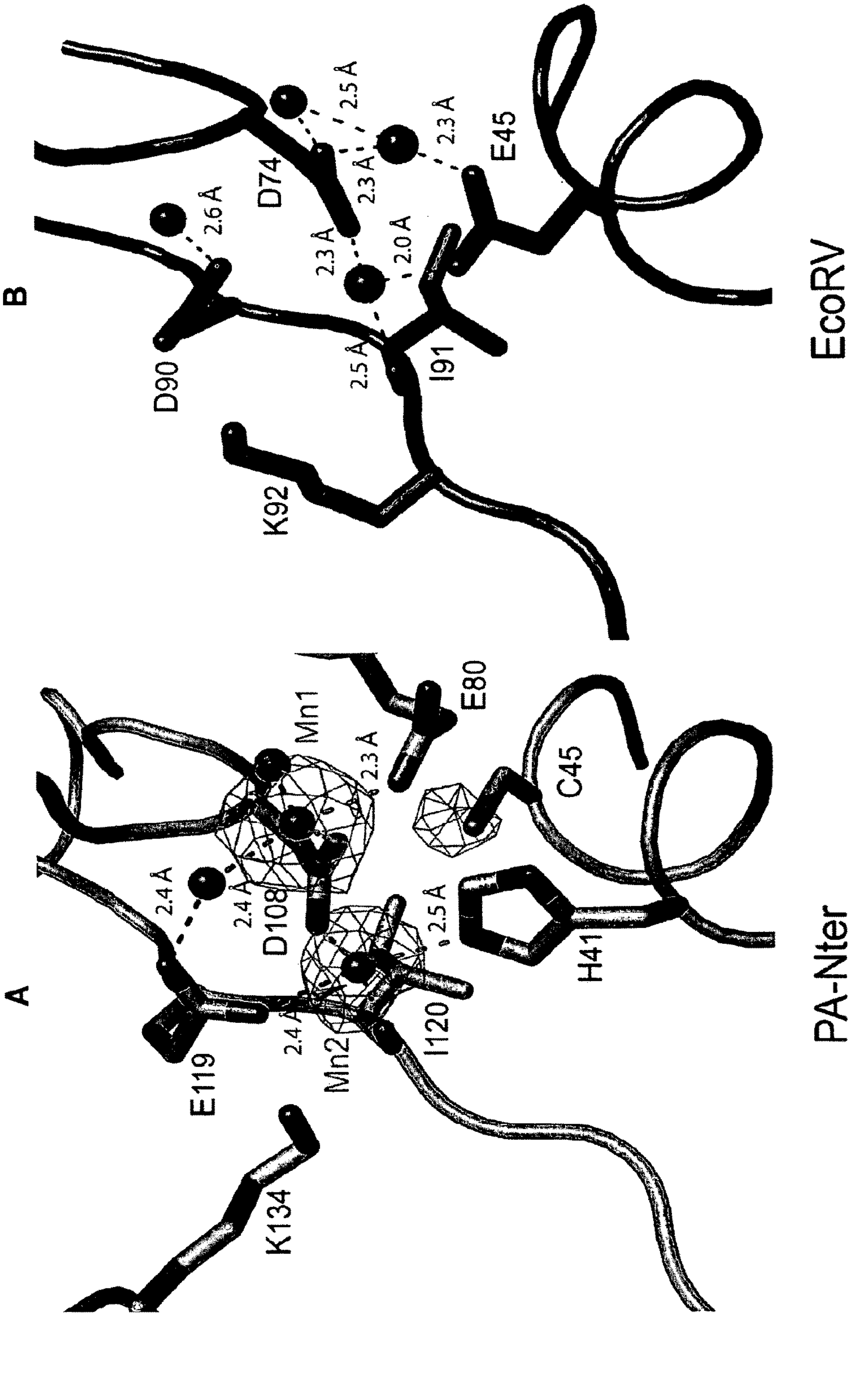
FIG. 15: Details of the manganese ion interactions with the active sites of influenza PA-Nter (SEQ ID NO: 22; molecule A) (left, A) and *E. coli* EcoRV restriction enzyme (product complex) (right, B). The active site elements and residues are shown respectively in light grey and dark grey (left) and dark grey (right). Manganese ions and water molecules are respectively medium grey and dark grey spheres. The anomalous difference map contoured at 3σ, calculated using manganese K edge (wavelength 1.89) diffraction data and model phases, is in dark grey. Peak heights are 14.1, 10.1, and 5.0 σ for Mn1, Mn2 and the sulphur of Cys45 respectively. Note that in metal dependent nucleases, the exact configuration of the metal ions and acidic side chains subtly depends on the reaction co-ordinate.
Figure 17:
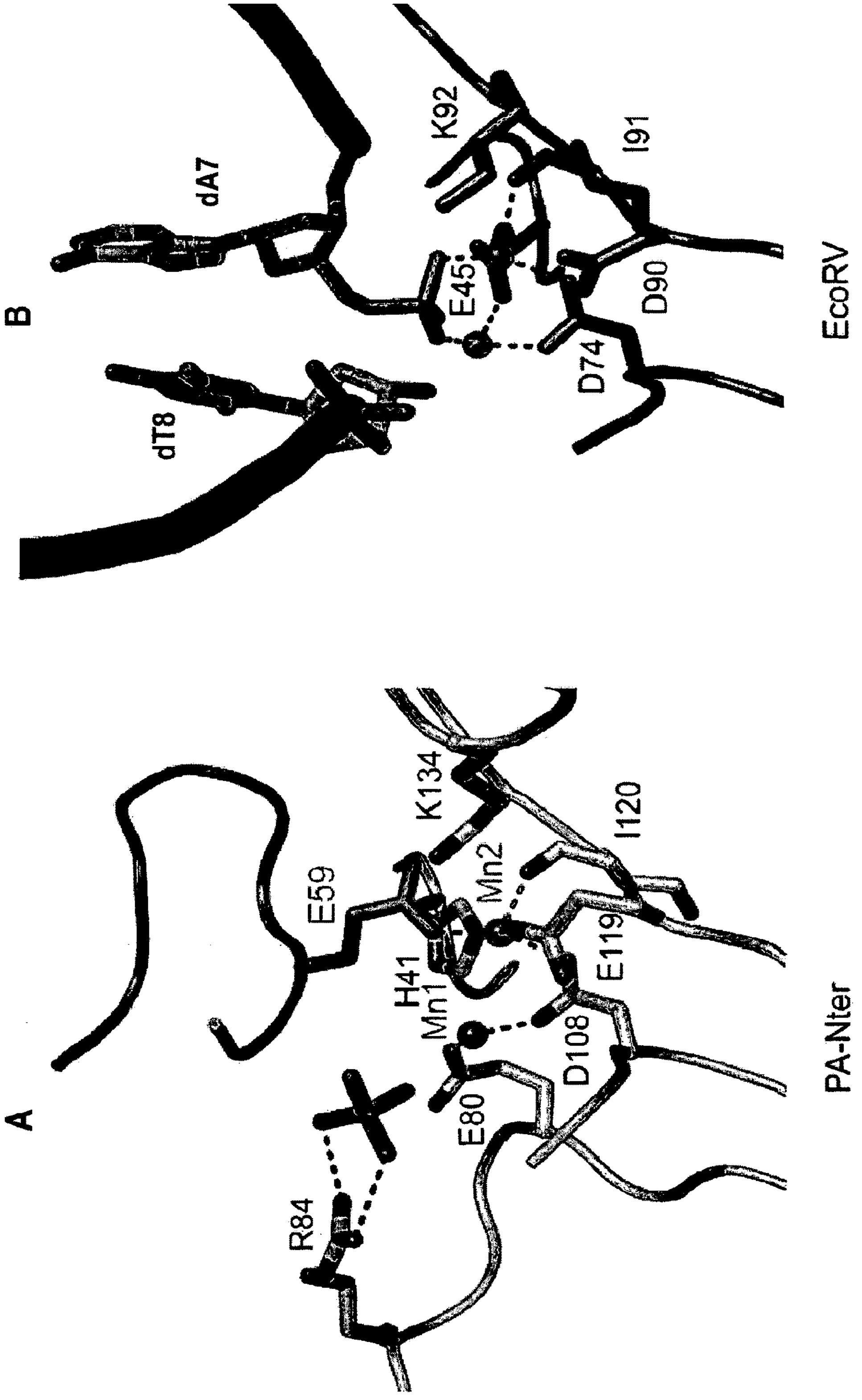
FIG. 17: Comparison of EcoRV product complex (B) and PA-Nter (SEQ ID NO: 22) with Glu66 from a neighboring molecule (A). The active site elements and residues of PA-Nter (SEQ ID NO: 22; molecule A) are shown in light grey with manganese ions in medium grey and the Glu66 containing loop of the adjacent molecule in light grey. In the same orientation, after superposition of the two structures, *E. coli* EcoRV restriction enzyme (PDB entry 1 STX) (Horton and Perona, supra) is shown in dark grey with the DNA bases in light grey and the manganese ions in medium grey. The carboxyl function of Glu59 superimposes on the scissile phosphate of dA7 whereas the well-ordered sulphate ion found in the active site of PA-Nter (SEQ ID NO: 22) occupies the position of the phosphate part of dT8.

To confirm that the conserved acidic residues of PA-Nter (SEQ ID NO: 22) are metal binding residues we calculated an anomalous difference map using data collected at the manganese K absorption edge. Two manganese ions were identified in each active site as adjacent anomalous peaks separated by about 3.8 Å (FIG. 15, left panel). The stronger peak (Mn1) is co-ordinated by Glu80, Asp108 and two water molecules; the weaker site (Mn2) by His41, Asp108, Glu119 and the carbonyl oxygen of Ile120. The cited residues are absolutely conserved in all influenza virus PA sequences (except for Ile120 which is conservatively substituted) (FIG. 11). The two metal sites correspond closely with those observed in restriction enzymes such as EcoRV (FIG. 15, right panel). His41 (positioned as Glu45 in EcoRV) from helix α3 could be important in conferring manganese specificity, since magnesium and calcium bind less readily to histidine. Manganese binding by His41 and the resulting stabilization of helix α3 could account for the additional helical content (estimated as 8-9 residues) detected upon incubating PA-Nter (SEQ ID NO: 22) with manganese (FIG. 3). In the crystal, Mn1 is also co-ordinated by Glu59 from a loop of an adjacent molecule. Superposition of DNA complexes of BamHI or EcoRV on PA-Nter (SEQ ID NO: 22) shows that the Glu59 carboxylate group corresponds closely to the position of the scissile phosphate group (FIG. 17). Thus our structure mimics a substrate or product complex.

Our structural and biochemical results combined with previous observations on the trimeric polymerase provide compelling evidence that PA-Nter (SEQ ID NO: 22) is the endonuclease that cleaves host mRNAs during cap-snatching. First, the domain has intrinsic RNA and DNA endonuclease activity which is preferentially activated by manganese, in accordance with observations reported for the viral RNPs (FIG. 6). Second, this activity is inhibited by a compound known to inhibit influenza endonuclease activity with a nearly identical $K_i$ (FIG. 9). Third, the domain contains a structural motif characteristic of the catalytic core of a broad family of nucleases, including type II endonucleases. The active site features a cluster of three acidic residues (Glu80, Asp108 and Glu119) and a putative catalytic lysine (Lys134) (FIGS. 14 to 16). Fourth, these acidic residues, together with His41, are all absolutely conserved in influenza viruses, co-ordinate two manganese ions in a configuration consistent with a two-metal dependent reaction mechanism as proposed for many nucleases (FIG. 15, left panel).

The invention claimed is:

1. An isolated polynucleotide encoding a polypeptide consisting of:

a)

i. amino acids 1 to 209 of the amino acid sequence of SEQ ID NO: 2 or a fragment thereof consisting of at least amino acids 15 to 196 of the amino acid sequence of SEQ ID NO: 2, or a variant consisting of at least 95% amino acid sequence identity to amino acids 1 to 209 of the amino acid sequence of SEQ ID NO: 2, or a fragment thereof consisting of at least 95% amino acid sequence identity to amino acids 15 to 196 of the amino acid sequence of SEQ ID NO: 2, ii. amino acids 1 to 206 of the amino acid sequence of SEQ ID NO: 4 or a fragment thereof consisting of at least amino acids 15 to 195 of the amino acid sequence of SEQ ID NO: 4, or a variant consisting of at least 95% amino acid sequence identity to amino acids 1 to 206 of the amino acid sequence of SEQ ID NO: 4, or a fragment thereof consisting of at least 95% amino acid sequence identity to amino acids 15 to 195 of the amino acid sequence of SEQ ID NO: 4, or iii. amino acids 1 to 189 of the amino acid sequence of SEQ ID NO: 6 or a fragment thereof consisting of at least amino acids 15 to 178 of the amino acid sequence of SEQ ID NO: 6, or a variant consisting of at least 95% amino acid sequence identity to amino acids 1 to 189 of the amino acid sequence of SEQ ID NO: 6, or a fragment thereof consisting of at least 95% amino acid sequence identity to amino acids 15 to 178 of the amino acid sequence of SEQ ID NO: 6, wherein said polypeptide has endonuclease activity of a PA subunit of a viral RNA-dependent RNA polymerase, and b)

i. a protease recognition site with or without an amino acid linker, and ii. a heterologous peptide or heterologous protein tag.

2. A recombinant vector comprising said isolated polynucleotide of claim 1.

3. A recombinant host cell comprising said isolated polynucleotide of claim 1.

4. The isolated polynucleotide of claim 1, wherein said polypeptide encoded by said isolated polynucleotide consists of amino acids 1 to 209 of the amino acid sequence set forth in SEQ ID NO: 2 linked to the amino acid sequence of SEQ ID NO: 19.

5. The isolated polynucleotide of claim 1, wherein said protease recognition site is a thrombin, Factor Xa, PreScission or TEV protease recognition site.

6. The isolated polynucleotide of claim 1, wherein said protease recognition site is the amino acid sequence of SEQ ID NO: 23.

7. The isolated polynucleotide of claim 6, wherein said protease recognition site is the amino acid sequence of SEQ ID NO: 21.

8. The isolated polynucleotide of claim 1, wherein said amino acid linker is the amino acid sequence of SEQ ID NO: 19.

9. The isolated polynucleotide of claim 1, wherein said heterologous peptide or heterologous protein tag is a tag that facilitates purification or detection of the polypeptide.

10. The isolated polynucleotide of claim 1, wherein said heterologous peptide or heterologous protein tag is selected from the group consisting of hemagglutinin-tag, FLAG-tag, myc-tag, poly-His-tag, glutathione-S-transferase-tag, maltose-binding-protein-tag, NusA-tag, thioredoxin-tag, and a fluorescent protein-tag.

11. The isolated polynucleotide of claim 10, wherein said fluorescent protein-tag is selected from the group consisting of a green fluorescent protein, a yellow fluorescent protein, a red fluorescent protein, and a cyan fluorescence protein.

12. An isolated polynucleotide encoding a polypeptide consisting of:

a)

i. amino acids 1 to 209 of the amino acid sequence of SEQ ID NO: 2 or a fragment thereof consisting of at least amino acids 15 to 196 of the amino acid sequence of SEQ ID NO: 2, or a variant consisting of at least 95% amino acid sequence identity to amino acids 1 to 209 of the amino acid sequence of SEQ ID NO: 2, or a fragment thereof consisting of at least 95% amino acid sequence identity to amino acids 15 to 196 of the amino acid sequence of SEQ ID NO: 2, ii. amino acids 1 to 206 of the amino acid sequence of SEQ ID NO: 4 or a fragment thereof consisting of at least amino acids 15 to 195 of the amino acid sequence of SEQ ID NO: 4, or a variant consisting of at least 95% amino acid sequence identity to amino acids 1 to 206 of the amino acid sequence of SEQ ID NO: 4, or a fragment thereof consisting of at least 95% amino acid sequence identity to amino acids 15 to 195 of the amino acid sequence of SEQ ID NO: 4 or iii. amino acids 1 to 189 of the amino acid sequence of SEQ ID NO: 6 or a fragment thereof consisting of at least amino acids 15 to 178 of the amino acid sequence of SEQ ID NO: 6, or a variant consisting of at least 95% amino acid sequence identity to amino acids 1 to 189 of the amino acid sequence of SEQ ID NO: 6, or a fragment thereof consisting of at least 95% amino acid sequence identity to amino acids 15 to 178 of the amino acid sequence of SEQ ID NO: 6, wherein said polypeptide has endonuclease activity of a PA subunit of a viral RNA-dependent RNA polymerase, and a heterologous peptide or heterologous protein tag.

13. A recombinant vector comprising said isolated polynucleotide of claim 12.

14. A recombinant host cell comprising said isolated polynucleotide of claim 12.

15. The isolated polynucleotide of claim 12, wherein said polypeptide encoded by said isolated polynucleotide consists of amino acids 1 to 209 of the amino acid sequence set forth in SEQ ID NO: 2 linked to the amino acid sequence of SEQ ID NO: 19.

16. The isolated polynucleotide of claim 12, wherein said heterologous peptide or heterologous protein tag is a tag that facilitates purification or detection of the polypeptide.

17. The isolated polynucleotide of claim 12, wherein said heterologous peptide or heterologous protein tag is selected from the group consisting of hemagglutinin-tag, FLAG-tag, myc-tag, poly-His-tag, glutathione-S-transferase-tag, maltose-binding-protein-tag, NusA-tag, thioredoxin-tag, and a fluorescent protein-tag.

18. The isolated polynucleotide of claim 17, wherein said fluorescent protein-tag is selected from the group consisting of a green fluorescent protein, a yellow fluorescent protein, a red fluorescent protein, and a cyan fluorescence protein.

* * * * *

UNITED STATES PATENT AND TRADEMARK OFFICE

CERTIFICATE OF CORRECTION

PATENT NO. : 9,890,368 B2
APPLICATION NO. : 14/519525
DATED : February 13, 2018
INVENTOR(S) : Denis Bouvier et al.

It is certified that error appears in the above-identified patent and that said Letters Patent is hereby corrected as shown below:

On the Title Page

Item (72) should be corrected to read:
--(72) Inventors: Denis Bouvier, Meylan (FR); Thibaut Crepin, Grenoble (FR); Rob Ruigrok, Sassenage (FR); Alexander Dias, Voiron (FR); Stephen Cusack, Seyssinet-Pariset (FR)--

Signed and Sealed this
Tenth Day of April, 2018

Andrei Iancu
*Director of the United States Patent and Trademark Office*